US012807650B2

(12) United States Patent
Keen et al.

(10) Patent No.: US 12,807,650 B2
(45) **Date of Patent: *Nov. 24, 2026**

(54) HETEROTANDEM BICYCLIC PEPTIDE COMPLEXES

(71) Applicant: BicycleTx Limited, Cambridge (GB)

(72) Inventors: Nicholas Keen, Carlisle, MA (US); Kevin Mcdonnell, Lexington, MA (US); Peter Park, Lincoln, MA (US); Punit Upadhyaya, Lexington, MA (US); Gemma Elizabeth Mudd, Cambridge (GB)

(73) Assignee: BicycleTx Limited, Cambridge (GB)

( * ) Notice: Subject to any disclaimer, the term of this patent is extended or adjusted under 35 U.S.C. 154(b) by 785 days.

This patent is subject to a terminal disclaimer.

(21) Appl. No.: 17/663,169

(22) Filed: May 12, 2022

(65) Prior Publication Data

US 2023/0008076 A1 Jan. 12, 2023

Related U.S. Application Data

(62) Division of application No. 16/372,692, filed on Apr. 2, 2019, now Pat. No. 11,453,703.

(30) Foreign Application Priority Data

Apr. 4, 2018 (GB) ..................................... 1805492
Dec. 21, 2018 (GB) ..................................... 1820981

(51) Int. Cl.

| | |
|---|---|
| ***C07K 14/00*** | (2006.01) |
| ***A61K 38/00*** | (2006.01) |
| ***A61K 38/12*** | (2006.01) |
| ***A61P 35/00*** | (2006.01) |
| ***C07K 7/06*** | (2006.01) |
| ***C07K 7/08*** | (2006.01) |
| ***C07K 7/50*** | (2006.01) |
| ***C07K 14/705*** | (2006.01) |
| ***C07K 14/715*** | (2006.01) |
| ***C07K 17/08*** | (2006.01) |

(52) U.S. Cl.

CPC ............ *C07K 14/001* (2013.01); *A61K 38/12* (2013.01); *A61P 35/00* (2018.01); *C07K 7/06* (2013.01); *C07K 7/08* (2013.01); *C07K 7/50* (2013.01); *C07K 14/70503* (2013.01); *C07K 14/70578* (2013.01); *C07K 14/715* (2013.01); *A61K 38/00* (2013.01); *C07K 17/08* (2013.01)

(58) Field of Classification Search

CPC .......... C07K 14/001; C07K 7/06; C07K 7/08; C07K 7/50; C07K 14/70503; C07K 14/70578; C07K 14/715; C07K 17/08; C07K 14/47; C07K 14/705; C07K 14/70575; C07K 14/78; A61K 38/12; A61K 38/00; A61P 35/00

See application file for complete search history.

(56) References Cited

U.S. PATENT DOCUMENTS

| | | | |
|---|---|---|---|
| 2,642,514 | A | 6/1953 | Herkenhoff |
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,595,756 | A | 1/1997 | Bally et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,326,144 | B1 | 12/2001 | Bawendi et al. |
| 6,468,808 | B1 | 10/2002 | Nie et al. |
| 6,552,065 | B2 | 4/2003 | Remiszewski et al. |
| 7,151,047 | B2 | 12/2006 | Chan |
| 7,192,785 | B2 | 3/2007 | Nie et al. |
| 7,390,799 | B2 | 6/2008 | Bruncko et al. |
| 8,138,347 | B2 | 3/2012 | Adams et al. |
| 8,680,022 | B2 | 3/2014 | Gregory et al. |
| 8,685,890 | B2 | 4/2014 | Winter et al. |
| 8,778,844 | B2 | 7/2014 | Winter et al. |
| 8,906,682 | B2 | 12/2014 | June et al. |
| 8,986,655 | B2 | 3/2015 | Weiss et al. |
| 9,518,081 | B2 | 12/2016 | Winter et al. |
| 9,644,201 | B2 | 5/2017 | Winter et al. |
| 9,657,288 | B2 | 5/2017 | Winter et al. |

(Continued)

FOREIGN PATENT DOCUMENTS

| | | | |
|---|---|---|---|
| CN | 101497878 | A | 5/2009 |
| CN | 105307686 | A | 2/2016 |

(Continued)

OTHER PUBLICATIONS

Product specification for 4-pentynoic acid from Sigma-Aldrich, downloaded May 29, 2025 from the internet. (Year: 2025).*

(Continued)

*Primary Examiner* — Joseph Fischer
(74) *Attorney, Agent, or Firm* — Wolf, Greenfield & Sacks, P.C.

(57) ABSTRACT

The present invention relates to heterotandem bicyclic peptide complexes which comprise a first peptide ligand, which binds to a component present on an immune cell, conjugated via a linker to a second peptide ligand, which binds to a component present on a cancer cell. The invention also relates to the use of said heterotandem bicyclic peptide complexes in preventing, suppressing or treating cancer.

28 Claims, 73 Drawing Sheets

Specification includes a Sequence Listing.

(56) References Cited

U.S. PATENT DOCUMENTS 9,670,482 B2 6/2017 Winter et al.
9,670,484 B2 6/2017 Winter et al.
9,670,521 B2 6/2017 Grabstein et al.
9,868,767 B2 1/2018 Pei et al.
9,932,367 B2 4/2018 Stace et al.
9,994,617 B2 6/2018 Tite et al.
10,118,947 B2 11/2018 Teufel et al.
10,294,274 B2 5/2019 Teufel et al.
10,441,663 B2 10/2019 Bennett et al.
10,532,106 B2 1/2020 Teufel et al.
10,624,968 B2 4/2020 Bennett et al.
10,626,147 B2 4/2020 Pei et al.
10,792,368 B1 10/2020 Teufel et al.
10,800,813 B2 10/2020 Tite et al.
10,857,196 B2 12/2020 Beswick et al.
10,870,679 B2 12/2020 Teufel et al.
10,875,894 B2 12/2020 Chen et al.
10,894,808 B2 1/2021 Teufel et al.
10,899,798 B2 1/2021 Bennett et al.
10,919,937 B2 2/2021 Beswick et al.
10,994,019 B2 5/2021 Teufel et al.
11,103,591 B2 8/2021 Teufel et al.
11,180,531 B2 11/2021 Beswick et al.
11,241,473 B2 2/2022 Beswick et al.
11,261,214 B2 3/2022 Chen et al.
11,306,123 B2 * 4/2022 Mudd ..................... A61P 35/00
11,312,749 B2 4/2022 Mudd et al.
11,332,500 B2 * 5/2022 Mudd .................... C07K 11/02
11,396,530 B2 7/2022 Beswick et al.
11,414,488 B2 8/2022 Bennett et al.
11,433,137 B2 9/2022 Bennett et al.
11,453,702 B2 9/2022 Beswick et al.
11,453,703 B2 9/2022 Keen et al.
11,484,602 B2 11/2022 Chen et al.
11,542,304 B2 1/2023 Chen et al.
11,613,560 B2 3/2023 Stephen et al.
11,623,012 B2 4/2023 Chen et al.
11,672,868 B2 6/2023 Teufel et al.
11,696,956 B2 7/2023 Chen et al.
11,730,819 B2 8/2023 Teufel et al.
11,746,126 B2 9/2023 Bennett et al.
11,814,447 B2 11/2023 Teufel et al.
11,833,211 B2 12/2023 Chen et al.
11,912,792 B2 2/2024 Beswick et al.
11,946,041 B2 4/2024 Chen et al.
11,970,553 B2 * 4/2024 Mudd ..................... A61P 35/00
12,049,520 B2 7/2024 Chen et al.
12,435,107 B2 * 10/2025 Mudd ..................... A61P 35/00
2002/0164788 A1 11/2002 Ellis
2005/0169931 A1 8/2005 Kinch et al.
2009/0222937 A1 9/2009 Arnould et al.
2009/0304721 A1 12/2009 Kinch et al.
2012/0101253 A1 4/2012 Heinis et al.
2012/0172235 A1 7/2012 Winter et al.
2013/0064791 A1 3/2013 Poelstra et al.
2013/0072598 A1 3/2013 Yang et al.
2014/0163201 A1 6/2014 Winter et al.
2014/0249292 A1 9/2014 Tite et al.
2014/0256596 A1 9/2014 Tite et al.
2014/0274759 A1 9/2014 Walker et al.
2015/0038434 A1 2/2015 Yang et al.
2015/0087810 A1 3/2015 Moore et al.
2016/0031939 A1 2/2016 Stace et al.
2016/0046721 A1 2/2016 Qian et al.
2016/0122430 A1 5/2016 Gish et al.
2016/0256579 A1 9/2016 Shalom
2016/0326232 A1 11/2016 Rosa et al.
2017/0067045 A1 3/2017 Winter et al.
2017/0190743 A1 7/2017 Pei et al.
2017/0204150 A1 7/2017 Liu et al.
2017/0304342 A1 10/2017 Cox et al.
2017/0306032 A1 10/2017 Gehlsen
2017/0360952 A1 12/2017 Schwartz et al.
2018/0169254 A1 6/2018 Bennett et al.
2018/0200378 A1 7/2018 Bennett et al.
2018/0280525 A1 10/2018 Teufel et al.
2018/0311300 A1 11/2018 Beswick et al.
2018/0318451 A1 11/2018 Skerra et al.
2018/0362585 A1 12/2018 Teufel et al.
2018/0371020 A1 12/2018 Bennett et al.
2019/0134213 A1 5/2019 Teufel et al.
2019/0184025 A1 6/2019 Chen et al.
2019/0263866 A1 * 8/2019 Chen ....................... A61P 35/00
2019/0307836 A1 10/2019 Keen et al.
2019/0389906 A1 * 12/2019 Beswick ................ A61P 35/00
2019/0389907 A1 12/2019 Teufel et al.
2020/0129630 A1 4/2020 Koehler et al.
2020/0131228 A1 4/2020 Beswick et al.
2020/0171161 A1 6/2020 Teufel et al.
2020/0190213 A1 6/2020 Preyer et al.
2020/0215199 A1 7/2020 Bennett et al.
2020/0255477 A1 8/2020 Chen et al.
2020/0283482 A1 9/2020 Keen et al.
2020/0289657 A1 9/2020 Teufel et al.
2020/0291096 A1 9/2020 Keen et al.
2020/0316209 A1 10/2020 Teufel et al.
2020/0338203 A1 10/2020 Chen et al.
2020/0354406 A1 11/2020 Stephen et al.
2020/0354456 A1 11/2020 Bennett et al.
2020/0407709 A1 12/2020 Chen et al.
2021/0040154 A1 2/2021 Mudd et al.
2021/0046145 A1 2/2021 Beswick et al.
2021/0069287 A1 3/2021 Mudd et al.
2021/0079045 A1 3/2021 Bennett et al.
2021/0101932 A1 4/2021 Chen et al.
2021/0101933 A1 4/2021 Chen et al.
2021/0101937 A1 4/2021 Mudd et al.
2021/0122785 A1 4/2021 Teufel et al.
2021/0122804 A1 4/2021 Teufel et al.
2021/0147484 A1 5/2021 Beswick et al.
2021/0147485 A1 5/2021 Teufel et al.
2021/0261620 A1 8/2021 Teufel et al.
2021/0269480 A1 9/2021 Beswick et al.
2021/0299210 A2 9/2021 Keen et al.
2022/0023432 A1 1/2022 Teufel et al.
2022/0024982 A1 1/2022 Chen et al.
2022/0031858 A1 2/2022 Mcdonnell et al.
2022/0054646 A1 2/2022 Chen et al.
2022/0064218 A1 3/2022 Baldassarre et al.
2022/0064221 A1 3/2022 Lani et al.
2022/0072140 A1 3/2022 Stace et al.
2022/0088118 A1 3/2022 Baldassarre et al.
2022/0088207 A1 3/2022 Chen et al.
2022/0089643 A1 3/2022 Beswick et al.
2022/0119488 A1 4/2022 Lani et al.
2022/0133732 A1 5/2022 Baldassarre et al.
2022/0133733 A1 5/2022 Baldassarre et al.
2022/0135614 A1 5/2022 Teufel et al.
2022/0184222 A1 6/2022 Bennett et al.
2022/0194983 A1 6/2022 Teufel et al.
2022/0213145 A1 7/2022 Chen et al.
2022/0227811 A1 7/2022 Mudd et al.
2022/0242911 A1 8/2022 Mudd et al.
2022/0257784 A1 8/2022 Upadhyaya et al.
2022/0275053 A1 9/2022 Upadhyaya et al.
2022/0281918 A1 9/2022 Van Rietschoten et al.
2022/0289792 A1 9/2022 Chen et al.
2022/0306689 A9 9/2022 Chen et al.
2022/0306694 A1 9/2022 Mudd
2022/0362390 A1 11/2022 Stace et al.
2022/0387611 A1 12/2022 Bennett et al.
2023/0002596 A1 1/2023 Zhang et al.
2023/0025916 A1 1/2023 Bennett et al.
2023/0025971 A1 1/2023 Bennett et al.
2023/0086865 A1 3/2023 Balmford et al.
2023/0106511 A1 4/2023 Balmford et al.
2023/0129258 A1 4/2023 Upadhyaya et al.
2023/0144799 A1 5/2023 Chen et al.
2023/0165966 A1 6/2023 Koehler et al.
2023/0181749 A1 6/2023 Dickson et al.
2023/0220008 A1 7/2023 Chen et al.
2023/0233698 A1 7/2023 Bennett et al.
2023/0287047 A1 9/2023 Beswick et al.
2023/0340020 A1 10/2023 Teufel et al.

(56) References Cited

U.S. PATENT DOCUMENTS

| | | | |
|---|---|---|---|
| 2024/0000957 A1 | 1/2024 | Chen et al. | |
| 2024/0082410 A1 | 3/2024 | Teufel et al. | |
| 2024/0108738 A1 | 4/2024 | Keen et al. | |
| 2024/0158444 A1 | 5/2024 | Bennett et al. | |
| 2024/0173422 A1 | 5/2024 | Beswick et al. | |
| 2024/0189436 A1 | 6/2024 | Chen et al. | |
| 2024/0197897 A1 | 6/2024 | Keen et al. | |
| 2024/0240255 A1 | 7/2024 | Blakemore et al. | |
| 2024/0325554 A1 | 10/2024 | Keen et al. | |
| 2024/0336656 A1 | 10/2024 | Mudd et al. | |

FOREIGN PATENT DOCUMENTS

| | | | | |
|---|---|---|---|---|
| EP | 2393520 A1 | 12/2011 | | |
| EP | 2970954 A1 | 1/2016 | | |
| EP | 3192802 A1 | 7/2017 | | |
| FR | 2932189 A1 | 11/2009 | | |
| GB | 1239978 A | 7/1971 | | |
| JP | 2006514104 A | 4/2006 | | |
| JP | 2011513298 A | 4/2011 | | |
| JP | 2011522794 A | 4/2011 | | |
| JP | 2013518807 A | 5/2013 | | |
| JP | 2016527180 A | 9/2016 | | |
| JP | 2018502825 A | 2/2018 | | |
| WO | WO9708320 A1 | 6/1997 | | |
| WO | WO9819705 A1 | 5/1998 | | |
| WO | WO0128683 A1 | 4/2001 | | |
| WO | WO0142246 A2 | 6/2001 | | |
| WO | WO0363794 A2 | 8/2003 | | |
| WO | WO2004005348 A1 | 1/2004 | | |
| WO | WO2004019973 A1 | 3/2004 | | |
| WO | WO0288112 A1 | 8/2004 | | |
| WO | WO2004077062 A2 | 9/2004 | | |
| WO | WO2004089925 A1 | 10/2004 | | |
| WO | WO2004106328 A1 | 12/2004 | | |
| WO | WO2005007623 A2 | 1/2005 | | |
| WO | WO2005103083 A2 | 11/2005 | | |
| WO | WO2005113554 A2 | 12/2005 | | |
| WO | WO2006029879 A2 | 3/2006 | | |
| WO | WO2006078161 A1 | 7/2006 | | |
| WO | WO2006078846 A1 | 7/2006 | | |
| WO | WO2006101187 A1 | 9/2006 | | |
| WO | WO2017102906 A1 | 9/2006 | | |
| WO | WO2006105021 A2 | 10/2006 | | |
| WO | WO2006122806 A2 | 11/2006 | | |
| WO | WO2007016176 A2 | 2/2007 | | |
| WO | WO2007044729 A2 | 4/2007 | | |
| WO | WO2007053452 A1 | 5/2007 | | |
| WO | WO2007070514 A1 | 6/2007 | | |
| WO | WO2007005874 A2 | 7/2007 | | |
| WO | WO2007084786 A1 | 7/2007 | | |
| WO | WO2007129161 A2 | 11/2007 | | |
| WO | WO2008033561 A2 | 3/2008 | | |
| WO | WO2008039218 A2 | 4/2008 | | |
| WO | WO2008134761 A2 | 6/2008 | | |
| WO | WO2008089627 A1 | 7/2008 | | |
| WO | WO2008109943 A1 | 9/2008 | | |
| WO | WO2008118802 A1 | 10/2008 | | |
| WO | WO2008132601 A1 | 11/2008 | | |
| WO | WO2008157490 A1 | 12/2008 | | |
| WO | WO2009009116 A2 | 1/2009 | | |
| WO | WO2009044273 A2 | 4/2009 | | |
| WO | WO2009073620 A2 | 6/2009 | | |
| WO | WO2009098450 A2 | 8/2009 | | |
| WO | WO2009114512 A1 | 9/2009 | | |
| WO | WO2010019570 A2 | 2/2010 | | |
| WO | WO2010077634 A1 | 7/2010 | | |
| WO | WO-2010089115 A1 * | 8/2010 | ............. | A61K 47/55 |
| WO | WO2010089117 A1 | 12/2010 | | |
| WO | WO2011018227 A2 | 2/2011 | | |
| WO | WO2011028683 A1 | 3/2011 | | |
| WO | WO2011056652 A1 | 5/2011 | | |
| WO | WO2011070024 A1 | 6/2011 | | |
| WO | WO2011079015 A1 | 6/2011 | | |
| WO | WO2011090760 A1 | 7/2011 | | |
| WO | WO2011107553 A1 | 9/2011 | | |
| WO | WO2011109400 A2 | 9/2011 | | |
| WO | WO2011131407 A1 | 10/2011 | | |
| WO | WO2011140249 A2 | 11/2011 | | |
| WO | WO2012032433 A1 | 3/2012 | | |
| WO | WO2012057624 A1 | 5/2012 | | |
| WO | WO2012142237 A1 | 10/2012 | | |
| WO | WO2012145493 A1 | 10/2012 | | |
| WO | WO2013050615 A1 | 4/2013 | | |
| WO | WO2013050617 A1 | 4/2013 | | |
| WO | WO2013079174 A1 | 6/2013 | | |
| WO | WO2013087699 A1 | 6/2013 | | |
| WO | WO2013119716 A1 | 8/2013 | | |
| WO | WO2013132044 A1 | 9/2013 | | |
| WO | WO2013050616 A1 | 11/2013 | | |
| WO | WO2013169264 A1 | 11/2013 | | |
| WO | WO2014008218 A1 | 1/2014 | | |
| WO | WO2014036357 A1 | 3/2014 | | |
| WO | WO2014044872 A1 | 3/2014 | | |
| WO | WO2014063012 A1 | 4/2014 | | |
| WO | WO2014142237 A1 | 9/2014 | | |
| WO | WO2014164693 A2 | 10/2014 | | |
| WO | WO2014167122 A1 | 10/2014 | | |
| WO | WO2014190257 A2 | 11/2014 | | |
| WO | WO2015116904 A1 | 6/2015 | | |
| WO | WO2015171938 A1 | 11/2015 | | |
| WO | WO2015179691 A2 | 11/2015 | | |
| WO | WO2016046574 A1 | 3/2016 | | |
| WO | WO-2016/067035 A1 | 5/2016 | | |
| WO | WO2016050361 A1 | 7/2016 | | |
| WO | WO2016171242 A1 | 10/2016 | | |
| WO | WO2016171272 A1 | 10/2016 | | |
| WO | WO2016174103 A1 | 11/2016 | | |
| WO | 2017046658 A1 | 3/2017 | | |
| WO | WO2017161069 A1 | 9/2017 | | |
| WO | WO-2017/173408 A1 | 10/2017 | | |
| WO | WO-2017/182672 A1 | 10/2017 | | |
| WO | WO2017191460 A1 | 11/2017 | | |
| WO | WO2017205738 A1 | 11/2017 | | |
| WO | WO2018096365 A1 | 5/2018 | | |
| WO | WO2018115203 A1 | 6/2018 | | |
| WO | WO2018115204 A1 | 6/2018 | | |
| WO | WO2018222987 A1 | 6/2018 | | |
| WO | WO2018127699 A1 | 7/2018 | | |
| WO | WO2018156740 A1 | 8/2018 | | |
| WO | WO2018197509 A1 | 11/2018 | | |
| WO | WO2018197893 A1 | 11/2018 | | |
| WO | WO2019002842 A1 | 1/2019 | | |
| WO | WO-2019025811 A1 * | 2/2019 | ............. | A61K 45/00 |
| WO | WO2019034866 A1 | 2/2019 | | |
| WO | WO2019034868 A1 | 2/2019 | | |
| WO | WO2019084060 A1 | 2/2019 | | |
| WO | WO2019094395 A2 | 5/2019 | | |
| WO | WO-2019/122860 A1 | 6/2019 | | |
| WO | WO-2019/122861 A1 | 6/2019 | | |
| WO | WO-2019/122863 A1 | 6/2019 | | |
| WO | WO-2019/162682 A1 | 8/2019 | | |
| WO | WO2019193328 A1 | 10/2019 | | |
| WO | WO2019136442 A1 | 11/2019 | | |
| WO | WO2019226617 A1 | 11/2019 | | |
| WO | WO-2019/243313 A1 | 12/2019 | | |
| WO | WO2019243329 A1 | 12/2019 | | |
| WO | WO2019243353 A1 | 12/2019 | | |
| WO | WO2019243455 A1 | 12/2019 | | |
| WO | WO2019243832 A1 | 12/2019 | | |
| WO | WO2019243833 A1 | 12/2019 | | |
| WO | WO2020084305 A1 | 4/2020 | | |
| WO | WO2020089627 A1 | 5/2020 | | |
| WO | WO2020120980 A1 | 6/2020 | | |
| WO | WO2020120981 A1 | 6/2020 | | |
| WO | WO2020120983 A1 | 6/2020 | | |
| WO | WO2020120984 A1 | 6/2020 | | |
| WO | WO2020128526 A1 | 6/2020 | | |
| WO | WO2020128527 A1 | 6/2020 | | |
| WO | WO2020148525 A1 | 7/2020 | | |
| WO | WO2020148526 A1 | 7/2020 | | |
| WO | WO2020148527 A1 | 7/2020 | | |
| WO | WO2020148528 A1 | 7/2020 | | |
| WO | WO2020148529 A1 | 7/2020 | | |

(56) References Cited

FOREIGN PATENT DOCUMENTS

| | | | |
|---|---|---|---|
| WO | WO2020148530 | A1 | 7/2020 |
| WO | WO2020165600 | A1 | 8/2020 |
| WO | WO2020178574 | A1 | 9/2020 |
| WO | WO-2020/201753 | A1 | 10/2020 |
| WO | WO2020225577 | A1 | 11/2020 |
| WO | WO2020229803 | A1 | 11/2020 |
| WO | WO-2021/019243 | A1 | 2/2021 |
| WO | WO2021019244 | A1 | 2/2021 |
| WO | WO2021019245 | A1 | 2/2021 |
| WO | WO2021019246 | A1 | 2/2021 |
| WO | WO2021028686 | A1 | 2/2021 |
| WO | WO2021171028 | A1 | 2/2021 |
| WO | WO2021171029 | A1 | 2/2021 |
| WO | WO-2021/064428 | A1 | 4/2021 |
| WO | WO2021038232 | A1 | 4/2021 |
| WO | WO2021074622 | A1 | 4/2021 |
| WO | WO2021074647 | A1 | 4/2021 |
| WO | WO-2021/105694 | A1 | 6/2021 |
| WO | WO2021148974 | A1 | 7/2021 |
| WO | WO2021234391 | A1 | 11/2021 |
| WO | WO2021250418 | A1 | 12/2021 |
| WO | WO2022038158 | A1 | 2/2022 |
| WO | WO2022148969 | A1 | 7/2022 |
| WO | WO2022148974 | A2 | 7/2022 |
| WO | WO2022148975 | A1 | 7/2022 |
| WO | WO2022148979 | A1 | 7/2022 |
| WO | WO2022029420 | A1 | 10/2022 |
| WO | WO2023089308 | A1 | 5/2023 |
| WO | WO2023031623 | A2 | 9/2023 |

OTHER PUBLICATIONS

Anonymous, "UPI000011DEEB," retrieved from the internet: URL:https://www.uniprot.org/uniparc/UPI000011DEEB, 2014, 2 pages.

Drumm et al., "Genetic Variation and Clinical Heterogeneity in Cystic Fibrosis", Annu. Rev. Pathol. Mech. Dis., 2012, 7:267-282.

Hurov et al., "Abstract 3257: Activation of CD137 using multivalent and tumor targeted Bicyclic peptides", Cancer Res, 2019, 79(13_ Supplement):3257, 3 pages.

Lowe, Derek, "Not alphafold's fault," blog—In the pipeline, 2022, 6 pages.

Lowe, Derek, "The good sides and bad sides of polar compounds," blog—In the pipeline, 2017, 15 pages.

Micoine et al., "A general strategy for ligation of organic and biological molecules to dawson and keggin polyoxotungstates", Org Chem. Lett., 2007, 9(20):3981-3984.

Nguyen, "Pancreatic Cancer", Merck Manual (https://www.merckmanuals.com/home/digestive-disorders/tumors-of-the-digestive-system/pancreatic-cancer?query=pancreatic%20cancer accessed Apr. 9, 21), 2021, 5 pages.

Solomons, "Organic Chemistry", 4th ed, 1988, p. 902 (3 pages).

Thornber, "Isosterism and molecular modification in drug design", Chem. Soc. Rev, 1979, 8(4):563-580.

Yampolsky et al., "The exchangeability of amino acids in proteins", Genetics, 2005, 170(4):1459-1472.

Zhang et al., "Characterization and application of three novel monoclonal antibodies against human 4-1BB: distinct epitopes of human 4-1BB on lung tumor cells and immune cells", Tissue Antigens, 2007, 70(6):470-479.

Adams et al., "Big Opportunities for Small Molecules in Immuno-oncology," Nature Reviews, 2015, 14:603-622.

Adams, "Molecular control of arterial-venous blood vessel identity," Journal of Anatomy, 2003, 202(1):105-112.

Adley et al., "Expression of membrane type 1 matrix metalloproteinase (MMP-14) in epithelial ovarian cancer: high level expression in clear cell carcinoma", Gynecologic oncology, 112(2):319-324.

Akanuma et al., "MicroRNA-133a regulates the mRNAs of two invadopodia-related proteins, FSCN1 and MMP14, in esophageal cancer," Br J Cancer. Jan. 7, 2014;110(1), 189-98.

Angelini et al., "Bicyclic peptide inhibitor reveals large contact interface with a protease target." ACS chemical biology 7, No. 5 (2012): 817-821.

Annunziata et al., "Phase 1, open-label study of MED1-547 in patients with relapsed or refractorysolid tumors," Invest New Druas, Feb. 2013, 31(1):77-84.

Anonymous, "Bicycle Conjugates", URL:https://web.archive.org/web/20210104063050/https://www.bicycletherapeutics.com/programs , 2021, 4 pages.

Anonymous, "Bicycle Therapeutics to Present New Translational Research for BT5528 and Preclinical Data for Tumor-targeted Immune Cell Agonists at the AACR Virtual Annual Meeting II," May 15, 2020; 2 pages. URL:https://www.businesswirc.com/news/home/20200515005111/cn/Bicycle-Therapeutics- to-Present-New-Translational-Research-for-BT5528-and-Preelinical-Data-for-Tumor-targeted-Immune-Cell-Aaon ists-at-the-AACR-Virtual-Ann ual-Meetina-II.

Anonymous, "Constrained Peptides Unconstrained Thinking Forward-Looking Statements", URL: https://investors.bicycletherapeutics.com/static-files/5f7f462f-2417-439d-b829-d723b3fd65f7, Aug. 2019, 26 pages.

Anthony et al., "Recapitulation of IVIG anti-inflammatory activity with a recombinant IgG Fc", Science Apr. 18, 2008;320(5874):373-376.

Arkadash et al., "Development of High Affinity and High Specificity Inhibitors of Matrix Metalloproteinase 14 through Computational Design and Directed Evolution" J. Biol. Chem. 2017, 292(8), 3481-3495.

Arnon et al., "The mechanisms controlling the recognition of tumor-and virus-infected cells by NKp46", Blood, Jan. 15, 2004;103(2):664-672.

Arnould et al., "Trastuzumab-based treatment of HER2-positive breast cancer: an antibody-dependent cellular cytotoxicity mechanism?", Br J Cancer, 2006, 94(2):259-267.

Askoxylakis et al., "A New Peptide Ligand for Targeting Human Carbonic Anhydrase IX, Identified through the Phage Display Technology", PLoS One, Dec. 2010, 5(12):10 pages.

Augoff et al., "Upregulated expression and activation of membrane-associated proteases in esophageal squamous cell carcinoma." Oncology reports, 2014, 31(6):2820-2826.

Ausiello et al., "Functional topography of discrete domains of human CD38," Tissue Antigens, Dec. 2000, 56(6):539-547.

Baek et al. "Effects of Histidine and Sucrose on the Biophysical Properties of a Monoclonal Antibody," Pharmaceutical Antibody, 2017, 34(3):629-639.

Banerji et al., "A Cancer research UK Phase I/IIA Trail of BT1718 (a first in class Bicycle Drug Conjugate) Given Intravenously in Patients with Advanced Solid Tumours," Journal of Clinical Oncology, Jan. 2018, 36(15):PS2610. (1 Page).

Banerji et al., "Preliminary pharmacokinetic assessment of BT1718: A phase I/IIa trial of BT1718 (a first in class Bicycle Toxin Conjugate) in patients with advanced solid tumours." In european journal of cancer, 2018, 103:E65-e65.

Barbas III et al., "Semisynthetic combinatorial antibody libraries: a chemical solution to the diversity problem," Proceedings of the National Academy of Sciences of the United States of America, May 1992, 89(10):4457-4461.

Barbolina et al., Microenvironmental regulation of membrane type 1 matrix metalloproteinase activity in ovarian carcinoma cells via collagen-induced EGR1 expression. Journal of Biological Chemistry, 2007, 282(7):4924-4931.

Bardia ct al., "Efficacy and safety of anti-trop-2 antibody drug conjugate sacituzumab govitecan (IMMU-132) in heavily pre-treated patients with metastatic triple-negative breast cancer." Journal of Clinical Oncology, 2017, 35(19):2141.

Bech et al., "Chemical Strategies for Half-Life Extension of Biopharmaceuticals: Lipidation and Its Alternatives," ACS Medicinal Chemistry Letters, Jun. 2018, 9(7):577-580.

Bennett et al., "Abstract 4481: BT5528, an EphA2-targeting Bicycle Toxin Conjugate (BTC): Profound efficacy without bleeding and coagulation abnormalities in animal models", Cancer Rescarch, 2019, 79(13 suppl):4481. 2 pages.

(56) References Cited

OTHER PUBLICATIONS

Bennett et al., "Abstract 5854: BT5528, a Bicycle Toxin Conjugate targeting EphA2 has potent anti-tumor activity without bleeding or coagulation abnormalities in preclinical models." Cancer Res., 2018, 78(13 suppl):5854.
Bennett et al., "Abstract 5855: Bicycle Drug Conjugates Targeting EphA2 for the Treatment of Solid Tumors: Discovery and Selection of BT5528", Cancer Research, 2018, 78(13 suppl):5855. 2 pages.
Bennett et al., "Development of BT1718, a Bicycle Drug Conjugate® (BDC) targeting MT1-MMP for treatment of solid tumours," European Journal of Cancer, Nov. 2016, 69(1):S21.
Bennett et al., "MMAE Delivery Using the Bicycle Toxin Conjugate BT5528," Mol Cancer Ther., Jul. 2020, 19(7):1385-1394.
Bennett et al., "The Mechanism of Action of BT1718, a Novel Small-Molecule Drug Conjugate for the Treatment of Solid Tumors Expressing MT1-MMP," AACR-NCI-EOrTC International Conference: Molecular Taroets and Cancer Therapeutics, Jan. 2018, 26-30.
Bennett, "BT1718, a Bicycle Drug Conjugate (BTC): Profound Efficacy Without Bleeding and Coaaulation Abnormalities in Animal Models," AACR Annual Meeting 2019, 4481, 2 pages.
Ben-Shmuel et al., "Unleashing Natural Killer Cells in the Tumor Microenvironment—The Next Generation of Immunotherapy?", Front Immunol., 2020, 11:275.
Berenson, "Multiple Myeloma," Merck Manual, Reterived from :https://www.merckmanuals.com/home/blood-disorders/plasma-cell-disorders/multiplemyeloma?query=multiple%20myeloma, Oct. 2022.
Berge et al., " Pharmaceutical Salts," Journal of Pharmaceutical Sciences, Jan. 1977, 66(1):1-19.
Berkel et al. "Binding of (5 S)-penicilloic acid to penicillin binding protein 3." ACS chemical biology 8, No. 10 (2013): 2112-2116.
Bernhagen et al., "Design, synthesis and characterization of different bicyclic peptides with enhanced binding and selectivity for various integrins", Reterived form : https://ec.europa.eu/research/participants/documents/downloadPublic?documentIds=080166c5acfd6757&appId=PPGMS, Oct. 14, 2016, XP55622035:1-6.
Beswick, Paul, "Bicycles—An entirely new class of therapeutics," accessed on https://www.bicycletherapeutics.com/wp-content/uploads/RSC-02-May-2019.pdf, 2019, 21 pages.
Bicycle Therapeutics, "Bicycle Therapeutics and Cancer Research UK Announce Inititation of FirstClinical Study of a Bicyclic Peptide (Bicycle®)," Press Release, Feb. 13, 2018, https://investors.bicycletherapeutics.com/node/6651/pdf.
Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.
BicycleTx Limited, "Study BT5528-100 in Patients With Advanced Solid Tumors Associated With EphA2 Expression," ClinicalTrials.gov Identifier NCT04180371. First Posted Nov. 27, 2019; Accessed Dec. 30, 2022: https://clinicaltrials.gov/ct2/show/NCT04180371.
Bilsky, Mark H., "Gliomas", Merck Manual (https://www.merckmanuals.com/professional/neurologic-disorders/intracranial-and-spinal-tumors/gliomas), May 2023, 8 pages.
Binda et al., "The EphA2 receptor drives self-renewal and tumorigenicity in stem-like tumor- propagating cells from human glioblastomas," Cancer Cell, Dec. 11, 2012, 22(6):765-780.
Biron et al., "Improving oral bioavailability of peptides by multiple N-methylation: somatostatin analogues," Angewandte Chemie International Edition, 2008, 47(14):2595-2599.
Blank et al., "Absence of Programmed Death Receptor 1 Alters Thymic Development and Enhances Generation of CD4/CD8 Double-Negative TCR-Transgenic T Cells " in Journal of Immunology, Nov. 2003, 171(19):4574-4581.
Bogaerts et al., "Individual patient data analysis to assess modifications to the RECIST criteria." European journal of cancer, 2009, 45(2):248-260.
Bolland et al., "Spontaneous autoimmune disease in Fc(gamma)RIIB-deficient mice results from strain-specific epistasis", Immunity, Aug. 2000, 13(2):277-285.
Booth et al., "Crowd control in the crypt," Nat Med., Dec. 2002, 8(12):1360-1361.
Borghaei et al., "Nivolumab versus docetaxel in advanced nonsquamous non-small-cell lung cancer." New England Journal of Medicine, 2015, 373(17):1627-1639.
Borrelli et al., "Cell Penetrating Peptides as Molecular Carriers for Anti-Cancer Agents," Molecules, Feb. 2018, 23(2):295. (28 pages).
Boruchov et al., "Activating and inhibitory IgG Fc receptors on human DCs mediate opposing functions", The Journal of Clinical Investigation, 2005, 115(10):2914-2923.
Bouchard et al., "Antibody-drug conjugates—a new wave of cancer drugs." Bioorganic & medicinal chemistry letters, 2014, 24(23):5357-5363.
Brahmer et al., "Nivolumab versus docetaxel in advanced squamous-cell non-small-cell lung cancer." New England Journal of Medicine, 2015, 373(2):123-135.
Brannan et al., "EphA2 in the early pathogenesis and progression of non-small cell lung cancer," Cancer Prev Res (Phila)., Dec. 2009, 2(12):1039-1049.
Brantley-Sieders et al., "Eph receptor tyrosine kinases in tumor and tumor microenvironment", Current Pharmaceutical Design, 2004, 10(27):3431-3442.
Brantley-Sieders et al., "Eph/Ephrin Profiling in Human Breast Cancer Reveals Significant Associations between Expression Level and Clinical Outcome", Plos One, 2011, 6(9):e24426.
Brantley-Sieders et al., "Impaired tumor microenvironment in EphA2-deficient mice inhibits tumor angiogenesis and metastatic progression," FASEB J., Nov. 2005, 19(13):1884-1886.
Bristol-Myers Squibb, "An Investigational Immuno-Therapy Study to Investigate the Safety and Effectiveness of Nivolumab, and Nivolumab Combination Therapy in Virus-Associated Tumors-Full Text View-Clinicaltrials." Gov.[(accessed on Jan. 30, 2021)] (2018).
Brown et al., "Blockade of programmed death-1 ligands on dendritic cells enhances T cell activation and cytokine production", Journal of Immunolgy, Feb. 2003, 170(3):1257-1266.
Cabanillas et al., "Phase I study of maytansine using a 3-day schedule," Cancer Treat Rep., Mar. 1978, 62(3):425-428.
Cancer Research UK, "Soft tissue sarcomas," Reterived from : http://aboutcancer.cancerresearchuk.org/about-cancer/soft-tissue-sarcoma, Sep. 2022.
Cancer Research UK, "Triple Negative Breast Cancer," Reterived from: https://www.cancerresearchuk.org/about-cancer/breast-cancer/stages-types-grades/types/triplenegative-breast-cancer#, Sep. 2022, 6 pages.
Cancer Research UK, "Types of lung cancer," Rctcrived form: https://www.cancerresearchuk.org/about-cancer/lung-cancer/stages-types-grades/types#, Sep. 2022.
Cancer Research UK, "Your mouth and cancer drugs," Reterived form : https://www.cancerresearchuk.org/about-cancer/cancer-in-general/treatment/cancer-drugs/sideeffects/your-mouth, Sep. 2022, 5 pages.
Caratelli et al., "FCγ Chimeric Receptor-Engineered T Cells: Methodology, Advantages, Limitations, and Clinical Relevance", Frontiers in Immunology, Apr. 27, 2017, :8:457, 8 pages.
Center for Panceratic and Biliary Diseases, "Bile Duct Cancer," University of Southern California,Department of Surgery. Retreived from https://web.archive.org/web/20171207023733/http://www.surgery.usc.edu:80/divisions/tumor/PancreasDiseases/web%20pages/BILIARY%20SYSTEM/cholangiocarcinoma.html.
Centers for Disease Control and Prevention, "What Can I Do to Reduce My Risk of Ovarian Cancer?", Division of Cancer Prevention and Control, Aug. 31, 2022. 1 page.
Chabner et al., "Initial clinical trials of maytansine, an antitumor plant alkaloid." Cancer Treat Rep., 1978, 62(3):429-433.
Chahinian et al., "Phase I study of weekly maytansine given by iv bolus or 24-hour infusion," Cancer Treat Rep., Nov. 1979, 63(11-12), 1953-1960.
Challita-Eid et al., "Enfortumab Vedotin Antibody-Drug Conjugate Targeting Nectin-4 Is a Highly Potent Therapeutic Agent in Multiple Preclinical Cancer Models", Cancer Research, 2016, 76(10):3003-3013.
Chan and Nie, "Quantum dot bioconjugates for ultrasensitive nonisotopic detection," Science, Sep. 25, 1998; 281(5385):2016-2018.

(56) References Cited

OTHER PUBLICATIONS

Chandrasekar, "Bladder Cancer," Merck Manual. ; Reterived form: https://www.merckmanuals.com/professional/genitourinary-disorders/genitourinary-cancers/bladder-cancer, Sep. 2022.
Chandrasekar, "Prostate Cancer," Merck Manual. Reterived from: https://www.merckmanuals.com/professional/genitourinary-disorders/genitourinary-cancers/prostate-cancer, Sep. 2022.
Chang et al., "Five different anti-prostate-specific membrane antigen (PSMA) Antibodies confirm PSMA expression in tumor-associated neovasculature," Cancer Res., Jul. 1, 1999, 59(13):3192-3198.
Chang ct al., "Subtiligasc: A Tool for Scmisynthesis of Proteins", Proc Natl Acad Sci, 1994, 91(26):12544-12548.
Chemnitz et al., "RNA fingerprints provide direct evidence for the inhibitory role of TGFβ and PD-1 on CD4+ T cells in Hodgkin lymphoma", Blood, 2007, 110(9):3226-3233.
Chen and Harrison, "Cell-Penetrating Peptides in Drug Development: Enabling Intracellular Targets," Biochemical Society Transactions, 2007, 35(4):821-825.
Chen et al., "Association of FCGR3A and FCGR3B copy number variations with systemic lupus erythematosus and rheumatoid arthritis in Taiwanese patients", Arthritis & Rheumatology, 2014, 66(11):3113-3121.
Chen et al., "Peptide ligands stabilized by small molecules," Angewandte Chemie International Edition, Feb. 3, 2014, 53(6):1602-1606.
Chen et al., "Structurally diverse cyclisation linkers impose different backbone conformations in bicyclic peptides," Chembiochem., May 7, 2012, 13(7):1032-1038.
Chen et al., "The Bicycle Platform: an Efficient Technology to Generate High Affinity, High Selectivity Molecules (Bicycles®) with Unique Drug Like Properties that are Amenable to Conjugation," URL:https://www.bicycletherapeutics.com/wp-content/uploads/16_PEGS-Bicycle_-30-04-2017-poster.pdf, Apr. 26, 2017, 1 page.
Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology", J Molecular Diagnostics, 2015, 17(3):251-264.
Cheng et al., "Blockade of EphA receptor tyrosine kinase activation inhibits vascular endothelial cell growth factor-induced angiogenesis," Mol Cancer Res., Nov. 2002, 1(1):2-11.
Cherney et al., "Macrocyclic Amino Carboxylates as Selective MMP-8 Inhibitors," Journal of Medicinal Chemistry, May 1998, 41(11):1749-1751.
Chiche et al., "Hypoxia-inducible carbonic anhydrase IX and XII promote tumor cell growth by counteracting acidosis through the regulation of the intracellular pH," Cancer Res., Jan. 1, 2009, 69(1):358-368.
Chinnery et al., "Viral antigen mediated NKp46 activation of NK cells results in tumor rejection via NK-DC crosstalk", Oncoimmunology, 2012, 1(6):874-883.
Christina Chun, "What are the most curable cancers?", Medical news Today(https://www.medicalnewstoday.com/articles/322700 Accessed May, 8, 2020), 2020, 8 pages.
Chung et al., "Bicycle synthesis through peptide macrocyclization using aziridine aldehydes followed by late stage disulfide bond installation." MedChemComm, 2023, 4(7):1124-1128.
Clarkson et al., "Treatment of refractory immune thrombocytopeniaurpura with an anti-Fc gamma-receptor antibody", The New England Journal of Medicine, 1986, 314(19):1236-1239.
Claus et al., "Tumor-targeted 4-1BB agonists for combination with T cell bispecific antibodies as off-the-shelf therapy", Sci Transl Med., Jun. 2019, 11(496):eaav5989. (12 Pages).
Clinicaltrials.gov, identifier NCT02426892, "Nivolumab and HPV-16 Vaccination in Patients with HPV-16 Positive Incurable Solid Tumors," https://clinicaltrials.gov/ct2/show/study/NCT02426892, 8 pages.
Clynes et al., "Inhibitory Fc receptors modulate in vivo cytotoxicity against tumor targets", Nature Medicine, Apr. 2000, 6(4):443-446.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013; EMA/749228/2013.
Connolly et al., "Complexities of TGF-β Targeted Cancer Therapy", Int'I J. Biological Sciences, 2012, 8(7):964-978.
Cook et al., "Pharmacokinetic (PK) Assessment of BT1718: A Phase 1/2a Study of BT1718, a First in Class Bicycle Toxin Conjugate (BTC), in Patients (PTS) with Advanced Solid Tumours," Annals of Oncology 2019; vol. 30, Jan. 2019, p. v174.
Cortes et al., "Phase II study of the halichondrin B analog cribulin mesylate in patients with locally advanced or metastatic breast cancer previously treated with an anthracycline, a taxane, and capecitabine." Journal of Clinical Oncology, 2010, 28(25):3922-3928.
Costello et al., "Defective expression and function of natural killer cell-triggering receptors in patients with acute myeloid leukemia", Blood, 2002, 99(10):3661-3667.
Crameri et al., "Construction and evolution of antibody-phage libraries by DNA shuffling," Nature Medicine, Jan. 1996, 2(1):100-102.
Cui, J. Jean., "A New Challenging and Promising Era of Tyrosine Kinase Inhibitors", ACS Med Chem Lett., 2014, 5(4):272-274.
Curiel et al., "Blockade of B7-H1 improves myeloid dendritic cell-mediated antitumor immunity", In Nature medicine, 2003, 9(5):562-567.
Dagher et al., "c-Kit and CD38 are expressed by long-term reconstituting hematopoietic cells present in the murinc yolk sac," Biol Blood Marrow Transplant, 1998, 4(2):69-74.
Davies et al., "Antibody VH Domains as Small Recognition Units," Bio/Technology, May 13, 1995, 13(5):475-479.
Davis et al., "Natural killer cells unleashed: Checkpoint receptor blockade and BiKE/TriKE utilization in NK-mediated anti-tumor immunotherapy", Scmin Immunol., 2017, 31:64-75.
Dawson et al., "Synthesis of proteins by native chemical ligation," Science, Nov. 1994, 266(5186):776-779.
De Kruif et al., "Selection and Application of Human Single Chain Fv Antibody Fragments from a Semi-synthetic Phage Antibody Display Library with Designed CDR3 Regions," Journal of Molecular Biology, Apr. 1995, 248(1):97-105.
De la Pena et al., "Expression of the matrix metalloproteases 2, 14, 24, and 25 and tissue inhibitor 3 as potential molecular markers in advanced human gastric cancer." Disease markers 2014 (2014).
Deaglio et al., "CD38 is a signaling molecule in B-cell chronic lymphocytic leukemia cells," Blood, Sep. 15, 2003, 102(6):2146-2155.
Debre et al., "Infusion of Fc gamma fragments for treatment of children with acute immunc thrombocytopeniaurpura", Lancct, 1993, 342(8877):945-949.
Deonarain et al., "Small-Format Drug Conjugates: A Viable Alternative to ADCs for Solid Tumours?", Antibodies (Basel), 2018, 7(2):16.
Derossi et al., "The third helix of the Antennapedia homeodomain translocates through biological membranes," Journal if Biological Chemistry, Apr. 1994, 269(14):10444-10450.
Deyle et al., "Phage Selection of Cyclic Peptides for Application in Research and Drug Development," Accounts of Chemical Research, 2017, 50(8):1866-1874.
Dharmadhikari, et al., "CD137 and CD137L signals are main drivers of type 1, cell-mediated immune responses." Oncoimmunology, 2016, 5(4):c1113367.
Di, "Strategic Approaches to Optimizing Peptide ADME Properties," Aaps J., Jan. 2015, 17(1):134-143.
Diamantis and Banerji, "Antibody-drug conjugates—an emerging class of cancer treatment." British journal of cancer, 2016, 114(4):362-367.
Diaz-Perlas et al., "Branched BBB-shuttle peptides: chemoselective modification of protcins to enhance blood-brain barrier transport," Chemical Science, Sep. 2018, 9(44):8409-8415.
Dong, et al. "Tumor-associated B7-H1 promotes T-cell apoptosis: a potential mechanism of immune evasion", Nature Medicine, 2002, 8(8):793-800.

(56) References Cited

OTHER PUBLICATIONS

Dorfman et al., "Programmed death-1 (PD-1) is a marker of germinal center-associated cells and angioimmunoblastic T-cell lymphoma." The American journal of surgical pathology, Jul. 2006, 30(7):802-810.
Driggers et al., "The exploration of macrocycles for drug discovery—an underexploited structural class," Nature Reviews Drug Discovery, Jul. 2008, 7(7):608-624.
Dubois ct al., "New ways to image and target tumour hypoxia and its molecular responses," Radiotherapy and Oncology, Sep. 2015, 116(3):352-357.
Dufort et al., "789: Generation of a Bicycle NK-TICA(TM), a novel NK cell engaging molecule to enhance targeted tumor cytotoxicity", Nov. 10, 2021, 9(Suppl 2):A824-A824. URL:https://jitc.bmj.com/contonl/jitc/9/SuppI_2/A824.full.pdf.
Dunne et al., "EphA2 Expression Is a Key Driver of Migration and Invasion and a Poor Prognostic Marker in Colorectal Cancer," Clin Cancer Res., Jan. 1, 2016, 22(1):230-242.
Duong and Rodan, "The role of integrins in osteoclast function," J Bone Miner Metab., 1999, 17(1):1-6.
Eagan et al., "Early clinical study of an intermittent schedule for maytansine (NSC-153858): brief communication." Journal of the National Cancer Institute, 1978, 60(1):93-96.
Eder et al., "A phage display derived stabilised bicyclic peptide targeting MMP-14 shows high imaging contrast in small animal PET imaging." In European Journal of Nuclear Medicine and Molecular Imaging, 42:S140-S141.
Eisenhauer et al., "New response evaluation criteria in solid tumours: revised RECIST guidclinc (version 1.1)." European journal of cancer, 2009, 45(2):228-247.
Ellenrieder et al., "Role of MT-MMPs and MMP-2 in pancreatic cancer progression." International Journal of Cancer, 2000, 85(1):14-20.
Elson-Schwab et al., "Guanidinylated neomycin delivers large, bioactive cargo into cells through a heparan sulfate-dependent pathway." Journal of Biological Chemistry, 2007, 282(18):13585-13591.
Fauriat et al., "Deficient expression of NCR in NK cells from acute myeloid leukemia: Evolution during leukemia treatment and impact of leukemia cells in NCRdull phenotype induction", Blood, 2007, 109(1):323-330.
Fehrenbacher et al., "Atezolizumab versus docetaxel for patients with previously treated non-small-cell lung cancer (POPLAR): a multicentre, open-label, phase 2 randomised controlled trial." The Lancet, 2016, 387(10030):1837-1846.
Felices et al., "Generation of BiKEs and TriKEs to Improve NK Cell-Mediated Targeting of Tumor Cells", Methods Mol Biol., 2016, 1441:333-346.
Felices et al., "Novel CD19-targeted TriKE restores NK cell function and proliferative capacity in CLL", Blood Adv., 2019, 3(6):897-907.
Fiacco et al., "N-Methyl Scanning Mutagenesis Generates Protease-Resistant G Protein Ligands with Improved Affinity and Selectivity," ChemBioChem, Sep. 2008, 9(14):2200-2203.
Figure 3.8 of "Immunobiology: The Immune System in Health and Disease," Garland Science, 2001.
Flaherty et al., "Nonclinical evaluation of GMA161—an antihuman CD16 (FcyRIII) monoclonal antibody for treatment of autoimmune disorders in CD16 transgenic mice", Toxicological Sciences, 2012, 125(1):299-309.
Forsberg, et al., "CD137 plays both pathogenic and protective roles in type 1 diabetes development in NOD mice." The Journal of Immunology, 2017, 198(10):3857-3868.
Francis ct al., "Bone and Soft Tissue Sarcomas: UK Incidence and Survival: 1996-2010," NationalCancer Intelligence Network, Nov. 2013, v2.0.
Fumet et al. "Phase Ib/II trial evaluating the safety, tolerability and immunological activity of durvalumab (MEDI4736)(anti-PD-L1) plus tremelimumab (anti-CTLA-4) combined with FOLFOX in patients with metastatic colorectal cancer." ESMO open, 2018, 3(4):e000375.
Funaro et al., "Human CD38 is associated to distinct molecules which mediate transmembrane signaling in different lineages." European journal of immunology, Oct. 1993, 23(10):2407-2411.
Funaro et al., "Involvement of the multilineage CD38 molecule in a unique pathway of cell activation and proliferation," J Immunol., Oct. 1990, 145(8):2390-2396.
Galsky et al., "Phase I trial of the prostate-specific membrane antigen-directed immunoconjugate MLN2704 in patients with progressive metastatic castration-resistant prostate cancer." Journal of clinical oncology, 2008, 26(13):2147-2154.
Gandhi et al., "MP69-11 Carbonic Anhydrase IX Assay: A Paradigm Shift in Diagnosis of Malignant Cystic Renal Lesions," J Urol., May 18, 2015, 193(4S):e870-e871.
Garcia-Iglesias ct al., "Low NKp30, NKp46 and NKG2D expression and reduced cytotoxic activity on NK cells in cervical cancer and precursor lesions", BMC Cancer, Jun. 16, 2009, 9:186, 8 pages.
Gauthier et al., "Multifunctional Natural Killer Cell Engagers Targeting NKp46 Trigger Protective Tumor Immunity", Ccll, 2019, 177(7):1701-1713.
Gelb et al., "Abstract 391: Molecular-based enrichment strategy for Nectin-4 targeted Bicycle toxin conjugate BT8009," Cancer Res., Jul. 1, 2021, 81(13 suppl):391 (poster).
Gelb et al., "Abstract A047: MT1-MMP Immunohistochemistry (IHC) analysis of tumor microarrays(TMAs) using a novel scoring system guides patient selection for BT1718 expansion cohorts," In Molecular Cancer Therapeutics, 2019, 18(12_Suppl):A047.
Gen path diagnostics, "Solid Tumors", Accessed on https://genpathdiagnostics.com/patients/oncology/solid-tumors/, Jun. 30, 2023, 4 pages.
Gentilucci et al., "Chemical Modifications Designed to Improve Peptide Stability: Incorporation of Non-Natural Amino Acids, Pseudo-Peptide Bonds, and Cyclization," Current Pharmacetical Design, 2010, 16(28):3185-3203.
Gleason ct al., "CD16×CD33 bispecific killer cell engager (BiKE) activates NK cells against primary MDS and MDSC CD33+ targets", Blood, 2014, 123(19):3016-3026.
Gokel et al., "Crown Ethers: Sensors for Ions and Molecular Scaffolds for Materials and Biological Models," Chem. Rev., 2004, 104(5):2723-2750.
Gradishar et al., "Significantly longer progression-free survival with nab-paclitaxel compared with docetaxel as first-line therapy for metastatic breast cancer." J Clin Oncol., 2009, 27(22):3611-3619.
Gresh, "Neuroblastoma," Merck Manual., Reterived form : https://www.msdmanuals.com/en-in/professional/pediatrics/pediatric-cancers/neuroblastoma, Sep. 2022, 4 pages.
Griffiths et al., "Isolation of high affinity human antibodies directly from large synthetic repertoires," EMBO Journal, Jul. 1994, 13(14):3245-3260.
Grisold et al., "Peripheral neuropathies from chemotherapeutics and targeted agents: diagnosis, treatment, and prevention." Neuro-oncology, 2012, 14(suppl_4):iv45-iv54.
Gu et al., "The influence of the penctrating peptide iRGD on the effect of paclitaxel-loaded MT1-AF7p-conjugated nanoparticles on glioma cells." Biomaterials, 2013, 34(21):5138-5148.
Guo et al., "Prognostic significance of combinations of RNA-dependent protein kinase and EphA2 biomarkers for NSCLC," J Thorac Oncol., Mar. 2013, 8(3):301-308.
Gupta et al., "Intracellular delivery of large molecules and small particles by cell-penetrating proteins and peptides," Advanced Drug Delivery Reviews, Feb. 2005, 57(4):637-651.
Hamanishi et al. "Programmed cell death 1 ligand 1 and tumor-infiltrating CD8+ T lymphocytes are prognostic factors of human ovarian cancer", Proc. Natl. Acad. Sci. USA, 2007, 104(9):3360-3365.
Han et al., "Altered NKp30, NKp46, NKG2D, and DNAM-1 Expression on Circulating Cells Is Associated with Tumor Progression in Human Gastric Cancer", Journal of Immunology Research, Sep. 3, 2018, 2018:6248590, 10 pages.

(56) References Cited

OTHER PUBLICATIONS

Hanna et al., "Randomized phase III trial of pemetrexed versus docetaxel in patients with non-small-cell lung cancer previously treated with chemotherapy." Journal of clinical oncology, 2004, 22(9):1589-1597.
Harrison ct al., "Abstract 5144: BT1718, a novel bicyclic peptide-maytansinoid Conjugate targeting MT1-MMP for the treatment of solid tumors: Design of bicyclic peptide and linker selection," Cancer Res., 2017, 77(13 suppl):5144.
Hart, et al., "De novo identification of lipid II binding lipopeptides with antibacterial activity against vancomycin-resistant bacteria." Chemical Science, 2017, 8(12):7991-7997.
Hart, et al., "Cell binding and internalization by filamentous phage displaying a cyclic Arg-Gly-Aspcontaining peptide", J. Biol. Chem., 1994, 269:12468-12474.
Hasmim et al., "Critical Role of Tumor Microenvironment in Shaping NK Cell Functions: Implication of Hypoxic Stress", Frontiers in Immunology, Sep. 23, 2015, 6:482, 9 pages.
He et al., "Matrix metalloproteinase-14 is a negative prognostic marker for patients with gastric cancer." Digestive diseases and sciences, 2013, 58:1264-1270.
Heinis et al, "Phage-encoded combinatorial chemical libraries based on bicyclic peptides." Nature Chemical Biology, Jul. 2009, 5(7):502-507.
Helft et al., "A phase I study of cantuzumab mertansine administered as a single intravenous infusion once weekly in patients with advanced solid tumors." Clinical cancer rescarch, 2004, 10(13):4363-4368.
Henriques et al., "Functional characterization of peripheral blood dendritic cells and monocytes in systemic lupus erythematosus", Rheumatology International, Apr. 2012, 32(4):863-869.
Herbst et al., "Pembrolizumab versus docetaxel for previously treated, PD-L 1-positive, advanced non-small-cell lung cancer (KEYNOTE-010): a randomised controlled tria", Lancet, Apr. 2016, 387(10027):1540-1550.
Hershman, "Thyroid Cancers," Merck Manual, Reterived from : https://www.merckmanuals.com/professional/endocrine-and-metabolic-disorders/thyroid-disorders/thyroid-cancers, Sep. 2020.
Hess et al., "Backbone Cyclic Peptidomimetic Melanocortin-4 Receptor Agonist as a Novel Orally Administrated Drug Lead for Treating Obesity," Journal of Medicinal Chemistry, Jan. 26, 2008, 51(4):1026-1034.
Hess et al., "Molecular Regulation of Tumor Cell Vasculogenic Mimicry by Tyrosinc Phosphorylation: Role of Epithelial Cell Kinase (Eck/EphA2", Cancer Research, 2001, 61(8):3250-3255.
Hikari et al., "Tags for labeling protein N-termini with subtiligase for proteomics", Bioorganic & Medicinal Chemistry Letters, Nov. 2008, 18 (22):6000-6003.
Hill et al: "Constraining Cyclic Peptides To Mimic Protein Structure Motifs", Angewandte Chemie International Edition, Nov. 24, 2014, 53(48):13020-13041.
Hinner et al., "Tumor-Localized Costimulatory T-Cell Engagement by the 4-1BB/HER2 Bispecific Antibody-Anticalin Fusion PRS-343", Clinical Cancer Research Oct. 2019, 23(19):5878-5889.
Hirano et al. "Blockade of B7-H1 and PD-1 by monoclonal antibodies potentiates cancer therapeutic immunity," Cancer Research, 2005, 65(3):1089-1096.
Hoogenboom et al., "By-passing immunisation. Human antibodies from synthetic repertoires of germline VH gene segments rearranged in vitro," Journal of Molecular Biology, Sep. 1992, 227(2):381-388.
Hoshino et al., "Mapping of the catalytic and epitopic sites of human CD38/NAD+ glycohydrolase to a functional domain in the carboxvl terminus," J Immunol., Jan. 15, 1997, 158(2):741-747.
Hsu et al., "Efficacy of plasmin-treated intravenous gamma-globulin for therapy of Kawasaki syndrome", The Pediatric Infectious Disease Journal, Jun. 1993, 12(6):509-512.
Hu-Lieskovan and Ribas, "New Combination Strategies Using Programmed Cell Death 1/Programmed Cell Death Ligand 1 Checkpoint Inhibitors as a Backbone," Cancer J., Jan./Feb. 2017, 23(1):10-22.
Hurov et al., "BT7480, a novel fully synthetic tumor-targeted immune cell agonist (TICA™) induces tumor localized CD137 agonism", Retrieved from the Internet: URL: https://www.bicycletherapeutics.com/wp-content/uploads/2020-06-16-BT7480-AACR-2020-poster-P5552_Final_CD137-in-title-002.pdf, Jun. 20, 2020, 1 page.
Ide et al., "A novel method for artificial lipid-bilayer formation," Biosensors and Bioelectronics, 2005, 21(4):672-677.
Inman et al., "PD-L1 (B7-H1) expression by urothelial carcinoma of the bladder and BCG-induced granulomata: associations with localized stage progression", Cancer, 2007, 109(8):1499-1505.
Ip et al., "Atypical localization of membrane type 1-matrix metalloproteinase in the nucleus is associated with aggressive features of hepatocellular carcinoma." Molecular Carcinogenesis: Published in cooperation with the University of Texas MD Anderson Cancer Center, 2007, 46(3):225-230.
Izawa et al., "$H_2O_2$ production within tumor microenvironment inversely correlated with infiltration of CD56(dim) NK cells in gastric and esophagcal cancer: possible mechanisms of NK cell dysfunction", Cancer Immunology, Immunotherapy, 2011, 60(12):1801-1810.
Jackson and Stover, "Using the lessons learned from the clinic to improve the preclinical development of antibody drug conjugates." Pharmaceutical rescarch, 2015, 32(11):3458-3469.
Jackson et al., "A human antibody-drug conjugate targeting EphA2 inhibits tumor growth in vivo", Cancer Research, Nov. 15, 2008, 68(22):9367-9374.
Jespers et al., "Selection of optical biosensors from chemisynthetic antibody libraries," Protein Engineering, Design and Selection, Oct. 2004, 17(10):709-713.
Jin et al., "αVβ3 Integrin-Targeted Radionuclide Therapy with 64Cu-cyclam-RAFT-c(-RGDfK-)4," Mol Cancer Ther., Sep. 2016, 15(9):2076-2085.
Johnson et al., "Melanoma-specific MHC-II expression represents a tumour- autonomous phenotype and predicts response to anti-PD-1/PD-L1 therapy", Nature Communications, Jan. 29, 2016, 7:10582(10 pages).
Johnson et al., "Relationships between drug activity in NCI preclinical in vitro and in vivo models and early clinical trials," British Journal of Cancer, 2001, 84(10):1424-1431.
Jones et al., "Randomized phase III study of docetaxel compared with paclitaxel in metastatic breast cancer." Journal of Clinical Oncology, 2005, 23(24):5542-5551.
Jones et al., "Targeting membrane proteins for antibody discovery using phage display," Scientific Reports, May 18, 2016, 6(1):1-11.
Kamat et al., "The clinical relevance of stromal matrix metalloproteinasc expression in ovarian cancer." Clinical Cancer Research, 2006, 12(6):1707-1714.
Kamijo et al., "Aberrant CD137 ligand expression induced by GATA6 overexpression promotes tumor progression in cutancous T-cell lymphoma." Blood, The Journal of the American Society of Hematology, 2018, 132(18):1922-1935.
Kanazawa et al., "Non-obese-diabetic mice: immune mechanisms of pancreatic β-cell destruction," Diabetologia, 1984, 27:113-115.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)." (2016): 5-5.
Kang, et al., "Anti-CD137 suppresses tumor growth by blocking reverse signaling by CD137 ligand." Cancer research, 2017, 77(21):5989-6000.
Keith, "Lung Carcinoma," Merck Manual, Reterived on: https://www.merckmanuals.com/professional/pulmonary-disorders/tumors-of-the-lungs/lung-carcinoma, Sep. 2021, 18 pages.
Kell, Douglas B., "The Transporter-Mediated Cellular Uptake and Efflux of Pharmaceutical Drugs and Biotechnology Projects: How and Why Phospholipid Bilayer Transport is Negligible in Real Biomembranes," Molecules, 2021, 26(5629):40 pages.

(56) References Cited

OTHER PUBLICATIONS

Kellog et al., "Disulfide-linked antibody—maytansinoid conjugates: Optimization of in vivo activity by varying the steric hindrance at carbon atoms adjacent to the disulfide linkage." Bioconjugate chemistry, 2011, 22(4):717-727.
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog." J. Org. Chem., 1985, 50(26):5834-5838.
Kerkela et al., "Differential patterns of stromelysin-2 (MMP-10) and MT1-MMP (MMP-14) expression in epithelial skin cancers." British journal of cancer, 2001, 84(5):659-669.
Kessenbrock et al., "Matrix metalloproteinases: regulators of the tumor microenvironment." Cell, 2010, 141(1):52-67.
Khan et al., "Engineering Lipid Bilayer Membranes for Protein Studies," International Journal of Molecular Sciences, Nov. 2013, 14(11):21561-21597.
Kikuchi et al., "Immunohistochemical detection of membrane-type-1-matrix metalloproteinasc in colorectal carcinoma." British journal of cancer, 2000, 83(2):215-218.
Kim et al., "Synergistic signals for natural cytotoxicity are required to overcome inhibition by c-Cbl ubiquitin ligase", Immunity, Feb. 26, 2010, 32(2):175-186.
Kim, et al., "Reverse signaling through the costimulatory ligand CD137L in epithelial cells is essential for natural killer cell-mediated acute tissue inflammation." Proceedings of the National Academy of Sciences, 2012, 109(1): E13-E22.
Kinch et al., "Predictive Value of the EphA2 Receptor Tyrosine Kinase in Lung Cancer Recurrence and Survival", Clin Cancer Res., 2003, 9(2):613-618.
Kitanaka ct al., "CD38 ligation in human B cell progenitors triggers tyrosinc Phosphorylation of CD19 and association of CD19 with lyn and phosphatidylinositol 3-kinase," J Immunol., 1997, 159(1):184-192.
Kitanaka et al., "CD38-mediated signaling events in murine pro-B cells expressing human CD38 with or without its cytoplasmic domain," J Immunol., Feb. 15, 1999, 162(4):1952-1958.
Kleinau et al., "Induction and suppression of collagen-induced arthritis is dependent on distinct fcgamma receptors", J Exp Med., May 2000, 191(9):1611-1616.
Knight et al., "Three genes for lupus nephritis in NZB×NZW mice," Journal of Experimental Medicine, Jun. 1978, 147(6):1653-1660.
Konishi et al., "B7-H1 Expression on Non-Small Cell Lung Cancer Cells and Its Relationship with Tumor-Infiltrating Lymphocytes and Their PD-1 Expression", Clin Cancer Res., 2004, 10(15):5094-5100.
Konopleva et al., "Ligation of cell surface CD38 protcin with agonistic monoclonal antibody induces a cell growth signal in myeloid leukemia cells," J Immunol., Nov. 1, 1998, 161(9):4702-4708.
Koo et al., "Reduction of the CD16-CD56bright NK Cell Subset Precedes NK Cell Dysfunction in Prostate Cancer", PLoS One, 2013, 8(11):c78049, 8 pages.
Kreidieh et al., "Overview, prevention and management of chemotherapy extravasation." World journal of clinical oncology, 2016, 7(1):87.
Krishnamoorthy et al., "Breaking the Permeability Barrier of *Escherichia coli* by Controlled Hyperporination of the Outer Membrane." Antimicrob Agents Chemother, 2016, 60(12):7372-7381.
Krop et al., "Trastuzumab emtansine versus treatment of physician's choice for pretreated HER2-positive advanced breast cancer (TH3RESA): a randomised, open-label, phase 3 trial." The Lancet Oncology, 2014, 15(7):689-699.
Kumagai et al., "Ligation of CD38 suppresses human B lymphopoiesis," J Exp Med., Mar. 1, 1995, 181(3):1101-1110.
Kylväjä, et al., "Penicillin binding protein 3 of *Staphylococcus aureus* NCTC 8325-4 binds and activates human plasminogen." BMC research notes, 2016, 9:1-10.
Landolt et al., "Clear cell renal cell carcinoma is linked to epithelial-to-mesenchymal transition and to fibrosis." Physiological reports, 2017, 5(11):e13305.
Lani et al., "Identification of high affinity, highly selective bicyclic peptides (Bicycles®) to transmembrane proteins using phage display screening on whole cells," Abstract, PEGS Summit, Boston, Massachusetts, May 2017, 1 page.
Lanman et al, "Analytical and Clinical Validation of a Digital Sequencing Panel for Quantitative, Highly Accurate Evaluation of Cell-Free Circulating Tumor DNA", PLoS One, 2015, 10(10):e0140712.
Lau,et al., "A penicillin-binding protein that can promote advanced-generation cephalosporin resistance and genome adaptation in the opportunistic pathogen Pseudomonas aeruginosa." International journal of antimicrobial agents, 55(3):105896.
Laudanski et al., "Increased serum level of membrane type 1-matrix metalloproteinase (MT1-MMP/MMP-14) in patients with breast cancer." Folia histochemica et cytobiologica, 2010, 48(1):101-103.
Lea and Simeonov, "Fluorescence polarization assays in small molecule screening," Expert Opinion in Drug Discovery, Jan. 2011, 6(1):17-32.
Lee and Aarhus, "ADP-ribosyl cyclase: an enzyme that cyclizes NAD+ into a calcium-mobilizing metabolite," Cell Regul., Mar. 1991, 2(3):203-209.
Lee et al., "ADP-ribosyl cyclase and CD38. Multi-functional enzymes in Ca+2 signaling, " Adv Exp Med Biol., 1997, 419:411-419.
Lee et al., "Structural determination of a cyclic metabolite of NAD+ with intracellular Ca2+-mobilizing activity," J Biol Chem., Jan. 25, 1989, 264(3):1608-1615.
Leighton, "Pharmacology Review: Kadeyla (ado-trastuzumab emtansine)," In Center for Drug Evaluation and Research Application No. 1254270rio1 sOOO., Feb. 2020.
Levi et al., "Characterization of tumor infiltrating Natural Killer cell subset", Oncotarget, May 30, 2015, 6(15):13835-13843.
Levine et al. "Methionine residues as endogenous antioxidants in proteins", PNAS, 1996, 93(26):15036-15040.
Li et al., "Fluorescent Mu selective opioid ligands from a mixture based cyclic peptide library." ACS combinatorial science, 2012, 14(12):673-679.
Li et al., "Targeting the Fc receptor in autoimmune disease", Expert Opinion on Therapeutic Targets, 2014, 18(3):335-350.
Li et al., "The overexpression membrane type 1 matrix metalloproteinase is associated | with the progression and prognosis in breast cancer." American Journal of Translational Research, 2015, 7(1):120.
Li et al., "Up-regulation of EphA2 and down-regulation of EphrinA1 are associated with the aggressive phenotype and poor prognosis of malignant glioma", Tomor Biology, 2010, 31(5):477-488.
Li, et al., "A novel strategy for in vitro selection of peptide-drug conjugates." Chemistry & biology, 2003, 10(3):233-239.
Li, et al., "Increasing the antimicrobial activity of nisin-based lantibiotics against Gram-negative pathogens." Applied and environmental microbiology, 2018, 84(12):e00052-18.
Lian at al, Screening Bicyclic Peptide Libraries for Protein-Protein Interaction Inhibitors: Discovery of Journal of the American Chemical Society, Aug. 14, 2013, 135(32):11990-11995.
Lian et al., "Cell-Permeable Bicyclic Peptide Inhibitors against Intracellular Proteins", Journal of the American Chemical Society, Jul. 2014, 136(28):9830-9833.
Lin et al., "EphA2 overexpression is associated with angiogenesis in ovarian cancer," Cancer, Jan. 15, 2007, 109(2):332-340.
Linch et al., "OX40 Agonists and Combination Immunotherapy: Putting the Pedal to the Metal," Frontiers in Oncology, Feb. 16, 2015, 5(34):1-14.
Linde et al., "Structure-Activity Relationship and Metabolic Stability Studies of Backbone Cyclization and N-Methylation of Melanocortin Peptides," Biopolymers, 2008, 90(5):671-682.
Lindstrom et al., "Myasthenia gravis," Advances in Immunology, Dec. 1988, 42:233-284.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway", Blood, 2007, 110(1):296-304.

(56) References Cited

OTHER PUBLICATIONS

Loktev et al., "Multicyclic Peptides as Scaffolds for the Development of Tumor Targeting Agents," Current Medicinal Chemistry, 2017, 24(999):2141-2155.
Lopus, Manu. "Antibody-DM1 conjugates as cancer therapeutics." Cancer letters, 2011, 307(2):113-118.
Lovering et al. "Escape from flatland: increasing saturation as an approach to improving clinical success." Journal of medicinal chemistry, 2009, 52(21):6752-6756.
Lovering, "Escape from Flatland 2: complexity and promiscuity," Medicinal Chemistry Communication, Dec. 2012, 4(3):515-519.
Lund et al., "CD38 signaling in B lymphocytes is controlled by its ectodomain but occurs independently of enzymatically generated ADP-ribose or cyclic ADP-ribose," J Immunol., Mar. 1, 1999, 162(5):2693-2702.
M.D. Anderson Cancer Center, "Nivolumab and HPV-16 Vaccination in Patients With HPV-16 Positive Incurable Solid Tumors," In ClinicalTrials.gov Identifier NCT02426892. Retreived form https://clinicaltrials.gov/ct2/show/study/NCT02426892, 2015.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):c1330235.
Macheboeuf et al., "Penicillin binding proteins: key players in bacterial cell cycle and drug resistance processes", FEMS Microbiol Rev., 2006, 30(5):673-691.
Mallone et al., "Signaling through CD38 induces NK cell activation," Int Immunol., Apr. 1, 2001, 13(4):397-409.
Mamessier et al., "Human breast tumor cells induce self-tolerance mechanisms to avoid NKG2D-mediated and DNAM-mediated NK cell recognition", Cancer Res., 2011, 71(21):6621-6632.
Manches et al., "In vitro mechanisms of action of rituximab on primary non-Hodgkin lymphomas", Blood, 2003, 101(3):949-954.
Mark, "Renal Cell Carcinoma," Merck Manual , Reterived form : https://www.merckmanuals.com/home/kidney-and-urinary-tract-disorders/cancers-of-the-kidney-and-genitourinary-tract/kidney-cancer, Sep. 2021.
Marks et al., "By-passing immunization. Human antibodies from V-gene libraries displayed on phage," Journal of Molecular Biology, Dec. 1991, 222(3):581-597.
Marme, "VEGFs, angiopoietins, Ephrins and their receptors: putative targets for tumor therapy?" Ann Hematol., 2002, 81(Suppl 2):S66.
Maron et al., "H-2K mutation controls immune response phenotype of autoimmune thyroiditis. Critical expression of mutant gene product in both thymus and thyroid glands," Journal of Experimental Medicine, Oct. 1980, 152(4):1115-1120.
McFarlin et al., "Experimental Allergic Encephalomyelitis in the Rat: Response to Encephalitogenic Proteins and Peptides," Science, Feb. 1973, 179(4072):478-480.
Merck Manual (https://www.merckanuals.com/home/blood-disorders/plasma-celldisorders/multiple-myeloma?q uery=pancreaticu ltiple%20myeloma accessed Apr. 9, 2021).
Merritt et al., "Analysis of EphA2 expression and mutant p53 in ovarian carcinoma," Cancer Biol Ther., Oct. 2006, 5(10):1357-1360.
Michel, et al., "Expression of soluble CD137 correlates with activation-induced cell death of lymphocytes." Cytokine, 2000, 12(6):742-746.
Milowsky et al., Phase 1/2 multiple ascending dose trial of the prostate-specific. Membrane antigen-targeted antibody drug conjugate MLN2704 in metastatic castration-resistant prostate cancer. In Urologic Oncology: Seminars and Original Investigations, 2016, 34(12):530-e15.
Mitra et al., "Structure—Activity Relationship Analysis of Peptides Targeting the EphA2 Receptor," Biochemistry, 2010, 49(31):6687-6695.
Mittler, el al., "Anti-CD137 antibodies in the treatment of autoimmune disease and cancer." Immunologic research, 2004, 29:197-208.
Miyoshi and Takai, "Nectin and nectin-like molecules: biology and pathology," Am J Nephrol., 2007, 27(6):590-604.
Mohammad et al., Prognostic value of membrane type 1 and 2 matrix metalloproteinase expression and gelatinase A activity in bladder cancer. The International journal of biological markers, 2010, 25(2):69-74.
Moore et al., "A novel bispecific antibody format enables simultaneous bivalent and monovalent co-engagement of distinct target antigens", Mabs, 2011, 3(6):546-557.
Moraes et al., "Immune checkpoint inhibitors (anti PD-1 or anti PD-L1) versus chemotherapy for second- or third-line treatment of metastatic non-small cell lung cancer," Cochrane Database Syst Rev., 2017, 2017(4):CD012644.
Moretta et al., "Surface NK receptors and their ligands on tumor cells", Seminars in Immunology, 2006, 18(3):151-158.
Morgan et al., "FcgammaRIIIA-158V and rheumatoid arthritis: a confirmation study", Rheumatology (Oxford), 2003, 42(4):528-533.
Morra et al., "CD38 is functionally dependent on the TCR/CD3 complex in human T cells," FASEB J., May 1998, 12(7):581-592.
Morrison, "Chemical Strategies for Bicyclic Peptide Formation," Univ. of Leeds, Sep. 2015, pp. 1-60.
Mudali et al., "Patterns of EphA2 protein expression in primary and metastatic pancreatic carcinoma and correlation with genetic status", Clinical & Experimental Metastasis, 2006, 23(7-8):357-365.
Mudd et al., "Identification and Optimization of EphA2-Selective Bicycles for the Delivery of Cytotoxic Payloads," J Med Chem., 2020, 63(8):4107-4116.
Mugera and Ward, "Acute toxicity of maytansine in F344 rats." Cancer Treatment Reports, 1977, 61(7):1333-1338.
Mulder et al., "Scaffold Optimization in Discontinuous Epitope Containing Protein Mimics of gp120 Using Smart Libraries," Org. Biomol. Chem., 2013, 11:2676-2684.
Mullis et al., "Specific synthesis of DNA in vitro via a polymerase-catalyzed chain reaction," Methods in Enzymology, Jan. 1987, 155:335-350.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate expression of activating Fc gamma receptors I and III and inhibiting Fc gamma receptor type II in the determination of joint inflammation and cartilage destruction during immune complex-mediated arthritis", Arthritis & Rheumatology, Jan. 2003, 48(1):255-265.
Nair et al., "Mimicry of Native Peptide Antigens by the Corresponding Retro-Inverso Analogs is Dependent on Their Intrinsic Structure and Interaction Propensities," The Journal of Immunology, 2003, 170(3):1362-1373.
Nakamoto and Bergemann, "Diverse roles for the Eph family of receptor tyrosine kinascs in carcinogenesis," Microsc Res Tech., Oct. 2002, 59(1):58-67.
Nakamura et al., "EPHA2/EFNA1 expression in human gastric cancer", Cancer Science, Jan. 2005, 96(1):42-47.
Nakamura et al., "Involvement of alpha(v)beta3 integrins in osteoclast function," J Bone Miner Metab., 2007, 25(6):337-344.
Nakanishi et al., "Overexpression of B7-H1 (PD-L1) significantly associates with tumor grade and postoperative prognosis in human urothelial cancers" Cancer Immunology, Immunotherapy, 2007, 56:1173-1182.
Nam et al., "The therapeutic potential of 4-1BB (CD137) in cancer", Current cancer drug targets, 2005, 5(5):357-363.
Nan et al., "Dual function glutamate-related ligands: discovery of a novel, potent inhibitor of glutamate carboxypeptidase II possessing mGluR3 agonist activity," J Med Chem., Mar. 9, 2000, 43(5):772-774.
National cancer institute, "Cancer prevention overview", (https://www.cancer.gov/about-cancer/causes-prevention/patient-prevention-overview-pdq accessed May 8, 2020), 2020, 12 pages.
National Cancer Institute, "What is Cancer", (https://www.cancer.gov/about-cancer/understanding/what-is-cancer, accessed Apr. 9, 2021), 10 pages.
National Cancer Institute, Understanding Cancer and Related Topics, (https://www.cancer.gov/about-cancer/understanding/what-is-cancer, accessed Apr. 9, 2021).

(56) References Cited

OTHER PUBLICATIONS

Nayyar et al., "Overcoming Resistance to Natural Killer Cell Based Immunotherapies for Solid Tumors", Feb. 11, 2019 ;9:51, 28 pages.
Neri and Supuran, "Interfering with pH regulation in tumours as a therapeutic strategy," Nature Review Drug Discovery, Sep. 2011, 10(10):767-777.
Nestor et al., "The Medicinal Chemistry of Peptides," Curr. Medicinal Chem, 2009, 16(33):4399-4418.
Nguyen, "Colorectal Cancer," Merck Manual, Reterived from https://www.merckmanuals.com/professional/gastrointestinal-disorders/tumors-of-the-gastrointestinal-tract/colorectal-cancer, 2021.
Nguyen, "Pancreatic Cancer", Merck Manual (https://merckmanuals.com/professional/gastrointestinal-disorders/tumors-of-the-gastrointestinal-tract/pancreatic-cancer?query=adenocarcinomas), Sep. 2022, 4 pages.
NIH National Human Genome Research Institute, "Animal Model," Genome.gov., Jan. 4, 2022.
Nishiwada et al., "Nectin-4 expression contributes to tumor proliferation, angiogenesis and patient prognosis in human pancreatic cancer," Journal of Experimental & Clinical Cancer Research, 2015, 34(1):30. (9 pages.).
Nissim et al., "Antibody fragments from a 'single pot' phage display library as immunochemical reagents," EMBO Journal, Feb. 1994, 13(3):692-698.
Nomi et al., "Clinical Significance and Therapeutic Potential of the Programmed Death-1 Ligand/Programmed Death-1 Pathway in Human Pancreatic Cancer", Clin Cancer Res., 2007, 13(7): 2151-2157.
Oehlke et al., "Cellular uptake of an alpha-helical amphipathic model peptide with the potential to deliver polar compounds into the cell interior non-endocytically," Biochimica et Biophysica Acta, Nov. 1998, 1414(1-2):127-139.
Okazaki et al., "A Rheostat for Immune Responses: the Unique Properties of PD-1 and Their Advantages for Clinical Application," Nat. Immunol., 2013, 14(12):1212-1218.
Okuyama et al., "Small-molecule mimics of an a-helix for efficient transport of proteins into cells," Nature Methods, Feb. 2007, 4(2):153-159.
Oliver et al., "Mouse CD38 is down-regulated on germinal center B cells and mature plasma cells," J Immunol., Feb. 1997, 158(3):1108-1115.
Ortiz et al., "Elucidating the interplay between IgG-Fc valency and FcγR activation for the design of immune complex inhibitors", Science Translational Medicine, Nov. 2016, 8(365):365ra158.
Pahwa et al., "Monitoring and inhibiting MT1-MMP during cancer initiation and progression." Cancers, 2014, 6(1):416-435.
Partida-Sanchez et al., "Cyclic ADP-ribose production by CD38 regulates intracellular calcium release, extracellular calcium influx and chemotaxis in neutrophils and is required for bacterial clearance in vivo," Nat Med., Nov. 2001, 7(11):1209-1216.
Partida-Sanchez et al., "Regulation of dendritic cell trafficking by the ADP-ribosyl cyclase CD38: impact on the development of humoral immunity," Immunity, Mar. 2004, 20(3):279-291.
Pasero et al., "Highly effective NK cells are associated with good prognosis in patients with metastatic prostate cancer", Oncotarget 6(16), Jun. 10, 2015, 14360-14373.
Pavlidou et al., "Nanodiscs Allow Phage Display Selection for Ligands to Non-Linear Epitopes on Membrane Proteins," PLoS One, Article No. e72272, Sep. 2013, 8(9):8 pages.
Pavlova et al., "A role for PVRL4-driven cell-cell interactions in tumorigenesis," Elife., Apr. 30, 2013, 2:c00358, 24 pages.
Pearson et al., "High-Level Clonal FGFR Amplification and Response to FGFR Inhibition in a Translational Clinical Trial", Cancer Discovery, 2016, 6(8):838-851.
Peng et al.,Combined features based on MT1-MMP expression, CD11b+ immunocytes density and LNR predict clinical outcomes of gastric cancer. Journal of translational medicine, 2013, 11(1):1-11.
Phichith, et al., "Novel peptide inhibiting both TEM-1 β-lactamase and penicillin-binding proteins." The FEBS Journal, 2010, 277(23):4965-4972.
Pickens et al., "Practical Considerations, Challenges and Limitations of Bioconjugation via Azide-Alkyne Cycloaddition," Bioconjugate Chem., 2018, 29:686-701.
Pietraszek et al., "Lumican: a new inhibitor of matrix metalloproteinase-14 activity," FEBS Lett., Nov. 28, 2014, 588(23):4319-4324.
Pivot et al., "Pooled analyses of eribulin in metastatic breast cancer patients with at least one prior chemotherapy." Annals of Oncology, 2016, 27(8):1525-1531.
Platonova et al., "Profound coordinated alterations of intratumoral NK cell phenotype and function in lung carcinoma", Cancer Res., 2011, 71(16):5412-5422.
Polakis, "Antibody Drug Conjugates for Cancer Therapy," Pharmacol Rev., Jan. 2016, 68(1):3-19.
Poliakov et al., "Diverse roles of eph receptors and ephrins in the regulation of cell migration and tissue assembly", Developmental Cell, Oct. 2004;7(4):465-480.
Poon et al., Preclinical safety profile of trastuzumab emtansine (T-DM1): mechanism of action of its cytotoxic component retained with improved tolerability. Toxicology and applied pharmacology, 2013, 273(2):298-313.
Poreba, "Protease-activated prodrugs: strategies, challenges, and future directions." The FEBS Journal, 2020, 287(10):1936-1969.
Pricop et al., "Differential modulation of stimulatory and inhibitory Fc gamma receptors on human monocytes by Th1 and Th2 cytokines", Journal of Immunology, 2001, 166(1):531-537.
Purdie and Benoiton, "Piperazinedione formation from esters of dipeptides containing glycine, alanine, and sarcosine: the kinetics in aqueous solution." Journal of the Chemical Society, Perkin Transactions 2, 1973, 14: 1845-1852.
Qi et al., "Serial determination of glomerular filtration rate in conscious mice using FITC-inulin clearance," American Journal of Physiology—Renal Physiology, Mar. 2004, 286(3):F590-F596.
Ramirez et al., "Defining causative factors contributing in the activation of hedgehog signaling in diffuse large B-cell lymphoma," Leuk Res., Oct. 2012, 36(10):1267-1273.
Randall et al., "Expression of murine CD38 defines a population of long-term reconstituting hematopoietic stem cells," Blood, May 15, 1996, 87(10):4057-4067.
Rataj et al., "High-affinity CD16-polymorphism and Fc-engineered antibodies enable activity of CD16-chimeric antigen receptor-modified T cells for cancer therapy", British Journal of Cancer, 2019, 120(1):79-87.
Ravetch et al., "IgG Fc receptors", Annual Review of Immunology, 2001:19:275-290.
Reagan-Shaw et al., "Dose translation from animal to human studies revisited, " FASEB J., Mar. 2008, 22(3):659-661.
Reinertsen et al., "B-Lymphocyte Alloantigens Associated with Systemic Lupus Erythematosus," The New England Journal of Medicine, Sep. 7, 1978, 299(10):515-518.
Remacle et al., "Membrane type I-matrix metalloproteinase (MT1-MMP) is internalised by two different pathways and is recycled to the cell surface." Journal of cell science, 2003, 116(19):3905-3916.
Remacle et al., "Novel MT1-MMP small-molecule inhibitors based on insights into hemopexin domain function in tumor growth," Cancer Res., May 1, 2012, 72(9):2339-2349.
Ridderstad and Tarlinton, "Kinetics of establishing the memory B cell population as revealed by CD38 expression," J Immunol., May 15, 1998, 160(10):4688-4695.
Riddle et al., "Tumor cell surface display of immunoglobulin heavy chain Fc by genc transfer as a means to mimic antibody therapy", Human Gene Therapy, 2005, 16(7):830-844.
Robert Gale, "Cancer treatment principles", Merck Manual consumer version (https://www.merckmanuals.com/home/cancer/prevention-and-treatment-of-cancer/cancer-treatment-principles?query=Cancer%20treatment Accessed May 8, 2020), Jul. 2018, 2 pages.
Robert Gale, "Overview of Cancer therapy", Merck Manual consumer version (https://www.merckmanuals.com/professional/

(56) References Cited

OTHER PUBLICATIONS hematology-and-oncology/principles-of-cancer-therapy/overview-of-cancer-therapy?query=Cancer Accessed May 8, 2020), Jul. 2018, 3 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, 2016, 7:413.
Rodan and Rodan, "Integrin function in osteoclasts," J Endocrinol., Sep. 1997, 154(Suppl):S47-S56.
Rodon et al., "Cantuzumab mertansine in a three-times a week schedule: a phase I and pharmacokinetic study." Cancer chemotherapy and pharmacology, 2008, 62(5):911-919.
Ross and Christiano, "Nothing but skin and bone," J Clin Invest., May 2006, 116(5):1140-1149.
Ross et al., "Bispecific T Cell Enager (BiTE) Antibody Constructs Can Mediate Bystander Tumor Cell Killing", PLoS One, Aug. 24, 2017, 12(8):1-24.
Rostovtsev et al., "A Stepwise Huisgen Cycloaddition Process: Copper(I)-Catalyzed Regioselective "Ligation" of Azides and Ter¬minal Alkynes," Angewandte Chemie, Jul. 2002, 41(14):2596-2599.
Roth et al., "Docetaxel, cisplatin, and fluorouracil; docetaxel and cisplatin; and epirubicin, cisplatin, and fluorouracil as systemic treatment for advanced gastric carcinoma: a randomized phase II trial of the Swiss Group for Clinical Cancer Research", J Clin Oncol. Aug. 1, 2007 , 25(22):3217-3023.
Rothwell et al., "Utility of ctDNA to support patient selection for early phase clinical trials: the Target study", Nature Medicine, 2019, 25(5):738-743.
Rudgers et al., "Binding properties of a peptide derived from beta-lactamasc inhibitory protein." Antimicrob Agents Chemother., 2001, 45(12):3279-3286.
Salmon et al., "Human receptors for immunoglobulin G: key elements in the pathogenesis of rheumatic disease", Arthritis & Rheumatology, 2001, 44(4):739-750.
Satoh et al., "Experimental allergic encephalomyelitis mediated by murine encephalitogenic T cell lines specific for myelin proteolipid apoprotein," Journal of Immunology, Jan. 1987, 138(1):179-184.
Sausville and Burger, "Contributions of Human Tumor Xenografts to Anticancer Drug Development," Cancer Res., 2006, 66(7):3351-3354.
Scagliotti et al., "Phase III study comparing cisplatin plus gemcitabine with cisplatin plus pemetrexed in chemotherapy-naive patients with advanced-stage non-small-cell lung cancer." Journal of clinical oncology, 2008, 26(21):3543-3551.
Schiller et al., "Comparison of four chemotherapy regimens for advanced non-small-cell lung cancer." New England Journal of Medicine, 2002, 346(2):92-98.
Schreiber et al., "Rapid, electrostatically assisted association of proteins," Nature Structural & Molecular Biology, May 1996, 3:427-431.
Schulke et al., "The homodimer of prostate-specific membrane antigen is a functional target for cancer therapy," Proc Natl Acad Sci U SA., Oct. 28, 2003, 100(22):12590-12595.
Seely and Frazier, "Regulatory Forum Opinion Piece*: Dispelling Confusing Pathology Terminology: Recognition and Interpretation of Selected Rodent Renal Tubule Lesions," Toxicol Pathol., 2015, 43(4):457-463.
Segal et al., "Results from an Integrated Safety Analysis of Urelumab, an Agonist Anti-CD137 Monoclonal Antibody", clinical Cancer research, 2017, 23(8):1929-1936.
Seiki et al., "Membrane-type I matrix metalloproteinase: a key enzyme for tumor invasion." Cancer letters, 2003, 194(1):1-11.
Scpiashvili et al., "Potentially novel candidate biomarkers for head and neck squamous cell carcinoma identified using an integrated cell line-based discovery strategy." Molecular & Cellular Proteomics, 2012, 11(11):1404-1415.
Shaabani et al., "A patent review on PD-1/PD-L 1 antagonists: small molecules, peptides, and macrocycles (2015-2018)," Expert Opinion on Therapeutic Patents, 2018, 28(9):665-678.
Shah et al., "Phase I study of IMGN901, a CD56-targeting antibody-drug conjugate, in patients with CD56-positive solid tumors." Investigational new drugs, 2016, 34:290-299.
Shah, "Update on metastatic gastric and esophageal cancers." Journal of clinical oncology 33, No. 16 (2015): 1760-1769.
Shao et al., "Copy number variation is highly correlated with differential gene expression: a pan-cancer study," BMC Medical Genetics, Nov. 9, 2019, 20(1):175.
Shao et al., "CD137 ligand, a member of the tumor necrosis factor family, regulates immune responses via reverse signal transduction." Journal of leukocyte biology, 2011, 89(1):21-29.
Sharma et al., "Plasmacytoid dendritic cells from mouse tumor-draining lymph nodes directly activate mature Tregs via indoleamine 2, 3-dioxygenase", The Journal of clinical investigation, 2007, 117(9):2570-2582.
Shen et al., "Non-clinical disposition and metabolism of DM1, a Component of Trastuzumab Emtansine (T-DM1), in Sprague Dawley Rats." Drug Metabolism Letters, 2015, 9(2):119-131.
Shen, et.al., "Evaluation of phage display discovered peptides as ligands for prostate-specific membrane antigen (PSMA). " PLoS One, 2013, 8(7):e68339.
Shi et al., "One-Bead-Two-Compound Thioether Bridged Macrocyclic (gamma)-AApeptide Screening Library Against EphA2," J Med Chem., Nov. 22, 2017, 60(22):9290-9298.
Shimauchi et al., "Augmented expression of programmed death-1 in both neoplastic and non-neoplastic CD4+ T-cells in adult T-cell leukemia/lymphoma", International journal of cancer, 2007, 121(12):2585-2590.
Sibaud et al., "Pigmentary disorders induced by anticancer agents. Part I: chemotherapy." In Annales de dermatologie et de venereologie, 2013, 140(3):183-196.
Siddharth et al., "Nectin-4 is a breast cancer stem cell marker that induces WNT/β-Catenin signaling via Pi3k/Akt axis," International Journal of Biochemistry and Cell Biology, 2017, 89:85-94.
Silver, "Multi-targeting by monotherapeutic antibacterials." Nat Rev Drug Discov., 2007, 6(1):41-55.
Smeenk et al., "Reconstructing the Discontinuous and Conformational β1/β3-Loop Binding Site on hFSH/hCG by Using Highly Constrained Multicyclic Peptides." ChemBioChem, 2015, 16(1):91-99.
Soderstrom, et al., "CD137: A checkpoint regulator involved in atherosclerosis." Atherosclerosis, 2018, 272:66-72.
Sordo-Bahamonde et al., "Mechanisms of Resistance to NK Cell Immunotherapy", Cancers (Basel). Apr. 7, 2020, 12(4):893.
Sounni et al. "MT1-MMP expression promotes tumor growth and angiogenesis through an up-regulation of vascular endothelial growth factor expression" FASEB J., 2002, 16(6):555-564.
Sporn et at, "Chemoprevention of cancer." Carcinogenesis, 2000, 21(3):525-530.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood, 2014, 124(21):1760.
Steck et al., "Inside-out red cell membrane vesicles: preparation and purification," Science, Apr. 10, 1970, 168(3928):255-257.
Stein et al., "Eph receptors discriminate specific ligand oligomers to determine alternative signaling complexes, attachment, and assembly responses", Genes Development, 1998, 12(5):667-678.
Stevenson et al., "Preliminary studies for an immunotherapeutic approach to the treatment of human myeloma using chimeric anti-CD38 antibody," Blood, Mar. 1, 1991, 77(5):1071-1079.
Stojanovic et al., "Natural killer cells and solid tumors", Journal of Innate Immunity, 2011, 3(4):355-364.
Stringaris et al., "Leukemia-induced phenotypic and functional defects in natural killer cells predict failure to achieve remission in acute myeloid leukemia", Haematologica, May 2014, 99(5):836-847.
Strome et al., "B7-H1 blockade augments adoptive T-cell immunotherapy for squamous cell carcinoma", Cancer Res., 2003, 63(19):6501-6505.

(56) References Cited

OTHER PUBLICATIONS

Stuart et al., "Collagen Autoimmune Arthritis," Annual Review of Immunology, 1984, 2:199-218.
Sun et al., "Carbohydrate and protein immobilization onto solid surfaces by sequential Diels-Alder and azide-alkyne cycloadditions," Bioconjugate Chemistry, Jan.-Feb. 2006, 17(1):52-57.
Sun et al., "NK cell receptor imbalance and NK cell dysfunction in HBV infection and hepatocellular carcinoma", Cellular & Molecular Immunology, May 2015, 12(3):292-302.
Suojanen et al., "A novel and selective membrane type-1 matrix metalloproteinase (MT1-MMP) inhibitor reduces cancer cell motility and tumor growth," Cancer Biology & Therapy, Dec. 2009, 8(24):2362-2370.
Supuran, "Carbonic anhydrases: novel therapeutic applications for inhibitors and activators," Nature Reviews Drug Discovery, Feb. 2008, 7(2):168-181.
Tandon et al., "Emerging strategies for EphA2 receptor targeting for cancer therapeutics" Expert Opinion on Therapeutic Targets, 2011, 15(1):31-51.
Tarazona et al., "Current progress in NK cell biology and NK cell-based cancer immunotherapy", Cancer Immunol Immunother, 2020, 69(5):879-899.
Tasch et al., "A unique folate hydrolase, prostate-specific membrane antigen (PSMA): a target for immunotherapy?", Crit Rev Immunol., 2001, 21(1-3):249-261.
Teitelbaum, "Osteoclasts, integrins, and osteoporosis," J Bone Miner Metab., Oct. 2000, 18(6):344-349.
Teitelbaum, "Osteoporosis and Integrins," The Journal of Clinical Endocrinology & Metabolism, Apr. 2005, 90(4):2466-2468.
Teti et al., "The Role of the AlphaVbeta3 Integrin in the Development of Osteolytic Bone Metastases: A Pharmacological Target for Alternative Therapy?", Calcified Tissue International, Oct. 2002, 71(4):293-299.
Tetu et al., "The influence of MMP-14, TIMP-2 and MMP-2 expression on breast cancer prognosis." Breast Cancer Research, 2006, 8(3):1-9.
Teufel et al., "Backbone-driven collapse in unfolded protein chains," J Mol Biol., Jun. 3, 2011, 409(2):250-262.
Thake et al., "Toxicity of Maytansine (NSC 153858) in dogs and monkeys." PB-US National Technical Information Service (1975), Feb. 1975, 244628.
Thevenard et al., "The YSNSG cyclopeptide derived from tumstatin inhibits tumor angiogenesis by down-regulating endothelial cell migration." International journal of cancer, 2010, 126(5):1055-1066.
Thompson et al., "Costimulatory B7-H1 in renal cell carcinoma patients: Indicator of tumor aggressiveness and potential therapeutic target", Proceedings of the National Academy of Sciences, 2004, 101(49):17174-17179.
Timmerman et al., "Rapid and Quantitative Cyclization of Multiple Peptide Loops onto Synthetic Scaffolds for Structural Mimicry of Protein Surfaces," ChemBioChem, 2005, 6(5):821-824.
Todisco et al., "CD38 ligation inhibits normal and leukemic myelopoiesis," Blood, Jan. 2000, 95(2):535-542.
Tolcher et al., "Cantuzumab mertansine, a maytansinoid immunoconjugate directed to the CanAg antigen: a phase I, pharmacokinetic, and biologic correlative study." Journal of clinical oncology, 2003, 21(2):211-222.
Toogood, "Small Molecule Immuno-oncology Therapeutic Agents," Bioorganic & Medicinal Chemistry Letters, 2018, 28(3):319-329.
Touati et al., "Phage Selection of Bicyclic Peptide Ligands and Development of a New Peptide Cyclisation Method", Thesc No. 5536, Oct. 2012, 117 pages.
Trouche et al., "Small multivalent architectures mimicking homotrimers of the TNF superfamily member CD40L: delineating the relationship between structure and effector function." Journal of the American Chemical Society, 2007, 129(44):13480-13492.
Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry." Human pathology, 2008, 39(5):731-739.
Tugyi et al., "Partial D-amino acid substitution: Improved enzymatic stability and preserved Ab recognition of a MUC2 epitope peptide," Proceedings of the National Academy of Sciences U.S.A., Jan. 2005, 102(2):413-418.
Tutt et al., "Abstract S3-01: the TNT trial: a randomized phase III trial of carboplatin (C) compared with docetaxel (D) for patients with metastatic or recurrent locally advanced triple negative or BRCA1/2 breast cancer (CRUK/07/012)." Cancer Research, May 2015, 75(9_Suppl):S3-01.
Uckun, "Regulation of human B-cell ontogeny," Blood, Nov. 1990, 76(10):1908-1923.
Ulasov et al., "Inhibition of MMP 14 potentiates the therapeutic effect of temozolomide and radiation in gliomas." Cancer medicine, 2013, 2(4):457-467.
Ün, Sanya. Charakterisierung von Peptiden für die Bindung essentieller Penicillin-bindender Proteine und die Variationen der Linkerlänge einzelkettiger TetR Varianten. Friedrich-Alexander-Universitaet Erlangen-Nuernberg (Germany), 2010. 139 pages.
Upadhyaya, "Activation of CD137 using multivalent and tumor targeted Bicyclic peptides." Cancer Research, Jul. 2019, 79(13 Suppl):3257-3257.
Van Eden et al., "Cloning of the mycobacterial epitope recognized by T lymphocytes in adjuvant arthritis," Nature, Jan. 14, 1988, 331(6152):171-173.
Van Glabbeke et al., "Progression-free rate as the principal end-point for phase II trials in soft-tissue sarcomas." European Journal of Cancer, 2002, 38(4):543-549.
Vandenbroucke and Libert, "Is there new hope for therapeutic matrix metalloproteinase inhibition?." Nature reviews Drug discovery, 2014, 13(12):904-927.
Walker-Daniels et al., "Overexpression of the EphA2 tyrosine kinase in prostate cancer", Prostate, 1999, 41(4):275-280.
Wallbrecher et al., "Exploration of the design principles of a cell-penetrating bicylic peptide scaffold," Bioconjug Chem., May 21, 2014, 25(5):955-964.
Wang et al., "Co-expression of MMP-14 and MMP-19 predicts poor survival in human glioma." Clinical and Translational Oncology, 2013, 15:139-145.
Wang et al., "MMP-14 overexpression correlates with poor prognosis in non-small cell lung cancer." Tumor Biology, 2014, 35:9815-9821.
Wang et al., "Probing for Integrin $\alpha v\beta 3$ Binding of RGD Peptides Using Fluorescence Polarization," Bioconjugate Chem., May-Jun. 2005, 16(3):729-734.
Wang, "An exact mathematical expression for describing competitive binding of two different ligands to a protein molecule." FEBS letters, 1995, 360(2):111-114.
Watanabe et al., "NK cell dysfunction with down-regulated CD16 and up-regulated CD56 molecules in patients with esophageal squamous cell carcinoma", Discases of the Esophagus, 2010, 23(8):675-681.
Waterhouse et al., "Safety profile of nivolumab administered as 30-min infusion: analysis of data from CheckMate 153," Cancer Chemother Pharmacol., Apr. 2018, 81(4):679-686.
Watts, "TNF/TNFR family members in costimulation of T cell responses", Annu. Rev, Immunol., Apr. 2005, 23:23-68.
Weber, J. "Immune Checkpoint Proteins: A New Therapeutic Paradigm for Cancer—Preclinical Background: CTLA-4 and PD-1 Blockade", Seminars in Oncology, Oct. 2010, 37(5):430-439.
Wei et al., "Discovery of Peptidomimetic Antibody-Drug Conjugate Linkers with Enhanced Protease Specificity," J. Med. Chem., 2018, 61(3):989-1000.
Wind et al., "Measuring carbonic anhydrase IX as a hypoxia biomarker: differences in concentrations in scrum and plasma using a commercial enzyme-linked immunosorbent assay due to influences of metal ions," Annals of Clinical Biochemistry, Mar. 2011, 48(2):112-120.
Winter et al., "Making antibodies by phage display technology," Annual Review of Immunology, 1994, 12:433-455.

(56) References Cited

OTHER PUBLICATIONS

Wu et al, "Structures of the CXCR4 chemokine GPCR with small-molecule and cyclic peptide antagonists," Science, Nov. 2010, 330(6007):1066-1071.
Wu et al., "A novel polymorphism of FcgammaRIIIa (CD16) alters receptor function and predisposes to autoimmune disease", The Journal of Clinical Investigation, 1997, 100(5):1059-1070.
Wu et al., "Design and Characterization of Novel EphA2 Agonists for Targeted Delivery of Chemotherapy to Cancer Cells," Chem. Biol., 2015, 22(7):876-887.
Wu et al., "Natural killer cells in cancer biology and therapy", Molecular Cancer, Aug. 6, 2020, 19(1):120, 26 pages.
Wu et al., "Immunohistochemical localization of programmed death-1 ligand-1 (PD-L1) in gastric carcinoma and its clinical significance" Acta histochemica, 2006, 108(1):19-24.
Wykosky et al., "EphA2 as a novel molecular marker and target in glioblastoma multiforme", Molecular Cancer Research, Oct. 2005, 3(10):541-551.
Xiong et al., "Crystal structure of the extracellular segment of integrin αVβ3 in complex with an Arg-Gly-Asp Ligand", Science, Apr. 2002, 296(5565):151-155.
Yang et al., "Overexpression of EphA2, MMP-9, and MVD-CD34 in hepatocellular carcinoma: Implications for tumor progression and prognosis," Hepatol Res., 2009, 39(12):1169-1177.
Yardley et al., "EMERGE: a randomized phase II study of the antibody-drug conjugate glembatumumab vedotin in advanced glycoprotein NMB-expressing breast cancer." Journal of clinical oncology: official journal of the American Society of Clinical Oncology, 2015, 33(14):1609.
Yoon et al., "An efficient strategy for cell-based antibody library selection using an integrated vector system," BMC Biotechnology, 2012, 12(62):10 pages.
Yoshihara et al., "Tags for labeling protein N-termini with subtiligase for proteomics," Bioorganic & Medicinal Chemistry Letters, Nov. 2008, 18(22):6000-6003.
Yu and Taylor, "A new strategy applied to the synthesis of an α-helical bicyclic peptide constrained by two overlapping i, i+ 7 side-chain bridges of novel design." Tetrahedron letters, 1996, 37(11):1731-1734.
Yuan et al., "Neuropilin-1 and the development progress of the same as a therapeutic target for malignant tumors," Tumor, 2016, 36:358-364.
Yuan et al., "Over-expression of EphA2 and EphrinA-1 in human gastric adenocarcinoma and its prognostic value for postoperative patients," Dig Dis Sci., Nov. 2009, 54(11):2410-2417.
Zarrabi et al., "Inhibition of matrix metalloproteinasc 14 (MMP-14)-mediated cancer cell migration." Journal of Biological Chemistry, 2011, 286(38):33167-33177.
Zelinski et al., "EphA2 Overexpression Causes Tumorigenesis of Mammary Epithelial Cells," Cancer research, Mar. 2001, 61(5):2301-2306.
Zervosen et al., "Development of New Drugs for an Old Target—The Penicillin Binding Proteins." Molecules. 2012:17 (11);12478-12505.
Zhang et al., "A new anti-HER2 antibody that enhances the anti-tumor efficacy of trastuzumab and pertuzumab with a distinct mechanism of action", Mol Immunol., 2020, 119:48-58.
Zhang et al., "FCGR2A and FCGR3A Polymorphisms Associated With Clinical Outcome of Epidermal Growth Factor Receptor-Expressing Metastatic Colorectal Cancer Patients Treated With Single-Agent Cetuximab", Journal of Clinical Oncology, 2007, 25(24):3712-3718.
Zhao el al., "Structural basis of specificity of a peptidyl urokinase inhibitor, upain-1," Journal of Structural Biology, Oct. 2007, 160(1):1-10.
Zhou et al., "Significance of semaphorin-3A and MMP-14 protein expression in non-small cell lung cancer", Oncology letters, 2014, 7(5):1395-1400.
Zhu et al., "High-affinity peptide against MT1-MMP for in vivo tumor imaging." Journal of controlled release, 2011, 150(3):248-255.
Zhuang et al., "Elevation of receptor tyrosine kinase EphA2 mediates resistance to trastuzumab therapy," Cancer Res., Jan. 1, 2010, 70(1):299-308.
Zilber et al., "CD38 expressed on human monocytes: a coaccessory molecule in the superantigeninduced proliferation," Proc Natl Acad Sci US A., Mar. 14, 2000, 97(6):2840-2845.
Zou et al., "PD-L1 (B7-H1) and PD-1 Pathway Blockade for Cancer Therapy: Mechanisms, Response Biomarkers and Combinations," Sci. Transl. Med., 2016, 8(328):328rv4., 1-14.
Zubiaur et al., "CD38 Ligation Results in Activation of the Raf-1/Mitogen-Activated |Protein Kinase and the CD3-zeta/zeta-Associated Protein-70 Signaling Pathways in Jurkat T Lymphocytes," J Immunol., Jul. 1, 1997, 159(1):193-205.
Zugazagoitia et al., "Current Challenges in Cancer Treatment," Clinical Therapies, 2016, 38(7):1551-1566.
Zupo et al., "CD38 signaling by agonistic monoclonal antibody prevents apoptosis of human germinal center B cells," Eur J Immunol., May 1994, 24(5):1218-1222.
PCT International Preliminary Report on Patentability received for PCT/EP2017/083953, dated Jul. 4, 2019, 7 pages.
PCT International Preliminary Report on Patentability received for PCT/EP2017/083954, dated Jul. 4, 2019, 7 pages.
PCT International Preliminary Report on Patentability received for PCT/EP2019/066010, dated Dec. 30, 2020, 9 pages.
PCT International Preliminary Report on Patentability received for PCT/EP2019/066066, dated Dec. 30, 2020, 8 pages.
PCT International Preliminary Report on Patentability received for PCT/EP2019/066273, dated Dec. 30, 2020, 8 pages.
PCT International Preliminary Report on Patentability received for PCT/EP2021/072866, dated Mar. 2, 2023, 13 pages.
PCT International Preliminary Report on Patentability received for PCT/GB2015/053247, dated May 11, 2017, 8 pages.
PCT International Preliminary Report on Patentability received for PCT/GB2018/050017, dated Jul. 18, 2019, 8 pages.
PCT International Preliminary Report on Patentability received for PCT/GB2018/052222, dated Feb. 13, 2020, 7 pages.
PCT International Preliminary Report on Patentability received for PCT/GB2019/050485, dated Sep. 3, 2020, 8 pages.
PCT International Preliminary Report on Patentability received for PCT/GB2019/053537, dated Jun. 24, 2021, 7 pages.
PCT International Preliminary Report on Patentability received for PCT/GB2019/053679, dated Jul. 1, 2021, 7 pages.
PCT International Preliminary Report on Patentability received for PCT/GB2019/053680, dated Jul. 1, 2021, 7 pages.
PCT International Preliminary Report on Patentability received for PCT/GB2020/050069, dated Jul. 29, 2021, 8 pages.
PCT International Preliminary Report on Patentability received for PCT/GB2020/050070, dated Jul. 29, 2021, 11 pages.
PCT International Preliminary Report on Patentability received for PCT/GB2020/050071, dated Jul. 29, 2021, 7 pages.
PCT International Preliminary Report on Patentability received for PCT/GB2020/050072, dated Jul. 29, 2021, 11 pages.
PCT International Preliminary Report on Patentability received for PCT/GB2020/050073, dated Jul. 29, 2021, 8 pages.
PCT International Preliminary Report on Patentability received for PCT/GB2020/050074, dated Jul. 29, 2021, 14 pages.
PCT International Preliminary Report on Patentability received for PCT/GB2020/052058, dated Mar. 10, 2022, 8 pages.
PCT International Preliminary Report on Patentability received for PCT/GB2020/052590, dated Apr. 28, 2022, 7 pages.
PCT International Preliminary Report on Patentability received for PCT/GB2021/050490, dated Sep. 9, 2022, 9 pages.
PCT International Preliminary Report on Patentability received for PCT/GB2021/050491, dated Sep. 9, 2022, 10 pages.
PCT International Preliminary Report on Patentability received for PCT/GB2022/050043, dated Jul. 20, 2023, 13 pages.
PCT International Preliminary Report on Patentability received for PCT/EP2018/060498, dated Nov. 7, 2019. 8 Pages.
PCT International Preliminary Report on Patentability received for PCT/EP2019/065993, dated Dec. 30, 2020, 7 pages.

(56) References Cited

OTHER PUBLICATIONS

PCT International Preliminary Report on Patentability received for PCT/GB2017/053560, dated Jun. 6, 2019, 7 pages.
PCT International Preliminary Report on Patentability received for PCT/GB2018/051779, dated Jan. 9, 2020, 6 pages.
PCT International Preliminary Report on Patentability received for PCT/GB2018/053676, dated Jul. 2, 2020, 7 pages.
PCT International Preliminary Report on Patentability received for PCT/GB2018/053678, dated Jul. 2, 2020, 9 pages.
PCT International Preliminary Report on Patentability received for PCT/GB2019/051740, dated Dec. 30, 2020, 8 pages.
PCT International Preliminary Report on Patentability received for PCT/GB2019/051741, dated Dec. 30, 2020, 7 pages.
PCT International Preliminary Report on Patentability received for PCT/GB2019/053020, dated May 6, 2021, 12 pages.
PCT International Preliminary Report on Patentability received for PCT/GB2019/053080, dated May 14, 2021, 16 pages.
PCT International Preliminary Report on Patentability received for PCT/GB2019/053536, dated Jun. 24, 2021, 07 pages.
PCT International Preliminary Report on Patentability received for PCT/GB2019/053539, dated Jun. 24, 2021, 7 pages.
PCT International Preliminary Report on Patentability received for PCT/GB2019/053540, dated Jun. 24, 2021, 8 pages.
PCT International Preliminary Report on Patentability received for PCT/GB2020/050505, dated Sep. 16, 2021, 7 pages.
PCT International Preliminary Report on Patentability received for PCT/GB2020/050874, dated Oct. 14, 2021, 11 pages.
PCT International Preliminary Report on Patentability received for PCT/GB2020/051140, dated Nov. 25, 2021, 8 pages.
PCT International Preliminary Report on Patentability received for PCT/GB2020/051144, dated Nov. 18, 2021, 9 pages.
PCT International Preliminary Report on Patentability received for PCT/GB2020/051827, dated Feb. 10, 2022, 8 pages.
PCT International Preliminary Report on Patentability received for PCT/GB2020/051829, dated Feb. 10, 2022 , 8 pages.
PCT International Preliminary Report on Patentability received for PCT/GB2020/051831, dated Feb. 10, 2022, 10 pages.
PCT International Preliminary Report on Patentability received for PCT/GB2020/051923, dated Feb. 24, 2022, 9 pages.
PCT International Preliminary Report on Patentability received for PCT/GB2020/052445, dated Apr. 14, 2022, 26 pages.
PCT International Preliminary Report on Patentability received for PCT/GB2020/052619, dated Apr. 28, 2022, 9 pages.
PCT International Preliminary Report on Patentability received for PCT/GB2020/053026, dated Jun. 9, 2022, 8 pages.
PCT International Preliminary Report on Patentability received for PCT/GB2021/051220, dated Dec. 1, 2022, 7 pages.
PCT International Preliminary Report on Patentability received for PCT/GB2021/051451, dated Dec. 22, 2022, 09 pages.
PCT International Preliminary Report on Patentability received for PCT/GB2021/052001, dated Feb. 16, 2023, 13 pages.
PCT International Preliminary Report on Patentability received for PCT/GB2022/050044, dated Jul. 20, 2023, 13 pages.
PCT International Preliminary Report on Patentability received for PCT/GB2022/050055, dated Jul. 20, 2023, 17 pages.
PCT International Preliminary Report on Patentability received for PCT/GB2017/051250, dated Nov. 15, 2018, 7 pages.
PCT International Preliminary Report on Patentability received for PCT/GB2018/051118, dated Nov. 7, 2019, 11 pages.
PCT International Search Report and Written Opinion received for PCT/EP2017/083953, dated May 9, 2018, 9 pages.
PCT International Search Report and Written Opinion received for PCT/EP2017/083954, dated May 4, 2018, 9 pages.
PCT International Search Report and Written Opinion received for PCT/EP2018/060498, dated Jul. 5, 2018, 13 pages.
PCT International Search Report and Written Opinion received for PCT/EP2019/065993, dated Sep. 24, 2019, 11 pages.
PCT International Search Report and Written Opinion received for PCT/EP2019/066010, dated Sep. 30, 2019, 12 pages.
PCT International Search Report and Written Opinion received for PCT/EP2019/066066, dated Oct. 1, 2019, 11 pages.
PCT International Search Report and Written Opinion received for PCT/EP2019/066273, dated Sep. 27, 2019, 11 pages.
PCT International Search Report and Written Opinion received for PCT/EP2021/072866, dated Dec. 21, 2021, 21 pages.
PCT International Search Report and Written Opinion received for PCT/GB2015/053247, dated Jan. 27, 2016, 12 pages.
PCT International Search Report and Written Opinion received for PCT/GB2017/051250, dated Aug. 4, 2017, 10 pages.
PCT International Search Report and Written Opinion received for PCT/GB2017/053560, dated Jul. 2, 2018, 9 pages.
PCT International Search Report and Written Opinion received for PCT/GB2018/050017, dated Mar. 23, 2018, 12 pages.
PCT International Search Report and Written Opinion received for PCT/GB2018/051118, dated Aug. 3, 2018, 20 pages.
PCT International Search Report and Written Opinion received for PCT/GB2018/051779, dated Sep. 3, 2018, 10 pages.
PCT International Search Report and Written Opinion received for PCT/GB2018/053676, dated Mar. 21, 2019, 12 pages.
PCT International Search Report and Written Opinion received for PCT/GB2018/053678, dated Mar. 20, 2019, 12 pages.
PCT International Search Report and Written Opinion received for PCT/GB2019/050485, dated Jun. 4, 2019, 12 Pages.
PCT International Search Report and Written Opinion received for PCT/GB2019/051740, dated Aug. 29, 2019, 11 pages.
PCT International Search Report and Written Opinion received for PCT/GB2019/051741, dated Aug. 5, 2019, 10 pages.
PCT International Search Report and Written Opinion received for PCT/GB2019/053020, dated Jun. 23, 2020, 19 pages.
PCT International Search Report and Written Opinion received for PCT/GB2019/053080, dated Feb. 7, 2020, 19 pages.
PCT International Search Report and Written Opinion received for PCT/GB2019/053536, dated Mar. 11, 2020, 11 pages.
PCT International Search Report and Written Opinion received for PCT/GB2019/053537, dated Mar. 11, 2020, 10 pages.
PCT International Search Report and Written Opinion received for PCT/GB2019/053539, dated Mar. 11, 2020, 8 pages.
PCT International Search Report and Written Opinion received for PCT/GB2019/053540, dated Mar. 11, 2020, 10 pages.
PCT International Search Report and Written Opinion received for PCT/GB2019/053679, dated Mar. 11, 2020, 12 pages.
PCT International Search Report and Written Opinion received for PCT/GB2019/053680, dated Mar. 11, 2020, 11 pages.
PCT International Search Report and Written Opinion received for PCT/GB2020/050069, dated Apr. 15, 2020, 10 pages.
PCT International Search Report and Written Opinion received for PCT/GB2020/050070, dated Jun. 23, 2020, 16 pages.
PCT International Search Report and Written Opinion received for PCT/GB2020/050071, dated May 12, 2020, 10 pages.
PCT International Search Report and Written Opinion received for PCT/GB2020/050072, dated Jun. 30, 2020, 16 pages.
PCT International Search Report and Written Opinion received for PCT/GB2020/050073, dated Apr. 7, 2020, 11 pages.
PCT International Search Report and Written Opinion received for PCT/GB2020/050074, dated Jun. 23, 2020, 21 pages.
PCT International Search Report and Written Opinion received for PCT/GB2020/050505, dated Apr. 28, 2020, 9 pages.
PCT International Search Report and Written Opinion received for PCT/GB2020/050874, dated Jun. 17, 2020, 15 pages.
PCT International Search Report and Written Opinion received for PCT/GB2020/051140, dated Aug. 20, 2020, 10 pages.
PCT International Search Report and Written Opinion received for PCT/GB2020/051144, dated Aug. 18, 2020, 12 pages.
PCT International Search Report and Written Opinion received for PCT/GB2020/051827, dated Nov. 3, 2020, 11 pages.
PCT International Search Report and Written Opinion received for PCT/GB2020/051829, dated Oct. 30, 2020, 11 pages.
PCT International Search Report and Written Opinion received for PCT/GB2020/051831, dated Nov. 4, 2020, 13 pages.
PCT International Search Report and Written Opinion received for PCT/GB2020/051923, dated Nov. 17, 2020, 12 pages.

(56) References Cited

OTHER PUBLICATIONS

PCT International Search Report and Written Opinion received for PCT/GB2020/052058, dated Nov. 12, 2020, 11 pages.
PCT International Search Report and Written Opinion received for PCT/GB2020/052445, dated Mar. 4, 2021, 34 pages.
PCT International Search Report and Written Opinion received for PCT/GB2020/052590, dated Jan. 28, 2021, 9 pages.
PCT International Search Report and Written Opinion received for PCT/GB2020/052619, dated Jan. 28, 2021, 12 pages.
PCT International Search Report and Written Opinion received for PCT/GB2020/053026, dated Mar. 23, 2021, 11 pages.
PCT International Search Report and Written Opinion received for PCT/GB2021/050490, dated May 19, 2021, 12 pages.
PCT International Search Report and Written Opinion received for PCT/GB2021/050491, dated May 14, 2021, 14 pages.
PCT International Search Report and Written Opinion received for PCT/GB2021/051220, dated Aug. 27, 2021, 12 pages.
PCT International Search Report and Written Opinion received for PCT/GB2021/051451, dated Sep. 22, 2021, 14 pages.
PCT International Search Report and Written Opinion received for PCT/GB2021/052001, dated Nov. 12, 2021, 11 pages.
PCT International Search Report and Written Opinion received for PCT/GB2022/050043, dated Nov. 17, 2022, 18 pages.
PCT International Search Report and Written Opinion received for PCT/GB2022/050044, dated Jun. 28, 2022, 19 pages.
PCT International Search Report and Written Opinion received for PCT/GB2022/050055, dated Apr. 19, 2022, 21 pages.
PCT International Search Report and Written Opinion received for PCT/GB2022/052249, dated Mar. 28, 2023, 14 pages.
PCT International Search Report and Written Opinion received for PCT/GB2022/052903, dated Mar. 13, 2023, 12 pages.
PCT International Search Report and Written Opinionreceived for PCT/GB2018/052222, dated Oct. 11, 2018, 9 pages.
U.S. Appl. No. 17/769,668, filed Apr. 15, 2022.
U.S. Appl. No. 18/021,748, filed Feb. 16, 2023.
U.S. Appl. No. 18/271,360, filed Jul. 7, 2023.
U.S. Appl. No. 18/271,593, filed Jul. 10, 2023.
U.S. Appl. No. 18/313,983, filed May 8, 2023.
U.S. Appl. No. 18/345,506, filed Jun. 30, 2023.
Rajendran et al., "CD137 signaling in Hodgkin and Reed-Sternberg cell lines induces IL-13 secretion, immune deviation and enhanced growth," Oncoimmunology, 2016, 5(6):e1160188(7 pages).
Palma et al., "CD137 and CD137 ligand constitutively coexpressed on human T and B leukemia cells signal proliferation and survival," Int. J. Cancer, Jan. 20, 2004, 108(3):390-398.
Ho et al., "Expression of CD137 on Hodgkin and Reed-Sternberg cells inhibits T-cell activation by eliminating CD137 ligand expression," Cancer Res., Jan. 15, 2013, 73(2):652-661.
Hacker et al., "Highly Constrained Bicyclic Scaffolds for the Discovery of Protease-Stable Peptides via mRNA Display", ACS Chem. Biol., 2017, 12(3):795-804.
Gfeller et al., "Current tools for predicting cancer-specific T cell immunity," Oncoimmunology 5:7: e1177691.
International Search Report and Written Opinion for PCT/GB2019/050951.
Liu et al. 2017 "Abstract 3642: Tumor-antigen expression-dependent activation of the CD137 costimulatory pathway by bispecific DART proteins," American Association for Cancer Research 77(13) supplement Jul. 2017, pp. 1-4.
Rhodes et al. 2017 "Bicyclic Peptides as Next-Generation Therapeutics" Chemistry 23(52): 12690-12703.
"Bicycle Therapeutics Investor Presentation", Retrieved from: https://investors.bicycletherapeutics.com/static-files/f456c054-95c8-4e19-a62a-fcf5feb0650b, Aug. 2024, 61 pages.
Anonymous, "Bicycle Therapeutics 2023 R&D Day Deck", Retrieved from: https://investors.bicycletherapeutics.com/static-files/46599fde-67dc-40a8-9deb-10ed8444f3le, Dec. 14, 2023, 155 pages.
Anonymous, "Bicycle Therapeutics BT8009 Regulatory Update", Retrieved from: https://investors.bicycletherapeutics.com/static-files/265210c3-233f-4dd8-af32-d34592398d85, Sep. 11, 2023, 23 pages.
Bader et al., "Abstract 3088: Breaking from the paradigm of antibody-drug conjugates: Evaluation of clinical pharmacokinetics and safety of Bicycle Toxin Conjugates® (BTCs)", American Society of Clinical Oncology Annual Meeting, May 31-Jun. 4, 2024, pp. 1-9.
Baldini et al., "Abstract 498: BT8009-100: A Phase I/II Study of Novel Bicyclic Peptide and MMAE Conjugate BT8009 in Patients (pts) with Advanced Malignancies Associated with Nectin-4 Expression, Including Urothelial Cancer (UC)", ASCO Genitourinary (GU) Cancers Symposium Conference, Feb. 17, 2023, pp. 1-6.
Banerji et al., "A Cancer Research UK phase I/IIa trial of BT1718 (a first in class Bicycle Toxin Conjugate) given intravenously in patients with advanced solid tumours", ASCO, Jun. 5, 2018, pp. 1-4.
Banerji et al., "A Cancer Research UK phase I/IIa trial of BT1718 (a first in class Bicycle Toxin Conjugate) given intravenously in patients with advanced solid tumours", NCRI, Oct. 1, 2018, 1 page.
Battula et al., "Abstract 4613: A novel fully synthetic dual targeted EphA2/CD137 Bicycle® peptide induces tumor localized CD137 agonism", American Association of Cancer Research, Jun. 22, 2020, pp. 1-4.
Battula et al., "Abstract P794: A novel fully synthetic dual targeted EphA2/4-1BB Bicycle® peptide induces tumor localized 4-1BB agonism", SITC, Nov. 9, 2019, pp. 1-4.
Bendell et al., "TPS3655: BT5528-100 Phase I/II Study; Safety, Pharmacokinetics & Preliminary Clinical Activity of BT5528 in Patients with Advanced Malignancies Associated with EphA2 Expression", ASCO, May 29, 2020, 1 page.
Bennett et al., "Abstract 1167/2: Development of BT1718, a novel Bicycle Drug Conjugate for the treatment of lung cancer", American Association of Cancer Research, Apr. 1, 2017, pp. 1-4.
Bennett et al., "Abstract 164: BT5528, an EphA2-targeting Bicycle Toxin Conjugate (BTC): profound efficacy without bleeding and coagulation abnormalities in animal models", EORTC, Nov. 13, 2018, pp. 1-6.
Bennett et al., "Abstract 5854: BT5528, a Bicycle Toxin Conjugate (BTC) targeting EphA2 has potent antitumour activity without bleeding or coagulation abnormalities in animal models", American Association of Cancer Research, Apr. 14, 2018, pp. 1-6.
Bennett et al., "Abstract 5855: Bicycle Toxin Conjugates (BTCs) targeting EphA2 for the treatment of solid tumours: Discovery and selection of BT5528", American Association of Cancer Research, Apr. 14, 2018, pp. 1-8.
Bennett et al., "Abstract C066: BT5528, a Bicycle Toxin Conjugate targeting EphA2: mechanism of action and clinical translation", AACR-NCI-EORTC, Oct. 29, 2019, pp. 1-6.
Bennett, "Abstract 4481: BT5528, an EphA2-targeting Bicycle® Toxin Conjugate (BTC): Profound efficacy without bleeding and coagulation abnormalities in animal models", AACR Annual Meeting, Apr. 4, 2019, 11 pages.
Bennett, "Bicycle Conjugates to Target Solid Tumors", Next Generation Conjugates Summit, Feb. 27, 2023, 23 pages.
Bennett, "BT5528: A Bicycle Toxin Conjugate Targeting EphA2 for the Treatment of Solid Tumours", 9th Annual World ADC Conference, Mar. 6, 2019, 13 pages.
Bournakas et al., "PBP inhibitors discovered using a modified phage display platform (Bicycles)", ESCMID, Oct. 11, 2022, 1 page.
Brandish, "Bicycle Therapeutics: Precision-guided immune agonism for the treatment of cancer", Immuno UK meeting, Sep. 30, 2022, 25 pages.
Campbell et al., "Poster 1197: A multi tumor survey of Nectin-4 expression to guide BT8009 indication selection", American Association of Cancer Research, Apr. 12, 2021, pp. 1-4.
Campbell et al., "Poster 5300: A survey of EphA2 expression by immunohistochemistry (IHC) in tumor tissue microarrays (TMAs) to support BT5528 indication selection", American Association of Cancer Research, Jun. 22, 2020, pp. 1-6.
Carabateas et al., "Strong Analgesics, Some 1-Substituted 4-Phenyl-4-Propionoxypiperidines", Journal of Medicinal and Pharmaceutical Chemistry, Sep. 1962, 5:913-919.
CAS No. 18226-42-1, "1,3,5-Tris(bromomethyl)benzene", Chemical Book, Retrieved from: https://www.chemicalbook.com/ProductChemicalPropertiesCB0500171_EN.htm, 2023, 2 pages.

(56) References Cited

OTHER PUBLICATIONS

Chen et al., "Abstract A8: Novel Multimers of Bicyclic Peptides Cluster and Activate CD137 (4-1BB): A Costimulatory T -Cell Checkpoint Receptor", PEGS, Nov. 12, 2018, pp. 1-7.
Cohen et al., "Abstract 2: Quantitation of CD137 and Nectin-4 expression across multiple tumor types to support indication selection for BT7480, a Bicycle tumor-targeted immune cell agonist™ (Bicycle TICA™)", SITC, Nov. 12, 2021, pp. 1-7.
Cohen et al., "Abstract 5555: Development of a CD137 receptor occupancy assay to support the phase I/II study of BT7480, a Bicycle® tumor-targeted immune cell agonist (Bicycle TICA™)", American Association of Cancer Research, Apr. 8, 2022, pp. 1-6.
Cohen et al., "Abstract A65: Development of a CD137 receptor occupancy assay to support the phase I/II study of BT7480, a Bicycle tumor-targeted immune cell agonist® (Bicycle TICA®)", AACR-BC-EORTC, Oct. 26, 2022, pp. 1-7.
Cohen, "Translating preclinical findings into clinical biomarker assays to support the Phase I/II study of BT7480, a Bicycle tumor-targeted immune cell agonist®", World Clinical Biomarkers & CDx Summit, Sep. 28, 2022, 21 pages.
Cohen, "Turning preclinical findings into clinic-ready biomarker assays to support BT7480 development", Markets and Markets Biomarker and Companion Diagnostics Conference, Feb. 15, 2023, 21 pages.
Cook et al., "Abstract 5764: Pharmacokinetic (PK) assessment of BT1718 : A phase 1/2a study of BT1718, a first in class bicycle toxin conjugate (BTC), in patients with advanced solid tumours", EMSO, Sep. 28, 2019, pp. 1-4.
Cooke, "Bicycles as precision guided therapeutics", UK Symposium: Advancing Drug Discovery for Oncology, Mar. 13, 2023, 15 pages.
Dufort et al., "Abstract 1340: Modulation of the natural killer cell immune response to tumor with a synthetic tumor-immune cell agonist, NK-TICA®", American Association for Cancer Research Annual Meeting, Apr. 8, 2024, pp. 1-6.
Dufort et al., "Abstract 15699: Generation of a Bicycle NK-TICA™, a novel NK cell engaging molecule designed to induce targeted tumor cytotoxicity", SITC, Nov. 12, 2022, pp. 1-5.
Dufort et al., Abstract 1806: Modulation of the natural killer (NK) cell immune response to tumor with novel synthetic tumor-immune cell agonist, NK-TICA™ American Association for Cancer Research Annual Meeting, Apr. 17, 2023, pp. 1-7.
Dufort et al., "Abstract 4233: Generation of a Bicycle NK-TICA™, a novel NK cell engaging molecule designed to induce targeted tumor cytotoxicity", American Association for Cancer Research, Apr. 8, 2022, pp. 1-5.
Dufort, "Bicycles: Bispecific, Precision-guided NK Cell Activators for the Treatment of Solid Tumors", Innate Killer Summit, Mar. 29, 2023, 23 pages.
Eder et al., "Bicyclic Peptides as a New Modality for Imaging and Targeting of Proteins Overexpressed by Tumors", Cancer Res., Feb. 15, 2019, 79(4):841-852.
Evans et al., "Abstract CT253: Phase 1/2 study of the safety, pharmacokinetics, and preliminary clinical activity of BT7480 in patients with Nectin-4 associated advanced malignancies", American Association for Cancer Research Annual Meeting, Apr. 18, 2023, pp. 1-5.
Frigerio, "Expanding the Potential of ADCs: Bicyclic Peptide (Bicycle®) Toxin Conjugates May Offer Advancements Over Traditional ADCs", World ADC, Mar. 20, 2023, 28 pages.
Frigerio, "Targeting Tumors with Bicycle Conjugates", PEGS Boston, May 17, 2023, 31 pages.
Gelb et al., "Abstract A047:MT1-MMP Immunohistochemistry (IHC) analysis of tumor microarrays (TMAs) using a novel scoring system guides patient selection for BT1718 expansion cohorts", AACR-NCI-EORTC, Oct. 27, 2019, pp. 1-7.
GenBank Accession No. CZR33441.1, "uncharacterized protein FPRO_01747 [Fusariumn proliferatum ET1]", National Center for Biotechnology Information, Retrieved from: https://www.ncbi.nlm.nih.gov/protein/1111492376, Dec. 6, 2016, 1 page.
Hadjicharalambous et al., "Investigating Penetration and Antimicrobial Activity of Vector Bicycle Conjugates", ACS Infectious Diseases, Jun. 12, 2024, 10(7):2381-2389.
Harrison et al., "Abstract 5144: BT1718, a novel bicyclic peptide-maytansinoid conjugate targeting MT1-MMP for the treatment of solid tumours: Design of bicyclic peptide and linker selection", AACR Annual meeting, Apr. 1, 2017, pp. 1-7.
Harrison et al., "Discovery and development of BT1718, a novel bicyclic peptidemaytansinoid conjugate targeting MT1-MMP for the treatment of solid tumours: In vitro and in vivo activities", PEGS, Apr. 30, 2017, 1 page.
Hu et al., "Lessons Learned from Molecular Scaffold Analysis", Journal of Chemical Information and Modeling, 2011, 51(8):1742-1753.
Hurov et al., "Abstract 1340: BT7455, a fully synthetic Bicycle tumor-targeted immune cell agonist®, leads to potent EphA2-dependent CD137 agonism and robust anti-tumor efficacy", SITC, Nov. 10, 2022, pp. 1-6.
Hurov et al., "Abstract 3257: Activation of 4-1BB using multivalent and tumour targeted bicyclic peptides", American Association of Cancer Research, Apr. 2, 2019, pp. 1-4.
Hurov et al., "Abstract 700: EphA2/CD137 Bicycle® tumor-targeted immune cell agonists (TICAs™) induce tumor regressions, immunogenic memory, and reprogramming of the tumor immune microenvironment", SITC, Nov. 9, 2020, pp. 1-4.
Hurov et al., "Abstract P398: Activation of the T cell costimulatory protein CD137 using multivalent bicyclic peptides", SITC, Nov. 6, 2018, pp. 1-5.
Hurov et al., "Abstract P782: A novel fully synthetic dual targeted Nectin-4/4-1BB Bicycle® peptide induces tumor localized 4-1BB agonism", SITC, Nov. 9, 2019, pp. 1-6.
Hurov et al., "BT7480, a novel fully synthetic Bicycle tumor-targeted immune cell agonist™ (Bicycle TICA™) induces tumor localized CD137 agonism", Journal for Immuno Therapy of Cancer, 2021, 9(11):e002883, pp. 1-13.
Hurov et al., "Poster 1728: Nectin-4-dependent immune cell stimulation and anti-tumor efficacy by BT7480, a Nectin-4/CD137 Bicycle® tumor-targeted immune cell agonist (TICA™)", American Association of Cancer Research, Apr. 12, 2021, pp. 1-6.
Hurov, "BT7480, a novel and fully synthetic Bicycle tumor-targeted immune cell agonist®", Festival of Biologics, Nov. 4, 2022, 23 pages.
Kanakia et al., "Development of CD137 (4-1BB) receptor occupancy assay using fluorescently labeled Bicycles®", AACR Tumor Immunology & Immunotherapy, Oct. 19, 2020, 5 pages.
Keen, "A novel fully synthetic dual targeted Nectin-4/4-1BB Bicycle® peptide induces tumor localized 4-1BB agonism", SITC, Nov. 6-10, 2019, 19 pages.
Keen, "BT5528, an EphA2-targeting Bicycle® Toxin Conjugate", World ADC congress, Oct. 11, 2019, 24 pages.
Keen, "BT7480, a novel Nectin-4 dependent agonist of the immune cell costimulatory receptor CD137", AACR Annual Meeting, Apr. 10-15 and May 17-21, 2021, 23 pages.
Kristensson et al., "Novel Bicyclic Peptide Multimers Activate T Cell Costimulatory Protein CD137", ELRIG Drug Discovery, Oct. 9, 2018, pp. 1-7.
Kristensson et al., "Novel Bicyclic Peptide Multimers Activate T Cell Costimulatory Protein CD137", Promega Biologics, Jul. 18, 2018, pp. 1-7.
Kumara et al., "Fusarium proliferatum, an endophytic fungus from Dysoxylum binectariferum Hook.f, produces rohitukine, a chromane alkaloid possessing anti-cancer activity", Antonie van Leeuwenhoek, 2012, 101(2):323-329.
Lahdenranta et al., "Abstract 1356: Transcriptional profiling of Bicycle® tumor-targeted CD137 agonist-treated mouse tumors revealed an early and rapid activation of myeloid cells followed by infiltration of cytotoxic T cells into the tumor", SITC, Nov. 10, 2022, pp. 1-9.
Lahdenranta et al., "Abstract 5301: Tumor-targeted activation of CD137 using Bicycle® molecules: New insights into mechanism of action and discovery of BT7455, a clinical candidate for the treatment of EphA2-expressing cancers", American Association for Cancer Research Annual Meeting, Apr. 9, 2024, pp. 1-5.

(56) References Cited

OTHER PUBLICATIONS

Lahdenranta et al., "Abstract A067: BT7480, a synthetic Bicycle tumor-targeted immune cell agonist® (Bicycle TICA®), induces reprogramming of the tumor immune microenvironment through tumor localized CD137 agonism", CICON, Sep. 29, 2022, pp. 1-9.
Lahdenranta et al., "Poster 1319: Rapid accumulation of cytotoxic payload in tumor tissue drives BT5528 activity in tumor models", American Association of Cancer Research, Apr. 12, 2021, pp. 1-4.
Lahdenranta et al., "Poster 1724: Microinjection of Nectin-4/CD137 tumor-targeted immune cell agonist (TICA™) activates the local tumor microenvironment", American Association of Cancer Research, Apr. 12, 2021, pp. 1-4.
Lahdenranta et al., "Poster 706: BT7480, a fully synthetic tumor-targeted immune cell agonist (TICA™) induces tumor localized CD137 agonism and modulation of tumor immune microenvironment", SITC, Nov. 9, 2020, pp. 1-6.
Loriot et al., "Abstract TPS4619: A phase 2/3 study of Bicycle® Toxin Conjugate zelenectide pevedotin (BT8009) targeting Nectin-4 in patients with locally advanced or metastatic urothelial cancer (1a/mUC) (Duravelo-2)", American Society of Clinical Oncology Annual Meeting, May 31-Jun. 4, 2024, 1 page.
Ludbrook, "Bicycle Toxin Conjugates to Target Solid Tumors", 3rd ADC Target Selection Summit, Dec. 6, 2023, 20 pages.
Luus et al., "Abstract 1832: EphA2-dependent CD137 agonism and anti-tumor efficacy by BT7455, a Bicycle tumor-targeted immune cell agonist®", American Association for Cancer Research Annual Meeting, Apr. 17, 2023, pp. 1-7.
McDonnell, "Bicycles for precision guided delivery", Boulder Peptide Symposium, Nov. 9, 2022, 29 pages.
McKean et al., "A Combined Phase I/II Study of BT8009 a Novel Bicycle® Toxin Conjugate with MMAE in Patients with Advanced Malignancies with Nectin-4", ASCO, Jun. 4, 2021, 1 page.
McKean et al., "BT8009-100 Phase I/II Study of Novel Bicyclic Peptide and MMAE Conjugate BT8009 in Patients with Advanced Malignancies Associated with Nectin-4 Expression", American Association for Cancer Research, Apr. 8-13, 2022, 17 pages.
McKean et al., "BT8009-100 Phase I/II Study of the Safety, Pharmacokinetics, & Preliminary Clinical Activity of BT8009 in Patients with Nectin-4 Expressing Advanced Malignancies", ESMO, Sep. 17, 2020, 1 page.
McKean, "A first in class phase I/II study of the novel bicyclic peptide and MMAE conjugate, BT5528, in patients with advanced malignancies associated with EphA2 expression", AACR-NCI-EORTC, Oct. 7-10, 2021, 19 pages.
Mistry et al., "Abstract 15523: Establishing the preclinical/translational PK/PD relationship for BT7480, a Nectin4/CD137 Bicycle tumor-targeted immune cell agonist™ (Bicycle TICA™)", SITC, Nov. 12, 2021, pp. 1-5.
Mistry et al., "Synthesis of Bicycle® Peptides using Gold-mediated Cysteine Arylation", European Peptide Synthesis Conference, Mar. 7, 2023, 1 page.
Mudd et al., "Bicyclic Peptides for Positron Emission Tomography (PET) Imaging of MT1-MMP Expressing tumours", PEGS, Apr. 30, 2017, 1 page.
Mudd et al., "Discovery of BT8009: A Nectin-4 Targeting Bicycle Toxin Conjugate for the Treatment of Cancer", Journal of Medicinal Chemistry, 2022, 65(21): 14261-14970.
Mudd et al., "Gold-Mediated Multiple Cysteine Arylation for the Construction of Highly Constrained Bicycle Peptides", Bioconjugate Chemistry, 2022, 33(8):1441-1445.
Mudd et al., "Potent anti-tumor activity of a Lead-212 labelled MT1-MMP targeting Bicycle Radionuclide ConjugateTM", TIDES USA—Oligonucleotide, May 8, 2023, pp. 1-7.
Newman et al., "Anti-Infectives Drug Discovery at Bicycle Therapeutics", ESCMID, Oct. 11, 2022, 1 page.
Newman, "Characterisation of novel, noncovalent cyclic peptide (Bicycles®) inhibitors of PBP3s from important Gram-negative pathogens", ESCMID, Oct. 11, 2022, 18 pages.
Ngo et al., "Abstract 333: Activity of the erythropoietin-producing hepatocellular A2 receptor (EphA2) targeting Bicycle® Toxin Conjugate (BTC™) BCY6033 in EGFR inhibitor resistant non-small cell lung cancer (NSCLC) patient derived xenografts", American Association for Cancer Research, Apr. 8, 2022, pp. 1-6.
Papadopoulos et al., "Abstract TPS2689: A Combined Phase I/II Study of a Novel Bicycle Tumor-targeted Immune Cell Agonist® BT7480 in Patients with Nectin-4 Associated Advanced Malignancies", ASCO, Jun. 6, 2022, 1 page.
Park et al., "Abstract 3756: Small Synthetic, Multivalent Bicyclic Peptides That Activate T Cell Costimulatory Protein CD137", American Association of Cancer Research, Apr. 14, 2018, pp. 1-9.
Park et al., "Abstract 3756: Small Synthetic, Multivalent Bicyclic Peptides That Activate T Cell Costimulatory Protein CD137", Cancer Res., Jul. 1, 2018, 78(13_Supplement):3756, 2 pages.
Park et al., "Abstract 3756: Small Synthetic, Multivalent Bicyclic Peptides That Activate T Cell Costimulatory Protein CD137", ELRIG Drug Discovery, Oct. 9, 2018, pp. 1-9.
Repash et al., "BT7480, a novel fully synthetic tumor-targeted immune cell agonist (TICA™) induces tumor localized CD137 agonism", AACR Tumor Immunology & Immunotherapy, Oct. 19, 2020, 10 pages.
Rezvaya et al., "Abstract 1207: NKp46 engaging Bicycle NK-TICA® drives tumor targeted cytotoxicity", SITC, Nov. 10, 2022, 1 page.
Rhodes et al., "Bicyclic Peptides as Next-Generation Therapeutics", Chemistry—A European Journal, 2017, 23(52):12690-12703.
Rietschoten et al., "Abstract 268: Small Synthetic, Multivalent Bicyclic Peptides That Activate T Cell Costimulatory Protein CD137", 35th European Peptide Symposium, Aug. 1, 2018, 1 page.
Rigby et al., "Abstract 4479: BT8009: A bicyclic peptide toxin conjugate targeting Nectin-4 (PVRL4) displays efficacy in preclinical tumor models", Cancer Res, 2019, 79(13_Supplement):4479, 3 pages.
Rigby et al., "Abstract C061: BT8009, a Bicycle® Toxin Conjugate targeting Nectin-4, shows target selectivity, and efficacy in preclinical large and small tumor models", AACR-NCI-EORTC, Oct. 29, 2019, pp. 1-9.
Rigby et al., "BT8009; A Nectin-4 Targeting Bicycle® Toxin Conjugate for Treatment of Solid Tumors", Molecular Cancer Therapeutics, 2022, 21(12):1-27.
Rigby, "Abstract 4479: BT8009: A bicyclic peptide toxin conjugate targeting Nectin-4 (PVRL4) displays efficacy in preclinical tumour models", AACR Annual Meeting, Apr. 2, 2019, 10 pages.
Santos et al., "Abstract 35472: Characterization of Nectin-4 protein expression in non-small cell lung cancer patients", AACR-BC-EORTC, Oct. 13, 2023, pp. 1-4.
Shah et al., "Abstract A28: Establishment of an ex vivo tissue culture platform as a preclinical model to assess the mechanism of action of Bicycle® tumor-targeted immune cell agonists in NSCLC", AACR-BC-EORTC, Oct. 26, 2022, pp. 1-8.
Singh et al., "Protein Engineering Approaches in the Post-Genomic Era", Current Protein and Peptide Science, 2017, 18(4):1-11.
Skynner et al., "BT1718, a novel Bicycle Drug Conjugate® shows potent anti-tumor activity in diverse cell-derived and patient-derived tumor xenograft models", PEGS, Apr. 30, 2017, 1 page.
Stanczuk et al., "Abstract 1388: Utility of humanized animal models for in vivo evaluation of NK-TICA®, novel Bicycle® tumor-targeted immune cell agonist® (Bicycle TICA®) designed to engage NK cells", SITC, Nov. 10, 2022, pp. 1-6.
Stanczuk et al., "Abstract 1826: Development of in vivo models for evaluation of NK-TICATM, novel Bicycle® tumortargeted immune cell agonist® designed to engage NK cells", American Association for Cancer Research Annual Meeting, Apr. 17, 2023, pp. 1-6.
Su, "Key DMPK Attributes of BT7480, a Bicycle Tumor-targeted Immune Cell AgonistTM Targeting Nectin-4 and Agonizing CD137", NEDMDG symposium, May 31, 2023, 20 pages.
Teufel et al., "Abstract 4920: Bicyclic Peptides for Positron Emission Tomography (PET) Imaging of MT1-MMP Expressing Tumors", American Association of Cancer Research, Apr. 1, 2017, pp. 1-8.
Tiberghien, "Highlighting the Potential of Bicycle Conjugates to Target Solid Tumours", World ADC, Mar. 20, 2023, 24 pages.
Uhlenbroich et al., "Abstract 0000: NKp46 engaging Bicycle NK-TICA™ drives tumor targeted cytotoxicity", PEGS Boston, May 17, 2023, 1 page.

(56) References Cited

OTHER PUBLICATIONS

Uhlenbroich, "Bicycles—a modality for Tumor-Targeted Immune Cell Agonism", Antibody Engineering & Therapeutics, Jun. 12, 2023, 23 pages.
Upadhyaya et al., "Abstract 888: An integrative approach to optimize a synthetic EphA2-dependent CD137 agonist: Balancing potency, physiochemical properties, and pharmacokinetics to achieve robust anti-tumor activity", SITC, Nov. 12, 2021, pp. 1-7.
Upadhyaya et al., "Anticancer immunity induced by a synthetic tumor-targeted CD137 agonist", Journal for Immunotherapy of Cancer, 2021, 9(1):e001762, pp. 1-10.
Upadhyaya et al., "Discovery and Optimization of a Synthetic Class of Nectin-4-Targeted CD137 Agonists for Immuno-oncology", Molecular Cancer Therapeutics, 2022, 65:9858-9872.
Upadhyaya, "Activation of CD137 using multivalent and tumour targeted bicyclic peptides", Peptide Congress, Retrieved from: https://www.bicycletherapeutics.com/wp-content/uploads/PU_2019-Peptide-Congress_publication.pdf, Apr. 2019, 25 pages.
Valko et al., "Application of biomimetic HPLC to estimate lipophilicity, protein and phospholipid binding of potential peptide therapeutics", ADMET and DMPK, 2018, 6(2):162-175.
Wagstaff et al., "An Assay for Periplasm Entry Advances the Development of Chimeric Peptide Antibiotics", ACS Infectious Diseases, 2020, 6(9):2355-2361.
Wallack et al., "Abstract P05: Investigating soluble Nectin-4 and EphA2 as cancer biomarkers in plasma", Bio-IT World, May 23, 2023, pp. 1-6.
Walsh et al., "Abstract 5807: Bicycle Toxin Conjugates® for the treatment of solid tumors", American Association for Cancer Research Annual Meeting, Apr. 9, 2024, pp. 1-7.
Wang et al., "Comprehensive Surfaceome Profiling to Identify and Validate Novel Cell-Surface Targets in Osteosarcoma", Molecular Cancer Therapeutics, Jun. 2022, 21(6):903-913.
Wang et al., "Integrative surfaceome profiling identifies immunotherapeutic targets in osteosarcoma and preclinical testing of BT1769, an MT1-MMP-targeted Bicycle® toxin conjugate, in osteosarcoma by the Pediatric Preclinical Testing Consortium (PPTC)", AACR Annual Meeting, Apr. 10-15 and May 17-21, 2021, 15 pages.
Xu et al., "The application of PK/PD modelling in the clinical development of BT5528—a novel toxin delivery platform", ACoP, Oct. 30-Nov. 2, 2022, 21 pages.
Zhang et al., "Propagated Perturbations from a Peripheral Mutation Show Interactions Supporting WW Domain Thermostability", Structure, Nov. 6, 2018, 26(11):1474-1485.
U.S. Appl. No. 18/427,414, Beswick et al., filed Jan. 30, 2024.
U.S. Appl. No. 18/742,691, Chen, filed Jun. 13, 2024.
U.S. Appl. No. 18/906,616, Beswick et al., filed Oct. 4, 2024.
Bicycle Therapuetics, Press Release: Bicycle Therapeutics to Present New BT1718 Data in the "New Drugs on the Horizon" Session at the 2018 American Association for Cancer Research Meeting. Apr. 3, 2018. Retrieved from: https://bicycletherapeutics.gcs-web.com/news-releases/news-release-details/bicycle-therapeutics-present-new-bt1718-data-new-drugs-horizon. 2 pages.
Van Rietschoten et al., Abstract 268: Small Synthetic, Multivalent Bicyclic Peptides That Activate T Cell Costimulatory Protein CD137. 35th European Peptide Symposium. Aug. 31, 2018. Retrieved from: https://www.bicycletherapeutics.com/wp-content/uploads/2022/06/8_35th-European-Peptide-symposium_CD137_31-08-2018.pdf. 1 page.

* cited by examiner

CD137 binder
(C-terminal

Peg12

EphA2 binder
(BCY6196 = 6099 peptide sequence— Sar10
spacer, N-terminal linkage)

A.

B.

D.

C.

| Patient ID: | 110003580 | 110006863 | 110003345 |
|---|---|---|---|
| % CD137+ T cells | 19.8 | 30.0 | 15.1 |
| % Nectin-4+ cells | 4.4 | 15.1 | 25.8 |

E.

BCY00009173

BCY00007985

BCY00008942

BCY00008943

BCY00009658

BCY00009659

BCY00010568

BCY00010570

BCY00010577

BCY00009407

BCY00010000

BCY00010567

BCY00010569

BCY00010571

BCY00010572

BCY00010573

BCY00010578

BCY00011373

BCY00011374

BCY00011375

BCY00011616

BCY00011617

BCY00011857

BCY00011858

BCY00011859

BCY00010580

BCY00010581

BCY00011017

BCY00011018

BCY00011019

BCY00011376

BCY00011377

BCY00011378

BCY00011379

BCY00011380

BCY00011381

HETEROTANDEM BICYCLIC PEPTIDE COMPLEXES

CROSS-REFERENCE TO RELATED APPLICATIONS

This application is a divisional of U.S. application Ser. No. 16/372,692, filed Apr. 2, 2019, which claims benefit of GB 1805492.4, filed Apr. 4, 2018, and GB 1820981.7, filed Dec. 21, 2018.

FIELD OF THE INVENTION

The present invention relates to heterotandem bicyclic peptide complexes which comprise a first peptide ligand, which binds to a component present on an immune cell, conjugated via a linker to a second peptide ligand, which binds to a component present on a cancer cell. The invention also relates to the use of said heterotandem bicyclic peptide complexes in preventing, suppressing or treating cancer.

SEQUENCE SUBMISSION

The present application is being filed along with a Sequence Listing in electronic format. The Sequence Listing is entitled “190883_SL”, which was created on May 11, 2022, and is 6,544 bytes in size. The information in the electronic format of the Sequence Listing is part of the present application and is incorporated herein by reference in its entirety.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu et al. (2007), Science 330, 1066-71), a cyclic peptide with the Arg-Gly-Asp motif binding to integrin αVb3 (355 $Å^2$) (Xiong et al. (2002), Science 296 (5565), 151-5) or the cyclic peptide inhibitor upain-1 binding to urokinase-type plasminogen activator (603 $Å^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-$(Xaa)_6$-Cys-$(Xaa)_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a heterotandem bicyclic peptide complex comprising:

(a) a first peptide ligand which binds to a component present on an immune cell; conjugated via a linker to (b) a second peptide ligand which binds to a component present on a cancer cell; wherein each of said peptide ligands comprise a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

According to a further aspect of the invention, there is provided a pharmaceutical composition comprising a heterotandem bicyclic peptide complex as defined herein in combination with one or more pharmaceutically acceptable excipients.

According to a further aspect of the invention, there is provided a heterotandem bicyclic peptide complex as defined herein for use in preventing, suppressing or treating cancer.

DETAILED DESCRIPTION OF THE INVENTION

Figure 1:
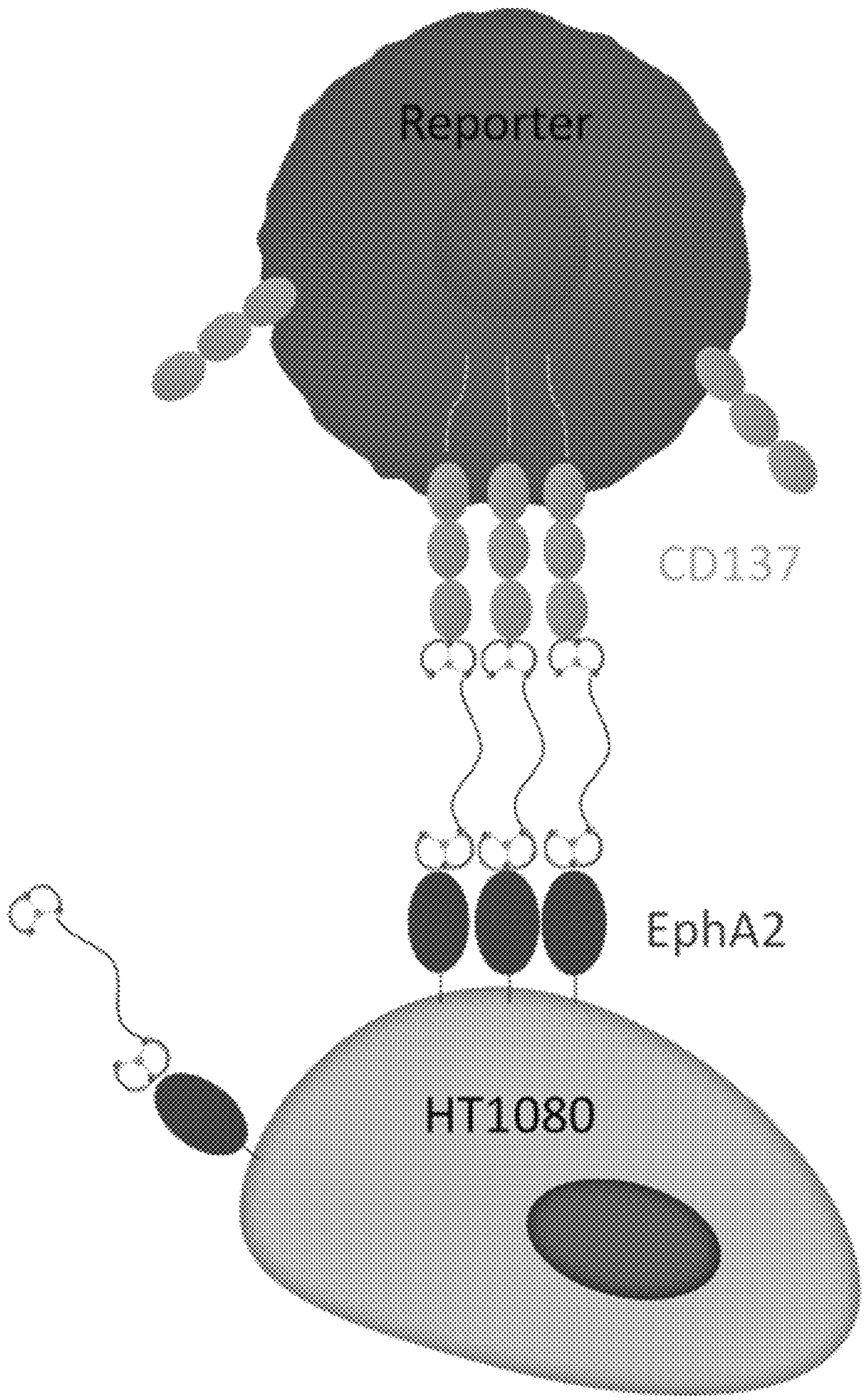
FIG. 1: Schematic representation of a heterotandem bicyclic peptide complex comprising an EphA2 and CD137 peptide ligand binding to both an immune cell and a cancer cell.

According to a first aspect of the invention, there is provided a heterotandem bicyclic peptide complex comprising:

(a) a first peptide ligand which binds to a component present on an immune cell; conjugated via a linker to (b) a second peptide ligand which binds to a component present on a cancer cell; wherein each of said peptide ligands comprise a polypeptide comprising at least three cysteine residues, separated by at least two loop sequences, and a molecular scaffold which forms covalent bonds with the cysteine residues of the polypeptide such that at least two polypeptide loops are formed on the molecular scaffold.

First Peptide Ligands

References herein to the term "immune cell" includes any cell within the immune system. Suitable examples include white blood cells, such as lymphocytes (e.g. T lymphocytes or T cells, B cells or natural killer cells). In one embodiment, the T cell is CD8 or CD4. In a further embodiment, the T cell is CD8. Other examples of immune cells include dendritic cells, follicular dendritic cells and granulocytes.

In one embodiment, the component present on an immune cell is CD137.

CD137 is a member of the tumour necrosis factor (TNF) receptor family. Its alternative names are tumour necrosis factor receptor superfamily member 9 (TNFRSF9), 4-IBB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice.

CD137 is a T-cell costimulatory receptor induced on TCR activation (Nam et al., Curr. Cancer Drug Targets, 5:357-363 (2005); Waits et al., Annu. Rev, Immunol., 23:23-68 (2005)).

In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et d-I., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun NH2-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

In one embodiment, the first peptide ligand comprises a CD137 binding bicyclic peptide ligand.

Suitable examples of CD137 binding bicyclic peptide ligands are disclosed in GB Patent Application Nos. 1712589.9 and 1802934.8, the peptides of which are incorporated herein by reference.

In one embodiment, the CD137 binding bicyclic peptide ligand comprises an amino acid sequence:
10);

(SEQ ID NO: 1)
$C_i$IEEGQY$C_{ii}$FADPY[Nle]$C_{iii}$;

(SEQ ID NO: 3)
$C_i$[tBuAla]PE[D-Ala]PY$C_{ii}$FADPY[Nle]$C_{iii}$;

(SEQ ID NO: 4)
$C_i$IEEGQY$C_{ii}$F[D-Ala]DPY[Nle]$C_{iii}$;

(SEQ ID NO: 5)
$C_i$[tBuAla]PK[D-Ala]PY$C_{ii}$FADPY[Nle]$C_{iii}$;

(SEQ ID NO: 6)
$C_i$[tBuAla]PE[D-Lys]PY$C_{ii}$FADPY[Nle]$C_{iii}$;

(SEQ ID NO: 7)
$C_i$[tBuAla]P[K(PYA)][D-Ala]PY$C_{ii}$FADPY[Nle]$C_{iii}$;

(SEQ ID NO: 8)
$C_i$[tBuAla]PE[D-Lys(PYA)]PY$C_{ii}$FADPY[Nle]$C_{iii}$;

-continued (SEQ ID NO: 9)
$C_i$IEE[D-Lys(PYA)]QY$C_{ii}$FADPY(Nle)$C_{iii}$;
and (SEQ ID NO: 10)
[d$C_i$][dI][dE][dE][K(PYA)][dQ][dY][d$C_{ii}$][dF][dA][dD][dP][dY][dNle][d$C_{iii}$];

wherein $C_i$, $C_{ii}$ and $C_{iii}$ represent first, second and third cysteine residues, respectively, Nle represents norleucine, tBuAla represents t-butyl-alanine, PYA represents 4-pentynoic acid, or a pharmaceutically acceptable salt thereof.

In one particular embodiment which may be mentioned, the CD137 binding bicyclic peptide ligand comprises an amino acid sequence:

(SEQ ID NO: 1)
$C_i$IEEGQY$C_{ii}$FADPY[Nle]$C_{iii}$;

wherein $C_i$, $C_{ii}$ and $C_{iii}$ represent first, second and third cysteine residues, respectively, Nle represents norleucine, or a pharmaceutically acceptable salt thereof.

In a further embodiment, the CD137 binding bicyclic peptide ligand comprises N- and C-terminal modifications and comprises:

Ac-A-(SEQ ID NO: 1)-Dap
(hereinafter referred to as BCY7732);

Ac-A-(SEQ ID NO: 1)-Dap(PYA)
(hereinafter referred to as BCY7741);

Ac-(SEQ ID NO: 3)-Dap
(hereinafter referred to as BCY9172);

Ac-(SEQ ID NO: 3)-Dap(PYA)
(hereinafter referred to as BCY11014);

Ac-A-(SEQ ID NO: 4)-Dap
(hereinafter referred to as BCY8045);

Ac-(SEQ ID NO: 5)-A
(hereinafter referred to as BCY8919);

Ac-(SEQ ID NO: 6)-A
(hereinafter referred to as BCY8920);

Ac-(SEQ ID NO: 7)-A
(hereinafter referred to as BCY8927);

Ac-(SEQ ID NO: 8)-A
(hereinafter referred to as BCY8928);

Ac-A-(SEQ ID NO: 9)-A
(hereinafter referred to as BCY7744);
and

Ac-[dA]-(SEQ ID NO: 10)-[dA]-$NH_2$
(hereinafter referred to as BCY11506);

wherein Ac represents an acetyl group, Dap represents diaminopropionic acid and PYA represents 4-pentynoic acid, or a pharmaceutically acceptable salt thereof.

In a further embodiment which may be mentioned, the CD137 binding bicyclic peptide ligand comprises N- and C-terminal modifications and comprises:

Ac-A-(SEQ ID NO: 1)-Dap (hereinafter referred to as BCY7732);

wherein Ac represents an acetyl group and Dap represents diaminopropionic acid, or a pharmaceutically acceptable salt thereof.

Second Peptide Ligands

References herein to the term "cancer cell" includes any cell which is known to be involved in cancer. Cancer cells are created when the genes responsible for regulating cell division are damaged. Carcinogenesis is caused by mutation and epimutation of the genetic material of normal cells, which upsets the normal balance between proliferation and cell death. This results in uncontrolled cell division and the evolution of those cells by natural selection in the body. The uncontrolled and often rapid proliferation of cells can lead to benign or malignant tumours (cancer). Benign tumors do not spread to other parts of the body or invade other tissues. Malignant tumors can invade other organs, spread to distant locations (metastasis) and become life-threatening.

In one embodiment, the cancer cell is selected from an HT1080, SC—OV-3, PC3, H1376, NCI-H292, LnCap, MC38, 4T1-D02 and RKO tumor cell.

In one embodiment, the component present on a cancer cell is EphA2.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

In one embodiment, the second peptide ligand comprises an EphA2 binding bicyclic peptide ligand.

Suitable examples of EphA2 binding bicyclic peptide ligands are disclosed in GB Patent Application Nos. 1721259.8 and 1804102.0, the peptides of which are incorporated herein by reference.

In one embodiment, the EphA2 binding bicyclic peptide ligand comprises an amino acid sequence:

(SEQ ID NO: 2)
$C_i$[HyP]LVNPL$C_{ii}$LHP[dD]W[HArg]$C_{iii}$;
and (SEQ ID NO: 11)
$C_i$LWDPTP$C_{ii}$ANLHL[HArg]$C_{iii}$;

wherein $C_i$, $C_{ii}$ and $C_{iii}$ represent first, second and third cysteine residues, respectively, HyP represents hydroxyproline, dD represents aspartic acid in D-configuration and HArg represents homoarginine, or a pharmaceutically acceptable salt thereof.

In one embodiment which may be mentioned, the EphA2 binding bicyclic peptide ligand comprises an amino acid sequence:

(SEQ ID NO: 2)
$C_i$[HyP]LVNPL$C_{ii}$LHP[dD]W[HArg]$C_{iii}$;

wherein $C_i$, $C_{ii}$ and $C_{iii}$ represent first, second and third cysteine residues, respectively, HyP represents hydroxyproline, dD represents aspartic acid in D-configuration and HArg represents homoarginine, or a pharmaceutically acceptable salt thereof.

In a further embodiment, the EphA2 binding bicyclic peptide ligand comprises N-terminal modifications and comprises:

A-HArg-D-(SEQ ID NO: 2) (hereinafter referred to as BCY9594);

[B-Ala]-[$Sar_{10}$]-A-[HArg]-D-(SEQ ID NO: 2) (hereinafter referred to as BCY6099);

[PYA]-[B-Ala]-[$Sar_{10}$]-A-[HArg]-D-(SEQ ID NO: 2) (hereinafter referred to asBCY6169);
and

[PYA]-[B-Ala]-[$Sar_{10}$]-VGP-(SEQ ID NO: 11) (hereinafter referred to as BCY8941);

wherein HArg represents homoarginine, PYA represents 4-pentynoic acid, $Sar_{10}$ represents 10 sarcosine units, B-Ala represents beta-alanine, or a pharmaceutically acceptable salt thereof.

In a further embodiment which may be mentioned, the EphA2 binding bicyclic peptide ligand comprises N-terminal modifications and comprises:

```
A-HArg-D-(SEQ ID NO: 2) (hereinafter referred to
as BCY9594).
```

wherein HArg represents homoarginine, or a pharmaceutically acceptable salt thereof.

In an alternative embodiment, the component present on a cancer cell is PD-1.

Programmed cell death 1 ligand 1 (PD-L1) is a 290 amino acid type I transmembrane protein encoded by the CD274 gene on mouse chromosome 19 and human chromosome 9. PD-L1 expression is involved in evasion of immune responses involved in chronic infection, e.g., chronic viral infection (including, for example, HIV, HBV, HCV and HTLV, among others), chronic bacterial infection (including, for example, *Helicobacter pylori*, among others), and chronic parasitic infection (including, for example, *Schistosoma mansoni*). PD-L1 expression has been detected in a number of tissues and cell types including T-cells, B-cells, macrophages, dendritic cells, and nonhaematopoietic cells including endothelial cells, hepatocytes, muscle cells, and placenta.

PD-L1 expression is also involved in suppression of anti-tumour immune activity. Tumours express antigens that can be recognised by host T-cells, but immunologic clearance of tumours is rare. Part of this failure is due to immune suppression by the tumour microenvironment. PD-L1 expression on many tumours is a component of this suppressive milieu and acts in concert with other immunosuppressive signals. PD-L1 expression has been shown in situ on a wide variety of solid tumours including breast, lung, colon, ovarian, melanoma, bladder, liver, salivary, stomach, gliomas, thyroid, thymic epithelial, head, and neck (Brown J A et al. 2003 Immunol. 170:1257-66; Dong H et al. 2002 Nat. Med. 8:793-800; Hamanishi J, et al. 2007 Proc. Natl. Acad. Sci. USA 104:3360-65; Strome S E et al. 2003 Cancer Res. 63:6501-5; Inman B A et al. 2007 Cancer 109:1499-505; Konishi J et al. 2004 Clin. Cancer Res. 10:5094-100; Nakanishi J et al. 2007 Cancer Immunol. Immunother. 56:1173-82; Nomi T et al. 2007 Clin. Cancer Res. 13:2151-57; Thompson R H et al. 2004 Proc. Natl. Acad. Sci. USA 101: 17174-79; Wu C et al. 2006 Acta Histochem. 108:19-24). In addition, the expression of the receptor for PD-L1, Programmed cell death protein 1 (also known as PD-1 and CD279) is upregulated on tumour infiltrating lymphocytes, and this also contributes to tumour immunosuppression (Blank C et al. 2003 Immunol. 171:4574-81). Most importantly, studies relating PD-L1 expression on tumours to disease outcome show that PD-L1 expression strongly correlates with unfavourable prognosis in kidney, ovarian, bladder, breast, gastric, and pancreatic cancer (Hamanishi J et al. 2007 Proc. Natl. Acad. Sci. USA 104:3360-65; Inman B A et al. 2007 Cancer 109:1499-505; Konishi J et al. 2004 Clin. Cancer Res. 10:5094-100; Nakanishi J et al. 2007 Cancer Immunol. Immunother. 56:1173-82; Nomi T et al. 2007 Clin. Cancer Res. 13:2151-57; Thompson R H et al. 2004 Proc. Natl. Acad. Sci. USA 101:17174-79; Wu C et al. 2006 Acta Histochem. 108:19-24). In addition, these studies suggest that higher levels of PD-L1 expression on tumours may facilitate advancement of tumour stage and invasion into deeper tissue structures.

The PD-1 pathway can also play a role in haematologic malignancies. PD-L1 is expressed on multiple myeloma cells but not on normal plasma cells (Liu J et al. 2007 Blood 110:296-304). PD-L1 is expressed on some primary T-cell lymphomas, particularly anaplastic large cell T lymphomas (Brown J A et al, 2003 Immunol. 170:1257-66). PD-1 is highly expressed on the T-cells of angioimmunoblastic lymphomas, and PD-L1 is expressed on the associated follicular dendritic cell network (Dorfman D M et al. 2006 Am. J. Surg. Pathol. 30:802-10). In nodular lymphocyte-predominant Hodgkin lymphoma, the T-cells associated with lymphocytic or histiocytic (L&H) cells express PD-1. Microarray analysis using a readout of genes induced by PD-1 ligation suggests that tumour-associated T-cells are responding to PD-1 signals in situ in Hodgkin lymphoma (Chemnitz J M et al. 2007 Blood 110:3226-33). PD-1 and PD-L1 are expressed on CD4 T-cells in HTLV-1-mediated adult T-cell leukaemia and lymphoma (Shimauchi T et al. 2007 Int. J. Cancer 121: 2585-90). These tumour cells are hyporesponsive to TCR signals.

Studies in animal models demonstrate that PD-L1 on tumours inhibits T-cell activation and lysis of tumour cells and in some cases leads to increased tumour-specific T-cell death (Dong H et al. 2002 Nat. Med. 8:793-800; Hirano F et al. 2005 Cancer Res. 65:1089-96). Tumour-associated APCs can also utilise the PD-1:PD-L1 pathway to control antitumour T-cell responses. PD-L1 expression on a population of tumour-associated myeloid DCs is upregulated by tumour environmental factors (Curiel T J et al. 2003 Nat. Med. 9:562-67). Plasmacytoid dendritic cells (DCs) in the tumour-draining lymph node of B16 melanoma express IDO, which strongly activates the suppressive activity of regulatory T-cells. The suppressive activity of IDO-treated regulatory T-cells required cell contact with IDO-expressing DCs (Sharma M D et al. 2007 Clin. Invest. 117:2570-82).

In one embodiment, the second peptide ligand comprises a PD-L1 binding bicyclic peptide ligand.

Suitable examples of PD-L1 binding bicyclic peptide ligands are disclosed in GB Patent Application Nos. 1820956.9 and 1820969.2, the peptides of which are incorporated herein by reference.

In one embodiment, the PD-L1 binding bicyclic peptide ligand comprises an amino acid sequence selected from:

(SEQ ID NO: 12)
$C_i$[HArg]DW$C_{ii}$HWTFSHGHP$C_{iii}$;

(SEQ ID NO: 13)
$C_i$SAGWLTM$C_{ii}$QKLHL$C_{iii}$;

and (SEQ ID NO: 14)
$C_i$SAGWLTM$C_{ii}$Q[K(PYA)]LHL$C_{iii}$;

wherein $C_i$, $C_{ii}$ and $C_{iii}$ represent first, second and third cysteine residues, respectively, HArg represents homoarginine and PYA represents 4-pentynoic acid, or a pharmaceutically acceptable salt thereof.

In a further embodiment, the PD-L1 binding bicyclic peptide ligand comprises N-terminal and/or C-terminal modifications and comprises:

[PYA]-[B-Ala]-[$Sar_{10}$]-(SEQ ID NO: 12) (hereinafter referred to as BCY8938);

[PYA]-[B-Ala]-[$Sar_{10}$]-SDK-(SEQ ID NO: 13) (hereinafter referred to as BCY10043);

$NH_2$-SDK-(SEQ ID NO: 13)-[$Sar_{10}$]-[K(PYA)] (hereinafter referred to as BCY10044);

$NH_2$-SDK-(SEQ ID NO: 14) (hereinafter referred to as BCY10045);
and

Ac-SDK-(SEQ ID NO: 14)-PSH (hereinafter referred to as BCY10861);

wherein PYA represents 4-pentynoic acid, B-Ala represents beta-alanine, $Sar_{10}$ represents 10 sarcosine units, or a pharmaceutically acceptable salt thereof.

In an alternative embodiment, the component present on a cancer cell is Nectin-4.

Nectin-4 is a surface molecule that belongs to the nectin family of proteins, which comprises 4 members. Nectins are cell adhesion molecules that play a key role in various biological processes such as polarity, proliferation, differentiation and migration, for epithelial, endothelial, immune and neuronal cells, during development and adult life. They are involved in several pathological processes in humans. They are the main receptors for poliovirus, herpes simplex virus and measles virus. Mutations in the genes encoding Nectin-1 (PVRL1) or Nectin-4 (PVRL4) cause ectodermal dysplasia syndromes associated with other abnormalities. Nectin-4 is expressed during foetal development. In adult tissues its expression is more restricted than that of other members of the family. Nectin-4 is a tumour-associated antigen in 50%, 49% and 86% of breast, ovarian and lung carcinomas, respectively, mostly on tumours of bad prognosis. Its expression is not detected in the corresponding normal tissues. In breast tumours, Nectin-4 is expressed mainly in triple-negative and ERBB2+ carcinomas. In the serum of patients with these cancers, the detection of soluble forms of Nectin-4 is associated with a poor prognosis. Levels of serum Nectin-4 increase during metastatic progression and decrease after treatment. These results suggest that Nectin-4 could be a reliable target for the treatment of cancer. Accordingly, several anti-Nectin-4 antibodies have been described in the prior art. In particular, Enfortumab Vedotin (ASG-22ME) is an antibody-drug conjugate (ADC) targeting Nectin-4 and is currently clinically investigated for the treatment of patients suffering from solid tumours.

In one embodiment, the second peptide ligand comprises a Nectin-4 binding bicyclic peptide ligand.

Suitable examples of Nectin-4 binding bicyclic peptide ligands are disclosed in GB Patent Application Nos 1810250.9, 1815684.4 and 1818499.4, the peptides of which are incorporated herein by reference.

In one embodiment, the Nectin-4 binding bicyclic peptide ligand comprises an amino acid sequence selected from:

$C_i$P[1Nal][dD]$C_{ii}$M[HArg]DWSTP[HyP]W$C_{iii}$ (SEQ ID NO: 15; hereinafter referred to as BCY8116);

$C_i$P[1Nal][dD]$C_{ii}$M[HArg]D[dW]STP[HyP][dW]$C_{iii}$ (SEQ ID NO: 16; hereinafter referred to as BCY11415); and -continued $C_i$P[1Nal][dK](Sar$_{10}$-(B-Ala))$C_{ii}$M[HArg]DWSTP[HyP]W$C_{iii}$ (SEQ ID NO: 17);
$C_i$PFG$C_{ii}$M[HArg]DWSTP[HyP]W$C_{iii}$ (SEQ ID NO: 18; hereinafter referred to as BCY11414);

wherein $C_i$, $C_{ii}$ and $C_{iii}$ represent first, second and third cysteine residues, respectively, 1NaI represents 1-naphthylalanine, HArg represents homoarginine, HyP represents hydroxyproline, $Sar_{10}$ represents 10 sarcosine units, B-Ala represents beta-alanine, or a pharmaceutically acceptable salt thereof.

In a further embodiment, the Nectin-4 binding bicyclic peptide ligand optionally comprises N-terminal modifications and comprises:

SEQ ID NO: 15 (hereinafter referred to as BCY8116);

[PYA]-[B-Ala]-[$Sar_{10}$]-(SEQ ID NO: 15) (hereinafter referred to as BCY8846);
SEQ ID NO: 16 (hereinafter referred to as BCY11415);

[PYA]-[B-Ala]-[$Sar_{10}$]-(SEQ ID NO: 16) (hereinafter referred to as BCY11942);
Ac-(SEQ ID NO: 17) (hereinafter referred to as BCY8831); and
SEQ ID NO: 18 (hereinafter referred to as BCY11414);

wherein PYA represents 4-pentynoic acid, B-Ala represents beta-alanine, $Sar_{10}$ represents 10 sarcosine units, or a pharmaceutically acceptable salt thereof.

In an alternative embodiment, the component present on a cancer cell is prostate-specific membrane antigen (PSMA).

Prostate-specific membrane antigen (PSMA) (also known as Glutamate carboxypeptidase II (GCPII), N-acetyl-L-aspartyl-L-glutamate peptidase I (NAALADase I) and NAAG peptidase) is an enzyme that in humans is encoded by the FOLH1 (folate hydrolase 1) gene. Human GCPII contains 750 amino acids and weighs approximately 84 kDa.

Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as potential biomarker for therapy and imaging of some cancers. In human prostate cancer, the higher expressing tumors are associated with quicker time to progression and a greater percentage of patients suffering relapse.

In one embodiment, the second peptide ligand comprises a PSMA binding bicyclic peptide ligand.

Suitable examples of PSMA binding bicyclic peptide ligands are disclosed in GB Patent Application Nos 1810318.4, 1810325.9 and 1820325.7, the peptides of which are incorporated herein by reference.

Linkers

It will be appreciated that the first peptide ligand may be conjugated to the second peptide ligand via any suitable linker. Typically the design of said linker will be such that the two Bicyclic peptides are presented in such a manner that they can bind unencumbered to their respective targets either alone or while simultaneously binding to both target receptors. Additionally, the linker should permit binding to both targets simultaneously while maintaining an appropriate distance between the target cells that would lead to the desired functional outcome. The properties of the linker may be modulated to increase length, rigidity or solubility to optimise the desired functional outcome. The linker may also be designed to permit the attachment of more than one Bicycle to the same target. Increasing the valency of either binding peptide may serve to increase the affinity of the heterotandem for the target cells or may help to induce oligomerisation of one or both of the target receptors.

In one embodiment, the linker is selected from the following sequences: —$CH_2$—, -$PEG_5$-, -$PEG_{10}$-, -$PEG_{12}$-, -$PEG_{23}$-, -$PEG_{24}$-, -$PEG_{15}$-$Sar_5$-, -$PEG_{10}$-$Sar_{10}$-, -$PEG_5$-$Sar_{15}$-, -$PEG_5$-$Sar_5$-, —B-Ala-$Sar_{20}$-, —B-Ala-$Sar_{10}$-$PEG_{10}$-, —B-Ala-$Sar_5$-$PEG_{15}$- and —B-Ala-$Sar_5$-$PEG_5$-.

Structural representations of suitable linkers are detailed below:

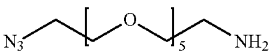

H2N-Peg5-N3
COM00000132

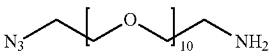

H2N-Peg10-N3
COM00000134

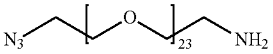

H2N-Peg23-N3
COM00000135

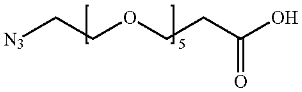

H2N-PEG5-COOH
COM00000467

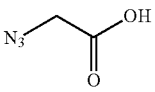

N3-CH2-COOH
COM00000468

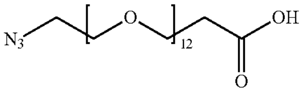

N3-PEG12-COOH
COM00000466

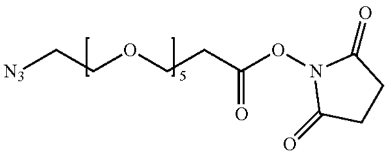

NHS-PEG5-N3

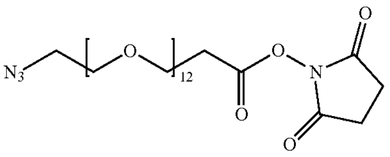

NHS-PEG12-N3

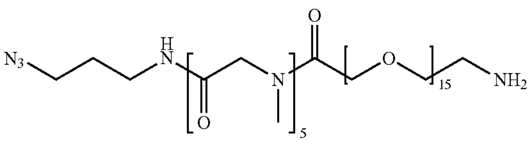

H2N-PEG15-SAR5-N3
COM00000128

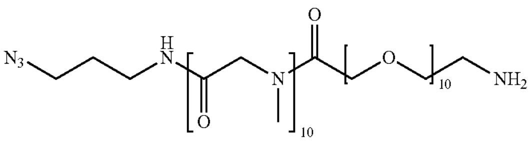

H2N-PEG10-SAR10-N3
COM00000129

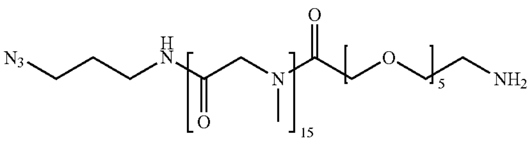

H2N-PEG5-SAR15-N3
COM00000130

-continued

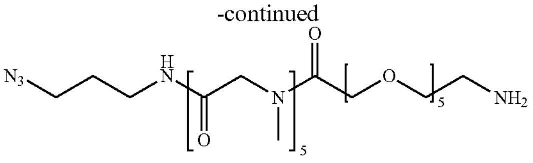

H2N-PEG5-SAR5-N3
COM00000131

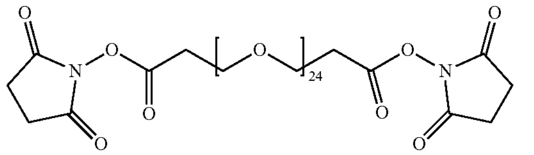

NHS-PEG24-NHS
COM00000469

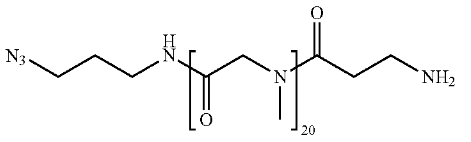

H2N-(B-Ala)-SAR20-N3
COM00000470

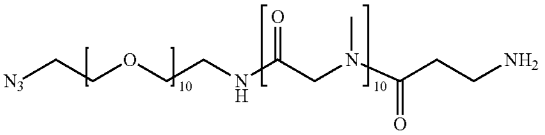

H2N-(B-Ala)-SAR10-PEG10-N3
COM00000471

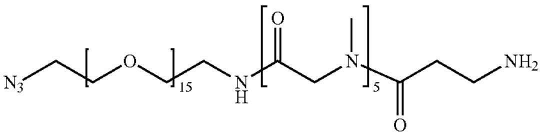

H2N-(B-Ala)-SAR5-PEG15-N3
COM00000472

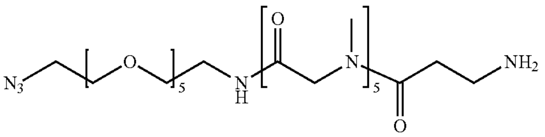

H2N-(B-Ala)-SAR5-PEG5-N3
COM00000473

Heterotandem Complexes

In one specific embodiment, the first peptide ligand comprises a CD137 binding bicyclic peptide ligand attached to a TATA scaffold, the second peptide ligand comprises an EphA2 binding bicyclic peptide ligand attached to a TATA scaffold and said heterotandem complex is selected from:

| Complex No. | EphA2 BCY No. | Attachment Point | Linker | CD137 BCY No. | Attachment Point |
|---|---|---|---|---|---|
| BCY9173 | BCY6169 | N-terminal PYA | -PEG$_{12}$- | BCY9172 | C-terminal Dap |
| BCY7985 | BCY6169 | N-terminal PYA | -PEG$_{12}$- | BCY7732 | C-terminal Dap |
| BCY8942 | BCY6169 | N-terminal PYA | -PEG$_{12}$- | BCY8045 | C-terminal Dap |
| BCY8943 | BCY8941 | N-terminal PYA | -PEG$_{12}$- | BCY7732 | C-terminal Dap |
| BCY9647 | BCY6099 | N-terminus | -PEG$_{10}$- | BCY7741 | C-terminal Dap(PYA) |
| BCY9648 | BCY6099 | N-terminus | -PEG$_{23}$- | BCY7741 | C-terminal Dap(PYA) |
| BCY9655 | BCY6099 | N-terminus | -PEG$_{15}$-Sar$_5$- | BCY7741 | C-terminal Dap(PYA) |
| BCY9656 | BCY6099 | N-terminus | -PEG$_{10}$-Sar$_{10}$- | BCY7741 | C-terminal Dap(PYA) |
| BCY9657 | BCY6099 | N-terminus | -PEG$_5$-Sar$_5$- | BCY7741 | C-terminal Dap(PYA) |
| BCY9658 | BCY6099 | N-terminus | -PEG$_5$-Sar$_5$- | BCY7741 | C-terminal Dap(PYA) |
| BCY9659 | BCY6099 | N-terminus | -PEG$_5$- | BCY7741 | C-terminal Dap(PYA) |
| BCY9758 | BCY6099 | N-terminus | -PEG$_{24}$- | BCY7732 | C-terminal Dap |
| BCY10568 | BCY6169 | N-terminal PYA | -PEG$_{12}$- | BCY8919 | Lys3 |
| BCY10570 | BCY6169 | N-terminal PYA | -PEG$_{12}$- | BCY8920 | dLys4 |
| BCY10574 | BCY9594 | N-terminus | -PEG$_5$- | BCY8927 | Lys (PYA)3 |
| BCY10575 | BCY9594 | N-terminus | -PEG$_5$- | BCY8928 | dLys (PYA)4 |
| BCY10576 | BCY9594 | N-terminus | -PEG$_5$- | BCY11014 | C-terminal Dap(PYA) |
| BCY10577 | BCY6169 | N-terminus | —$CH_2$— | BCY9172 | C-terminal Dap |

Figure 2:
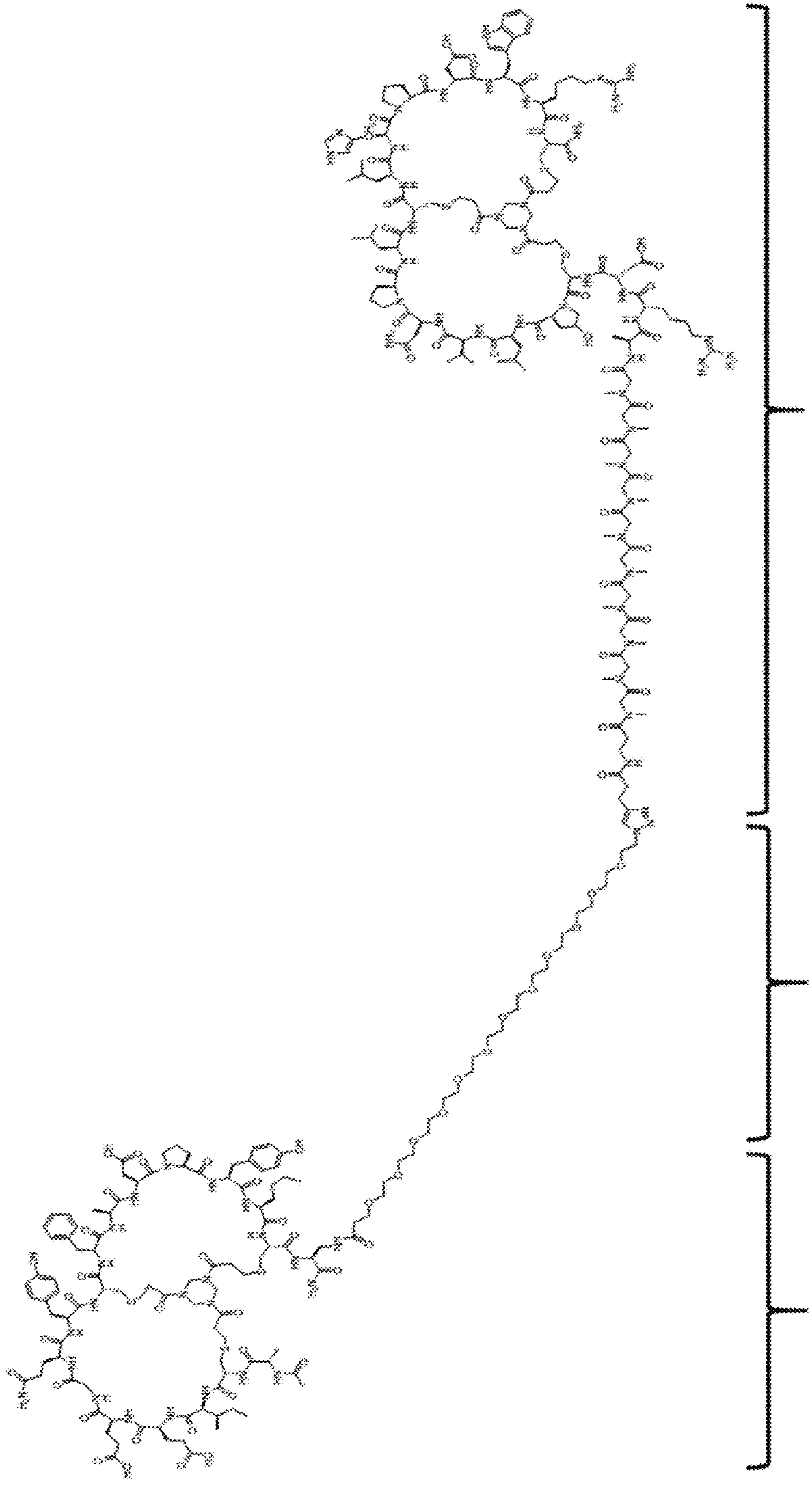
FIG. 2: Structure and composition of the EphA2-CD137 heterotandem bicyclic peptide complex BCY7985.

The heterotandem bicyclic peptide complex BCY7985 consists of a CD137-specific peptide BCY7859 linked to the N-terminal PYA group of an EphA2-specific peptide BCY6169 via PEG$_{12}$ (shown pictorially in FIG. 2).

CD137 is a homotrimeric protein and the natural ligand CD137L exists as a homotrimer either expressed on immune cells or secreted. The biology of CD137 is highly dependent on multimerization to induce CD137 activity in immune cells. One way to generate CD137 multimerization is through cellular cross-linking of the CD137 specific agonist through interaction with a specific receptor present on another cell.

EphA2 is highly expressed on tumour cells and oligomerization of this receptor tyrosine kinase by Ephrin-A ligands drives its activation. Without being bound by theory, the inventors believe that a EphA2-CD137 heterotandem consisting of one EphA2-specific peptide coupled to one CD137-specific peptide acts to cross-link CD137. The implication is that CD137 would be multimerized and activated in the presence of EphA2 on cells such as tumour cells. This would drive 00137 immune cell activation in the local tumour environment (FIG. 1).

Figure 3:
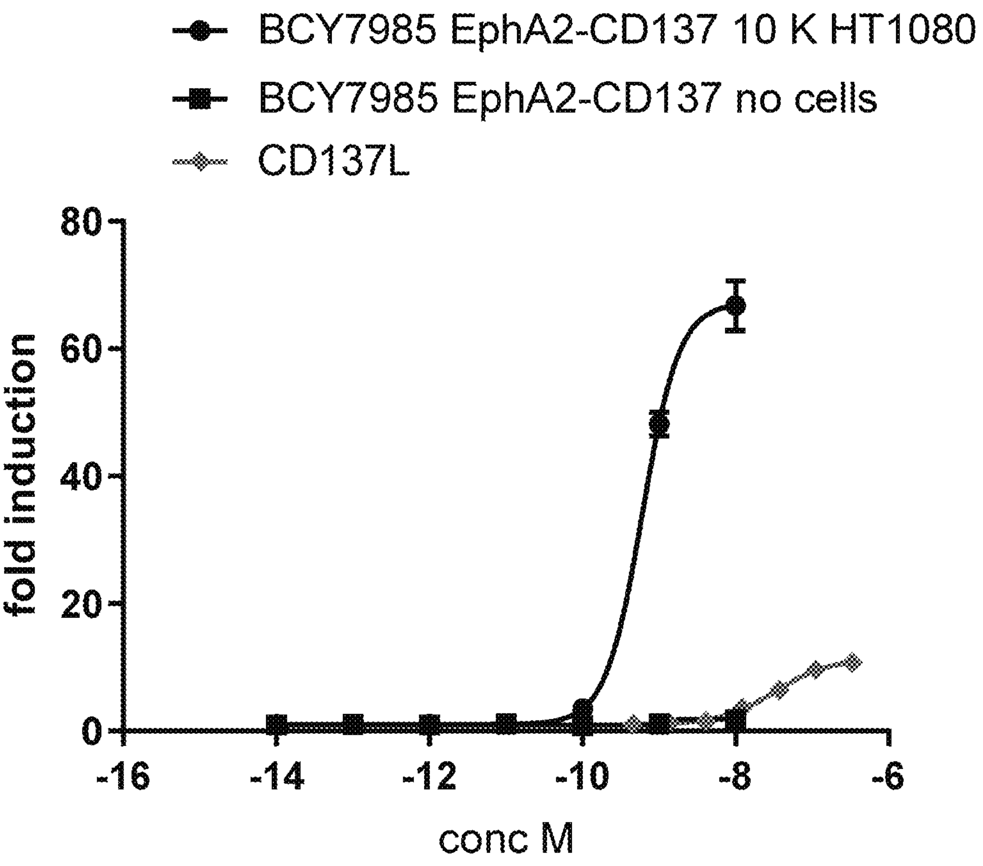
FIG. 3: Analysis of the EphA2-CD137 heterotandem bicyclic peptide complex BCY7985 in the Promega CD137 luciferase reporter assay (CS196008) in the presence of EphA2-expressing HT1080 cells.

This hypothesis was tested in the 00137 cellular activity reporter assay described herein and the results are shown herein in FIG. 3 wherein it can be seen that BCY7985 showed strong induction of CD137 cell activity in the Promega CD137 luciferase reporter assay (CSi196008) in the presence of EphA2-expressing HT1080 cells.

In one alternative specific embodiment, the first peptide ligand comprises a 00137 binding bicyclic peptide ligand attached to a TATA scaffold, the second peptide ligand comprises a Nectin-4 binding bicyclic peptide ligand attached to a TATA scaffold and said heterotandem complex is selected from:

| Complex No. | Nectin-4 BCY No. | Attachment Point | Linker | CD137 BCY No. | Attachment Point |
|---|---|---|---|---|---|
| BCY8854 | BCY8846 | N-terminal PYA | -PEG$_{12}$- | BCY7732 | C-terminal Dap |
| BCY9350 | BCY11942 | N-terminal PYA | -PEG$_{12}$- | BCY7732 | C-terminal Dap |
| BCY9351 | BCY8846 | N-terminal PYA | -PEG$_{12}$- | BCY8045 | C-terminal Dap |
| BCY9399 | BCY8116 | N-terminus | -PEG$_{10}$- | BCY7741 | C-terminal Dap(PYA) |
| BCY9400 | BCY8116 | N-terminus | -PEG$_{23}$- | BCY7741 | C-terminal Dap(PYA) |
| BCY9401 | BCY8116 | N-terminus | -B-Ala-Sar$_{20}$- | BCY7741 | C-terminal Dap(PYA) |
| BCY9403 | BCY8116 | N-terminus | -B-Ala-Sar$_{10}$-PEG$_{10}$- | BCY7741 | C-terminal Dap(PYA) |
| BCY9405 | BCY8116 | N-terminus | -B-Ala-Sar$_5$-PEG$_{15}$- | BCY7741 | C-terminal Dap(PYA) |
| BCY9406 | BCY8116 | N-terminus | -B-Ala-Sar$_5$-PEG$_{15}$- | BCY7741 | C-terminal Dap(PYA) |
| BCY9407 | BCY8116 | N-terminus | -PEG$_{15}$-Sar$_5$- | BCY7741 | C-terminal Dap(PYA) |
| BCY9408 | BCY8116 | N-terminus | -PEG$_{10}$-Sar$_{10}$- | BCY7741 | C-terminal Dap(PYA) |
| BCY9409 | BCY8116 | N-terminus | -PEG$_5$-Sar$_{15}$- | BCY7741 | C-terminal Dap(PYA) |
| BCY9410 | BCY8116 | N-terminus | -PEG$_5$-Sar$_5$- | BCY7741 | C-terminal Dap(PYA) |
| BCY9411 | BCY8116 | N-terminus | -PEG$_5$- | BCY7741 | C-terminal Dap(PYA) |
| BCY9759 | BCY8116 | N-terminus | -PEG$_{24}$- | BCY7732 | C-terminal Dap |
| BCY10000 | BCY8846 | N-terminal PYA | -PEG$_{12}$- | BCY9172 | C-terminal Dap |

-continued

| Complex No. | Nectin-4 BCY No. | Attachment Point | Linker | CD137 BCY No. | Attachment Point |
|---|---|---|---|---|---|
| BCY10567 | BCY8846 | N-terminal PYA | -$PEG_{12}$- | BCY8919 | Lys3 |
| BCY10569 | BCY8846 | N-terminal PYA | -$PEG_{12}$- | BCY8920 | dLys4 |
| BCY10571 | BCY8116 | N-terminus | -$PEG_5$- | BCY8927 | Lys(PYA)3 |
| BCY10572 | BCY8116 | N-terminus | -$PEG_5$- | BCY8928 | dLys (PYA)4 |
| BCY10573 | BCY8116 | N-terminus | -$PEG_5$- | BCY11014 | C-terminal Dap(PYA) |
| BCY10578 | BCY8846 | N-terminal PYA | —$CH_2$— | BCY9172 | C-terminal Dap |
| BCY10917 | BCY8831 | dLys($Sar_{10}$)-(B-Ala))4 | -$PEG_{12}$- | BCY11014 | C-terminal Dap(PYA) |
| BCY11020 | BCY8831 | dLys($Sar_{10}$)-(B-Ala))4 | -$PEG_5$- | BCY11014 | C-terminal Dap(PYA) |
| BCY11373 | BCY8116 | N-terminus | —$CH_2$— | BCY8927 | Lys(PYA)3 |
| BCY11374 | BCY8116 | N-terminus | —$CH_2$— | BCY8928 | dLys (PYA)4 |
| BCY11375 | BCY8116 | N-terminus | —$CH_2$— | BCY11014 | C-terminal Dap(PYA) |
| BCY11616 | BCY8116 | N-terminus | -$PEG_5$- | BCY7744 | dLys (PYA)4 |
| BCY11617 | BCY8116 | N-terminus | -$PEG_5$- | BCY11506 | Lys(PYA)4 |
| BCY11857 | BCY11414 | N-terminus | -$PEG_5$- | BCY7744 | dLys (PYA)4 |
| BCY11858 | BCY11414 | N-terminus | -$PEG_5$- | BCY8928 | dLys (PYA)4 |
| BCY11859 | BCY11415 | N-terminus | -$PEG_5$- | BCY8928 | dLys (PYA)4 |

Without being bound by theory, the inventors believe that a Nectin-4-CD137 heterotandem consisting of one Nectin-4-specific peptide coupled to one CD137-specific peptide acts to cross-link CD137 in the same manner as described hereinbefore for EphA2.

In one embodiment, the Nectin-4-CD137 heterotandem is other than any one or more of: BCY11857, BCY11858 and/or BCY11859.

In one alternative specific embodiment, the first peptide ligand comprises a CD137 binding bicyclic peptide ligand attached to a TATA scaffold, the second peptide ligand comprises a PD-L1 binding bicyclic peptide ligand attached to a TATA scaffold and said heterotandem complex is selected from:

| Complex No. | PD-L1 BCY No. | Attachment Point | Linker | CD137 BCY No. | Attachment Point |
|---|---|---|---|---|---|
| BCY8939 | BCY8938 | N-terminal PYA | -$PEG_{12}$- | BCY7732 | C-terminal Dap |
| BCY10580 | BCY10043 | N-terminal PYA | -$PEG_{12}$- | BCY9172 | C-terminal Dap |
| BCY10581 | BCY10044 | C-terminal Lys(PYA) | -$PEG_{12}$- | BCY9172 | C-terminal Dap |
| BCY10582 | BCY10045 | Lys(PYA)9 | -$PEG_{12}$- | BCY9172 | C-terminal Dap |
| BCY11017 | BCY10861 | Lys(PYA)9 | -$PEG_{12}$- | BCY8919 | Lys3 |
| BCY11018 | BCY10861 | Lys(PYA)9 | -$PEG_{12}$- | BCY8920 | dLys4 |
| BCY11019 | BCY10861 | Lys(PYA)9 | -$PEG_{12}$- | BCY9172 | C-terminal Dap |
| BCY11376 | BCY10861 | Lys(PYA)9 | —$CH_2$— | BCY8919 | Lys3 |
| BCY11377 | BCY10861 | Lys(PYA)9 | —$CH_2$— | BCY8920 | dLys4 |
| BCY11378 | BCY10861 | Lys(PYA)9 | —$CH_2$— | BCY9172 | C-terminal Dap |
| BCY11379 | BCY10861 | Lys(PYA)9 | -$PEG_5$- | BCY8919 | Lys3 |
| BCY11380 | BCY10861 | Lys(PYA)9 | -$PEG_5$- | BCY8920 | dLys4 |
| BCY11381 | BCY10861 | Lys(PYA)9 | -$PEG_5$- | BCY9172 | C-terminal Dap |

Without being bound by theory, the inventors believe that a PD-L1-CD137 heterotandem consisting of one PD-L1-specific peptide coupled to one CD137-specific peptide acts to cross-link CD137 in the same manner as described hereinbefore for EphA2.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) $4^{th}$ ed., John Wiley & Sons, Inc.), which are incorporated herein by reference.

NOMENCLATURE

Numbering

When referring to amino acid residue positions within compounds of the invention, cysteine residues ($C_i$, $C_{ii}$ and $C_{iii}$) are omitted from the numbering as they are invariant, therefore, the numbering of amino acid residues within SEQ ID NO: 1 is referred to as below:

(SEQ ID NO: 1)

$C_i$-$I_1$-$E_2$-$E_3$-$G_4$-$Q_5$-$Y_6$-$C_{ii}$-$F_7$-$A_8$-$D_9$-$P_{10}$-$Y_{11}$-$[Nle]_{12}$-$C_{iii}$.

For the purpose of this description, all bicyclic peptides are assumed to be cyclised with TBMB (1,3,5-tris(bromomethyl)benzene) or 1,1,1"-(1,3,5-triazinane-1,3,5-triyl)triprop-2-en-1-one (TATA) and yielding a tri-substituted structure. Cyclisation with TBMB and TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal βAla-Sar10-Ala tail would be denoted as:

(SEQ ID NO: X)

βAla-Sar10-A-.

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —$COO^-$), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the invention contain an amine function, these may form quaternary ammonium salts, for example by reaction with an alkylating agent according to methods well known to the skilled person. Such quaternary ammonium compounds are within the scope of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Ca-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise 3-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

- Incorporating hydrophobic moieties that exploit the hydrophobic effect and lead to lower off rates, such that higher affinities are achieved,
- Incorporating charged groups that exploit long-range ionic interactions, leading to faster on rates and to higher affinities (see for example Schreiber et al, Rapid, electrostatically assisted association of proteins (1996), Nature Struct. Biol. 3, 427-31); and
- Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}H$ (D) and $^{3}H$ (T), carbon, such as $^{11}C$, $^{13}C$ and $^{14}C$, chlorine, such as $^{31}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}S$, copper, such as $^{64}Cu$, gallium, such as $^{67}Ga$ or $^{68}Ga$, yttrium, such as $^{90}Y$ and lutetium, such as $^{177}Lu$, and Bismuth, such as $^{213}Bi$.

Certain isotopically-labelled peptide ligands of the invention, for example, those incorporating a radioactive isotope, are useful in drug and/or substrate tissue distribution studies, and to clinically assess the presence and/or absence of the Nectin-4 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}H$ (T), and carbon-14, i.e. $^{14}C$, are particularly useful for this purpose in view of their ease of incorporation and ready means of detection.

Substitution with heavier isotopes such as deuterium, i.e. $^{2}H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment, the molecular scaffold may be a macromolecule. In one embodiment, the molecular scaffold is a macromolecule composed of amino acids, nucleotides or carbohydrates.

In one embodiment, the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3,5-Triacryloylhexahydro-1,3,5-triazine ('TATA'), or a derivative thereof.

In one embodiment, the molecular scaffold is 2,4,6-tris(bromomethyl)mesitylene. This molecule is similar to 1,3,5-tris(bromomethyl)benzene (TBMB) but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl)amine, tris-(2-maleimidoethyl)benzene, tris-(maleimido)benzene. An example of an αβ unsaturated carbonyl containing compound is 1,1',1"-(1,3,5-triazinane-1,3,5-triyl)triprop-2-en-1-one (TATA) (Angewandte Chemie, International Edition (2014), 53(6), 1602-1606). An example of an α-halomethylcarbonyl containing compound is N,N',N"-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

According to a further aspect of the invention, there is provided a heterotandem bicyclic peptide complex as defined herein for use in preventing, suppressing or treating cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Example 1: Synthesis of Linkers

COM128

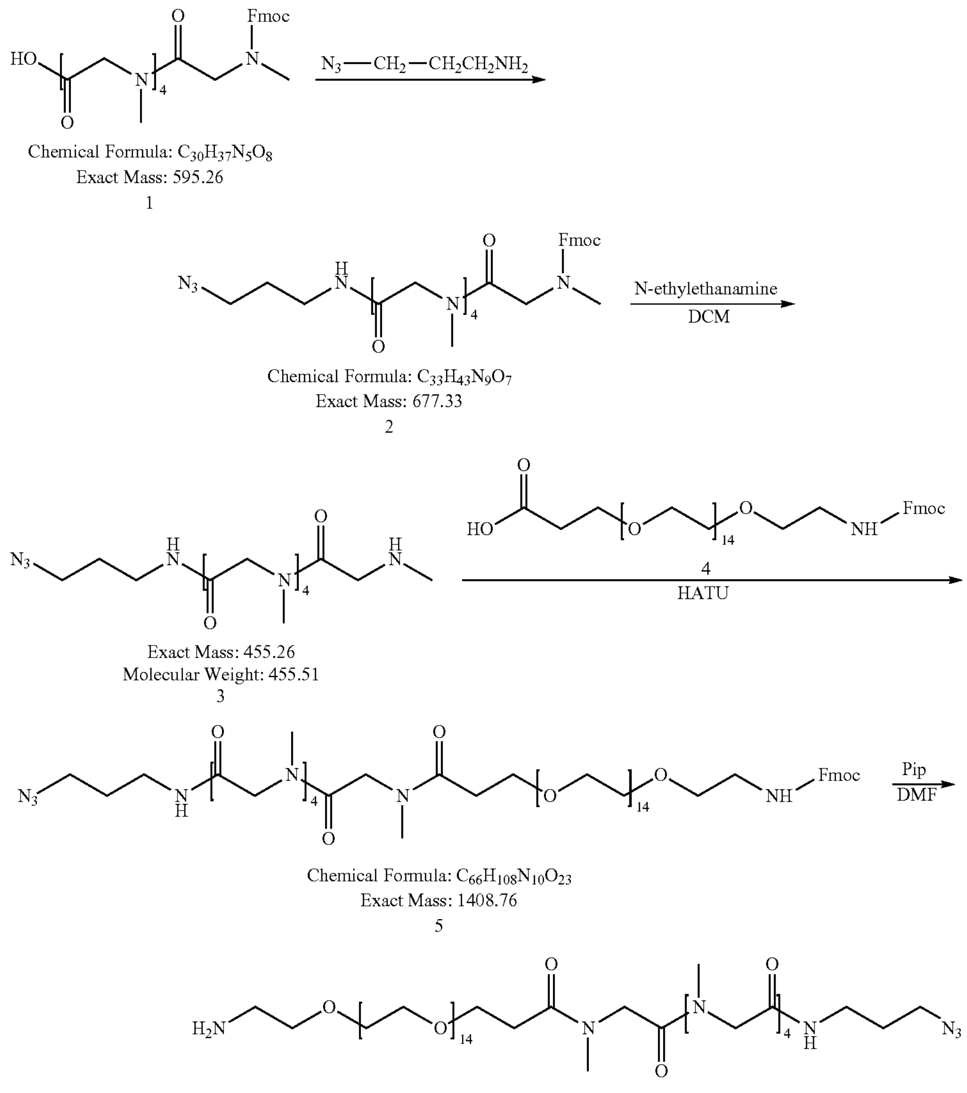

COM00000128

A mixture of compound 1 (700.0 mg, 1.18 mmol, 1.0 eq), 3-azidopropan-1-amine (117.66 mg, 1.18 mmol, 1.0 eq), EDCl (270.4 mg, 1.41 mmol, 1.2 eq), HOBt (190.6 mg, 1.41 mmol, 1.2 eq) was dissolved in DCM (20 mL, pre-degassed and purged with $N_2$ for 3 times), and then the mixture was stirred at 20-25° C. for 1 hr under $N_2$ atmosphere. LC-MS showed compound 1 was consumed completely and one main peak with desired m/z (calculated MW: 677.33, observed m/z: 678.2 ($[M+H]^+$)) was detected. The solvent was evaporated to produce compound 2 (600 mg, crude) was obtained as a white solid.

A mixture of compound 2 (600.0 mg, 885.3 μmol, 1.0 eq), N-ethylethanamine (1.29 g, 15.19 mmol, 1.50 mL, 17.2 eq) was dissolved in DCM (3 mL, pre-degassed and purged with $N_2$ for 3 times), and then the mixture was stirred at 25-30° C. for 2 hr under $N_2$ atmosphere. LC-MS showed compound 2 was consumed completely and one main peak with desired m/z (calculated MW: 455.51, observed m/z: 456.3 ($[M+H]^+$)) was detected. The solvent was evaporated to produce compound 3 (400 mg, crude) was obtained as colorless oil.

A mixture of compound 3 (150.0 mg, 329.3 μmol, 1.0 eq), compound 4 (320.1 mg, 329.3 μmol, 1.0 eq), HATU (125.2 mg, 329.3 μmol, 1.0 eq), DIEA (42.6 mg, 329.3 μmol, 57.4 μL, 1.0 eq) was dissolved in DMF (2 mL, pre-degassed and purged with $N_2$ for 3 times), and then the mixture was stirred at 25-30° C. for 2 under $N_2$ atmosphere. LC-MS showed compound 3 was consumed completely and one main peak with desired m/z (calculated MW: 1408.76, observed m/z: 705.3 ($[M/2+H]^+$)) was detected. The solvent was evaporated to produce compound 5 (400 mg, crude) was obtained as yellow oil.

Compound 5 (400 mg, 283.77 μmol, 1.0 eq) was dissolved in DMF (4 mL, pre-degassed and purged with $N_2$ for 3 times), following by addition of piperidine (862.2 mg, 10.13 mmol, 1 mL, 35.7 eq), and then the mixture was stirred at 25-30° C. for 15 min under $N_2$ atmosphere. LC-MS showed compound 5 was consumed completely and one main peak with desired m/z (calculated MW: 1187.37, observed m/z: 594.4 ($[M/2+H^+]$, 1187.4 ($[M+H]^+$)) was detected. The solvent was evaporated to produce COM128 (250 mg, crude) was obtained as colorless oil.

COM129

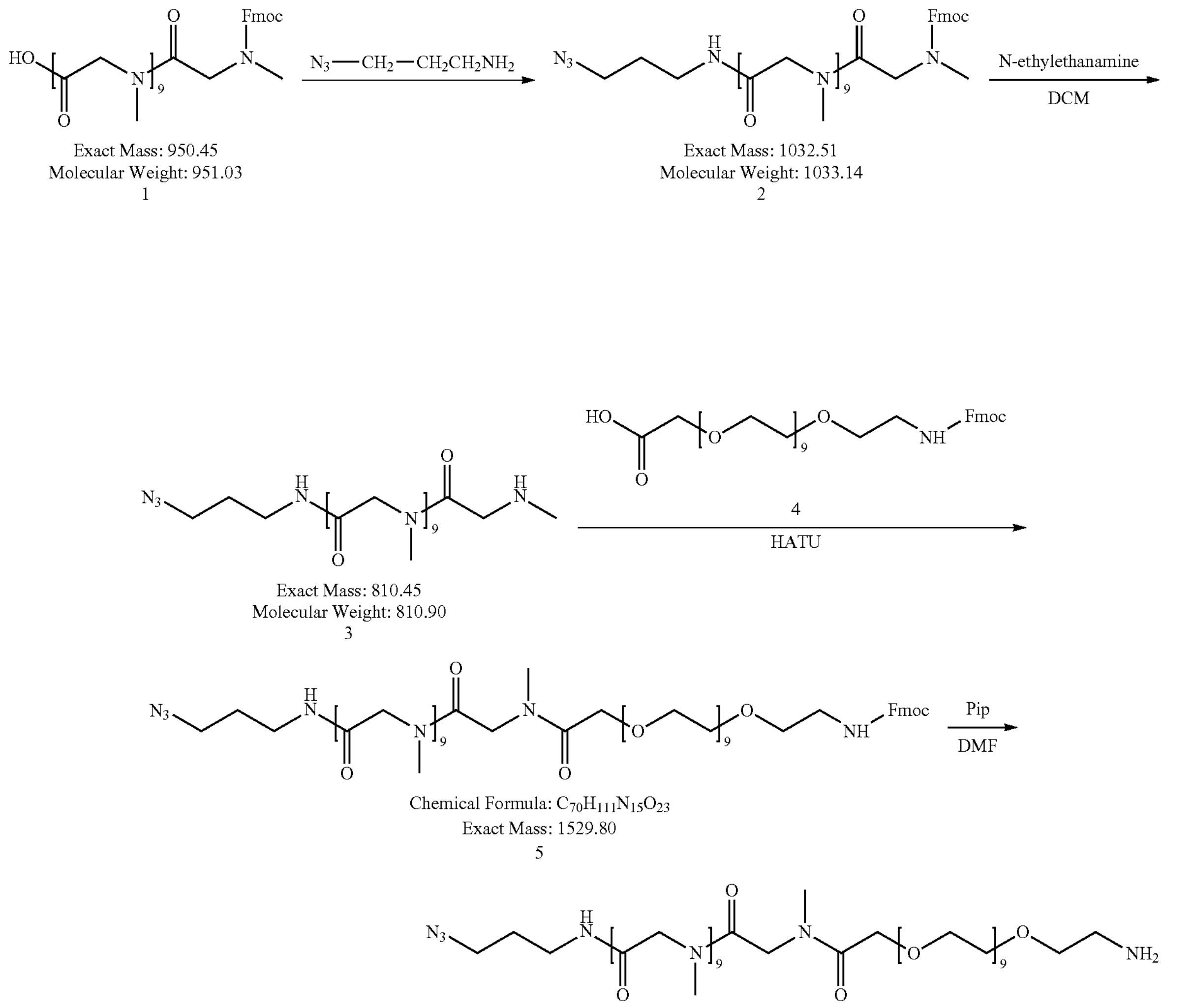

Exact Mass: 950.45
Molecular Weight: 951.03
1

Exact Mass: 1032.51
Molecular Weight: 1033.14
2

Exact Mass: 810.45
Molecular Weight: 810.90
3

Chemical Formula: $C_{70}H_{111}N_{15}O_{23}$
Exact Mass: 1529.80
5

COM00000129

A mixture of compound 1 (1.4 g, 1.47 mmol, 1.0 eq), 3-azidopropan-1-amine (162.1 mg, 1.62 mmol, 1.1 eq), EDCl (338.6 mg, 1.77 mmol, 1.2 eq), HOBt (238.7 mg, 1.77 mmol, 1.2 eq) was dissolved in DCM (5 mL, pre-degassed and purged with $N_2$ for 3 times), and then the mixture was stirred at 20-25° C. for 1 hr under $N_2$ atmosphere. LC-MS showed compound 1 was consumed completely and one main peak with desired m/z (calculated MW: 1033.14, observed m/z: 1033.2 ($[M+H]^+$)) was detected. The reaction mixture was treated with a few drops of 1 M HCl, and the organic layer was evaporated under reduced pressure to remove solvent. Compound 2 (1.1 g, crude) was obtained as yellow oil.

A mixture of compound 2 (1.1 g, 1.06 mmol, 1 eq), N-ethylethanamine (3.89 g, 53.24 mmol, 5.48 mL, 50 eq) was dissolved in DCM (5 mL, pre-degassed and purged with $N_2$ for 3 times), and then the mixture was stirred at 20-25° C. for 1 hr under $N_2$ atmosphere. LC-MS showed compound 2 was consumed completely and one main peak with desired m/z (calculated MW: 810.90, observed m/z: 810.9 ($[M+H]^+$)) was detected. The reaction mixture was evaporated under reduced pressure and compound 3 (810 mg, crude) was obtained as a white solid.

A mixture of compound 3 (810.0 mg, 998.9 μmol, 1.0 eq), compound 4 (810.7 mg, 1.10 mmol, 1.1 eq), HATU (455.8 mg, 1.20 mmol, 1.2 eq), DIEA (258.2 mg, 2.00 mmol, 348.0 μL, 2.0 eq) was dissolved in DMF (2 mL, pre-degassed and purged with $N_2$ for 3 times), and then the mixture was stirred at 25-30° C. for 2 under $N_2$ atmosphere. LC-MS showed compound 3 was consumed completely and one main peak with desired m/z (calculated MW: 1530.72, observed m/z: 765.5 ($[M/2+H]^+$)) was detected. The reaction mixture was treated with a few drops of 1 M HCl, and the organic layer was collected and evaporated under reduced pressure to remove solvent. Compound 5 (1.1 g, crude) was obtained as a yellow solid.

Compound 5 (1 g, 653.29 μmol, 1 eq) was dissolved in DCM (10 mL, pre-degassed and purged with $N_2$ for 3 times), following by addition of piperidine (2.39 g, 32.66 mmol, 3.36 mL, 50 eq), and then the mixture was stirred at 25-30° C. for 2 hr under $N_2$ atmosphere. LC-MS showed Compound 5 was consumed completely and one main peak with desired m/z (calculated MW: 1308.47, observed m/z: 1308.4 ($[M+H]^+$)) was detected. The residue was purified by prep-HPLC (TFA condition: Phase A: 0.075% TFA in $H_2O$, phase B: MeCN, Column: Luna 200*25 mm 10 um, C18, 110A and Gemin150*30 mm, C18, 5 um, 110A, connection, 50° C.). COM129 (700 mg, 463.72 μmol, 70.98% yield) was obtained as a yellow solid.

COM130

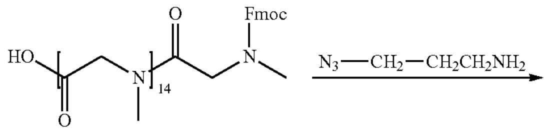

Exact Mass: 1305.64
Molecular Weight: 1306.44
1

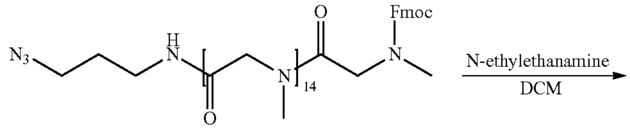

Exact Mass: 1387.70
Molecular Weight: 1388.55

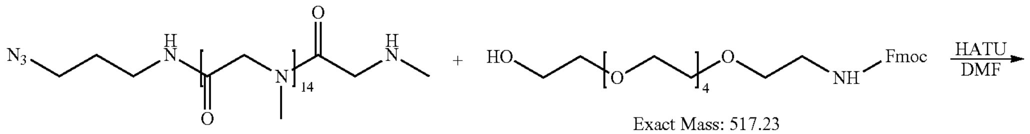

Exact Mass: 1165.63
Molecular Weight: 1166.31
3

Exact Mass: 517.23
Molecular Weight: 517.58
4

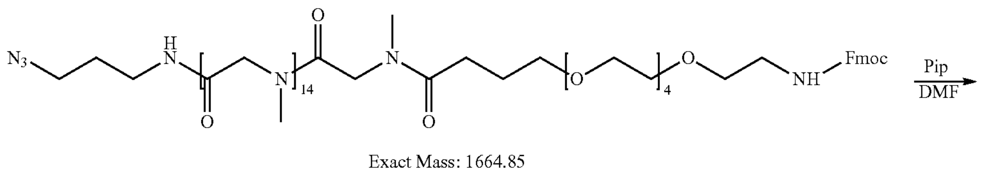

Exact Mass: 1664.85
Molecular Weight: 1665.87
5

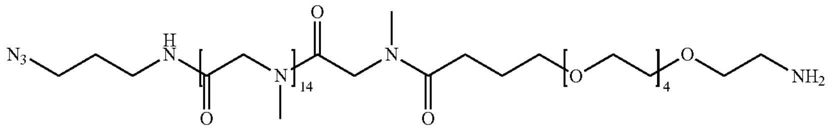

COM00000130

A mixture of Compound 1 (291 mg, 222.75 μmol, 1.0 eq), 3-azidopropan-1-amine (24.53 mg, 245.02 μmol, 1.1 eq), EDCl (51.24 mg, 267.30 μmol, 1.2 eq), HOBt (36.12 mg, 267.30 μmol, 1.2 eq) was dissolved in DCM (3 mL, pre-degassed and purged with $N_2$ for 3 times), and then the mixture was stirred at 20-25° C. for 1 hr under $N_2$ atmosphere. LC-MS showed Compound 1 was consumed completely and one main peak with desired m/z (MW: 1388.53, observed m/z: 694.7 ($[M/2+H]^+$)) was detected. The residue was purified by prep-HPLC (neutral condition). Compound 2 (200 mg, 144.04 μmol, 64.66% yield) was obtained as a white solid.

A mixture of Compound 2 (200 mg, 144.04 μmol, 1.0 eq), N-ethylethanamine (210.7 mg, 2.88 mmol, 297 μL, 20.0 eq) was dissolved in DCM (3 mL, pre-degassed and purged with $N_2$ for 3 times), and then the mixture was stirred at 20-25° C. for 1 hr under $N_2$ atmosphere. LC-MS showed Compound 2 was consumed completely and one main peak with desired m/z (MW: 1166.29, observed m/z: 1166.3 ($[M+H]^+$)) was detected. The reaction mixture was evaporated and Compound 3 (150 mg, crude) was obtained as yellow oil.

A mixture of compound 3 (150 mg, 128.61 μmol, 1.0 eq), compound 4 (75 mg, 144.91 μmol, 1.13 eq), HATU (58.7 mg, 154.34 μmol, 1.2 eq) and DIEA (33.24 mg, 257.23 μmol, 44.80 μL, 2.0 eq) was dissolved in DMF (5 mL, pre-degassed and purged with $N_2$ for 3 times), and then the mixture was stirred at 20-25° C. for 2 hr under $N_2$ atmosphere. LC-MS showed compound 3 was consumed completely and one main peak with desired m/z (MW: 1665.84, observed m/z: 833.2 ($[M/2+H]^+$)) was detected. The solvent was removed under reduced pressure and compound 5 (300 mg, crude) was obtained as yellow oil.

To crude compound 5 (300 mg, dissolved in 10 mL DMF) was added piperidine (2 mL), and the mixture was stirred at 30° C. for 2 hr. LCMS indicated one main peak with desired m/z (MW: 1443.60 observed m/z: 722.7 ($[M/2+H]^+$)) was detected. The residue was purified by prep-HPLC (neutral condition). COM130 (140 mg, 58.19 μmol, 32.31% yield, 60% purity) was obtained as a white solid.

COM131

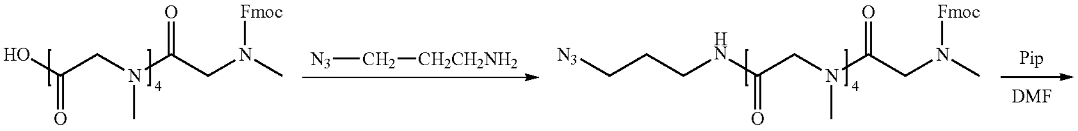

Exact Mass: 595.26
Molecular Weight: 595.64
1

Exact Mass: 677.33
Molecular Weight: 677.75
2

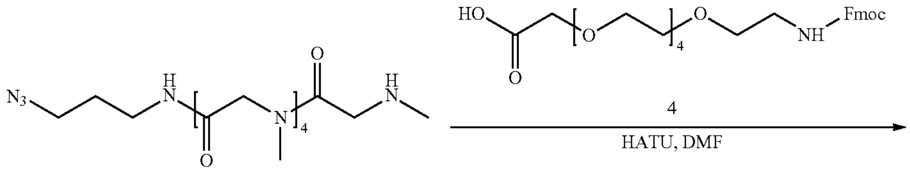

Exact Mass: 455.26
Molecular Weight: 455.51
3

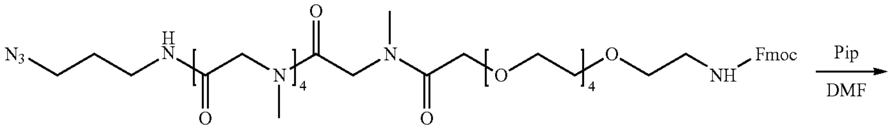

Exact Mass: 954.48
Molecular Weight: 955.06
5

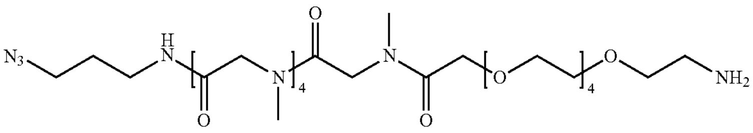

COM00000131

A mixture of compound 1 (700.0 mg, 1.18 mmol, 1.0 eq), 3-azidopropan-1-amine (117.7 mg, 1.18 mmol, 1.0 eq), HOBt (190.6 mg, 1.41 mmol, 1.2 eq), EDCl (270.4 mg, 1.41 mmol, 1.2 eq) was dissolved in DCM (20 mL, pre-degassed and purged with $N_2$ for 3 times), and then the mixture was stirred at 25-30° C. for 2 hr under $N_2$ atmosphere. LC-MS showed compound 1 was consumed completely and one main peak with desired m/z (calculated MW: 677.75, observed m/z: 678.2 ($[M+H]^+$)) was detected. The reaction mixture was treatment with a few drops of 1 M HCl, and the organic layer was collected and evaporated under reduced pressure. Compound 2 (600.0 mg, crude) was obtained as a white solid.

Compound 2 (600.0 mg, 885.2 μmol, 1.0 eq) was dissolved in DMF (3 mL, pre-degassed and purged with $N_2$ for 3 times), and then piperidine (1.29 g, 15.19 mmol, 1.50 mL, 17.2 eq) was added and the mixture was stirred at 25-30° C. for 2 hr under $N_2$ atmosphere. LC-MS showed compound 2 was consumed completely and one main peak with desired m/z (calculated MW: 455.51 observed m/z: 456.3 ($[M+H]^+$)) was detected. The reaction mixture was purified by prep-HPLC (TFA condition), and compound 3 (400.0 mg, 879.1 μmol) was obtained as colorless oil.

A mixture of compound 3 (250.0 mg, 548.83 μmol, 1.0 eq), compound 4 (284.1 mg, 548.83 μmol, 1 eq), HATU (229.6 mg, 603.72 μmol, 1.1 eq), DIEA (141.9 mg, 1.10 mmol, 191.19 μL, 2.0 eq) in DCM (20 mL, pre-degassed and purged with $N_2$ for 3 times), and then the mixture was stirred at 25-30° C. for 2 hr under $N_2$ atmosphere. LC-MS showed compound 3 was consumed completely and one main peak with desired m/z (calculated MW: 955.06, observed m/z: 955.6 ($[M+H]^+$)) was detected. The residue was purified by prep-HPLC (TFA condition). Compound 5 (400.0 mg, 419.1 μmol) was obtained as a white solid A mixture of Compound 5 (400.0 mg, 418.82 μmol, 1.0 eq) was dissolved in DMF (4 mL, pre-degassed and purged with $N_2$ for 3 times), and then piperidine (862.2 mg, 10.13 mmol, 1 mL, 24.2 eq) was added and the mixture was stirred at 25-30° C. for 2 hr under $N_2$ atmosphere. LC-MS showed Compound 5 was consumed completely and one main peak with desired m/z (MW: 732.83 observed m/z: 733.3 ($[M+H]^+$)) was detected. The residue was purified by prep-HPLC (TFA condition). COM131 (200 mg, 272.9 μmol) was obtained as colorless oil.

COM470

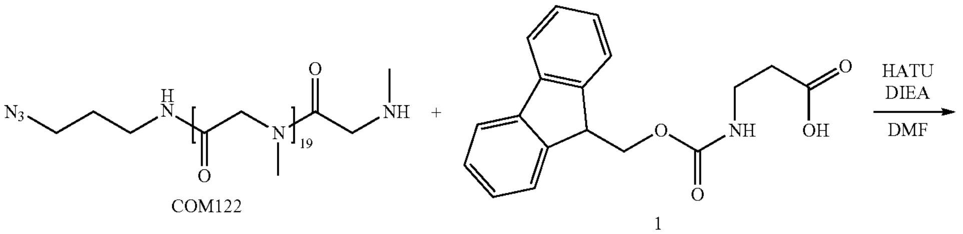

COM122

1

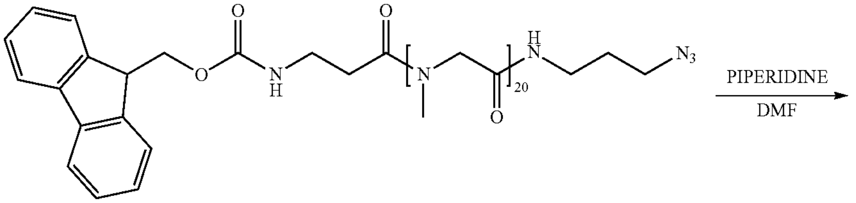

2

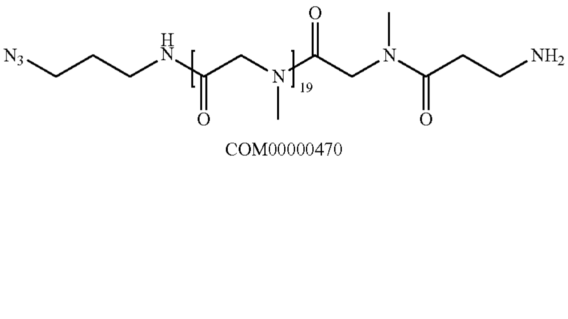

COM00000470

To a solution of COM122 (228 mg, 149.83 μmol, 1.0 eq), Compound 1 (51.31 mg, 164.82 μmol, 1.1 eq) in DMF (6 mL) was added HATU (85.40 mg, 224.75 μmol, 1.5 eq) and DIEA (19.37 mg, 149.83 μmol, 26.10 μL, 1.0 eq). The mixture was stirred at 25-30° C. for 2 hr. LC-MS showed Compound 1 was consumed completely and one main peak with desired m/z (MW: 1814.99, observed m/z: 908.2 ([M/2+H]$^+$)) was detected. The reaction mixture was concentrated under reduced pressure to remove solvent to give a residue. The residue was purified by prep-HPLC (neutral condition). Compound 2 (54 mg, 29.75 μmol, 19.86% yield) was obtained as a white solid.

To a solution of Compound 2 (54 mg, 29.8 μmol, 1.0 eq) in DMF (2 mL) was added piperidine (61 mg, 715 μmol, 71 μL, 24.0 eq). The mixture was stirred at 25-30° C. for 2 hr. LC-MS showed Compound 2 was consumed completely and one main peak with desired m/z (MW: 1592.75 observed m/z: 796.27 ([M/2+H]$^+$)) was detected. The reaction mixture was concentrated under reduced pressure to remove solvent to give a residue. The residue was purified by prep-HPLC (TFA condition). COM470 (40 mg, 25.11 μmol, 84.41% yield) was obtained as a white solid.

COM471

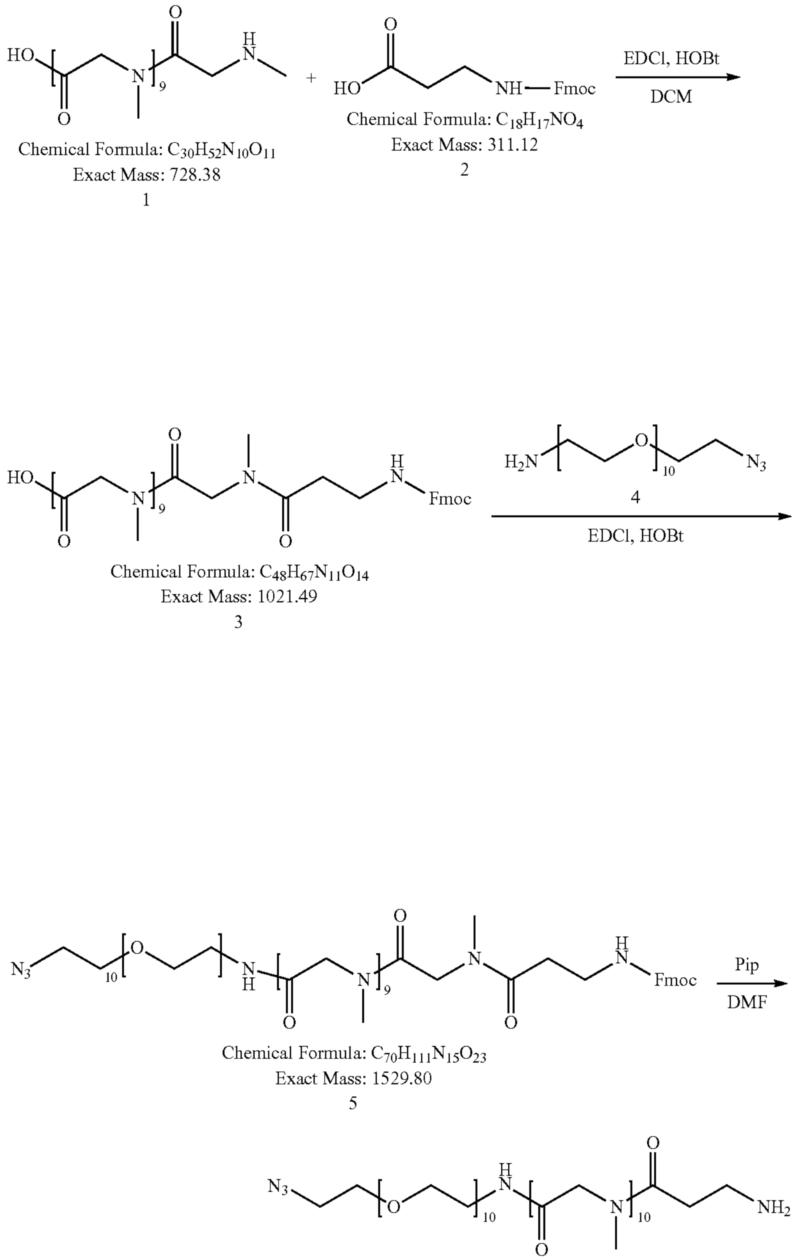

Chemical Formula: $C_{30}H_{52}N_{10}O_{11}$
Exact Mass: 728.38
1

Chemical Formula: $C_{18}H_{17}NO_4$
Exact Mass: 311.12
2

Chemical Formula: $C_{48}H_{67}N_{11}O_{14}$
Exact Mass: 1021.49
3

Chemical Formula: $C_{70}H_{111}N_{15}O_{23}$
Exact Mass: 1529.80
5

H2N-(B-Ala)-Sar10-Peg10-N3
COM00000471

A mixture of compound 1 (900 mg, 1.23 mmol, 1.0 eq) and compound 2 (1.0 g, 3.21 mmol, 2.6 eq) was dissolved in DCM (20 mL), following by addition of (284.0 mg, 1.48 mmol, 1.2 eq), HOBt (200.2 mg, 1.48 mmol, 1.2 eq). The mixture was stirred at 25° C. for 2 hr. LC-MS showed compound 1 was consumed completely and one peak with desired m/z (calculated MW: 1021.49, observed m/z: 1022.2 ($[M+H]^+$)) was detected. The reaction mixture was concentrated under reduced pressure to remove solvent. The residue was purified by prep-HPLC (TFA condition). Compound 3 (0.900 g, 880.53 μmol, 71.30% yield) was obtained as a white solid.

A mixture of compound 3 (500.0 mg, 489.19 μmol, 1.0 eq), compound 4 (257.6 mg, 489.19 μmol, 1.0 eq) was dissolved in DCM (5 mL), following by addition of HOBt (132.2 mg, 978.37 μmol, 2.0 eq), EDCl (187.6 mg, 978.37 μmol, 2.0 eq). The mixture was stirred at 25-30° C. for 2 hrs. LC-MS showed compound 3 was consumed completely and one main peak with desired m/z (MW: 1529.80 observed m/z: 765.9 ($[M/2+H]^+$) was detected. The reaction mixture was concentrated under reduced pressure to remove solvent to give a residue. The residue was purified by prep-HPLC (neutral condition). Compound 3 (420 mg, 246.94 μmol, 50.48% yield) was obtained as colorless oil.

Compound 5 (420 mg, 274.38 μmol, 1.0 eq) was dissolved in DMF (4 mL), following by addition of piperidine (865.2 mg, 10.16 mmol, 1 mL, 37 eq). The mixture was stirred at 25-30° C. for 2 hr. LC-MS showed compound 5 was consumed completely and one main peak with desired m/z (calculated MW: 1308.48, observed m/z: 654.8 ($[M/2+H]^+$) was detected. The crude product was purified by prep-HPLC (TFA condition). COM471 (386 mg, 265.50 μmol, 96.76% yield) was obtained as colorless oil.

COM472

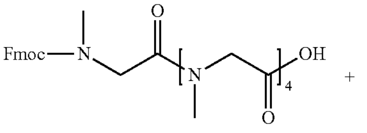

Chemical Formula: $C_{30}H_{37}N_5O_8$
Exact Mass: 595.26
1

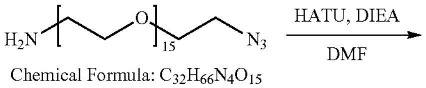

Chemical Formula: $C_{32}H_{66}N_4O_{15}$
Exact Mass: 746.45
2

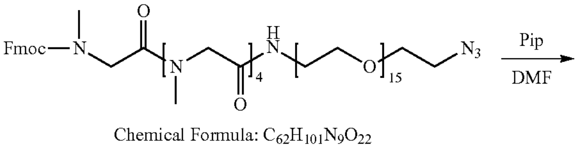

Chemical Formula: $C_{62}H_{101}N_9O_{22}$
Exact Mass: 1323.71
3

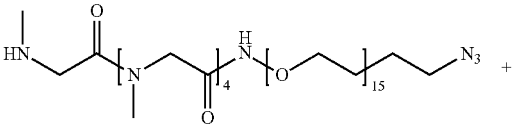

COM126

-continued

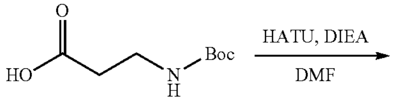

4

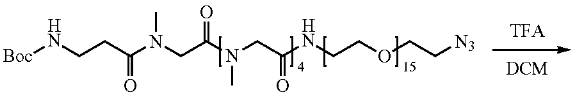

5

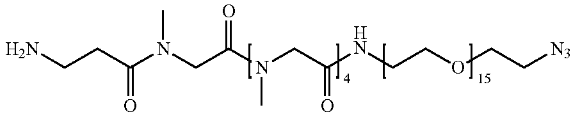

COM00000472

A mixture of compound 1 (0.5 g, 839.43 μmol, 1.0 eq), compound 2 (627.0 mg, 839.43 μmol, 1.0 eq) and DIEA (217.0 mg, 1.68 mmol, 292.4 μL, 2.0 eq) was dissolved in DMF (2 mL), then HATU (319.2 mg, 839.4 μmol, 1.0 eq) was added to the mixture. The mixture was then stirred at 25° C. for 30 min. TLC ($DCM:CH_3OH=10:1$, $R_f=0.24$) showed compound 1 was consumed completely and one new spot formed. The solvent was evaporated to produce compound 3 (0.45 g, 339.75 μmol, 40.47% yield, crude) as colorless oil, which was used in next step without further purification.

Compound 3 (450.0 mg, 339.75 μmol, 1.0 eq) was dissolved in DMF (8 mL), following by addition of piperidine (2 mL). The mixture was stirred for 15 mins at 25° C. LC-MS showed compound 3 was consumed completely and one main peak with desired (calculated MW: 1102.27, observed m/z: 552.1 ($[M/2+H]^+$)) was detected. The residue was purified by prep-HPLC (TFA condition). Compound 3 (370.0 mg, 335.67 μmol, 98.80% yield) was obtained as colorless oil.

To a solution of COM126 (60 mg, 54.45 μmol, 1.0 eq), compound 4 (15.5 mg, 81.68 μmol, 1.5 eq) in DMF (5 mL) was added HATU (31 mg, 81.68 μmol, 1.5 eq) and DIEA (10.5 mg, 61.68 μmol, 15 μL, 1.5 eq). The mixture was stirred at 30° C. for 2 hr. LC-MS showed COM126 was consumed completely and one main peak with desired was detected. The mixture was evaporated to remove solvent, and compound 5 (30 mg, crude) was obtained as colorless oil, which was used in next step without further purification.

Compound 5 (30 mg, 23.57 μmol, 1.0 eq) was dissolved DCM (4.5 mL), and then TFA (0.5 mL) was added and the mixture was stirred at 25-30° C. for 2 hr. LC-MS showed compound 5 was consumed completely and one main peak with desired was detected. The residue was purified by prep-HPLC (TFA condition). COM472 (10 mg, 8.52 μmol) was obtained as white solid.

COM473

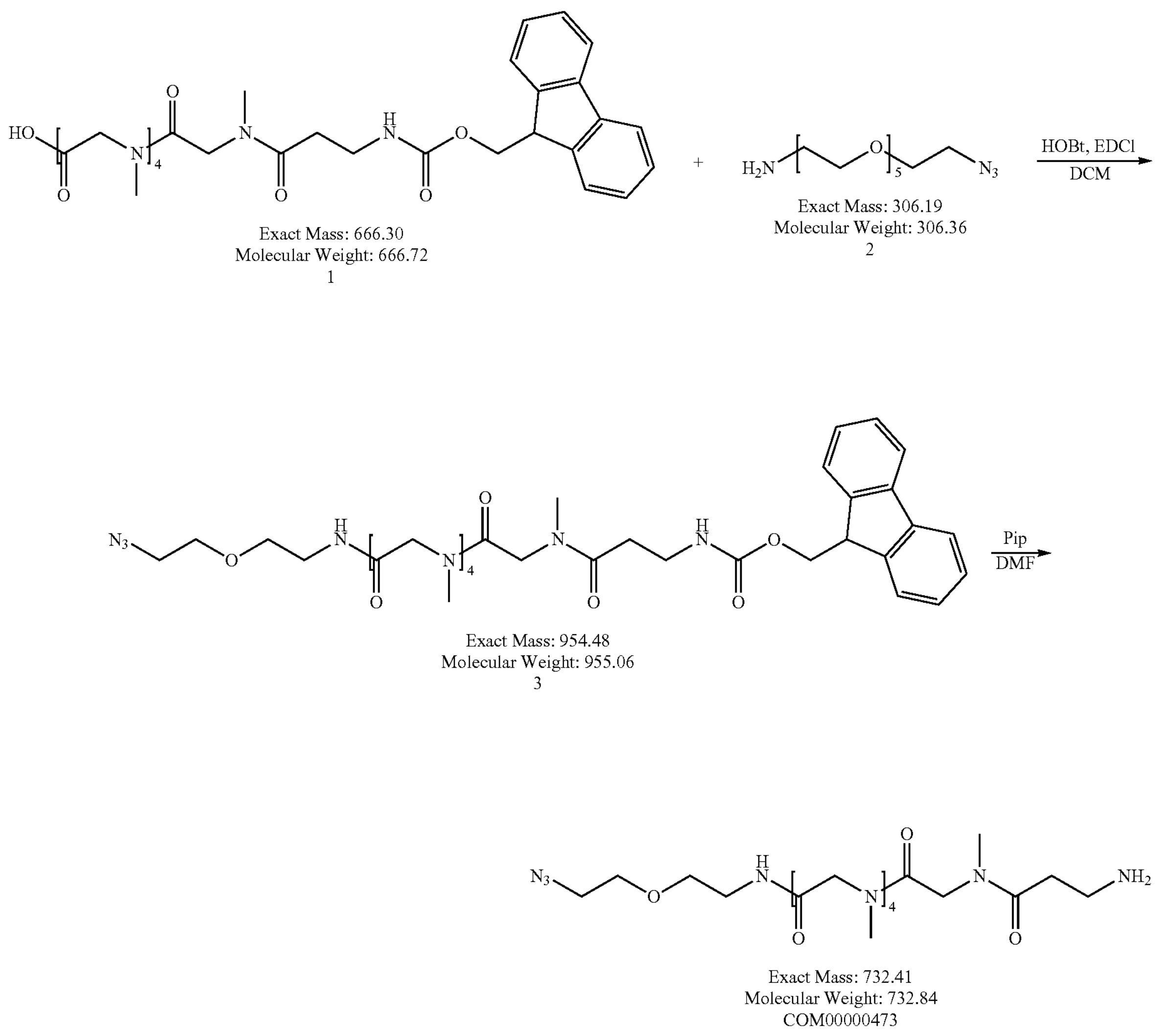

A mixture of compound 1 (300 mg, 449.96 μmol, 1.0 eq), compound 2 (138 mg, 449.96 μmol, 1.0 eq), HOBt (122 mg, 899.93 μmol, 2.0 eq), EDCl (173 mg, 899.93 μmol, 2.0 eq) was dissolved in DCM (10 mL, pre-degassed and purged with $N_2$ for 3 times), and then the mixture was stirred at 20-25° C. for 1 hr under $N_2$ atmosphere. LC-MS showed compound 1 was consumed completely and one main peak with desired (MW: 955.06, observed m/z: 955.3 ($[M+H]^+$)) was detected. The reaction mixture was concentrated under reduced pressure to remove solvent. The mixture was evaporated under reduced pressure and compound 3 (300 mg, crude) was obtained as yellow oil.

Compound 3 (300 mg, 314.12 μmol, 1.0 eq) was dissolved in DMF (4 mL), and then piperdine (1 mL) was added and the mixture was stirred at 20-25° C. for 1 hr. LC-MS showed compound 3 was consumed completely and one main peak with desired m/z (MW: 732.83 observed m/z: 733.2 ($[M+H]^+$)) was detected. The residue was purified by prep-HPLC (neutral condition). COM473 (160 mg, 218.33 μmol, 69.51% yield) was obtained as a colorless oil.

Example 2: Synthesis of EphA2/CD137 Binding Heterotandem Bicyclic Peptides BCY9173

Procedure for Preparation of BCY9172-PEG12-$N_3$

BCY00009172 + NHS-PEG12-$N_3$

1

$NaHCO_3$

MeCN/$H_2O$

BCY00009172-PEG12-$N_3$

2

BCY9172 (520 mg, 248.16 μmol, 1 eq) and compound 1 (370 mg, 499.47 μmol, 2.01 eq), were dissolved in in DMF (5 mL) was added DIEA (48.11 mg, 372.24 μmol, 64.84 μL, 1.5 eq) and then the mixture was stirred at 30° C. for 12 hr. LC-MS showed BCY9172 was consumed completely and one main peak with desired m/z (calculated MW: 2721.12 observed m/z: 1360.9 ($[M/2+H]^+$)) was detected. The reaction mixture was purified by prep-HPLC (TFA condition)

and compound 2 (284 mg, 101.10 μmol, 40.74% yield, 96.87% purity) was obtained as a white solid.

CuSO4
VcNa
THPTA
BCY00009172-PEG12-$N_3$ + BCY00006169
t-BuOH/$H_2O$
2
BCY00009173

Procedure for Preparation of BCY9173

This reaction was performed in two independent containers in parallel. For one container, Compound 2 (100 mg, 36.75 μmol, 1.0 eq) and BCY6169 (120 mg, 36.78 μmol, 1.0 eq) were first dissolved in 10 mL of t-BuOH/$H_2O$ (1:1), and then $CuSO_4$ (0.4 M, 91.9 μL, 1.0 eq), VcNa (0.4 M, 183.8 μL, 2.0 eq) and THPTA (0.4 M, 91.9 μL, 1.0 eq) was added. Finally 1 M $NH_4HCO_3$ was added to adjust pH to 8. All solvents here were degassed and purged with $N_2$ for 3 times. The reaction mixture was stirred at 40° C. for 16 hr under $N_2$ atmosphere. LC-MS showed compound 2 was consumed completely and one main peak with desired m/z (calculated MW: 5983.85 observed m/z: 997.6600 ($[M/6+H]^+$) and 1197.2300 ($[M/5+H]^+$)). The reaction mixture was purified by prep-HPLC (TFA condition) and BCY9173 (218 mg, 34.97 μmol, 47.58% yield, 96% purity) was obtained as a white solid.

BCY7985

General Procedure for Preparation of BCY7859

N3-PEG12-COOH
1) HOSu, EDCl, DMA/DCM
2) BCY00007732, DIEA, DMF
BCY00007859

To a solution of N3-PEG12-COOH (250 mg, 388 μmol) and HOSu (67.0 mg, 583 μmol) in DMA (4.5 mL) and DCM (1.5 mL) was added EDCl (89.3 mg, 466 μmol) with stirring at 20° C. for 16 hr. To another 50 mL of round flask containing a mixture of BCY7732 (855 mg, 388 μmol) in 5 mL of DMA was added DIEA (186 mg, 1.44 mmol, 250 μL) with stirring for 10 min. Then the initial reaction mixture was added to the flask with further stirring at 20° C. for additional 5 hr. LC-MS (ES8396-307-P1B1) showed BCY7732 was consumed completely and one main peak with desired mass was detected. The resulting reaction mixture was purified directly by prep-HPLC (TFA condition) to give compound BCY7859 (621 mg, 200 μmol, 51.6% yield, TFA salt) as a white solid.

General Procedure for Preparation of BCY6169

BCY00006099
PYA-NHS
DIEA, DMA
BCY00006169

To a solution of BCY6099 (300 mg, 94.3 μmol) in DMA (2 mL) was added DIEA (36.6 mg, 283 μmol, 49.3 μL) with stirring for 10 min. After, PYA-NHS (36.8 mg, 189 μmol) was added with further stirring at 20° C. for additional 15 hr. LC-MS showed BCY6099 was consumed completely and one main peak with desired mass was detected. The reaction mixture was purified by prep-HPLC (neutral condition) to give compound BCY6169 (299 mg, 86.2 μmol, 91.5% yield) as a white solid.

General Procedure for Preparation of BCY7985

BCY00006169 + BCY00007859
Vc, $CuSO_4$
DMF, $H_2O$
BCY00007985

To a solution of BCY7859 (220 mg, 77.8 μmol) and BCY6169 (251 mg, 77.1 μmol) in DMF (5 mL) purged by nitrogen for 2 hr was added aqueous ascorbic acid solution (0.8 M, 963 μL) followed by adding aqueous $CuSO_4$ (0.8 M, 289 μL) under nitrogen atmosphere. Then the mixture was stirred at 20° C. for 2 hr. LC-MS showed BCY6169 was consumed completely and one main peak with desired mass was detected. The reaction mixture was directly purified by prep-HPLC (TFA condition) to give compound BCY7985 (283 mg, 43.4 μmol, 56.3% yield, TFA) as a white solid.

BCY8942

General Procedure for Preparation of BCY8940

BCY00008045 + N3—PEG12—COOH
EDCl, HOSu
DMA•DCM
BCY00008940

To a solution of N3-PEG12-COOH (120 mg, 186 μmol, 1.0 eq) in DMA (3 mL) and DCM (1 mL) was added HOSu (32.2 mg, 280 μmol, 1.5 eq) with stirring. Then EDCl (42.9 mg, 224 μmol, 1.2 eq) was added to the mixture with further stirring for additional 7 hr at 20° C. LCMS showed the activated ester was formed completely. To another flask with BCY8045 (410 mg, 186 μmol, 1.0 eq) in DMA (3 mL) was added DIEA (120 mg, 932 μmol, 162 μL, 5.0 eq) with stirring, then the activated ester was added and the mixture was stirred for 18 hr at 20° C. LC-MS showed one main peak with desired m/z was detected. The reaction mixture was concentrated in vacuum to remove the DCM. The resulting mixture was purified by prep-HPLC (TFA condition) to give BCY8940 (190 mg, 67.2 μmol, 36.1% yield) as a white solid.

General Procedure for Preparation of BCY8942

BCY00006169
BCY00008940
Vc, $CuSO_4$, DMF, $H_2O$
BCY00008942

To a solution of BCY8940 (28.6 mg, 10.1 μmol, 1.1 eq) and BCY6169 (30.0 mg, 9.19 μmol, 1.0 eq) in DMF (2.0 mL) was added (2R)-2-[(1S)-1,2-dihydroxyethyl]-3, 4-dihydroxy-2H-furan-5-one (1.0 M, 92.0 μL) and $CuSO_4$ (1.0 M, 27.6 μL) with stirring under nitrogen atmosphere for 2 hr at 20° C. LC-MS showed BCY6169 was consumed completely and one main peak with desired m/z (calculated MW: 6089.91 observed m/z: 1218.4 ($[M/5+H]^+$), 1016.0 ($[M/6+H]^+$), 870.7 ($[M/7+H]^+$) was detected. The reaction mixture was purified by prep-HPLC (TFA condition) to give compound BCY8942 (15.4 mg, 2.46 μmol, 26.8% yield, 97.3% purity) as a white solid.

BCY8943

General Procedure for Preparation of BCY8941

BCY00006015 +

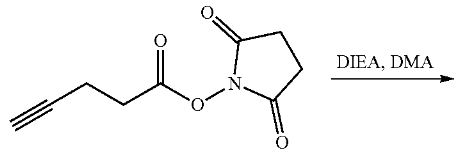

BCY00008941

To a solution of BCY6015 (a peptide identical to BCY8941 except for the absence of a PYA moiety; 100 mg, 32.9 μmol) in DMA (2 mL) was added DIEA (12.8 mg, 98.7 μmol, 17.2 μL) with stirring for 10 min. Then (2,5-dioxopyrrolidin-1-yl) pent-4-ynoate (12.8 mg, 65.8 μmol) was added to the mixture, following with further stirring at 20° C. for 16 hr. LC-MS showed compound 1 was consumed completely and one main peak with desired m/z (calculated MW: 3119.60, observed m/z: 1040.5 ([M/3+H]$^+$) was detected. The mixture was purified by prep-HPLC (neutral condition) to give compound BCY8941 (90.0 mg, 28.9 μmol, 87.7% yield) as a white solid.

General Procedure for Preparation of BCY8943

BCY00008941 BCY00007859 / Vc, $CuSO_4$, DMF, $H_2O$ BCY00008943

To a solution of BCY7859 (which may be prepared as described in BCY7985; 40.0 mg, 14.2 μmol) and BCY8941 (42.0 mg, 13.5 μmol) in DMSO (2 mL, pre-purged by nitrogen for 1 hr) was added (2R)-2-[(1S)-1,2-dihydroxyethyl]-3,4-dihydroxy-2H-furan-5-one (1.0 M, 270 μL) and $CuSO_4$ (1.0 M, 80.9 μL). The mixture was purged with nitrogen for 3 times and stirred at 15° C. for 2 hr. LC-MS showed BCY8941 was consumed completely and one main peak with desired m/z (calculated MW: 5946.77, observed m/z: 1190.2 ([M/5+H]$^+$), 991.5 ([M/6+H]$^+$), 849.9 ([M/7+H]$^+$) was detected. The reaction mixture was purified by prep-HPLC (A: 0.075% TFA in $H_2O$, B: ACN) to give compound BCY8943 (11.5 mg, 1.90 μmol, 14.1% yield, 98.1% purity) as a white solid.

BCY9647

Procedure for Preparation of Compound 2

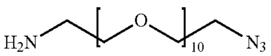

+

Exact Mass: 526.32139
Molecular Weight: 526.62144

COM00000134

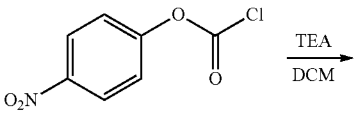

Exact Mass: 200.98
Molecular Weight: 201.56

1

-continued

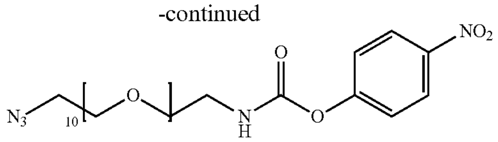

Exact Mass: 691.32760
Molecular Weight: 691.72446

2

To a solution of COM134 (30.0 mg, 57.0 μmol, 1.0 eq), compound 1 (17.2 mg, 85.3 μmol, 1.5 eq) in DCM (0.5 mL) was added TEA (8.65 mg, 11.9 μL, 1.5 eq). The mixture was stirred at 25° C. for 1 hr. LC-MS showed COM134 was consumed completely and one main peak with desired mass (calculated MW: 691.72, observed m/z: 692.3 ([M+H]$^+$) and 709.3 ([M+NH4]$^+$)) was detected. The reaction mixture was concentrated under reduced pressure, and then lyophilized to produce crude compound 2 (30.5 mg, crude) as a white Procedure for Preparation of Compound-3

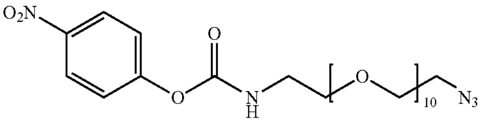

+

Exact Mass: 691.32760
Molecular Weight: 691.72446

2

BCY000069099 DIEA / DMF

Exact Mass: 3180.55
Molecular Weight: 3182.66

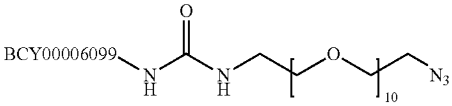

Exact Mass: 3732.85
Molecular Weight: 3735.28

3

To a solution of compound 2 (10 mg, 1.0 eq) in DMF (1 mL) was added BCY6099 (46 mg, 1.0 eq) and DIEA (5.61 mg, 7.55 μL, 3.0 eq). The mixture was stirred at 30° C. for 2 hr. LC-MS showed compound 2 was consumed completely and one main peak with desired m/z (calculated MW: 3735.28 observed m/z: 1245.9 ([M/3+H]$^+$) and 934.5 ([M/4+H]$^+$)) was detected. The reaction mixture was filtered and concentrated under reduced pressure to give a residue. The crude product was purified by reversed-phase HPLC (TFA condition). Compound 3 (34 mg, 62.96% yield, 100% purity) was obtained as a white solid.

Procedure for Preparation of BCY9647

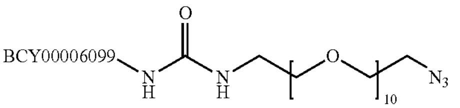

+

Exact Mass: 3732.85
Molecular Weight: 3735.28

3

-continued

BCY00007741

$CuSO_4$, VcNa THPTA t-BuOH:H2O

Exact Mass: 2279.93
Molecular Weight: 2281.54

BCY00009647

Exact Mass: 6012.79
Molecular Weight: 6016.82

A mixture of Compound 3 (34 mg, 9.10 μmol, 1.0 eq), BCY7741 (23 mg, 10.08 μmol, 1.11 eq), and THPTA (0.4 M, 11.4 μL, 0.5 eq) was dissolved in t-BuOH/$H_2O$ (1:1, 2 mL, pre-degassed and purged with $N_2$ for 3 times), and then $CuSO_4$ (0.4 M, 11.4 μL, 0.5 eq) and VcNa (0.4 M, 22.8 μL, 1 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed compound 3 was consumed completely and one main peak with desired m/z (calculated MW: 6016.82, observed m/z: 1204.1 ([M/5+H]$^+$), 1003.5 ([M/6+H]$^+$), 860.3 ([M/7+H]$^+$)). The reaction mixture was directly purified by prep-HPLC (TFA condition). BCY9647 (31.2 mg, 54.67% yield, 95.96% purity) was obtained as a white solid.

BCY9648

Procedure for Preparation of Compound 2

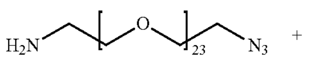

Exact Mass: 1098.66219
Molecular Weight: 1099.30472

COM00000135

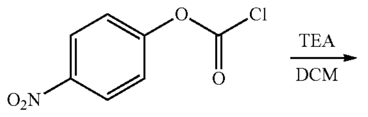

Exact Mass: 200.98
Molecular Weight: 201.56

1

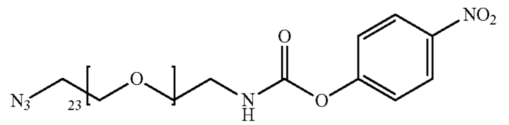

Exact Mass: 1263.66839
Molecular Weight: 1264.40774

2

To a solution of COM135 (30 mg, 27.29 μmol, 1.0 eq), compound 1 (8.25 mg, 40.94 μmol, 1.5 eq) in DCM (0.5 mL) was added TEA (4.14 mg, 40.94 μmol, 5.70 μL, 1.5 eq). The mixture was stirred at 25-30° C. for 1 hr. LC-MS showed COM135 was consumed completely and one main peak with desired mass [calculated MW: 1264.41, observed m/z: 1281.4 ([M+$NH_4$]$^+$), 649.8 ([M/2+H]$^+$)] was detected. The reaction mixture was concentrated under reduced pressure to remove solvent to give a residue. The residue was purified by prep-HPLC (TFA condition) to give compound 2 (18 mg, 14.2 μmol, 52.14% yield).

Procedure for Preparation of Compound 3

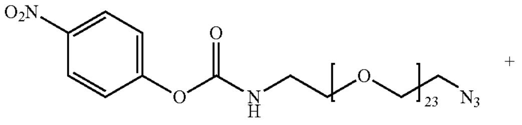

Exact Mass: 1263.66839
Molecular Weight: 1264.40774

2

BCY000069099

DIEA

DMF

Exact Mass: 3180.55
Molecular Weight: 3182.66

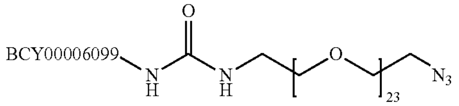

Exact Mass: 4305.19
Molecular Weight: 4307.96

3

To a solution of compound 3 (9 mg, 7.12 μmol, 1 eq) in DMF (1 mL) was added BCY6099 (23 mg, 7.23 μmol, 1.02 eq) and DIEA (2.76 mg, 21.35 μmol, 3.72 μL, 3.0 eq). The mixture was stirred at 30° C. for 2 hr. LC-MS showed compound 2 was consumed completely and one main peak with desired m/z (calculated MW: 4307.96 observed m/z: 1436.9 ([M/3+H]$^+$), 1077.9 ([M/4+H]$^+$), 862.5 ([M/5+H]$^+$)) was detected. The reaction mixture was filtered and concentrated under reduced pressure to give a residue. The crude product was purified by reversed-phase HPLC (TFA condition). Compound 3 (14.6 mg, 47.61% yield, 100% purity) was obtained as a white solid.

Procedure for Preparation of RCY9648

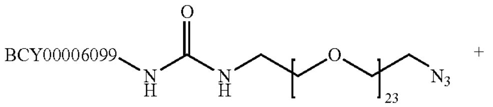

Exact Mass: 4305.19
Molecular Weight: 4307.96

3

BCY00007741

$CuSO_4$, VcNa THPTA t-BuOH:H2O

Exact Mass: 2279.93
Molecular Weight: 2281.54

BCY00009648

Exact Mass: 6585.13
Molecular Weight: 6589.50

A mixture of compound 3 (14.6 mg, 3.39 μmol, 1 eq), BCY7741 (8.5 mg, 3.73 μmol, 1.1 eq) and THPTA (0.4 M, 4.3 μL, 0.5 eq) was dissolved in t-BuOH/$H_2O$ (1:1, 2 mL, pre-degassed and purged with $N_2$ for 3 times), and then $CuSO_4$ (0.4 M, 4.3 μL, 0.5 eq) and VcNa (0.4 M, 8.6 μL, 1.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed compound 3 was consumed completely and one main peak with desired m/z (MW: 6589.50 observed m/z: 1098.8 ([M/6+H]$^+$), 942.1 ([M/7+H]$^+$), 824.6 ([M/8+H]$^+$)). The reaction mixture was directly purified by prep-HPLC (TFA condition). BCY9648 (14.7 mg, 63.34% yield, 96.22% purity) was obtained as a white solid.

BCY9655

Procedure for Preparation of Compound 2

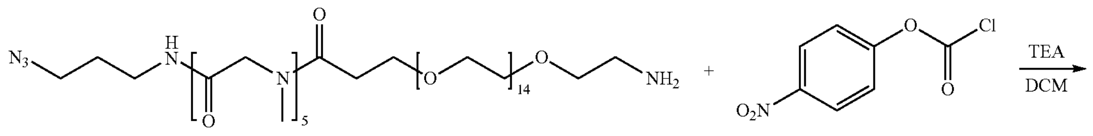

Exact Mass: 1186.69
Molecular Weight: 1187.38

COM00000128

Exact Mass: 200.98
Molecular Weight: 201.56

1

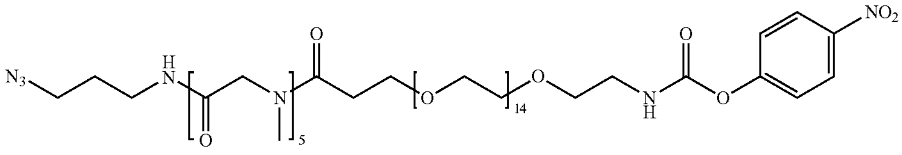

Exact Mass: 1351.70
Molecular Weight: 1352.48

2

To a solution of COM128 (120 mg, 101.06 μmol, 1.0 eq), compound 1 (25 mg, 124.03 μmol, 1.25 eq) in DCM (0.5 mL) was added TEA (15.34 mg, 151.59 μmol, 21.10 μL, 1.5 eq). The mixture was stirred at 25° C. for 1 hr. LC-MS showed one new peak with desired m/z (calculated MW: 1352.48, observed m/z: 676.8 ($[M/2+H]^+$), 1369.3 ($[M+NH4]^+$)) was detected. The reaction mixture was concentrated under reduced pressure to remove solvent to give a residue. The residue was purified by prep-HPLC (neutral condition). Compound 2 (14 mg, 8.99 μmol, 8.90% yield, 86.86% purity) was obtained as colorless oil.

Procedure for Preparation of Compound 3

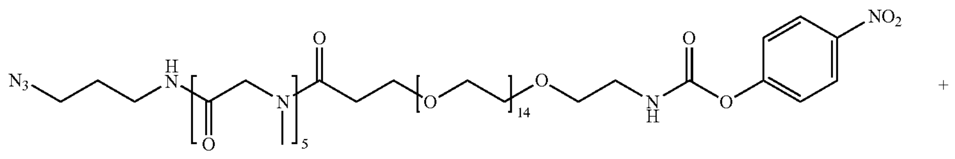

Exact Mass: 1351.70
Molecular Weight: 1352.48

2

BCY00006099

Exact Mass: 3180.55
Molecular Weight: 3182.66

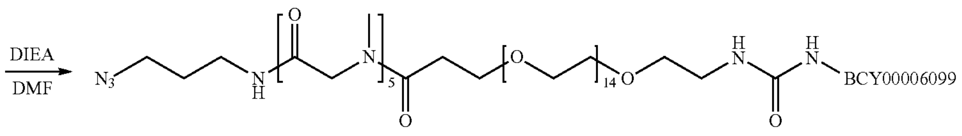

Exact Mass: 4393.22
Molecular Weight: 4396.03

3

To a solution of compound 2 (7 mg, 5.18 μmol, 1.0 eq) and BCY6099 (16 mg, 5.03 μmol, 1.0 eq) in DMF (2 mL) was added DIEA (2.01 mg, 15.53 μmol, 2.70 μL). The mixture was stirred at 30° C. for 2 hrs. LC-MS showed compound 2 was consumed completely and one main peak with desired m/z (calculated MW: 4396.02, observed m/z: 879.8 ($[M/5+H]^+$) and 1099.8 ($[M/4+H]^+$)) was detected. The reaction mixture was filtered and concentrated under reduced pressure to give a residue. The crude product was purified by reversed-phase HPLC (0.1% TFA condition). Compound 3 (11.8 mg, 48.29% yield, 93.11% purity) was obtained as a white solid.

Procedure for Preparation of BCY9655

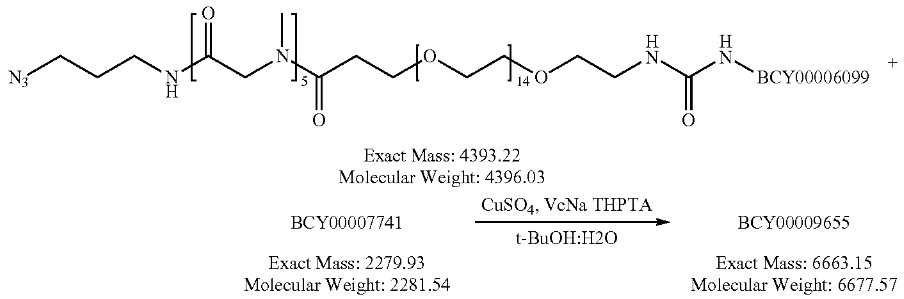

A mixture of Compound 3 (11.8 mg, 2.69 μmol, 1.0 eq), BCY7741 (7.0 mg, 3.07 μmol, 1.14 eq), and THPTA (0.4 M, 6.8 μL, 1 eq) was dissolved in t-BuOH/$H_2O$ (1:1, 2 mL, pre-degassed and purged with $N_2$ for 3 times), and then $CuSO_4$ (0.4 M, 6.8 μL, 1.0 eq) and VcNa (0.4 M, 13.6 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed compound 3 was consumed completely and one main peak with desired m/z (calculated MW: 6677.57, observed m/z: 1113.7 ($[M/6+H]^+$), 954.7 ($[M/7+H]^+$)). The reaction mixture was directly purified by prep-HPLC (TFA condition). BCY9655 (1.9 mg, 0.26 μmol, 9.65% yield, 91.15% purity) was obtained as a white solid.

BCY9656

Procedure for Preparation of Compound 2

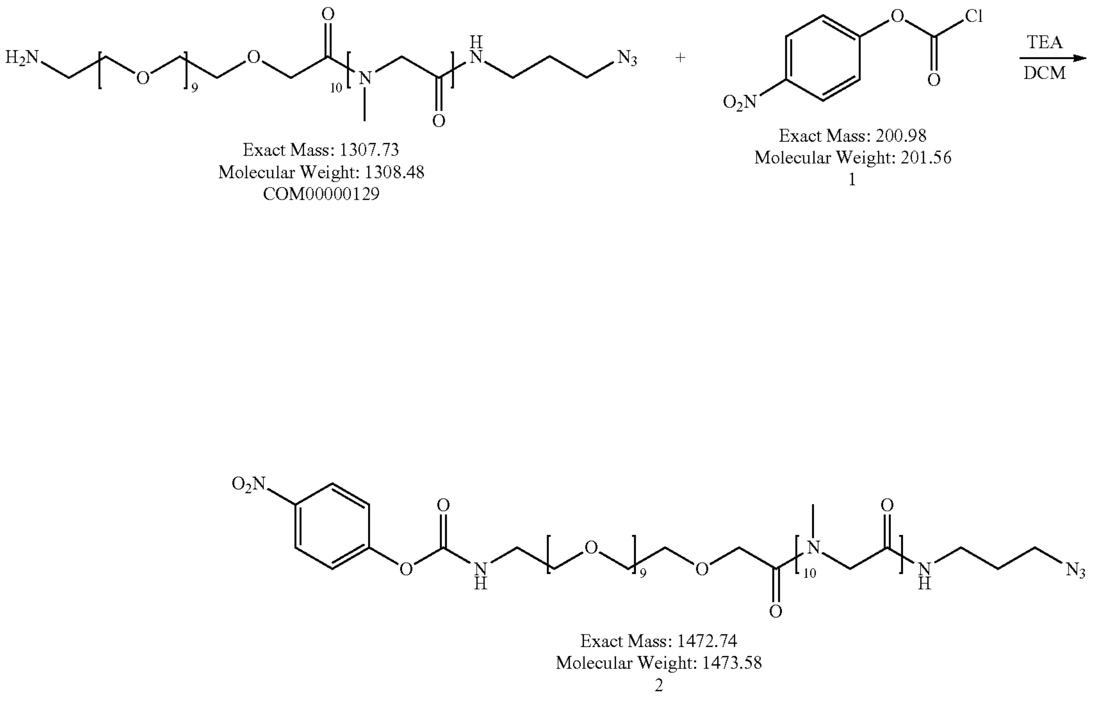

To a solution of COM129 (30.0 mg, 22.93 μmol, 1.0 eq), compound 1 (6.9 mg, 34.39 μmol, 1.5 eq) in DCM (3 mL) was added TEA (3.5 mg, 34.39 μmol, 4.8 μL, 1.5 eq). The mixture was degassed and purged with $N_2$ for 3 times, and then the mixture was stirred at 25° C. for 1 hr under $N_2$ atmosphere. LC-MS showed COM129 was consumed completely and one main peak with desired m/z (calculated MW: 1473.58, observed m/z: 737.3 ($[M/2+H]^+$)) was detected. The reaction mixture was concentrated under reduced pressure to remove solvent to give a residue. The residue was purified by prep-HPLC (neutral condition) to produce Compound 2 (12.3 mg, 8.35 μmol, 36.41% yield) as a white solid.

Procedure for Preparation of Compound 3

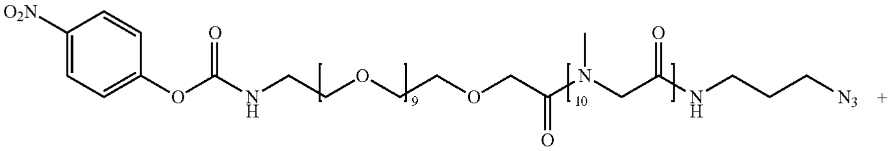

Exact Mass: 1472.74
Molecular Weight: 1473.58
2

\+ BCY00006099
Exact Mass: 3732.85
Molecular Weight: 3735.28

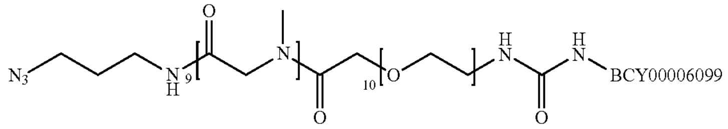

Exact Mass: 4514.26
Molecular Weight: 4517.13
3

To a solution of compound 2 (9.26 mg, 6.28 μmol, 1.0 eq) and BCY6099 (10 mg, 3.14 μmol, 0.5 eq) in DMF (3 mL) was added TEA (0.7 mg, 6.93 μmol, 1 μL, 1.1 eq). The mixture was degassed and purged with $N_2$ for 3 times, and then the mixture was stirred at 25-30° C. for 1 hr under $N_2$ atmosphere. LC-MS showed compound 2 was consumed completely and one main peak with desired m/z (calculated MW: 4517.12, observed m/z: 1129.8 ($[M/4+H]^+$), 904.1 ($[M/5+H]^+$), 753.7 ($[M/6+H]^+$)) was detected. The reaction mixture was filtered and concentrated under reduced pressure to give a residue. The crude product was purified by reversed-phase HPLC (TFA condition). Compound 3 (12 mg, 72.36% yield, 85.58% purity) was obtained as a white solid.

Procedure for Preparation of BCY9656

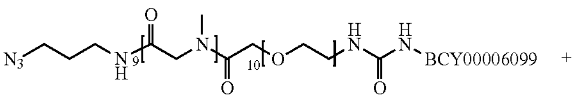

Exact Mass: 4514.26
Molecular Weight: 4517.13
3

-continued

BCY00007741
Exact Mass: 2279.93
Molecular Weight: 2281.54

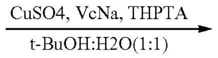

BCY00009656
Exact Mass: 6794.19
Molecular Weight: 6798.67

A mixture of Compound 3 (11 mg, 2.44 μmol, 1.0 eq), BCY7741 (6.0 mg, 2.63 μmol, 1.08 eq), and THPTA (0.4 M, 6.1 μL, 1.0 eq) was dissolved in t-BuOH/$H_2O$ (1:1, 2 mL, pre-degassed and purged with $N_2$ for 3 times), and then $CuSO_4$ (0.4 M, 6.1 μL, 1.0 eq) and VcNa (0.4 M, 12.2 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z (calculated MW: 6798.66, observed m/z: 1133.8 ($[M/6+H]^+$), 971.9 ($[M/7+H]^+$), 850.7 ($[M/8+H]^+$)) was detected. The reaction mixture was directly purified by prep-HPLC (TFA condition). BCY9656 (6.8 mg, 37.36% yield, 90.97% purity) was obtained as a white solid.

BCY9657

Procedure for Preparation of Compound 2

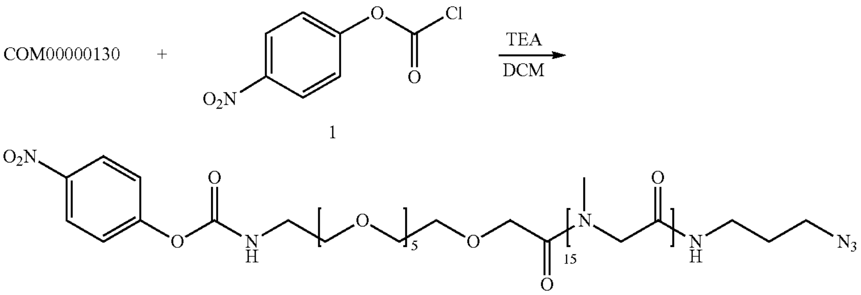

1

2

To a solution of COM130 (30.0 mg, 20.78 μmol, 1.0 eq), compound 1 (6.3 mg, 31.17 μmol, 1.5 eq) in DCM (3 mL) was added TEA (3.2 mg, 31.17 μmol, 4.4 μL, 1.5 eq). The mixture was stirred at 25-30° C. for 1 hr. LC-MS showed COM130 was consumed completely and one main peak with desired m/z (calculated MW: 1608.7, observed m/z: 804.8 ([M/2+H]$^+$)) was detected. The reaction mixture was concentrated under reduced pressure and lyophilized to produce compound 2 (7.9 mg, crude) as a white solid.

Procedure for Preparation of Compound 3

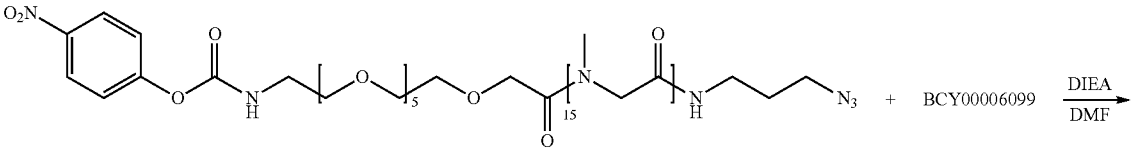

2

[BCY00006099]-[COM00000130]

3

To a solution of compound 2 (7.9 mg, 4.91 μmol, 1.0 eq) and BCY6099 (16 mg, 5.03 μmol, 1.02 eq) in DMF (1 mL) was added DIEA (1.9 mg, 14.73 μmol, 2.6 μL, 3.0 eq). The mixture was stirred at 30° C. for 2 hrs. LC-MS showed compound 2 was consumed completely and one main peak with desired m/z (calculated MW: 4652.25, observed m/z: 1551.3 ([M/3+H]$^+$), 1163.6 ([M/4]$^+$), 931.1 ([M/5+H]$^+$), 776.1 ([M/6+H]$^+$)) was detected. The reaction mixture was filtered and concentrated under reduced pressure to give a residue. The crude product was purified by reversed-phase HPLC (TFA condition). Compound 3 (13.3 mg, 2.86 μmol, 53.22% yield, 91.42% purity) was obtained as a white solid.

Procedure for Preparation of BCY9657

[BCY00006099]-[COM00000130] +

3

BCY00007741

$CuSO_4$ VcNa THPTA t-BuOH/$H_2O$

BCY00009657

A mixture of Compound 3 (13.3 mg, 2.86 μmol, 1.0 eq), BCY7741 (7.0 mg, 3.07 μmol, 1.03 eq), and THPTA (0.4 M, 7.5 μL, 1.0 eq) was dissolved in t-BuOH/$H_2O$ (1:1, 2 mL, pre-degassed and purged with $N_2$ for 3 times), and then $CuSO_4$ (0.4 M, 7.5 μL, 1 eq) and VcNa (0.4 M, 15 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 6933.78, observed m/z: 1156.7 ([M/6+H]$^+$), 991.4 ([M/7+H]$^+$), 867.4 ([M/8+H]$^+$)] was detected. The reaction mixture was directly purified by prep-HPLC (TFA condition). BCY9657 (8.4 mg, 40.21% yield, 94.9% purity) was obtained as a white solid.

BCY9658

Procedure for Preparation of Compound 2

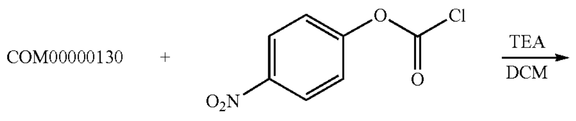

1

-continued

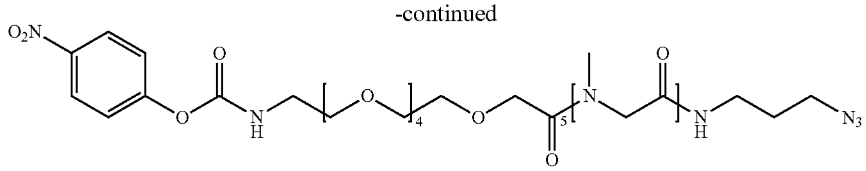

2

To a solution of COM131 (167.0 mg, 227.89 μmol, 1.0 eq), compound 1 (55.0 mg, 272.87 μmol, 1.2 eq) in DCM (5 mL) was added TEA (36.4 mg, 359.23 μmol, 50.0 μL, 1.6 eq). The mixture was stirred at 25-30° C. for 1 hr. LC-MS showed one main peak with desired m/z (MW: 897.93 observed 920.3 ([M+Na$^+$]) was detected. The reaction mixture was concentrated under reduced pressure to remove solvent to give a residue. The residue was purified by prep-HPLC (TFA condition). Compound 2 (35 mg, 33.74 μmol, 14.81% yield, 86.56% purity) was obtained as colorless oil.

Procedure for Preparation of Compound 3

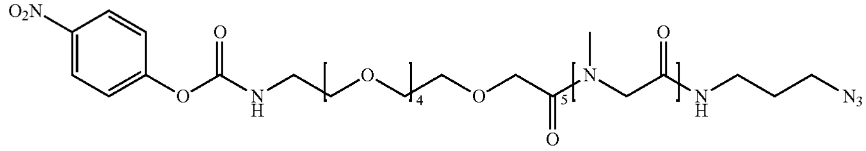

2

+ BCY00006099

TEA

DMF

[BCY00006099]-[COM00000131]

3

To a solution of compound 2 (15 mg, 16.71 μmol, 1.0 eq) and BCY6099 (53 mg, 16.65 μmol, 1.0 eq) in DMF (2 mL) was added DIEA (6.48 mg, 65.05 μmol, 50.1 μL, 4.0 eq). The mixture was stirred at 30° C. for 2 hrs. LC-MS showed compound 2 was consumed completely and one main peak with desired m/z (MW: 3941.47 observed m/z: 986.0 ([M/4+H]$^+$)) was detected. The reaction mixture was filtered and concentrated under reduced pressure to give a residue. The crude product was purified by reversed-phase HPLC (TFA condition). [BCY6099]—[COM131] (5 mg, 50.48% yield, 94.96% purity) was obtained as a white solid.

Procedure for Preparation of BCY9658

[BCY00006099]-[COM00000131] +

3

BCY00007741

$CuSO_4$ VcNa THPTA t-BuOH/$H_2O$

BCY00009658

A mixture of Compound 3 (35 mg, 8.88 μmol, 1.0 eq), BCY7741 (21 mg, 9.20 μmol, 1.03 eq), and THPTA (0.4 M, 22.2 μL, 1.0 eq) was dissolved in t-BuOH/$H_2O$ (1:1, 2 mL, pre-degassed and purged with $N_2$ for 3 times), and then $CuSO_4$ (0.4 M, 22.2 μL, 1.0 eq) and VcNa (0.4 M, 44.4 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 6223.01 observed m/z: 1038.0 ([M/6+H]$^+$) and 889.8 ([M/8+H]$^+$)] was detected. The reaction mixture was directly purified by prep-HPLC (TFA condition). BCY9658 (13.2 mg, 21.54% yield, 90.16% purity) was obtained as a white solid.

BCY9659

Procedure for Preparation of Compound 2

COM00000132 +

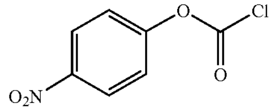

1

TEA

DCM

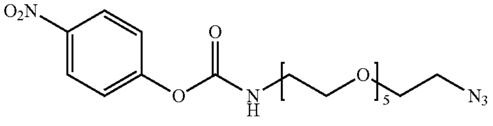

2

To a solution of COM132 (20.0 mg, 65.28 μmol, 1.0 eq), compound 1 (15.8 mg, 78.34 μmol, 1.2 eq) in DCM (5 mL) was added TEA (36.4 mg, 359.23 μmol, 50 μL, 5.5 eq). The mixture was stirred at 25° C. for 1 hr. LC-MS one main peak with desired m/z (MW: 471.46, observed m/z: 489.2 ([M+$NH_4$]$^+$)) was detected. The reaction mixture was concentrated under reduced pressure to give compound 2 (26 mg, crude) colorless oil.

Procedure for Preparation of Compound 3

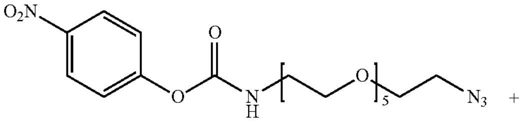

2

BCY00006099 TEA DMF [BCY00006099]-[COM00000132]

3

To a solution of compound 2 (15.0 mg, 4.71 μmol, 1.0 eq) and BCY6099 (3.33 mg, 7.07 μmol, 1.5 eq) in DMF (3 mL) was added TEA (0.7 mg, 6.93 μmol, 1 μL, 1.5 eq). The mixture was stirred at 30° C. for 2 hrs. LC-MS showed compound 2 was consumed completely and one main peak with desired m/z (MW: 3515.01, observed m/z: 1172.1 ($[M/3+H]^+$) 879.5 ($[M/4+H]^+$)) was detected. The reaction mixture was filtered and concentrated under reduced pressure to give a residue. The crude product was purified by reversed-phase HPLC (TFA condition). Compound 3 (12.7 mg, 3.26 μmol, 69.23% yield, 90.3% purity) was obtained as a white solid.

Procedure for Preparation of BCY9659

[BCY00006099]-[COM00000132] +

3

BCY00007741 $CuSO_4$ VcNa THPTA t-BuOH/$H_2O$ BCY00009659

A mixture of Compound 3 (12.7 mg, 2.89 μmol, 1.0 eq), BCY7741 (6.80 mg, 2.98 μmol, 1.03 eq), and THPTA (1.3 mg, 2.99 μmol, 1.03 eq) was dissolved in t-BuOH/$H_2O$ (1:1, 2 mL, pre-degassed and purged with $N_2$ for 3 times), and then $CuSO_4$ (0.4 M, 7.3 μL, 1.0 eq) and VcNa (0.4 M, 14.6 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5796.54 observed m/z: 1159.8 ([M/5+H]) 966.7 ($[M/6+H]^+$)] was detected. The reaction mixture was directly purified by prep-HPLC (TFA condition). BCY9659 (6.2 mg, 1.06 μmol, 36.58% yield, 98.86% purity) was obtained as a white solid.

BCY9758

Procedure for Preparation of Compound 2

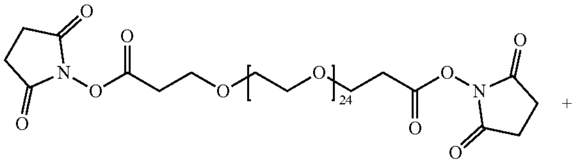

1

BCY00006099 2.0 eq DIPEA Dry DMF BCY00006099-PEG24-NHS ester

2

To a solution of compound 1 (5.0 mg, 3.54 μmol, 1.0 eq), BCY6099 (11.3 mg, 3.54 μmol, 1.0 eq) in DMF (3 mL) was added DIEA (0.9 mg, 7.07 μmol, 1.2 μL, 2.0 eq). The mixture was stirred at 25-30° C. for 20 min. LC-MS showed one peak with desired m/z (MW: 4481.11, observed m/z: 1101.3 ($[M/4+H]^+$)) was detected. The reaction mixture was filtered and concentrated under reduced pressure and lyophilized to give compound 2 (15 mg, crude) as a white solid.

Procedure for Preparation of BCY9758

BCY00006099-PEG24-NHS ester + BCY00007732 2.0 eq DIPEA Dry DMF

2

BCY00009758

To a solution of compound 2 (15 mg, 3.35 μmol, 1.0 eq) and BCY7732 (14.74 mg, 6.69 μmol, 2.0 eq) in DMF (3 mL) was added DIEA (0.9 mg, 7.07 μmol, 1.2 μL, 2.1 eq). The mixture was stirred at 25-30° C. for 2 hrs. LC-MS showed compound 2 was consumed completely and one main peak with desired m/z (MW: 6567.48, observed m/z: 1095.1 ([M/6+H]), 938.8 ($[M/7+H]^+$)) was detected. The reaction mixture was filtered and concentrated under reduced pressure to give a residue. The crude product was purified by reversed-phase HPLC (TFA condition). BCY9758 (5.8 mg, 24.26% yield, 91.97% purity) was obtained as a white solid.

BCY10568

Procedure for Preparation of BCY8919-PEG12-$N_3$

BCY00008919 + NHS-PEG12-$N_3$ DIEA DMSO

1

BCY00008919-PEG12-$N_3$

2

BCY8919 (80.0 mg, 38.47 μmol, 1.0 eq) and compound 1 (29.6 mg, 40.01 μmol, 1.04 eq) were dissolved in DMSO (1 mL). The solution was then added with DIPEA (7.46 mg, 55.71 μmol, 10.0 μl, 1.5 eq), and then the mixture was stirred at 25-30° C. for 2 hr. LC-MS showed majority of BCY8919 was consumed and one main peak with desired m/z (calculated MW: 2705.16, observed m/z: 1353.1 ($[M/2+H]^+$)) was detected. The reaction mixture was purified by prep-HPLC (TFA condition) and compound 2 (18.6 mg, 6.86 μmol, 17.83% yield, 99.76% purity) was obtained as a white solid.

Procedure for Preparation of BCY10568

BCY00008919-PEG12—$N_3$ +

2

BCY00006169 $CuSO_4$ VcNa THPTA t-BuOH/$H_2O$ BCY00010568

Compound 2 (9.0 mg, 3.33 μmol, 1.0 eq) and BCY6169 (11.0 mg, 3.36 μmol, 1.01 eq) were first dissolved in 2 mL of t-BuOH/$H_2O$ (1:1), and then $CuSO_4$ (0.4 M, 8.3 μL, 1.0 eq), VcNa (1.4 mg, 7.06 μmol, 2.1 eq) and THPTA (1.4 mg, 3.22 μmol, 1.0 eq) were added. Finally 0.4 M $NH_4HCO_3$ was added to adjust pH to 8. All solvents here were degassed and purged with $N_2$ for 3 times. The reaction mixture was stirred at 30° C. for 16 hr under $N_2$ atmosphere. LC-MS showed compound 2 was consumed completely and one main peak with desired m/z (calculated MW: 5967.90, observed m/z: 995.00 ([M/5+H]$^+$) and 1194.70 ([M/6+H]$^+$)). The reaction mixture was purified by prep-HPLC (TFA condition) and BCY10568 (13.4 mg, 2.16 μmol, 69.44% yield, 96.3% purity) was obtained as a white solid.

BCY10570

Procedure for Preparation of BCY8920-PEG12-$N_3$

BCY00008920 + NHS—PEG12—$N_3$
1
DIEA
DMSO
BCY00008920-PEG12—$N_3$
2

To a solution of BCY8920 (37 mg, 17.31 μmol, 1.0 eq) and compound 1 (15 mg, 20.25 μmol, 1.2 eq) in DMSO (2 mL) was added DIEA (3.36 mg, 25.96 μmol, 4.5 μL, 1.5 eq). The mixture was stirred at 30° C. for 12 hr. LC-MS showed BCY8920 was consumed completely and one main peak with desired m/z (calculated MW: 2763.2, observed m/z: 689.07 ([M/4−H$^+$])) was detected. The reaction mixture was concentrated under reduced pressure to remove solvent and produced a residue. The residue was then purified by prep-HPLC (neutral condition). Compound 2 (22.8 mg, 8.15 μmol, 47.09% yield, 98.78% purity) was obtained as a white solid.

Procedure for Preparation of BCY10570

BCY00008920-PEG12—$N_3$ +
2
BCY00006169
$CuSO_4$
VcNa
THPTA
t-BuOH/$H_2O$
BCY00010570

Compound 2 (6 mg, 2.17 μmol, 1.0 eq) and BCY6169 (7.08 mg, 2.17 μmol, 1.0 eq) were first dissolved in 2 mL of t-BuOH/$H_2O$ (1:1), and then $CuSO_4$ (0.4 M, 5.4 μL, 1.0 eq), VcNa (0.4 M, 10.8 μL, 2.0 eq) and THPTA (0.4 M, 5.4 μL, 1.0 eq) was added. Finally 0.2 M $NH_4HCO_3$ was added to adjust pH to 8. All solvents here were degassed and purged with $N_2$ for 3 times. The reaction mixture was stirred at 30° C. for 4 hr under $N_2$ atmosphere. LC-MS showed compound 2 was consumed completely and one main peak with desired m/z (MS: 6025.93, observed m/z: 1004.56 ([M/6]+H$^+$) and 861.48 ([M/7+H$^+$])) was detected. The reaction mixture was filtered and concentrated under reduced pressure to give a residue. The crude product was purified by prep-HPLC (TFA condition). BCY10570 (7.2 mg, 1.17 μmol, 53.90% yield, 97.95% purity) was obtained as a white solid.

BCY10574

Procedure for Preparation of Compound 2

BCY00009594 + NHS—PEG5—$N_3$
1
DIEA
DMSO
BCY00009594-PEG5—$N_3$
2

To a solution of BCY9594 (65 mg, 27.07 μmol, 1 eq), Compound 1 (12.00 mg, 27.75 μmol, 1.02 eq) in DMSO (1 mL) was added DIEA (5.25 mg, 40.61 μmol, 7.07 μL, 1.5 eq). The mixture was stirred at 25-30° C. for 2 hr. LC-MS showed BCY9594 was consumed completely and one main peak with desired m/z (calculated MW: 2718.13, observed m/z: 906.04 ([M/3+H]$^+$), 1359.07 ([M/2+H]$^+$)) was detected. The reaction mixture was concentrated under reduced pressure to remove solvent to give a residue. The residue was purified by prep-HPLC (TFA condition). Compound 2 (42.6 mg, 15.67 μmol, 57.89% yield, 100% purity) was obtained as a white solid.

Procedure for Preparation of BCY10574

BCY00009594-PEG5—$N_3$ +
2
BCY00008927
$CuSO_4$
VcNa
THPTA
t-BuOH/$H_2O$
BCY00010574

A mixture of Compound 2 (20 mg, 7.36 μmol, 1.0 eq), BCY8927 (17 mg, 7.87 μmol, 1.07 eq), and THPTA (0.4 M, 18.4 μL, 1.0 eq) was dissolved in t-BuOH/$H_2O$ (1:1, 2 mL, pre-degassed and purged with $N_2$ for 3 times), and then $CuSO_4$ (0.4 M, 18.4 μL, 1.0 eq) and VcNa (0.4 M, 36.8 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 2 was consumed completely and one main peak with desired m/z (calculated MW: 4877.68, observed m/z: 1219.42 ([M/4+H]$^+$) and 975.54 ([M/5+H]$^+$)) was detected. The reaction mixture was directly purified by prep-HPLC (TFA condition).

BCY10574 (17.6 mg, 3.41 μmol, 46.29% yield, 94.40% purity) was obtained as a white solid.

BCY10575

Procedure for Preparation of Compound 2

BCY00009594 + NHS—PEG5—$N_3$
1
DIEA
DMSO
BCY00009594-PEG5—$N_3$
2

To a solution of BCY9594 (65 mg, 27.07 μmol, 1 eq), Compound 1 (12.0 mg, 27.75 μmol, 1.02 eq) in DMSO (1 mL) was added DIEA (5.25 mg, 40.61 μmol, 7.07 μL, 1.5 eq). The mixture was stirred at 25-30° C. for 2 hr. LC-MS showed Compound 1 was consumed completely and one main peak with desired m/z [calculated MW: 2718.13 observed m/z: 906.04 ([M/3+H]$^+$) and 1359.07 ([M/2+H]$^+$)] was detected. The reaction mixture was concentrated under reduced pressure to remove solvent to give a residue. The residue was purified by prep-HPLC (TFA condition). Compound 2 (42.6 mg, 15.67 μmol, 57.89% yield, 100% purity) was obtained as a white solid.

Procedure for Preparation of BCY10575

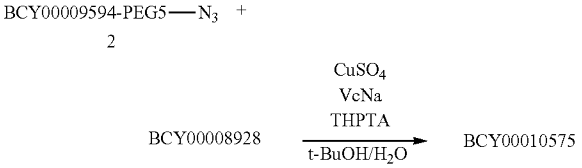

A mixture of Compound 2 (20 mg, 7.36 μmol, 1.0 eq), BCY8928 (17 mg, 7.67 μmol, 1.04 eq), and THPTA (0.4 M, 18.4 μL, 1.0 eq) was dissolved in t-BuOH/$H_2O$ (1:1, 2 mL, pre-degassed and purged with $N_2$ for 3 times), and then $CuSO_4$ (0.4 M, 18.4 μL, 1.0 eq) and VcNa (0.4 M, 36.8 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 2 was consumed completely and one main peak with desired m/z [calculated MW: 4935.71, observed m/z: 1234.59 ($[M/4+H]^+$) and 987.71 ($[M/5+H]^+$)] was detected. The reaction mixture was directly purified by prep-HPLC (TFA condition).

BCY10575 (12 mg, 2.37 μmol, 32.27% yield, 97.67% purity) was obtained as a white solid.

BCY10576

Procedure for Preparation of Compound 2

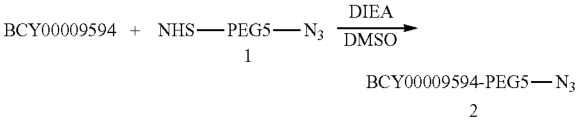

To a solution of BCY9594 (30.0 mg, 12.50 μmol, 1.0 eq), Compound 1 (5.54 mg, 12.81 μmol, 1.02 eq) in DMSO (1 mL) was added DIEA (2.42 mg, 18.74 μmol, 3.3 μL, 1.5 eq). The mixture was stirred at 25-30° C. for 2 hr. LC-MS showed Compound 1 was consumed completely and one main peak with desired m/z [calculated MW: 2718.13, observed m/z: 906.45 ([M/3+H]+) and 1359.50 ([M/2+H]+)] was detected. The reaction mixture was concentrated under reduced pressure to remove solvent to give a residue. The residue was purified by prep-HPLC (TFA condition). Compound 2 (16 mg, 5.80 μmol, 46.42% yield, 98.54% purity) was obtained as a white solid.

Procedure for Preparation of BCY10576

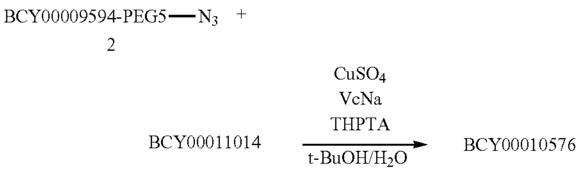

A mixture of compound 2 (17.0 mg, 6.25 μmol, 1.0 eq), BCY11014 (13.6 mg, 6.25 μmol, 1.0 eq), and THPTA (0.4 M, 1.8 μL, 2.0 eq) was dissolved in t-BuOH/$H_2O$ (1:1, 2 mL, pre-degassed and purged with $N_2$ for 3 times), and then $CuSO_4$ (0.4 M, 15.6 μL, 1.0 eq) and VcNa (0.4 M, 1.84 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed majority of compound 2 was consumed and one main peak with desired m/z [calculated MW: 4893.63, observed m/z: 1224.7 ($[M/4+H]^+$) and 980.0 ($[M/6+H]^+$)] was detected. The reaction mixture was directly purified by prep-HPLC (TFA condition).

BCY10576 (20.5 mg, 4.13 μmol, 66.02% yield, 98.57% purity) was obtained as a white solid.

BCY10577

Procedure for Preparation of Compound 2

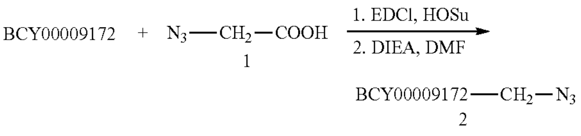

To a solution of compound 1 (5.0 mg, 49.5 μmol, 1.0 eq) in DMF (1 mL) was added EDCl (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then BCY9172 (53 mg, 25.29 μmol, 0.47 eq) and DIEA (3.27 mg, 25.29 μmol, 4.4 μL, 0.47 eq) were added to the reaction mixture. The mixture was stirred at 25-30° C. for 2 hr. LC-MS showed BCY9172 was consumed completely and one main peak with desired m/z (MW: 2178.46, observed m/z: 1089.5700 ($[(M/2+H^+])$) was detected. The reaction mixture was concentrated under reduced pressure to remove solvent and produced a residue. The residue was then purified by prep-HPLC (neutral condition). Compound 2 (30 mg, 13.77 μmol, 54.45% yield, 100% purity) was obtained as a white solid.

Procedure for Preparation of BCY10577

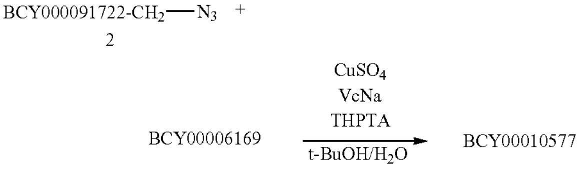

Compound 2 (20 mg, 9.18 μmol, 1.0 eq) and BCY6169 (32.95 mg, 10.10 μmol, 1.1 eq) were first dissolved in 2 mL of t-BuOH/$H_2O$ (1:1), and then $CuSO_4$ (0.4 M, 23 μL, 1 eq), VcNa (0.4 M, 46 μL, 2.0 eq) and THPTA (0.4 M, 23 μL, 1.0 eq) were added. Finally 1 M $NH_4HCO_3$ was added to adjust pH to 8. All solvents here were degassed and purged with $N_2$ for 3 times. The reaction mixture was stirred at 30° C. for 4 hr under $N_2$ atmosphere. LC-MS showed compound 2 was consumed completely and one main peak with desired m/z (calculated MW: 5441.20, observed m/z: 1361.8 ($[M/4+H]^+$)) was detected. The reaction mixture was filtered and concentrated under reduced pressure to give a residue. The crude product was purified by prep-HPLC (TFA condition). BCY10577 (16.2 mg, 2.98 μmol, 32.43% yield) was obtained as a white solid.

Example 3: Synthesis of Nectin-4/CD137 Binding Heterotandem Bicyclic Peptides BCY8854

General Procedure for Preparation of BCY8846

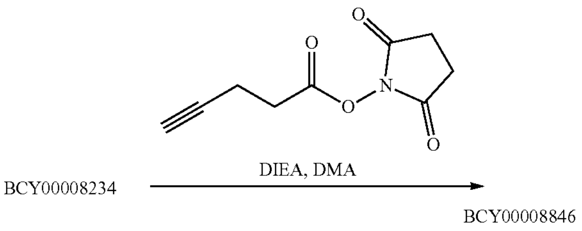

To a solution of BCY8234 (a peptide identical to BCY8846 except for the absence of a PYA moiety; 300 mg, 102 μmol, 1.0 eq) in DMA (3 mL) was added DIEA (52.5 mg, 406 μmol, 70.8 μL, 4.0 eq) with stirring for 10 min. Then (2,5-dioxopyrrolidin-1-yl) pent-4-ynoate (25.8 mg, 132 μmol, 1.3 eq) was added thereto and the mixture was further stirred at 20° C. for additional 16 hr. LC-MS showed BCY8234 was consumed completely and one main peak with desired m/z (calculated MW: 3034.43, observed m/z: 1011.8 ([M/3+H]$^+$), 1517.0 ([M/2+H]$^+$)) was detected. The reaction mixture was purified by prep-HPLC (neutral condition) to give compound BCY8846 (290 mg, 95.6 μmol, 94.1% yield) as a white solid.

General Procedure for Preparation of BCY8854

BCY00008846 —BCY00007859 / Vc, $CuSO_4$, DMF, $H_2O$→ BCY00008854

To a solution of BCY8846 (234 mg, 77.1 μmol, 1.0 eq) in DMF (5 mL) was added BCY7859 (which may be prepared as described in BCY7985; 220 mg, 77.8 μmol, 1.0 eq), followed by addition (2R)-2-[(1S)-1,2-dihydroxyethyl]-3,4-dihydroxy-2H-furan-5-one (0.80 M, 963 μL, 1.0 eq) and $CuSO_4$ (0.80 M, 289 μL, 0.3 eq). The mixture was stirred at 20° C. for 2 hr. LC-MS showed BCY8846 was consumed completely and one main peak with desired m/z (Calculated MW: 5861.59, observed m/z: 837.9 ([M/7+H]$^+$), 977.6 ([M/6+H]$^+$), 1173.3 ([M/5+H]$^+$)) was detected. The reaction mixture was purified by prep-HPLC (A: 0.075% TFA in $H_2O$, B: ACN) to give compound BCY8854 (292 mg, 46.8 μmol, 60.8% yield, 95.9% purity, TFA) as a white solid.

BCY9350

General Procedure for Preparation of BCY8782-PYA

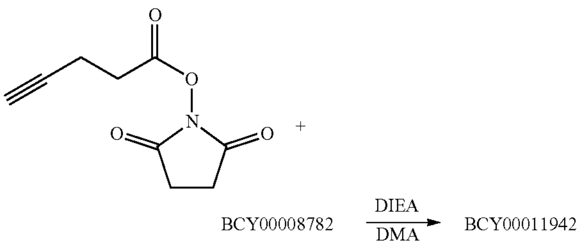

To a solution of BCY8782 (a peptide identical to BCY11942 except for the absence of a PYA moiety; 20.0 mg, 6.77 μmol, 1.0 eq) in DMA (1 mL) was added DIEA (4.37 mg, 33.9 μmol, 5.90 μL, 5.0 eq) and (2,5-dioxopyrrolidin-1-yl) pent-4-ynoate (2.64 mg, 13.5 μmol, 2.0 eq) with stirring for 12 hr at 25° C. LC-MS showed BCY8782 was consumed completely and one main peak with desired m/z (calculated MW: 3034.43, observed m/z: 1012.1 [M/3+H]$^+$) was detected. The reaction mixture was purified by prep-HPLC (neutral condition) to give BCY11942 (20.0 mg, 6.00 μmol, 88.6% yield, 91.0% purity) as a white solid.

General Procedure for Preparation of BCY9350

BCY00011942 + BCY0007859 —Vc, $CuSO_4$ / DMF→ BCY00009350

To a solution of BCY11942 (20 mg, 6.59 μmol, 1.0 eq) and BCY7859 (which may be prepared as described in BCY7985; 20.5 mg, 7.25 μmol, 1.1 eq) in DMF (1 mL) was added (2R)-2-[(1S)-1,2-dihydroxyethyl]-3, 4-dihydroxy-2H-furan-5-one (0.4 M, 330 μL, 20.0 eq) and $CuSO_4$ (0.4 M, 98.9 μL, 6.0 eq) were added to the mixture. The mixture was stirred at 25° C. for 2 hr. LC-MS showed BCY8782-PYA was consumed completely and one main peak with desired m/z (calculated MW: 5861.59, observed m/z: 1173.3 [M/5+H]$^+$) was detected. The reaction mixture was purified by prep-HPLC (A: 0.075% TFA in $H_2O$, B: ACN) to give BCY9350 (14.5 mg, 2.40 μmol, 36.5% yield, 97.2% purity) as a white solid.

BCY9351

General Procedure for Preparation of BCY9351

BCY00008940 + BCY00008846 —Vc, $CuSO_4$ / DMF→ BCY00009351

To a solution of BCY8940 (which may be prepared as described in BCY8942; 9.4 mg, 3.33 μmol, 1.01 eq) and BCY8846 (10.0 mg, 3.30 μmol, 1.0 eq) in DMF (1 mL) was added Vc (0.4 M, 165 μL, 20.0 eq) and $CuSO_4$ (0.4 M, 49.4 μL, 6.0 eq) under nitrogen atmosphere. The mixture was stirred at 25° C. for 1 hr. LC-MS showed BCY8940 was consumed completely and one main peak with desired m/z (calculated MW: 5861.59, observed m/z: 975.4 [M/6+H]$^+$, 1172.3 [M/5+H]$^+$) was detected. The reaction mixture was purified by prep-HPLC (A: 0.075% TFA in $H_2O$, B: ACN) to give BCY9351 (5.30 mg, 0.904 μmol, 26.3% yield, 96.0% purity) as a white solid.

BCY9399

Procedure for Preparation of Compound 2

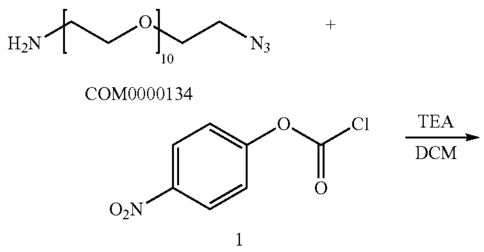

-continued

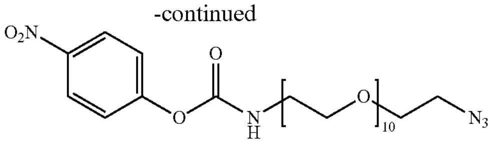

2

To a solution of COM134 (30 mg, 56.97 μmol), Compound 1 (17.22 mg, 85.45 μmol) in DCM (0.5 mL) was added TEA (8.65 mg, 85.45 μmol, 11.9 μL). The mixture was stirred at 25° C. for 1 hr. LC-MS showed COM134 was consumed completely and one main peak with desired m/z (calculated MW: 691.72, observed m/z: 692.3 ($[M+H]^+$) and 709.3 ($[M+NH4]^+$)) was detected. The reaction mixture was concentrated under reduced pressure to remove solvent to give a residue. The residue was purified by prep-HPLC (neutral condition). Compound 2 (30.5 mg) was obtained as a colorless oil.

Procedure for Preparation of Compound 3

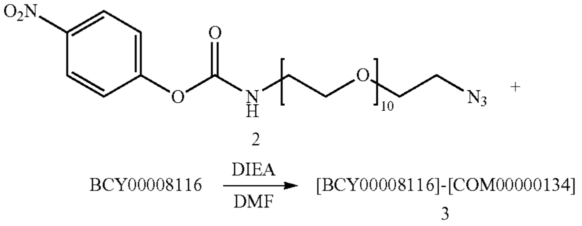

To a solution of Compound 2 (15 mg, 21.68 μmol) and BCY8116 (47 mg, 21.68 μmol) in DMF (1 mL) was added DIEA (8.41 mg, 65.05 μmol, 11.33 μL). The mixture was stirred at 30° C. for 2 hrs. LC-MS showed Compound 2 was consumed completely and one main peak with desired m/z (MW: 2725.1 observed m/z: 1362.7 ($[M/2+H]^+$), 909.0 ($[M/3+H]^+$)) was detected. The reaction mixture was filtered and concentrated under reduced pressure to give a residue. The crude product was purified by reversed-phase HPLC (TFA condition). Compound 3 (20 mg, 33.41% yield, 98.71% purity) was obtained as a white solid.

Procedure for Preparation of BCY9399

[BCY00008116]-[COM00000134] +
3

BCY00007741 —CuSO4 VcNa THPTA / t-BuOH/H2O→ BCY00009399

A mixture of Compound 3 (20.0 mg, 5.35 μmol, 1.0 eq), BCY7741 (13.0 mg, 5.70 μmol, 1.01 eq), and THPTA (0.4 M, 13.4 μL, 1.0 eq) was dissolved in t-BuOH/$H_2O$ (1:1, 2 mL, pre-degassed and purged with $N_2$ for 3 times), and then $CuSO_4$ (0.4 M, 13.4 μL, 1.0 eq) and VcNa (0.4 M, 26.8 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5006.64 observed m/z: 834.9 ($[M/6+H]^+$), 1002.3 ($[M/5+H]^+$), 1252.4 ($[M/4+H]^+$)] was detected. The reaction mixture was directly purified by prep-HPLC (TFA condition). BCY9399 (9.1 mg, 27.20% yield, 96.29% purity) was obtained as a white solid.

BCY9400

Procedure for Preparation of Compound 2

COM00000135 +

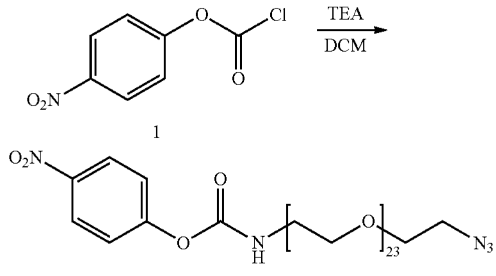

To a solution of COM135 (which may be prepared as described in BCY9648; 30.0 mg, 27.29 μmol), Compound 1 (8.3 mg, 40.94 μmol) in DCM (2 mL) was added TEA (4.14 mg, 40.94 μmol, 5.7 μL). Then the reaction mixture was stirred at 25-30° C. for 1 hr. LC-MS showed COM135 was consumed completely and one main peak with desired m/z (calculated MW: 1264.40, observed m/z: 1281.4 ($[M+NH_4]^+$)) was detected. The reaction mixture was concentrated under reduced pressure to remove solvent to give a residue. The residue was purified by prep-HPLC (neutral condition) to give compound 2 (18 mg) as a white solid.

Procedure for Preparation of Compound 3

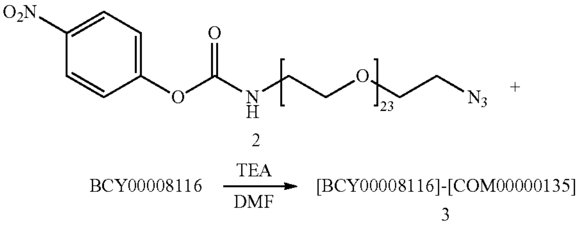

To a solution of Compound 2 (15.5 mg, 7.12 μmol) and BCY8116 (9 mg, 7.12 μmol) in DMF (2 mL) was added DIEA (1.4 mg, 10.68 μmol, 1.9 μL). The mixture was stirred at 30° C. for 2 hrs. LC-MS showed Compound 2 was consumed completely and one main peak with desired m/z (MW: 3297.78, observed m/z: 1099.7 ($[M/3+H]^+$)) was detected. The reaction mixture was filtered and concentrated under reduced pressure to give a residue. The crude product was purified by reversed-phase HPLC (TFA condition). Compound 3 (19.5 mg, 5.91 μmol, 33.41% yield, 83.07% purity) was obtained as a white solid.

Procedure for Preparation of BCY9400

[BCY00008116]-[COM00000135] +
3

BCY00007741 —CuSO4 VcNa THPTA / t-BuOH/H2O→ BCY00009400

A mixture of Compound 3 (19.5 mg, 5.91 μmol), BCY7741 (14 mg, 6.14 μmol, 1.01 eq), and THPTA (0.4 M, 15 μL, 1 eq) was dissolved in t-BuOH/$H_2O$ (1:1, 2 mL, pre-degassed and purged with $N_2$ for 3 times), and then $CuSO_4$ (0.4 M, 15 µL, 1 eq) and VcNa (0.4 M, 30 µL, 2 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5579.31 observed m/z: 930.5 ([M/6+H]$^+$), 1116.6 ([M/5+H]$^+$)] was detected. The reaction mixture was directly purified by prep-HPLC (TFA condition). BCY9400 (13.9 mg, 2.33 µmol, 27.20% yield, 93.56% purity) was obtained as a white solid.

BCY9401

Procedure for Preparation of Compound 3

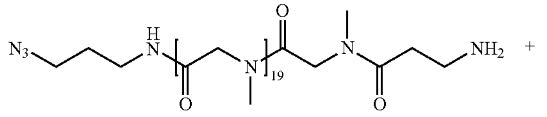

Exact Mass: 1591.85429
Molecular Weight: 1592.75832
1
COM00000470

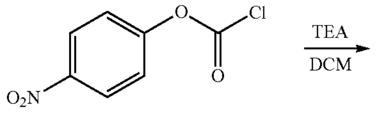

Exact Mass: 200.98289
Molecular Weight: 201.56396
2

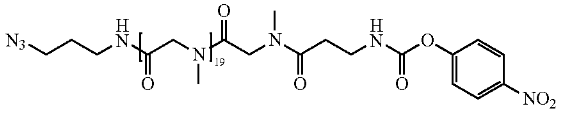

Exact Mass: 1756.86049
Molecular Weight: 1757.86134
3

To a solution of Compound 1 (50.0 mg, 31.39 µmol, 1 eq), Compound 2 (6.6 mg, 32.96 µmol, 1.05 eq) in DCM (2 mL) was added TEA (4.8 mg, 47.09 µmol, 6.6 µL, 1.5 eq). The mixture was stirred at 25-30° C. for 2 hr. LC-MS showed Compound 1 was consumed completely and one main peak with desired m/z (MW: 1757.86 observed m/z: 879.10 ([M/2+H]$^+$)) was detected. The reaction mixture was concentrated under reduced pressure to remove solvent to give a residue. The residue was purified by prep-HPLC (TFA condition). Compound 3 (0.02 g, 6.56 µmol, 20.91% yield, 57.7% purity) was obtained as a white solid.

Procedure for Preparation of Compound 4

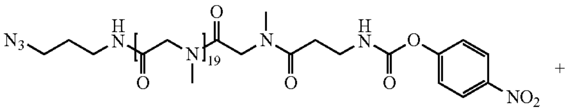

3

BCY00008116 DIEA DMF [BCY00008116]-[COM00000122]

4

To a solution of Compound 3 (20 mg, 11.38 µmol, 1 eq), BCY8116 (25 mg, 11.51 µmol, 1.01 eq) in DMF (4 mL) was added DIEA (2.2 mg, 17.07 µmol, 2.97 µL, 1.5 eq). The mixture was stirred at 25-30° C. for 12 hr. LC-MS showed Compound 3 was consumed completely and one main peak with desired m/z (MW: 3791.23, observed m/z: 1263.2 ([M/3+H]$^+$)) was detected. The reaction was directly purified by prep-HPLC (neutral condition). Compound 4 (10 mg, 2.43 µmol, 21.33% yield, 92% purity) was obtained as colorless oil.

Procedure for Preparation of BCY9401

[BCY00008116]-[COM00000122] +

4

BCY00007741 CuSO4, VcNa, THPTA t-BuOH/$H_2O$ BCY00009401

A mixture of Compound 4 (10 mg, 2.43 µmol, 0.9 eq), BCY7741 (6.32 mg, 2.77 µmol, 1.0 eq) and THPTA (0.4 M, 6.7 µL, 1.0 eq) was dissolved in t-BuOH/$H_2O$ (1:1, 2 mL, pre-degassed and purged with $N_2$ for 3 times), and then $CuSO_4$ (0.4 M, 6.7 µL, 1.0 eq) and VcNa (0.4 M, 13.4 µL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 4 was consumed completely and one main peak with desired m/z [MW: MW: 6072.77, observed m/z: 1012.00 ([M/6+H]$^+$)] was detected. The reaction mixture was directly purified by prep-HPLC (TFA condition). BCY9401 (8.4 mg, 1.56 µmol, 59.31% yield, 95.52% purity) was obtained as a white solid.

BCY9403

Procedure for Preparation of Compound 2

COM00000471 +

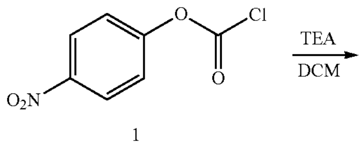

1

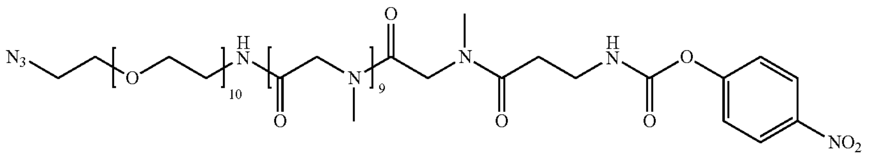

2

To a solution of COM471 (100.0 mg, 76.42 μmol, 1.0 eq), 4-nitrophenylchloroformate (16.2 mg, 80.25 μmol, 1.05 eq) in DCM (10 mL) was added TEA (11.6 mg, 114.64 μmol, 16.0 μL, 1.5 eq). The mixture was stirred at 25-30° C. for 2 hr. LC-MS showed COM471 was consumed completely and one main peak with desired m/z (MW: 1473.58, observed m/z: 736.83 ([M/2+H]$^+$)) was detected. The reaction mixture was concentrated under reduced pressure to remove solvent to give a residue. The residue was purified by prep-HPLC (TFA condition). Compound 2 (62.8 mg, 42.67 μmol, 55.84% yield, 48.37% purity) was obtained as a white oil.

Procedure for Preparation of Compound 3

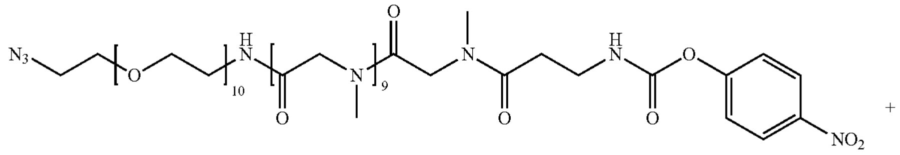

2

BCY00008116
DIEA
DMF
[BCY00008116]-[COM00000471]
3

To a solution of Compound 2 (44 mg, 29.46 μmol, 1.0 eq), BCY8116 (63 mg, 29.18 μmol, 1.0 eq) in DMF (2 mL) was added DIEA (5.66 mg, 43.77 μmol, 7.62 μL, 1.5 eq). The mixture was stirred at 40° C. for 12 hr. LC-MS showed Compound 2 was consumed completely and one main peak with desired m/z (MW: 3506.95, observed m/z: 1168.58 ([M/3+H]$^+$)) was detected. The residue was purified by prep-HPLC (TFA condition). Compound 3 (20 mg, 5.42 μmol, 18.57% yield, 95.04% purity) was obtained as a white solid.

Procedure for Preparation of BCY9403

[BCY00008116]-[COM00000471] +
3
BCY00007741
$CuSO_4$ VcNa THPTA
t-BuOH/$H_2O$
BCY00009403

A mixture of Compound 3 (10.0 mg, 2.71 μmol, 1.0 eq), BCY7741 (6.83 mg, 2.99 μmol, 1.1 eq), and THPTA (0.4 M, 7 μL, 1.0 eq) was dissolved in t-BuOH/$H_2O$ (1:1, 2 mL, pre-degassed and purged with $N_2$ for 3 times), and then $CuSO_4$ (0.4 M, 7 μL, 1.0 eq) and VcNa (0.4 M, 14 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5788.49, observed m/z: 1157.00 ([M/5+H]$^+$) and 964.60 ([M/6+H]$^+$)] was detected. The reaction mixture was directly purified by prep-HPLC (TFA condition). BCY9403 (2.1 mg, 0.34 μmol, 11.93% yield, 93.80% purity) was obtained as a white solid.

BCY9405

Procedure for Preparation of Compound 2

COM00000472 +

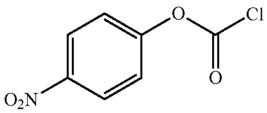

1

TEA
DCM

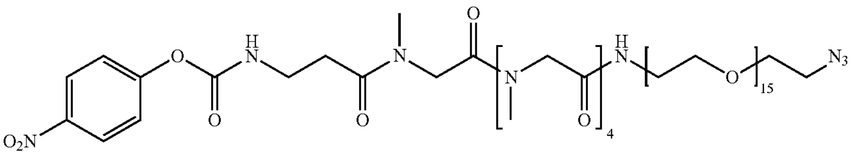

2

To a solution of COM472 (44.7 mg, 38.1 μmol), Compound 1 (9.2 mg, 45.72 μmol) in DCM (4 mL) was added TEA (5.8 mg, 57.14 μmol, 8 μL). The mixture was stirred at 25° C. for 2 hr. LC-MS showed COM472 was consumed completely and one main peak with desired m/z (MW: 1338.45, observed m/z: 686.23 ([M/2+NH4$^+$])) was detected. The reaction mixture was concentrated under reduced pressure to remove solvent to give a residue. The residue was purified by prep-HPLC (neutral condition). Compound 2 (20 mg, 14.94 μmol, 39.2% yield) was obtained as colorless oil.

Procedure for Preparation of Compound 3

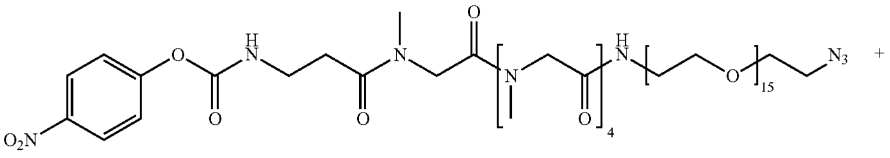

2

BCY00008116
DIEA
DMF
[BCY00008116]-[COM00000472]
3

To a solution of Compound 2 (20 mg, 14.94 μmol) and BCY8116 (38.96 mg, 17.93 μmol) in DMF (4 mL) was added DIEA (1.9 mg, 14.94 μmol, 2.6 μL). The mixture was stirred at 30° C. for 2 hrs. LC-MS showed Compound 2 was consumed completely and one main peak with desired m/z (MW: 3371.82, observed m/z: 1123.94 ([M/3+H$^+$])) was detected. The reaction mixture was filtered and concentrated under reduced pressure to give a residue. The crude product was purified by reversed-phase HPLC (TFA condition). Compound 3 (10 mg, 99.07% yield, 19.66 purity) was obtained as a white solid.

Procedure for Preparation of BCY9405

[BCY00008116]-[COM00000472] +
3

BCY00007741
$CuSO_4$
VcNa
THPTA
t-BuOH/$H_2O$
BCY00009405

A mixture of Compound 3 (10.0 mg, 2.97 μmol, 1.0 eq), BCY7741 (7.4 mg, 3.26 μmol, 1.1 eq), and THPTA (1.3 mg, 2.97 μmol, 1.0 eq) was dissolved in t-BuOH/$H_2O$ (1:1, 2 mL, pre-degassed and purged with $N_2$ for 3 times), and then $CuSO_4$ (0.4 M, 7.5 μL, 1.0 eq) and VcNa (0.4 M, 151 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5653.36, observed m/z: 1130.47 ([M/5+H]$^+$)] was detected. The reaction mixture was directly purified by prep-HPLC (TFA condition). BCY9405 (7.8 mg, 46.08% yield, 97.8% purity) was obtained as a white solid.

BCY9406

Procedure for Preparation of Compound 2

COM00000473 +

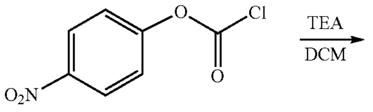

1

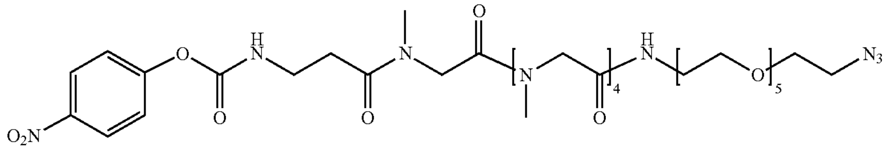

2

To a solution of COM473 (130.0 mg, 177.40 μmol, 1.0 eq), (4-nitrophenyl) carbonochloridate (36.4 mg, 180.59 μmol, 1.02 eq) in DCM (3 mL) was added TEA (27.0 mg, 266.09 μmol, 37 μL, 1.5 eq). The mixture was stirred at 35° C. for 2 hr. LC-MS showed COM473 was consumed completely and one main peak with desired m/z (MW: 897.93, observed m/z: 897.65 ([M+H]$^+$), 914.60 ([M+NH4]$^+$)) was detected. The reaction mixture was concentrated under reduced pressure to remove solvent to give a residue. The residue was purified by prep-HPLC (TFA condition). Compound 2 (90 mg, 95.87 μmol, 54.04% yield, 95.65% purity) was obtained as colorless oil.

Procedure for Preparation of Compound 3

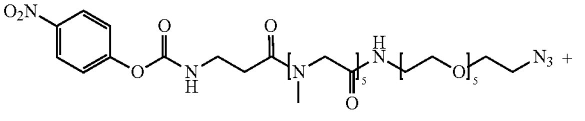

2

BCY00008116 DIEA DMF [BCY00008116]-[COM00000473]

3

To a solution of Compound 2 (10 mg, 11.14 μmol, 1 eq), BCY8116 (25 mg, 11.51 μmol, 1.03 eq) in DMF (2 mL) was added DIEA (2.16 mg, 16.71 μmol, 2.91 μL, 1.5 eq). The mixture was stirred at 25-30° C. for 12 hr. LC-MS showed one main peak with desired m/z (MW: 2931.30, observed m/z: 977.00 ([M/3+H]$^+$)) was detected. The reaction mixture was filtered and concentrated under reduced pressure to give a residue. The crude product was purified by reversed-phase HPLC (FTA condition). Compound 3 (15 mg, 5.12 μmol, 45.79% yield, 99.66% purity) was obtained as a white solid.

Procedure for Preparation of BCY9406

[BCY00008116]-[COM00000473] +

3

BCY00007741 $CuSO_4$ VcNa THPTA t-BuOH/$H_2O$ BCY00009406

A mixture of Compound 3 (15 mg, 5.12 μmol, 1.0 eq), BCY7741 (12 mg, 5.26 μmol, 1.03 eq), and THPTA (0.4 M, 12.8 μL, 1.0 eq) was dissolved in t-BuOH/$H_2O$ (1:1, 2 mL, pre-degassed and purged with $N_2$ for 3 times), and then $CuSO_4$ (0.4 M, 12.8 μL, 1.0 eq) and VcNa (0.4 M, 25.6 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5212.84 observed m/z: 1042.74 ([M/4+H]$^+$)] was detected. The reaction mixture was directly purified by prep-HPLC (TFA condition). BCY9406 (14.4 mg, 2.57 μmol, 50.21% yield, 93.01% purity) was obtained as a white solid.

BCY9407

Procedure for Preparation of Compound 2

COM00000128 +

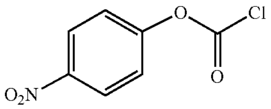

1

DIEA DCM

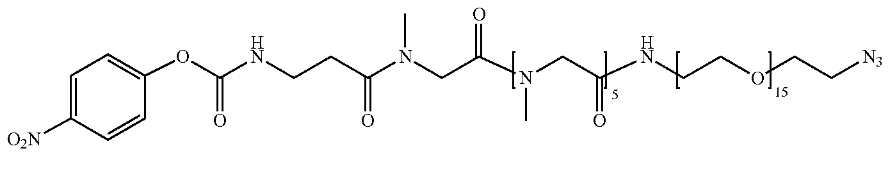

2

To a solution of COM128 (60 mg, 50.53 μmol, 1.0 eq), compound 1 (13 mg, 64.50 μmol, 1.28 eq), DIEA (9.80 mg, 75.80 μmol, 13.20 μL, 1.5 eq) in DCM (5 mL) was degassed and purged with $N_2$ for 3 times, and then the mixture was stirred at 25-30° C. for 1 hr under $N_2$ atmosphere. LC-MS showed COM128 was consumed completely and one main peak with desired m/z (calculated MW: 1352.48, observed m/z: 676.7 ([M/2+H]$^+$)) was detected. The reaction mixture was concentrated under reduced pressure to remove solvent to give a residue. The residue was purified by prep-HPLC (TFA condition). Compound 2 (12 mg, 8.87 μmol, 17.56% yield) was obtained as colorless oil.

Procedure for Preparation of [BCY8116]—[COM128]

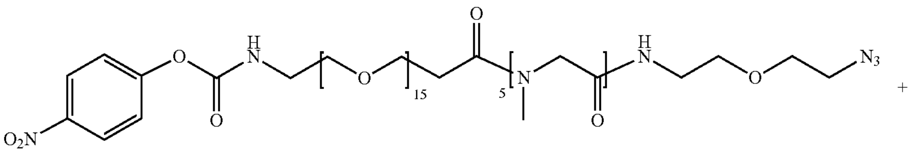

2

BCY00008116 TEA DMF [BCY00008116]-[COM00000128]

To a solution of compound 2 (7 mg, 5.18 μmol, 1.0 eq) and BCY8116 (11 mg, 5.06 μmol, 1.0 eq), DIEA (2.01 mg, 15.53 μmol, 2.70 μL, 3.0 eq) in DMF (3 mL) was degassed and purged with $N_2$ for 3 times, and then the mixture was stirred at 25-30° C. for 1 hr under $N_2$ atmosphere. LC-MS showed one main peak with desired m/z (calculated MW: 3385.85, observed m/z: 1129.3 ([M/3+H]$^+$)) was detected. The reaction mixture was filtered and concentrated under reduced pressure to give a residue. The crude product was purified by reversed-phase HPLC (TFA condition). [BCY8116]—[COM128] (15.6 mg, 4.46 μmol, 86.13% yield, 96.75% purity) was obtained as a white solid Procedure for Preparation of BCY9407

[BCY00008116]-[COM00000128] +

BCY00007741 $CuSO_4$ VcNa THPTA t-BuOH/$H_2O$ BCY00009407

A mixture of [BCY8116]—[COM128] (15.6 mg, 4.61 μmol, 1.0 eq), BCY7741 (11 mg, 4.82 μmol, 1.05 eq), and THPTA (0.8 M, 5.8 μL, 1.0 eq) was dissolved in t-BuOH/$H_2O$ (1:1, 2 mL, pre-degassed and purged with $N_2$ for 3 times), and then $CuSO_4$ (0.4 M, 11.6 μL, 1.0 eq) and VcNa (0.4 M, 23.2 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed one peak with desired m/z (calculated MW: 5667.39, observed m/z: 945.6 ([M/6+H]$^+$) and 1134.2 ([M/5+H]$^+$)) was detected. The reaction mixture was directly purified by prep-HPLC (TFA condition). BCY9407 (1.3 mg, 0.23 μmol, 4.33% yield, 86.90% purity) was obtained as a white solid.

BCY9408

Procedure for Preparation of Compound 2

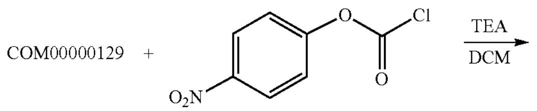

1

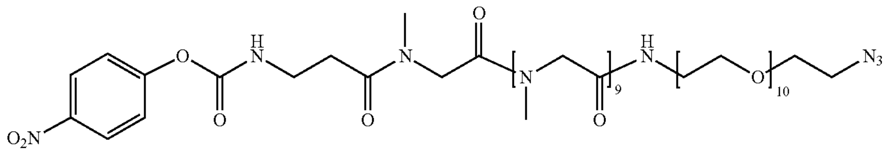

2

To a solution of COM129 (45.0 mg, 34.39 μmol, 1.0 eq), compound 1 (15.0 mg, 74.42 μmol, 2.1 eq) in DCM (5 mL) was added TEA (5.5 mg, 53.88 μmol, 7.5 μL, 1.5 eq), and then the mixture was stirred at 25-30° C. for 1 hr under $N_2$ atmosphere. LC-MS showed COM129 was consumed completely and one main peak with desired m/z (MW: 1473.58, observed m/z: 737.3 ([M/2+H]$^+$)) was detected. The reaction mixture was concentrated under reduced pressure to remove solvent to give a residue. The residue was purified by prep-HPLC (TFA condition). Compound 2 (9 mg, 6.11 μmol, 17.01% yield, 95.76% purity) was obtained as a white solid.

Procedure for Preparation of Compound 3

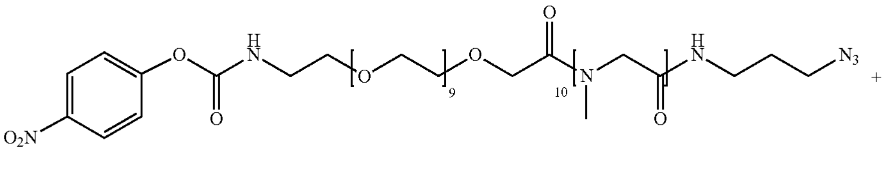

2

BCY00008116
TEA
DCM
[BCY00008116]-[COM00000129]
3

To a solution of compound 2 (9.0 mg, 6.11 μmol, 1.0 eq) and BCY8116 (13.3 mg, 6.11 μmol, 1.0 eq) in DMF (3 mL) was added DIEA (2.4 mg, 18.32 μmol, 3.2 μL, 3.0 eq). All solvents were degassed and purged with $N_2$ for 3 times, and then the mixture was stirred at 25-30° C. for 1 hr under $N_2$ atmosphere. LC-MS showed compound 2 was consumed completely and one main peak with desired m/z (MW: 3506.95, observed m/z: 877.4 ([M/4+H]$^+$) and m/z: 1169.6 ([M/3+H]$^+$)) was detected. The reaction mixture was filtered and concentrated under reduced pressure to give a residue. The crude product was purified by reversed-phase HPLC (TFA condition). Compound 3 (7.2 mg, 2.05 μmol, 31.93% yield, 95% purity) was obtained as a white solid.

Procedure for Preparation of BCY9408

[BCY00008116]-[COM00000129] +
3

[BCY00007741]
$CuSO_4$
VcNa
THPTA
t-BuOH/$H_2O$
BCY00009408

A mixture of Compound 3 (7.2 mg, 2.05 μmol, 1.0 eq), BCY7741 (5.0 mg, 2.19 μmol, 1.03 eq), and THPTA (0.4 M, 5.1 μL, 1.0 eq) was dissolved in t-BuOH/$H_2O$ (1:1, 2 mL, pre-degassed and purged with $N_2$ for 3 times), and then $CuSO_4$ (0.4 M, 5.1 μL, 1.0 eq) and VcNa (0.4 M, 10.2 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5788.49 observed m/z: 968.9 ([M/6+H]$^+$) and 1158.0 ([M/5+H]$^+$)] was detected. The reaction mixture was directly purified by prep-HPLC (TFA condition). BCY9408 (3.1 mg, 4.97 e-1 μmol, 24.23% yield, 92.87% purity) was obtained as a white solid.

BCY9409

Procedure for Preparation of Compound 2

COM00000130 +

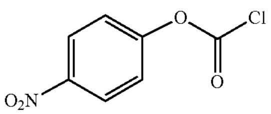

1

TEA
DCM

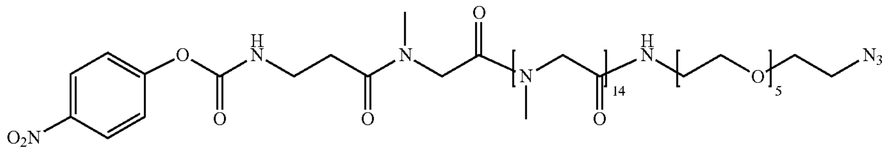

2

To a solution of compound 1 (30 mg, 20.78 μmol), COM130 (6.28 mg, 31.17 μmol) in DCM (3 mL) was added TEA (3.15 mg, 31.17 μmol, 4.34 μL, 1.5 eq). The mixture was stirred at 25-30° C. for 1 hr. LC-MS showed compound 1 was consumed completely and one main peak with desired m/z (MW: 1608.70 observed m/z: 804.8 ([M/2+H]$^+$) was detected. The reaction mixture was concentrated under reduced pressure and then lyophilized to give Compound 2 (10.2 mg, crude) as a white solid.

Procedure for Preparation of Compound 3

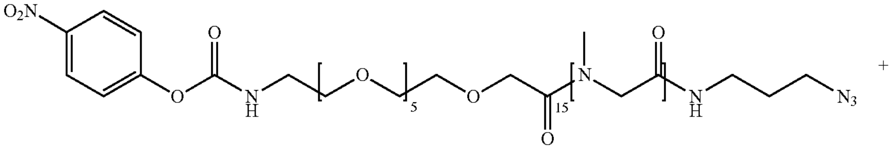

2

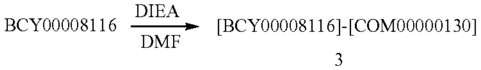

3

To a solution of compound 2 (10.2 mg, 6.34 μmol) and BCY8116 (13.50 mg, 6.22 μmol) in DMF (2 mL) was added DIEA (0.8 mg, 6.22 μmol, 1.1 μL, 1.0 eq). The mixture was stirred at 30° C. for 2 hr. LC-MS detected desired m/z (MW: 3642.08, observed m/z: 1214.4 ([M/3+H]$^+$). The reaction mixture was filtered and concentrated under reduced pressure to give a residue. The crude product was purified by reversed-phase HPLC (TFA condition). Compound 3 (15.0 mg, 4.12 μmol, 62.94% yield, 95% purity) was obtained as a white solid.

Procedure for Preparation of BCY9409

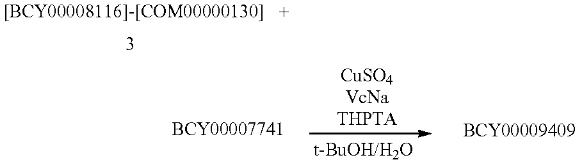

A mixture of Compound 3 (15 mg, 4.12 μmol, 1.0 eq), BCY7741 (10 mg, 4.38 μmol, 1.03 eq), and THPTA (0.4 M, 10.3 μL, 1.0 eq) was dissolved in t-BuOH/$H_2O$ (1:1, 2 mL, pre-degassed and purged with $N_2$ for 3 times), and then $CuSO_4$ (0.4 M, 10.3 μL, 1.0 eq) and VcNa (0.4 M, 20.6 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 5923.61, observed m/z: 988.2 ([M/6+H]$^+$)] was detected. The reaction mixture was directly purified by prep-HPLC (TFA condition). BCY9409 (3.1 mg, 0.52 μmol, 12.62% yield, 90.89% purity) was obtained as a white solid.

BCY9410

Procedure for Preparation of Compound 2

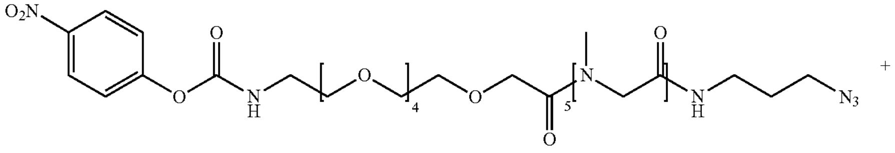

2

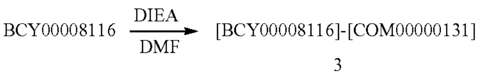

3

To a solution of COM131 (167.0 mg, 227.89 μmol, 1.0 eq), compound 1 (55.0 mg, 272.87 μmol, 1.2 eq) in DCM (5 mL) was added TEA (36.4 mg, 359.23 μmol, 50.0 μL, 1.6 eq). The mixture was stirred at 25-30° C. for 1 hr. LC-MS showed one main peak with desired m/z (MW: 897.93 observed 920.3 ([M+Na$^+$]) was detected. The reaction mixture was concentrated under reduced pressure to remove solvent to give a residue. The residue was purified by prep-HPLC (TFA condition). Compound 2 (35 mg, 33.74 μmol, 14.81% yield, 86.56% purity) was obtained as colorless oil.

Procedure for Preparation of Compound 3

[BCY00008116]-[COM00000131] +
3

BCY00007741 —CuSO$_4$ VcNa THPTA / t-BuOH/H$_2$O→ BCY00009410

To a solution of compound 2 (20 mg, 22.27 μmol, 1.0 eq) and BCY8116 (48 mg, 22.09 μmol, 1.0 eq) in DMF (2 mL) was added DIEA (8.64 mg, 66.82 μmol, 11.64 μL, 3.0 eq). The mixture was stirred at 30° C. for 2 hr. LC-MS showed compound 3 was consumed completely and one main peak with desired m/z (MW: 2931.32, observed m/z: 977.7 ([M+H]$^+$)) was detected. The residue was purified by prep-HPLC (TFA condition). Compound 3 (40 mg, 13.08 μmol, 58.7% yield, 95.82% purity) was obtained as a white solid.

Procedure for Preparation of BCY9410

[BCY00008116]-[COM00000131] +
3

BCY00007741 —CuSO$_4$ VcNa THPTA / t-BuOH/H$_2$O→
BCY00009410

A mixture of Compound 3 (40 mg, 13.08 μmol, 1.0 eq), BCY7741 (35 mg, 15.34 μmol, 1.17 eq), and THPTA (0.4 M, 34 μL, 1.0 eq) was dissolved in t-BuOH/H$_2$O (1:1, 2 mL, pre-degassed and purged with N$_2$ for 3 times), and then CuSO$_4$ (0.4 M, 34 μL, 1.0 eq) and VcNa (0.4 M, 68 μL, 2.0 eq) were added under N$_2$. The pH of this solution was adjusted to 8 by dropwise addition of 0.2 M NH$_4$HCO$_3$ (in 1:1 t-BuOH/H$_2$O) and the solution turned to light yellow. The reaction mixture was stirred at 25-30° C. for 12 hr under N$_2$ atmosphere. LC-MS showed Compound 3 was consumed completely and one main peak with desired m/z [MW: 5212.85, observed m/z: 1043.2 ([M/5+H]$^+$)] was detected. The reaction mixture was directly purified by prep-HPLC (TFA condition). BCY9410 (38.6 mg, 6.78 μmol, 49.71% yield, 91.6% purity) was obtained as a white solid.

BCY9411

Procedure for Preparation of Compound 2

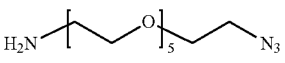
+

COM00000132

-continued

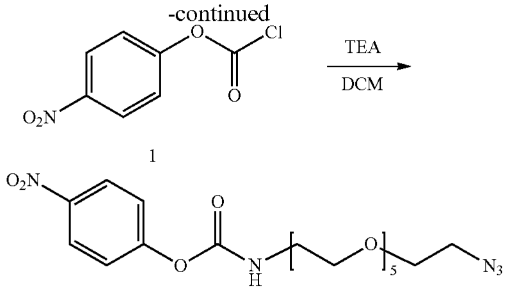

1

2

To a solution of COM132 (5 mg, 16.32 μmol, 1 eq), Compound 1 (4 mg, 19.85 μmol, 1.22 eq) in DCM (5 mL) was added TEA (2.8 mg, 24.48 μmol, 3.4 μL, 1.5 eq). The mixture was stirred at 25° C. for 1 hr. LC-MS showed one peak with desired m/z (calculated MW: 471.46, observed m/z: 489.2 ([M+NH4]$^+$)) was detected. The reaction mixture was concentrated under reduced pressure to remove solvent, and then lyophilized to give compound 2 (8 mg, crude) as a white solid.

Procedure for Preparation of Compound 3

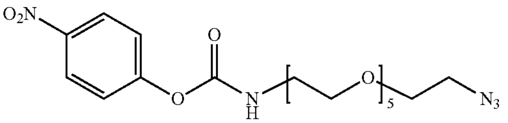
+

2

BCY00008116 —DIEA / DMF→
[BCY00008116]-[COM00000132]
3

To a solution of Compound 2 (3.3 mg, 6.9 μmol, 1.5 eq) and BCY8116 (10.0 mg, 4.6 μmol, 1.0 eq) in DMF (5 mL) was added DIEA (0.7 mg, 6.90 μmol, 1 μL, 1.5 eq). The mixture was stirred at 30° C. for 2 hrs. LC-MS showed Compound 2 was consumed completely and one main peak with desired m/z (calculated MW: 2504.83, observed m/z: 1252.3 ([M/2+H]$^+$)) was detected. The reaction mixture was filtered and concentrated under reduced pressure to give a residue. The crude product was purified by reversed-phase HPLC (TFA condition). Compound 3 (4.2 mg, 1.51 μmol, 32.78% yield, 90% purity) was obtained as a white solid.

Procedure for Preparation of BCY9411

[BCY00008116]-[COM00000132] +
3

BCY00007741 —CuSO$_4$ VcNa THPTA / t-BuOH/H$_2$O→
BCY00009411

A mixture of Compound 3 (4.2 mg, 1.68 μmol, 1.0 eq), BCY7741 (4.0 mg, 1.75 μmol, 1.05 eq), and THPTA (0.04 M, 84 μL, 2.0 eq) was dissolved in t-BuOH/H$_2$O (1:1, 2 mL, pre-degassed and purged with N$_2$ for 3 times), and then CuSO$_4$ (0.04 M, 84 μL, 2.0 eq) and VcNa (0.04 M, 168 μL, 4.0 eq) were added under N$_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 3 was consumed completely and one main peak with desired m/z [MW: 4786.37 observed m/z: 1596.2 ([M/3+H]$^+$), 1196.9 ([M/4+H]$^+$)] was detected. The reaction mixture was directly purified by prep-HPLC (TFA condition). BCY9411 (4.1 mg, 0.86 μmol, 50.20% yield, 98.26% purity) was obtained as a white solid.

BCY9759

Procedure for Preparation of Compound 2

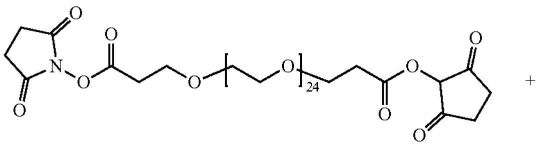

1

BCY00008116

2.0 eq DIPEA

Dry DMF

BCY00008116-PEG24-NHS ester

2

To a solution of compound 1 (5.0 mg, 3.54 μmol, 1.0 eq), BCY8116 (7.7 mg, 3.54 μmol, 1.0 eq) in DMF (3 mL) was added DIEA (0.9 mg, 7.07 μmol, 1.2 μL, 2.0 eq). The mixture was stirred at 0° C. for 20 min. LC-MS detected mass corresponding to compound 2 with NHS group falling off (calculated MW: 3470.95, hydrolyzed MW: 3373.81, observed m/z: 1125.0 ([M/3+H]$^+$). The reaction mixture was filtered and concentrated under reduced pressure and lyophilized to give compound 2 (15 mg, crude) was obtained as a white solid.

Procedure for Preparation of BCY9759

BCY00008116-PEG24-NHS ester +

2

BCY00007732

2.0 eq DIPEA

Dry DMF

BCY00009759

To a solution of compound 2 (20 mg, 5.76 μmol, 1.0 eq) and BCY7732 (12.7 mg, 5.76 μmol, 1.0 eq) in DMF (3 mL) was added DIEA (1.5 mg, 11.52 μmol, 2.0 μL, 2.0 eq). The mixture was stirred at 25-30° C. for 2 hrs. LC-MS showed compound 2 was consumed completely and one main peak with desired m/z (MW: 5557.3, observed m/z: 927.0 ([M/6+H]$^+$) and 1112.2 ([M/5+H]$^+$)) was detected. The reaction mixture was filtered and concentrated under reduced pressure to give a residue. The crude product was purified by reversed-phase HPLC (TFA condition). BCY9759 (2.3 mg, 6.92% yield, 96.29% purity) was obtained as a white solid.

BCY10000

Procedure for Preparation of BCY9172-PEG12-$N_3$

BCY00009172 +

NHS-PEG12-$N_3$

1

DIEA

DMF

BCY00009172-PEG12-$N_3$

2

BCY9172 (520 mg, 248.16 μmol, 1.0 eq) and compound 1 (370 mg, 499.47 μmol, 2.01 eq) were dissolved in DMF (5 mL), then the mixture was added with DIEA (48.11 mg, 372.24 μmol, 64.84 μL, 1.5 eq) and stirred at 30° C. for 12 hr. LC-MS showed BCY9172 was consumed completely and one main peak with desired m/z (calculated MW: 2721.12, observed m/z: 1360.9 ([M/2+H]$^+$)) was detected. The reaction mixture was purified by prep-HPLC (TFA condition) and compound 2 (284 mg, 101.10 μmol, 40.74% yield, 96.87% purity) was obtained as a white solid.

Procedure for Preparation of BCY10000

BCY00009172-NHS-PEG12-$N_3$ +

2

BCY00008846

$CuSO_4$

VcNa

THPTA t-BuOH/$H_2O$

BCY00010000

This reaction was performed in two independent containers in parallel. For one container, Compound 2 (142 mg, 52.18 μmol, 1.0 eq) and BCY8846 (157 mg, 51.74 μmol, 1.0 eq) were first dissolved in 10 mL of t-BuOH/$H_2O$ (1:1), and then $CuSO_4$ (0.4 M, 130.5 μL, 1.0 eq), VcNa (0.4 M, 261.0 μL, 2.0 eq) and THPTA (0.4 M, 130.5 μL, 1.0 eq) were added. Finally 1 M $NH_4HCO_3$ was added to adjust pH to 8. All solvents here were degassed and purged with $N_2$ for 3 times. The reaction mixture was stirred at 30° C. for 12 hr under $N_2$ atmosphere. LC-MS showed compound 2 was consumed completely and one main peak with desired m/z (calculated MW: 5755.54, observed m/z: 959.60 ([M/6+H]$^+$) and 1151.55 ([M/5+H]$^+$)) was detected. The reaction mixture was purified by prep-HPLC (TFA condition) and BCY10000 (314.9 mg, 51.99 μmol, 49.82% yield, 95.03% purity) was obtained as a white solid.

BCY10567

Procedure for Preparation of BCY8919-PEG12-$N_3$

BCY00008919 +

NHS-PEG12-$N_3$

1

DIEA

DMSO

BCY00008919-PEG12-$N_3$

2

BCY8919 (60.0 mg, 28.85 μmol, 1.0 eq) and compound 1 (22.2 mg, 30.01 μmol, 1.04 eq) were dissolved in DMSO (1 mL). The solution was added with DIPEA (5.6 mg, 43.28 μmol, 7.6 μl, 1.5 eq), and then the mixture was stirred at 25-30° C. for 2 hr. LC-MS showed BCY8919 was consumed completely and one main peak with desired m/z (calculated MW: 2705.16, observed m/z: 1353.15 ($[M/2+H]^+$)) was detected. The reaction mixture was purified by prep-HPLC (TFA condition) and compound 2 (BCY8919-PEG12-$N_3$, 18.5 mg, 6.77 μmol, 23.47% yield, 99.04% purity) was obtained as a white solid.

Procedure for Preparation of BCY10567

BCY00008919-NHS-PEG12-$N_3$ +

2

BCY00008846

$CuSO_4$
VcNa
THPTA
t-BuOH/$H_2O$

BCY00010567

Note: This reaction has been performed twice, and the first one is described below.

Compound 2 (9.0 mg, 3.33 μmol, 1.0 eq) and BCY8846 (10.1 mg, 3.33 μmol, 1.0 eq) were first dissolved in 2 mL of t-BuOH/$H_2O$ (1:1), and then $CuSO_4$ (0.4 M, 8.3 μL, 1.0 eq), VcN (1.3 mg, 6.56 μmol, 2.0 eq) and THPTA (1.4 mg, 3.22 μmol, 1.0 eq) were added. Finally 0.4 M $NH_4HCO_3$ was added to adjust pH to 8. All solvents here were degassed and purged with $N_2$ for 3 times. The reaction mixture was stirred at 30° C. for 16 hr under $N_2$ atmosphere. LC-MS showed compound 2 was consumed completely and one main peak with desired m/z (calculated MW: 5739.58, observed m/z: 956.75 ($[M/6+H]^+$)). The reaction mixture was purified by prep-HPLC (TFA condition) and BCY10567 (6.85 mg, 1.18 μmol, 35.48% yield, 98.91% purity) was obtained as a white solid.

BCY10569

Procedure for Preparation of Compound 3

BCY00008920 +

NHS-PEG12-$N_3$

2

DIEA
DMF

BCY00008920-PEG12-$N_3$

3

A mixture of compound BCY8920 (40.0 mg, 18.71 μmol, 1.0 eq.), compound 2 (16.0 mg, 21.6 μmol, 1.15 eq.) and DIEA (5.0 μL, 28.0 μmol, 1.5 eq.) was dissolved in DMF. The reaction mixture was stirred at 40° C. for 1 hr, till LC-MS showed one main peak with desired m/z (calculated MW: 2763.2, observed m/z: 912.17 ($[(M-28)/2+H]^+$) was detected. The reaction mixture was then concentrated under reduced pressure to remove solvent and produced a residue, following by purification by prep-HPLC (TFA condition). Compound 3 (23.4 mg, 8.47 μmol, 45.25% yield, 99.0% purity) was obtained as a white solid.

Procedure for Preparation of BCY10569

BCY00008920-NHS-PEG12-$N_3$ +

3

BCY00008846

$CuSO_4$
VcNa
THPTA
DMF

BCY00010569

A mixture of compound 3 (5.0 mg, 1.81 μmol, 1.0 eq.), BCY8846 (5.8 mg, 1.9 μmol, 1.05 eq.), and THPTA (1.0 mg, 2.3 μmol, 1.3 eq.) was dissolved in t-BuOH/$H_2O$ (1:1, 1 mL, pre-degassed and purged with $N_2$ for 3 times), and then $CuSO_4$ (0.4 M, 5.0 μL, 1.0 eq.) and VcNa (0.4 M, 5.0 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 3 was consumed completely and one main peak with desired m/z (calculated MW: 5797.62, observed m/z: 1160.7 ($[M/5+H]^+$) was detected. The reaction mixture was filtered and concentrated under reduced pressure to give a residue. The crude product was purified by prep-HPLC (TFA condition), and BCY10569 (5.7 mg, 1.18 μmol, 52.25% yield, 96.16% purity) was obtained as a white solid.

BCY10571

Procedure for Preparation of BCY8116-PEG5-$N_3$

BCY00008116 +

NHS-PEG5-$N_3$

1

DIEA
DMSO

BCY00008116-PEG5-$N_3$

2

BCY8116 (60 mg, 27.62 μmol, 1.0 eq) and compound 1 (12.0 mg, 27.75 μmol, 1.0 eq) were first dissolved in DMSO (1 mL), then the mixture was added with DIEA (5.4 mg, 41.43 μmol, 7.22 μL, 1.5 eq). The mixture was stirred at 30° C. for 12 hr. LC-MS showed one main peak with desired m/z (MW: 2489.82. observed m/z: 1245.1700 ($[M/2+H]^+$)) was detected. The reaction mixture was concentrated under reduced pressure to remove solvent to give a residue. The residue was purified by prep-HPLC (TFA condition). Compound 2 (48 mg, 19.28 μmol, 69.80% yield, 100% purity) was obtained as a white solid.

Procedure for Preparation of BCY10571

BCY00008116-PEG5-$N_3$ +

2

BCY00008927

$CuSO_4$
VcNa
THPTA
t-BuOH/$H_2O$

BCY00010571

This reaction was performed in two independent containers in parallel. For one container, Compound 2 (10 mg, 4.02 μmol, 1.0 eq) and BCY8927 (9 mg, 4.17 μmol, 1.04 eq) were first dissolved in 2 mL of t-BuOH/$H_2O$ (1:1), and then $CuSO_4$ (0.4 M, 10.0 μL, 1.0 eq), VcNa (0.4 M, 20.1 μL, 2.0 eq) and THPTA (0.4 M, 10.0 μL, 1 eq) were added. Finally 0.4 M $NH_4HCO_3$ was added to adjust pH to 8. All solvents here were degassed and purged with $N_2$ for 3 times. The reaction mixture was stirred at 30° C. for 4 hr under $N_2$ atmosphere. LC-MS showed compound 3 was consumed completely and one main peak with desired m/z (MW: 4649.36, observed m/z: 1162.57 ($[M/4+H]^+$), 1549.69 ($[M/3+H]^+$)) was detected. The residue was purified by prep-HPLC (TFA condition). BCY10571 (13 mg, 2.79 μmol, 34.88% yield, 96.48% purity) was obtained as a white solid.

BCY10572

Procedure for Preparation of BCY8116-PEG5-$N_3$

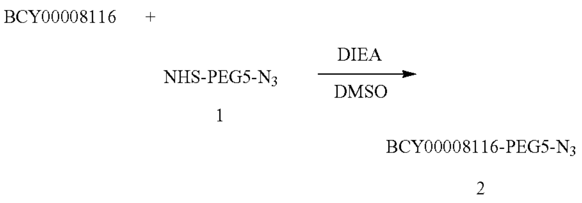

BCY8116 (60 mg, 27.62 μmol, 1.0 eq) and compound 1 (12.0 mg, 27.75 μmol, 1.0 eq) were first dissolved in DMSO (1 mL), then the mixture was added with DIEA (5.4 mg, 41.43 μmol, 7.22 μL, 1.5 eq). The mixture was stirred at 30° C. for 12 hr. LC-MS showed one main peak with desired m/z (MW: 2489.82. observed m/z: 1245.1700 ($[M/2+H]^+$)) was detected. The reaction mixture was concentrated under reduced pressure to remove solvent to give a residue. The residue was purified by prep-HPLC (TFA condition). Compound 2 (48 mg, 19.28 μmol, 69.80% yield, 100% purity) was obtained as a white solid.

Procedure for Preparation of BCY10572

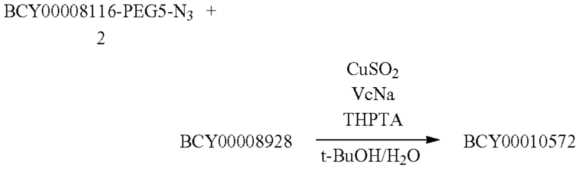

This reaction was performed in two independent containers in parallel. For one container, Compound 2 (10 mg, 4.02 μmol, 1.0 eq) and BCY8928 (9 mg, 4.06 μmol, 1.01 eq) were first dissolved in 2 mL of t-BuOH/$H_2O$ (1:1), and then $CuSO_4$ (0.4 M, 10.1 μL, 1 eq), VcNa (0.4 M, 20.2 μL, 2.0 eq) and THPTA (0.4 M, 10.1 μL, 1.0 eq) was added. Finally 0.4 M $NH_4HCO_3$ was added to adjust pH to 8. All solvents here were degassed and purged with $N_2$ for 3 times. The reaction mixture was stirred at 30° C. for 4 hr under $N_2$ atmosphere. LC-MS showed compound 1 was consumed completely and one main peak with desired m/z (MW: 4707.40. observed m/z: 1568.29 ($[M/3+H]^+$) and 1176.83 ($[M/4+H]^+$)) was detected. The reaction mixture was concentrated under reduced pressure to remove solvent to give a residue. The residue was purified by prep-HPLC (TFA condition). BCY10572 (21 mg, 4.46 μmol, 55.7% yield, 97.51% purity) was obtained as a white solid.

BCY10573

Procedure for Preparation of Compound 2

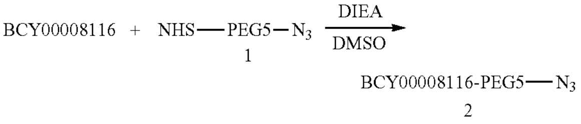

To a solution of BCY8116 (35 mg, 16.11 μmol, 1 eq), Compound 1 (7.00 mg, 16.19 μmol, 1 eq) in DMSO (1 mL) was added DIEA (3.12 mg, 24.17 μmol, 4.21 μL, 1.5 eq). The mixture was stirred at 25-30° C. for 2 hr. LC-MS showed majority of BCY8116 was consumed and one main peak with desired m/z (calculated MW: 2489.82, observed m/z: 1245.37 ($[M/2+H]^+$) and 830.25 ($[M/3+H]^+$)) was detected. The reaction mixture was concentrated under reduced pressure to remove solvent to give a residue. The residue was purified by prep-HPLC (TFA condition). Compound 2 (26.8 mg, 10.76 μmol, 66.81% yield, 100% purity) was obtained as a white solid.

Procedure for Preparation of BCY10573

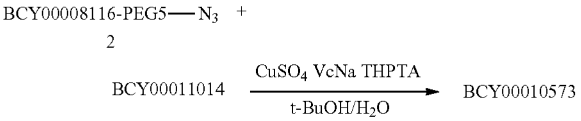

A mixture of Compound 2 (15 mg, 6.02 μmol, 1.0 eq), BCY11014 (13.50 mg, 6.21 μmol, 1.03 eq), and THPTA (0.4 M, 15.1 μL, 1.0 eq) was dissolved in t-BuOH/$H_2O$ (1:1, 2 mL, pre-degassed and purged with $N_2$ for 3 times), and then $CuSO_4$ (0.4 M, 15.1 μL, 1.0 eq) and VcNa (0.4 M, 30.2 μL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 2 was consumed completely and one main peak with desired m/z [MW: 4665.32, observed m/z: 1167.50 ($[M/4+H^+]$)] was detected. The reaction mixture was directly purified by prep-HPLC (TFA condition). BCY10573 (11.5 mg, 2.42 μmol, 40.14% yield, 98.11% purity) was obtained as a white solid.

BCY10578

Procedure for Preparation of Compound 2

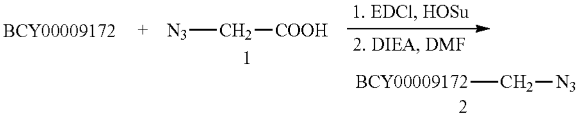

Compound 1 (5.0 mg, 49.5 μmol, 1.0 eq) was first activated by mixing with EDCl (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then compound BCY9172 (80.0 mg, 38.18 μmol, 0.8 eq.) and DIEA (6.3 mg, 8.5 μL, 49.5 μmol, 1.0 eq.) were added to this mixture, and stirred at 40° C. for 1 hr, till LC-MS showed one main peak with desired m/z (calculated MW: 2178.46, observed m/z: 1089.44 ($[M/2+H]^+$) was detected. The reaction mixture was then concentrated under reduced pressure to remove solvent and produced a residue, following by purification by prep-HPLC (TFA condition). Compound 2 (15 mg, 6.88 μmol, 18.66% yield, 73.3% purity) was obtained as a white solid.

Procedure for Preparation of BCY10578

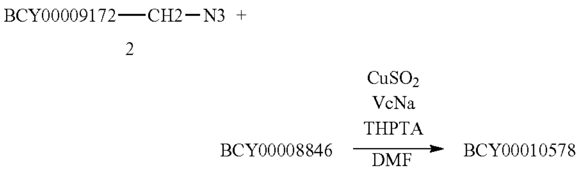

A mixture of compound 2 (9.8 mg, 4.5 μmol, 1.0 eq.), BCY8846 (14.0 mg, 4.6 μmol, 1.0 eq.), and THPTA (2.0 mg, 4.6 μmol 1.0 eq.) was dissolved in t-BuOH/$H_2O$ (1:1, 1 mL, pre-degassed and purged with $N_2$ for 3 times), and then $CuSO_4$ (0.4 M, 12 μL, 1.0 eq.) and VcNa (0.4 M, 24 μL, 2.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 2 was consumed completely and one main peak with desired m/z (calculated MW: 5212.88, observed m/z: 1304.2 ($[M/4+H]^+$)) was detected. The reaction mixture was filtered and concentrated under reduced pressure to give a residue. The crude product was purified by prep-HPLC (TFA condition), and BCY10578 (13.78 mg, 2.64 μmol, 58.66% yield, 96.23% purity) was obtained as a white solid.

BCY10917

Procedure for Preparation of BCY8831-PEG12-$N_3$

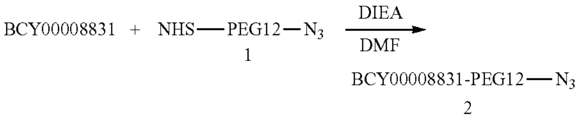

BCY8831 (40.0 mg, 13.29 μmol, 1.0 eq) and compound 1 (10.5 mg, 14.17 μmol, 1.07 eq) were dissolved in DMF (1 mL). The solution was added with DIPEA (2.6 mg, 20.09 μmol, 3.5 μl, 1.5 eq), and then the mixture was stirred at 30° C. for 16 hr. LC-MS showed BCY8831 was consumed completely and one main peak with desired m/z (calculated MW: 3635.16 observed m/z: 1212.0 ($[M/3+H]^+$)) was detected. The reaction mixture was purified by prep-HPLC (TFA condition) and compound 2 (22.0 mg, 5.83 μmol, 43.85% yield, 96.39% purity) was obtained as a white solid.

Procedure for Preparation of BCY10917

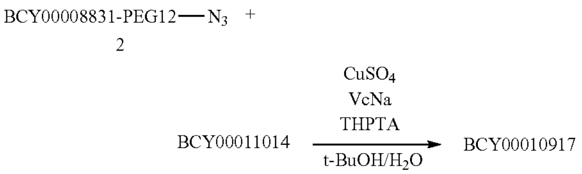

Note: Two batches were made, and the first one was written for final report.

Compound 2 (10.0 mg, 2.75 μmol, 1.0 eq) and BCY11014 (5.98 mg, 2.75 μmol, 1.0 eq), were first dissolved in 2 mL of t-BuOH/$H_2O$ (1:1), and then $CuSO_4$ (0.4 M, 13.7 μL, 2.0 eq), VcNa (1.1 mg, 5.55 μmol, 2.0 eq) and THPTA (1.2 mg, 2.76 μmol, 1.0 eq) was added. Finally 1 M $NH_4HCO_3$ was added to adjust pH to 8. All solvents here were degassed and purged with $N_2$ for 3 times. The reaction mixture was stirred at 30° C. for 16 hr under $N_2$ atmosphere. LC-MS showed compound 2 was consumed completely and one main peak with desired m/z (calculated MW: 5810.66 observed m/z: 1163.0 ($[M/5+H]^+$)). The reaction mixture was purified by prep-HPLC (TFA condition) and BCY10917 (6.4 mg, 1.07 μmol, 39.03% yield, 97.49% purity) was obtained as a white solid.

BCY11020

Procedure for Preparation of BCY8831-PEG5-$N_3$

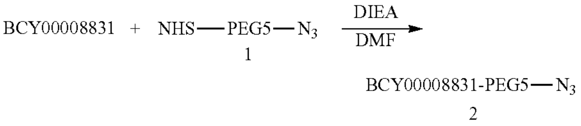

BCY8831 (25.0 mg, 8.31 μmol, 1.0 eq) and compound 1 (3.9 mg, 9.02 μmol, 1.09 eq), were dissolved in DMF (1 mL). The solution was added with DIPEA (1.6 mg, 12.46 μmol, 2.2 μl, 1.5 eq), and then the mixture was stirred at 35° C. for 2 hr. LC-MS showed BCY8831 was consumed completely and one main peak with desired m/z (calculated MW: 3326.79 observed m/z: 1109.66 ($[M/3+H]^+$)) was detected. The reaction mixture was purified by prep-HPLC (TFA condition) and compound 2 (7.3 mg, 2.09 μmol, 25.20% yield, 95.41% purity) was obtained as a white solid.

Procedure for Preparation of BCY11020

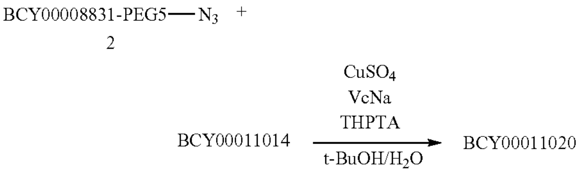

Compound 2 (7.3 mg, 2.19 μmol, 1.0 eq) and BCY11014 (4.8 mg, 2.19 μmol, 1.0 eq), were first dissolved in 2 mL of t-BuOH/$H_2O$ (1:1), and then $CUSO_4$ (0.4 M, 5.5 μL, 1.0 eq), VcNa (1.0 mg, 5.05 μmol, 2.3 eq) and THPTA (1.0 mg, 2.30 μmol, 1.0 eq) was added. Finally 1 M $NH_4HCO_3$ was added to adjust pH to 8. All solvents here were degassed and purged with $N_2$ for 3 times. The reaction mixture was stirred at 30° C. for 12 hr under $N_2$ atmosphere. LC-MS showed compound 2 was consumed completely and one main peak with desired m/z (calculated MW: 5502.29, observed m/z: 1101.74 ($[M/5+H]^+$)) was detected. The reaction mixture was purified by prep-HPLC (TFA condition) and BCY11020 (3.3 mg, 0.577 μmol, 26.30% yield, 96.24% purity) was obtained as a white solid.

BCY11373

Procedure for Preparation of Compound 2

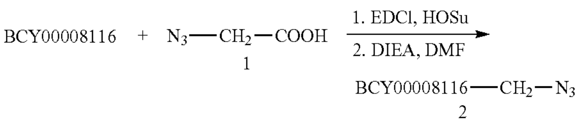

To a solution of compound 1 (5.0 mg, 49.5 μmol, 1.0 eq) in DMF (1 mL) was added EDCl (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.3 mL of this mixture was added with BCY8116 (30.0 mg, 13.81 μmol, 0.28 eq.) and DIEA (2.4 μL, 13.81 μmol, 0.28 eq.), and stirred at 25-30° C. for 2 hr. LC-MS showed BCY8116 was consumed completely and one main peak with desired m/z (calculated MW: 2255.53, observed m/z: 1128.34 ($[M/2+H]^+$) was detected. The reaction mixture was then concentrated under reduced pressure to remove solvent and produced a residue, following by purification by prep-HPLC (TFA condition). Compound 2 (21 mg, 8.9 μmol, 64.43% yield, 95.56% purity) was obtained as a white solid.

Procedure for Preparation of BCY11373

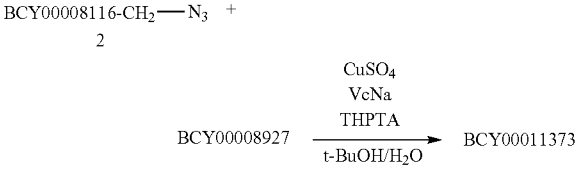

A mixture of compound 2 (5 mg, 2.22 μmol, 1.0 eq.), BCY8928 (4.79 mg, 2.22 μmol, 1.0 eq.), and THPTA (1.0 mg, 2.30 μmol, 1.0 eq.) was dissolved in t-BuOH/$H_2O$ (1:1, 1 mL, pre-degassed and purged with $N_2$ for 3 times), and then $CuSO_4$ (0.4 M, 5.6 μL, 1.0 eq.) and VcNa (0.4 M, 5.6 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 2 was consumed completely and one main peak with desired m/z (calculated MW: 4415.07, observed m/z: 1471.5 ($[M/3+H]^+$ and 1103.8 ($[M/4+H]^+$) was detected. The reaction mixture was filtered and concentrated under reduced pressure to give a residue. The crude product was purified by prep-HPLC (TFA condition), and BCY11373 (4.9 mg, 1.03 μmol, 46.26% yield, 92.4% purity) was obtained as a white solid.

BCY11374

Procedure for Preparation of BCY11374

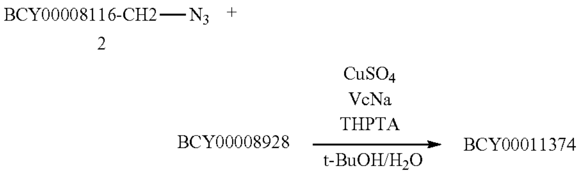

A mixture of compound 2 (which may be prepared as described in the procedure for preparing BCY11373; 5 mg, 2.22 μmol, 1.0 eq.), BCY8928 (4.9 mg, 2.22 μmol, 1.0 eq.), and THPTA (1.0 mg, 2.30 μmol, 1.0 eq.) was dissolved in t-BuOH/$H_2O$ (1:1, 1 mL, pre-degassed and purged with $N_2$ for 3 times), and then $CuSO_4$ (0.4 M, 5.6 μL, 1.0 eq.) and VcNa (0.4 M, 5.6 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 2 was consumed completely and one main peak with desired m/z (calculated MW: 4473.11, observed m/z: 1491.5 ($[M/3+H]^+$ and 1118.5 ($[M/4+H]^+$) was detected. The reaction mixture was filtered and concentrated under reduced pressure to give a residue. The crude product was purified by prep-HPLC (TFA condition), and BCY11374 (4.1 mg, 1.27 μmol, 38.04% yield, 92.0% purity) was obtained as a white solid.

BCY11375

Procedure for Preparation of BCY11375

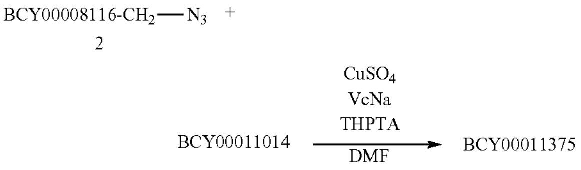

A mixture of compound 2 (which may be prepared as described in BCY11373; 5 mg, 2.22 μmol, 1.0 eq.), BCY11014 (4.8 mg, 2.22 μmol, 1.0 eq.), and THPTA (0.5 mg, 2.30 μmol, 1.0 eq.) was dissolved in t-BuOH/$H_2O$ (1:1, 1 mL, pre-degassed and purged with $N_2$ for 3 times), and then $CuSO_4$ (0.4 M, 5.6 μL, 1.0 eq.) and VcNa (0.4 M, 5.6 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS detected some desired m/z (calculated MW: 4431.03, observed m/z: 1107.59 ($[M/4+H]^+$ and 1477.90 ($[M/3+H]^+$). The reaction mixture was filtered and concentrated under reduced pressure to give a residue. The crude product was purified by prep-HPLC (TFA condition), and BCY11375 (6 mg, 1.31 μmol, 59.13% yield, 96.8% purity) was obtained as a white solid.

BCY11616

Procedure for Preparation of Compound 3

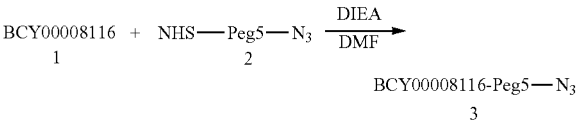

A mixture of compound BCY8116 (30.0 mg, 13.81 μmol, 1.0 eq.), compound 2 (6.0 mg, 13.88 μmol, 1.0 eq.) and DIEA (2.4 μL, 13.82 μmol, 1.0 eq.) was dissolved in DMF. The reaction mixture was stirred at 40° C. for 1 hr, till LC-MS showed compound 1 was consumed completely and one main peak with desired m/z (calculated MW: 2489.82, observed m/z: 1245.4 ($[M/2+H]^+$) was detected. The reaction mixture was then concentrated under reduced pressure to remove solvent and produced a residue, following by purification by prep-HPLC (TFA condition). Compound 3 (27 mg, 10.29 μmol, 74.52% yield, 94.9% purity) was obtained as a white solid.

Procedure for Preparation of BCY11616

BCY00008116-Peg5—$N_3$ +

3

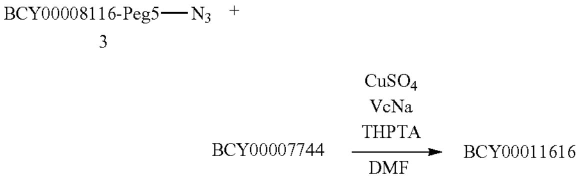

BCY00007744 → BCY00011616

A mixture of compound 3 (5 mg, 2.01 μmol, 1.0 eq.), BCY7744 (5.2 mg, 2.21 μmol, 1.1 eq.), and THPTA (1.0 mg, 2.30 μmol, 1.0 eq.) was dissolved in t-BuOH/$H_2O$ (1:1, 1 mL, pre-degassed and purged with $N_2$ for 3 times), and then $CuSO_4$ (0.4 M, 5.0 μL, 1.0 eq.) and VcNa (0.4 M, 5.0 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 3 was consumed completely and one main peak with desired m/z (calculated MW: 4827.46, observed m/z: 1207.12 ([M/4+H]$^+$) was detected. The reaction mixture was filtered and concentrated under reduced pressure to give a residue. The crude product was purified by prep-HPLC (TFA condition), and BCY11616 (4.7 mg, 1.0 μmol, 48.48% yield, 94.7% purity) was obtained as a white solid.

BCY11617

Procedure for Preparation of BCY11617

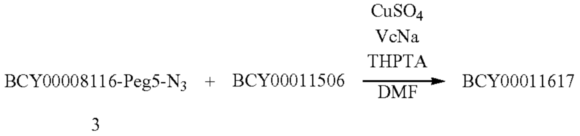

BCY00008116-Peg5-$N_3$ + BCY00011506 → BCY00011617

3

A mixture of compound 3 (which may be prepared as described in the procedure for preparing BCY11616; 5 mg, 2.01 μmol, 1.0 eq.), BCY11506 (5.2 mg, 2.21 μmol, 1.1 eq.), and THPTA (1.0 mg, 2.30 μmol, 1.1 eq.) was dissolved in t-BuOH/$H_2O$ (1:1, 1 mL, pre-degassed and purged with $N_2$ for 3 times), and then $CuSO_4$ (0.4 M, 5.0 μL, 1.0 eq.) and VcNa (0.4 M, 5.0 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 3 was consumed completely and one main peak with desired m/z (calculated MW: 4828.45, observed m/z: 1206.97 ([M/4+H]$^+$) and 965.91 ([M/5+H]$^+$)) was detected. The reaction mixture was filtered and concentrated under reduced pressure to give a residue. The crude product was purified by prep-HPLC (TFA condition), and BCY11617 (3.2 mg, 0.63 μmol, 31.37% yield, 95.05% purity) was obtained as a white solid.

BCY11857

Procedure for Preparation of BCY11414-PEG5-$N_3$

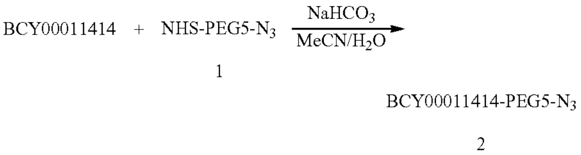

BCY00011414 + NHS-PEG5-$N_3$ →

1

BCY00011414-PEG5-$N_3$

2

BCY11414 (60.0 mg, 29.06 μmol, 1.0 eq) and compound 1 (13.0 mg, 30.06 μmol, 1.03 eq) were dissolved in 2 mL of MeCN/$H_2O$ (1:1). Adjust pH to 8 with $NaHCO_3$ (0.4 M), and then the mixture was stirred at 25-30° C. for 2 hr. LC-MS showed one main peak with desired m/z (calculated MW: 2381.72, observed m/z: 1191.07 ([M/2+H]$^+$)) was detected. The reaction mixture was purified by prep-HPLC (TFA condition) and compound 2 (38.0 mg, 15.9 μmol, 54.71% yield, 97.35% purity) was obtained as a white solid.

Procedure for Preparation of BCY11857

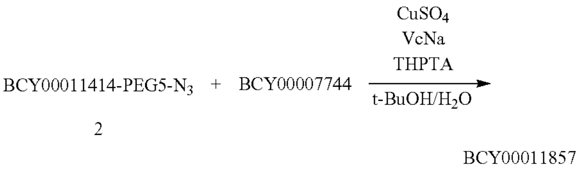

BCY00011414-PEG5-$N_3$ + BCY00007744 →

2

BCY00011857

Compound 2 (10.0 mg, 4.20 μmol, 1.0 eq) and BCY7744 (11.5 mg, 4.92 μmol, 1.2 eq) were first dissolved in 2 mL of t-BuOH/$H_2O$ (1:1), and then $CuSO_4$ (0.4 M, 11.0 μL, 1.0 eq), VcNa (2.0 mg, 10 μmol, 2.4 eq) and THPTA (2.0 mg, 4.6 μmol, 1.1 eq) were added. Finally 0.2 M $NH_4HCO_3$ was added to adjust pH to 8. All solvents here were degassed and purged with $N_2$ for 3 times. The reaction mixture was stirred at 30° C. for 16 hr under $N_2$ atmosphere. LC-MS showed compound 2 was consumed completely and one main peak with desired m/z (calculated MW: 4719.37, observed m/z: 1180.24 ([M/4+H]$^+$)). The reaction mixture was purified by prep-HPLC (TFA condition) and BCY11857 (10.3 mg, 2.18 μmol, 51.90% yield, 96.02% purity) was obtained as a white solid.

BCY11858

Procedure for Preparation of BCY11414-PEG5-$N_3$

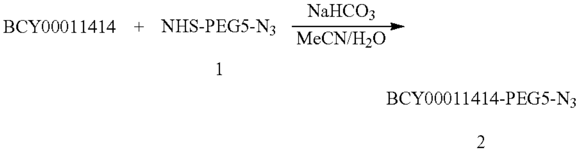

BCY00011414 + NHS-PEG5-$N_3$ →

1

BCY00011414-PEG5-$N_3$

2

BCY11414 (60.0 mg, 29.06 μmol, 1.0 eq) and compound 1 (13.0 mg, 30.06 μmol, 1.03 eq), were dissolved in 2 mL of MeCN/$H_2O$ (1:1). Adjust pH to 8 with $NaHCO_3$ (0.4 M), and then the mixture was stirred at 25-30° C. for 2 hr. LC-MS showed one main peak with desired m/z (calculated MW: 2381.72, observed m/z: 1191.07 ([M/2+H]$^+$)) was detected. The reaction mixture was purified by prep-HPLC (TFA condition) and compound 2 (38.0 mg, 15.9 μmol, 54.71% yield, 97.35% purity) was obtained as a white solid.

Procedure for Preparation of BCY11858

$CuSO_4$
VcNa
THPTA
BCY00011414-PEG5-$N_3$ + BCY00008928
t-BuOH/$H_2O$
2
BCY00011858

Compound 2 (20.0 mg, 8.40 μmol, 1.0 eq) and BCY8928 (22.0 mg, 9.92 μmol, 1.1 eq) were first dissolved in 2 mL of t-BuOH/$H_2O$ (1:1), and then $CuSO_4$ (0.4 M, 21.0 μL, 1.0 eq), VcNa (4.0 mg, 20.19 μmol, 2.4 eq) and THPTA (4.0 mg, 9.20 μmol, 1.1 eq) were added. Finally 0.4 M $NH_4HCO_3$ was added to adjust pH to 8. All solvents here were degassed and purged with $N_2$ for 3 times. The reaction mixture was stirred at 30° C. for 16 hr under $N_2$ atmosphere. LC-MS showed compound 2 was consumed completely and one main peak with desired m/z (calculated MW: 4599.30, observed m/z: 920.38 ($[M/5+H]^+$), 1150.79 ($[M/4+H]^+$), 1533.35 ($[M/3+H]^+$)). The reaction mixture was purified by prep-HPLC (TFA condition) and BCY11858 (16.9 mg, 3.67 μmol, 43.43% yield, 99.25% purity) was obtained as a white solid.

BCY11859

Procedure for Preparation of BCY11415-PEG5-$N_3$

BCY00011415 + NHS-PEG5-$N_3$
$NaHCO_3$
MeCN/$H_2O$
1
BCY00011415-PEG5-$N_3$
2

BCY11415 (30.0 mg, 13.81 μmol, 1.0 eq) and compound 1 (6.0 mg, 30.06 μmol, 1.0 eq), were dissolved in 2 mL of MeCN/$H_2O$ (1:1). Adjust pH to 8 with $NaHCO_3$ (0.4 M), and then the mixture was stirred at 25-30° C. for 2 hr. LC-MS showed one main peak with desired m/z (calculated MW: 2489.82, observed m/z: 1245.18 ($[M/2+H]^+$)) was detected. The reaction 25 mixture was purified by prep-HPLC (TFA condition) and compound 2 (24.0 mg, 9.63 μmol, 69.7% yield, 99.28% purity) was obtained as a white solid.

Procedure for Preparation of BCY11859

$CuSO_4$
VcNa
THPTA
BCY00011415-PEG5-$N_3$ + BCY00008928
t-BuOH/$H_2O$
2
BCY00011859

Compound 2 (20.0 mg, 8.03 μmol, 1.0 eq) and BCY8928 (21.0 mg, 9.47 μmol, 1.1 eq) were first dissolved in 2 mL of t-BuOH/$H_2O$ (1:1), and then $CuSO_4$ (0.4 M, 21.0 μL, 1.0 eq), VcNa (4.0 mg, 2.5 eq) and THPTA (4.0 mg, 1.1 eq) was added. Finally 1 M $NH_4HCO_3$ was added to adjust pH to 8. All solvents here were degassed and purged with $N_2$ for 3 times. The reaction mixture was stirred at 30° C. for 16 hr under $N_2$ atmosphere. LC-MS showed compound 2 was consumed completely and one main peak with desired m/z (calculated MW: 4707.40, observed m/z: 941.7 ($[M/5+H]^+$), 1176.9 ($[M/4+H]^+$), 1569.6 ($[M/3+H]^+$)). The reaction mixture was purified by prep-HPLC (TFA condition) and BCY11859 (19.2 mg, 4.01 μmol, 49.87% yield, 98.22% purity) was obtained as a white solid.

Example 4: Synthesis of PD-L1/CD137 Binding Heterotandem Bicyclic Peptides BCY8939

General Procedure for Preparation of BCY8939

N3-PEG12-COOH
1) HOSu, EDCl
2) BCY00007732, DIEA
BCY00007859

To a solution of N3-PEG12-COOH (250 mg, 388 μmol) and HOSu (67.0 mg, 583 μmol) in DMA (4.5 mL) and DCM (1.5 mL) was added EDCl (89.3 mg, 466 μmol) with stirring at 20° C. for 16 hr. LCMS showed the desired intermediate was formed completely. BCY7732 (854.97 mg, 388.37 μmol, 1 eq) and DIEA (186 mg, 1.44 mmol, 250 μL) were added to the mixture with further stirring at 20° C. for additional 5 hr. LC-MS showed BCY7732 was consumed completely and one main peak with desired mass was detected. The reaction mixture was purified by prep-HPLC (TFA condition) to give compound BCY7859 (621 mg, 200.58 μmol, 51.65% yield, 95% purity, TFA) as a white solid. Calculated MW: 2817.16, observed m/z: 942.7 $[M/3+H]^+$ General Procedure for Preparation of BCY8939

BCY00007859
BCY00008938
Vc, CuSO4, DMF
BCY00008939

To a solution of BCY7859 (31.1 mg, 11.0 μmol) and BCY8938 (30.0 mg, 10.0 μmol) in DMF (2 mL) was added (2R)-2-[(1S)-1,2-dihydroxyethyl]-3,4-dihydroxyl-2H-furan-5-one (1 M, 100 μL) and $CuSO_4$ (1 M, 30.0 μL) with stirring under nitrogen atmosphere for 2 hr at 20° C. LC-MS showed BCY7859 was consumed completely and one main peak with desired mass was detected. The reaction mixture was purified by prep-HPLC (TFA condition) to give compound BCY8939 (16.1 mg, 2.72 μmol, 27.1% yield, 98.3% purity) as a white solid. Calculated MW: 5823.49, observed m/z: 1165.4 $[M/5+H]^+$, 971.0 $[M/6+H]^+$, 832.9$[M/7+H]^+$

BCY10580

Procedure for Preparation of BCY9172-PEG12-$N_3$

BCY00009172 + NHS-PEG12-$N_3$
DIEA
DMSO
1
BCY00009172-PEG12-$N_3$
2

BCY9172 (100.0 mg, 47.72 μmol, 1 eq) and compound 1 (40.0 mg, 54.00 μmol, 1.13 eq) in DMSO (2 mL) was added DIEA (9.25 mg, 71.58 μmol, 12.47 μL, 1.5 eq). The mixture was stirred at 30° C. for 12 hr. LC-MS showed BCY9172 was consumed completely and one main peak with desired m/z (MW: 2721.12, observed m/z: 1361.07 ($[(M/2+H^+])$) was detected. The reaction mixture was concentrated under reduced pressure to remove solvent and produced a residue.

The residue was then purified by prep-HPLC (neutral condition). Compound 2 (48 mg, 17.44 µmol, 45.68% yield, 98.87% purity) was obtained as a white solid.

Procedure for Preparation of BCY10580

BCY00009172-PEG12-$N_3$ + BCY00010043
2
$CuSO_4$
VcNa
THPTA
t-BuOH/$H_2O$
BCY00010580

Compound 2 (20 mg, 7.35 µmol, 1.0 eq) and BCY10043 (23.1 mg, 7.35 µmol, 1.0 eq) were first dissolved in 2 mL of t-BuOH/$H_2O$ (1:1), and then $CuSO_4$ (0.4 M, 18.4 µL, 1.0 eq), VcNa (0.4 M, 36.8 µL, 2.0 eq) and THPTA (0.4 M, 18.4 µL, 1.0 eq) were added. Finally 1 M $NH_4HCO_3$ was added to adjust pH to 8. All solvents here were degassed and purged with $N_2$ for 3 times. The reaction mixture was stirred at 30° C. for 4 hr under $N_2$ atmosphere. LC-MS showed compound 3 was consumed completely and one main peak with desired m/z (MW: 5855.74 observed m/z: 976.40 ([M/6+H]$^+$) and 1171.67 ([M/5+H]$^+$)) was detected. The residue was purified by prep-HPLC (TFA condition). BCY10580 (29 mg, 4.85 µmol, 65.95% yield, 97.879% purity) was obtained as a white solid.

BCY10581

Procedure for Preparation of BCY9172-PEG12-$N_3$

BCY00009172 + NHS-PEG12-$N_3$
1
DIEA
DMSO
BCY00009172-PEG12-$N_3$
2

BCY9172 (100 mg, 47.72 µmol, 1 eq) an compound 1 (40.00 mg, 54.00 µmol, 1.13 eq) in DMSO (2 mL) was added DIEA (9.25 mg, 71.58 µmol, 12.47 µL, 1.5 eq). The mixture was stirred at 30° C. for 12 hr. LC-MS showed BCY9172 was consumed completely and one main peak with desired m/z (MW: 2721.12, observed m/z: 1361.07 ([(M/2+H$^+$])) was detected. The reaction mixture was concentrated under reduced pressure to remove solvent and produced a residue. The residue was then purified by prep-HPLC (neutral condition). Compound 2 (48 mg, 17.44 µmol, 45.68% yield, 98.87% purity) was obtained as a white solid.

Procedure for Preparation of BCY10581

BCY00009172-PEG12-$N_3$ + BCY00010044
2
$CuSO_4$
VcNa
THPTA
t-BuOH/$H_2O$
BCY00010581

Compound 2 (12 mg, 4.41 µmol, 1 eq) and BCY10044 (14.08 mg, 4.41 µmol, 1 eq) were first dissolved in 2 mL of t-BuOH/$H_2O$ (1:1), and then $CuSO_4$ (0.4 M, 11.02 µL, 1 eq), VcNa (0.4 M, 22.05 µL, 2 eq) and THPTA (0.4 M, 10.04 µL, 1 eq) was added. Finally 1 M $NH_4HCO_3$ was added to adjust pH to 8. All solvents here were degassed and purged with $N_2$ for 3 times. The reaction mixture was stirred at 30° C. for 4 hr under $N_2$ atmosphere. LC-MS showed compound 3 was consumed completely and one main peak with desired m/z (MW: 5912.84, observed m/z: 985.90 ([M/6+H]$^+$) and 1183.28 ([M/5+H]$^+$)) was detected. The residue was purified by prep-HPLC (TFA condition). BCY10581 (9.3 mg, 1.47 µmol, 33.36% yield, 93.541% purity) was obtained as a white solid.

BCY10582

Procedure for Preparation of Compound 2

BCY00009172 + NHS-PEG12-$N_3$
1
DIEA
DMSO
BCY00009172-PEG12-$N_3$
2

To a solution of BCY9172 (100.0 mg, 47.7 µmol, 1.0 eq), Compound 1 (40.0 mg, 54.0 µmol, 1.13 eq) in DMSO (2 mL) was added DIEA (9.2 mg, 71.6 µmol, 12.5 µL, 1.5 eq). The mixture was stirred at 30° C. for 12 hr. LC-MS showed BCY9172 was consumed completely and one main peak with desired m/z (calculated MW: 2721.12, observed m/z: 1361.07 ([M/2+H]$^+$)) was detected. The reaction mixture was concentrated under reduced pressure to remove solvent to give a residue. The residue was purified by prep-HPLC (TFA condition). Compound 2 (37 mg, 13.60 µmol, 28.49% yield) was obtained as a white solid.

Procedure for Preparation of BCY10582

BCY00009172-PEG12-$N_3$ + BCY00010045
2
$CuSO_4$
VcNa
THPTA
t-BuOH/$H_2O$
BCY00010582

A mixture of Compound 2 (16.0 mg, 5.9 µmol, 1.0 eq), BCY10045 (14.0 mg, 6.0 µmol, 1.01 eq), and THPTA (0.4 M, 14.7 µL, 1.0 eq) was dissolved in t-BuOH/$H_2O$ (1:1, 2 mL, pre-degassed and purged with $N_2$ for 3 times), and then $CuSO_4$ (0.4 M, 14.7 µL, 1.0 eq) and VcNa (0.4 M, 29.4 µL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed Compound 2 was consumed completely and one main peak with desired m/z [calculated MW: 5073.89, observed m/z: 1015.24 ([M/5+H]$^+$) and 1268.97 ([M/4+H]$^+$) was detected. The reaction mixture was directly purified by prep-HPLC (TFA condition). BCY10582 (10 mg, 1.92 µmol, 32.58% yield, 97.21% purity) was obtained as a white solid.

BCY11017

Procedure for Preparation of BCY11017

BCY00008919-PEG12-$N_3$ + BCY00010861

2

$CuSO_4$
VcNa
THPTA
t-BuOH/
$H_2O$

BCY00011017

Compound 2 (which may be prepared as described in the procedure for preparing BCY10567; 7.0 mg, 2.59 μmol, 1.0 eq) and BCY10861 (7.03 mg, 2.59 μmol, 1.0 eq), were first dissolved in 2 mL of t-BuOH/$H_2O$ (1:1), and then $CuSO_4$ (0.4 M, 13.0 μL, 2.0 eq), VcNa (1.0 mg, 5.03 μmol, 2.0 eq) and THPTA (1.1 mg, 2.53 μmol, 1.0 eq) were added. Finally 1 M $NH_4HCO_3$ was added to adjust pH to 8. All solvents here were degassed and purged with $N_2$ for 3 times. The reaction mixture was stirred at 35° C. for 16 hr under $N_2$ atmosphere. LC-MS showed compound 2 was consumed completely and one main peak with desired m/z (calculated MW: 5421.30, observed m/z: 1084.7 ($[M/5+H]^+$)). The reaction mixture was purified by prep-HPLC (TFA condition) and BCY11017 (6.6 mg, 1.17 μmol, 45.24% yield, 96.16% purity) was obtained as a white solid.

BCY11018

Procedure for Preparation of BCY11018

BCY00008920-PEG12-$N_3$ + BCY00010861

2

$CuSO_4$
VcNa
THPTA
t-BuOH/
$H_2O$

BCY00011018

Compound 2 (which may be prepared as described in the procedure for preparing BCY10570; 6.0 mg, 2.17 μmol, 1.0 eq) and BCY10861 (5.9 mg, 2.17 μmol, 1.0 eq), were first dissolved in 2 mL of t-BuOH/$H_2O$ (1:1), and then $CuSO_4$ (0.4 M, 11.0 μL, 2.0 eq), VcNa (1.0 mg, 2.3 eq) and THPTA (1.1 mg, 1.0 eq) was added. Finally 1 M $NH_4HCO_3$ was added to adjust pH to 8. All solvents here were degassed and purged with $N_2$ for 3 times. The reaction mixture was stirred at 35° C. for 16 hr under $N_2$ atmosphere. LC-MS showed compound 2 was consumed completely and one main peak with desired m/z (calculated MW: 5479.34, observed m/z: 1096.40 ($[M/5+H]^+$)). The reaction mixture was purified by prep-HPLC (TFA condition) and BCY11018 (2.3 mg, 0.40 μmol, 18.31% yield, 94.73% purity) was obtained as a white solid.

BCY11019

Procedure for Preparation of BCY11019

BCY00009172-PEG12-$N_3$ + BCY00010861

2

$CuSO_4$
VcNa
THPTA
t-BuOH/
$H_2O$

BCY00011019

Compound 2 (which may be prepared as described in the procedure for preparing BCY10581; 8.0 mg, 2.94 μmol, 1.0 eq) and BCY10861 (8.0 mg, 2.95 μmol, 1.0 eq), were first dissolved in 2 mL of t-BuOH/$H_2O$ (1:1), and then $CuSO_4$ (0.4 M, 14.7 μL, 2.0 eq), VcNa (1.2 mg, 6.05 μmol, 2.0 eq) and THPTA (1.3 mg, 2.99 μmol, 1.0 eq) was added. Finally 1 M $NH_4HCO_3$ was added to adjust pH to 8. All solvents here were degassed and purged with $N_2$ for 3 times. The reaction mixture was stirred at 35° C. for 16 hr under $N_2$ atmosphere. LC-MS showed compound 2 was consumed completely and one main peak with desired m/z (calculated MW: 5437.26, observed m/z: 1088.09 ($[M/5+H]^+$) and 1360.19 ($[M/4+H]^+$)). The reaction mixture was purified by prep-HPLC (TFA condition) and BCY11019 (7.6 mg, 1.36 μmol, 46.09% yield, 96.95% purity) was obtained as a white solid.

BCY11376

Procedure for Preparation of Compound 2

BCY00008919 + $N_3$—$CH_2$—COOH

1

1. EDCl,
HOSu
2. DIEA,
DMF

BCY00008919-$CH_2$—$N_3$

2

To a solution of compound 1 (5.0 mg, 49.5 μmol, 1.0 eq) in DMF (1 mL) was added EDCl (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.2 mL of this mixture was added with BCY8919 (20.0 mg, 9.62 μmol) and DIEA (1.7 μL, 9.62 μmol). The mixture was stirred at 25-30° C. for 2 hr. LC-MS showed BCY8919 was consumed completely and one main peak with desired m/z (calculated MW: 2162.51, observed m/z: 1081.8 ($[M/2+H]^+$)) was detected. The reaction mixture was then concentrated under reduced pressure to remove solvent and produced a residue, following by purification by prep-HPLC (TFA condition). Compound 2 (12 mg, 5.55 μmol, 56.28% yield, 97.54% purity) was obtained as a white solid.

Procedure for Preparation of BCY11376

BCY00008919-$CH_2$—$N_3$ + BCY00010861

2

$CuSO_4$
VcNa
THPTA
t-BuOH/
$H_2O$

BCY00011376

A mixture of compound 2 (3 mg, 1.39 μmol, 1.0 eq.), BCY10861 (3.8 mg, 1.40 μmol, 1.0 eq.), and THPTA (1.2 mg, 2.76 μmol, 2.0 eq.) was dissolved in t-BuOH/$H_2O$ (1:1, 1 mL, pre-degassed and purged with $N_2$ for 3 times), and then $CuSO_4$ (0.4 M, 3.5 μL, 1.0 eq.) and VcNa (0.4 M, 3.5 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed BCY10861 was consumed completely and one main peak with desired m/z (calculated MW: 4878.64, observed m/z: 1220.8 ([M/4+H]$^+$) was detected. The reaction mixture was filtered and concentrated under reduced pressure to give a residue. The crude product was purified by prep-HPLC (TFA condition), and BCY11376 (1.9 mg, 1.0 μmol, 27.01% yield, 96.2% purity) was obtained as a white solid.

BCY11377

Procedure for Preparation of Compound 2

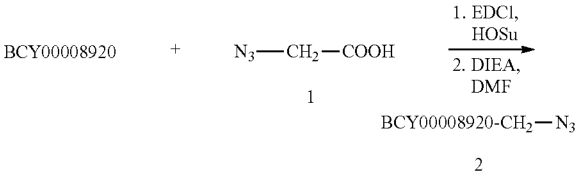

To a solution of compound 1 (5.0 mg, 49.5 μmol, 1.0 eq) in DMF (1 mL) was added EDCl (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.2 mL of this mixture was added with BCY8920 (20.0 mg, 9.36 μmol) and DIEA (1.2 mg, 9.36 μmol). The mixture was stirred at 25-30° C. for 2 hr. LC-MS showed BCY8920 was consumed completely and one main peak with desired m/z (calculated MW: 2220.54, observed m/z: 1110.90 ([M/2+H]$^+$) was detected. The reaction mixture was then concentrated under reduced pressure to remove solvent and produced a residue, following by purification by prep-HPLC (TFA condition). Compound 2 (12 mg, 5.15 μmol, 56.28% yield, 95.3% purity) was obtained as a white solid.

Procedure for Preparation of BCY11377

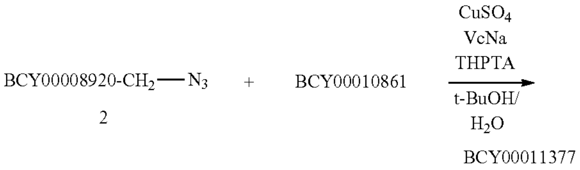

A mixture of compound 2 (3 mg, 1.35 μmol, 1.0 eq.), BCY10861 (3.8 mg, 1.35 μmol, 1.0 eq.), and THPTA (0.6 mg, 1.0 eq.) was dissolved in t-BuOH/$H_2O$ (1:1, 1 mL, pre-degassed and purged with $N_2$ for 3 times), and then $CuSO_4$ (0.4 M, 3.4 μL, 1 eq.) and VcNa (0.4 M, 3.4 μL, 1 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed one main peak with desired m/z (calculated MW: 4936.68, observed m/z: 1234.9 ([M/4+H]$^+$) was detected. The reaction mixture was filtered and concentrated under reduced pressure to give a residue. The crude product was purified by prep-HPLC (TFA condition), and BCY11377 (3.5 mg, 0.66 μmol, 48.86% yield, 93.1% purity) was obtained as a white solid.

BCY11378

Procedure for Preparation of Compound 2

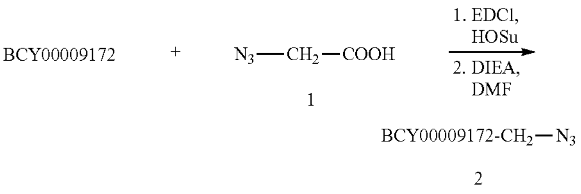

To a solution of compound 1 (5.0 mg, 49.5 μmol, 1.0 eq) in DMF (1 mL) was added EDCl (8.5 mg, 54.8 μmol, 1.1 eq) and HOSu (5.7 mg, 49.5 μmol, 1.0 eq). The mixture was stirred at 25-30° C. for 30 min. TLC indicated compound 1 was consumed completely and one new spot formed. Then 0.2 mL of this mixture was added to BCY9172 (20.0 mg, 9.54 μmol) and DIEA (1.7 μL, 9.62 μmol). The mixture was stirred at 25-30° C. for 2 hr. LC-MS showed compound 1 was consumed completely and one main peak with desired m/z (calculated MW: 2176.49, observed m/z: 1090.0 ([M/2+H]$^+$) was detected. The reaction mixture was then concentrated under reduced pressure to remove solvent and produced a residue, following by purification by prep-HPLC (TFA condition). Compound 2 (20.2 mg, 7.48 μmol, 78.34% yield, 80.57% purity) was obtained as a white solid.

Procedure for Preparation of BCY11378

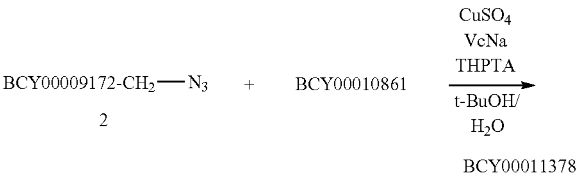

A mixture of compound 2 (5 mg, 2.30 μmol, 1.0 eq.), BCY10861 (6.24 mg, 2.30 μmol, 1.0 eq.), and THPTA (1.0 mg, 1.0 eq.) was dissolved in t-BuOH/$H_2O$ (1:1, 1 mL, pre-degassed and purged with $N_2$ for 3 times), and then $CuSO_4$ (0.4 M, 5.8 μL, 1.0 eq.) and VcNa (0.4 M, 5.8 μL, 1.0 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 2 hr under $N_2$ atmosphere. LC-MS showed compound 3 was consumed completely and one main peak with desired m/z (calculated MW: 4894.61, observed m/z: 1224.3 ([M/4+H]$^+$) was detected. The reaction mixture was filtered and concentrated under reduced pressure to give a residue. The crude product was purified by prep-HPLC (TFA condition), and BCY11378 (1.2 mg, 0.34 μmol, 10.07% yield, 94.3% purity) was obtained as a white solid.

BCY11379

Procedure for Preparation of BCY8919-PEG5-$N_3$

BCY00008919 + NHS-PEG5-$N_3$
1
$NaHCO_3$
MeCN/$H_2O$
BCY00008919-PEG5—$N_3$
2

BCY8919 (30.0 mg, 14.43 μmol, 1.0 eq) and compound 1 (6.3 mg, 14.57 μmol, 1.01 eq), were dissolved in a mixture of MeCN (1 mL) and $H_2O$ (1 mL). The solution was added with 1 M $NaHCO_3$ to adjust pH to 8, and then the mixture was stirred at 35° C. for 2 hr. LC-MS showed BCY8919 was consumed completely and one main peak with desired m/z (calculated MW: 2396.79, observed m/z: 1198.74 ($[M/2+H]^+$) and 799.50 ($[M/4+H]^+$)) was detected. The reaction mixture was purified by prep-HPLC (TFA condition) and compound 2 (20 mg, 8.07 μmol, 55.92% yield, 96.68% purity) was obtained as a white solid.

Procedure for Preparation of BCY11379

BCY00008919-PEG5-$N_3$ + BCY00010861
2
$CuSO_4$
VcNa
THPTA
t-BuOH/
$H_2O$
BCY00011379

Compound 2 (3.0 mg, 1.25 μmol, 1.0 eq) and BCY10861 (3.4 mg, 1.25 μmol, 1.0 eq) were first dissolved in 2 mL of t-BuOH/$H_2O$ (1:1), and then $CuSO_4$ (0.4 M, 7 μL, 2.24 eq), VcNa (1 mg, 5.04 μmol, 4.03 eq) and THPTA (1 mg, 2.30 μmol, 1.84 eq) was added. Finally 1 M $NH_4HCO_3$ was added to adjust pH to 8. All solvents here were degassed and purged with $N_2$ for 3 times. The reaction mixture was stirred at 25-30° C. for 16 hr under $N_2$ atmosphere. LC-MS showed compound 2 was consumed completely and one main peak with desired m/z (calculated MW: 5112.93 observed m/z: 1022.96 ($[M/5+H]^+$) and 1278.74 ($[M/4+H]^+$)). The reaction mixture was purified by prep-HPLC (TFA condition) and BCY11379 (3.4 mg, 0.615 μmol, 52.00% yield, 97.88% purity) was obtained as a white solid.

BCY11380

Procedure for preparation of BCY8920-PEG5-$N_3$

BCY00008920 + NHS-PEG5-$N_3$
1
$NaHCO_3$
MeCN/$H_2O$
BCY00008920-PEG5-$N_3$
2

BCY8920 (30.0 mg, 14.04 μmol, 1.0 eq) and compound 1 (6.1 mg, 14.11 μmol, 1.01 eq), were dissolved in a mixture of MeCN (1 mL) and $H_2O$ (1 mL). The solution was added with 1 M $NaHCO_3$ to adjust pH to 8, and then the mixture was stirred at 35° C. for 2 hr. LC-MS showed BCY8920 was consumed completely and one main peak with desired m/z (calculated MW: 2454.83, observed m/z: 1227.63 ($[M/2+H]^+$) and 818.66 ($[M/3+H]^+$)) was detected. The reaction mixture was purified by prep-HPLC (TFA condition) and compound 2 (20 mg, 8.03 μmol, 57.21% yield, 98.56% purity) was obtained as a white solid.

Procedure for Preparation of BCY11380

BCY00008920-PEG5-$N_3$ + BCY00010861
2
$CuSO_4$
VcNa
THPTA
t-BuOH/
$H_2O$
BCY00011380

Compound 2 (3.5 mg, 1.43 μmol, 1.0 eq) and BCY10861 (3.9 mg, 1.44 μmol, 1.0 eq) were first dissolved in 2 mL of t-BuOH/$H_2O$ (1:1), and then $CUSO_4$ (0.4 M, 8 μL, 2.24 eq), VcNa (1 mg, 5.04 μmol, 3.52 eq) and THPTA (1 mg, 2.30 μmol, 1.61 eq) were added. Finally 1 M $NH_4HCO_3$ was added to adjust pH to 8. All solvents here were degassed and purged with $N_2$ for 3 times. The reaction mixture was stirred at 25-30° C. for 16 hr under $N_2$ atmosphere. LC-MS showed majority of compound 2 was consumed and one main peak with desired m/z (calculated MW: 5170.97, observed m/z: 1034.28 ($[M/5+H]^+$) and 1293.10 ($[M/4+H]^+$)). The reaction mixture was purified by prep-HPLC (TFA condition) and BCY11380 (1.6 mg, 0.296 μmol, 20.77% yield, 96.77% purity) was obtained as a white solid.

BCY11381

Procedure for Preparation of BCY8920-PEG5-$N_3$

BCY00009172 + NHS-PEG5-$N_3$
1
$NaHCO_3$
MeCN/$H_2O$
BCY00009172-PEG5-$N_3$
2

BCY9172 (30.0 mg, 14.32 μmol, 1.0 eq) and compound 1 (6.2 mg, 14.34 μmol, 1.0 eq), were dissolved in a mixture of MeCN (1 mL) and $H_2O$ (1 mL). The solution was added with 1 M $NaHCO_3$ to adjust pH to 8, and then the mixture was stirred at 35° C. for 2 hr. LC-MS showed BCY9172 was consumed completely and one main peak with desired m/z (calculated MW: 2412.75, observed m/z: 1206.72 ($[M/2+H]^+$)) was detected. The reaction mixture was purified by prep-HPLC (TFA condition) and compound 2 (15 mg, 6.14 μmol, 42.87% yield, 98.75% purity) was obtained as a white solid.

Procedure for Preparation of BCY11381

BCY00009172-PEG5-$N_3$ + BCY00010861
2
$CuSO_4$
VcNa
THPTA
t-BuOH/
$H_2O$
BCY00011381

Compound 2 (3.0 mg, 1.24 μmol, 1.0 eq) and BCY10861 (3.4 mg, 1.25 μmol, 1.01 eq) were first dissolved in 2 mL of t-BuOH/$H_2O$ (1:1), and then $CuSO_4$ (0.4 M, 7 μL, 2.25 eq), VcNa (1 mg, 5.04 μmol, 4.06 eq) and THPTA (1 mg, 2.30 μmol, 1.85 eq) were added. Finally 1 M $NH_4HCO_3$ was added to adjust pH to 8. All solvents here were degassed and purged with $N_2$ for 3 times. The reaction mixture was stirred at 25-30° C. for 16 hr under $N_2$ atmosphere. LC-MS showed one peak with desired m/z (calculated MW: 5128.89, observed m/z: 1026.05 ($[M/5+H]^+$) and 1282.50 ($[M/4+H]^+$)). The reaction mixture was purified by prep-HPLC (TFA condition) and BCY11381 (1.6 mg, 0.295 μmol, 23.73% yield, 94.59% purity) was obtained as a white solid.

Example 5: Production of CD137 Monoclonal Antibody Agonist

The sequence of the CD137 monoclonal antibody agonist that was used for comparison to CD137 multimers in the experiments presented herein was disclosed in U.S. Pat. No. 7,288,638. The IgG4 isotype antibody was expressed using the ExpiCHO Expression System (Thermo Fisher Scientific) following transient transfection of the DNA expression construct. The antibody was purified by Protein A affinity chromatography and formulated in phosphate-buffered solution (PBS) pH 7.2. Purity analysis using HPLC-SEC (column GF-250, Agilent) indicated that the monomer rate of CD137 monoclonal antibody is approximately 95%. Binding activity analysis indicated that the CD137 monoclonal antibody with a concentration higher than 1 μg/ml can bind to CHO cells expressing CD137. Endotoxin analysis using the ToxinSensor™ Chromogenic LAL Endotoxin Assay Kit (Genscript) indicated that the CD137 monoclonal antibody preparation contained <7 EU/mg of endotoxin.

Biological Data

1. CD137 Biacore Experimental Description

Biacore experiments were performed to determine $k_a$ ($M^{-1}s^{-1}$), $k_d$ ($s^{-1}$), $K_D$ (nM) values of heterotandem peptides binding to human CD137 protein. Recombinant human CD137 (R&D systems) was resuspended in PBS and biotinylated using EZ-Link™ Sulfo-NHS-LC-LC-Biotin reagent (Thermo Fisher) as per the manufacturer's suggested protocol. The protein was desalted to remove uncoupled biotin using spin columns into PBS.

For analysis of peptide binding, a Biacore T200 or a Biacore 3000 instrument was used with a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μl/min. For capture of streptavidin, the protein was diluted to 0.2 mg/ml in 10 mM sodium acetate (pH 4.5) and captured by injecting 120 μl of onto the activated chip surface. Residual activated groups were blocked with a 7 min injection of 1 M ethanolamine (pH 8.5) and biotinylated CD137 captured to a level of 270-1500 RU. Buffer was changed to PBS/0.05% Tween 20 and a dilution series of the peptides was prepared in this buffer with a final DMSO concentration of 0.5%. The top peptide concentration was 500 nM with 6 further 2-fold or 3-fold dilutions. The SPR analysis was run at 25° C. at a flow rate of 90 μl/min with 60 seconds association and 900 seconds dissociation. After each cycle a regeneration step (10 μl of 10 mM glycine pH 2) was employed. Data were corrected for DMSO excluded volume effects as needed. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain heterotandem peptides were tested in this assay and the results are shown in Table 1 below

TABLE 1

CD137 Biacore Assay Data with Heterotandem Peptides

| Complex ID | SPR ($K_D$)(nM) |
|---|---|
| BCY9173 | 7.98 |
| BCY7985 | 143 |
| BCY8942 | 853 |
| BCY8943 | 156 |
| BCY9647 | 206 |
| BCY9648 | 202 |
| BCY9655 | 199 |
| BCY9656 | 159 |
| BCY9657 | 256 |
| BCY9658 | 152 |
| BCY9659 | 88.1 |
| BCY9758 | 189 |
| BCY8854 | 108 |
| BCY9350 | 69.4 |
| BCY9351 | 3640 |
| BCY9399 | 73 |
| BCY9400 | 53 |
| BCY9408 | 105 |
| BCY9409 | 97.7 |
| BCY9410 | 65.8 |
| BCY9411 | 71.1 |
| BCY9759 | 44.3 |
| BCY10000 | 6.19 |
| BCY10571 | 12.03 |
| BCY10572 | 5.00 |
| BCY10573 | 3.39 |

2. Nectin-4 Biacore Experimental Description

Biacore experiments were performed to determine $k_a$ ($M^{-1}s^{-1}$), $k_d$ ($s^{-1}$), $K_D$ (nM) values of heterotandem peptides binding to human Nectin-4 protein (obtained from Charles River). Human Nectin-4 (residues Gly32-Ser349; NCBI RefSeq: NP_112178.2) with a gp67 signal sequence and C-terminal FLAG tag was cloned into pFastbac-1 and baculovirus made using standard Bac-to-Bac™ protocols (Life Technologies). Sf21 cells at $1\times10^6$ $ml^{-1}$ in Excell-420 medium (Sigma) at 27° C. were infected at an MOI of 2 with a P1 virus stock and the supernatant harvested at 72 hours. The supernatant was batch bound for 1 hour at 4° C. with Anti-FLAG M2 affinity agarose resin (Sigma) washed in PBS and the resin subsequently transferred to a column and washed extensively with PBS. The protein was eluted with 100 μg/ml FLAG peptide. The eluted protein was concentrated to 2 ml and loaded onto an S-200 Superdex column (GE Healthcare) in PBS at 1 ml/min. 2 ml fractions were collected and the fractions containing Nectin-4 protein were concentrated to 16 mg/ml.

The protein was randomly biotinylated in PBS using EZ-Link™ Sulfo-NHS-LC-LC-Biotin reagent (Thermo Fisher) as per the manufacturer's suggested protocol. The protein was extensively desalted to remove uncoupled biotin using spin columns into PBS.

For analysis of peptide binding, a Biacore 3000 instrument was used with a CM5 chip (GE Healthcare). Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 minute injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μl/min. For capture of streptavidin, the protein was diluted to 0.2 mg/ml in 10 mM sodium acetate (pH 4.5) and captured by injecting 120 μl of streptavidin onto the activated chip surface. Residual activated groups were blocked with a 7 minute injection of 1 M ethanolamine (pH 8.5) and biotinylated Nectin-4 captured to a level of 1,200-1,800 RU. Buffer was changed to PBS/0.05% Tween 20 and a dilution series of the peptides was prepared in this buffer with a final DMSO concentration of 0.5%. The top peptide concentration was 100 nM with 6 further 2-fold dilutions. The SPR analysis was run at 25° C. at a flow rate of 50 μl/min with 60 seconds association and dissociation between 400 and 1,200 seconds depending upon the individual peptide. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain heterotandem peptides of the invention were tested in the above mentioned Nectin-4 binding assays and the results are shown in Table 2 below:

TABLE 2

Nectin-4 Biacore Assay Data with Heterotandem Peptides

| Complex ID | SPR $K_D$(nM) |
|---|---|
| BCY8854 | 2.76 |
| BCY9350 | >200 nM |
| BCY9351 | 2.47 |
| BCY9399 | 1.67 |
| BCY9400 | 1.8 |
| BCY9408 | 1.57 |
| BCY9409 | 1.66 |
| BCY9410 | 1.49 |
| BCY9411 | 1.48 |
| BCY9759 | 2.14 |
| BCY10000 | 2.26 |

3. EphA2 Biacore Experimental Description

Biacore experiments were performed to determine $k_a$ ($M^{-1}s^{-1}$), $k_d$ ($s^{-1}$), $K_D$ (nM) values of heterotandem peptides binding to human EphA2 protein.

EphA2 were biotinylated with EZ-Link™ Sulfo-NHS-LC-Biotin for 1 hour in 4 mM sodium acetate, 100 mM NaCl, pH 5.4 with a 3× molar excess of biotin over protein. The degree of labelling was determined using a Fluorescence Biotin Quantification Kit (Thermo) after dialysis of the reaction mixture into PBS. For analysis of peptide binding, a Biacore T200 instrument was used with a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μl/min. For capture of streptavidin, the protein was diluted to 0.2 mg/ml in 10 mM sodium acetate (pH 4.5) and captured by injecting 120 μl onto the activated chip surface. Residual activated groups were blocked with a 7 min injection of 1 M ethanolamine (pH 8.5):HBS-N (1:1). Buffer was changed to PBS/0.05% Tween 20 and biotinylated EphA2 was captured to a level of 500-1500 RU using a dilution of protein to 0.2 μM in buffer. A dilution series of the peptides was prepared in this buffer with a final DMSO concentration of 0.5% with a top peptide concentration was 50 or 100 nM and 6 further 2-fold dilutions. The SPR analysis was run at 25° C. at a flow rate of 90 μl/min with 60 seconds association and 900-1200 seconds dissociation. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain heterotandem peptides of the invention were tested in the EphA2 binding assays and the results are shown in Table 3 below:

TABLE 3

EphA2 Biacore Assay Data with Heterotandem Peptides

| Complex ID | SPR $K_D$(nM) |
|---|---|
| BCY9173 | 2.1 |
| BCY7985 | 2 |
| BCY8942 | 1.7 |
| BCY8943 | >200 nM |
| BCY9647 | 1.69 |
| BCY9648 | 1.75 |
| BCY9655 | 1.33 |
| BCY9656 | 0.75 |
| BCY9657 | 1.1 |
| BCY9658 | 1.9 |
| BCY9659 | 1.03 |
| BCY9758 | 1.5 |

4. CD137 Reporter Assay Co-Culture with Tumour Cells

Culture medium referred to as R1 media is prepared by adding 1% FBS to RPMI-1640 (component of Promega kit CS196005). Serial dilutions of test articles in R1 are prepared in a sterile 96 well-plate. Use 25 μl per well of test articles or R1 (as a background control) to designated wells in white cell culture plate. Tumour cells* are harvested and resuspended at a concentration of 400,000 cells/mL in R1 media. Twenty five (25) μL/well tumour cells are used in white cell culture plate. Jurkat cells (Promega kit CS196005, 0.5 mL) are thawed in the water bath and then added to 5 ml pre-warmed R1 medium. Twenty five (25) μL/well Jurkat cells are used in white cell culture plate. Incubate the cells and test articles for 6 h at 37° C., 5% $CO_2$. At the end of 6 h, add 75 μl/well Bio-Glo™ (Promega) and incubate for 10 min before reading luminescence in a plate reader (Clariostar, BMG). The fold change relative to cells (Jurkat cells+Cell line used in co-culture) is calculated and plotted in GraphPad Prism as log(agonist) vs response to determine EC50 (nM) and Fold Induction over background (Max)

The tumour cell type used in co-culture is dependent on the tumour target specific for heterotandem as is shown in Table 4 below:

TABLE 4

Cell Lines Used for each Tumour Target

| Tumour target | Cell line used in co-culture |
|---|---|
| EphA2 | A549, SC-OV-3, PC3, LNCaP |
| Nectin-4 | HT1376, NCI-H292 |
| PD-L1 | RKO |

Data is presented in FIG. 3 which shows that the EphA2-CD137 heterotandem BCY7985 showed strong induction of CD137 cell activity in the Promega CD137 luciferase reporter assay in the presence of EphA2-expressing HT1080 cells. There is no CD137 induction by the heterotandem in the absence of HT1080 cells.

Figure 4:
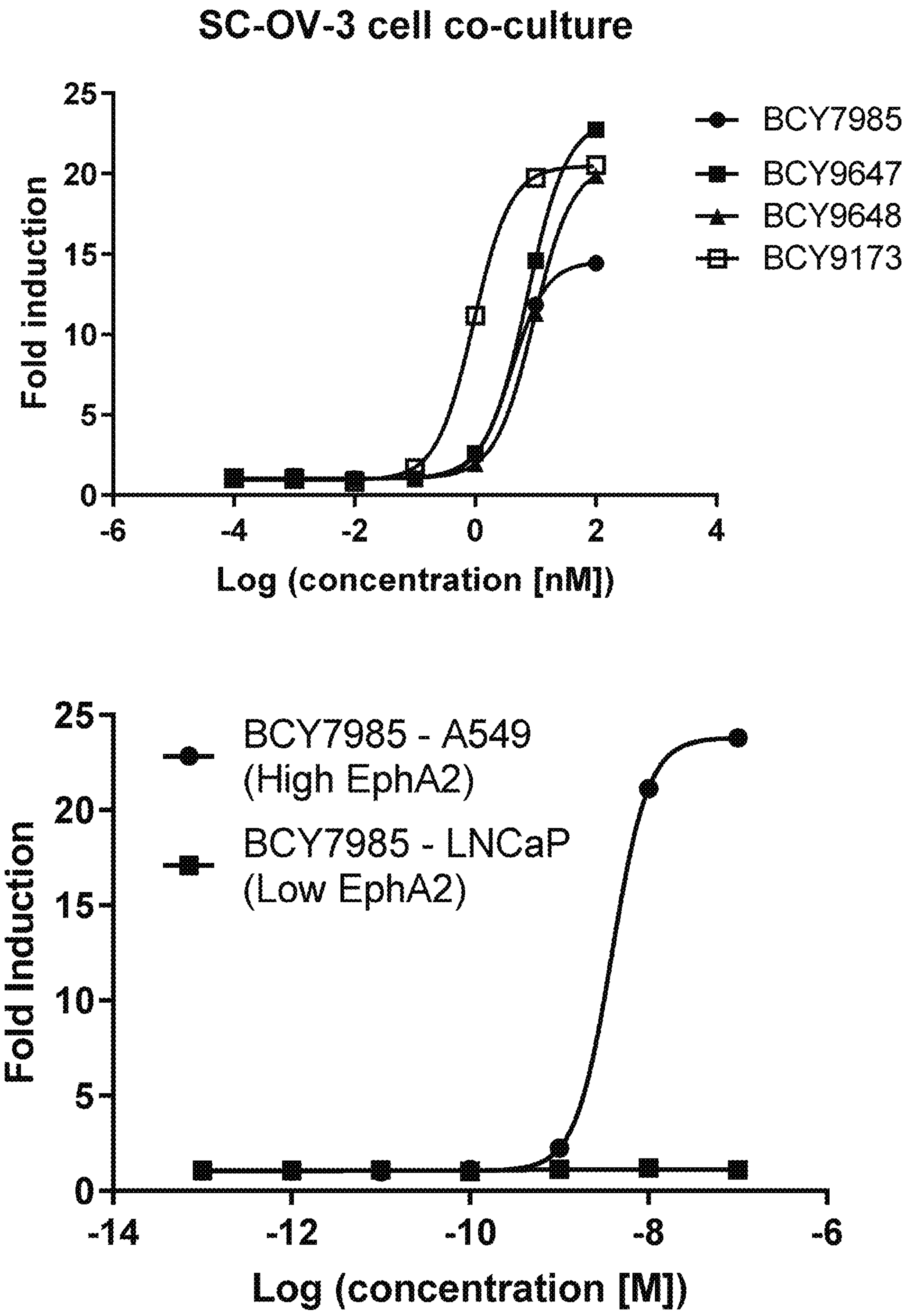
FIG. 4: EphA2/CD137 heterotandems are active in CD137 reporter assay and the fold induction of activation is dependent on tumour target expression level on the cell line used in co-culture.

Data is presented in FIG. 4 which shows that EphA2/CD137 heterotandems induce strong CD137 activation in CD137 reporter assay and the fold induction of activation is dependent on tumour target expression level on the cell line (A549 and SC—OV-3:EphA2 High and LNCaP:EphA2 Low) used in co-culture.

Figure 6:
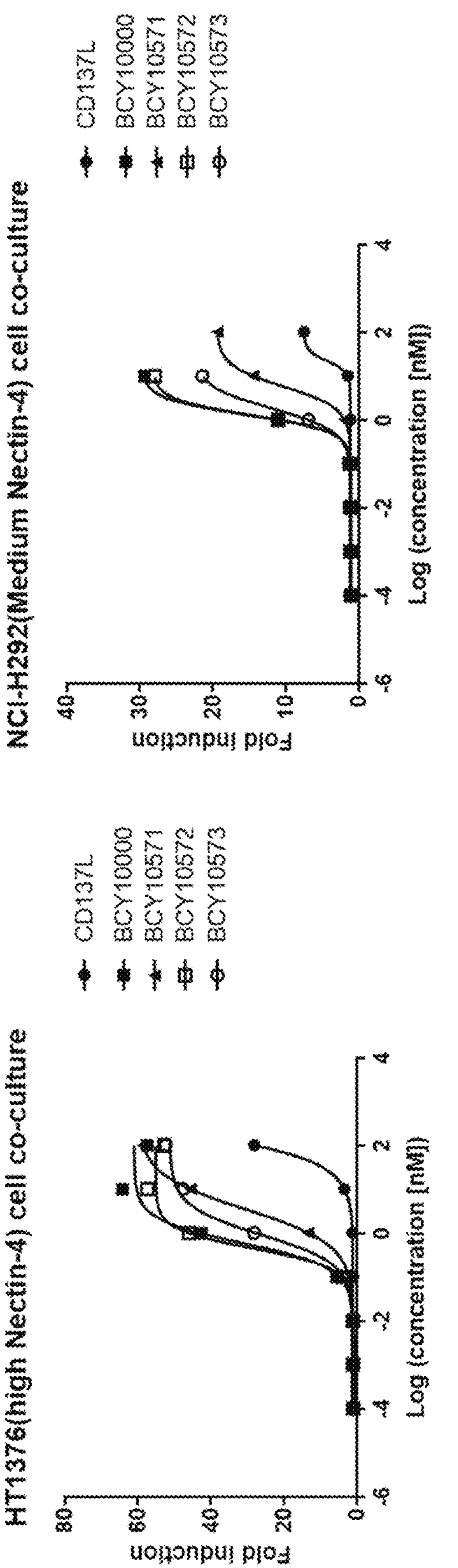
FIG. 6: Nectin-4/CD137 heterotandems are active in CD137 reporter assay and the fold induction of activation is dependent on tumour target expression level on the cell line (HT1376:Nectin-4 high and NCI-H292: Nectin-4 Medium) used in co-culture.

Data is presented in FIG. 6 which shows that Nectin-4/CD137 heterotandems induce strong CD137 activation in CD137 reporter assay and the fold induction of activation is dependent on tumour target expression level on the cell line (HT1376:Nectin-4 high and NCI-H292: Nectin-4 Medium) used in co-culture.

Figure 9:
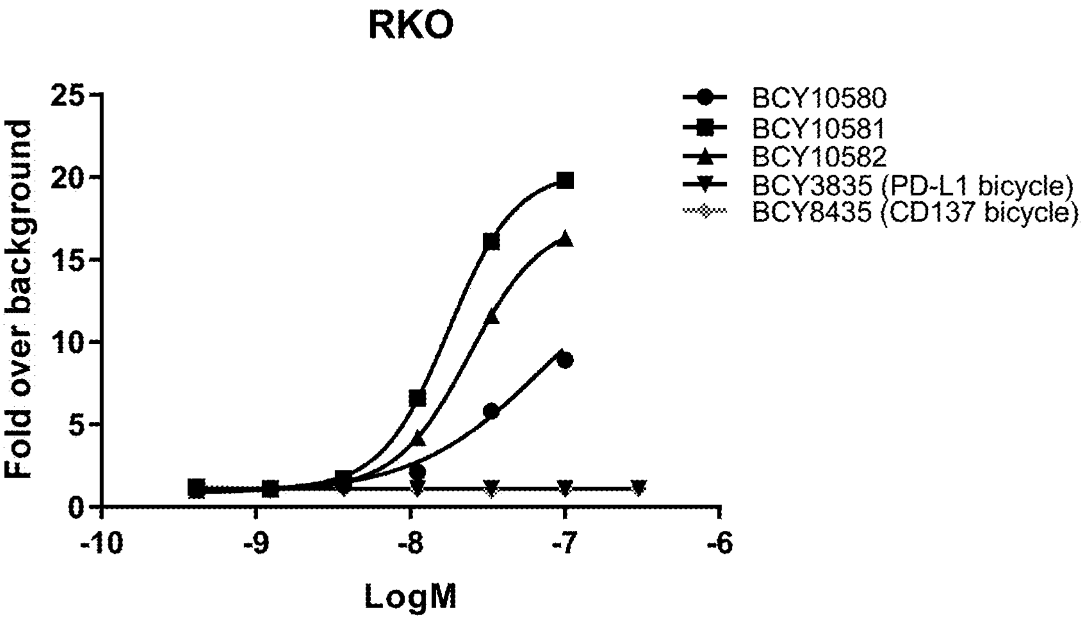
FIG. 9: PD-L1/CD137 heterotandems are active in CD137 reporter assay in presence of PD-L1 expressing cell line RKO.

Data is presented in FIG. 9 which shows that PD-L1/CD137 heterotandems induce strong activation of 00137 in the 00137 reporter assay in presence of PD-L1 expressing cell line. A summary of the EC50 (nM) and Fold Induction induced by heterotandem peptides in CD137 reporter assay in co-culture with different cells lines are reported in Table 5 below:

TABLE 5

Fold Induction induced by Heterotandem Peptides in CD137 Reporter Assay

| Complex ID | Tumour Target | Cell Line used in Coculture | EC50 (nM) | Fold Induction over Background |
|---|---|---|---|---|
| BCY9173 | EphA2 | SC-OV-3 | 0.94 | 21 |
| BCY7985 | EphA2 | SC-OV-3 | 4.0 | 15 |
| BCY8942 | EphA2 | PC3 | — | <2 fold induction at 100 nM |
| BCY8943 | EphA2 | PC3 | — | <2 fold induction at 100 nM |
| BCY9647 | EphA2 | SC-OV-3 | 7.2 | 24 |
| BCY9648 | EphA2 | SC-OV-3 | 9.3 | 20 |
| BCY9655 | EphA2 | SC-OV-3 | 4.1 | 6 |
| BCY9656 | EphA2 | SC-OV-3 | 1.1 | 3 |
| BCY9657 | EphA2 | SC-OV-3 | 9.0 | 26 |
| BCY9658 | EphA2 | SC-OV-3 | 6.2 | 11 |
| BCY9659 | EphA2 | SC-OV-3 | 9.9 | 7 |
| BCY9758 | EphA2 | SC-OV-3 | 1.2 | 7 |
| BCY10568 | EphA2 | PC3 | 0.25 | 32 |
| BCY10570 | EphA2 | PC3 | 0.41 | 38 |
| BCY10574 | EphA2 | PC3 | 1.0 | 32 |
| BCY10575 | EphA2 | PC3 | 0.62 | 38 |
| BCY10576 | EphA2 | PC3 | 0.51 | 38 |
| BCY10577 | EphA2 | PC3 | 0.28 | 37 |
| BCY8854 | Nectin4 | H1376 | 1.2 | 30 |
| BCY9350 | Nectin4 | H1376 | — | <2 fold induction at 100 nM |
| BCY9351 | Nectin4 | H1376 | — | <2 fold induction at 100 nM |
| BCY9399 | Nectin4 | H1376 | 11 | 13 |
| BCY9400 | Nectin4 | H1376 | 2.9 | 13 |
| BCY9401 | Nectin4 | H1376 | 18 | 70 |
| BCY9407 | Nectin4 | H1376 | 3.4 | 29 |
| BCY9408 | Nectin4 | H1376 | 1.1 | 20 |
| BCY9409 | Nectin4 | H1376 | 1.2 | 24 |
| BCY9410 | Nectin4 | H1376 | 1.3 | 24 |
| BCY9411 | Nectin4 | H1376 | 14 | 41 |
| BCY9759 | Nectin4 | H1376 | 2.7 | 15 |
| BCY10000 | Nectin4 | H1376 | 0.58 | 61 |
| BCY10567 | Nectin4 | H1376 | 1.7 | 45 |
| BCY10569 | Nectin4 | H1376 | 1.2 | 52 |
| BCY10571 | Nectin4 | H1376 | 3.5 | 60 |
| BCY10572 | Nectin4 | H1376 | 0.44 | 55 |
| BCY10573 | Nectin4 | H1376 | 0.90 | 55 |

TABLE 5-continued

Fold Induction induced by Heterotandem Peptides in CD137 Reporter Assay

| Complex ID | Tumour Target | Cell Line used in Coculture | EC50 (nM) | Fold Induction over Background |
|---|---|---|---|---|
| BCY10578 | Nectin4 | H1376 | 0.42 | 58 |
| BCY10917 | Nectin4 | H1376 | 0.27 | 54 |
| BCY11020 | Nectin4 | H1376 | 0.26 | 47 |
| BCY11373 | Nectin4 | H1376 | 0.16 | 74 |
| BCY11374 | Nectin4 | H1376 | 0.091 | 72 |
| BCY11375 | Nectin4 | H1376 | 0.23 | 72 |
| BCY8939 | mouse PD-L1 | MC38 | — | <2 fold induction at 100 nM |
| BCY10580 | PD-L1 | RKO | 28 | 3 |
| BCY10581 | PD-L1 | RKO | 18 | 6 |
| BCY10582 | PD-L1 | RKO | 28 | 4 |
| BCY11017 | PD-L1 | RKO | 66 | 4 |
| BCY11018 | PD-L1 | RKO | 27 | 7 |
| BCY11019 | PD-L1 | RKO | 18 | 6 |
| BCY11376 | PD-L1 | RKO | 127 | 9 |
| BCY11377 | PD-L1 | RKO | 40 | 6 |
| BCY11378 | PD-L1 | RKO | 80 | 3 |
| BCY11379 | PD-L1 | RKO | 68 | 6 |
| BCY11380 | PD-L1 | RKO | 34 | 7 |
| BCY11381 | PD-L1 | RKO | 105 | 7 |

5. Primary Human T Cells-A549 Co-Culture (Tumour Cell Killing)

PBMC were isolated from three healthy donors and added to Nuclight Red labelled tumour target cells (human lung carcinoma cells A549©, ATCC CLL-185™) at two defined ratios in the presence of anti-CD3 stimulation at two concentrations. Tumour cell: PBMC co-cultures were incubated with the lead bicycles at three concentrations. All test conditions were also plated onto tumour cells in the absence of stimulated PBMC in order to detect direct tumour cell cytotoxicity. Tumour killing was evaluated by counting viable Nuclight red positive tumour cells over time. In addition, a Caspase 3/7 dye was used to identify apoptotic tumour cells. Cultures were analysed using an IncuCyte S3 machine which allows real-time live cell fluorescence imaging. Co-cultures were imaged for 72 hours. Each condition was established in triplicate.

Figure 5:
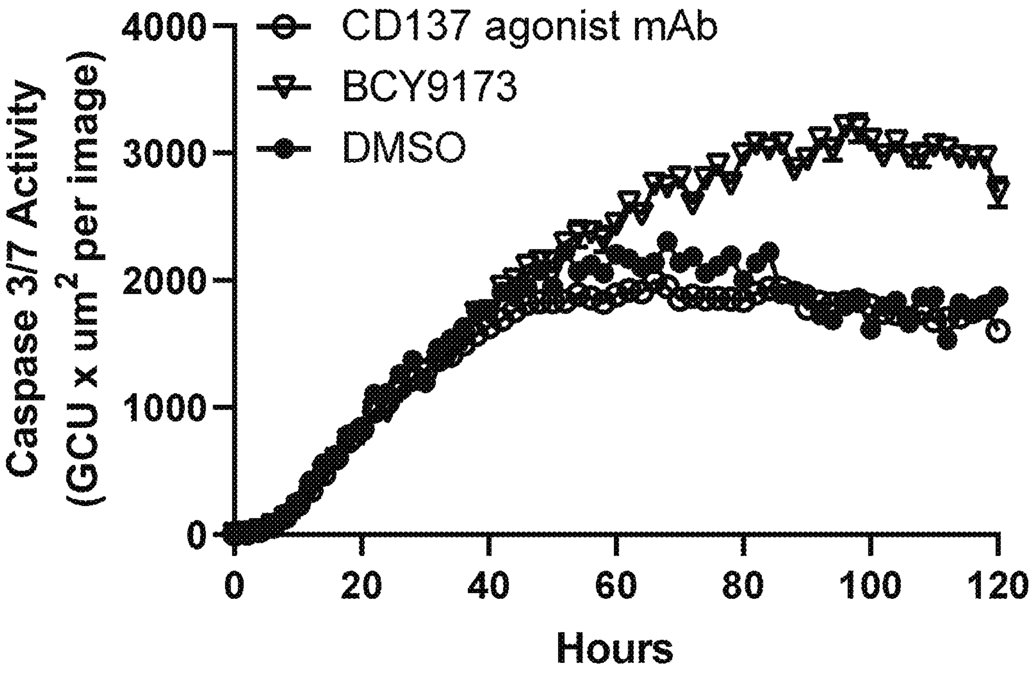
FIG. 5: EphA2/CD137 heterotandems induce tumour cell killing in primary human T-cell and cancer cell co-culture assay. Tumour cell killing is evaluated by counting viable Nuclight red positive tumour cells over time. A Caspase 3/7 dye is used to identify apoptotic tumour cells.

Data is presented in FIG. 5 which demonstrates that EphA2/CD137 heterotandems induce tumour cell killing in primary human T-cell and cancer cell co-culture assay. Anti-CD137 mAb agonist is used as a control.

6. Human PBMC-4T1 Co-Culture (Cytokine Release) Assay

Mouse mammary gland tumor cell line 4T1-1 (4T1-Parental) and murine Nectin-4 overexpressing 4T1 (4T1-D02) were cultured in RPM11640 supplemented with 10% heat-inactivated Fetal Bovine Serum, 100 I·U/ml Penicillin and 100 I·U/Streptomycin, 20 mM HEPES, 1× Non-Essential Amino Acids, and 2 mM L-Glutamine (RPMI working medium). Frozen PBMCs from healthy human donors were thawed and washed one time in room temperature PBS, and then resuspended in RPMI working medium. For tumor cell and PBMC co-culture, 10000 PBMCs and 2000 tumor cells (5:1) were mixed and plated in each well of a 384 well plate. For stimulating human PBMCs, 125 ng/ml of soluble anti-CD3 mAb (clone OKT3) was added to the culture on day 0. Test, control compounds or vehicle controls were added to respective wells and brought the final volume per well to 100 ul. Plates were incubated in a 37° C. cell culture incubator with 5% $CO_2$ for up to three days. Supernatants were collected 48 hours after stimulation, and human IL-2 and IFNγ were detected using HTRF assays. Raw data were analyzed using Excel or Prism software to generate standard curves to interpolate protein concentrations. Data represents one study with three different donor PBMC tested in experimental duplicates.

Figure 7:
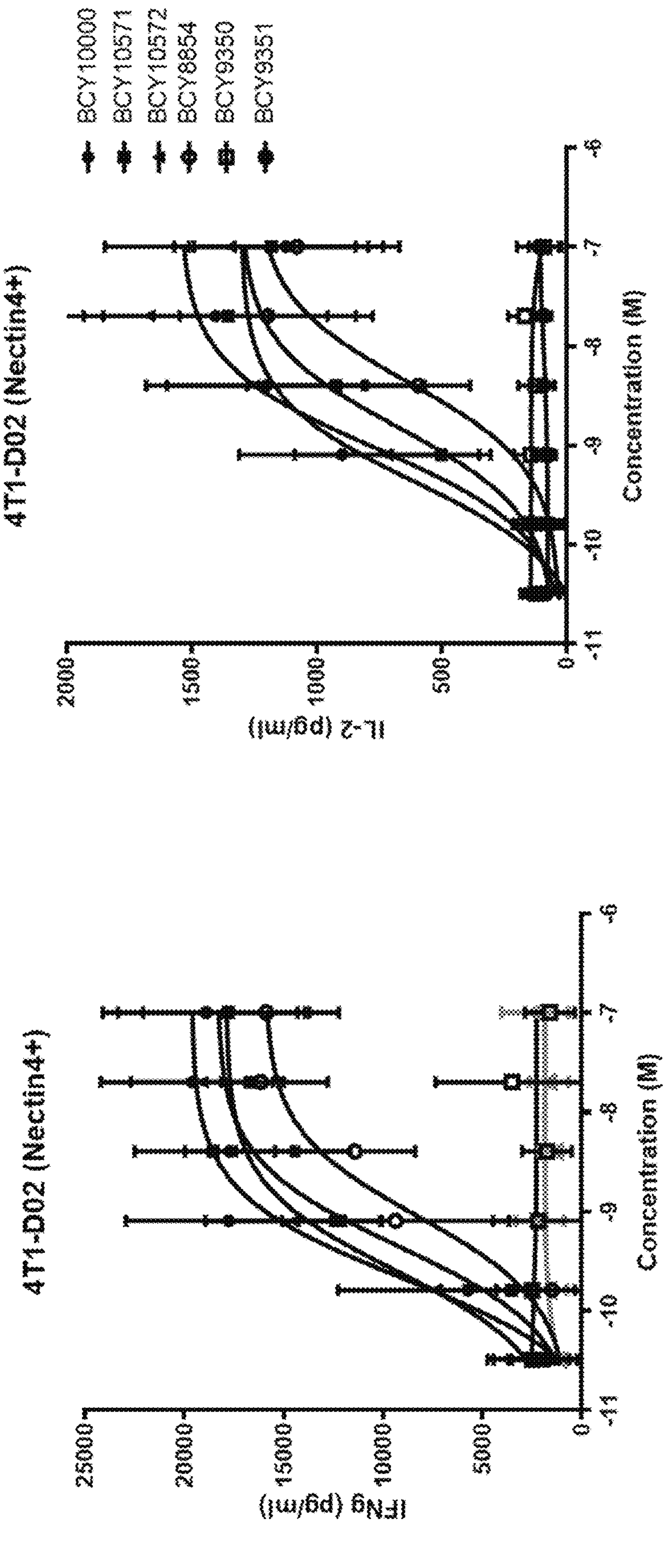
FIG. 7: Nectin-4/CD137 heterotandems induce IL-2 and IFN-γ cytokine secretion in a PBMC-4T1 co-culture assay. BCY9350 and BCY9351 are non-binding controls for Nectin-4 and CD137 respectively.

Data presented in FIG. 7 demonstrates that Nectin-4/CD137 heterotandems induce robust IL-2 and IFN-γ cytokine secretion in a PBMC-4T1 co-culture assay. BCY9350 and BCY9351 are non-binding controls for Nectin-4 and CD137 respectively.

A summary of the EC50 (nM) and maximum IFN-γ cytokine secretion (pg/ml) induced by selected Nectin-4/CD137 heterotandem peptides in Human PBMC-4T1 co-culture (cytokine release) assay is reported in Table 6 below:

TABLE 6

EC50 and maximum IFN-y cytokine secretion induced by selected Nectin-4/CD137 heterotandem peptides in Human PBMC-4T1 co-culture (cytokine release) assay

| Complex ID | Cell line | EC50 (nM) | max IFN-y (pg/ml) |
|---|---|---|---|
| BCY8854 | 4T1-D02(Nectin4+) | 0.89 | 15962 |
| BCY9350 | 4T1-D02(Nectin4+) | — | No Activity up to 1 μM |
| BCY9351 | 4T1-D02(Nectin4+) | — | No Activity up to 1 μM |
| BCY10000 | 4T1-D02(Nectin4+) | 0.21 | 19642 |
| BCY10571 | 4T1-D02(Nectin4+) | 0.44 | 18349 |
| BCY10572 | 4T1-D02(Nectin4+) | 0.25 | 17915 |

7. Ex Vivo Culture Protocol

Primary patient derived tumour cells from Discovery Life Sciences (DLS) are thawed gently in 10 mL pre-warmed wash medium spiked fresh with Benzonase. The 3D spheroid kit from Greiner (cat #655840) is used to maintain cells in culture for 2 days. Briefly, tumour cells are counted with trypan blue using a haemocytometer. The cells are centrifuged at 1500 rpm for 5 min to wash, and the pellet is resuspended in 100 μL per $1\times10^6$ cells N3D nanoshuttle. To make them magnetic, cells are spun down at 1500 rpm for 5 min and resuspended; this process is repeated for a total of 4 times. After the final spin, cells are resuspended in the appropriate amount of fresh Lung DTC medium (DLS) to give 50,000-100,000 cells per well in 100 μL/well. Greiner cell-repellent, 96-well plates (cat #655976) are used for this experiment. If there are cell clumps or debris visible, sample is applied to a 70-100 μm filter before plating. At least 50,000 cells per sample are reserved for a Day 0 flow cytometry panel, these cells are stained, fixed, and stored at 4° C. for later flow analysis. Control/test compound dilutions are prepared in a separate plate at 2× in Lung DTC medium, and 100 μL/well of these 2× drug solutions are added to the wells as described by the plate map. The assay plate is then placed onto the 96-well magnetic spheroid drive in a humidified chamber at 37 C, 5% $CO_2$. At 24 h, the magnetic spheroid drive is removed. At 48 h, medium is collected for cytokine analysis and cells are collected for a Day 2 flow cytometry panel. Cytokines are quantified using a custom-built cytokine/chemokine panel (IP-10, Granzyme B, IFNγ, IL-2, IL-6, TNFα, IL-8, MIP-1a, MIP-1b, MCP-1, IL-10, MIG) from R&D systems on a Luminex reader. Flow panels: Day 0=Live/Dead, CD45, EpCAM, Nectin4, CD3, CD4, CD8, CD137; Day 2=Live/Dead, CD45, EpCAM, Nectin4, CD3, CD8, Ki67, and counting beads. Flow data is analysed with Flowjo software.

Figure 8:
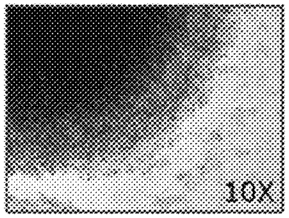
FIG. 8: Nectin-4/CD137 heterotandems induce target dependent cytokine release in ex-vivo cultures of primary patient-derived lung tumours. (A) Ex vivo patient derived tumour cells form 3D spheroids within 4 h in culture, 10× image under light microscope. (B) Flow analysis of Nectin-4 expression in patient derived tumour samples from 3 donors. (C) Table indicates % $CD137^+$ T cells and Nectin-$4^+$ cells in 3 donor samples. (D) Heatmap indicating % change in immune markers (normalized to vehicle) in response to treatment with control/test compounds. (E) % CD8 $^+$ki$67^+$ T cells in response to treatment with control/test compounds (vehicle indicated with dotted line).
Figure 8:
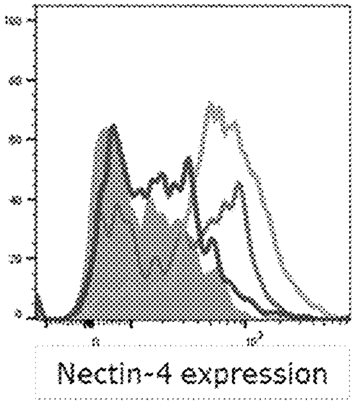
Figure 8:
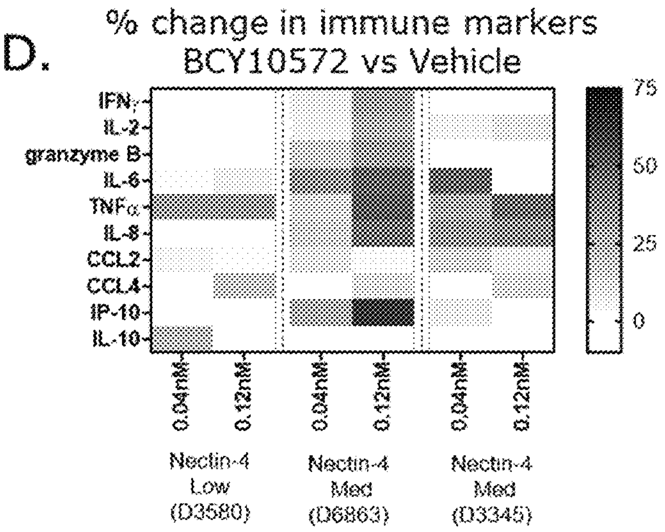
Figure 8:
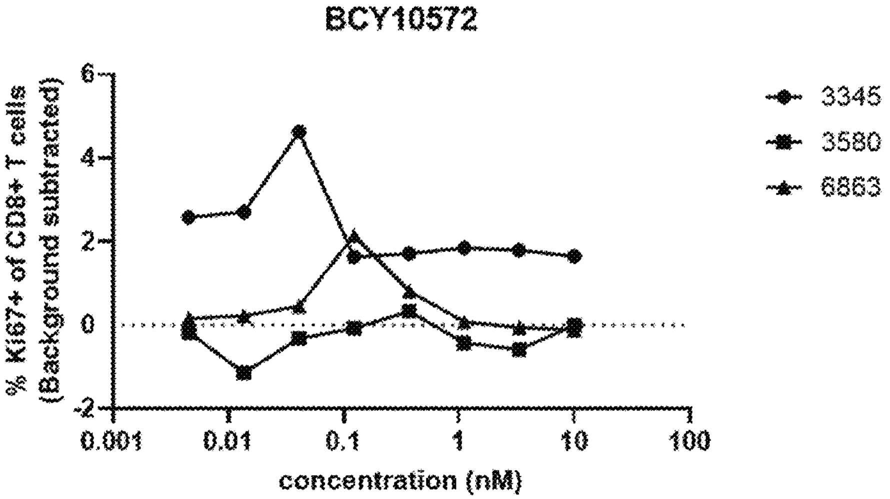

Data shown in FIG. 8 demonstrate that Nectin-4/CD137 heterotandems induce target dependent cytokine release in ex-vivo cultures of primary patient-derived lung tumours. Treatment of BCY10572 induced Nectin-4 dependent change in several immune markers (normalized to vehicle) and in % $CD8^+ki67^+$ T cells in patient-derived samples.

8. Pharmacokinetics of CD137 Bispecifics in SD Rats

Male SD Rats were dosed with 2 mg/kg of each Bicycle multimer formulated in 25 mM Histidine HCl, 10% sucrose pH 7. Serial bleeding (about 80 μL blood/time point) was performed via submadibular or saphenous vein at each time point. All blood samples were immediately transferred into prechilled microcentrifuge tubes containing 2 μL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 μL of the supernatant samples were directly injected for LC-MS/MS analysis using an Orbitrap Q Exactive in positive ion mode to determine the concentrations of Bicycle multimer. Plasma concentration versus time data were analyzed by non-compartmental approaches using the Phoenix WinNonlin 6.3 software program. C0, Cl, Vdss, T½, AUC(0-last), AUC(0-inf), MRT(0-last), MRT(0-inf) and graphs of plasma concentration versus time profile were reported.

Figure 10:
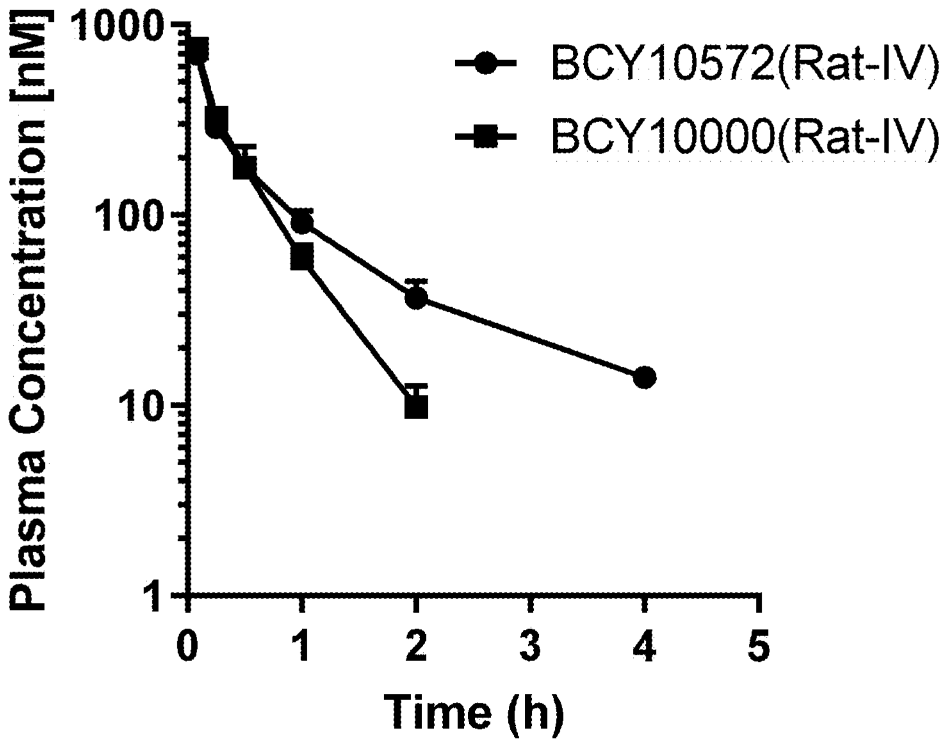
FIG. 10: Pharmacokinetics of heterotandems in SD Rats: BCY10572 and BCY10000 were dosed IV at 2 mg/kg (n=3).
Figure 11:
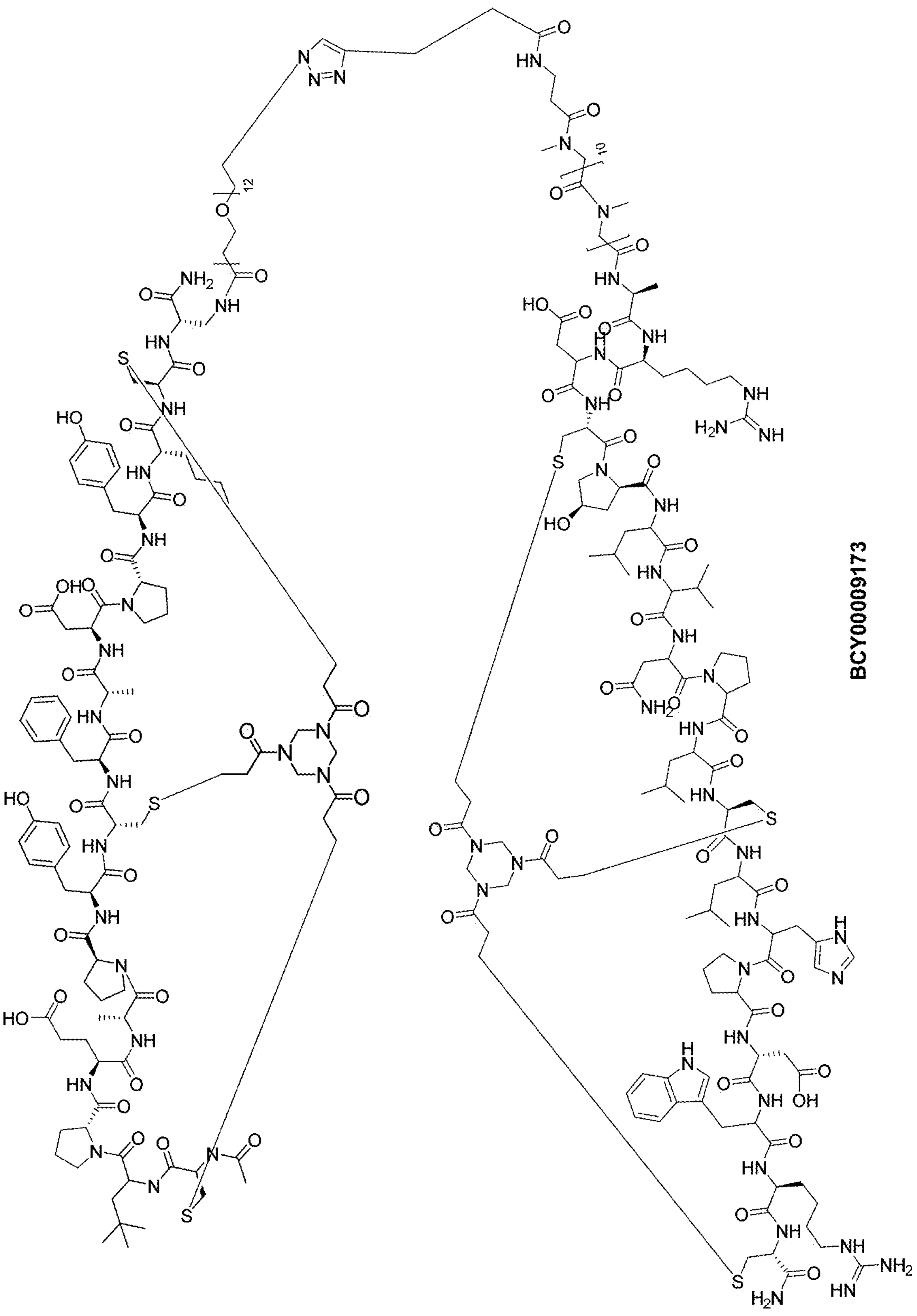
FIG. 11: Formula of BCY9173.
Figure 12:
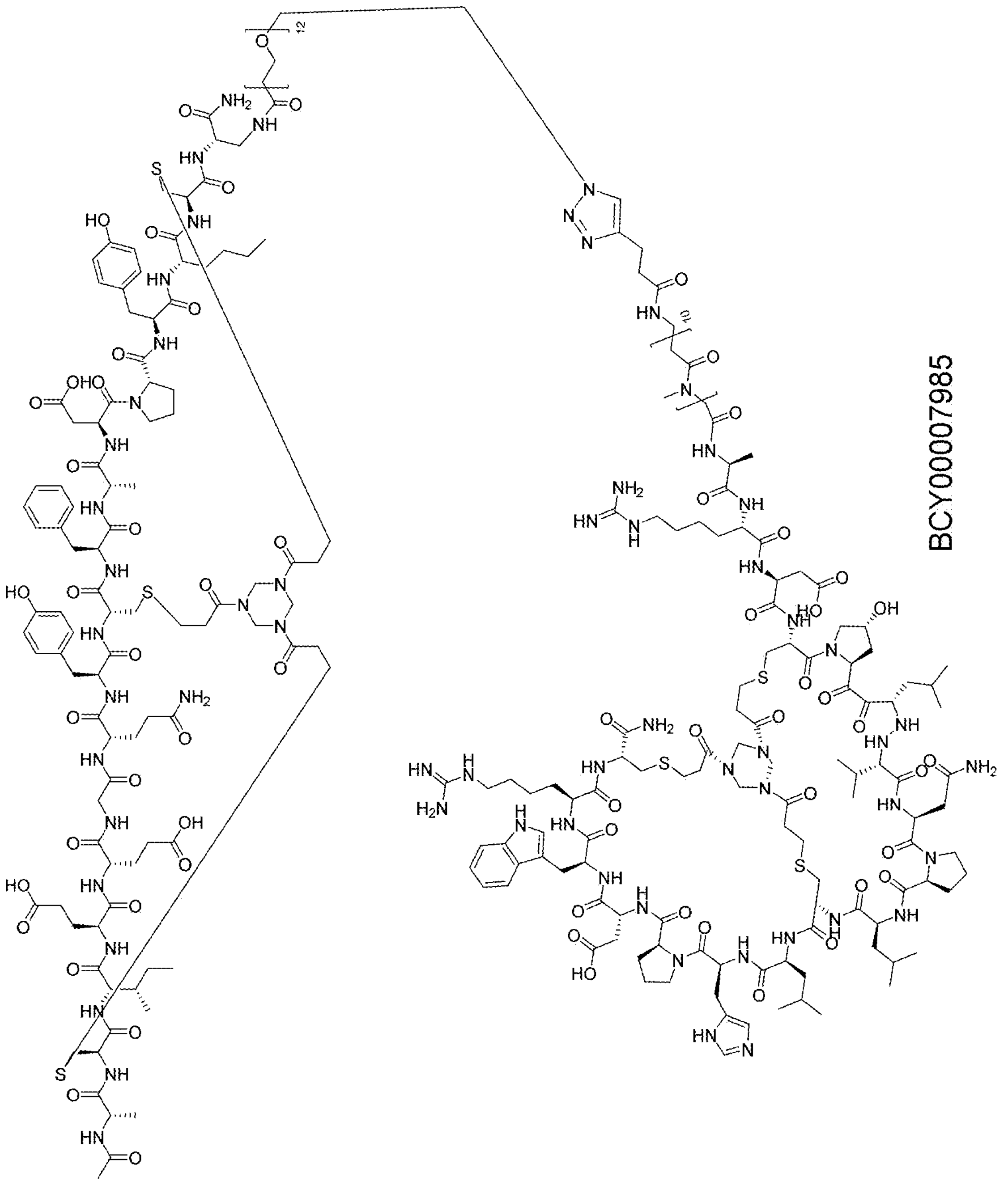
FIG. 12: Formula of BCY7985.
Figure 13:
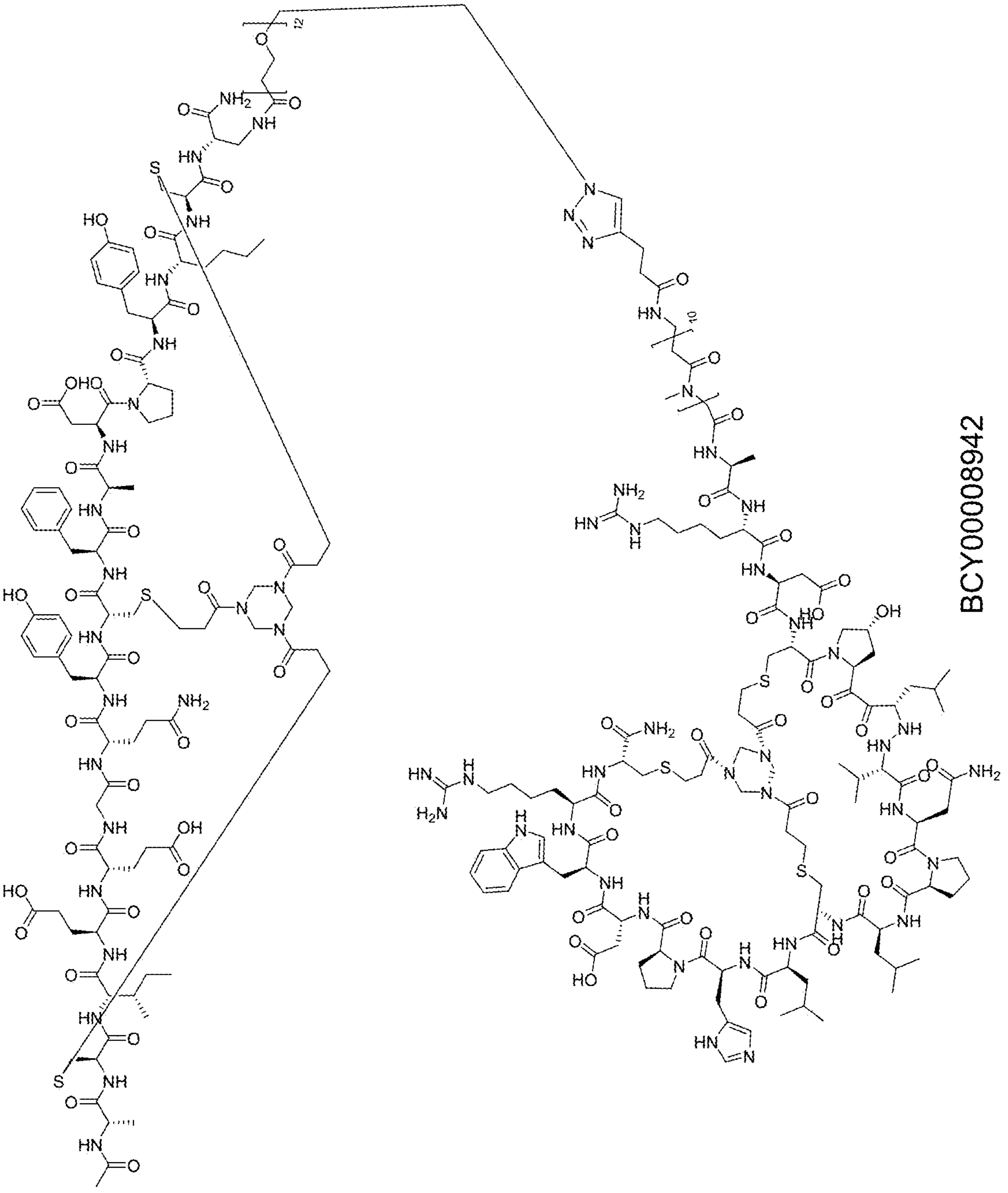
FIG. 13: Formula of BCY8942.
Figure 14:
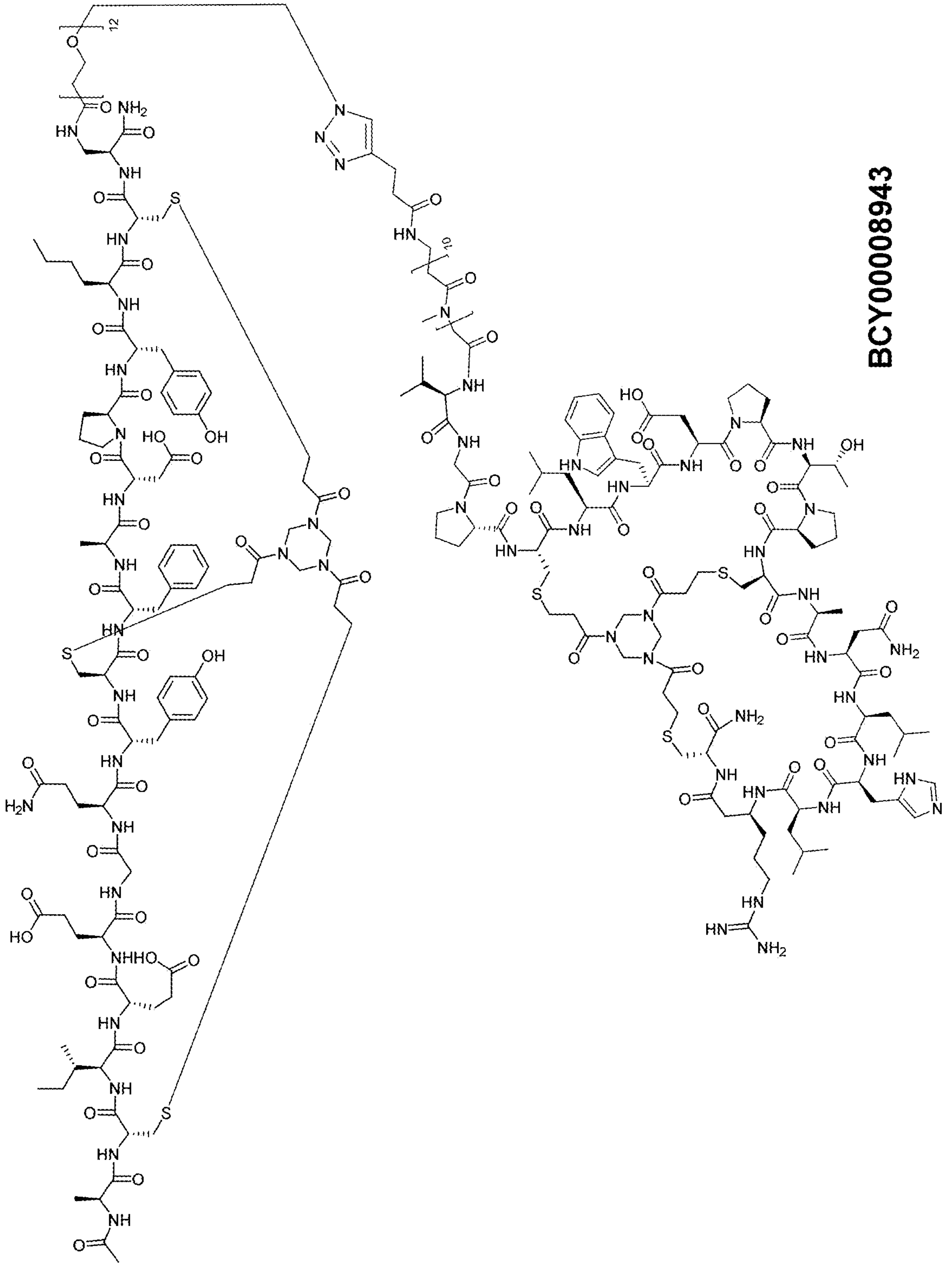
FIG. 14: Formula of BCY8943.
Figure 15:
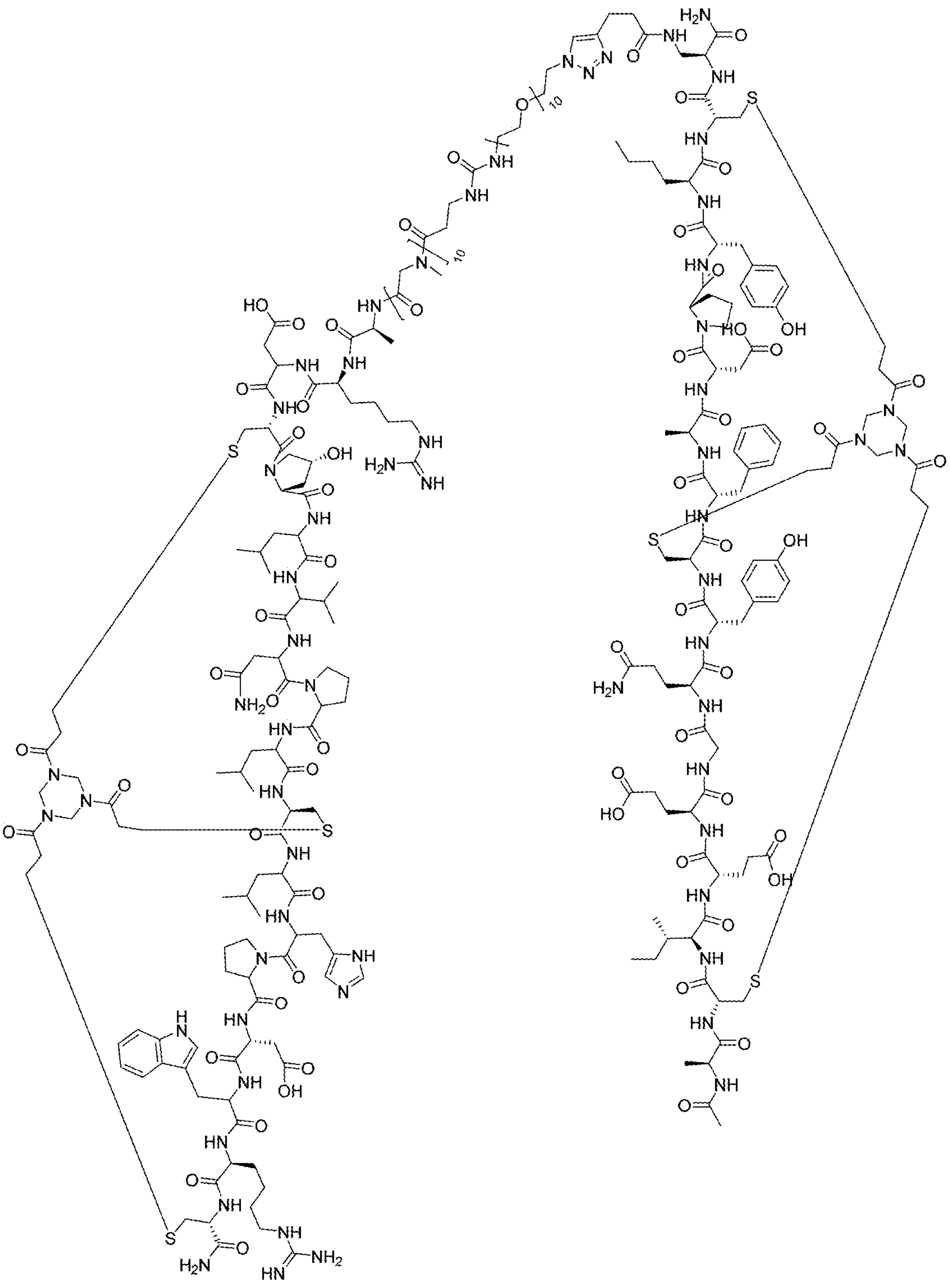
FIG. 15: Formula of BCY9647.
Figure 16:
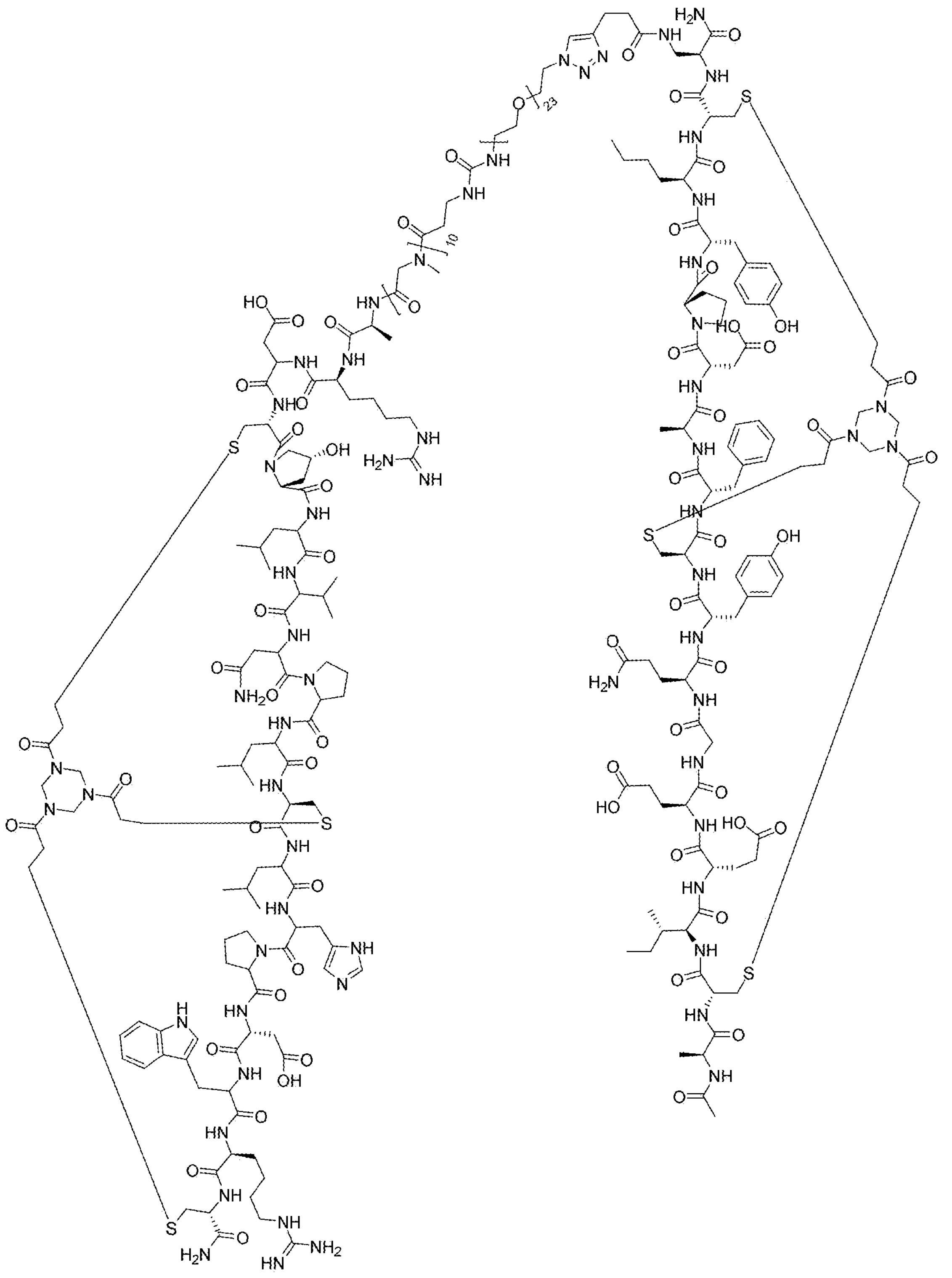
FIG. 16: Formula of BCY9648.
Figure 17:
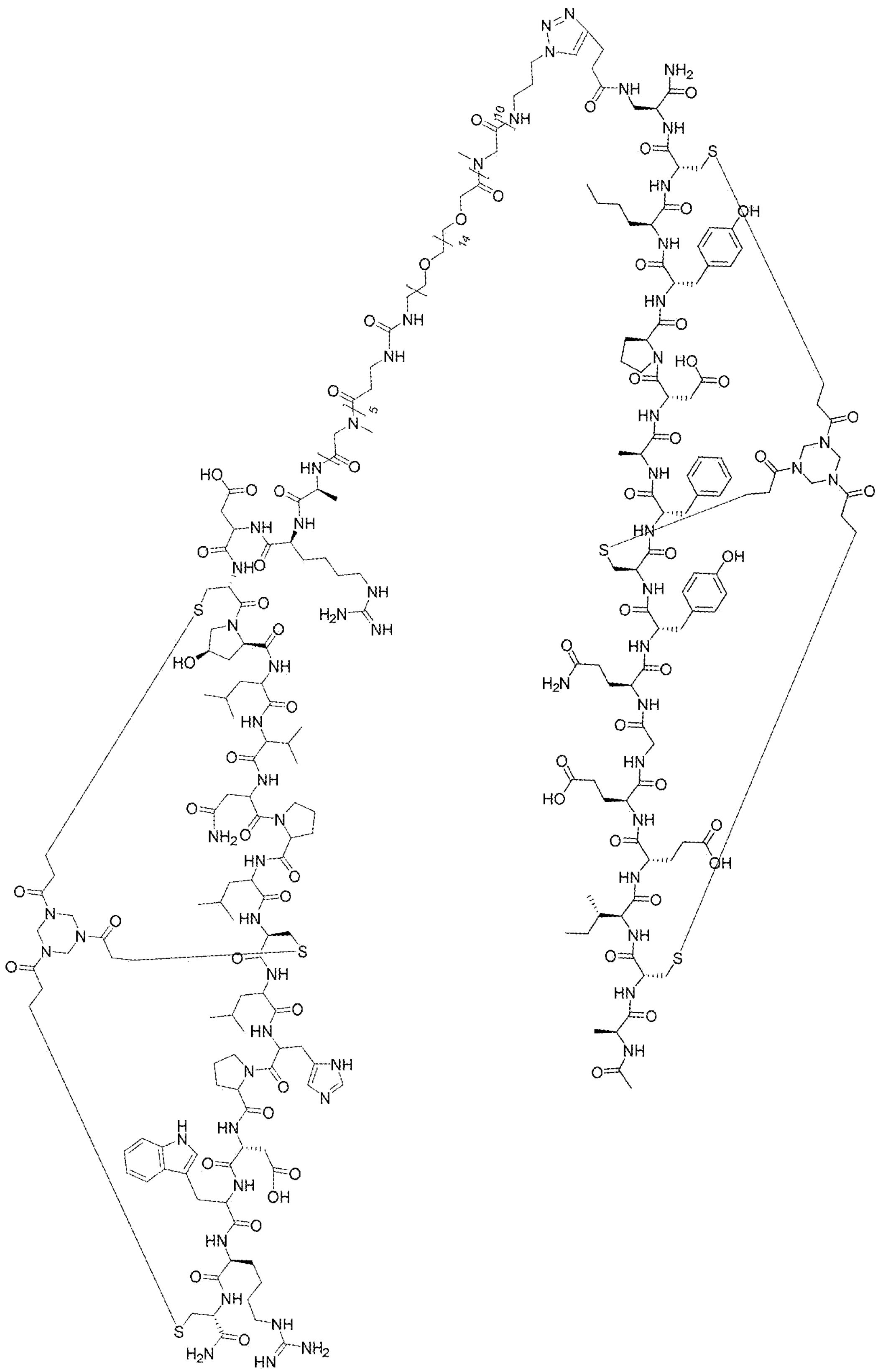
FIG. 17: Formula of BCY9655.
Figure 18:
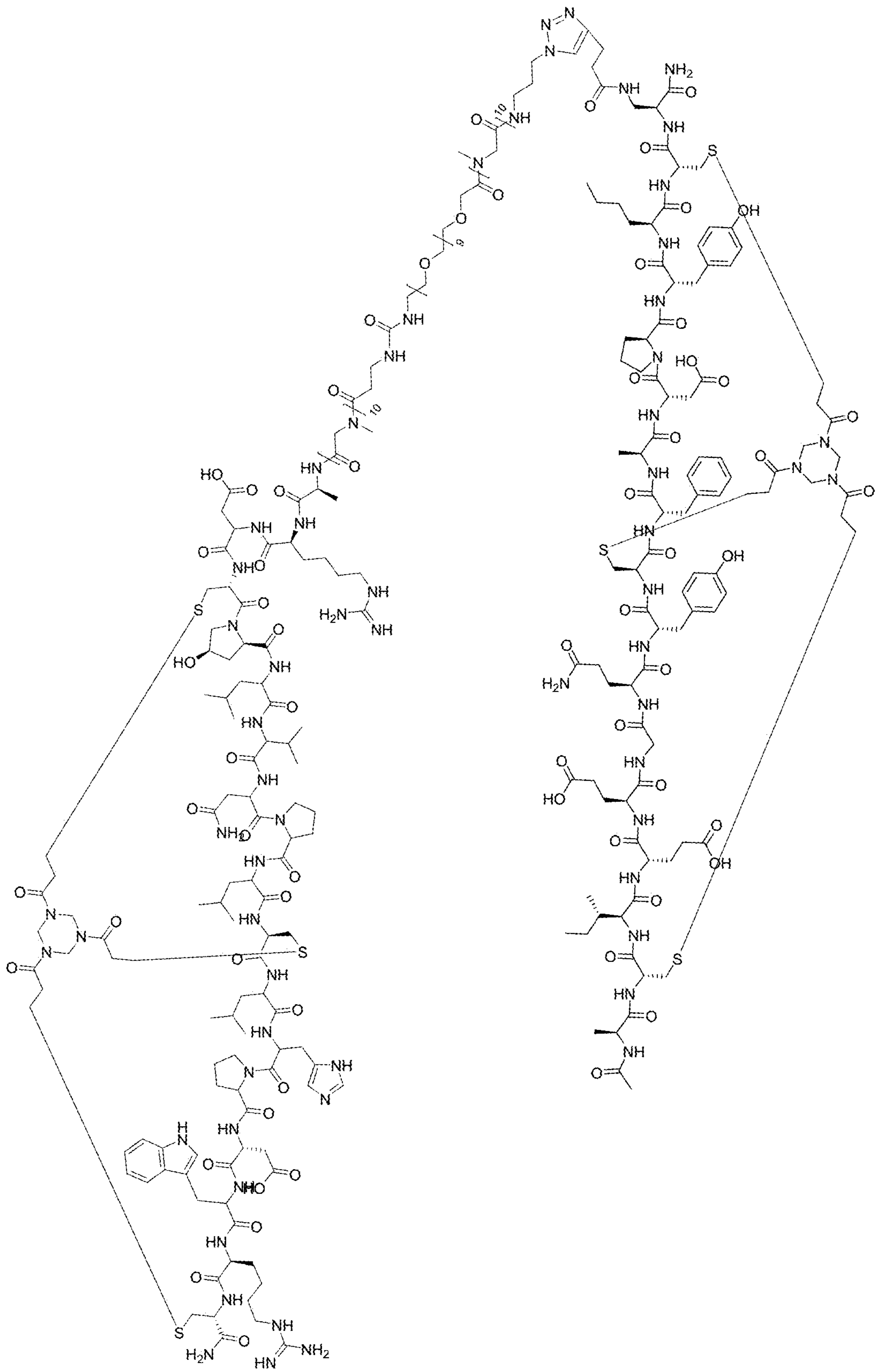
FIG. 18: Formula of BCY9656.
Figure 19:
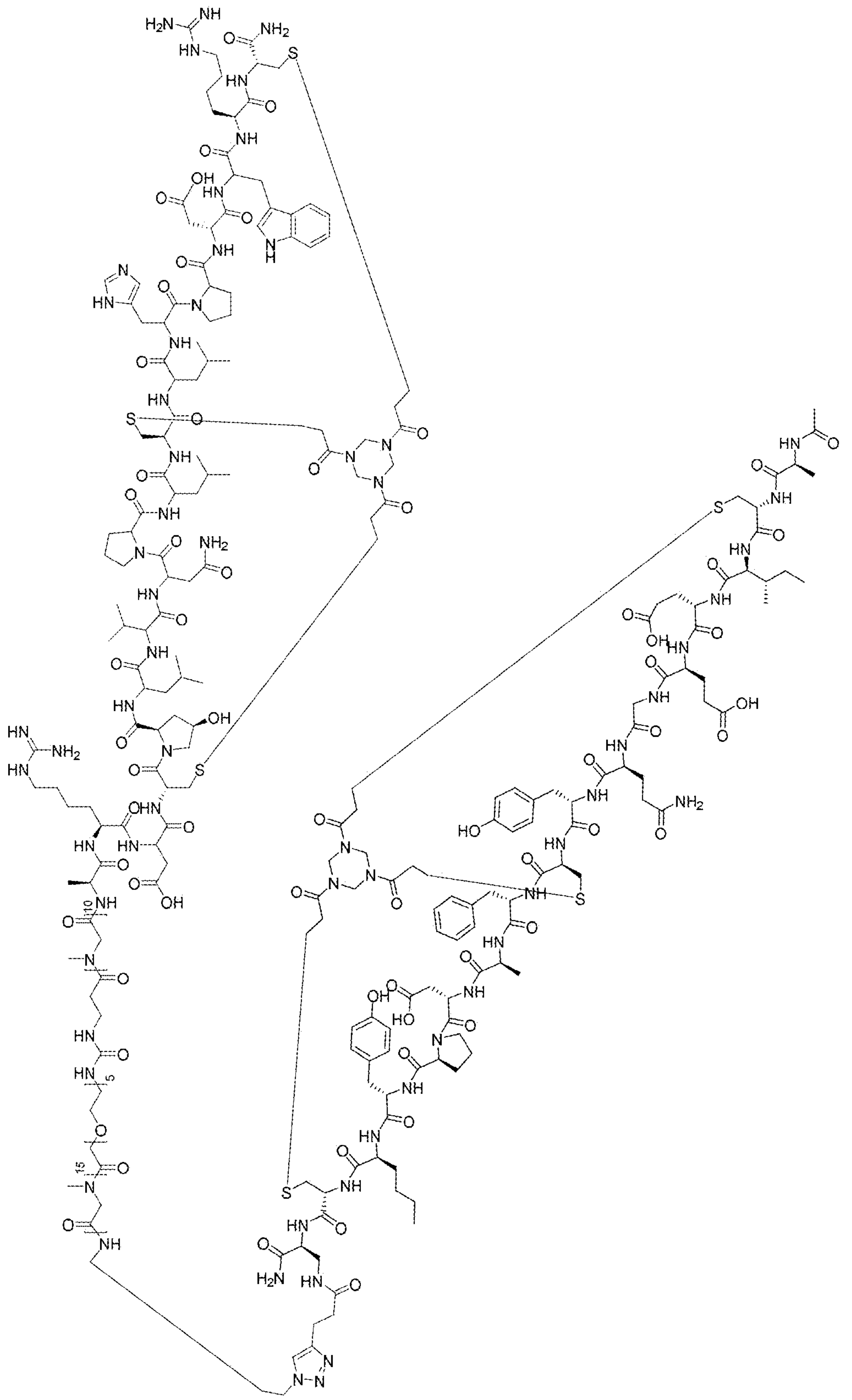
FIG. 19: Formula of BCY9657.
Figure 20:
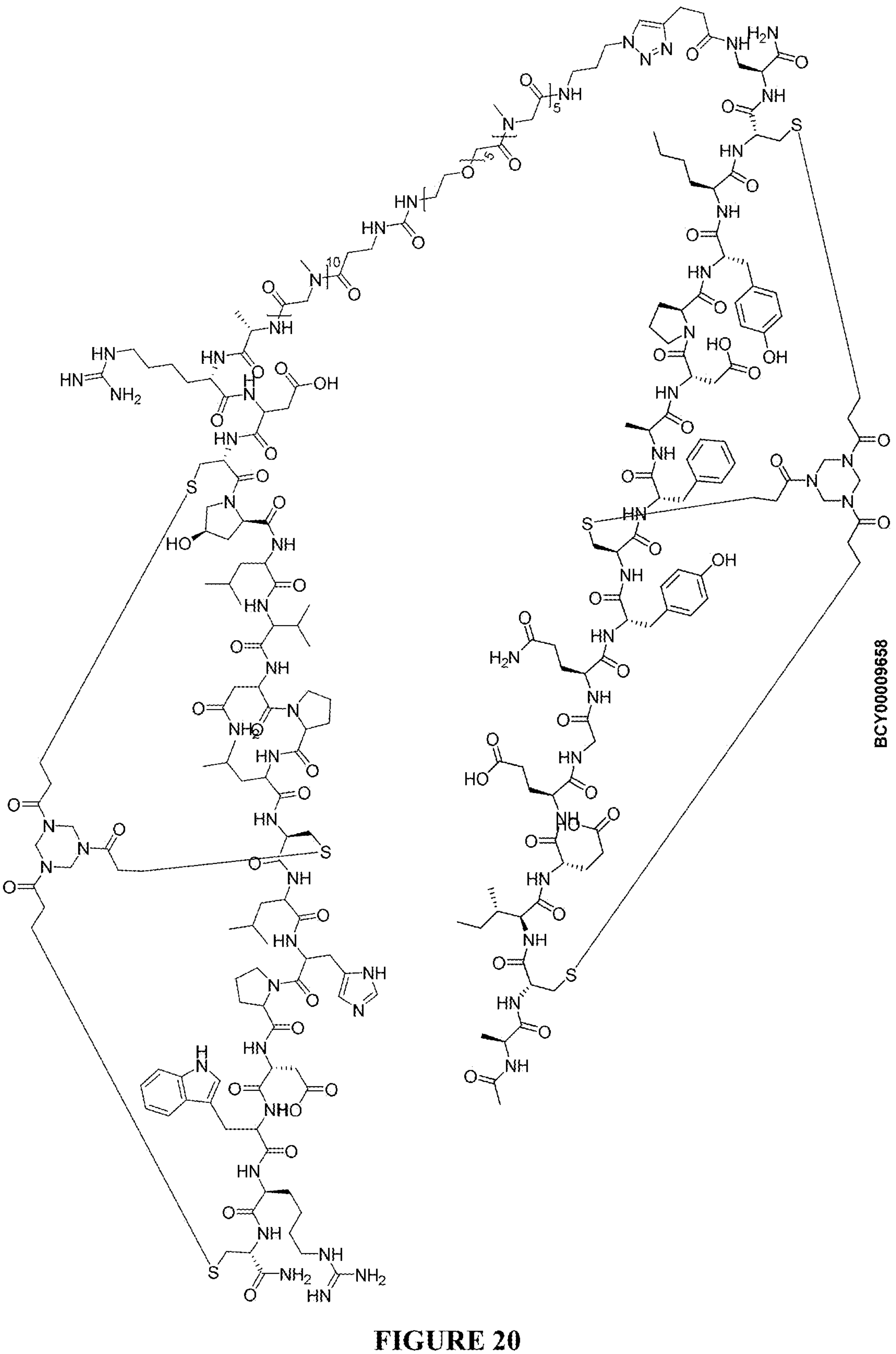
FIG. 20: Formula of BCY9658.
Figure 21:
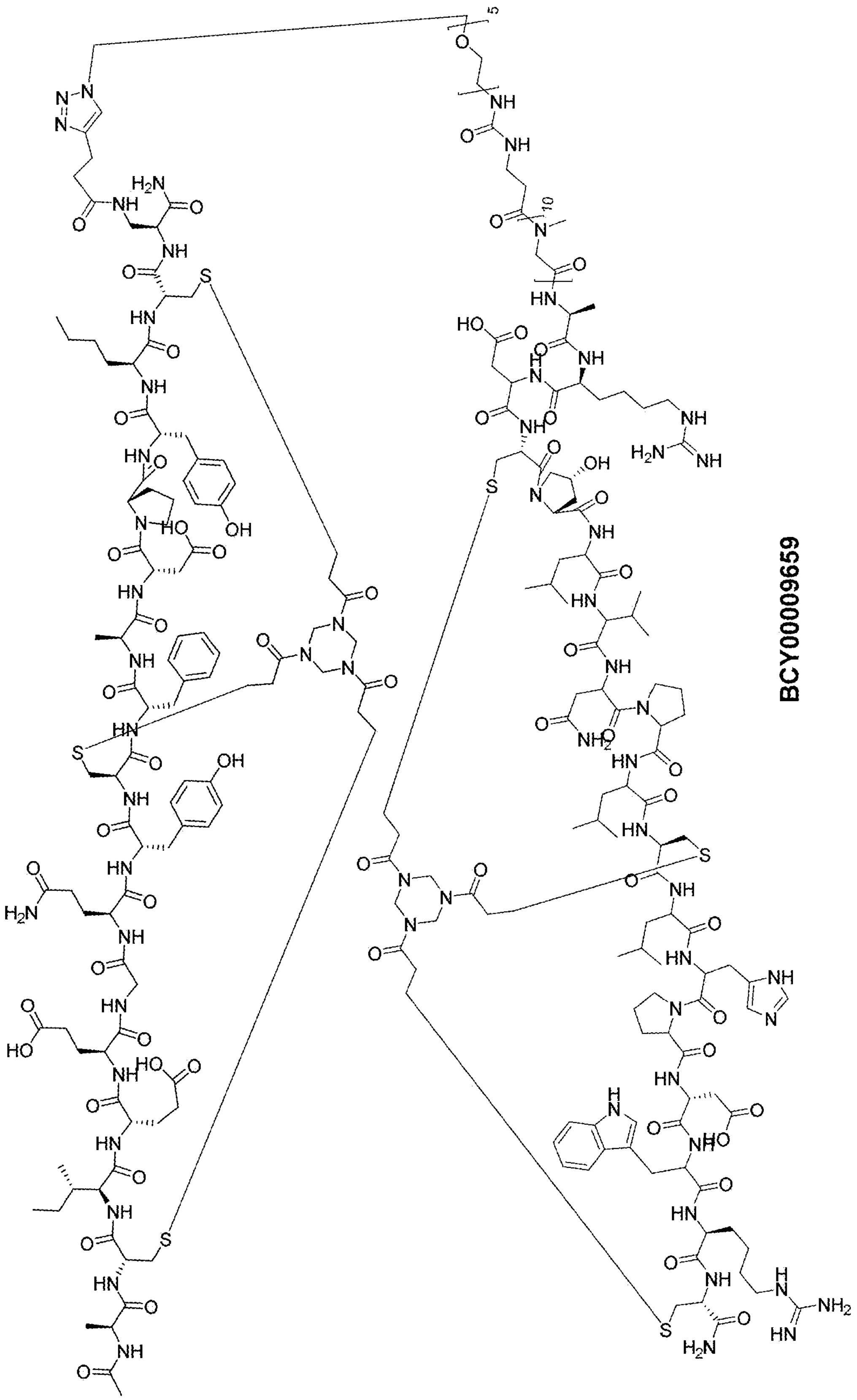
FIG. 21: Formula of BCY9659.
Figure 22:
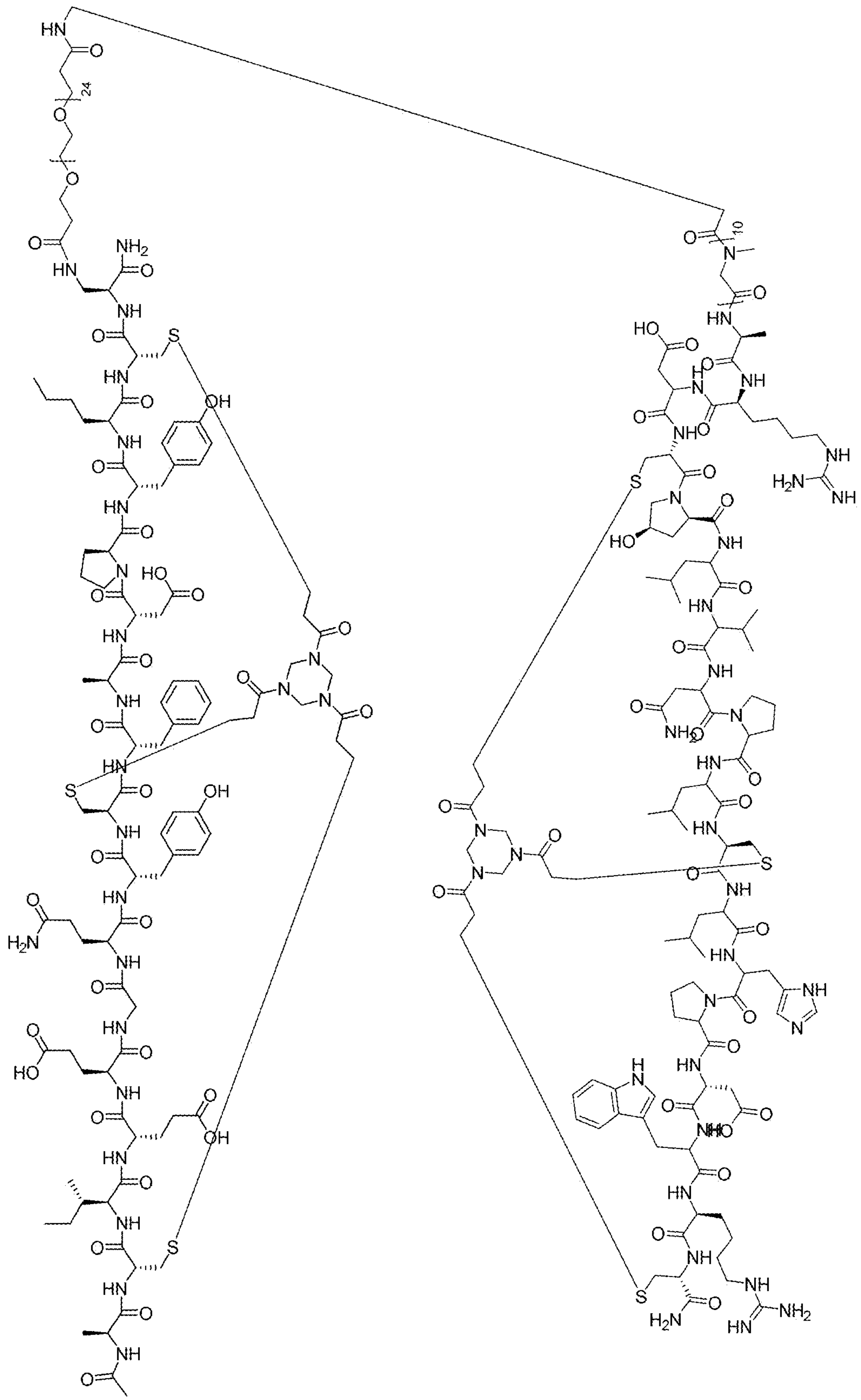
FIG. 22: Formula of BCY9758.
Figure 23:
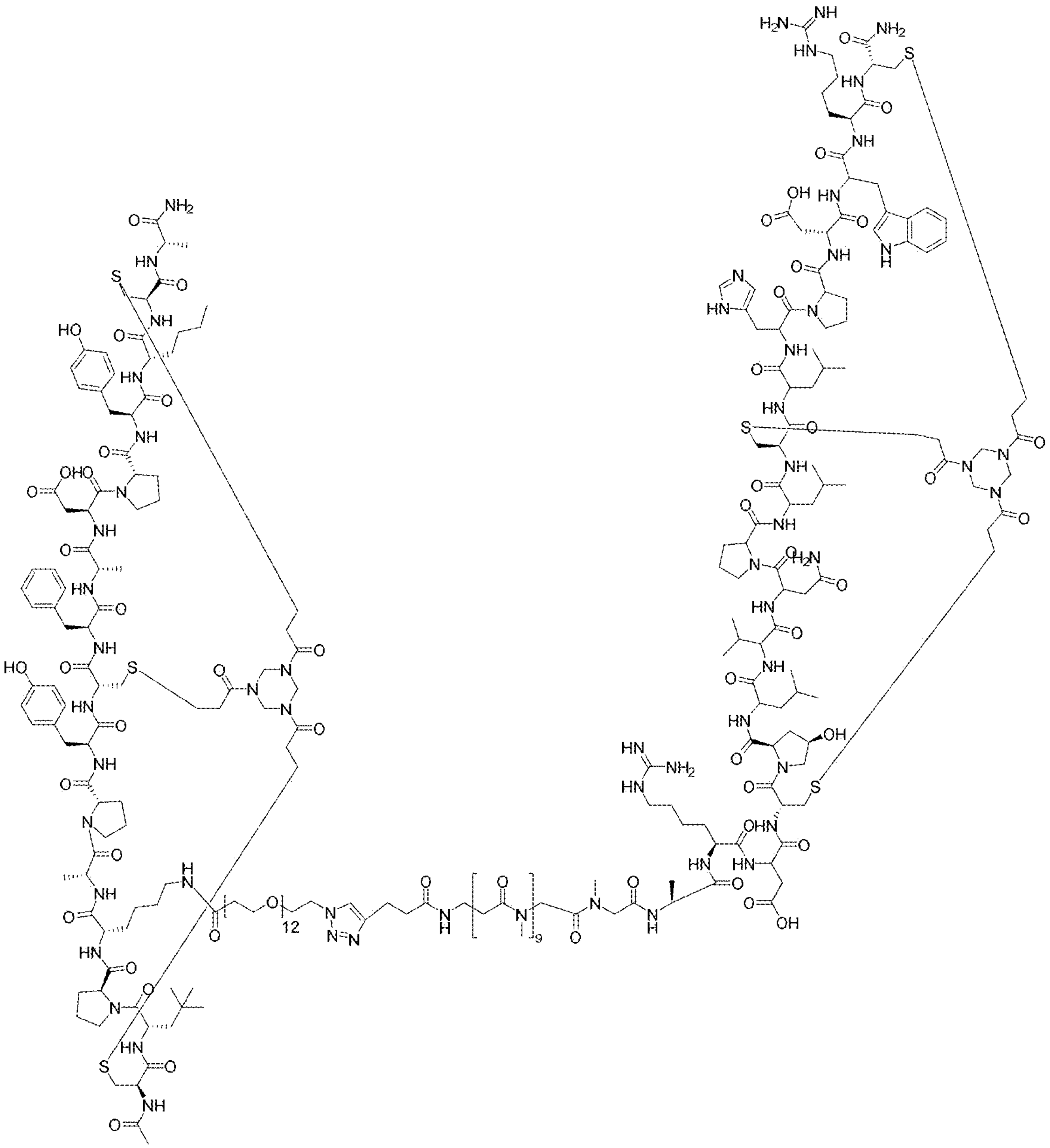
FIG. 23: Formula of BCY10568.
Figure 24:
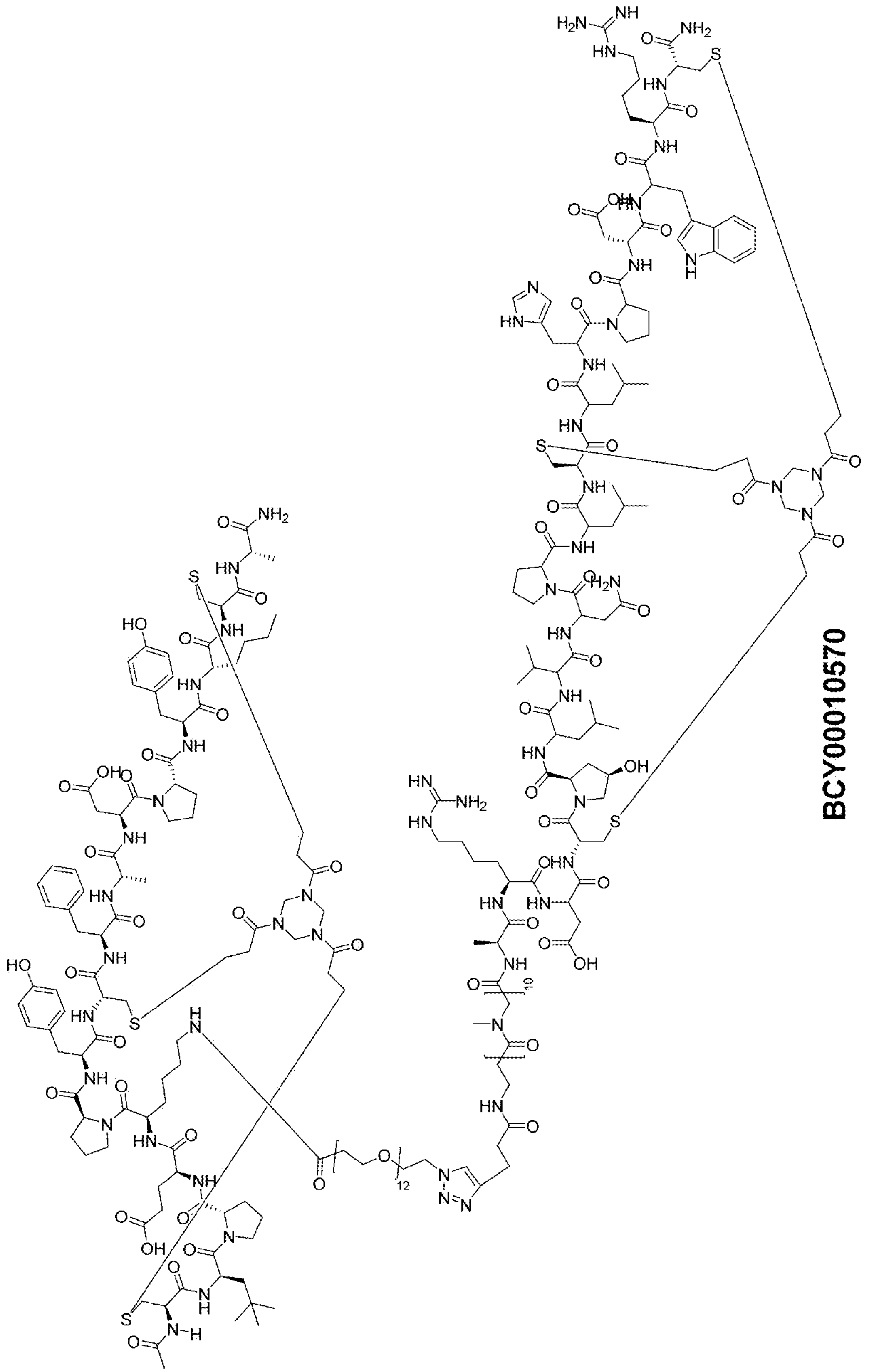
FIG. 24: Formula of BCY10570.
Figure 25:
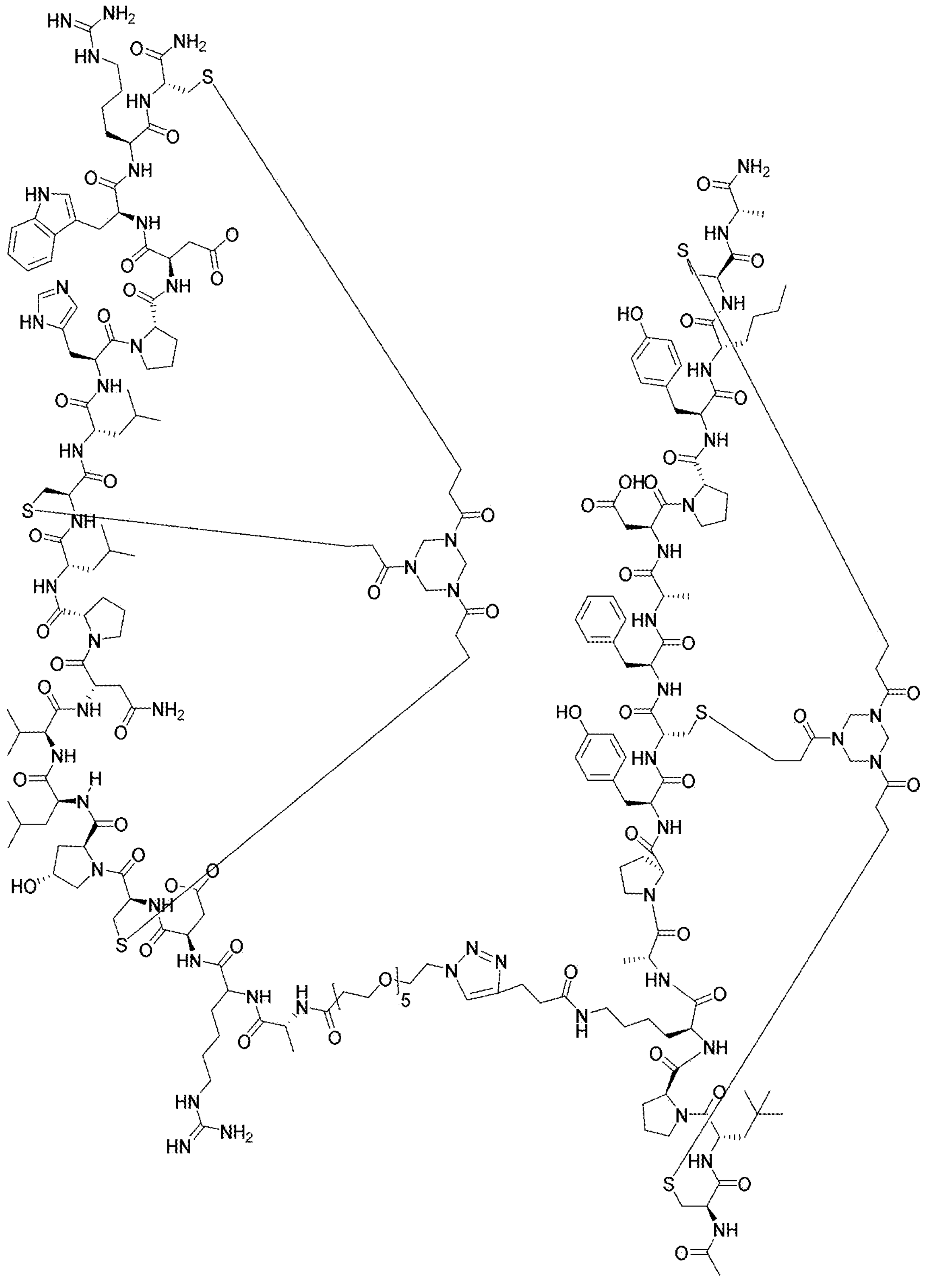
FIG. 25: Formula of BCY10574.
Figure 26:
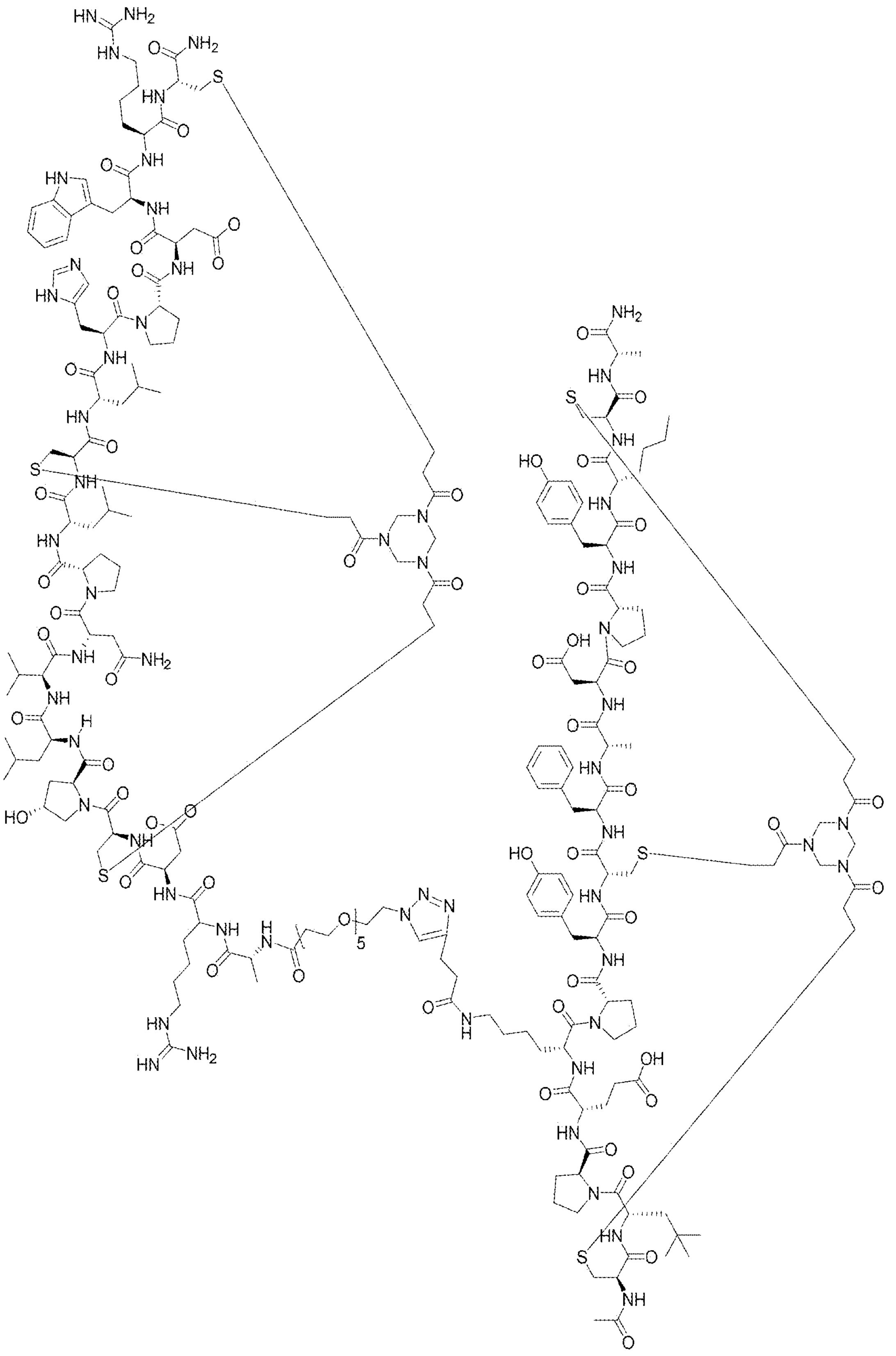
FIG. 26: Formula of BCY10575.
Figure 27:
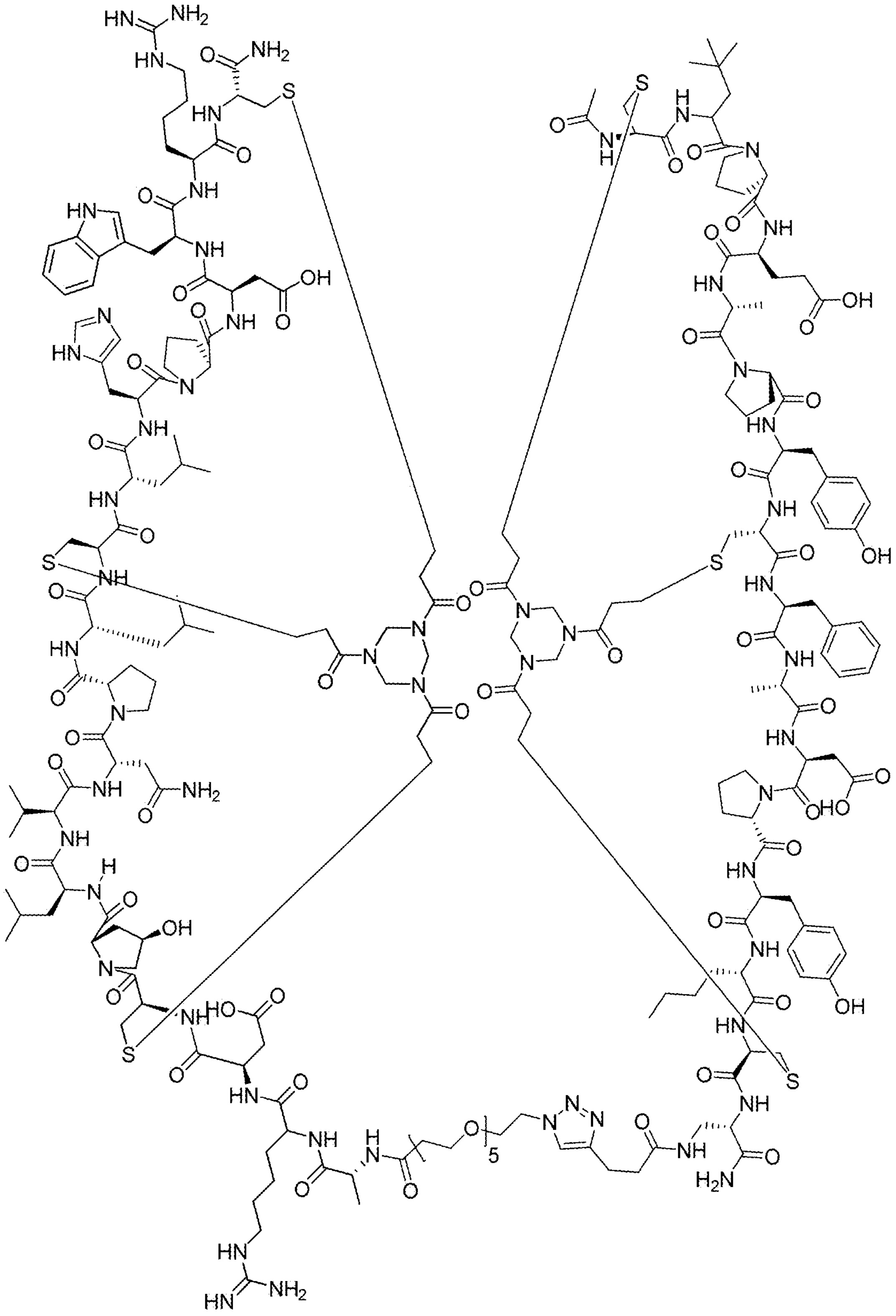
FIG. 27: Formula of BCY10576.
Figure 28:
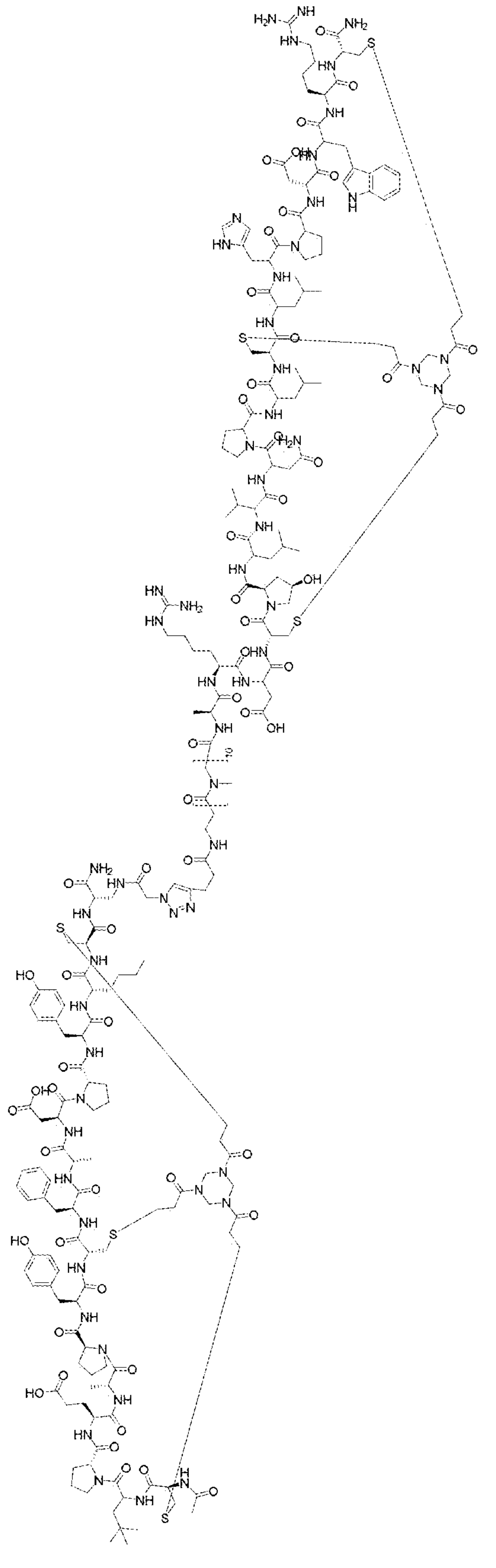
FIG. 28: Formula of BCY10577.
Figure 29:
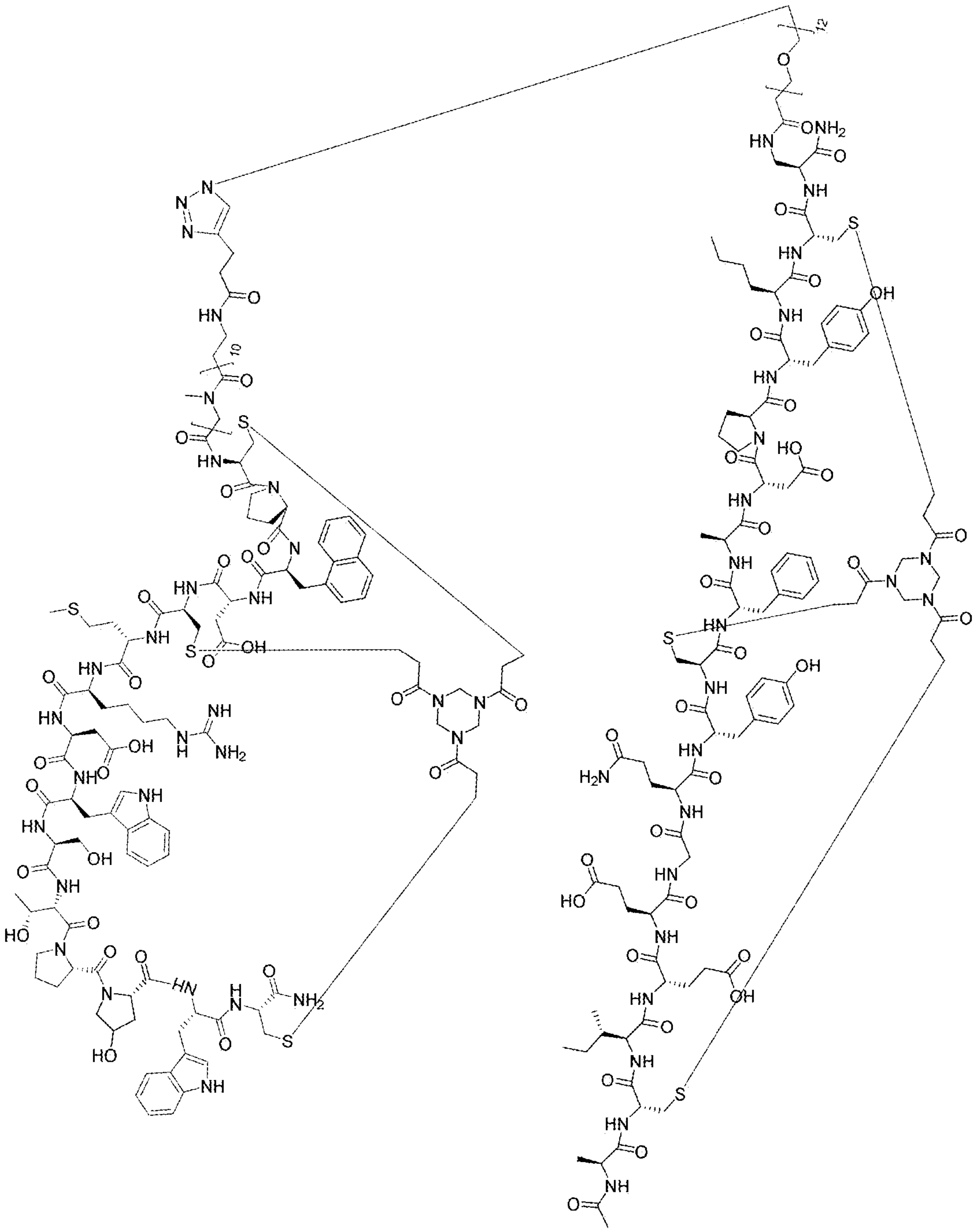
FIG. 29: Formula of BCY8854.
Figure 30:
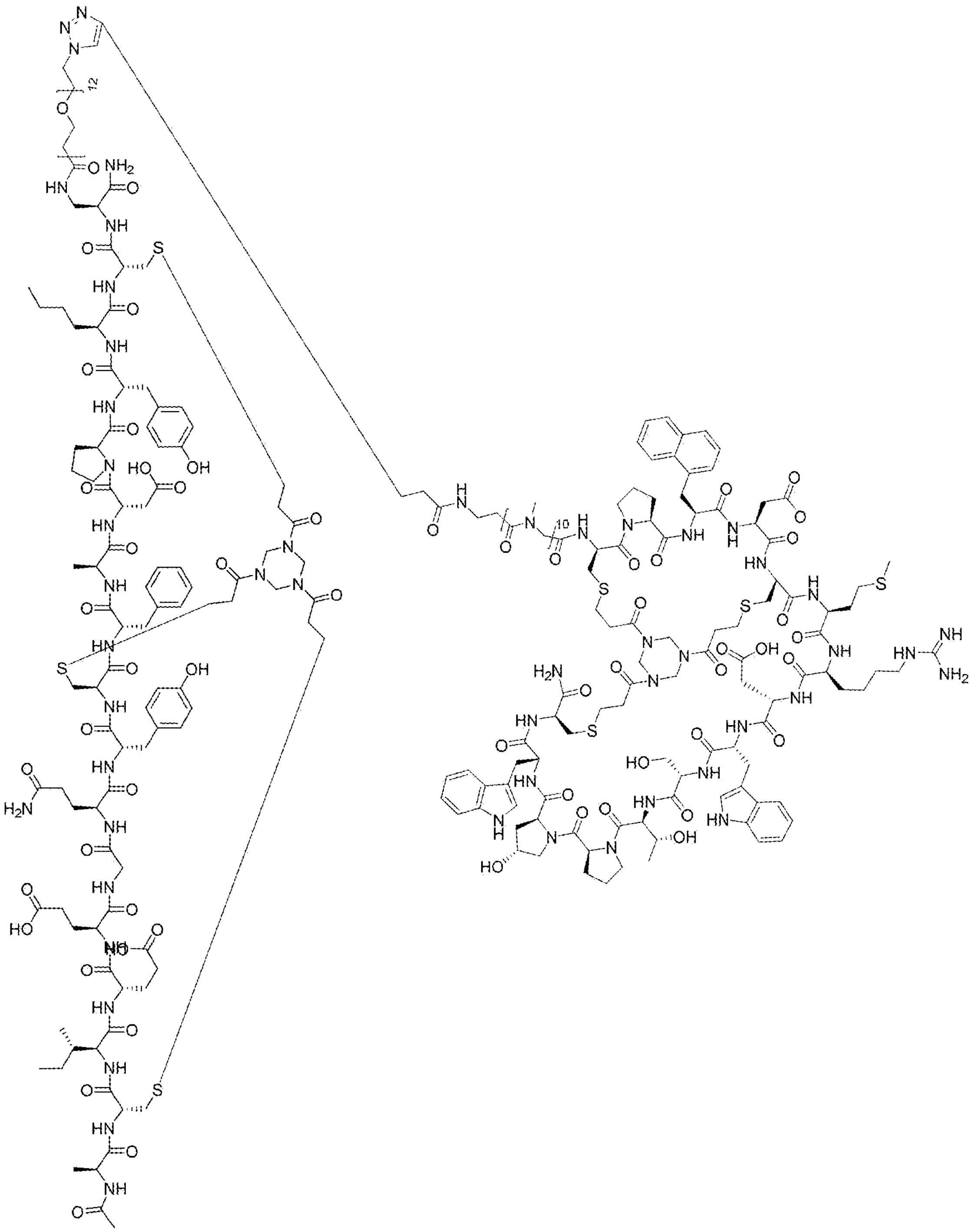
FIG. 30: Formula of BCY9350.
Figure 31:
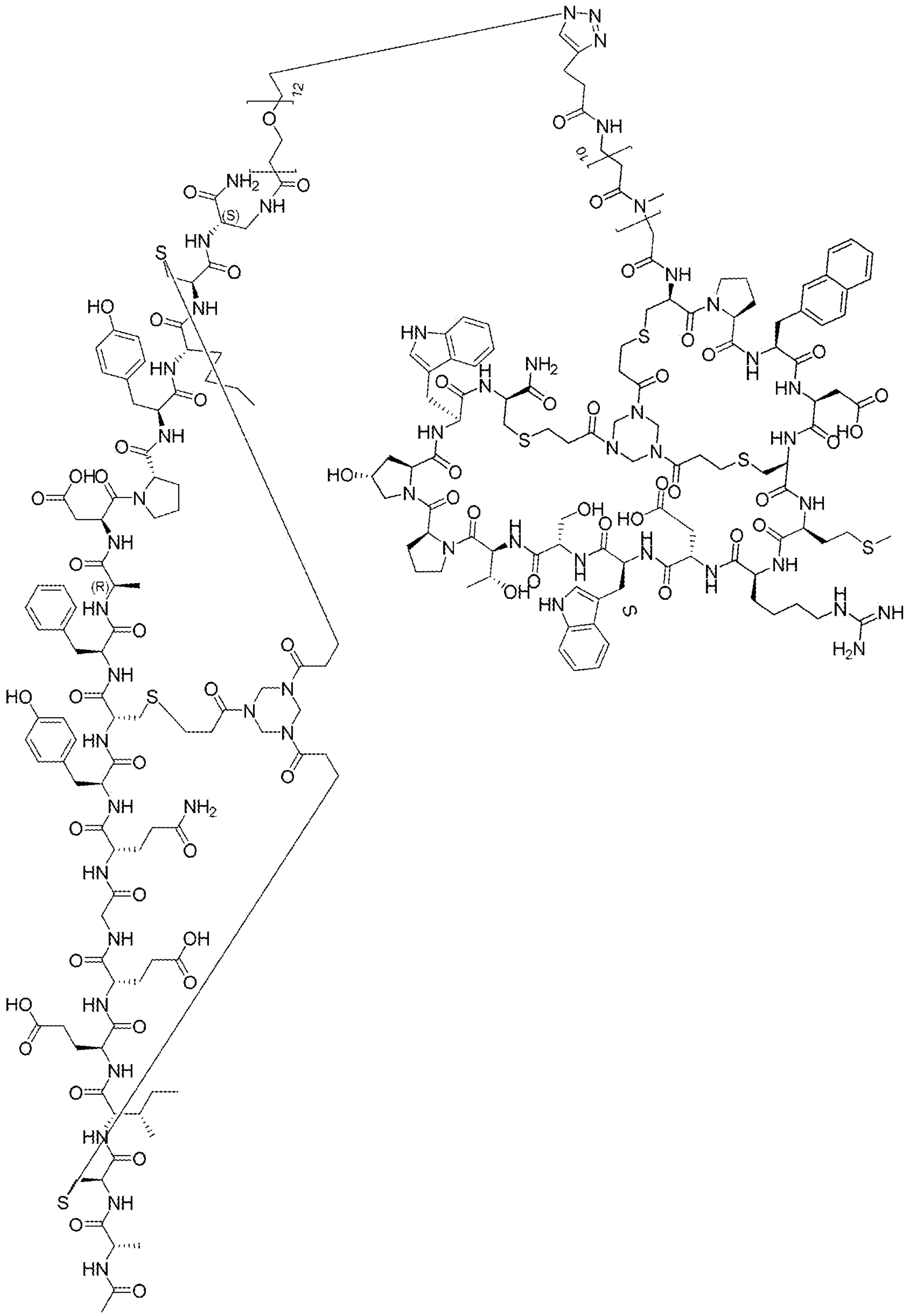
FIG. 31: Formula of BCY9351.
Figure 32:
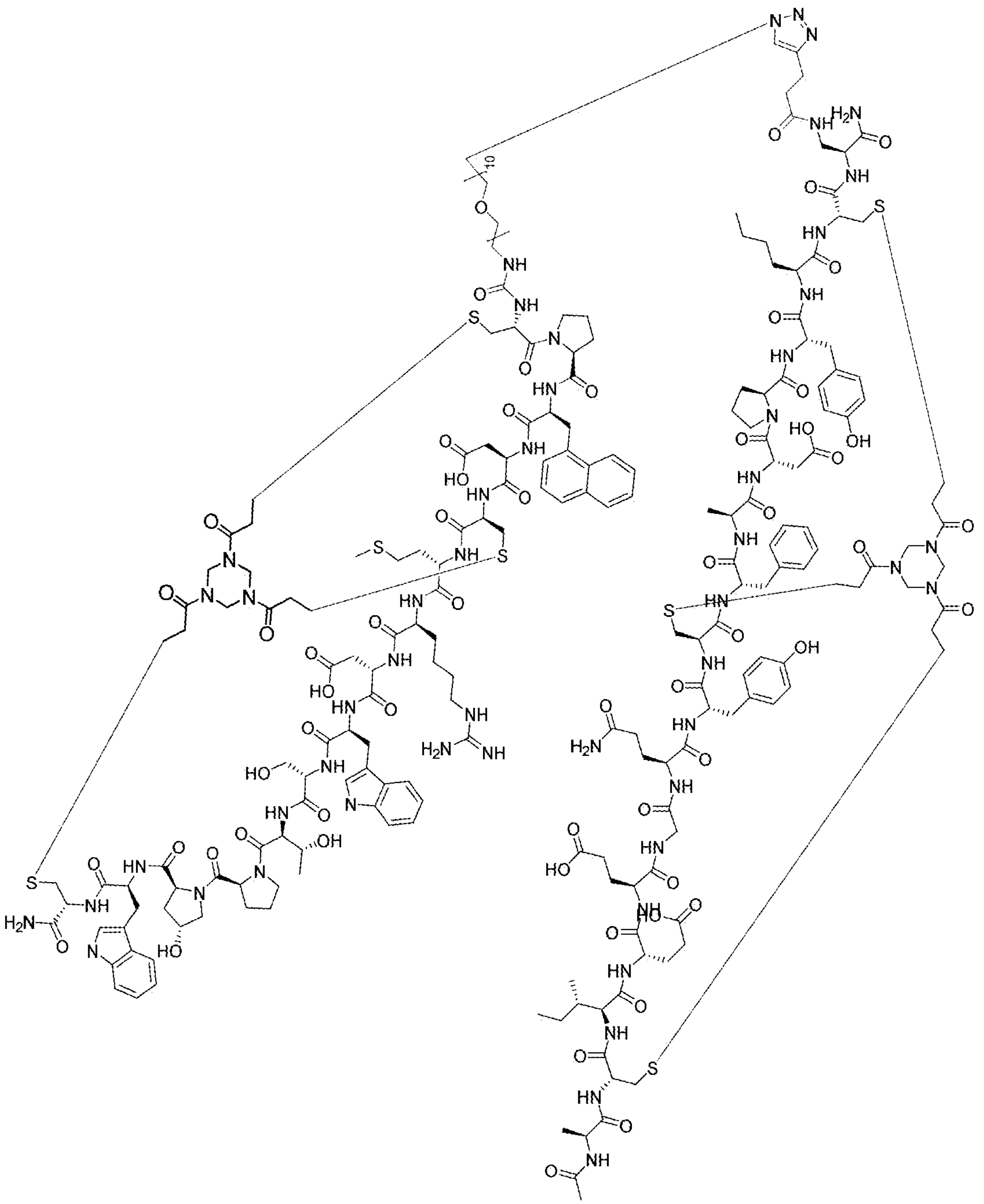
FIG. 32: Formula of BCY9399.
Figure 33:
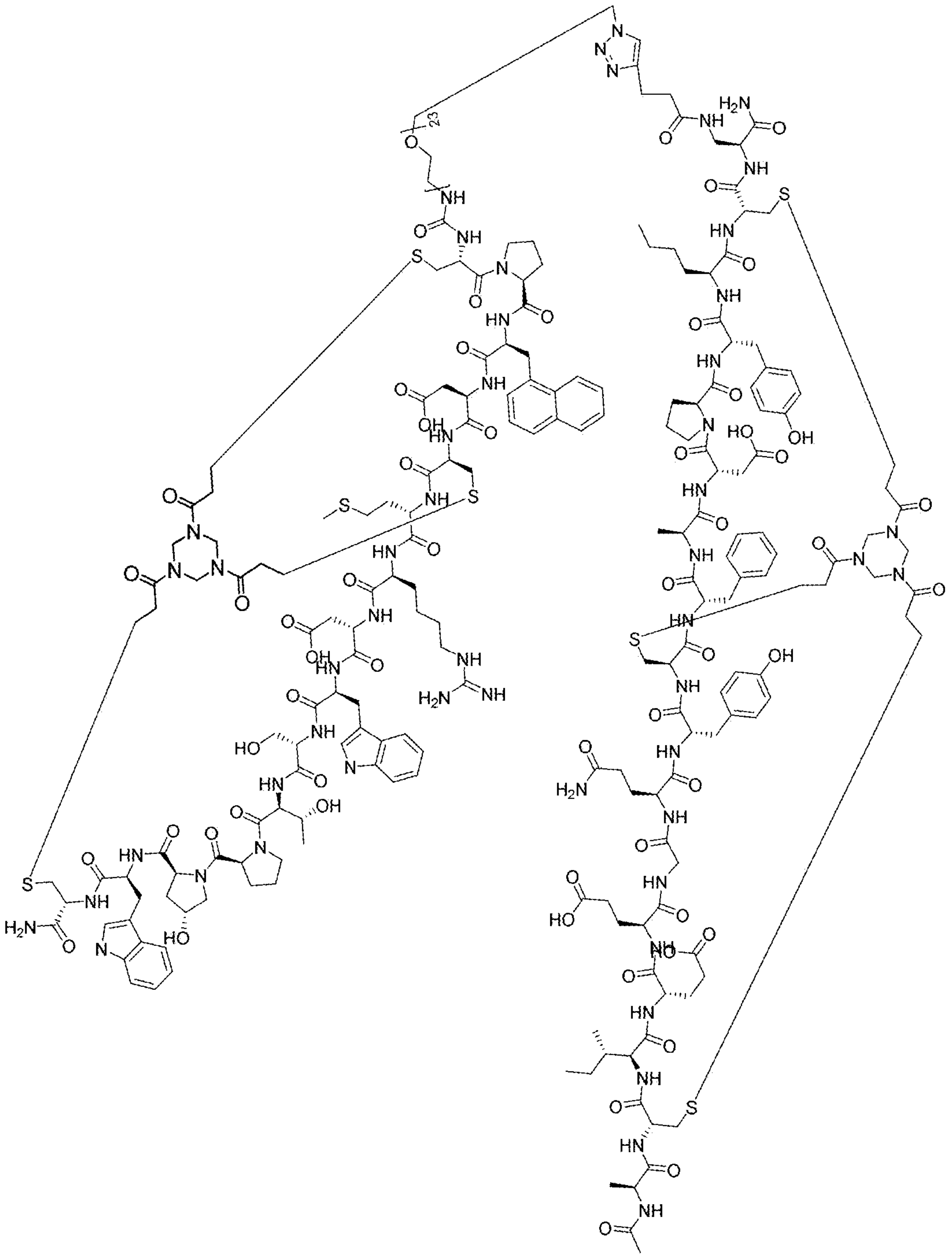
FIG. 33: Formula of BCY9400.
Figure 34:
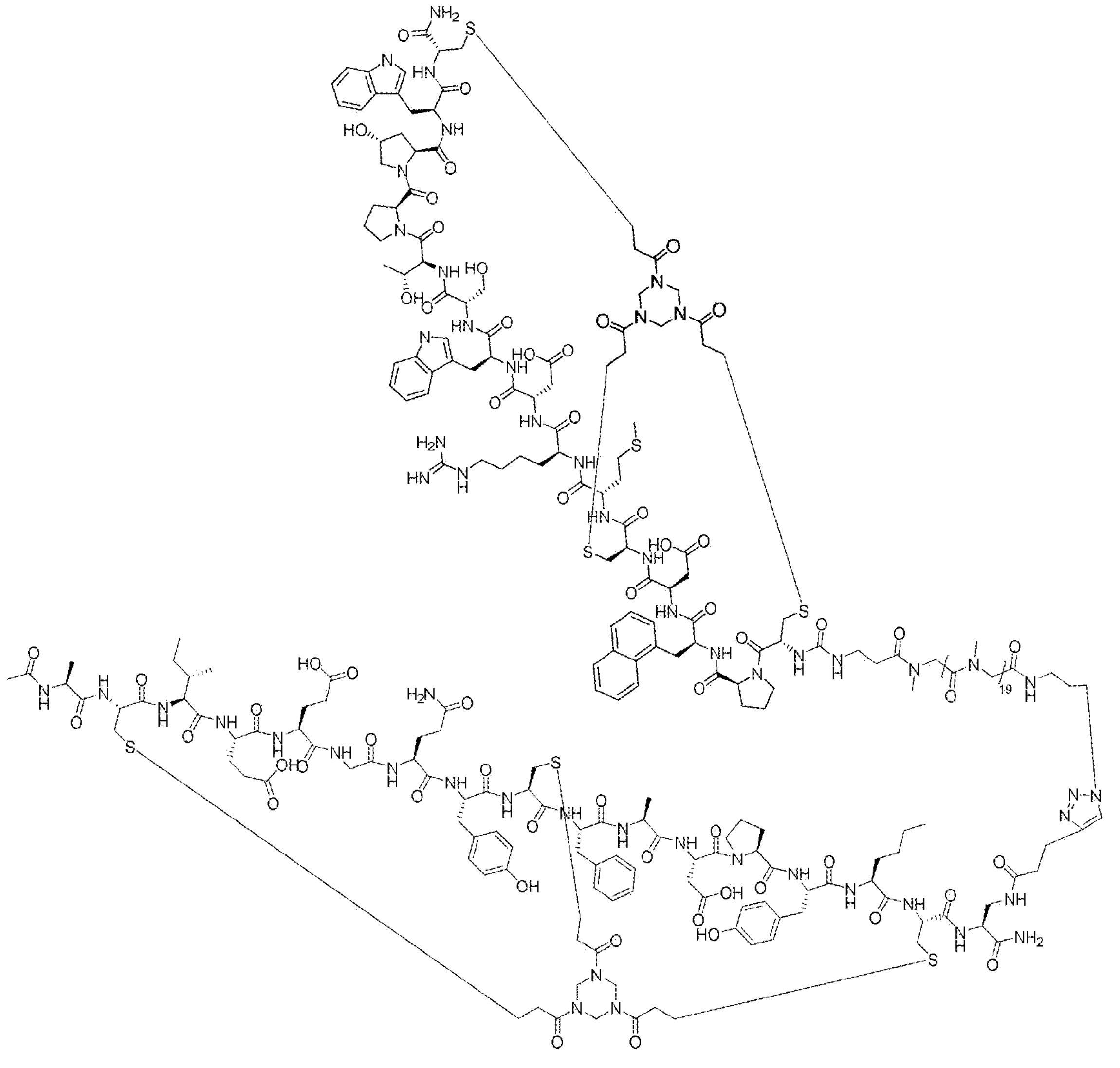
FIG. 34: Formula of BCY9401.
Figure 35:
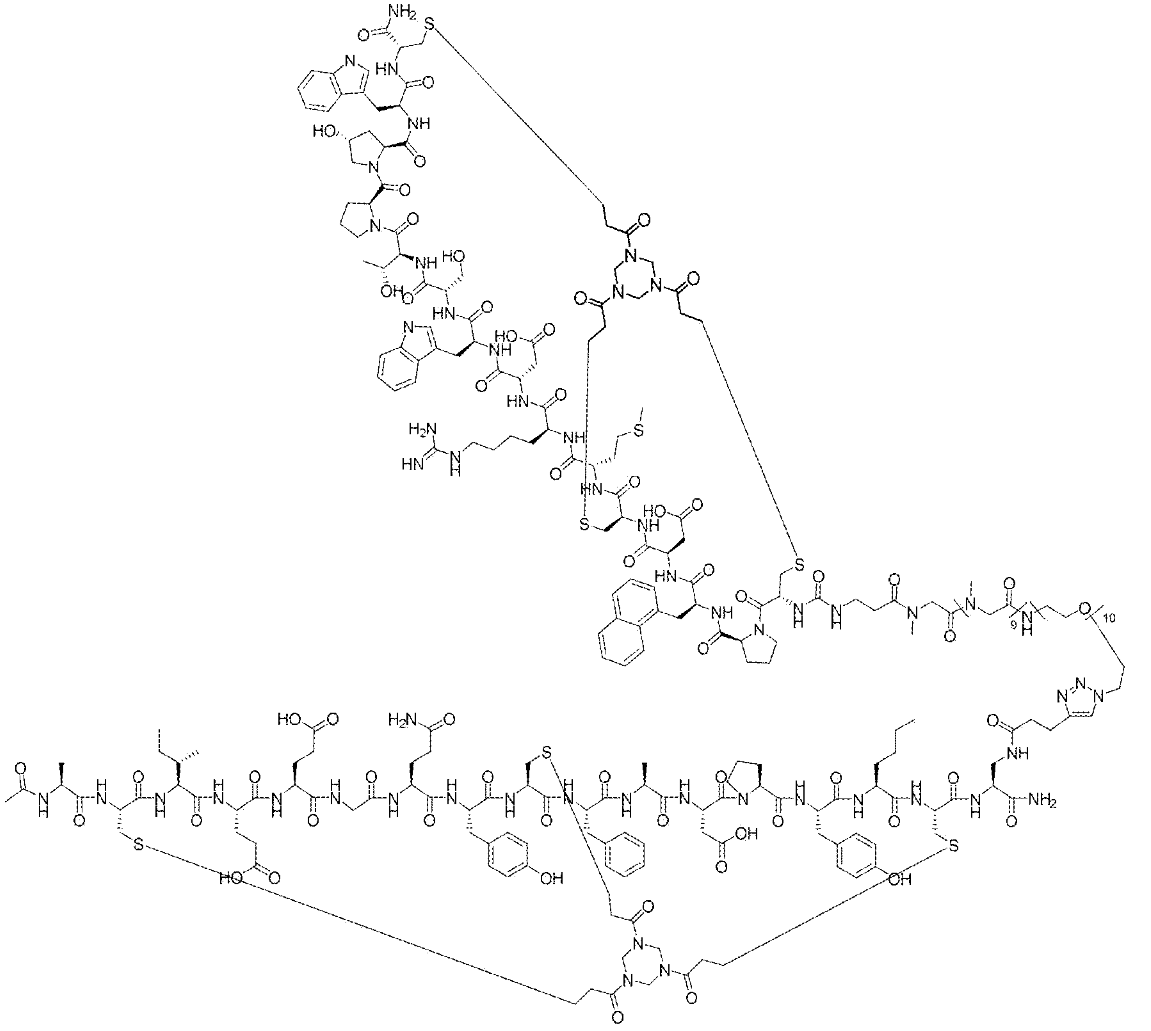
FIG. 35: Formula of BCY9403.
Figure 36:
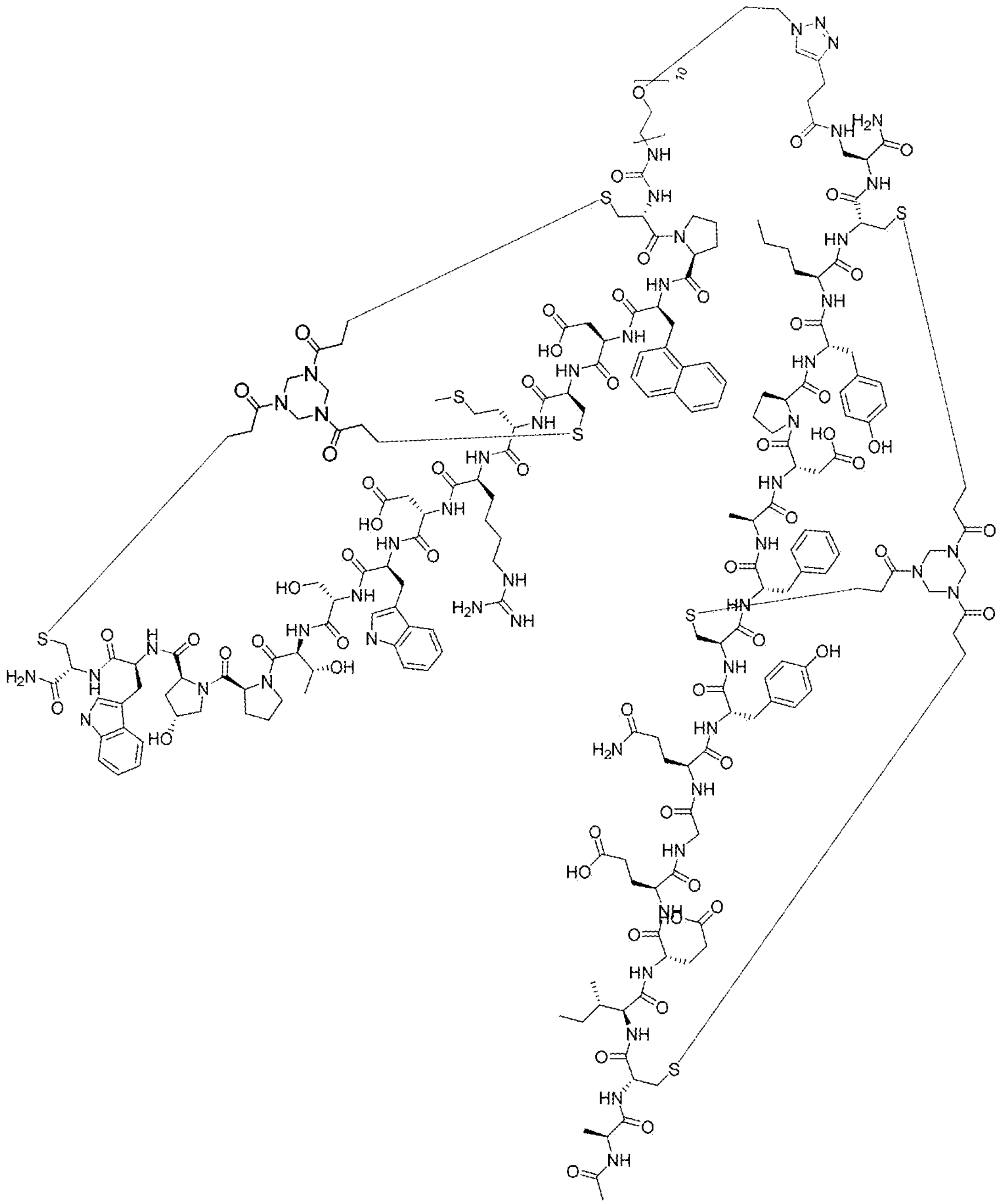
FIG. 36: Formula of BCY9405.
Figure 37:
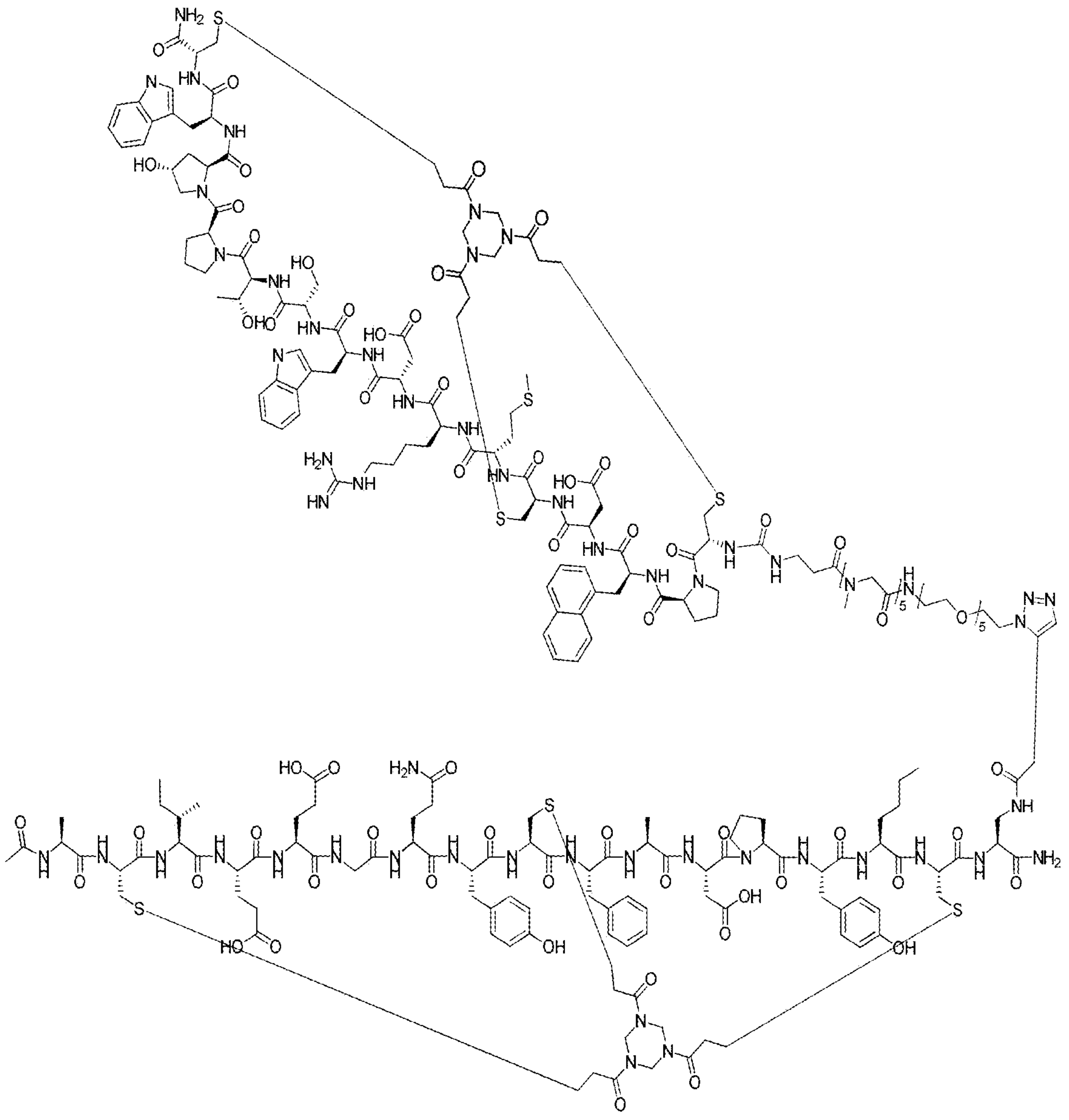
FIG. 37: Formula of BCY9406.
Figure 38:
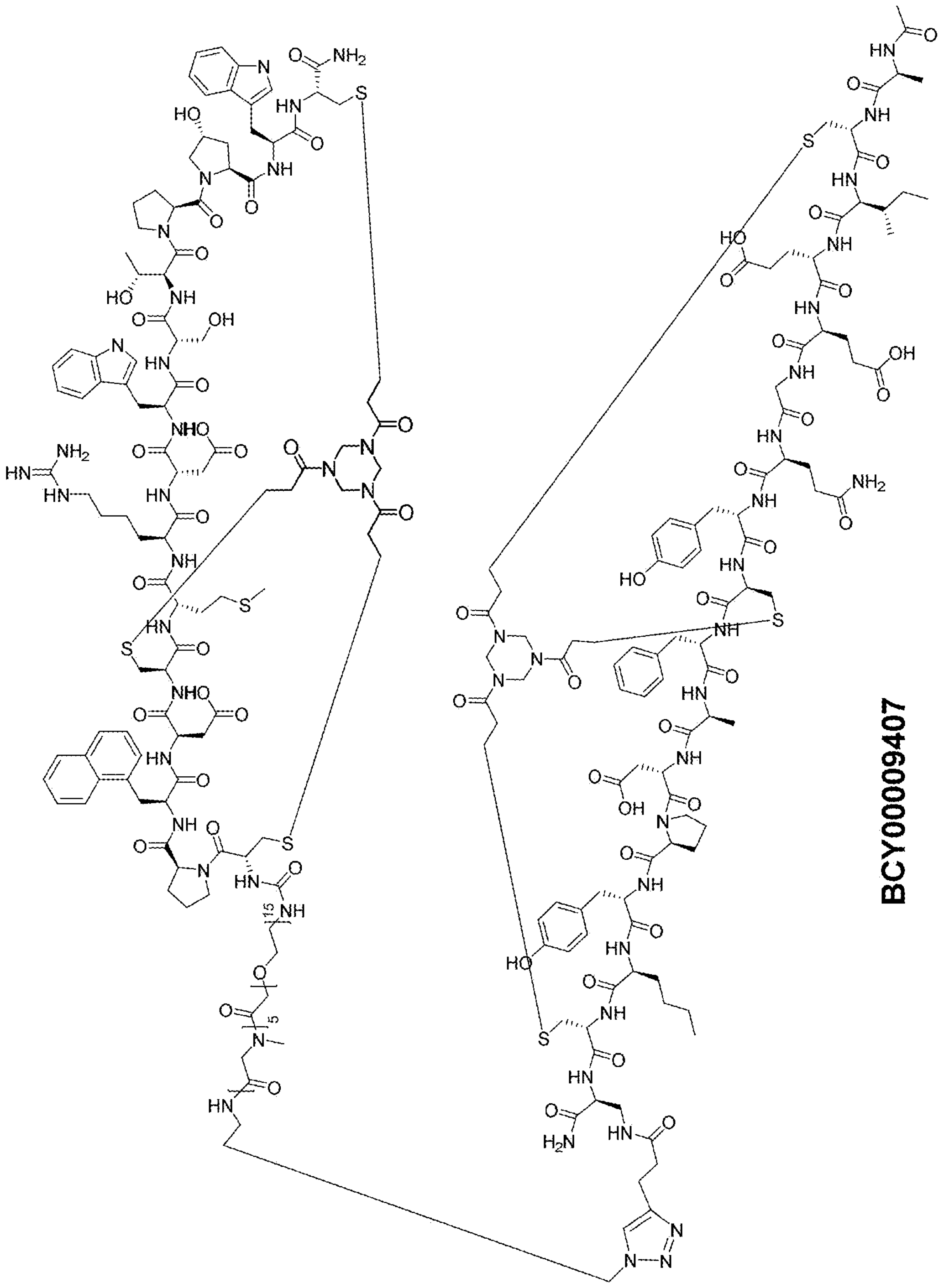
FIG. 38: Formula of BCY9407.
Figure 39:
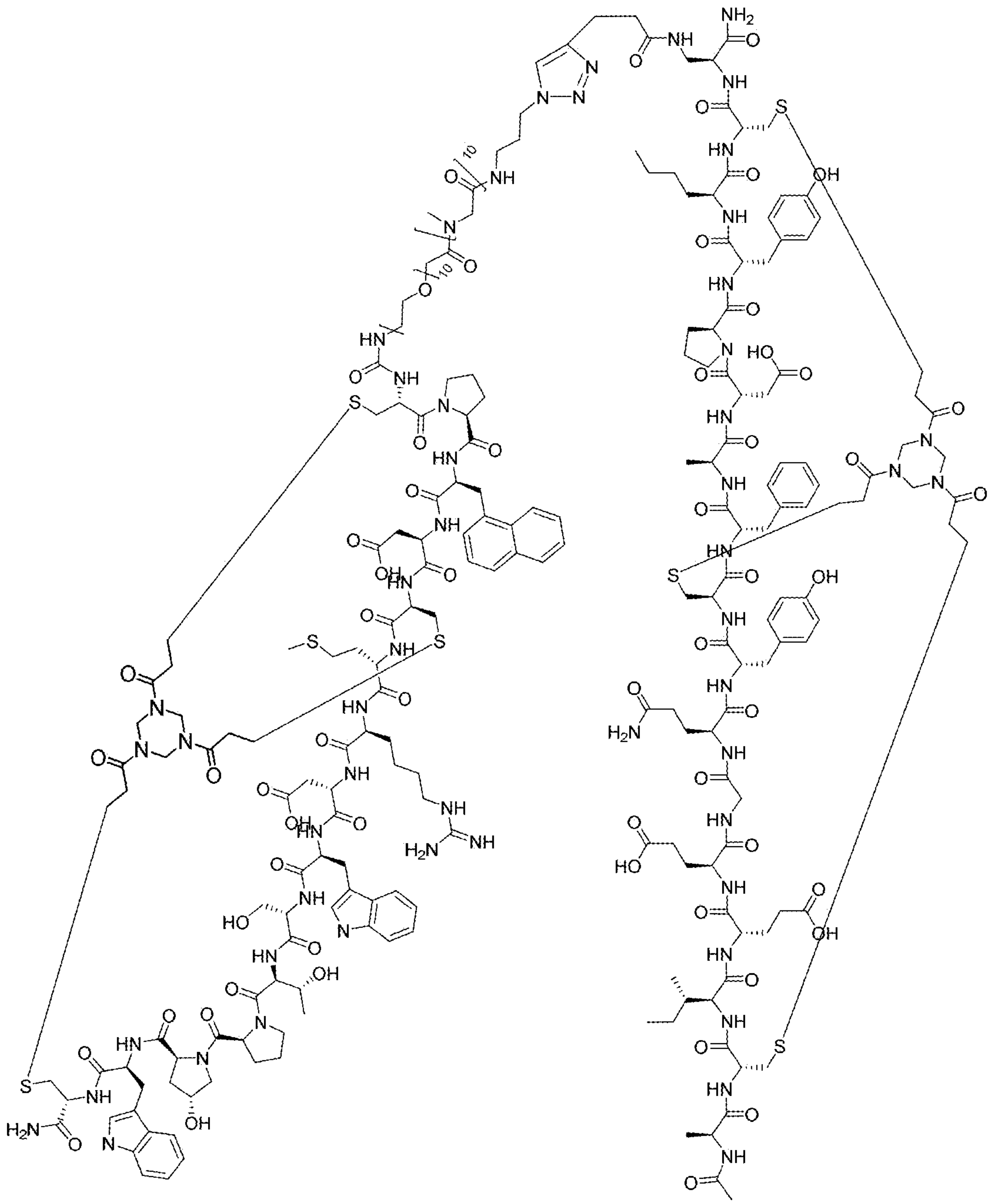
FIG. 39: Formula of BCY9408.
Figure 40:
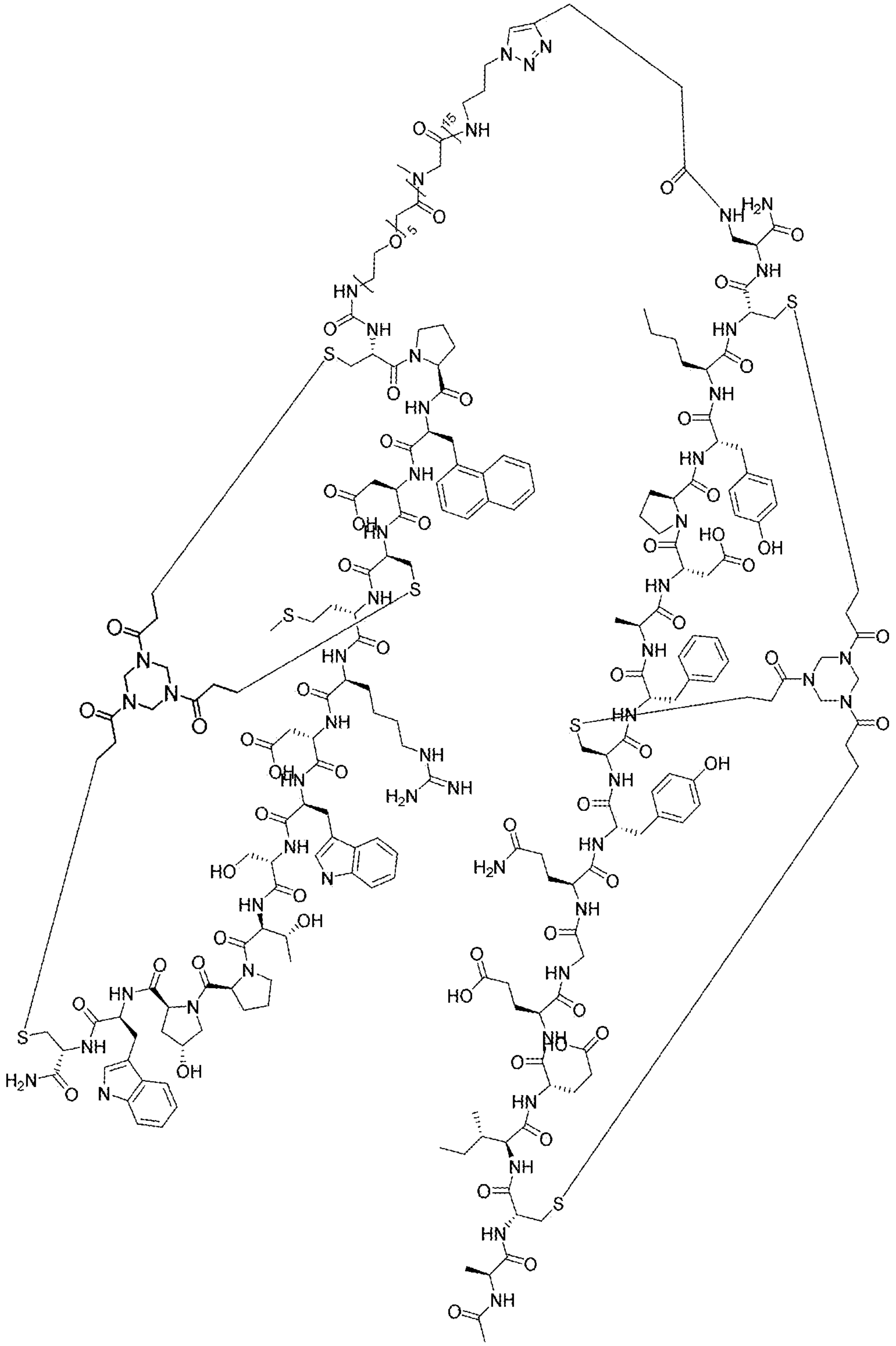
FIG. 40: Formula of BCY9409.
Figure 41:
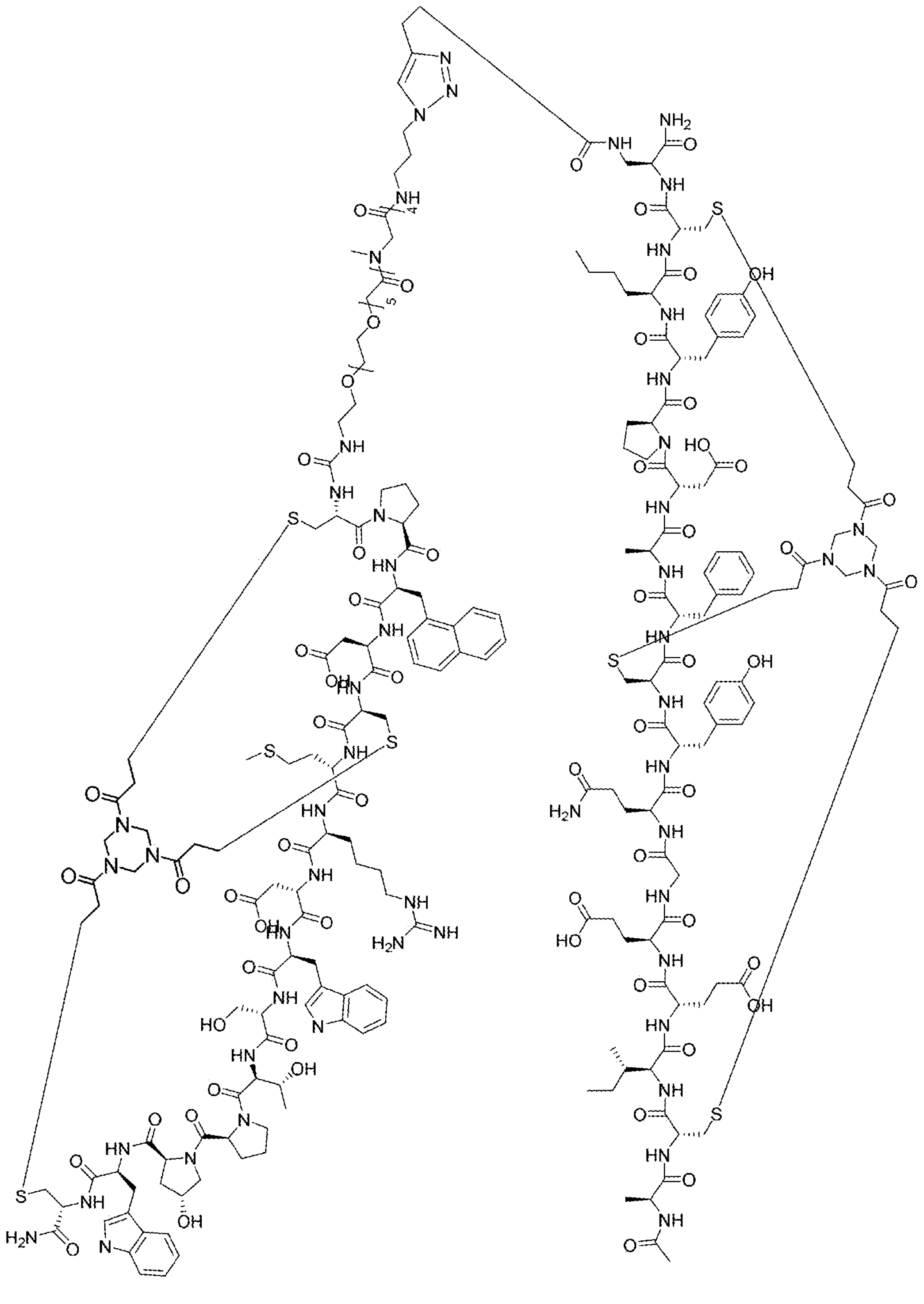
FIG. 41: Formula of BCY9410.
Figure 42:
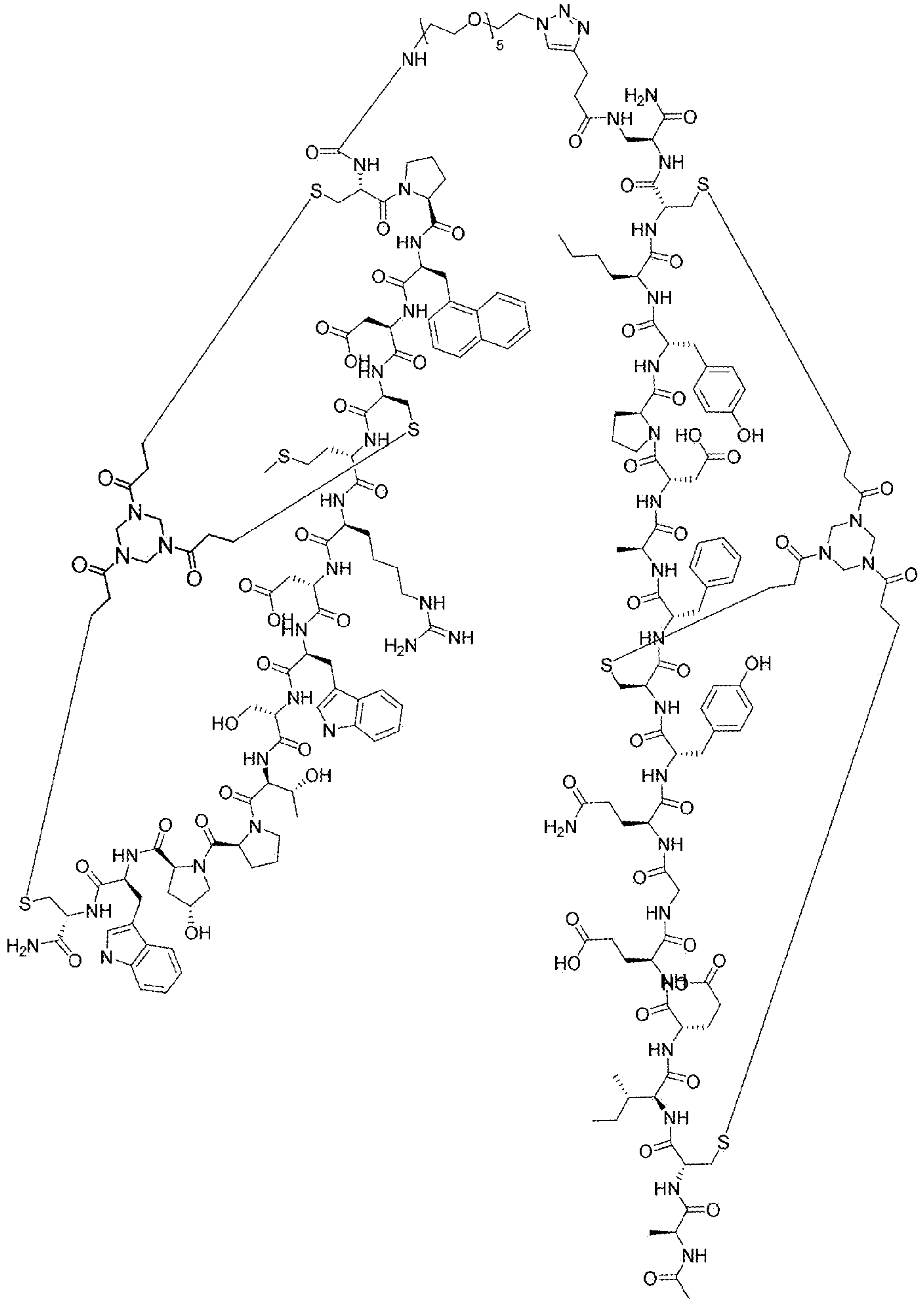
FIG. 42: Formula of BCY9411.
Figure 43:
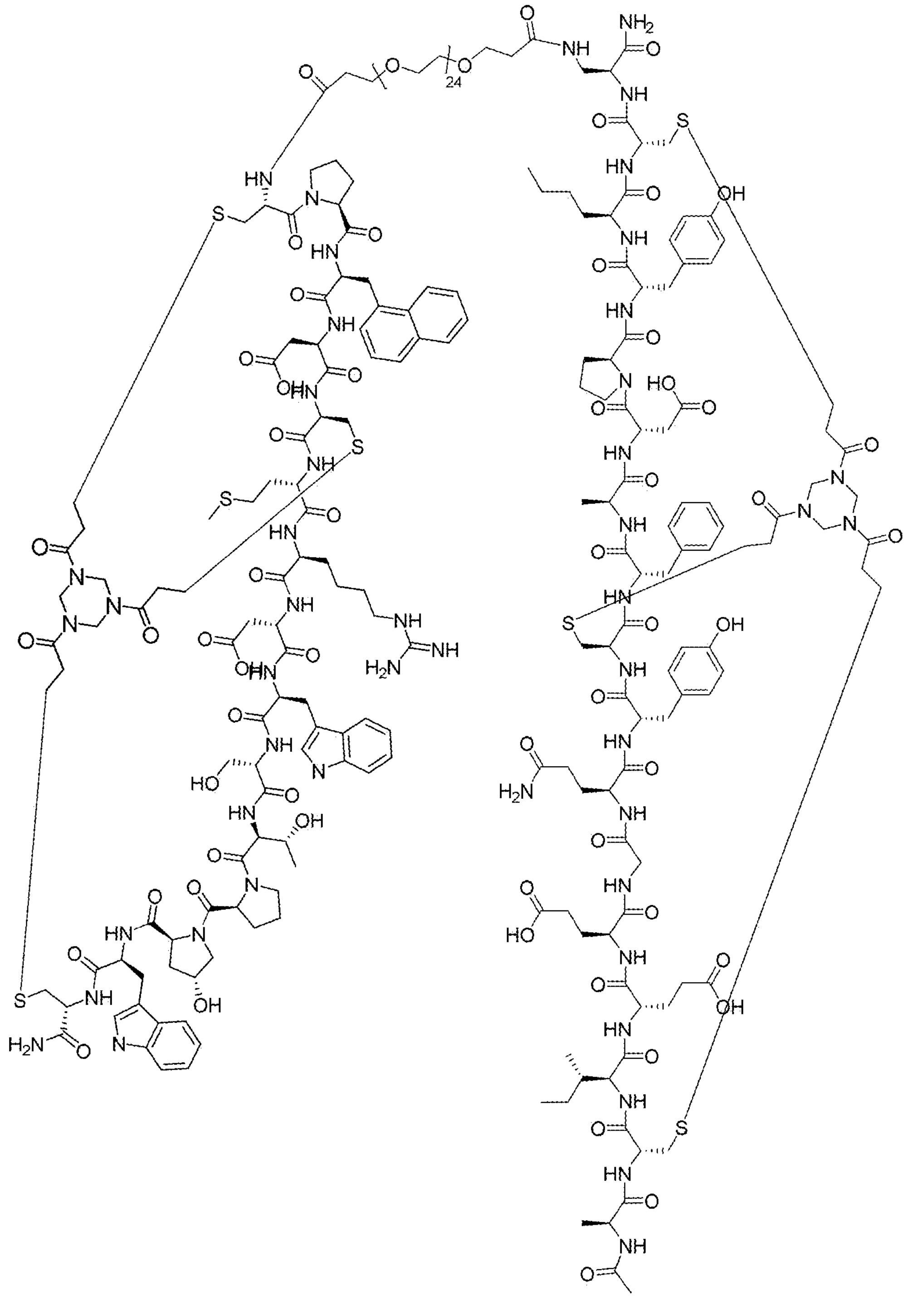
FIG. 43: Formula of BCY9759.
Figure 44:
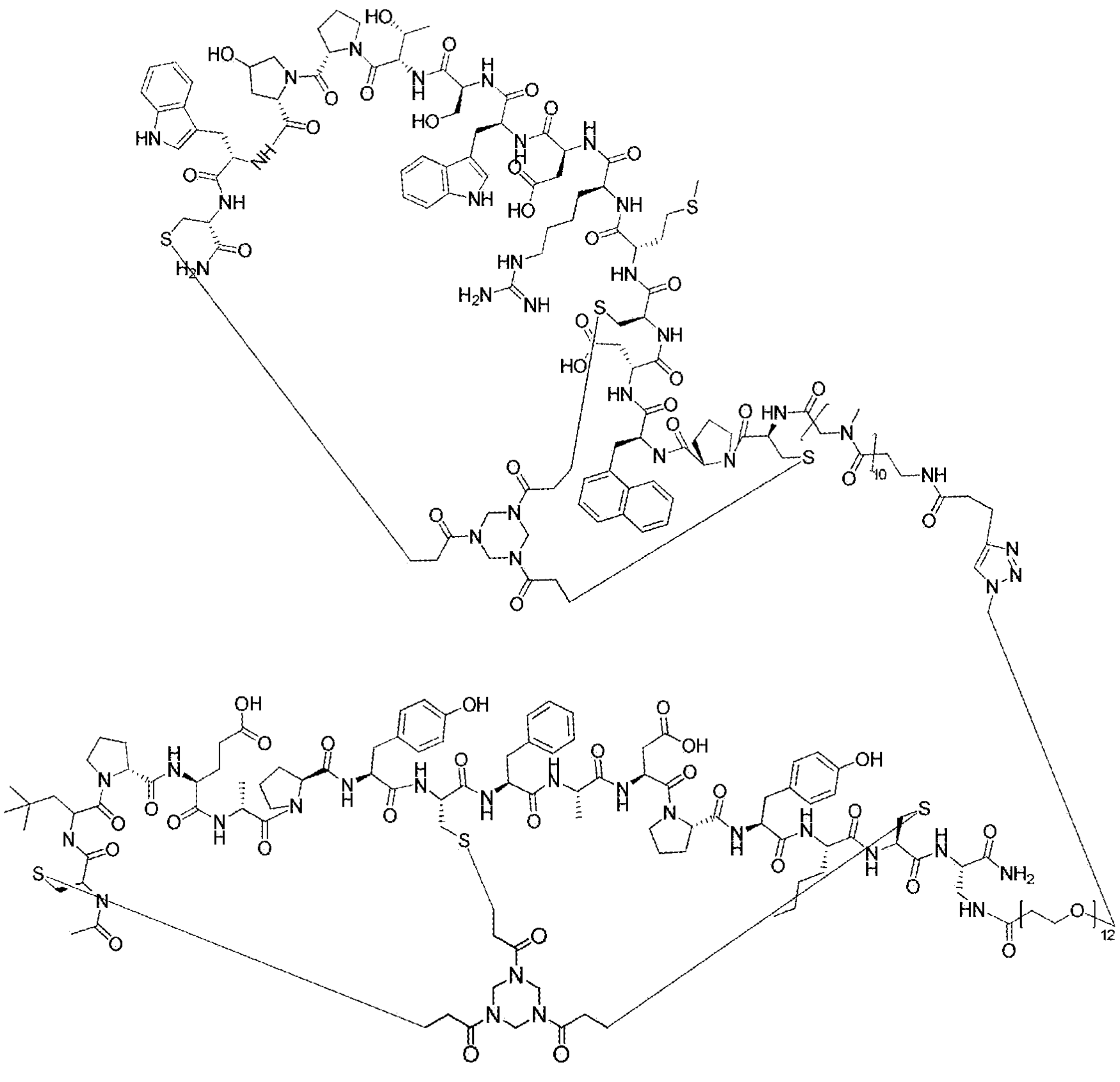
FIG. 44: Formula of BCY10000.
Figure 45:
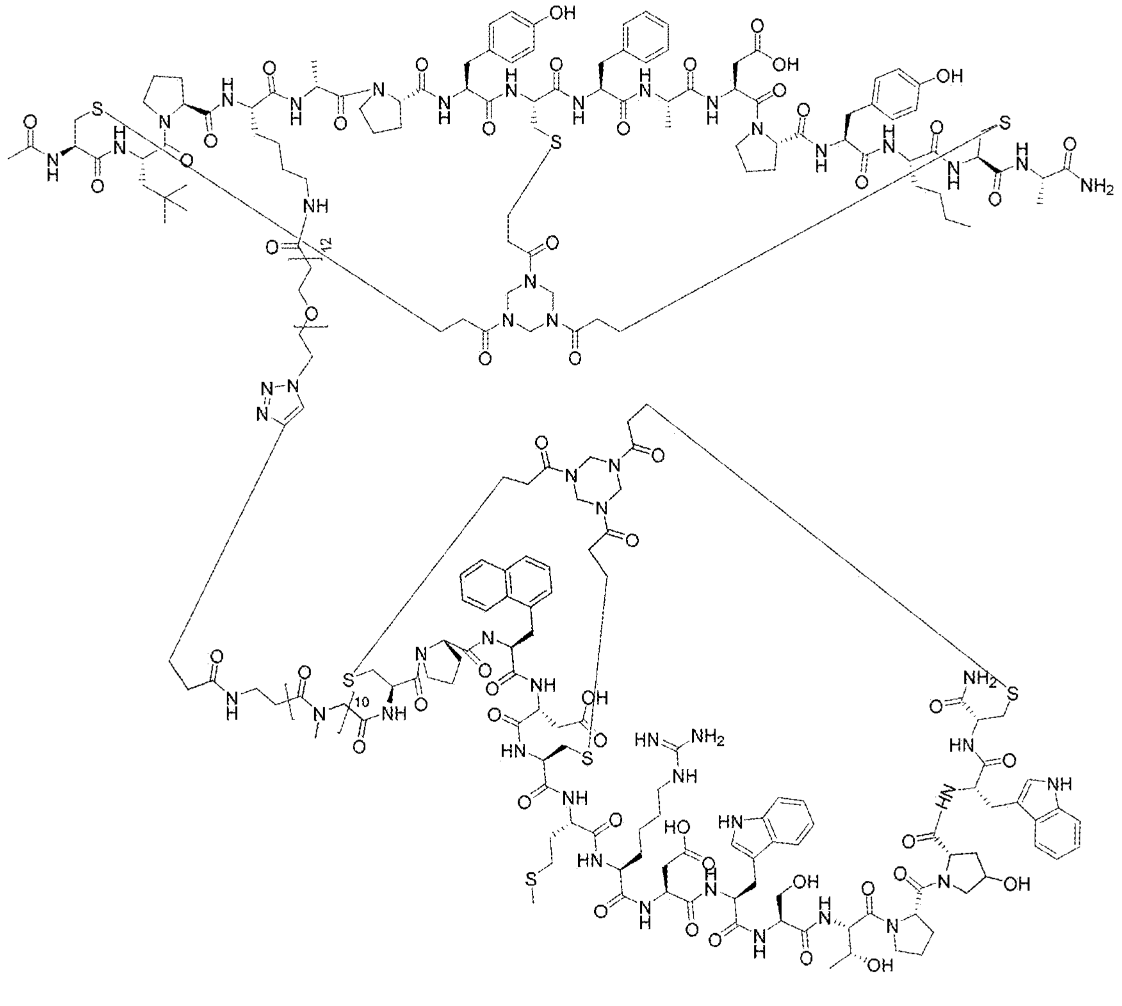
FIG. 45: Formula of BCY10567.
Figure 46:
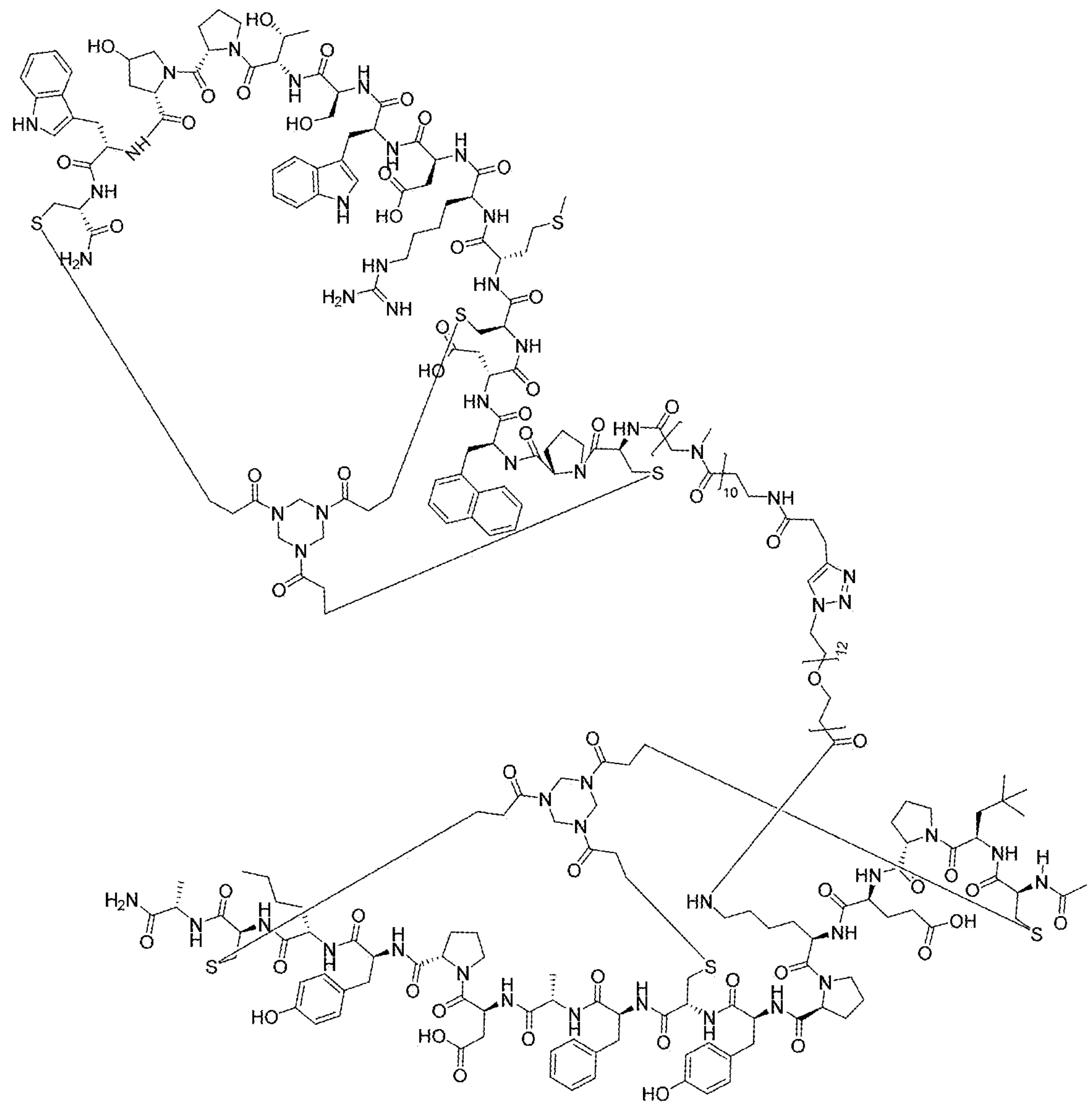
FIG. 46: Formula of BCY10569.
Figure 47:
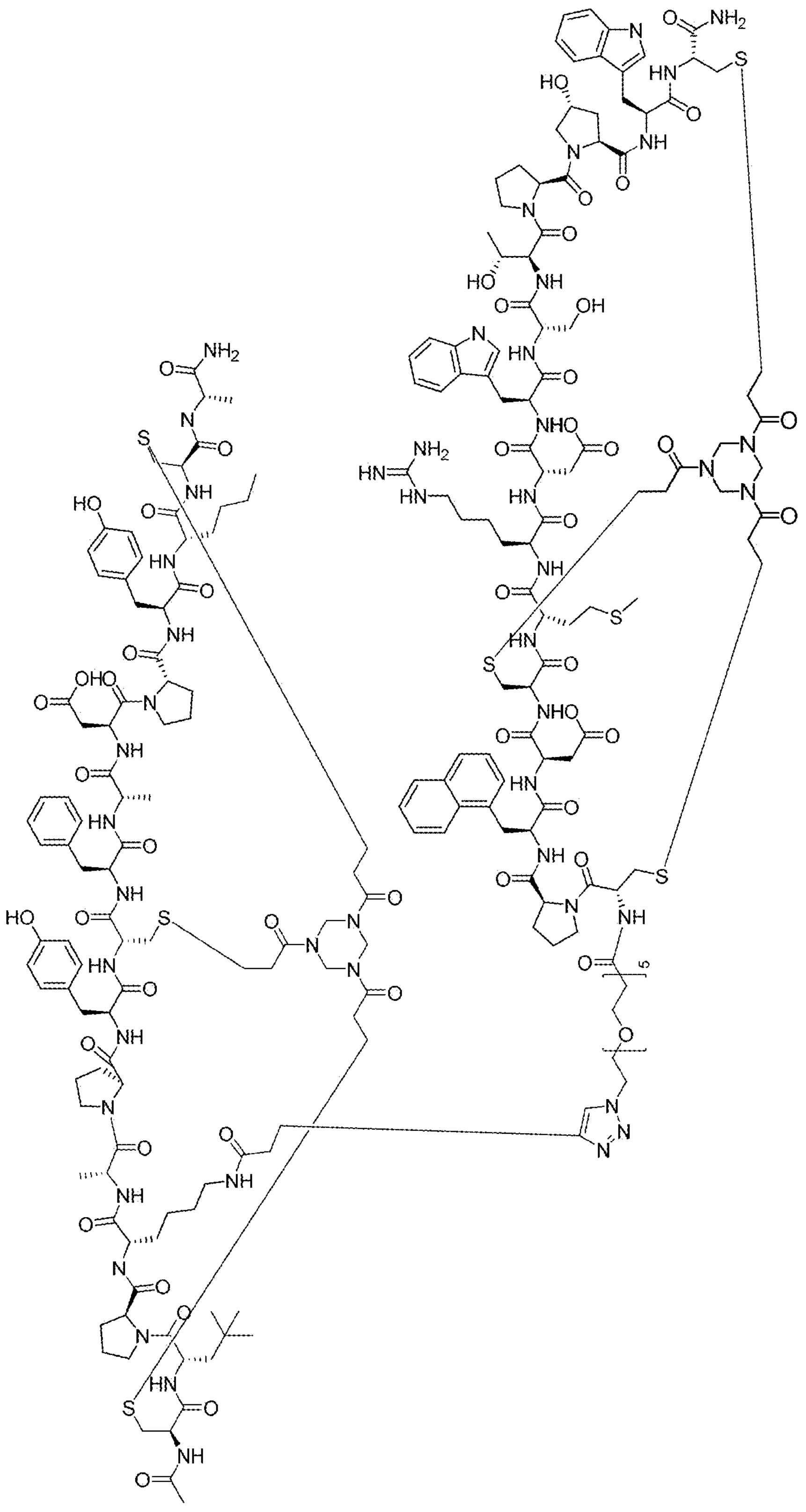
FIG. 47: Formula of BCY10571.
Figure 48:
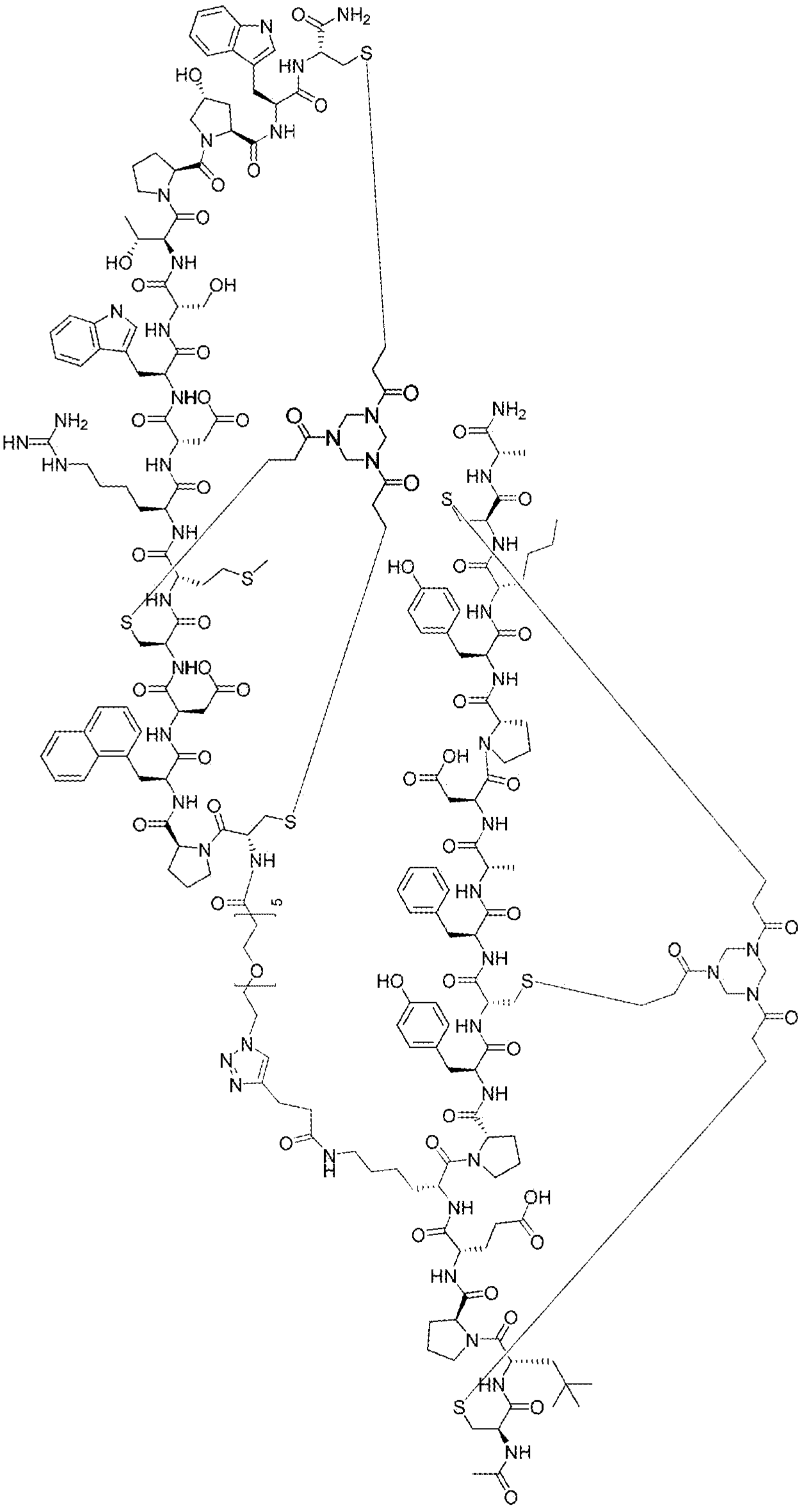
FIG. 48: Formula of BCY10572.
Figure 49:
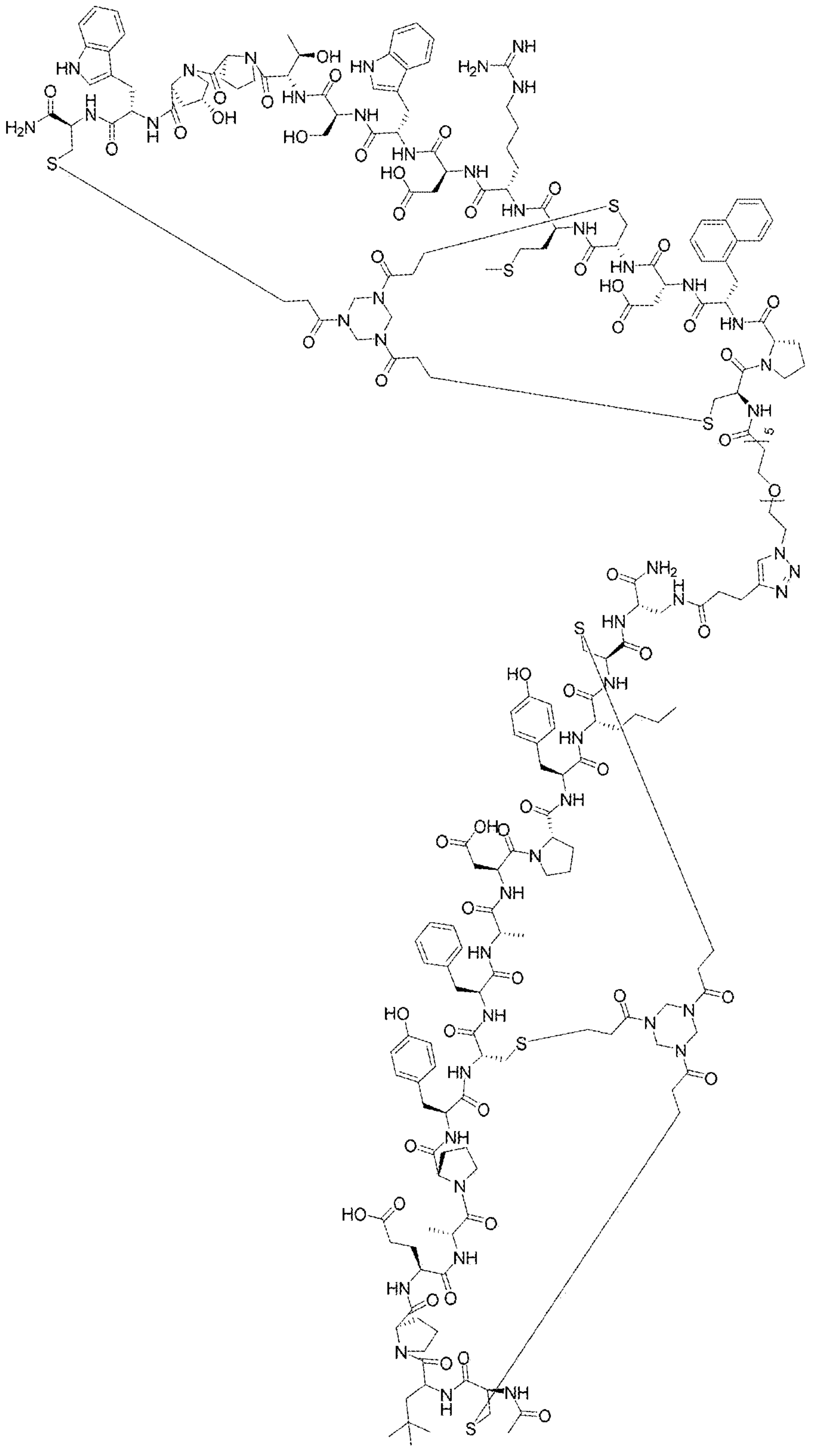
FIG. 49: Formula of BCY10573.
Figure 50:
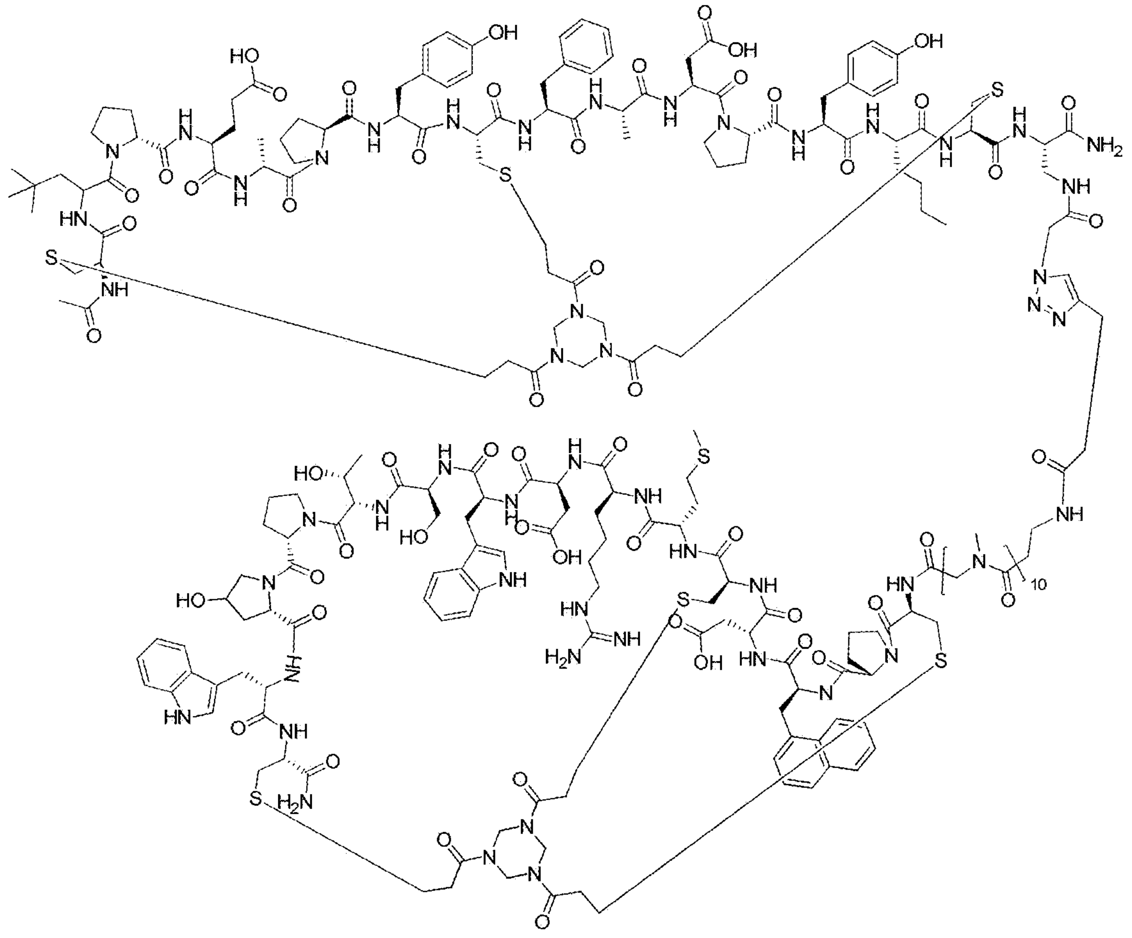
FIG. 50: Formula of BCY10578.
Figure 51:
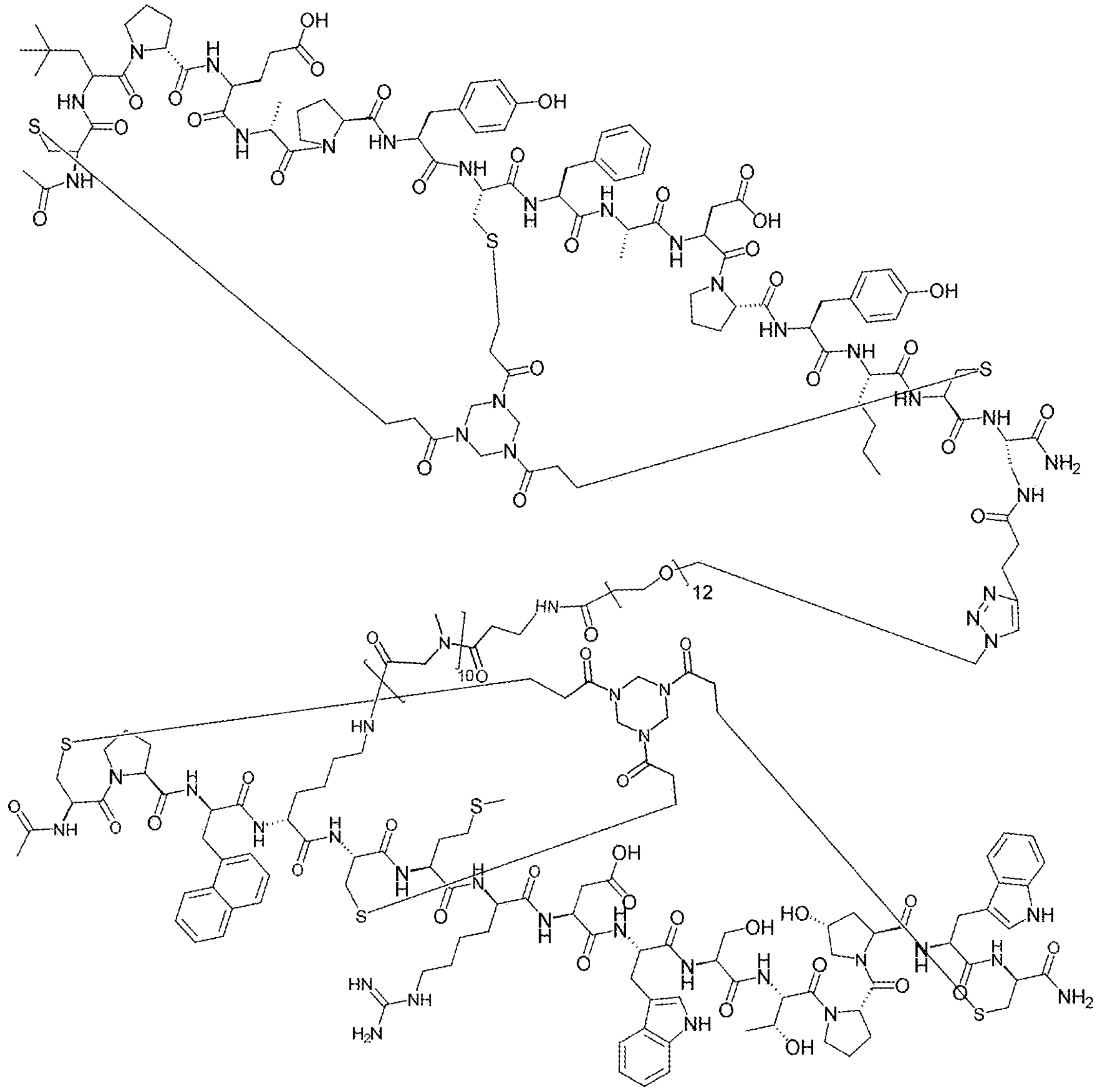
FIG. 51: Formula of BCY10917.
Figure 52:
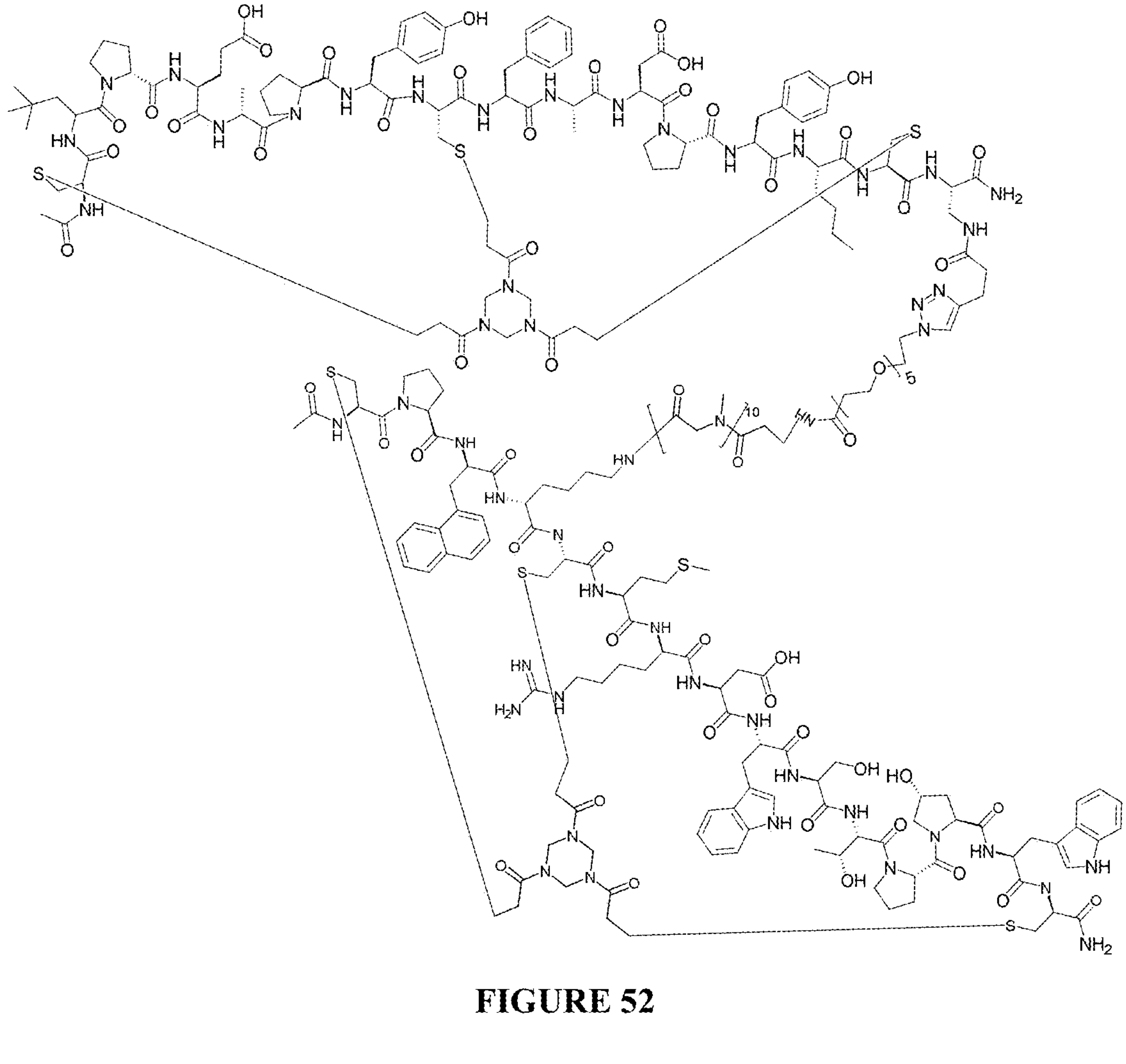
FIG. 52: Formula of BCY11020.
Figure 53:
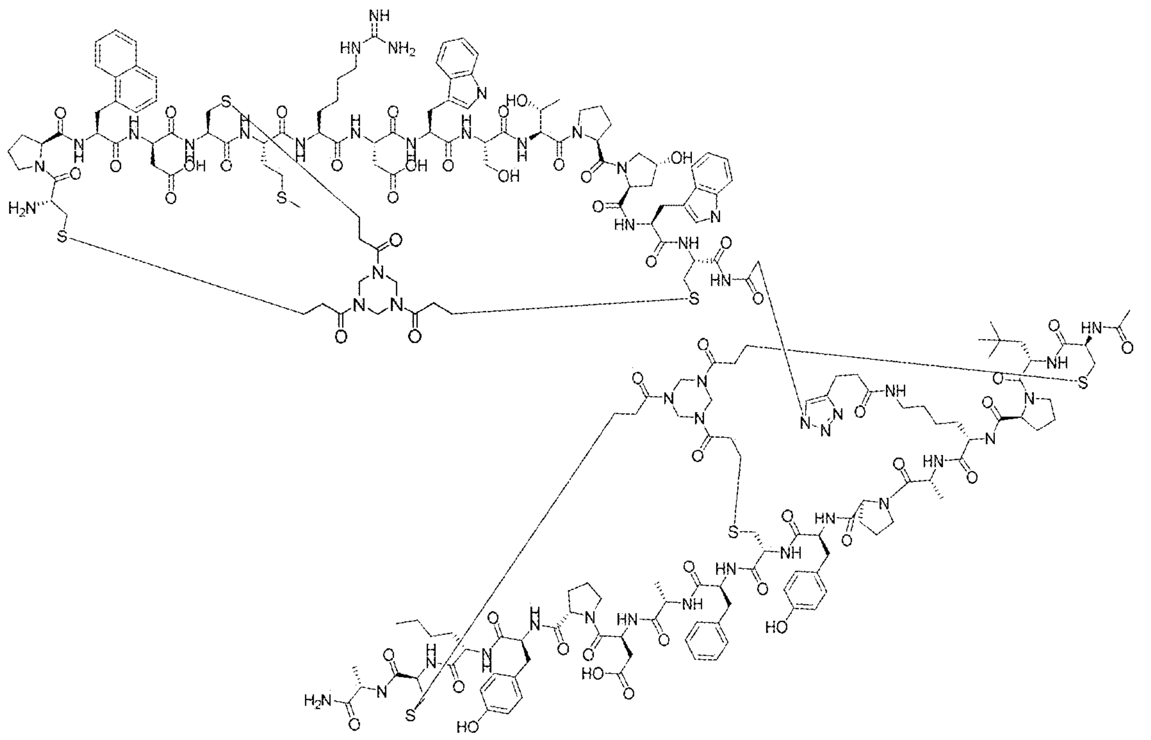
FIG. 53: Formula of BCY11373.
Figure 54:
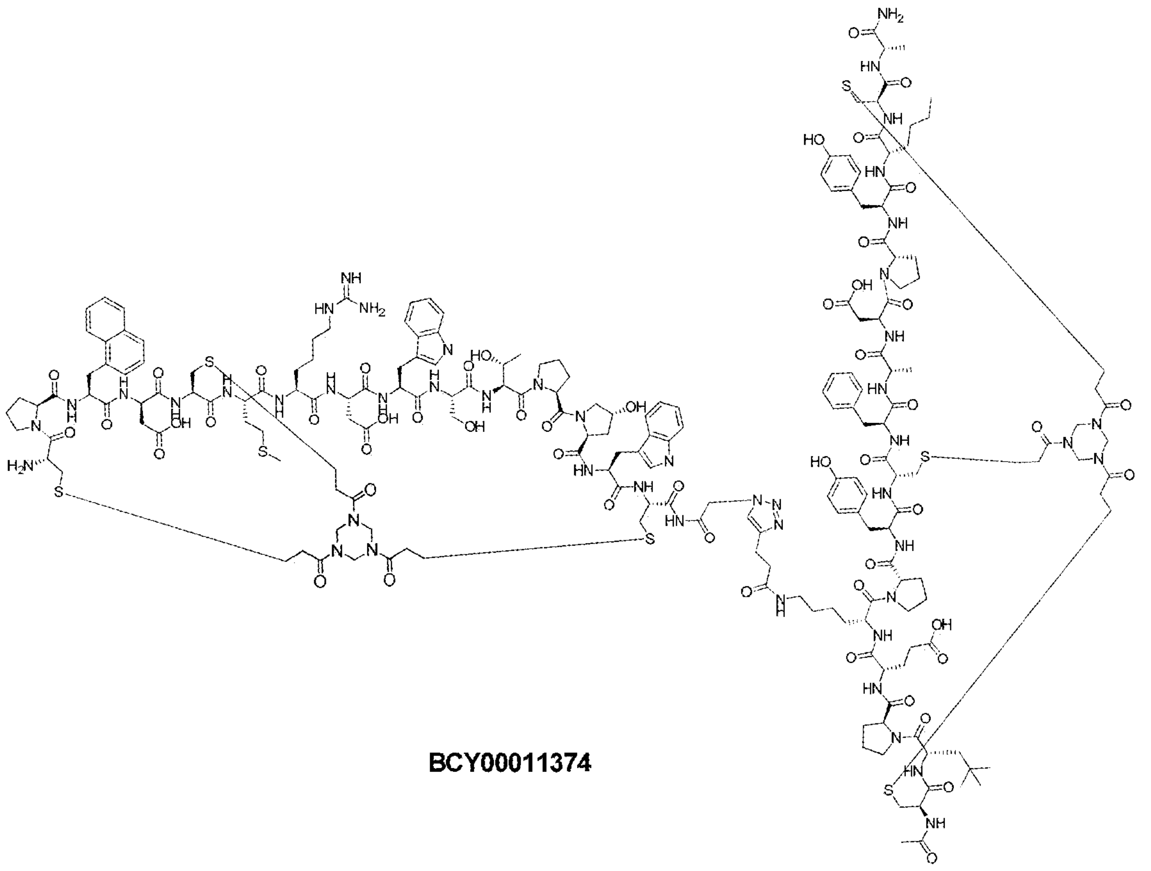
FIG. 54: Formula of BCY11374.
Figure 55:
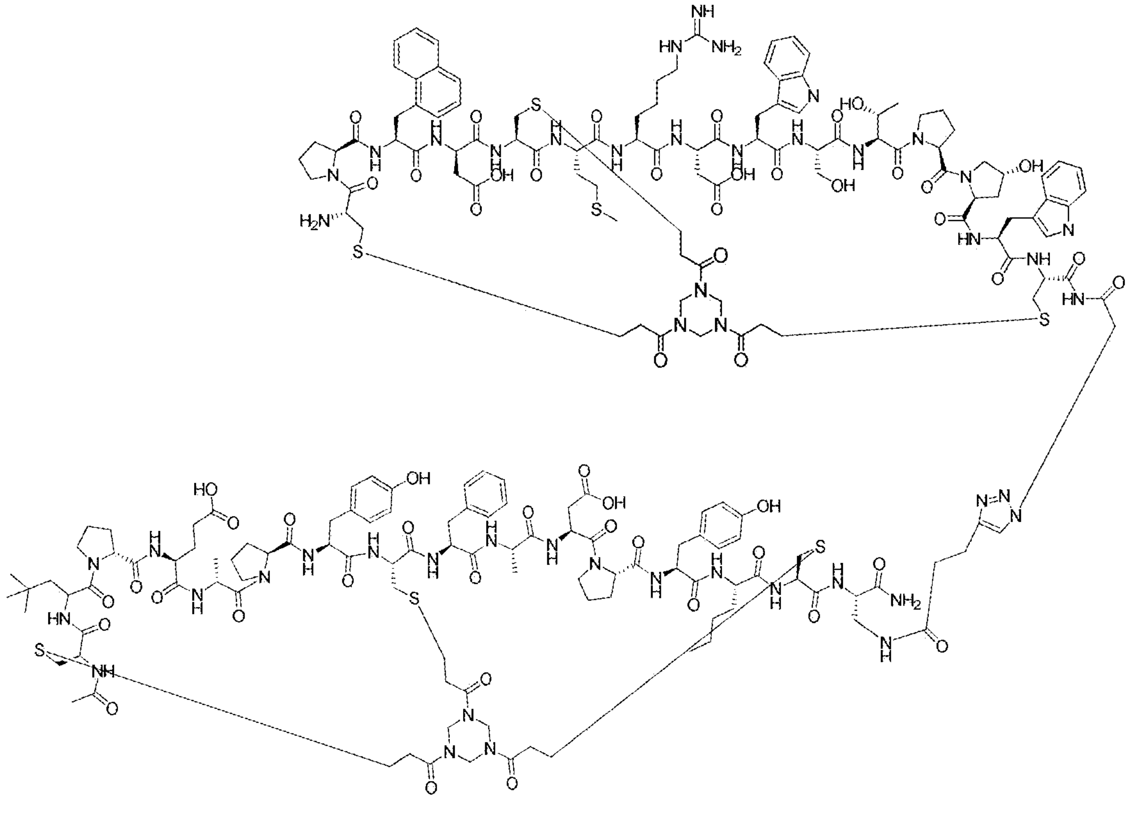
FIG. 55: Formula of BCY11375.
Figure 56:
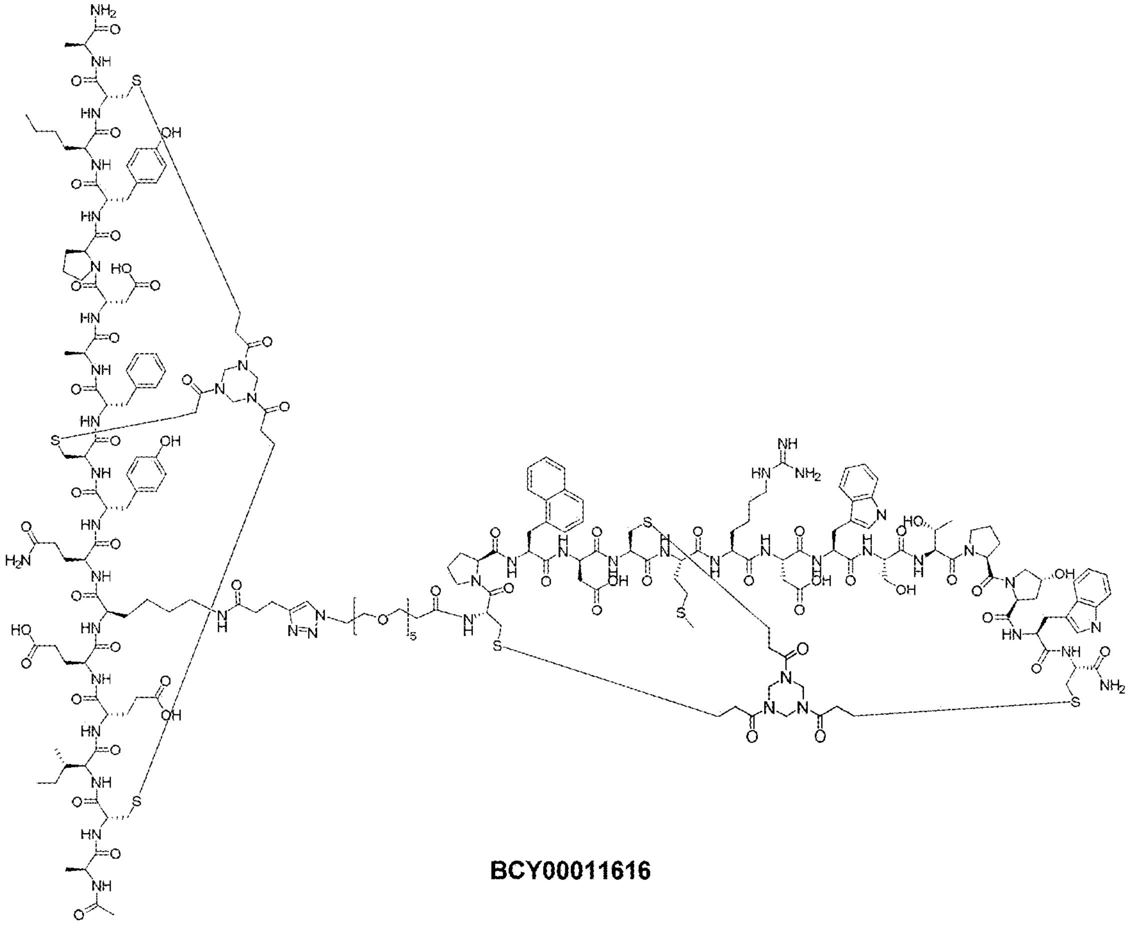
FIG. 56: Formula of BCY11616.
Figure 57:
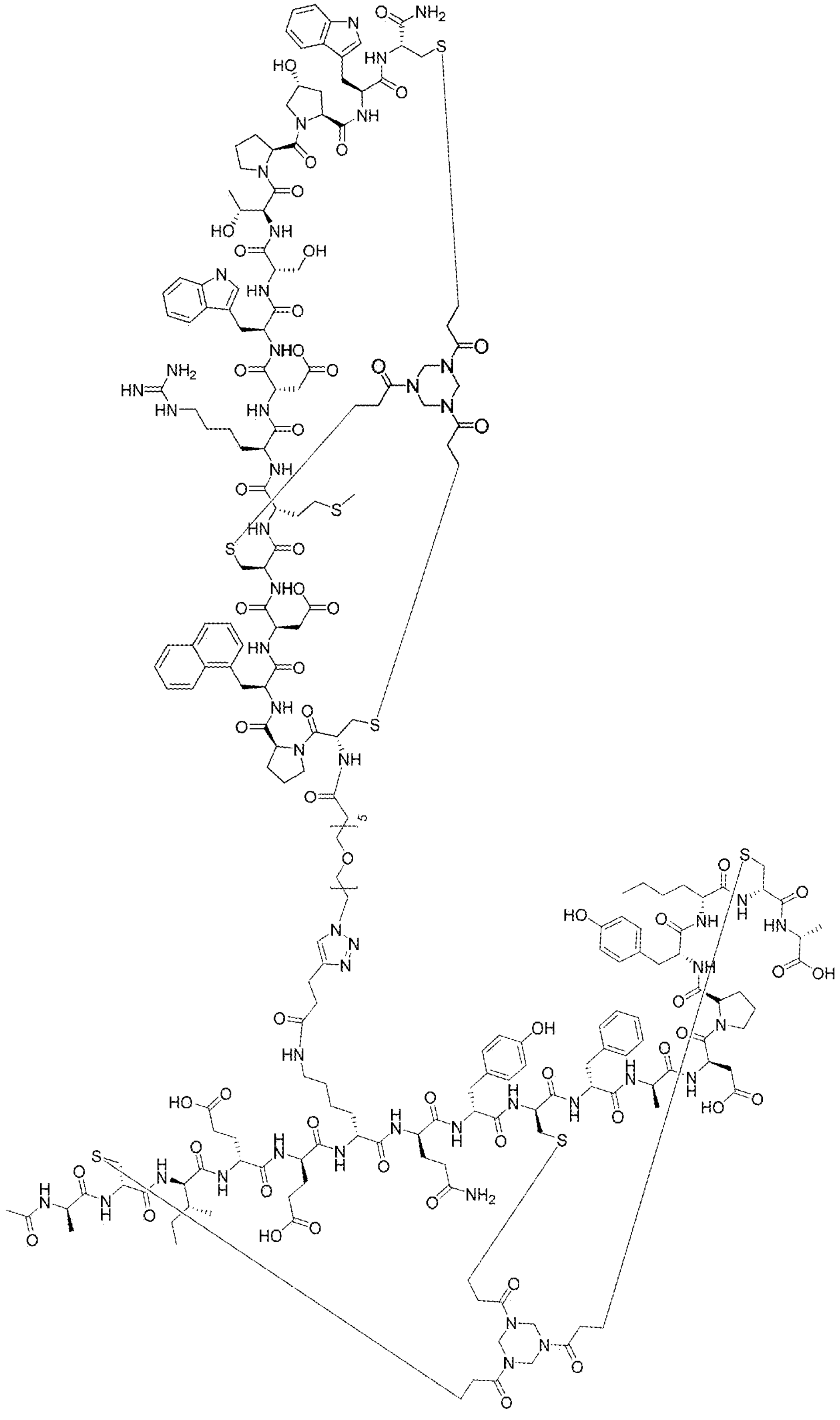
FIG. 57: Formula of BCY11617.
Figure 58:
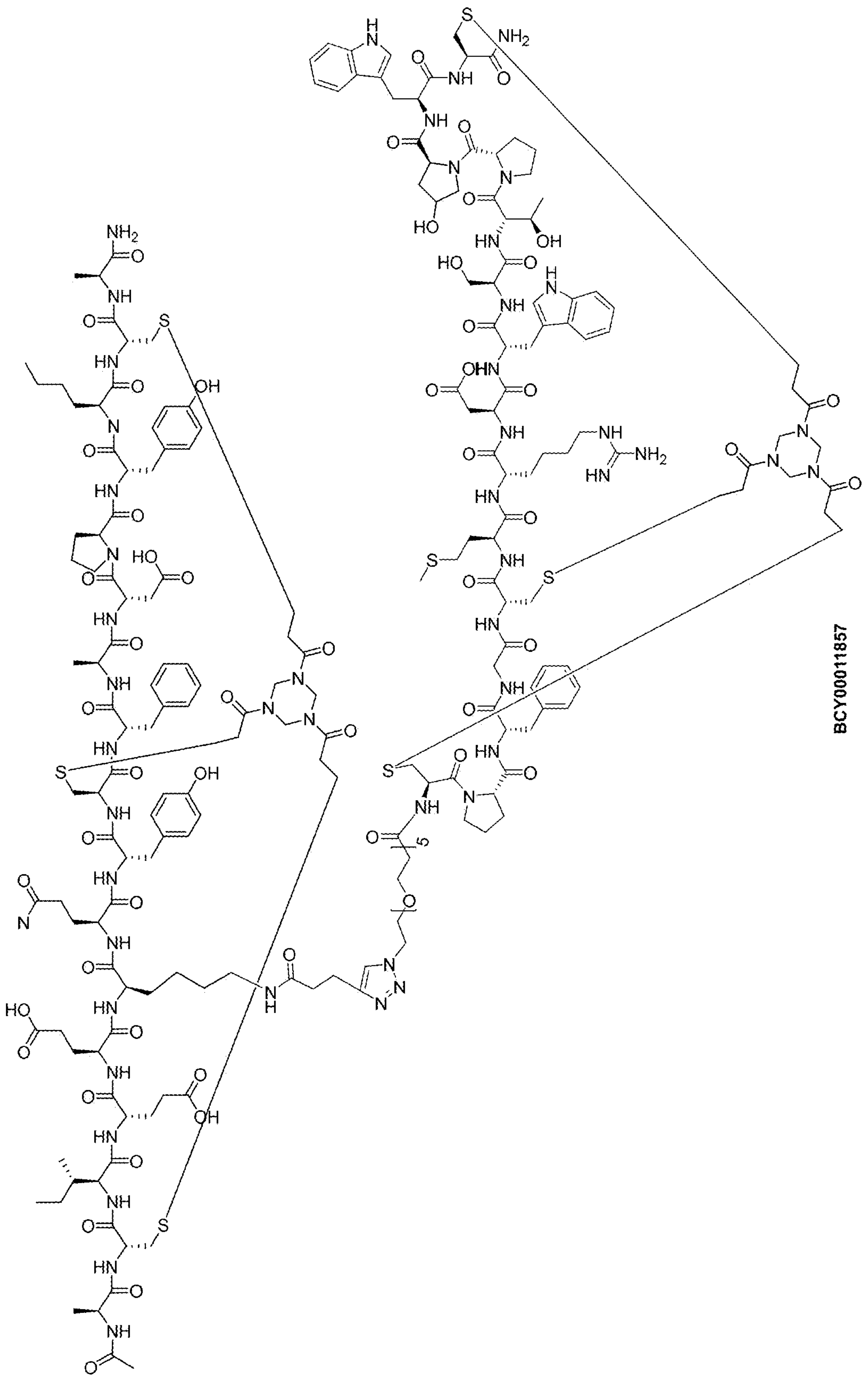
FIG. 58: Formula of BCY11857.
Figure 59:
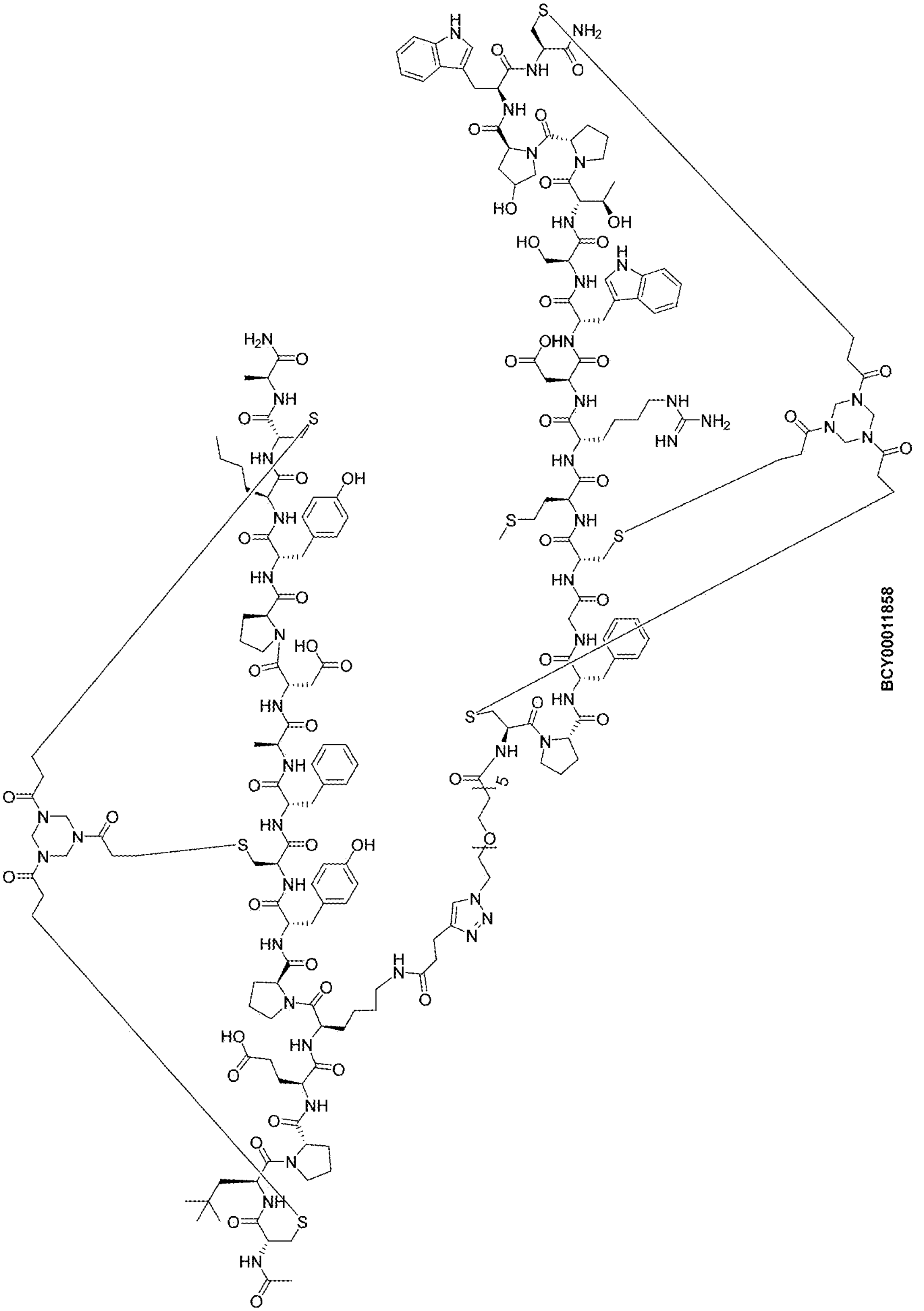
FIG. 59: Formula of BCY11858.
Figure 60:
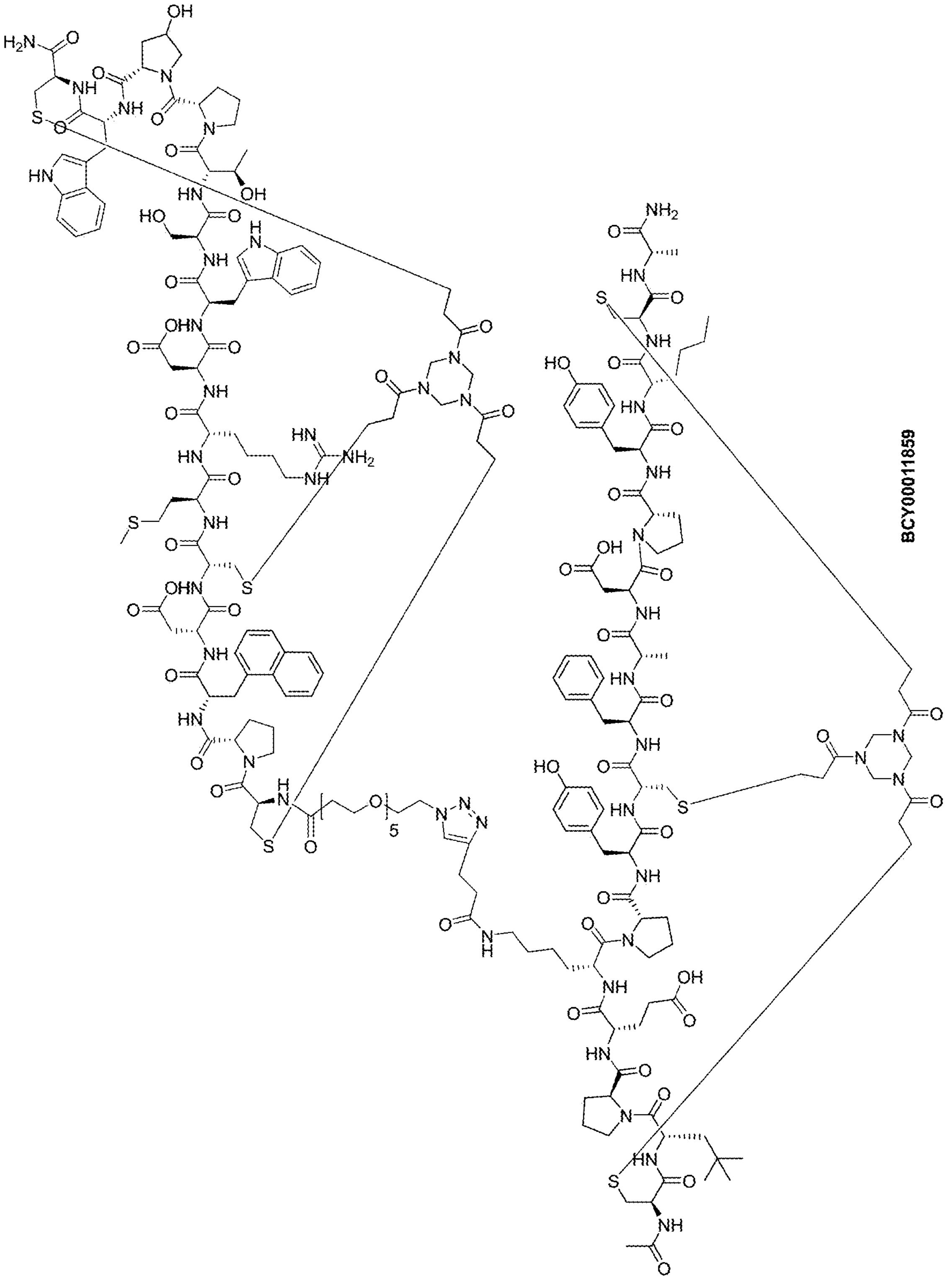
FIG. 60: Formula of BCY11859.
Figure 61:
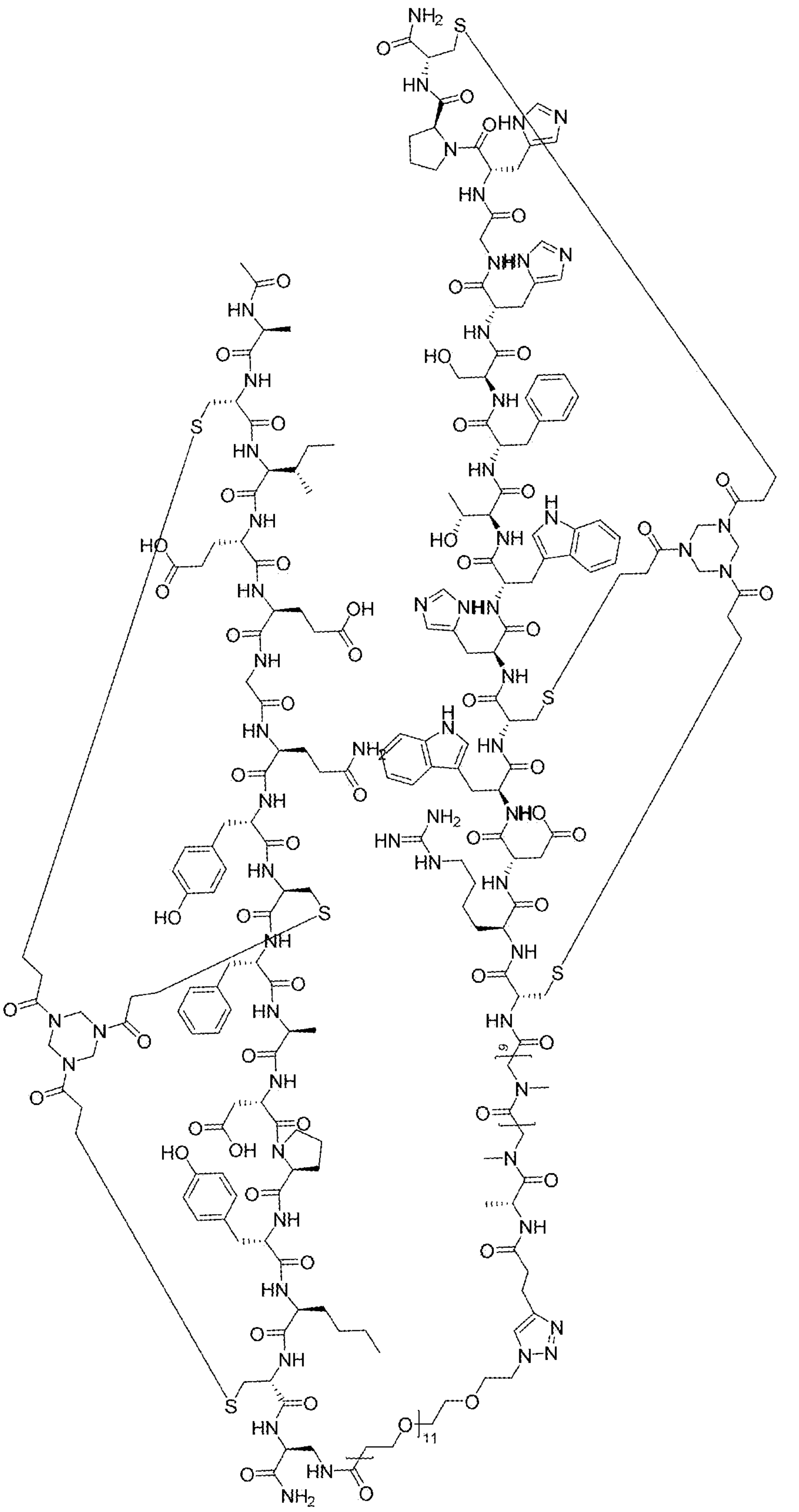
FIG. 61: Formula of BCY8939.
Figure 62:
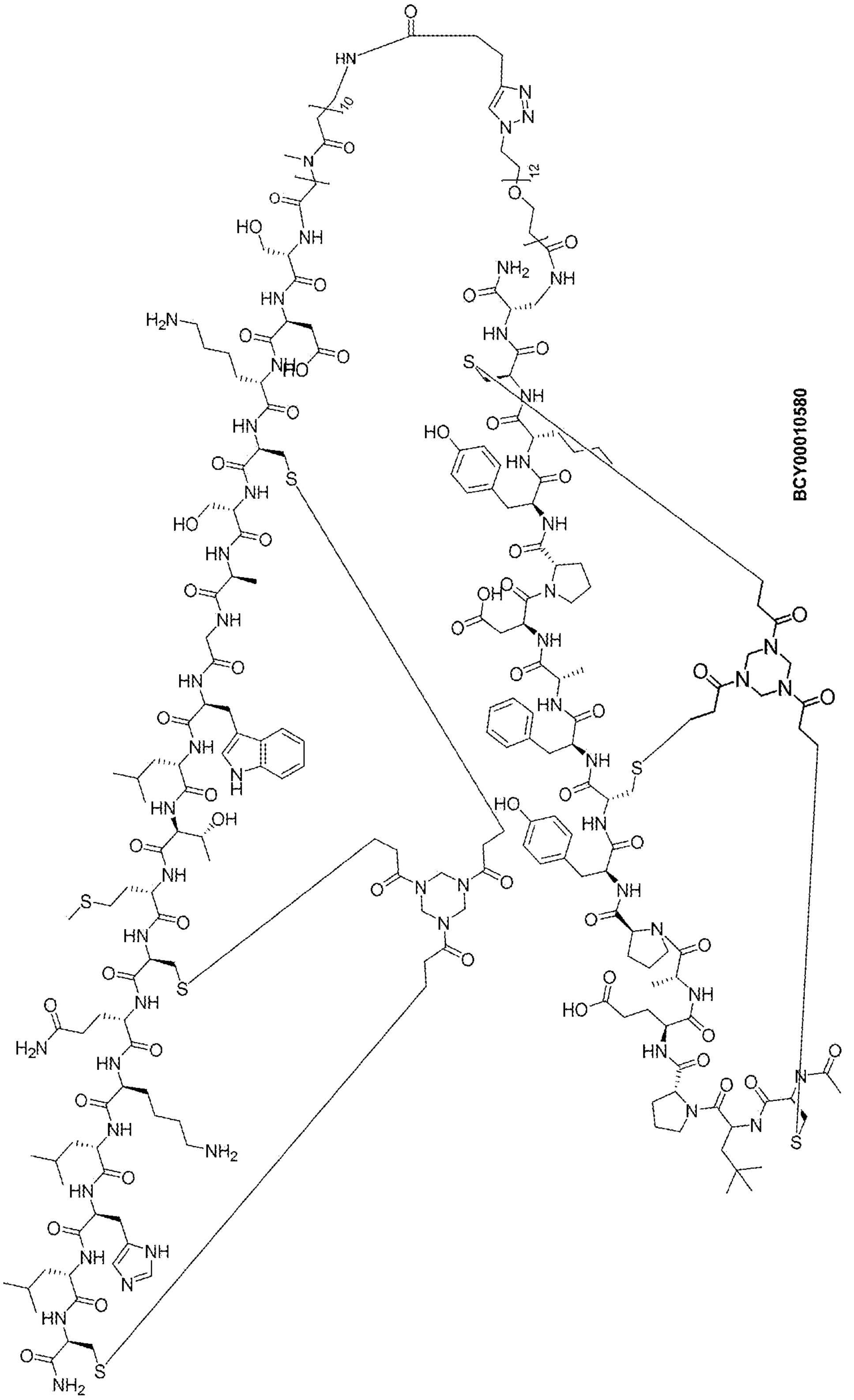
FIG. 62: Formula of BCY10580.
Figure 63:
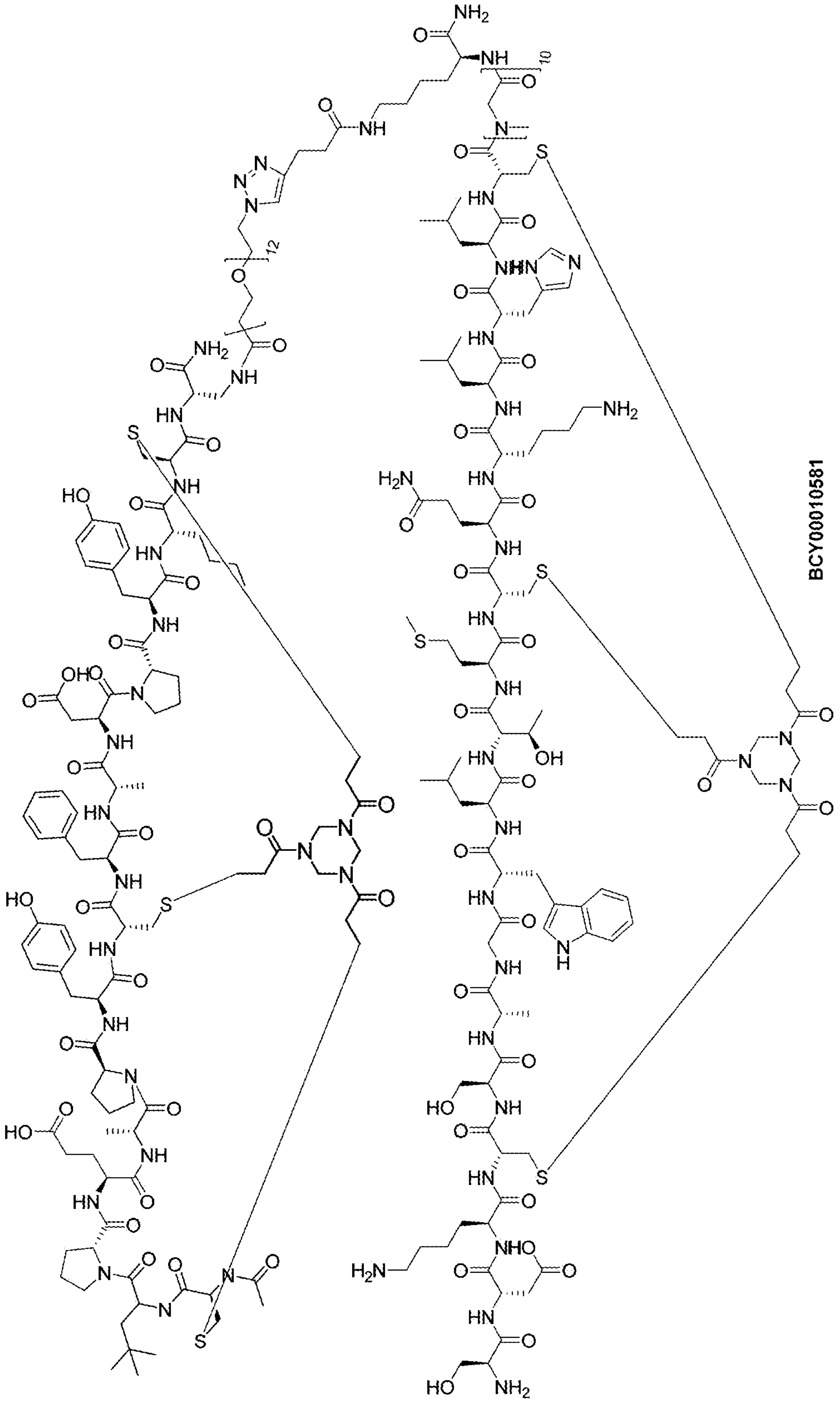
FIG. 63: Formula of BCY10581.
Figure 64:
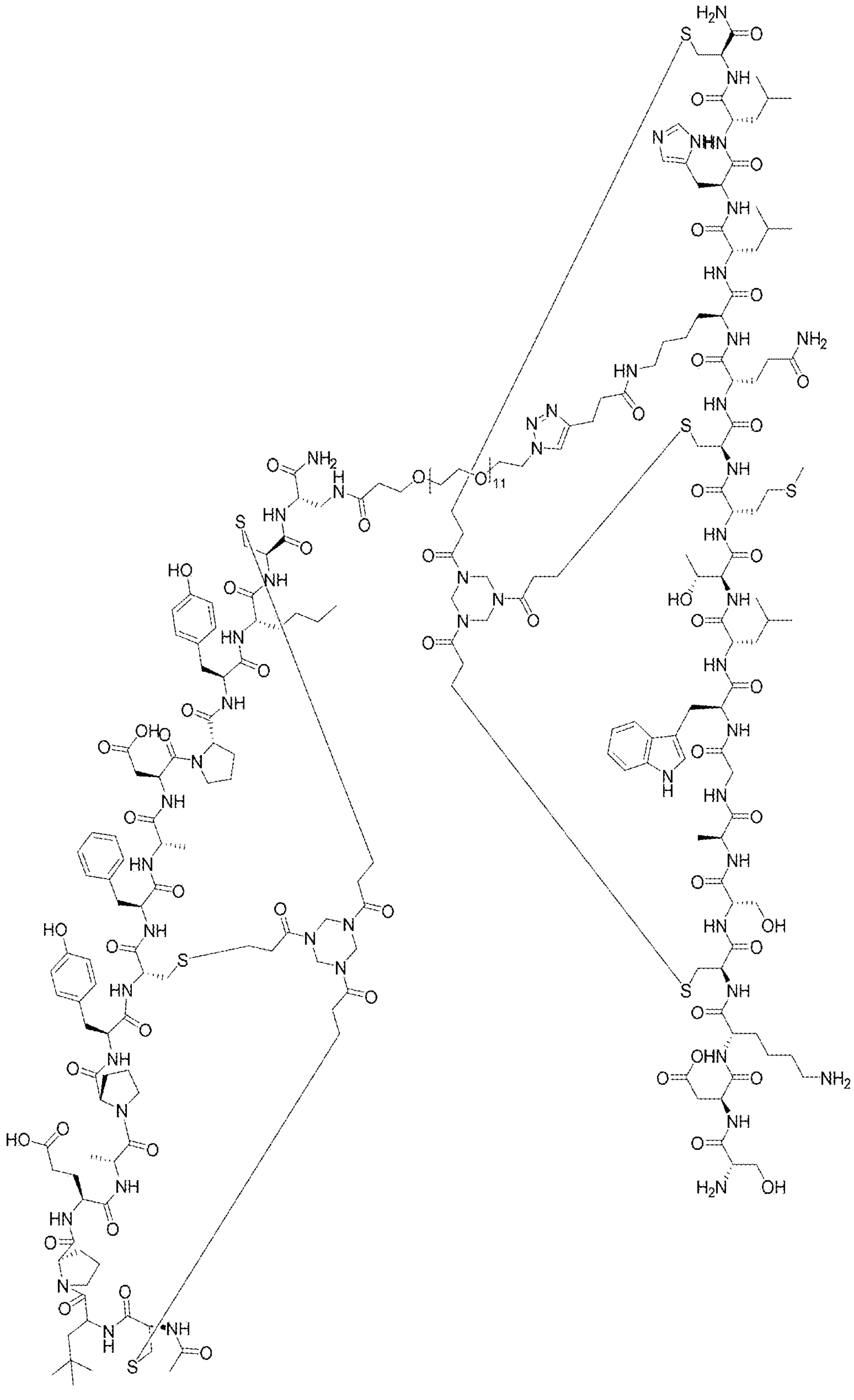
FIG. 64: Formula of BCY10582.
Figure 65:
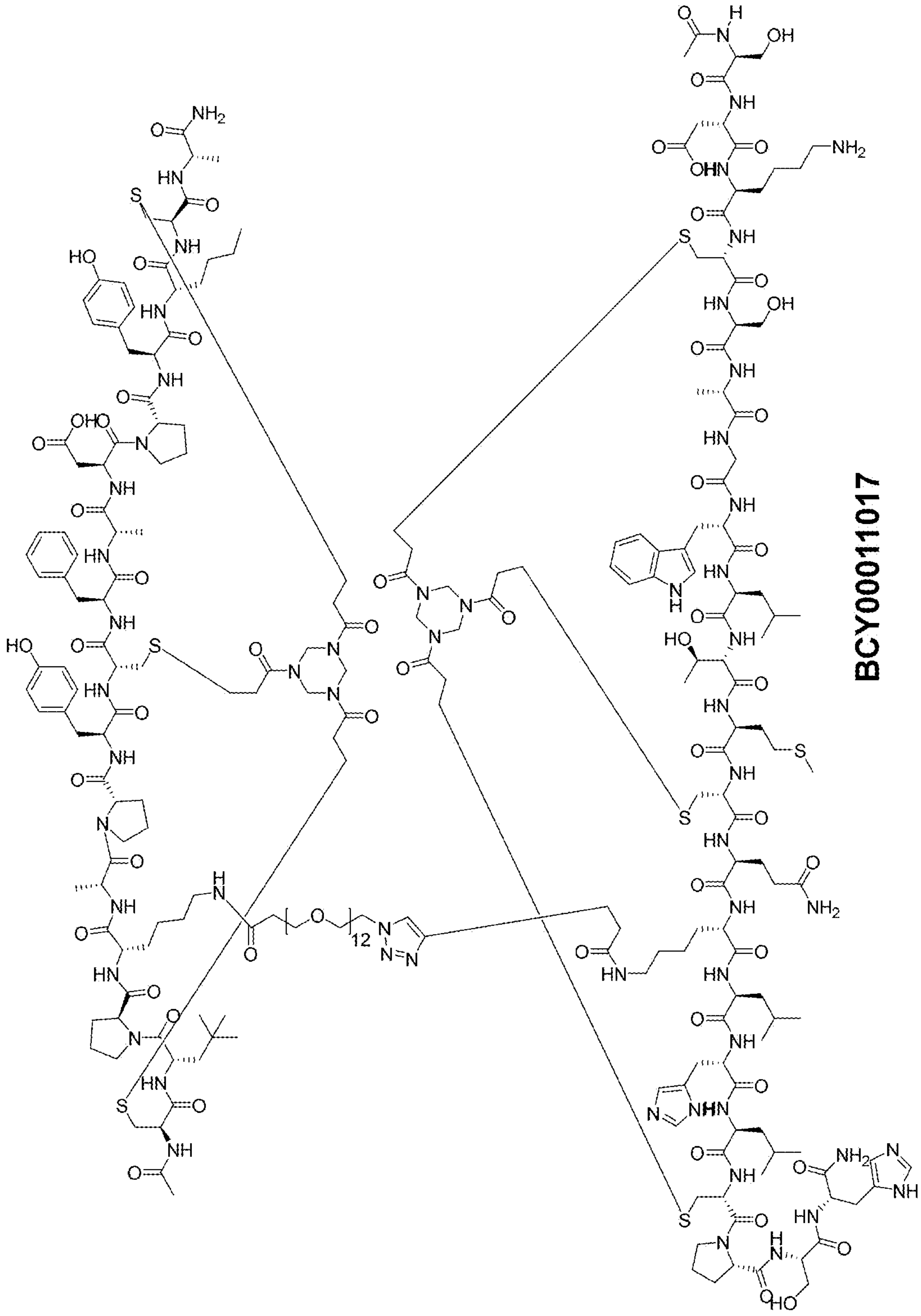
FIG. 65: Formula of BCY11017.
Figure 66:
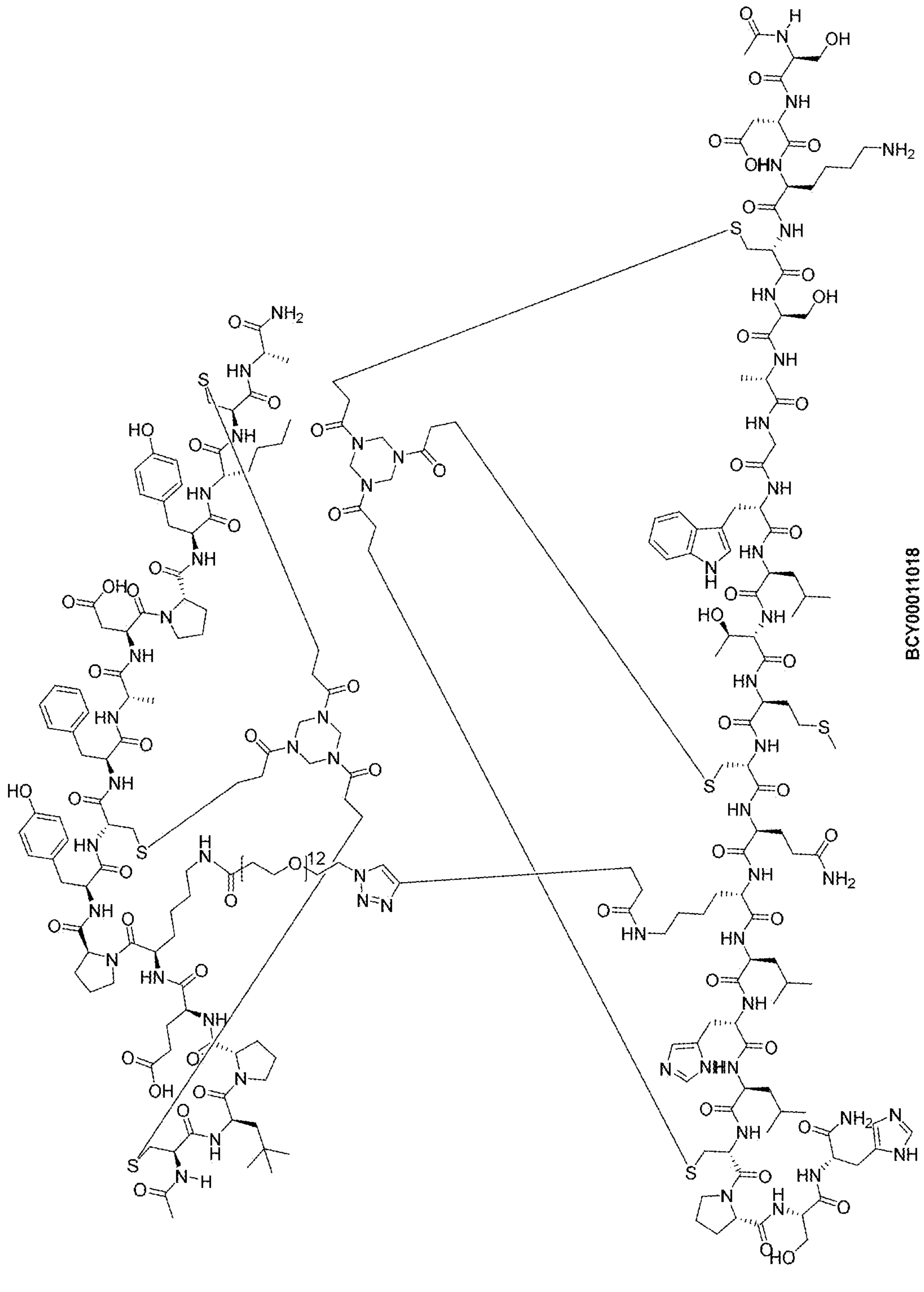
FIG. 66: Formula of BCY11018.
Figure 67:
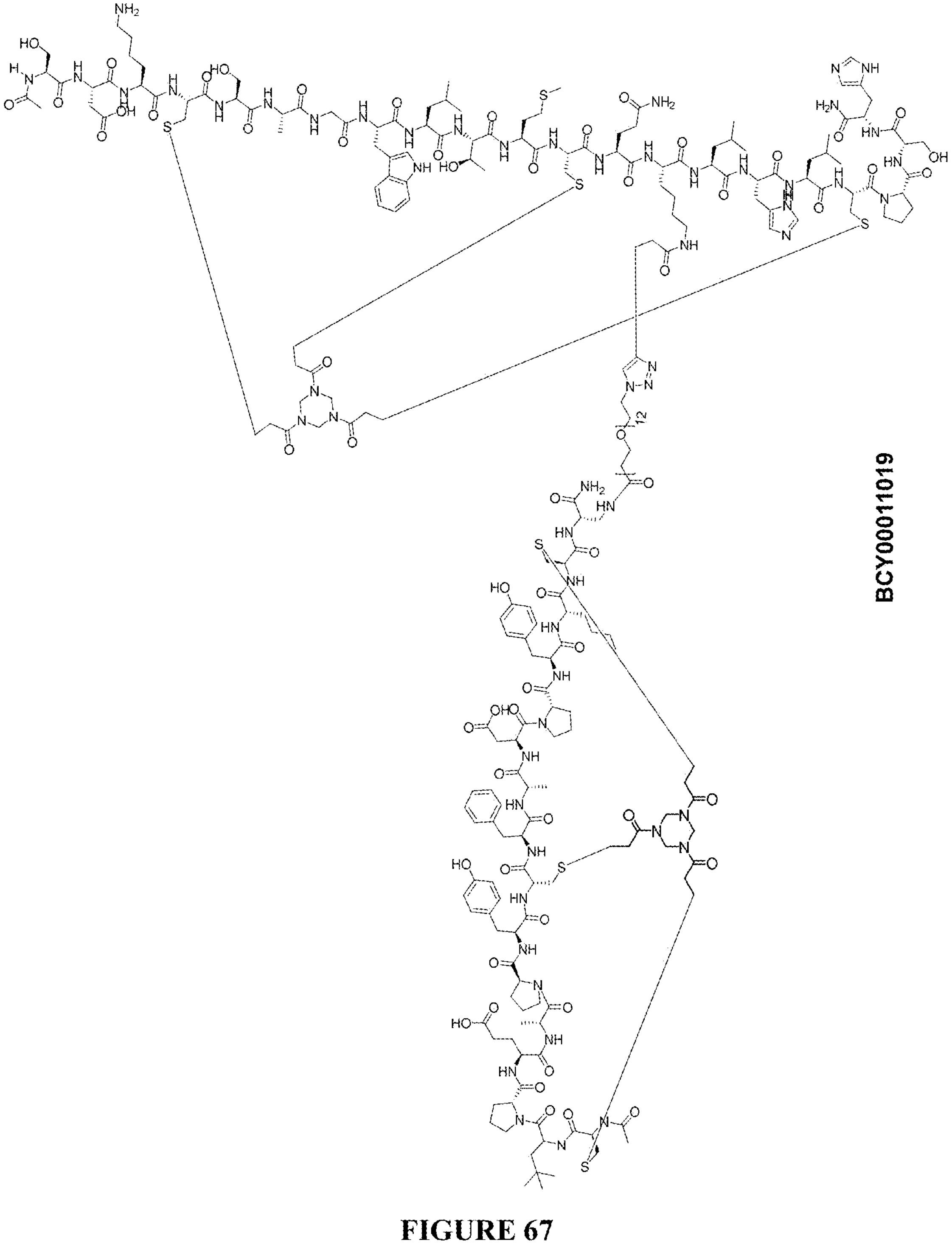
FIG. 67: Formula of BCY11019.
Figure 68:
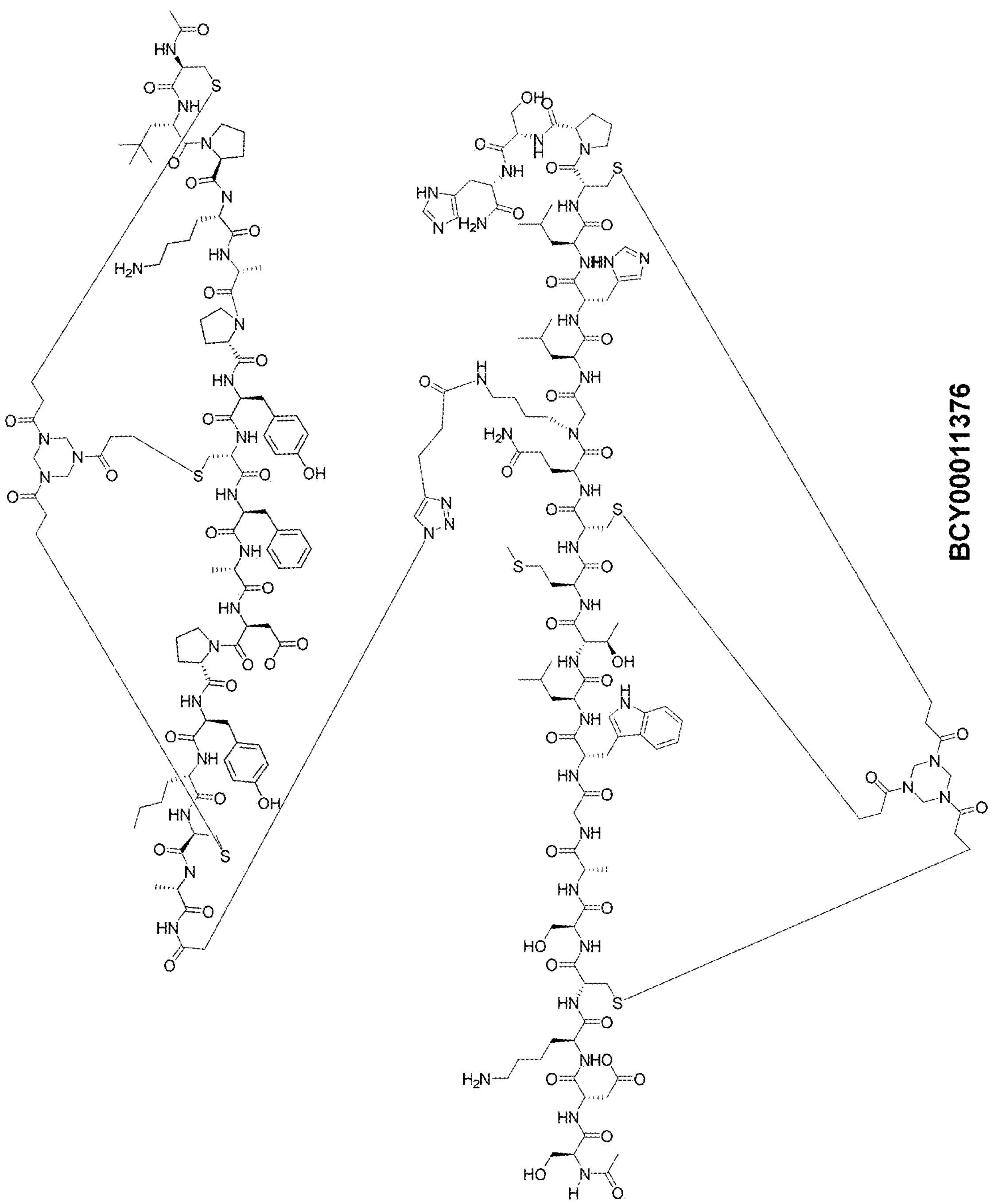
FIG. 68: Formula of BCY11376.
Figure 69:
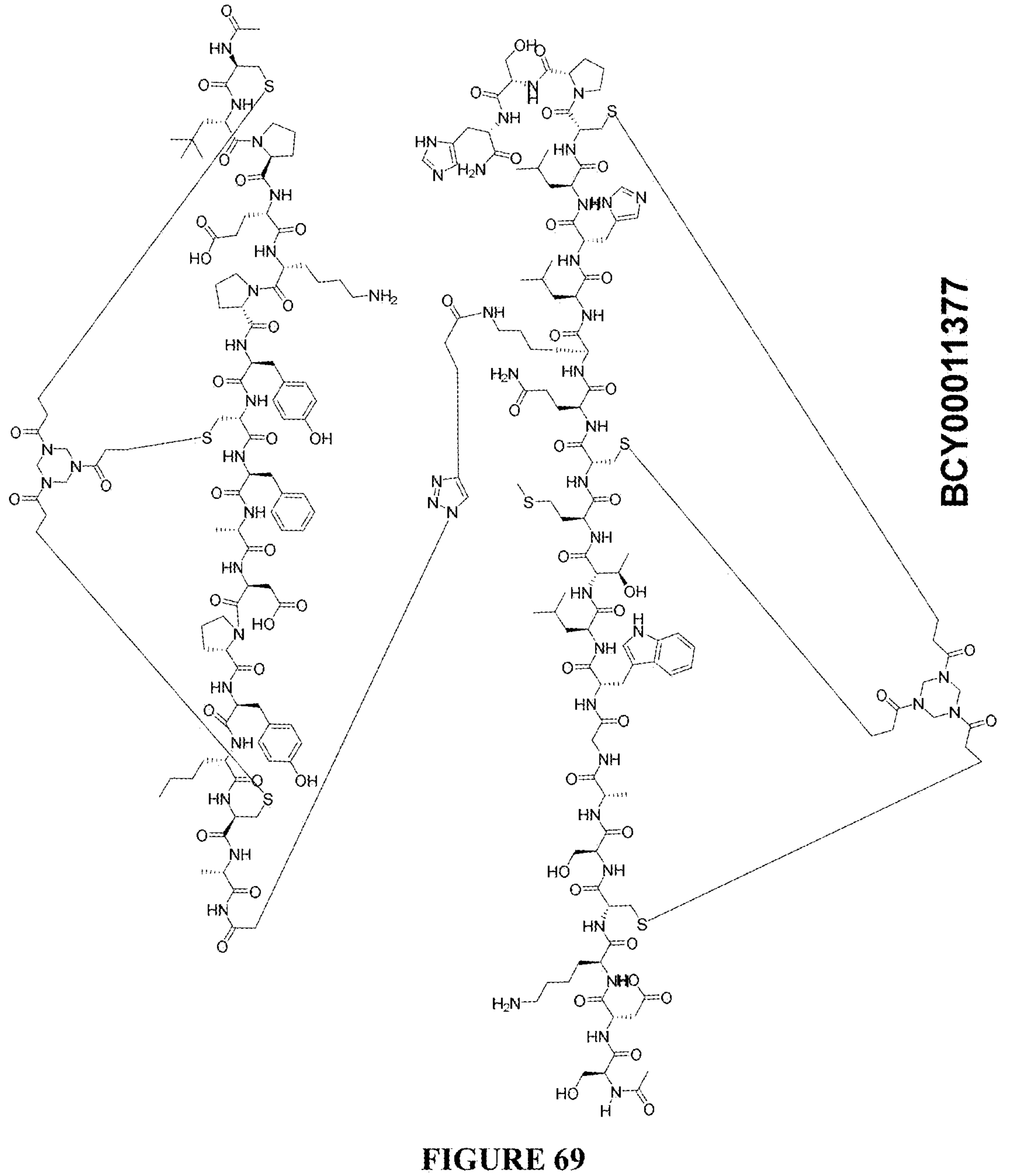
FIG. 69: Formula of BCY11377.
Figure 70:
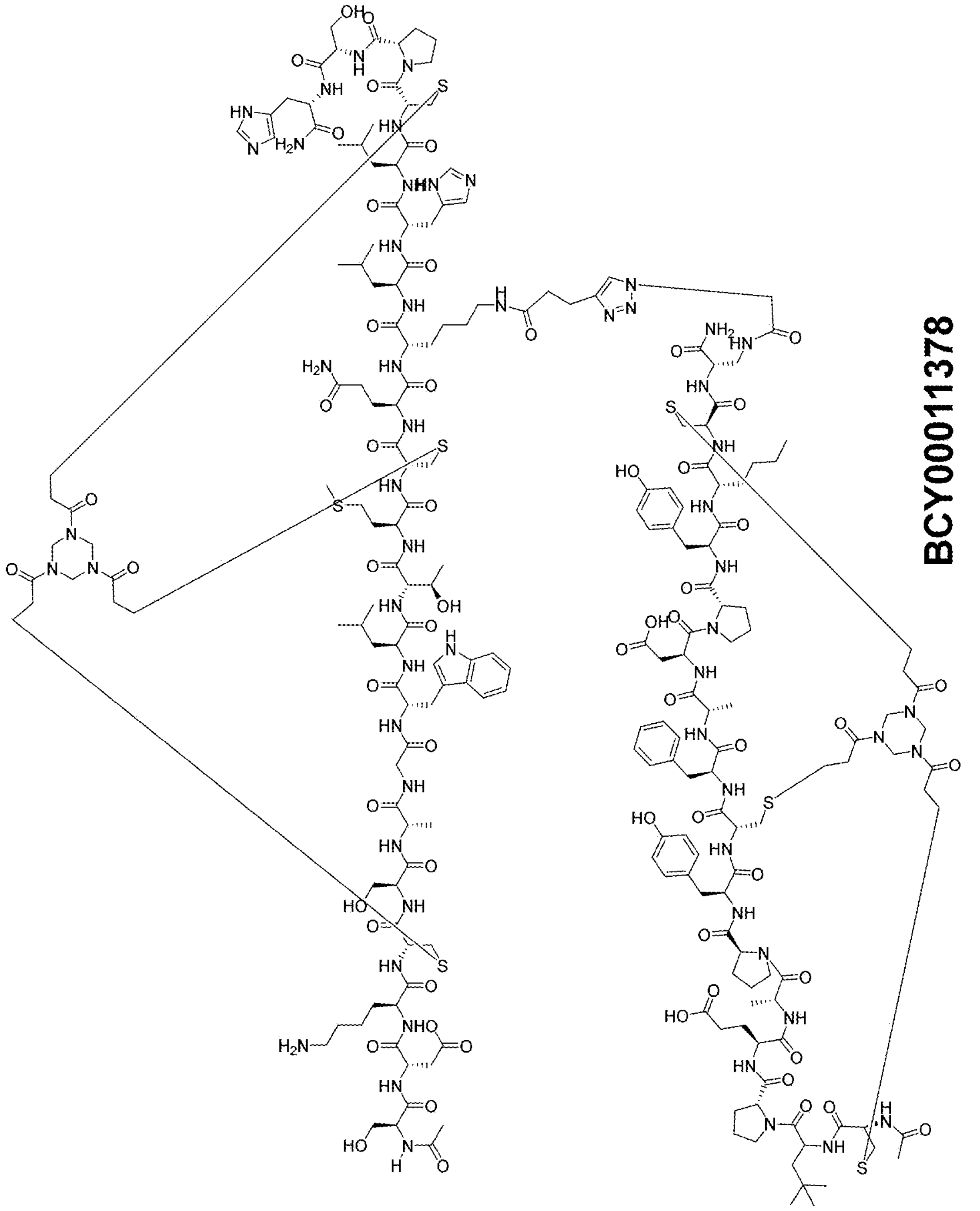
FIG. 70: Formula of BCY11378.
Figure 71:
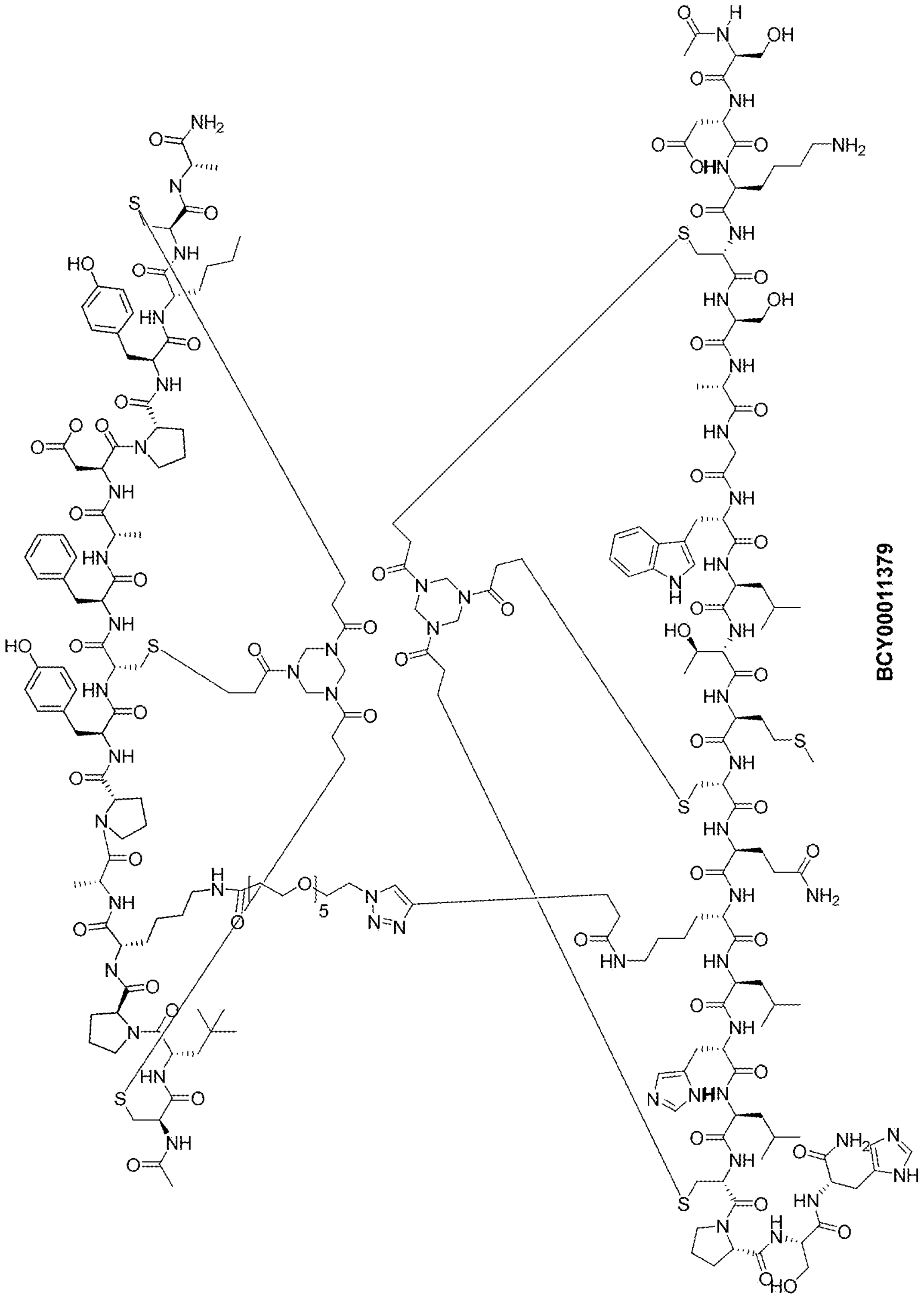
FIG. 71: Formula of BCY11379.
Figure 72:
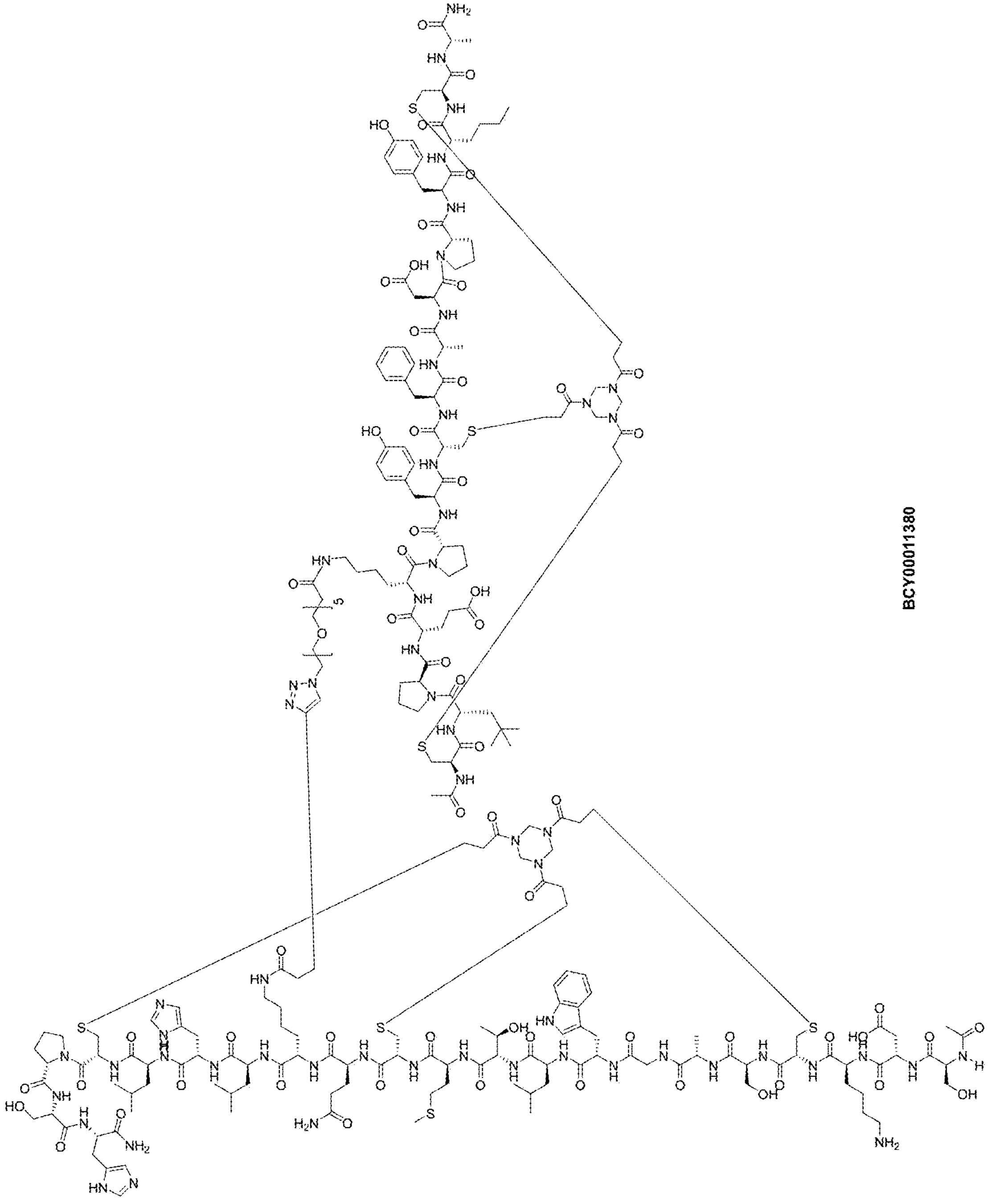
FIG. 72: Formula of BCY11380.
Figure 73:
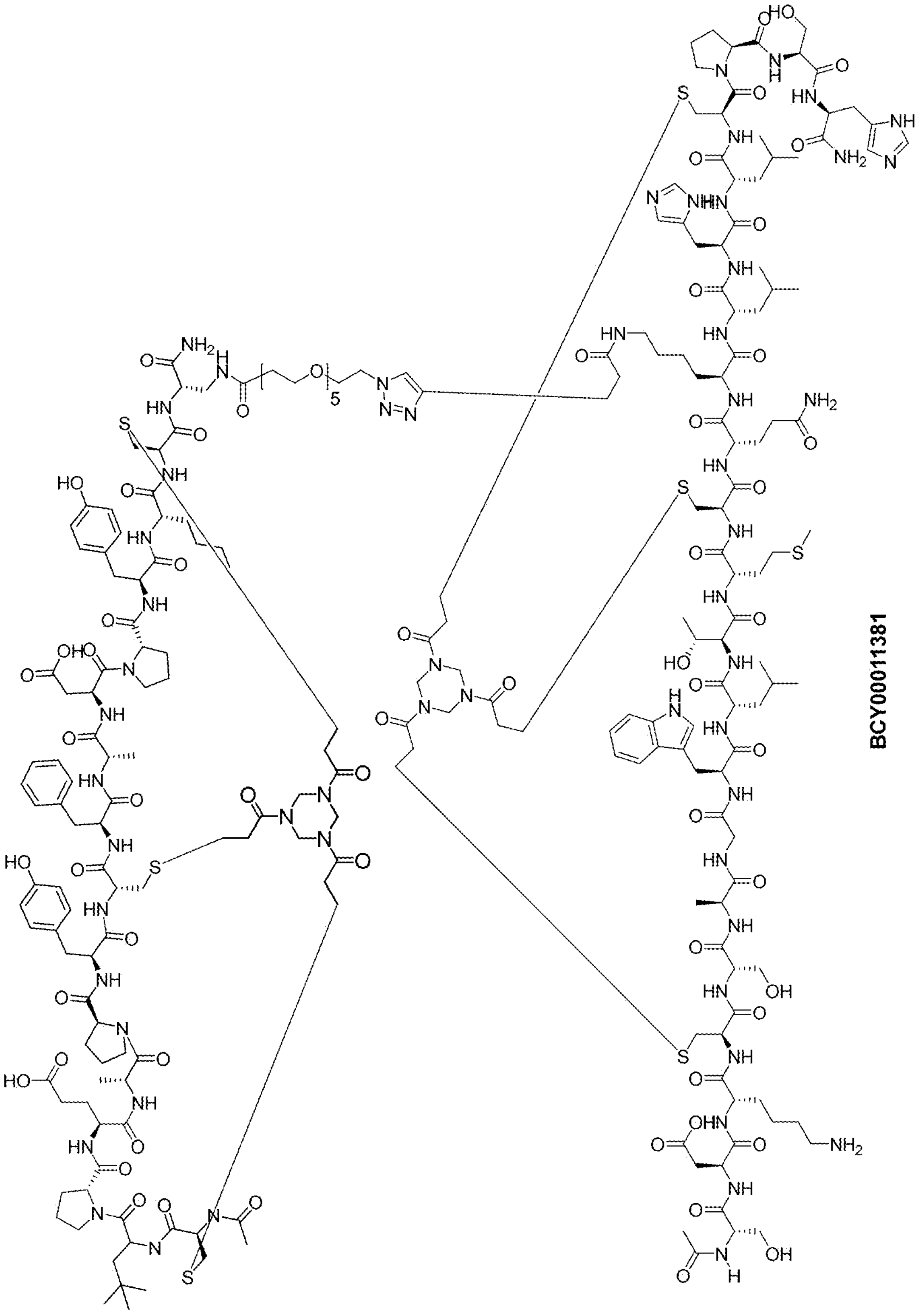
FIG. 73: Formula of BCY11381.

FIG. 10 shows the plasma concentration vs time curve of BCY10572 and BCY10000 from a 2 mg/kg IV dose in SD Rat (n=3). The pharmacokinetic parameters from the experiment are as shown in Table 7:

TABLE 7

Pharmacokinetic Parameters of plasma concentration vs time curve of BCY10572 and BCY10000

| Compound | T1/2(h) | Clp (ml/min/kg) | Vdss (L/kg) |
|---|---|---|---|
| BCY10000 | 0.357 | 16.1 | 0.395 |
| BCY10572 | 0.926 | 15.6 | 0.882 |

The invention claimed is:

1. A heterotandem bicyclic peptide complex comprising:

(a) a first peptide ligand which binds to CD137 on an immune cell;

conjugated via a linker to (b) a second peptide ligand which binds to a component present on a cancer cell, wherein the component present on the cancer cell is Nectin-4; wherein each of said peptide ligands comprises a polypeptide comprising three cysteine residues, separated by two loop sequences, and a molecular scaffold which forms covalent bonds with the cysteine residues of the polypeptide such that two polypeptide loops are formed on the molecular scaffold, wherein the first peptide ligand is a CD137 binding bicyclic peptide ligand comprising an amino acid sequence selected from:

CiIEEGQYCiiFADPY[Nle]Ciii (SEQ ID NO: 1);

Ci[tBuAla]PE[D-Ala]PYCiiFADPY[Nle]Ciii (SEQ ID NO: 3);

CiIEEGQYCiiF[D-Ala]DPY[Nle]Ciii (SEQ ID NO: 4);

Ci[tBuAla]PK[D-Ala]PYCiiFADPY[Nle]Ciii (SEQ ID NO: 5);

Ci[tBuAla]PE[D-Lys]PYCiiFADPY[Nle]Ciii (SEQ ID NO: 6);

Ci[tBuAla]P[K(PYA)][D-Ala]PYCiiFADPY[Nle]Ciii (SEQ ID NO: 7);

Ci[tBuAla]PE[D-Lys(PYA)]PYCiiFADPY[Nle]Ciii (SEQ ID NO: 8);

CiIEE[D-Lys(PYA)]QYCiiFADPY(Nle)Ciii (SEQ ID NO: 9); and

[dCi][dE][dE][K(PYA)][dQ][dY][dCii][dF][dA][dD][dP][dY][dNle][dCiii] (SEQ ID NO: 10); and wherein the second peptide ligand is a Nectin-4 binding bicyclic peptide ligand comprising an amino acid sequence selected from:

```
                                                  (SEQ ID NO: 15)
CiP[1Nal][dD]CiiM[HArg]DWSTP[HyP]WCiii;

                                                  (SEQ ID NO: 16)
CiP[1Nal][dD]CiiM[HArg|D[dW]STP[HyP][dW|Ciii;
```

-continued (SEQ ID NO: 17)
CiP[1Nal][dK](Sar10-(B-Ala))CiiM[HArg]DWSTP][HyP]WCiii;
and (SEP ID NO: 18)
CiPFGCiiM[HArg]DWSTP[HyP]WCiii;

wherein Ci, Cii and Ciii represent first, second and third cysteine residues, respectively, Nle represents norleucine, tBuAla represents t-butyl-alanine, PYA represents 4-pentynoic acid, 1Nal represents 1-naphthylalanine, HArg represents homoarginine, HyP represents hydroxyproline, dD represents aspartic acid in D-configuration, Sar10 represents 10 sarcosine units, B-Ala represents beta-alanine, or a pharmaceutically acceptable salt of said heterotandem bicyclic peptide complex.

2. The heterotandem bicyclic peptide complex, or a pharmaceutically acceptable salt thereof, as defined in claim 1, wherein the CD137 binding bicyclic peptide ligand comprises N- and C-terminal modifications and comprises an amino acid sequence selected from:

Ac-A-CiIEEGQYCiiFADPY[Nle]Ciii-Dap (Ac-A-(SEQ ID NO: 1)-Dap);

Ac-A-CiIEEGQYCiiFADPY[Nle]Ciii-Dap(PYA) (Ac-A-(SEQ ID NO: 1)-Dap(PYA));

Ac-Ci[tBuAla]PE[D-Ala]PYCiiFADPY[Nle]Ciii-Dap (Ac-(SEQ ID NO: 3)-Dap);

Ac-Ci[tBuAla]PE[D-Ala]PYCiiFADPY[Nle]Ciii-Dap(PYA) (Ac-(SEQ ID NO: 3)-Dap(PYA));

Ac-A-CiIEEGQYCiiF[D-Ala]DPY[Nle]Ciii-Dap (Ac-A-(SEQ ID NO: 4)-Dap);

Ac-Ci[tBuAla]PK[D-Ala]PYCiiFADPY|Nle]Ciii-A (Ac-(SEQ ID NO: 5)-A);

Ac-CiltBuAla]PE[D-Lys]PYCiiFADPY[Nle]Ciii-A (Ac-

-continued (SEQ ID NO: 6)-A);

Ac-Ci[tBuAla]P[K(PYA)|[D-Ala]PYCiiFADPY|Nle]Ciii-A (Ac-(SEQ ID NO: 7)-A);

Ac-Ci[tBuAla]PE[D-Lys(PYA)]PYCiiFADPY[Nle]Ciii-A (Ac-(SEQ ID NO: 8)-A);

Ac-A-CiIEE[D-Lys(PYA)]QYCiiFADPY(Nle)Ciii-A (Ac-A-(SEQ ID NO: 9)-A); and

[dA]-NH2 (Ac-[dA]-(SEQ ID NO: 10)-[dA]-$NH_2$);

wherein Ac represents an acetyl group, Dap represents diaminopropionic acid and PYA represents 4-pentynoic acid.

3. The heterotandem bicyclic peptide complex, or a pharmaceutically acceptable salt thereof, as defined in claim 1, wherein the Nectin-4 binding bicyclic peptide ligand comprises an amino acid sequence selected from:

CiP[1Nal][dD]CiiM[HArg]DWSTP[HyP]WCiii (SEQ ID NO: 15);

[PYA]-[B-Ala]-[Sar10]-CiP[1Nal][dD]CiiM[HArg]DWSTP[HyP]WCiii ([PYA]-[B-Ala]-[Sar10]-(SEQ ID NO: 15));

CiP[1Nal][dD]CiiM[HArg]D[dW]STP[HyP][dW]Ciii (SEQ ID NO: 16);

[PYA]-[B-Ala]-[Sar10]-CiP[1Nal][dD]CiiM[HArg]D[dW]STP[HyP][dW]Ciii ([PYA]-[B-Ala]-[Sar10]-(SEQ ID NO: 16));

Ac-CiP[1Nal][dK](Sar10-(B-Ala))CiiM[HArg]DWSTP[HyP]WCiii (Ac-(SEQ ID NO: 17)); and CiPFGCiiM[HArg]DWSTP[HyP]WCiii (SEQ ID NO: 18);

wherein PYA represents 4-pentynoic acid, B-Ala represents beta-alanine, Sar10 represents 10 sarcosine units.

4. The heterotandem bicyclic peptide complex, or a pharmaceutically acceptable salt thereof, as defined in claim 1, which is a CD137/Nectin-4 complex selected from:

BCY8854
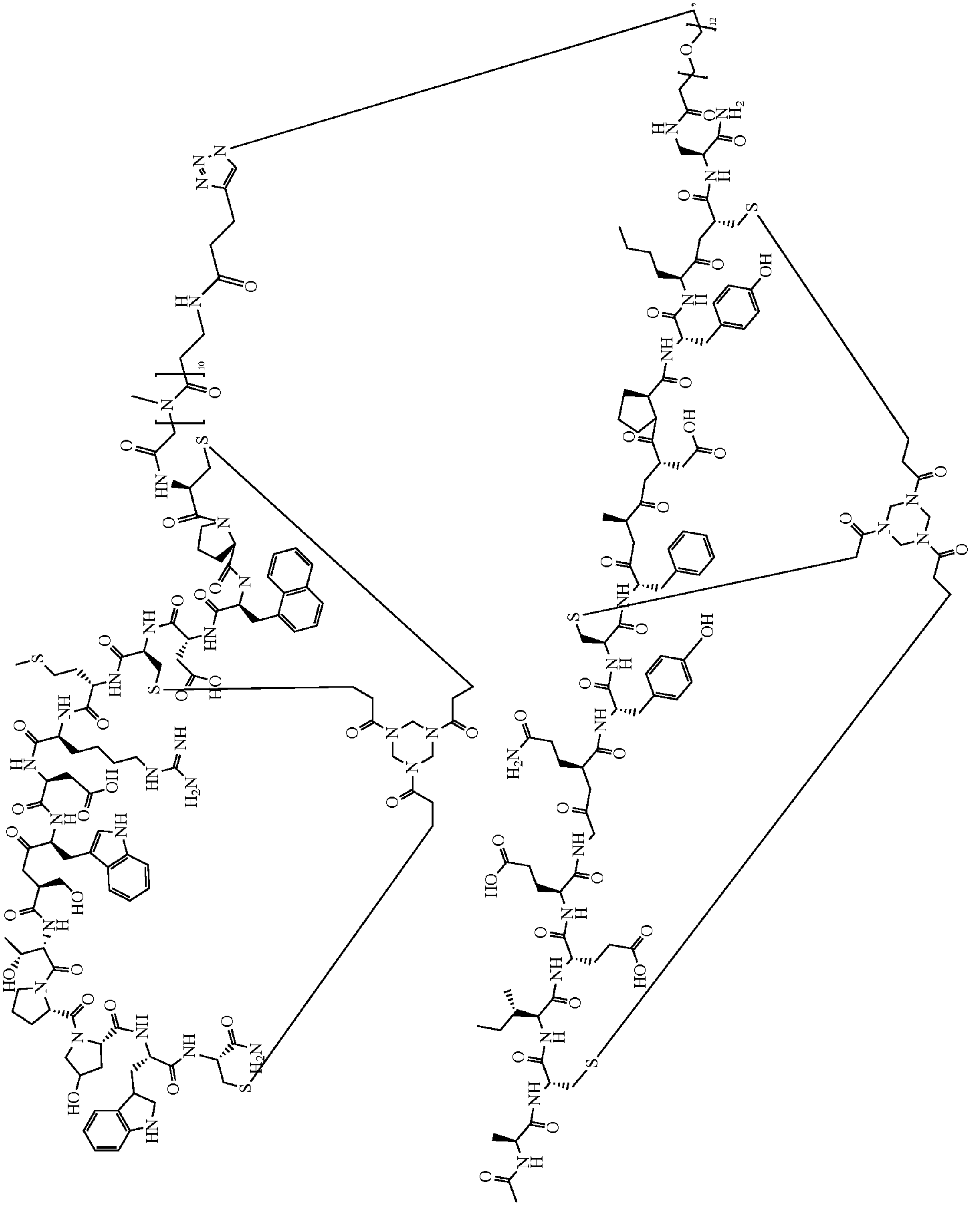

BCY9350
-continued
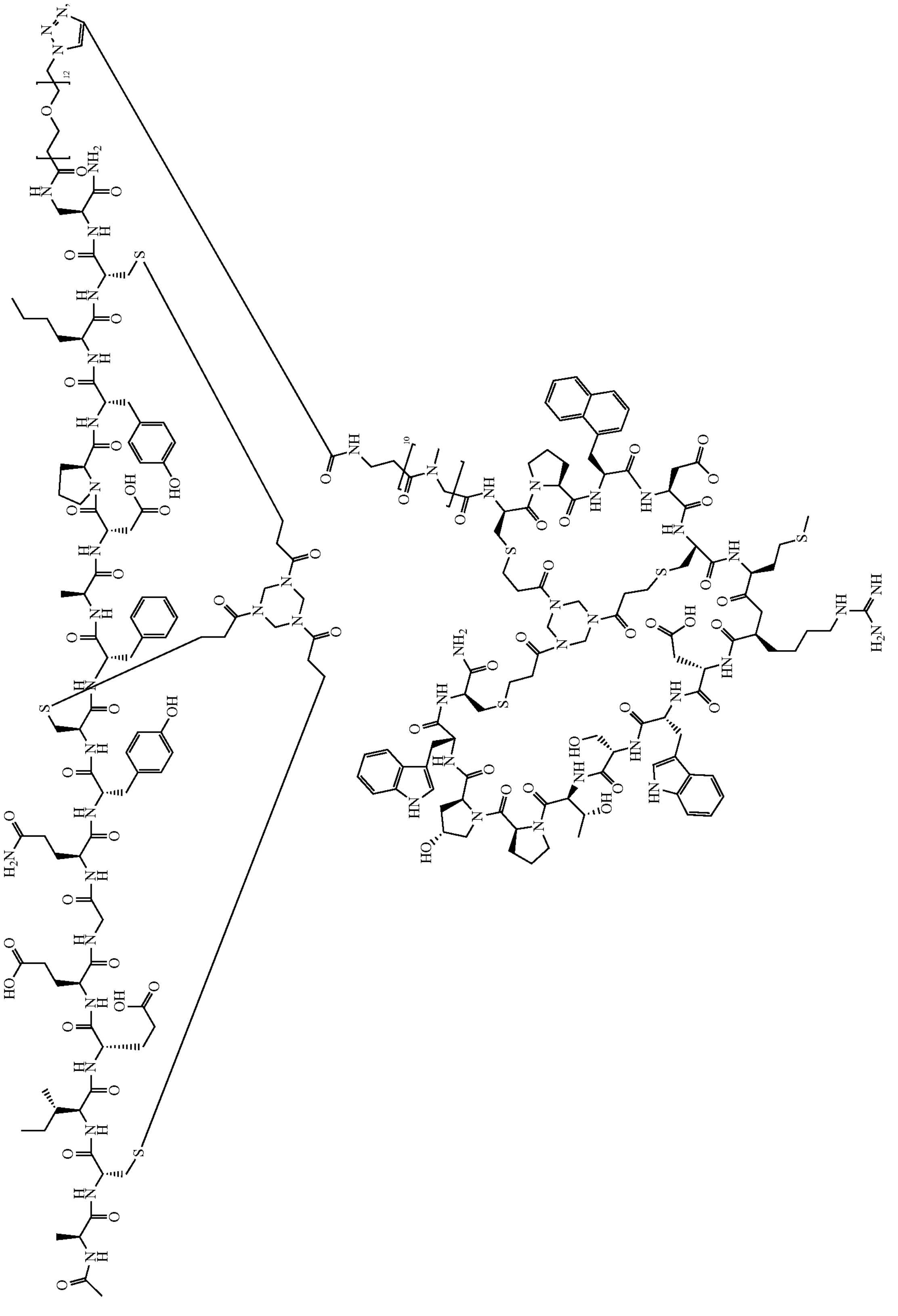

-continued
BCY9351
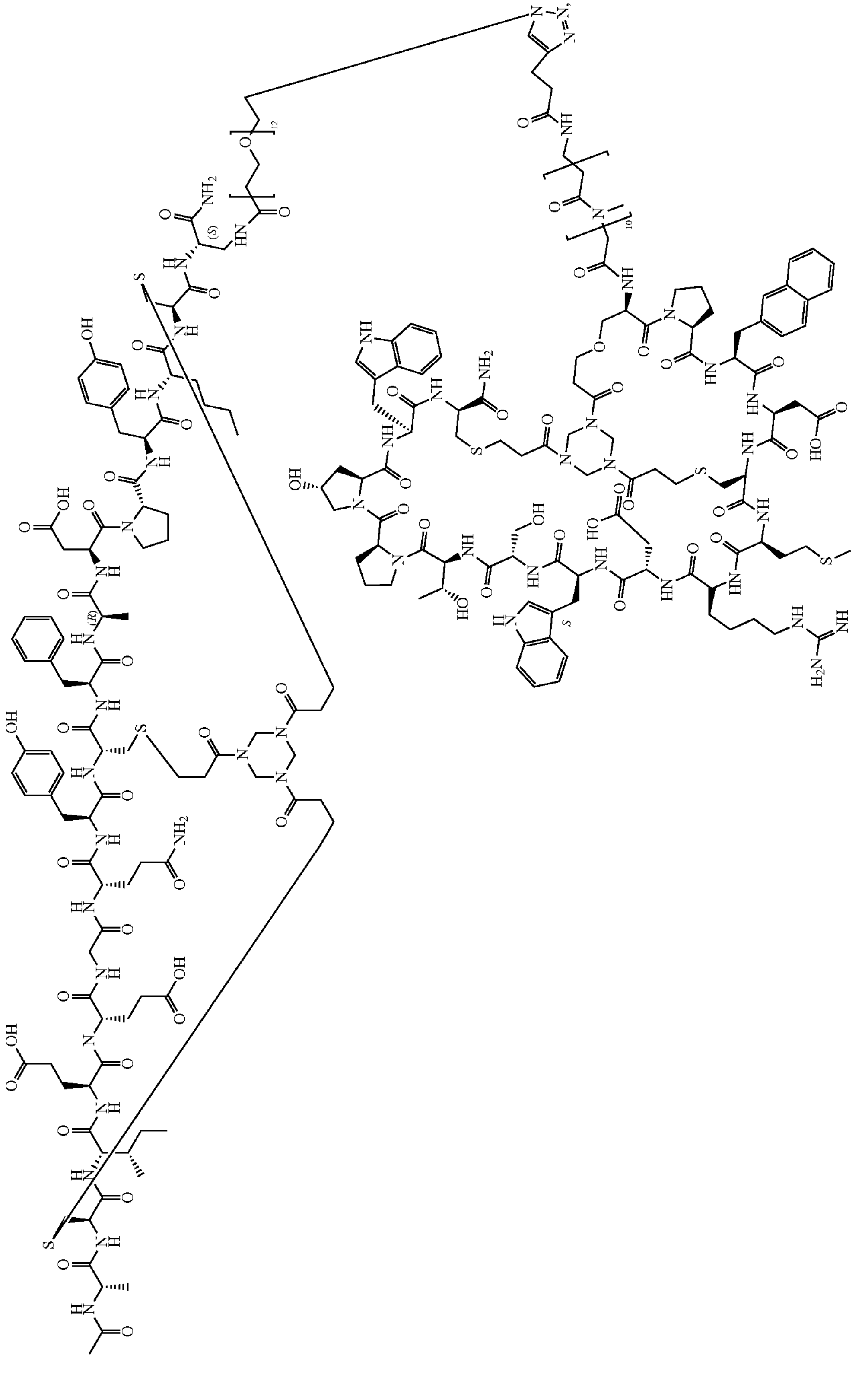

-continued
BCY9399
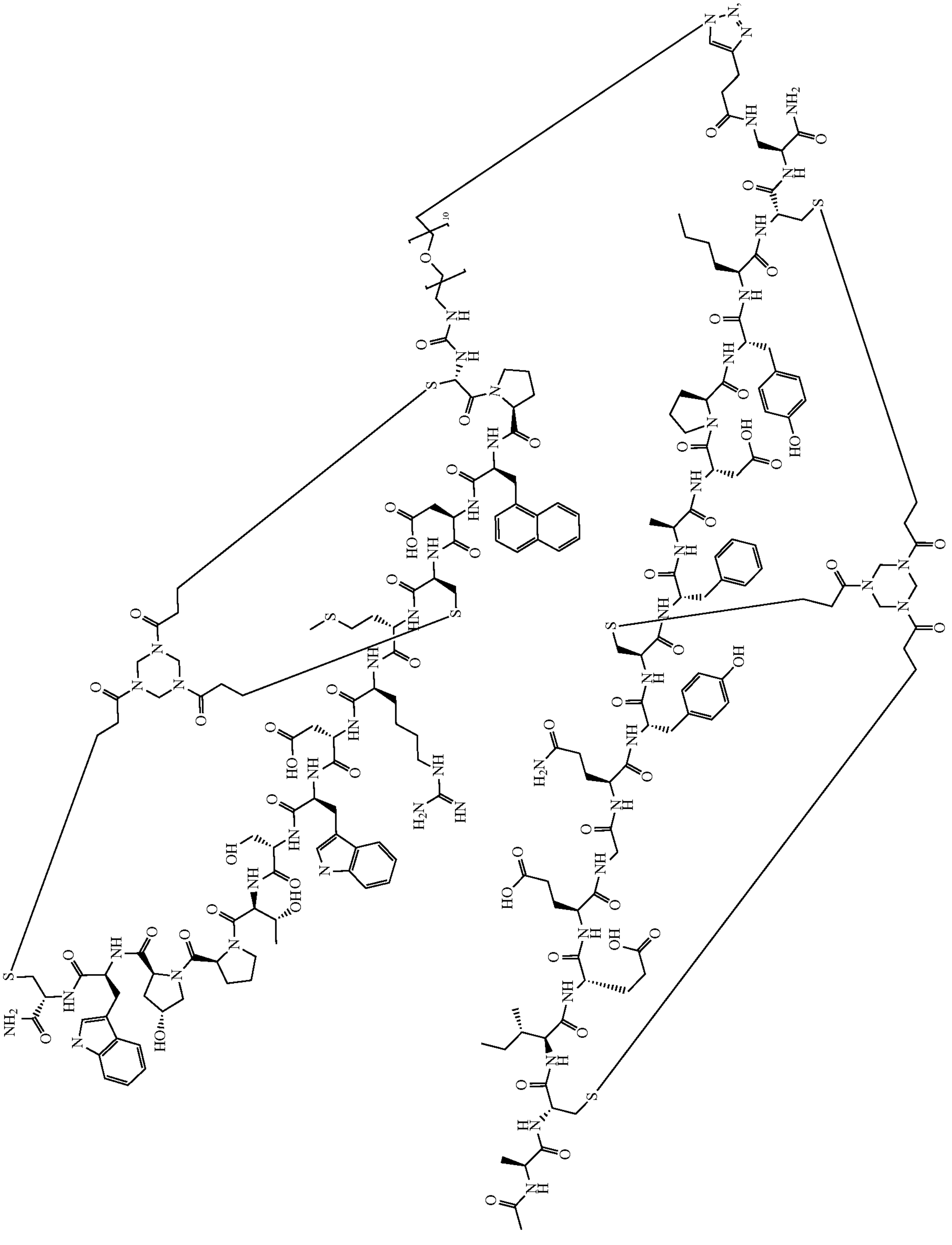

-continued
BCY9400
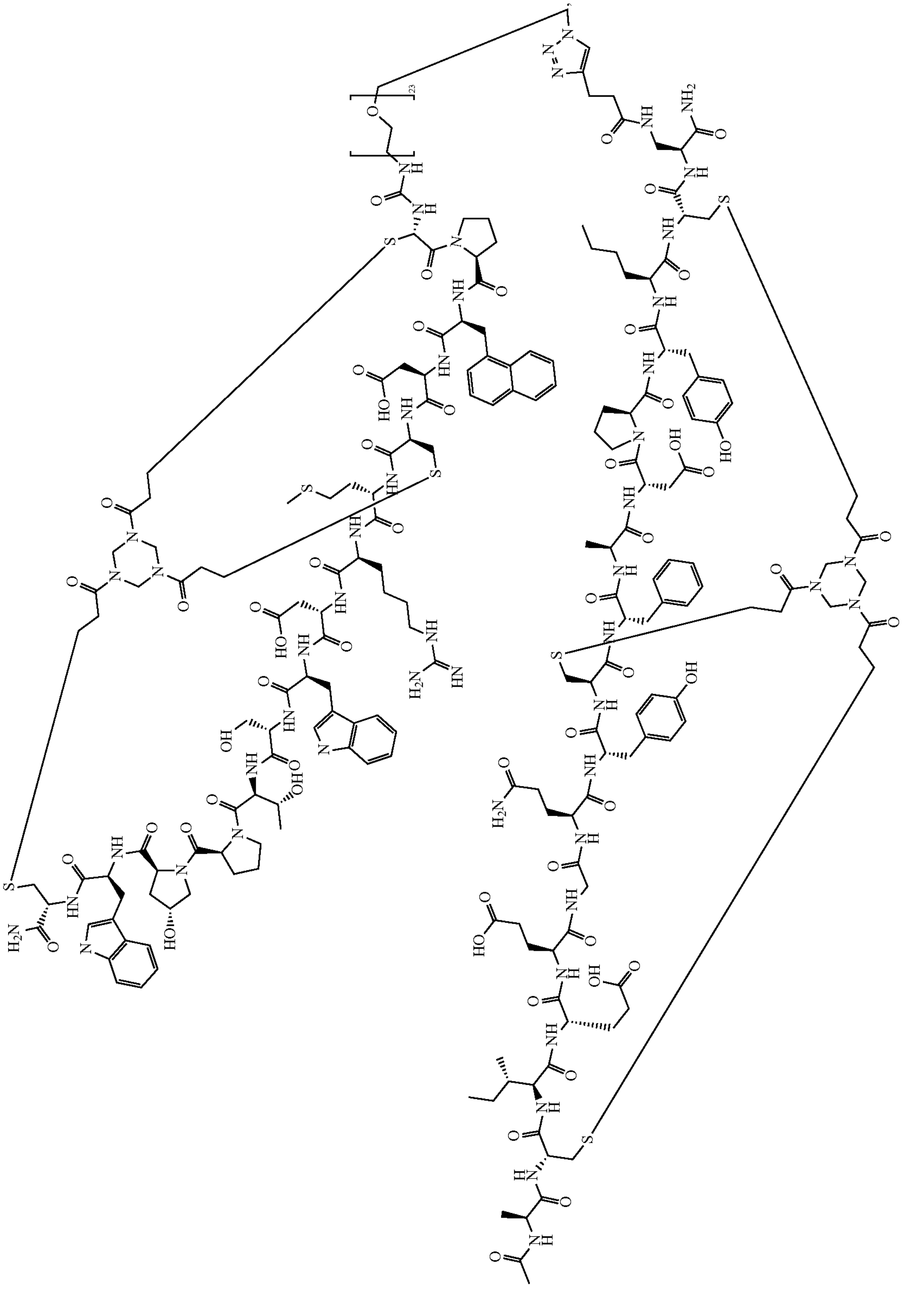

-continued
BCY9401
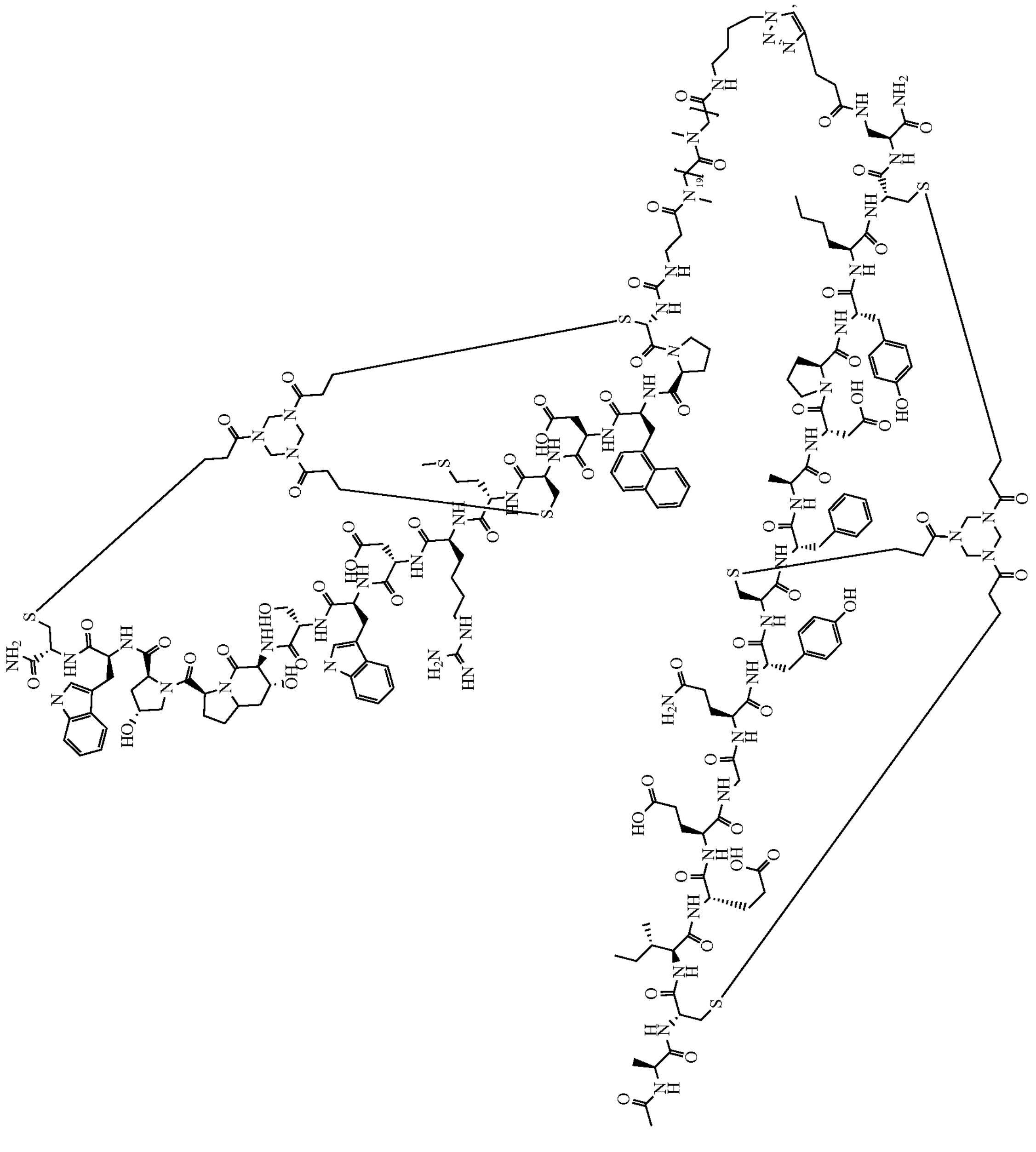

BCY9403
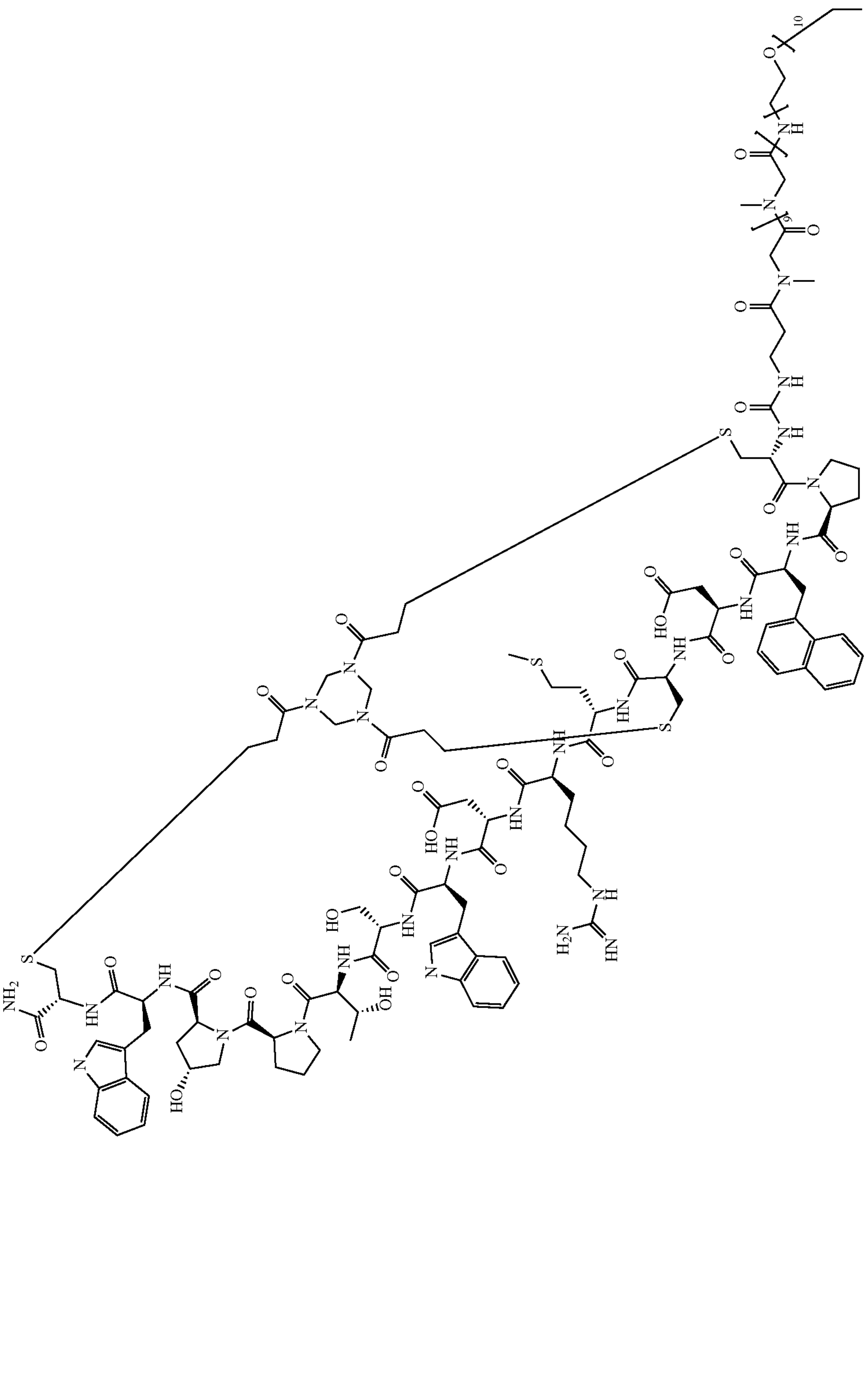

-continued
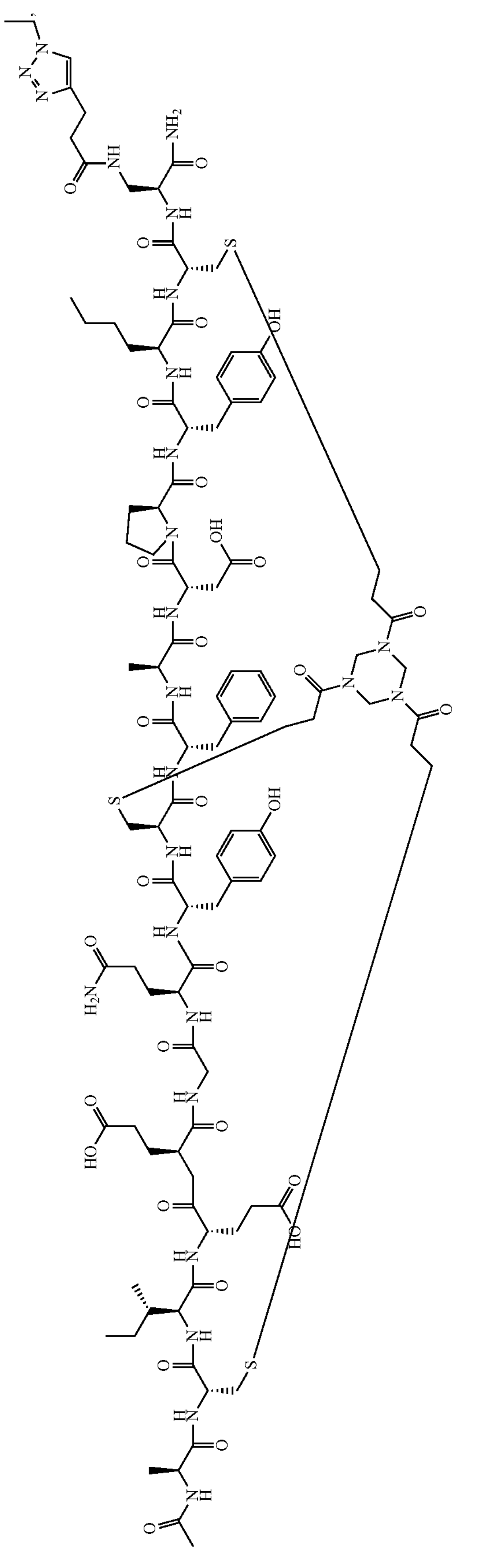

BCY9405
-continued
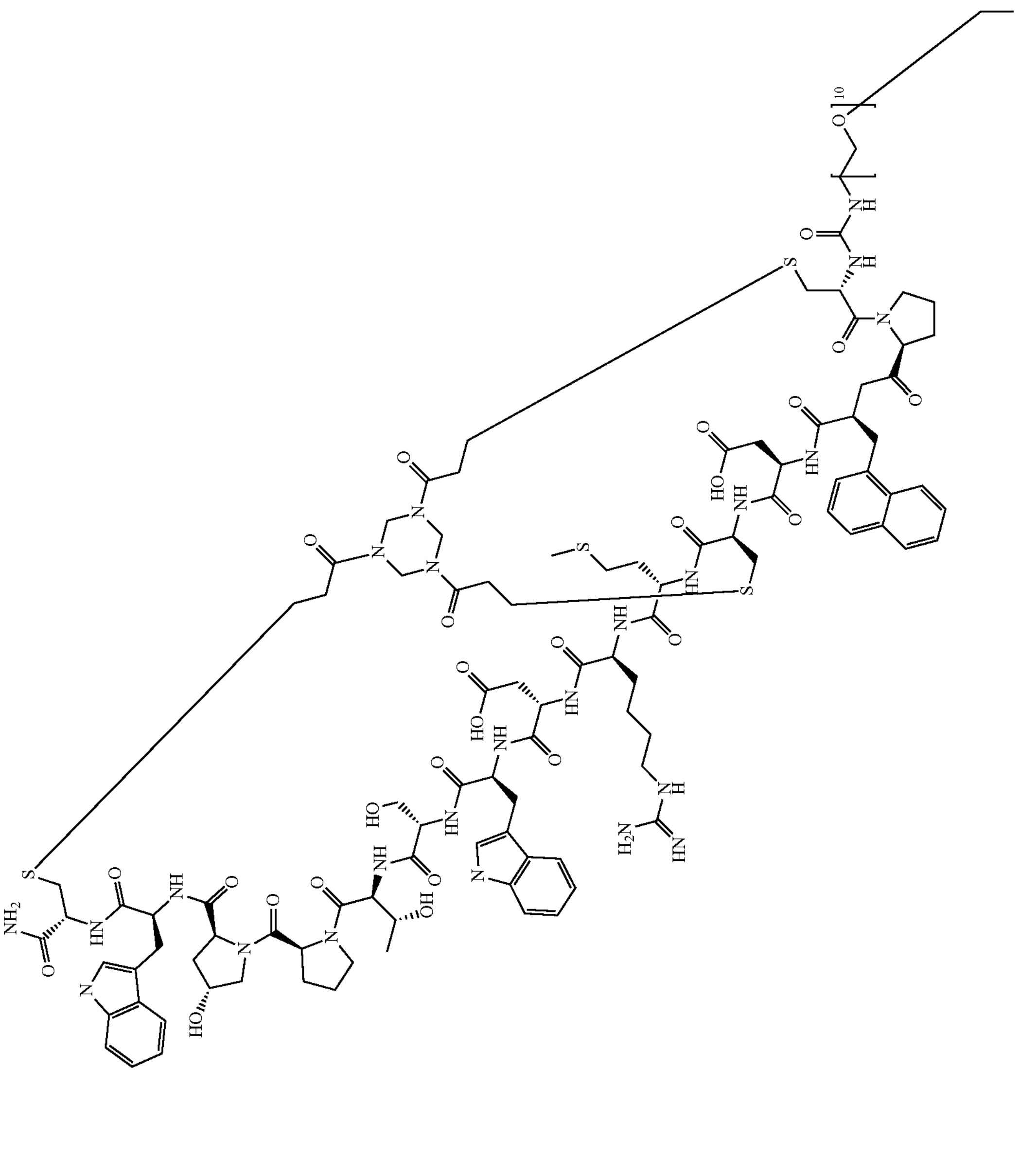

-continued
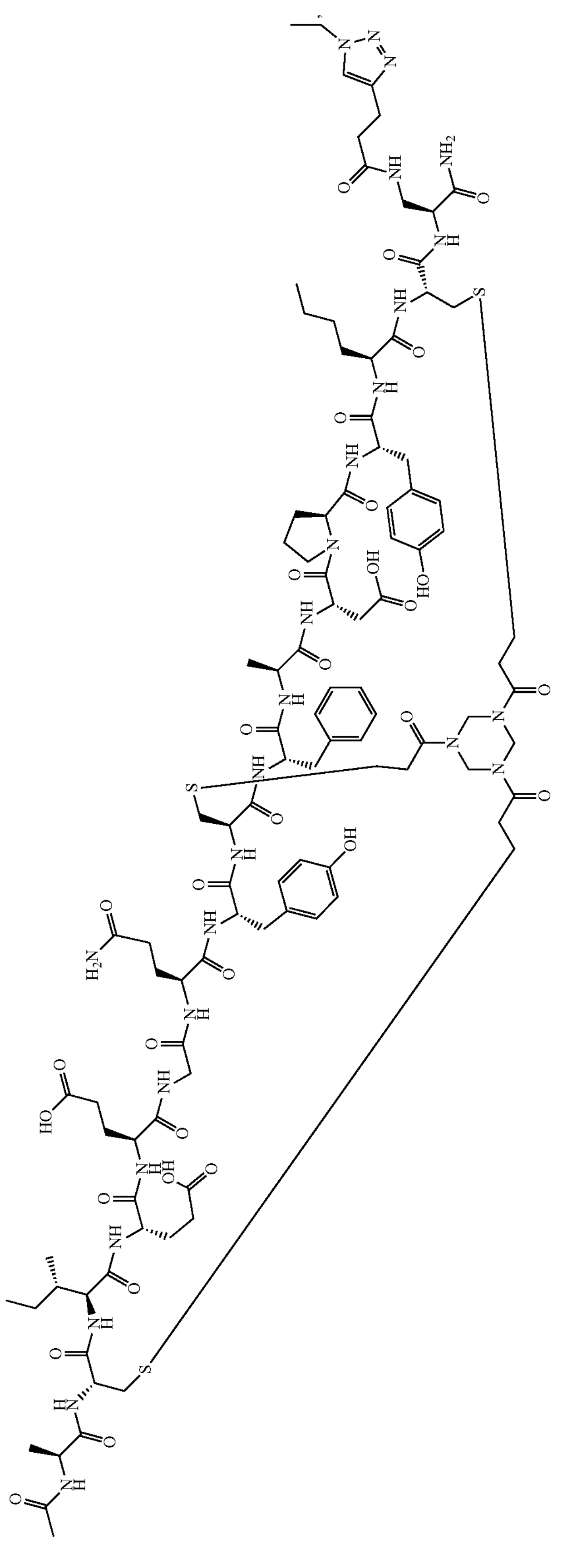

-continued
BCY9406
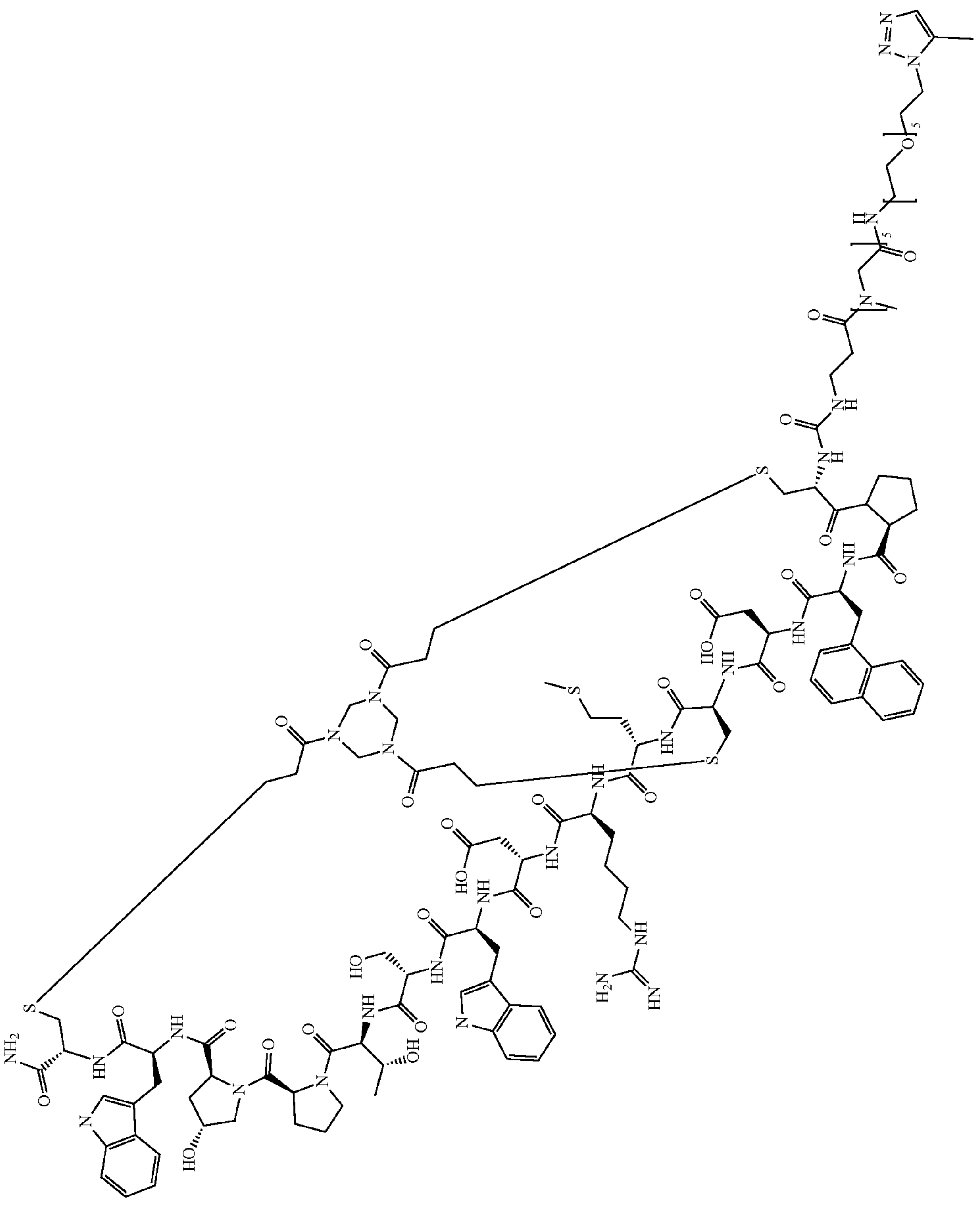

-continued
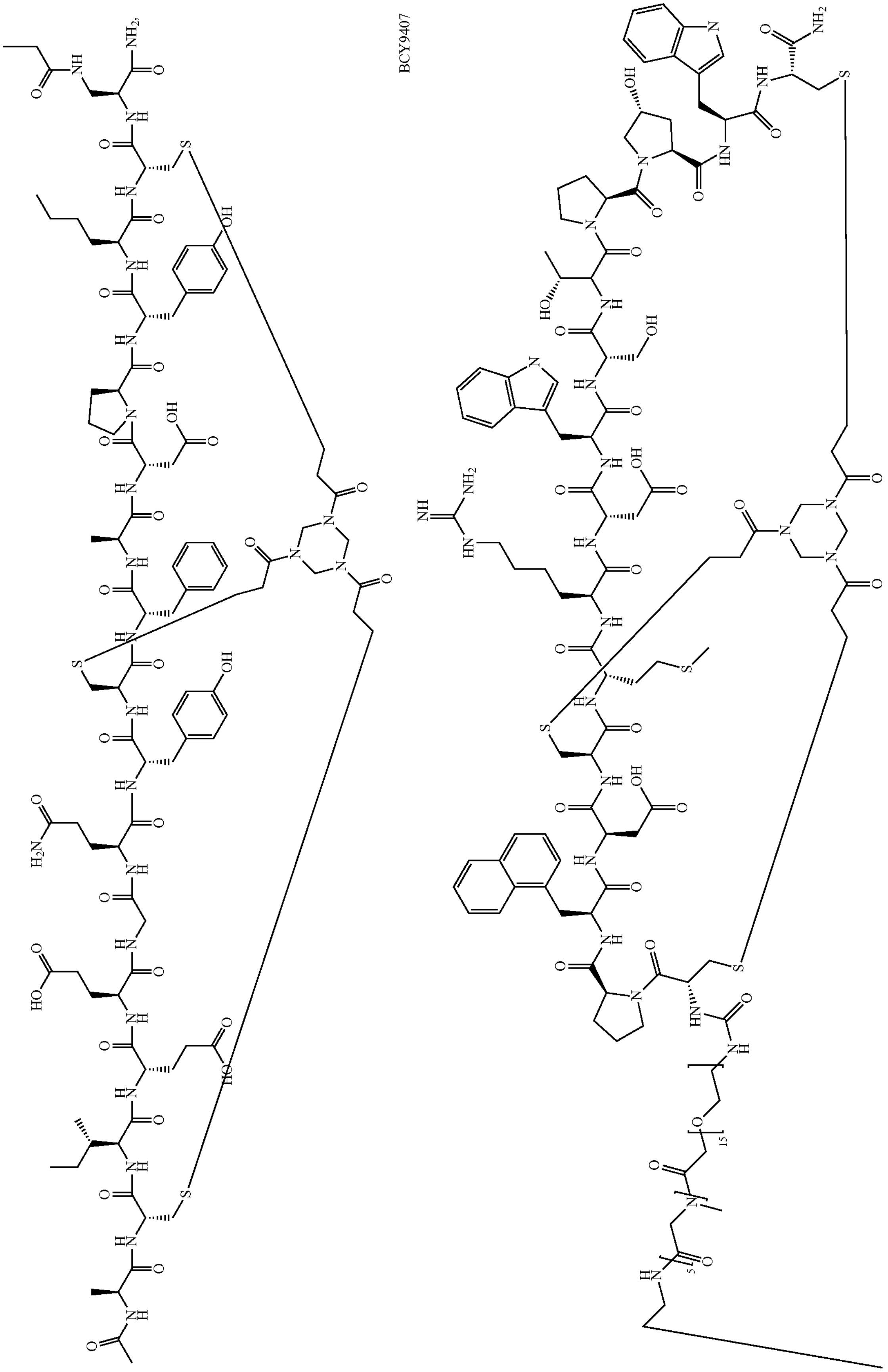
BCY9407

-continued
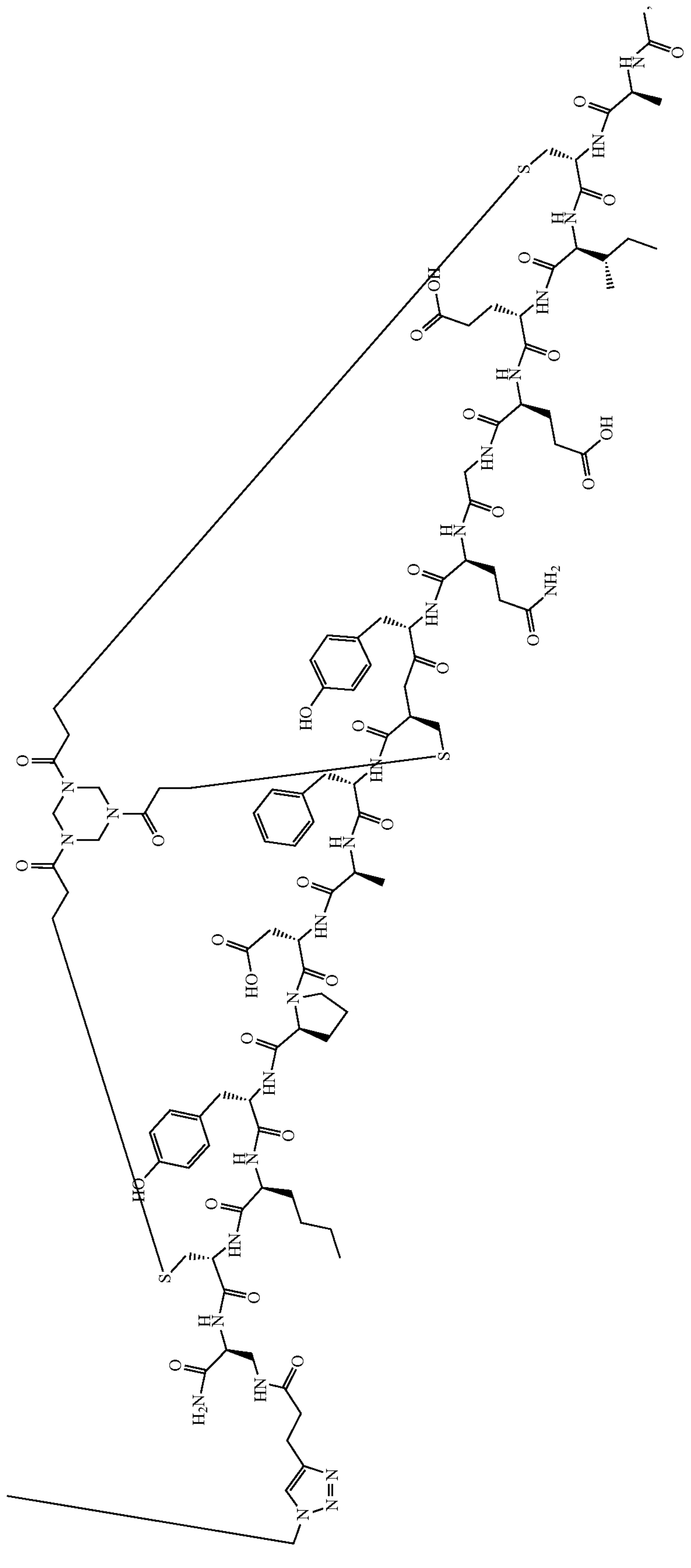

-continued
BCY9408
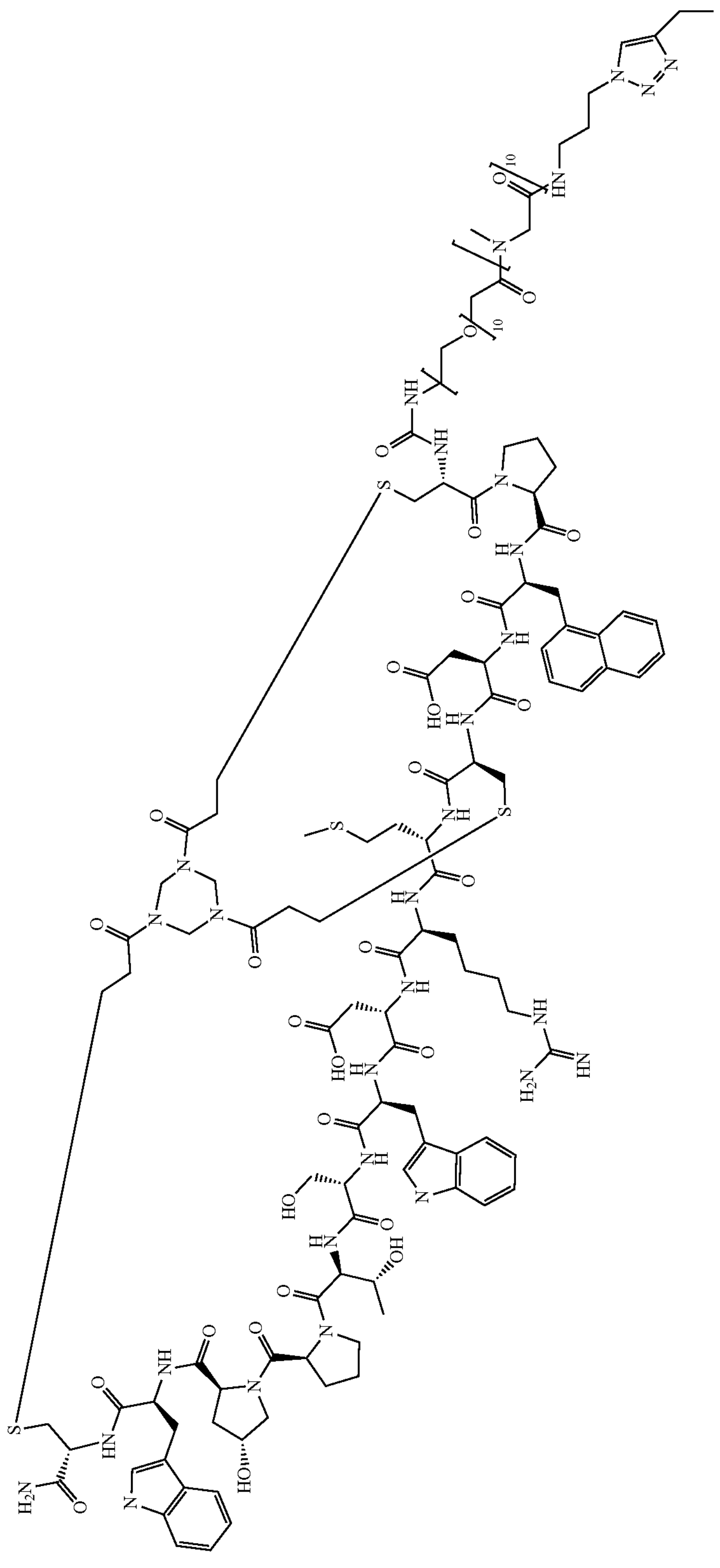

-continued
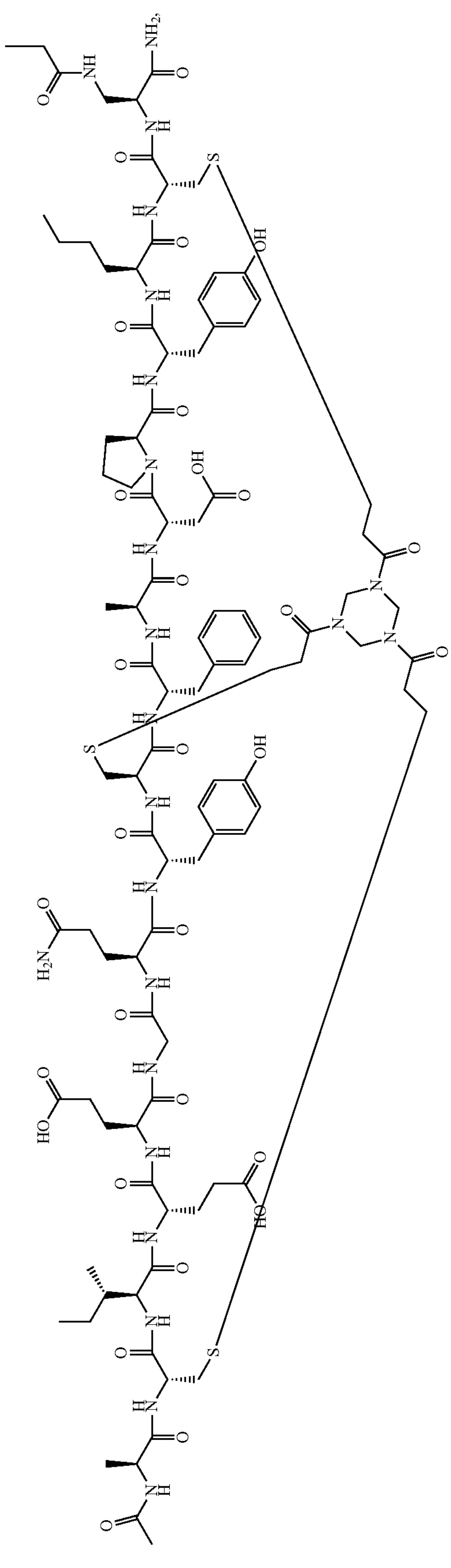
BCY9409
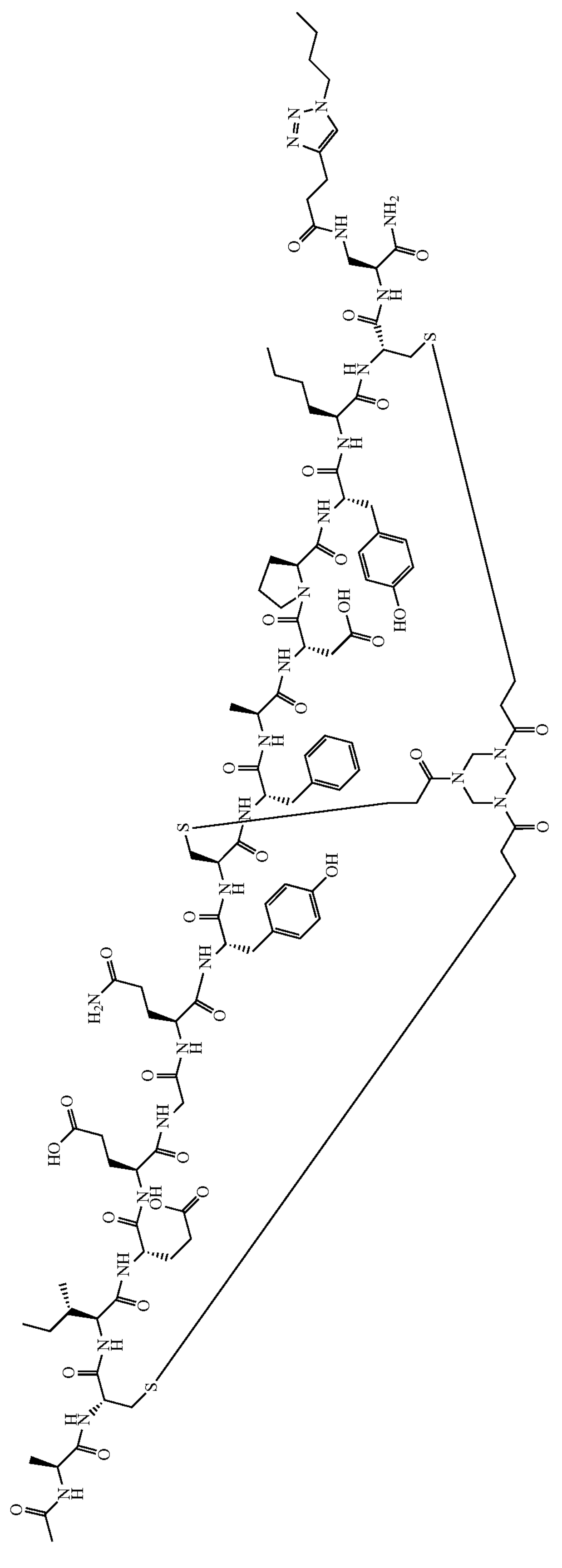

-continued
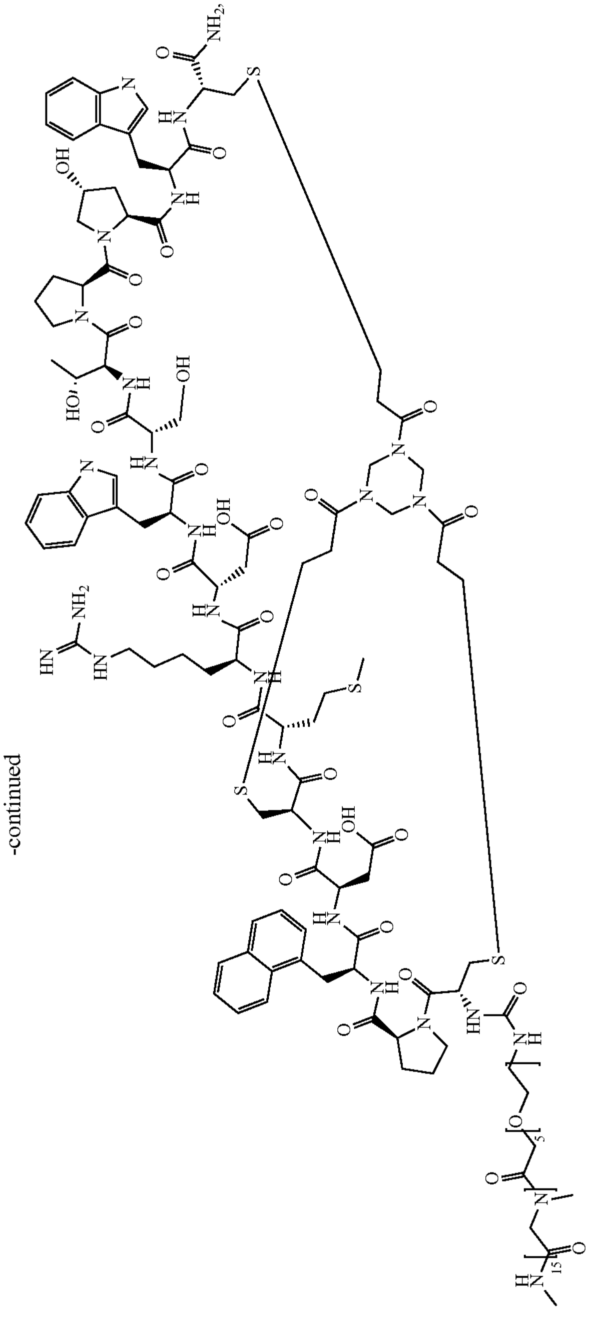
BCY9410
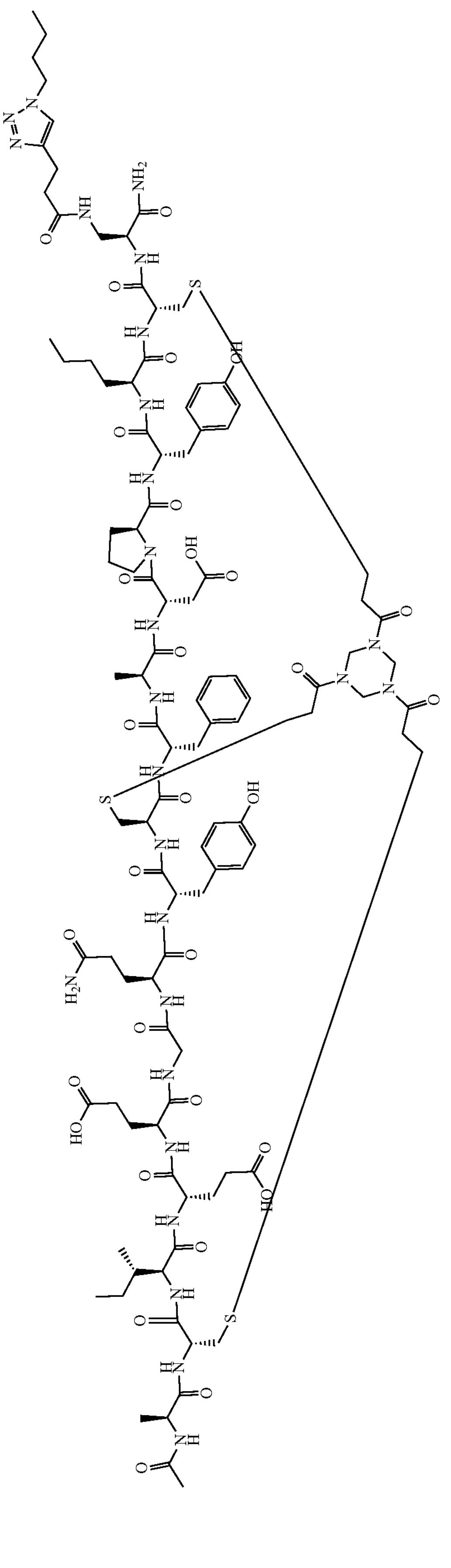

-continued
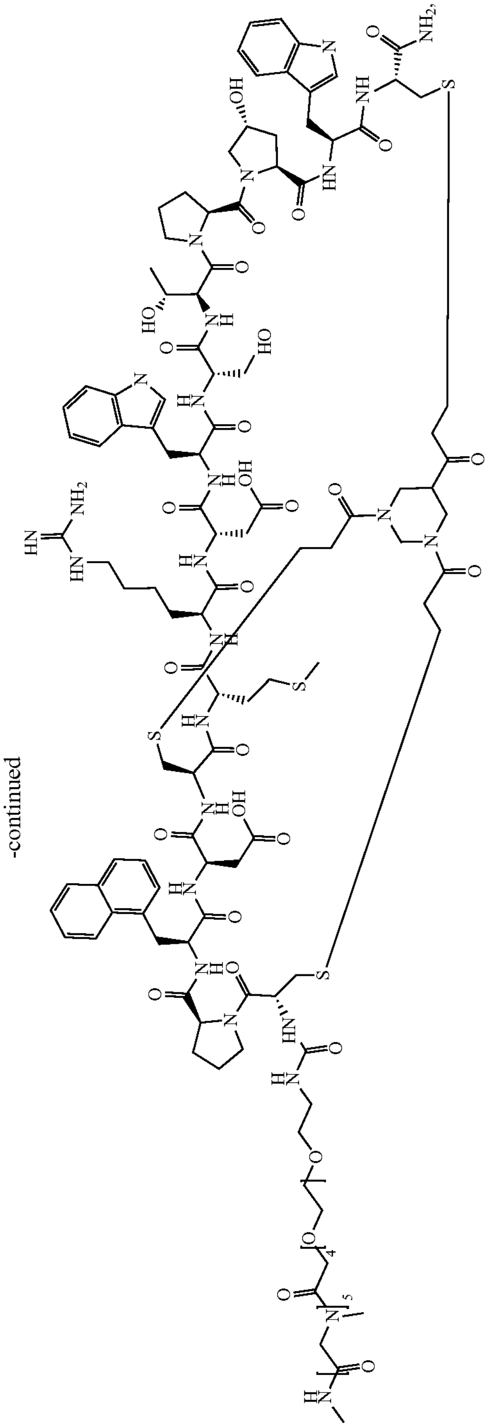
BCY9411
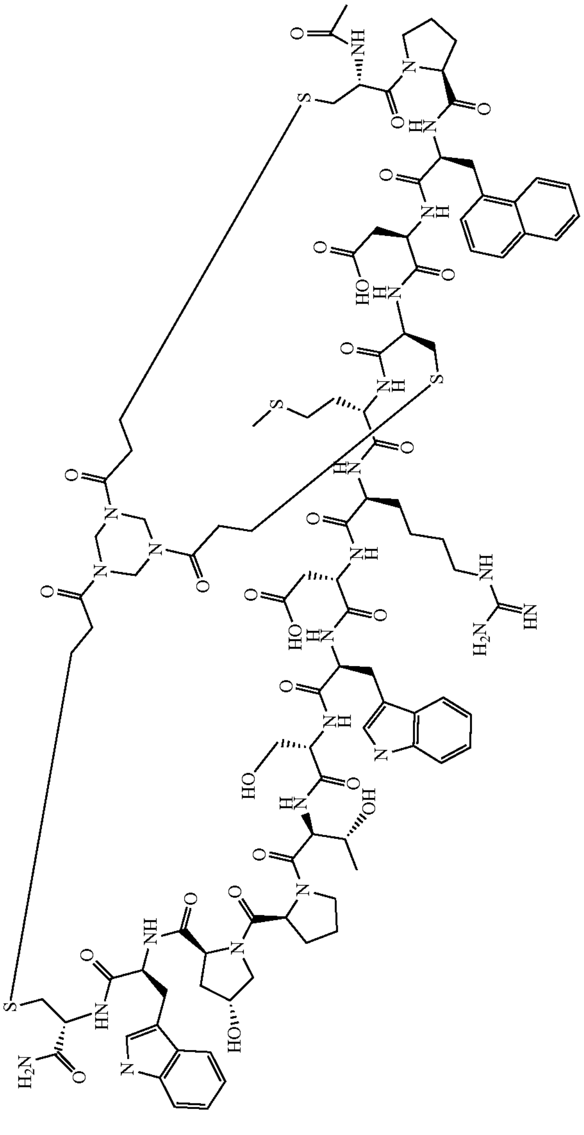

-continued
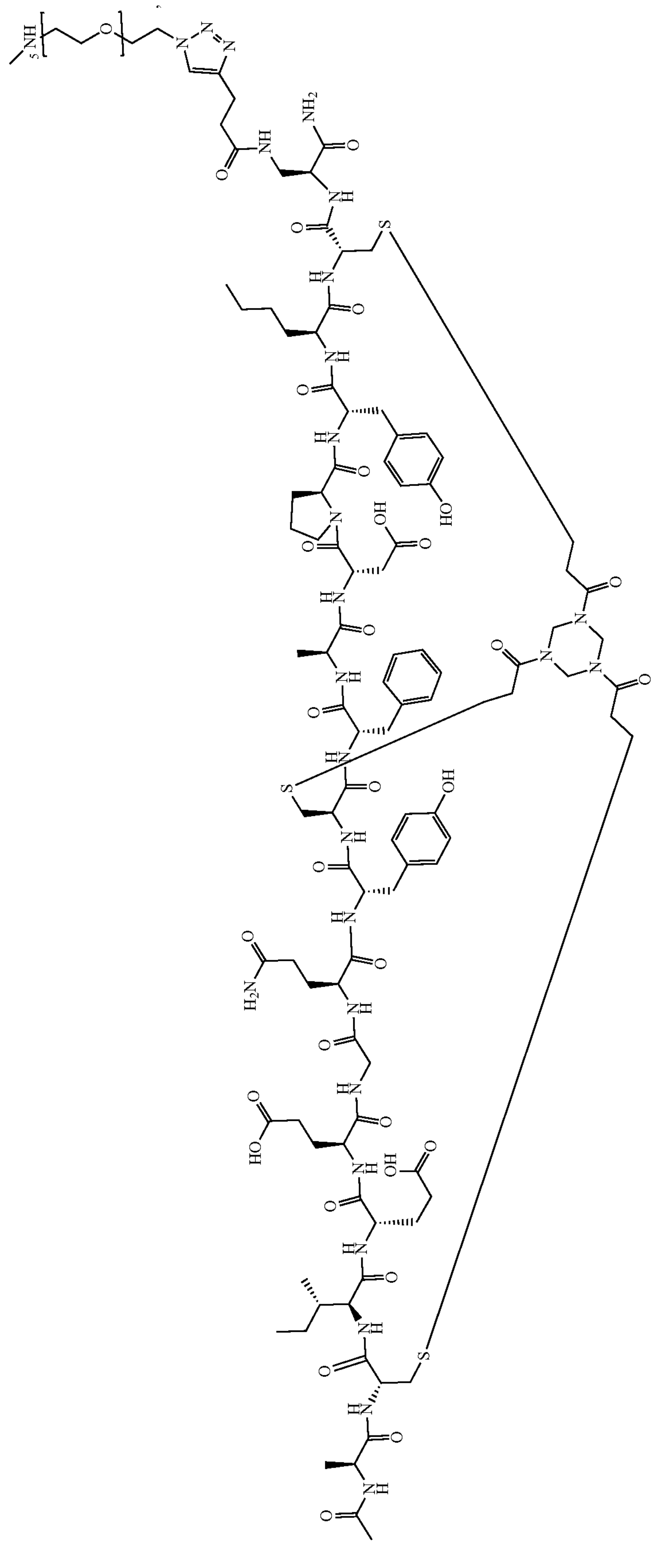

BCY9759
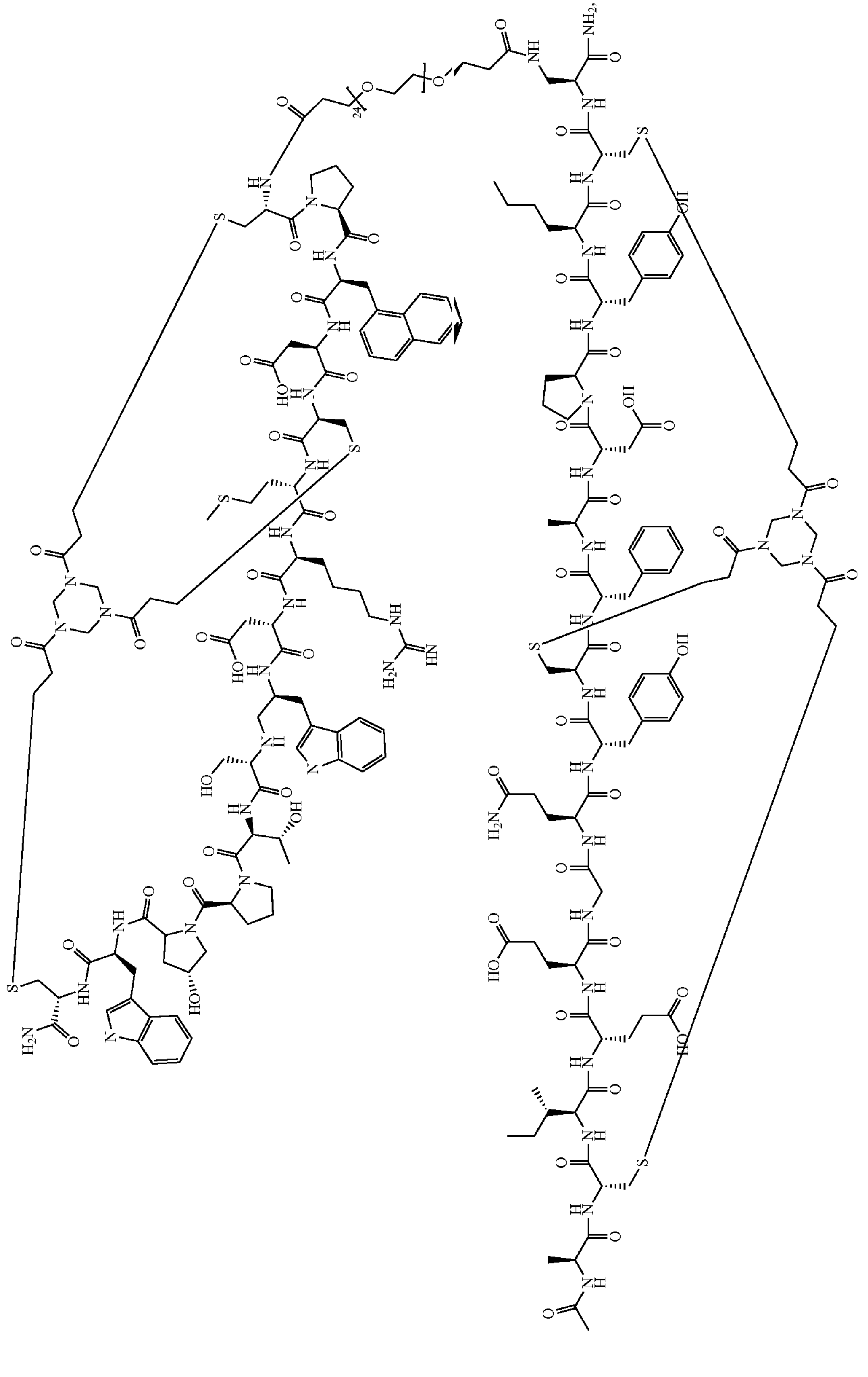

-continued
BCY10000
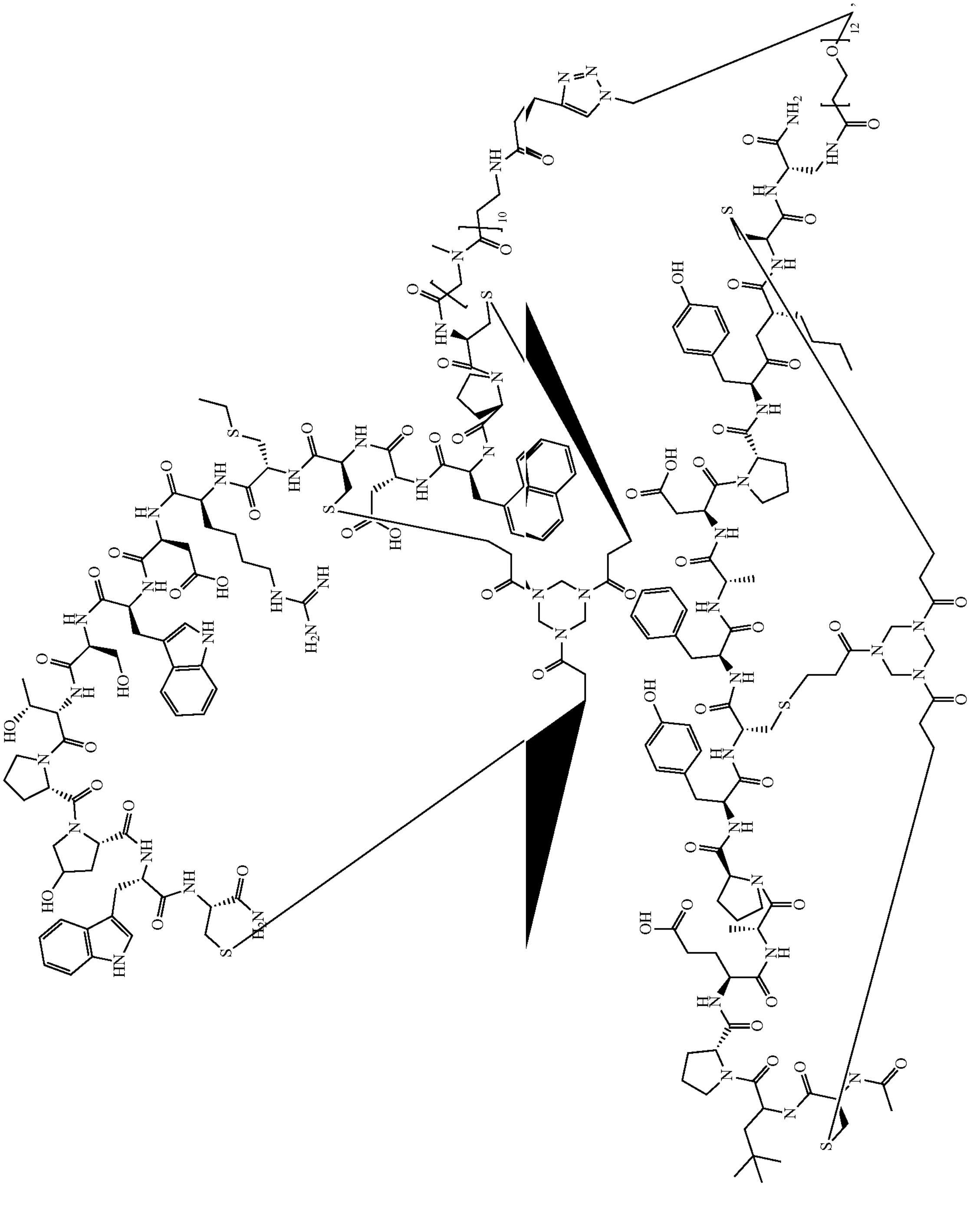

-continued
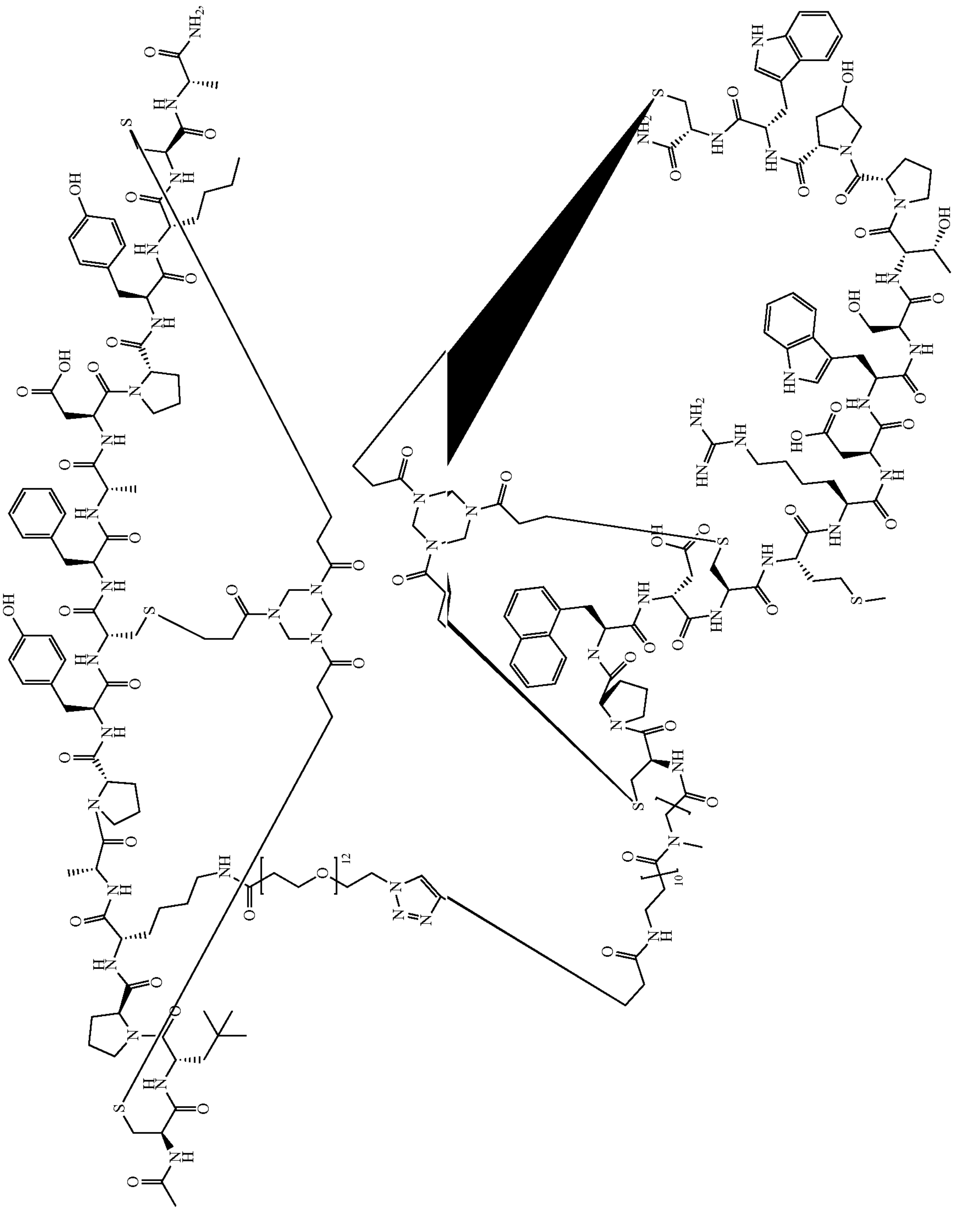
BCY10567

-continued
BCY10569
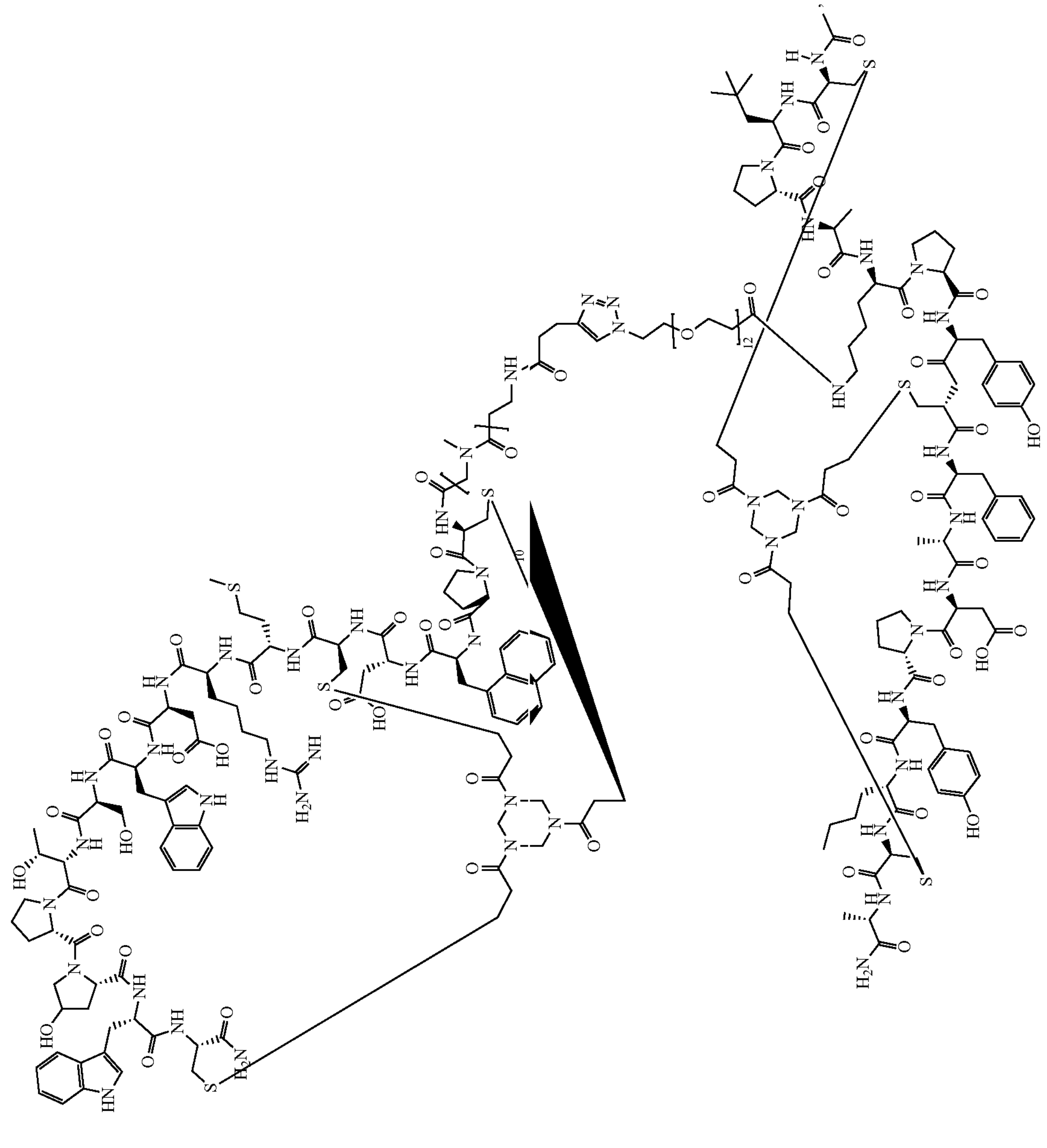

-continued
BCY10571
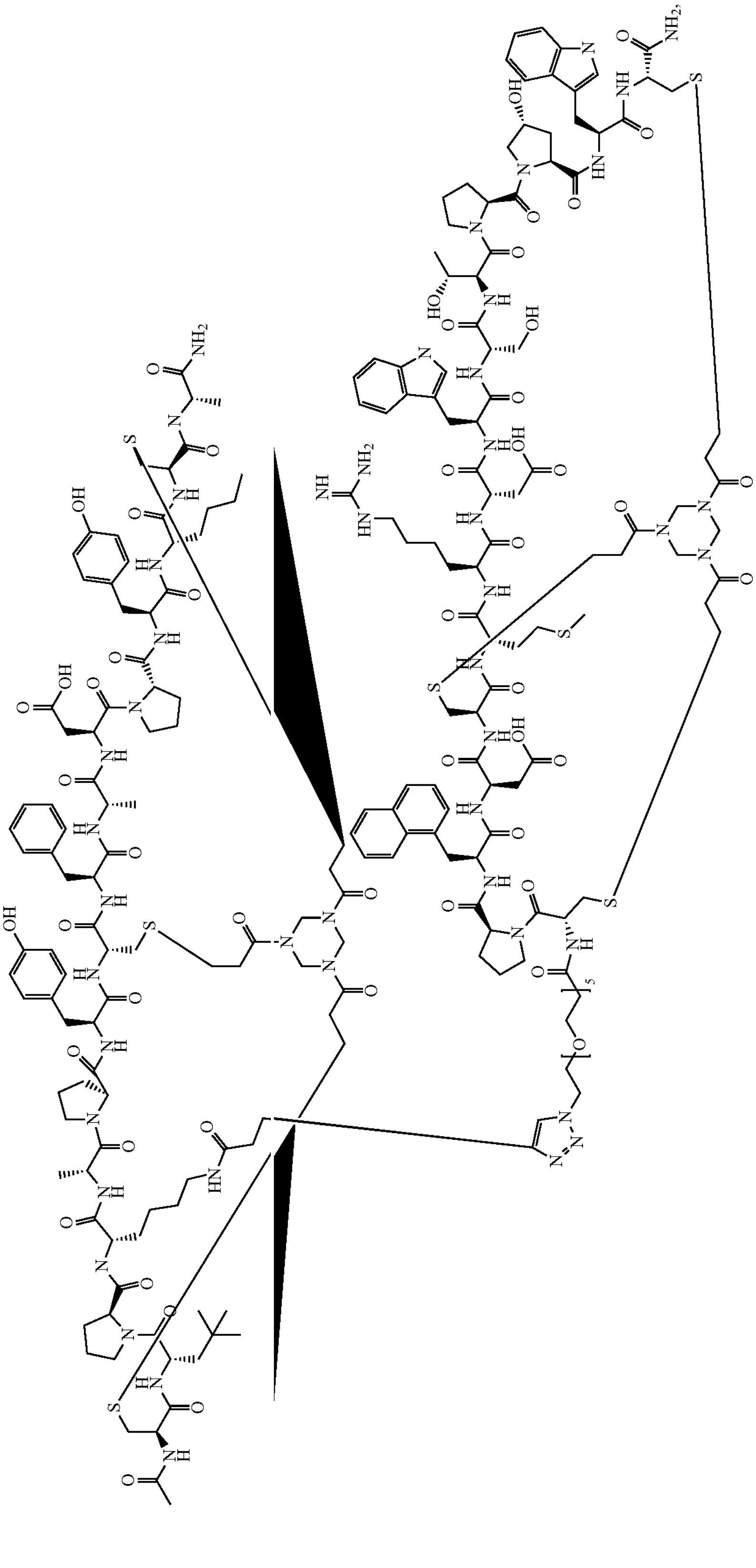

-continued
BCY10572
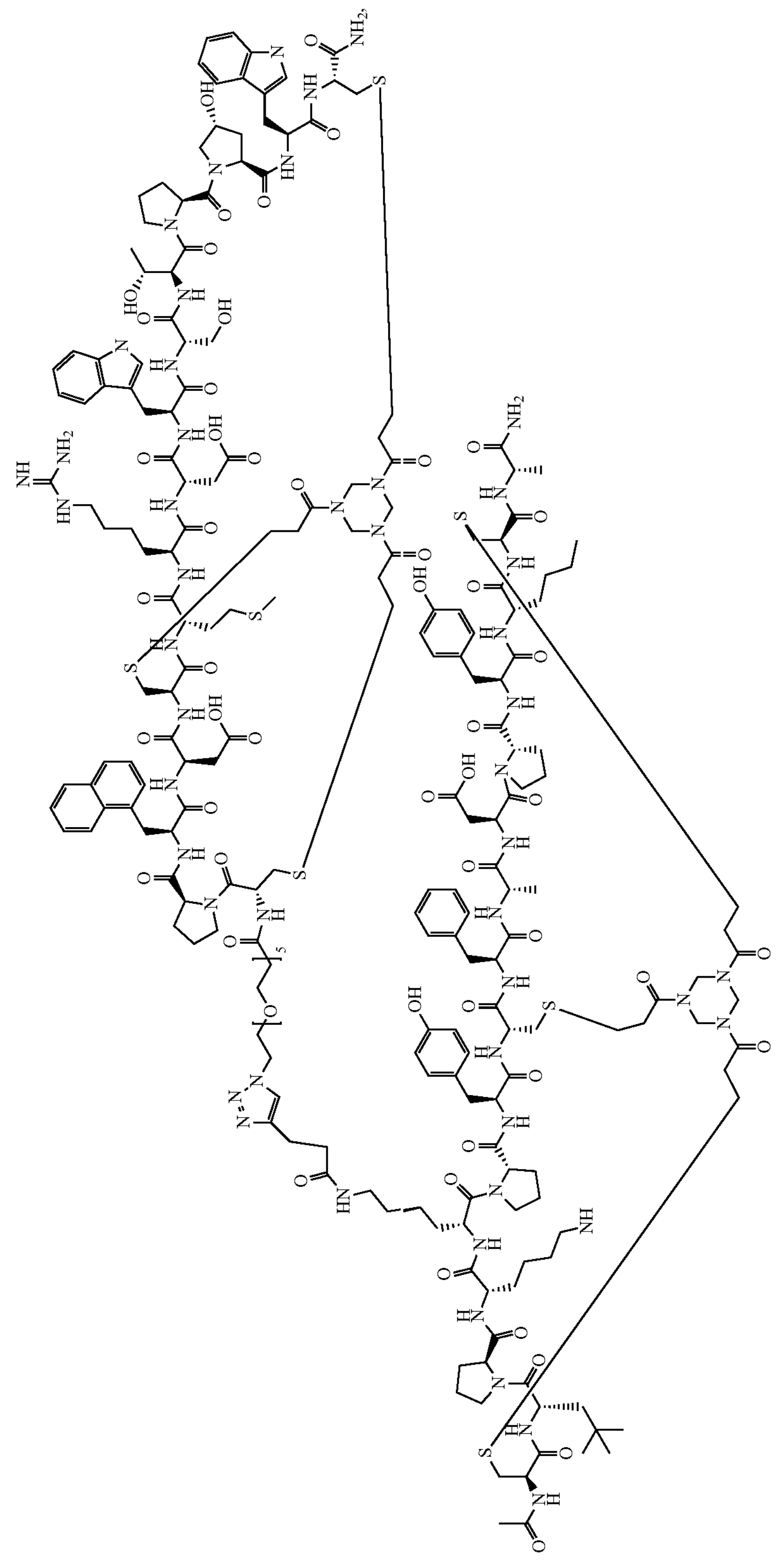
BCY10573
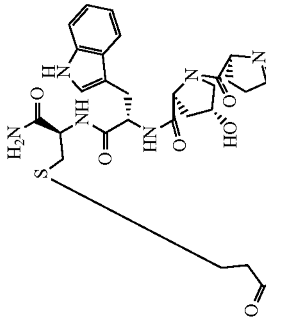

-continued
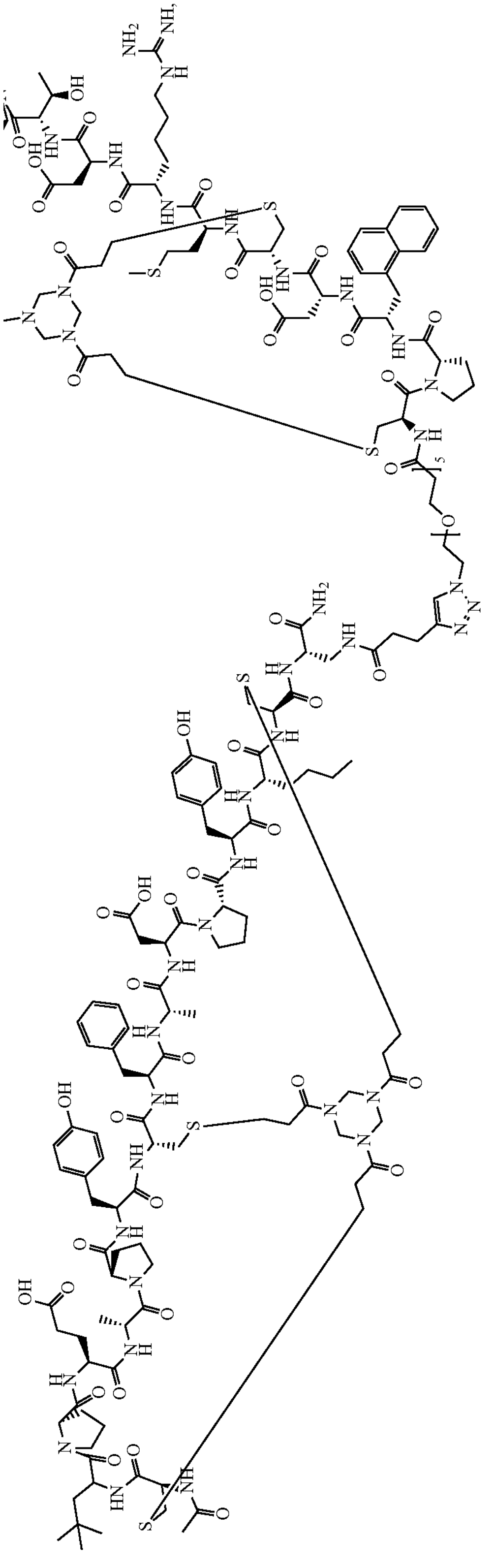

BCY10578
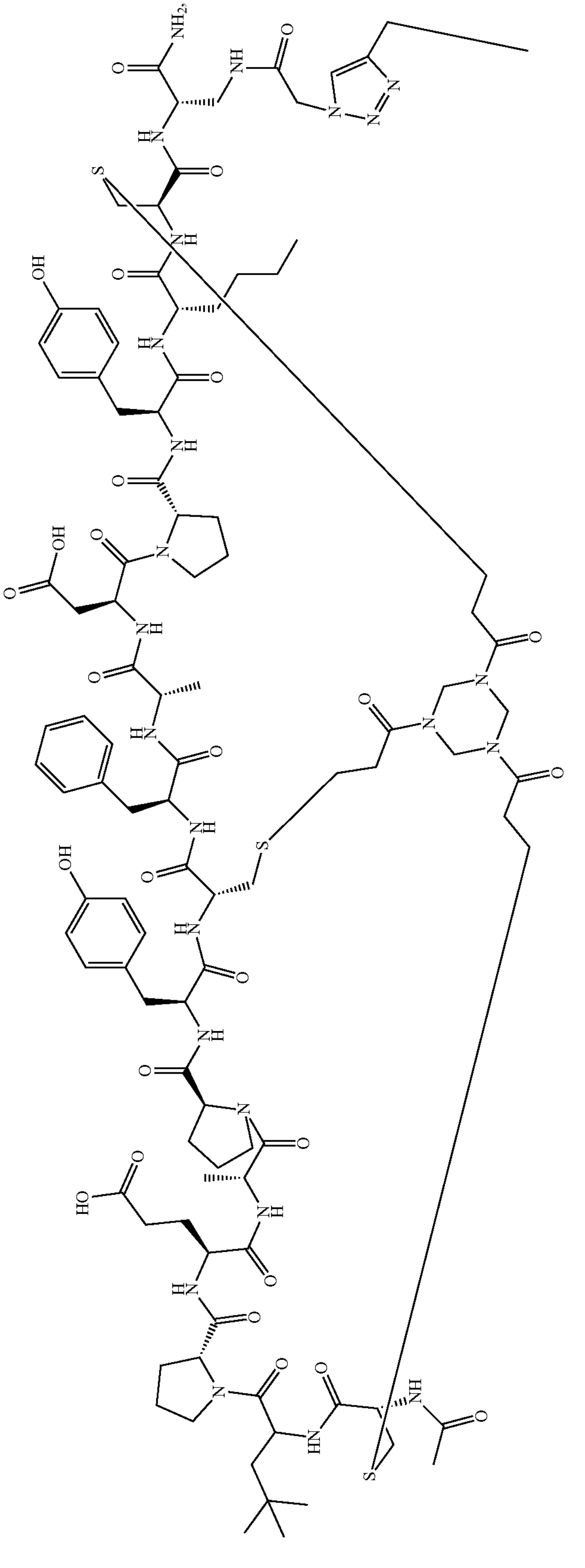

-continued
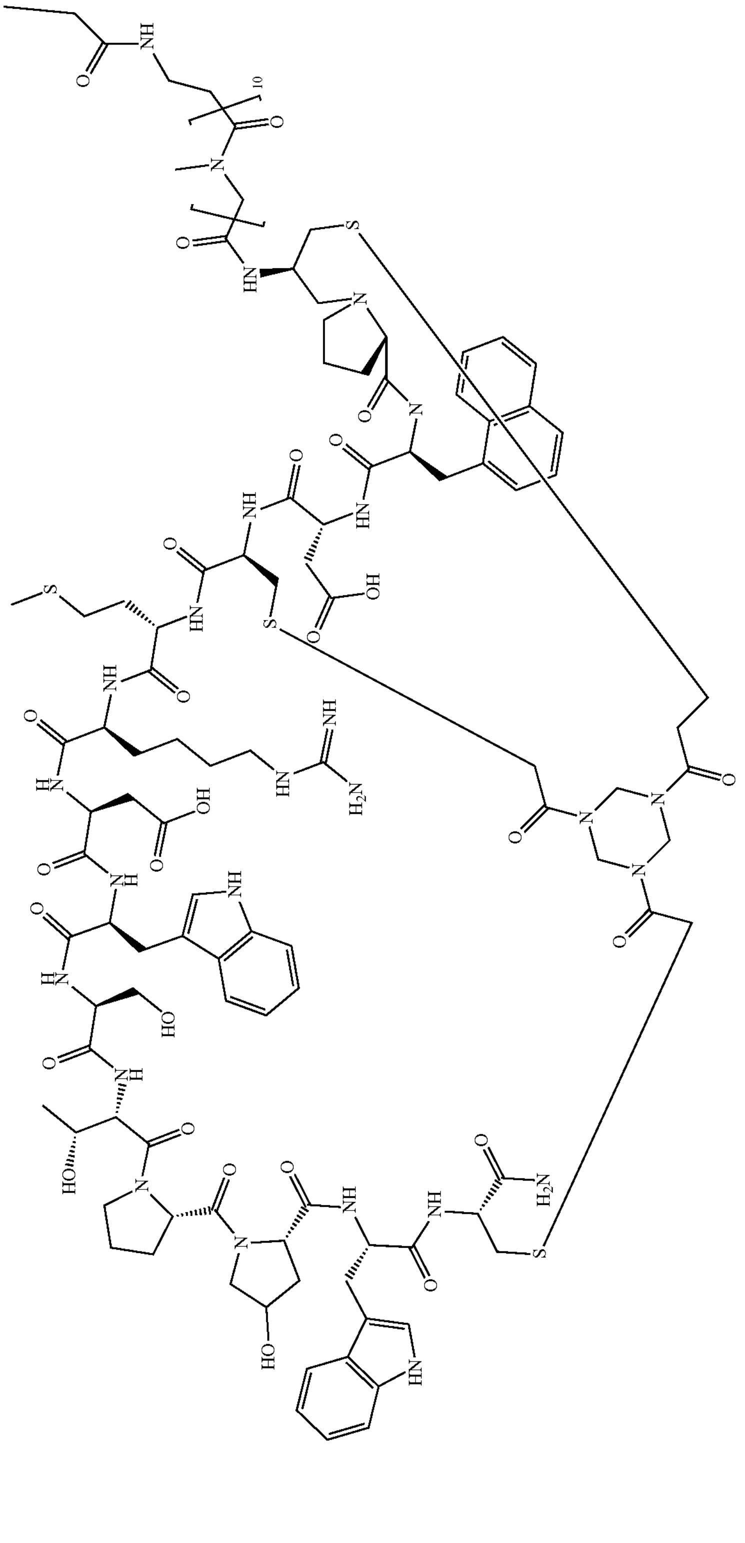

-continued
BCY10917
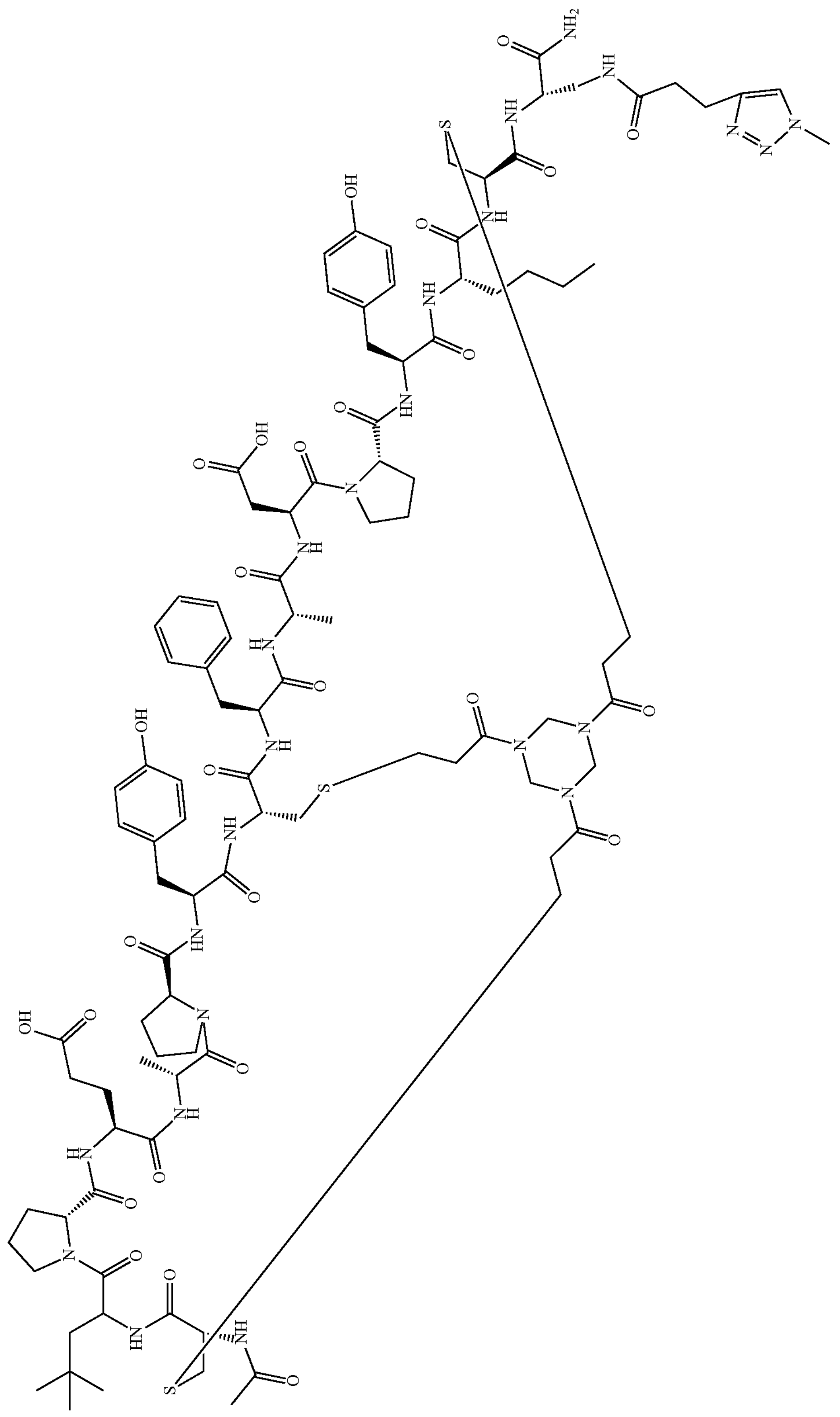

-continued
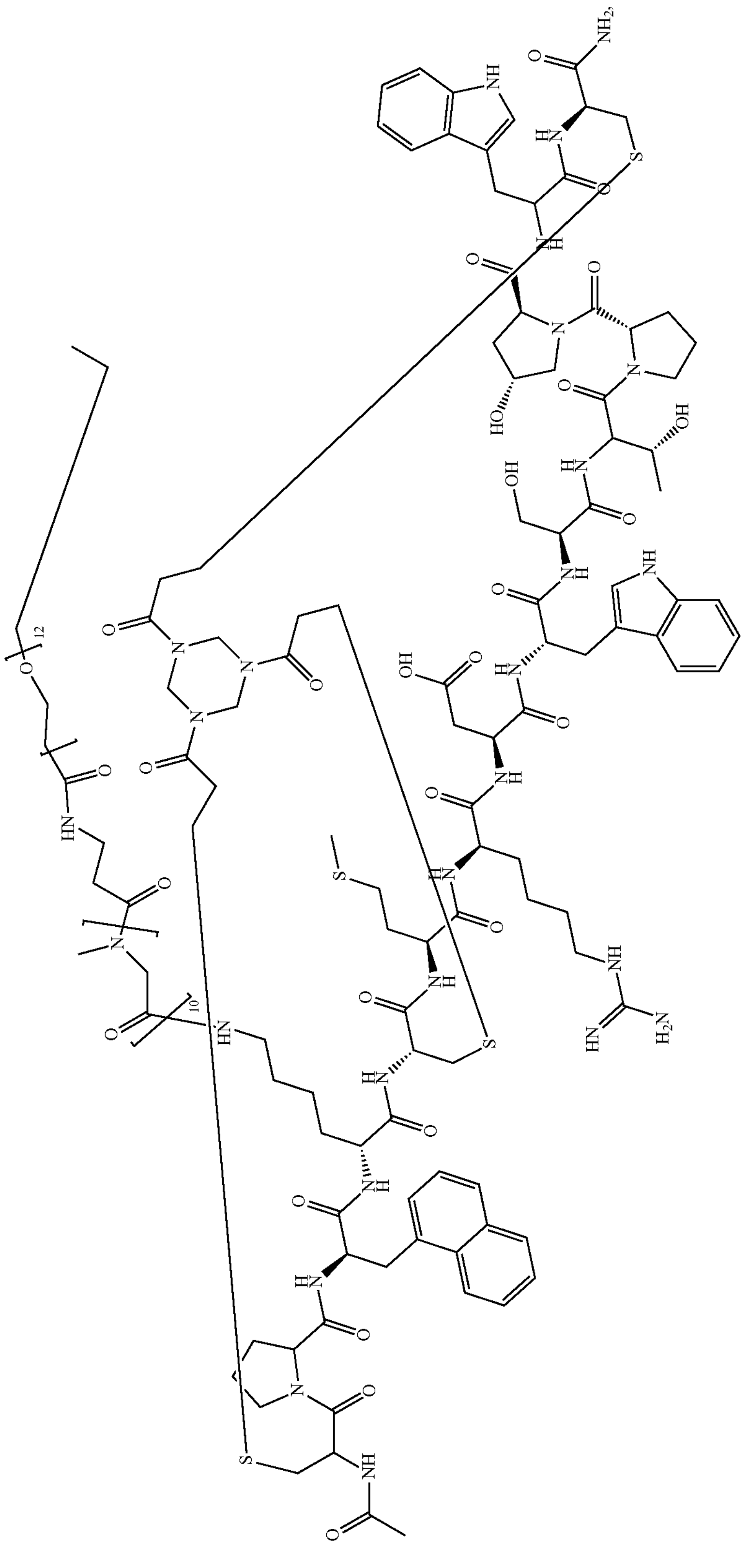

-continued
BCY11020
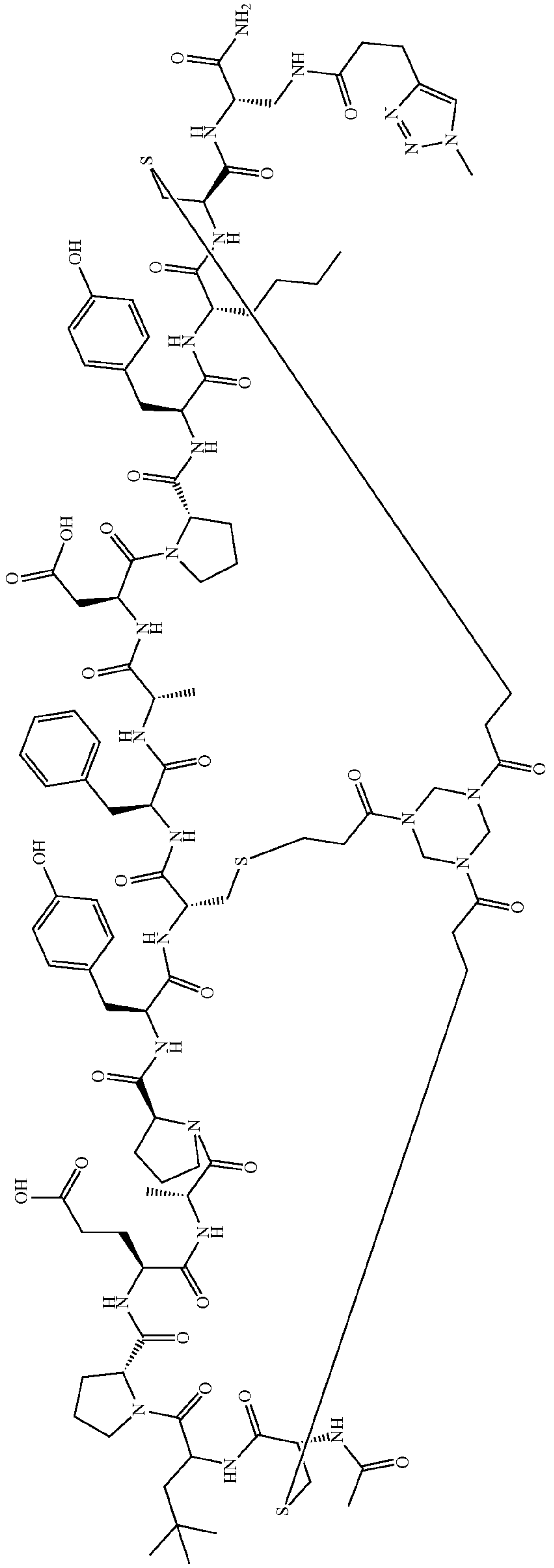

-continued
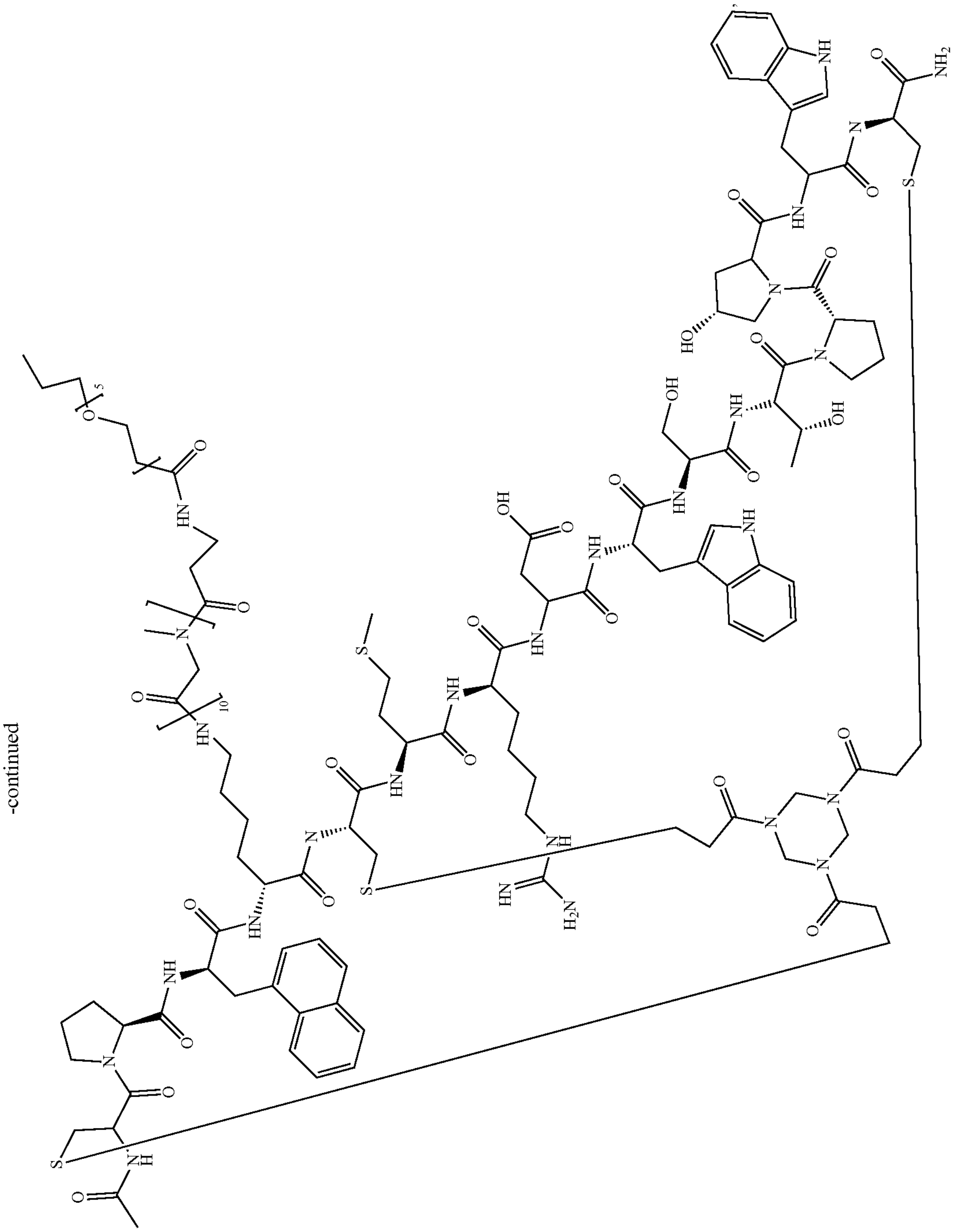

-continued
BCY11373
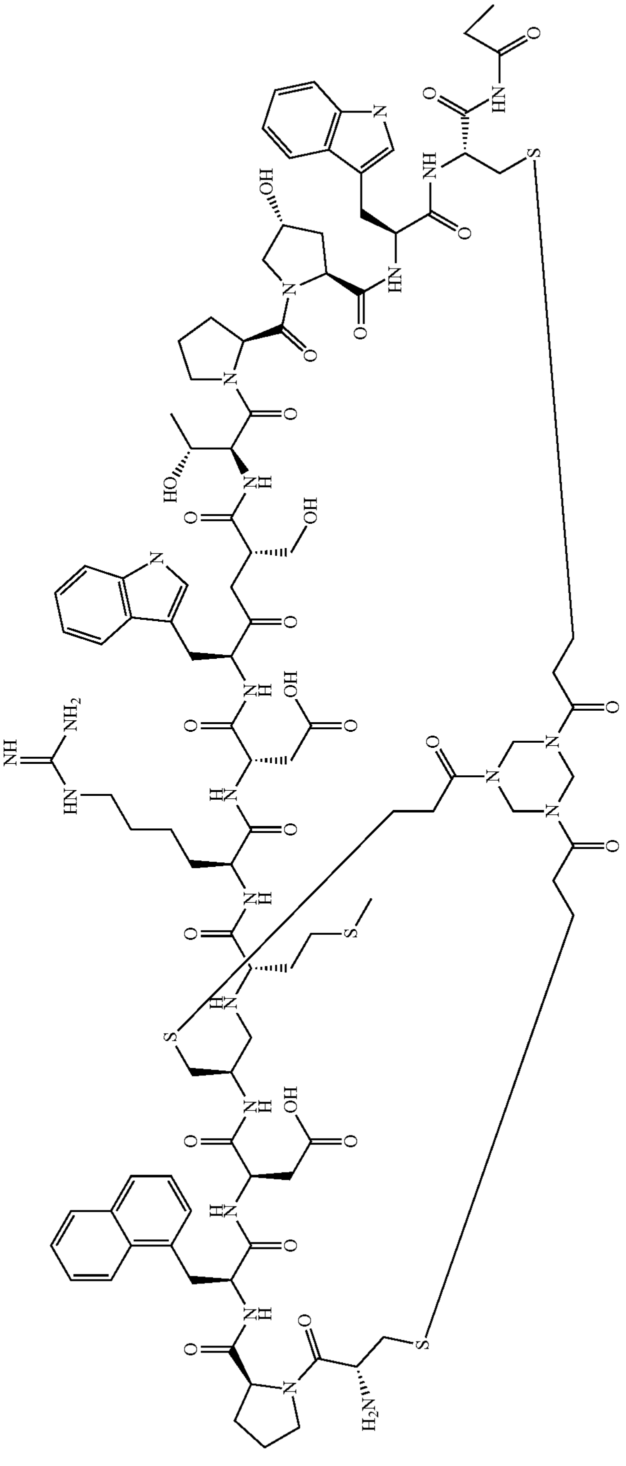

-continued
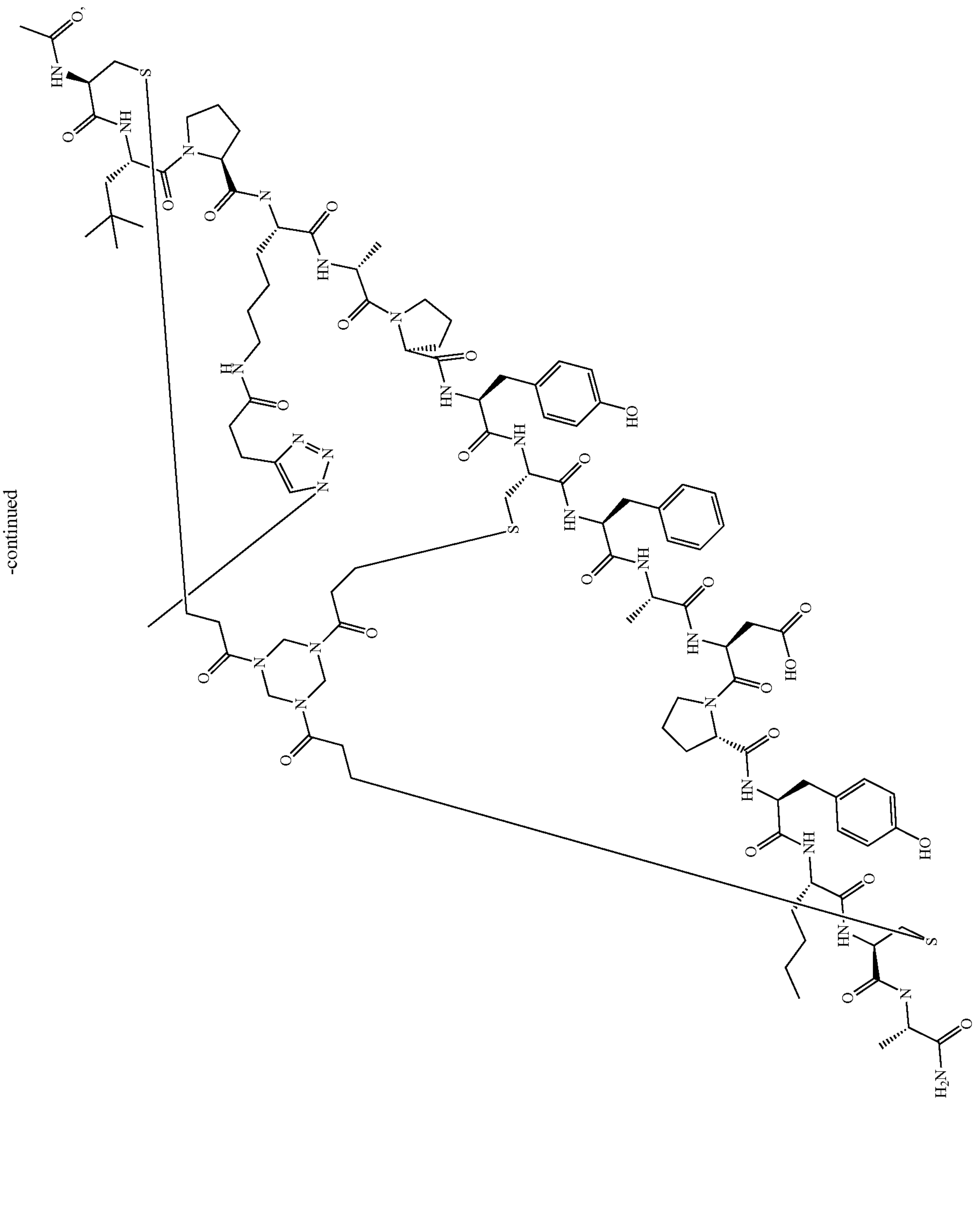

-continued
BCY11374
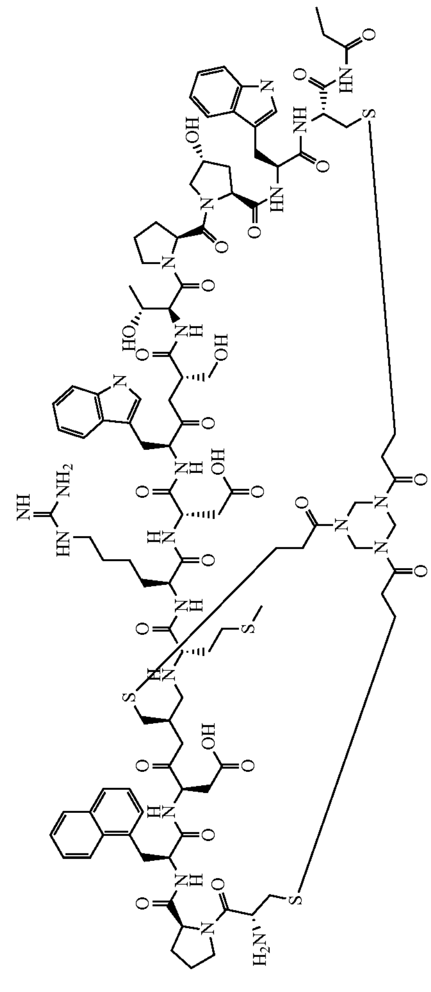

-continued
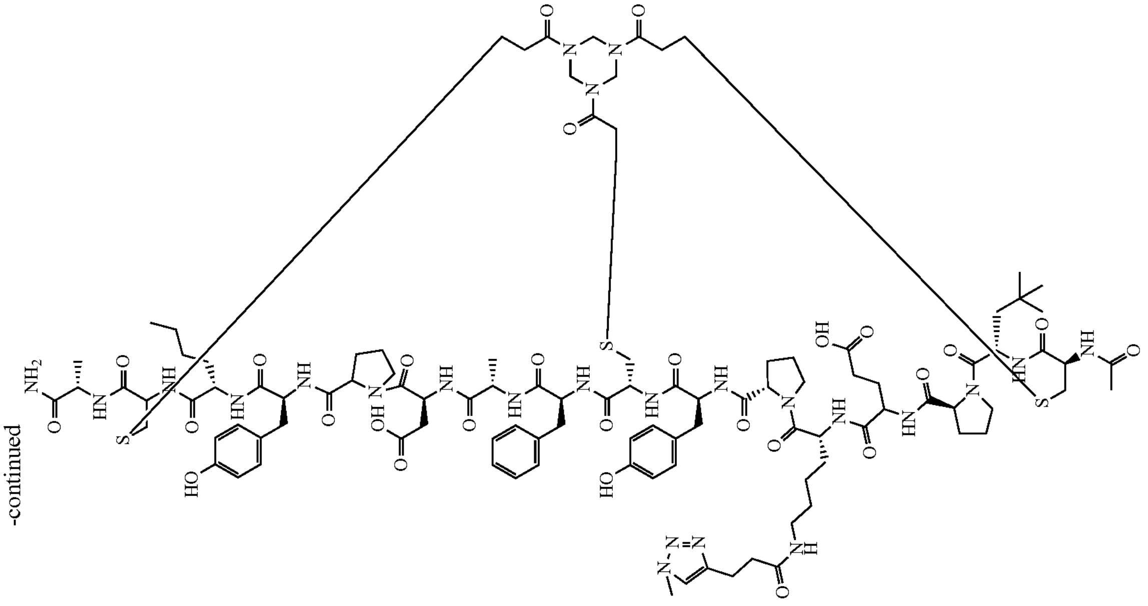

-continued
BCY11375
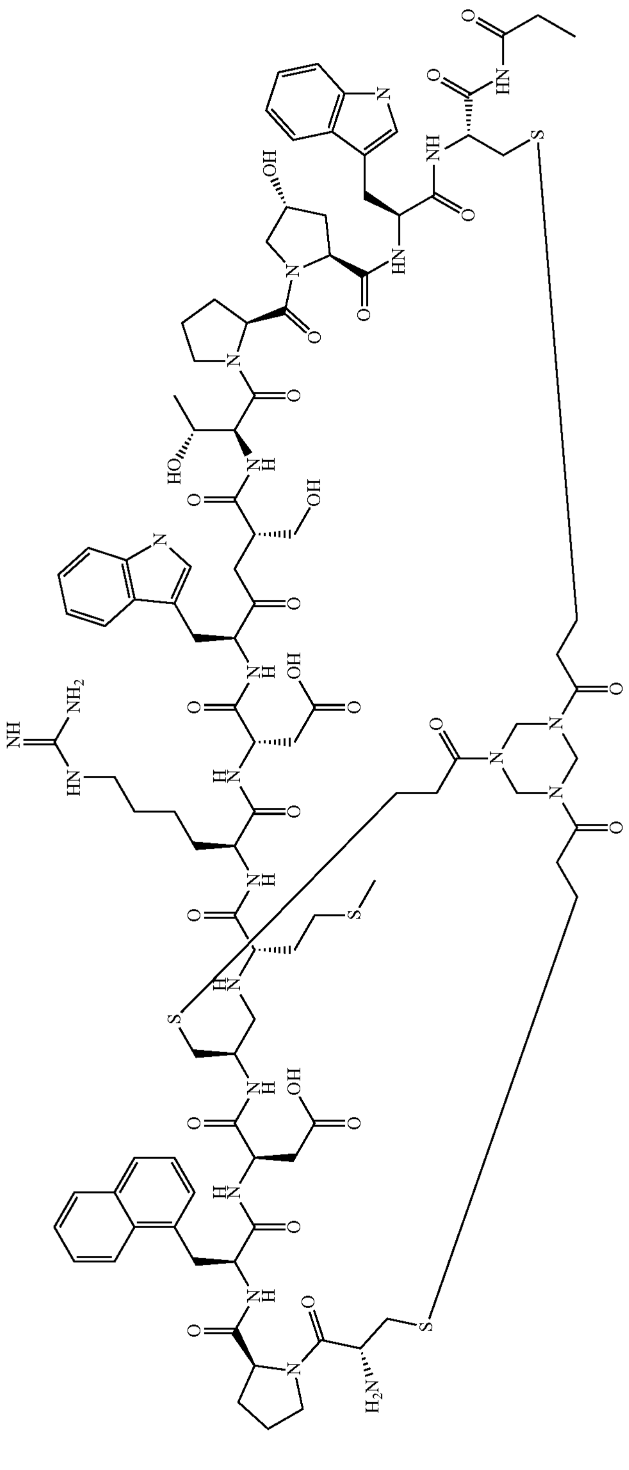

-continued
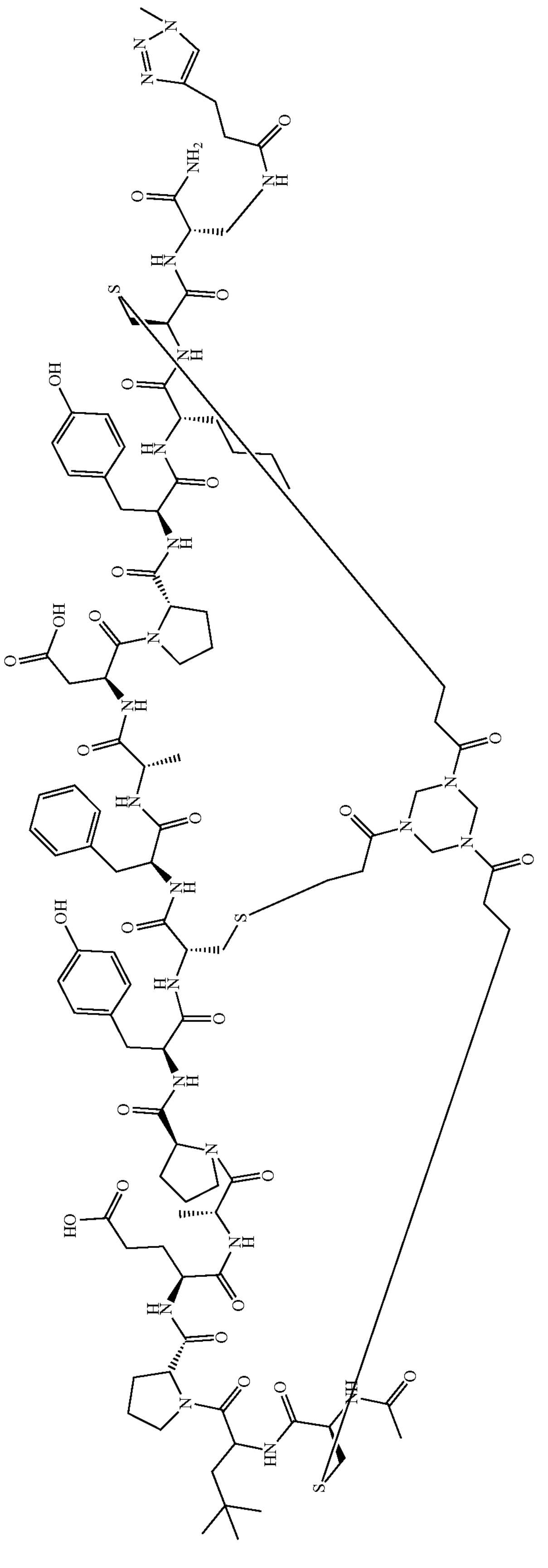

BCY11616
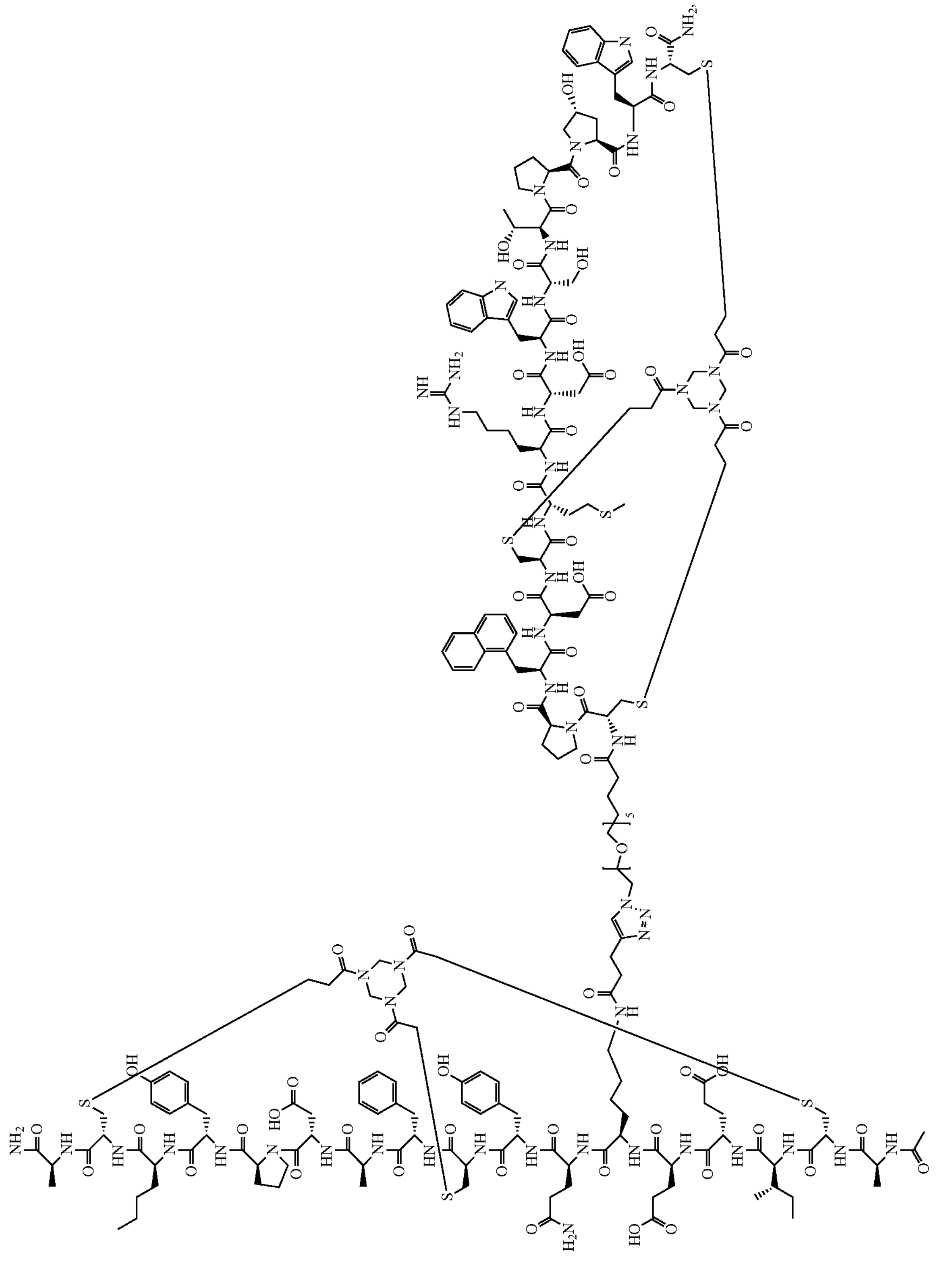

-continued
BCY11617
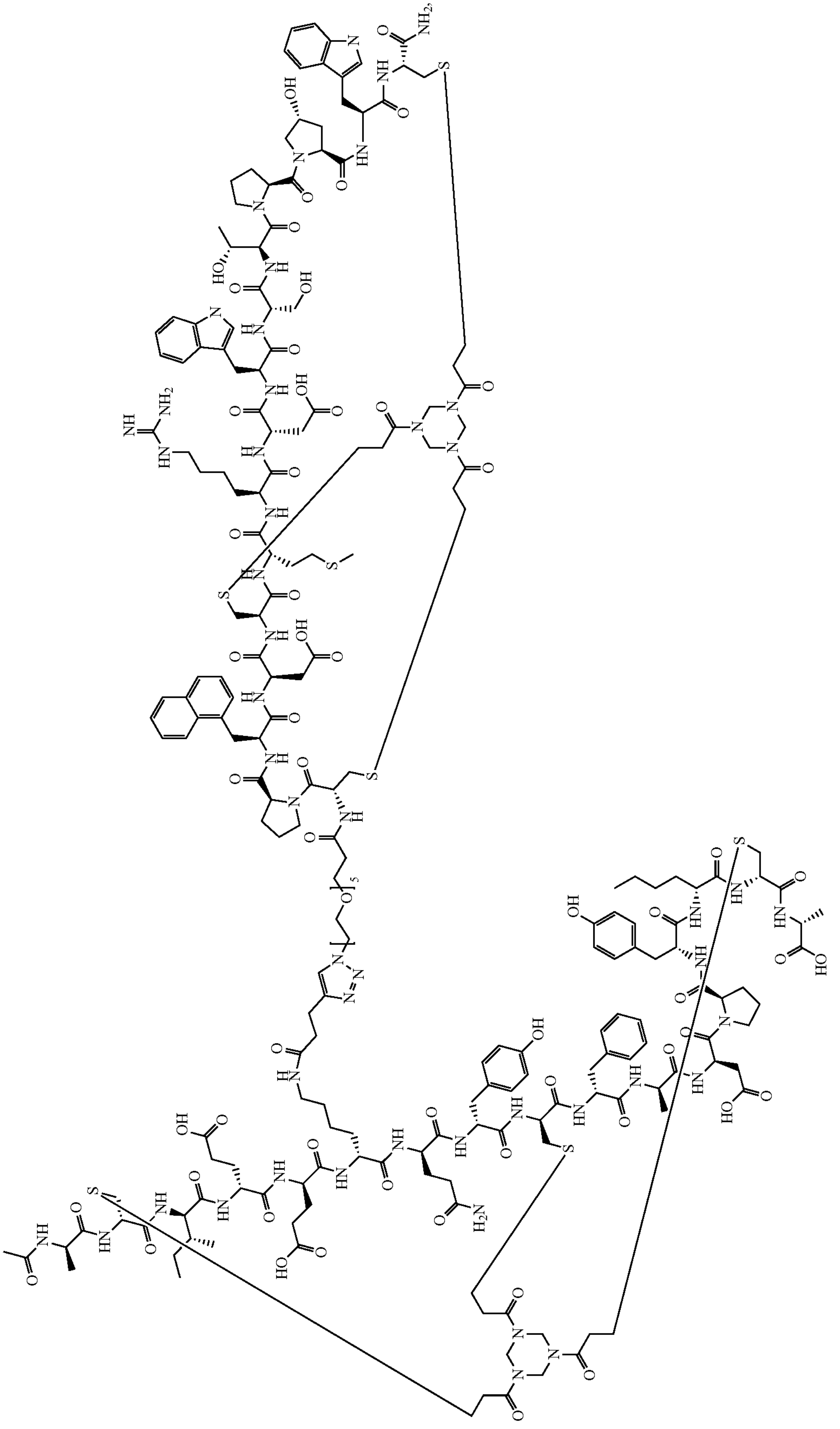

-continued
BCY11857
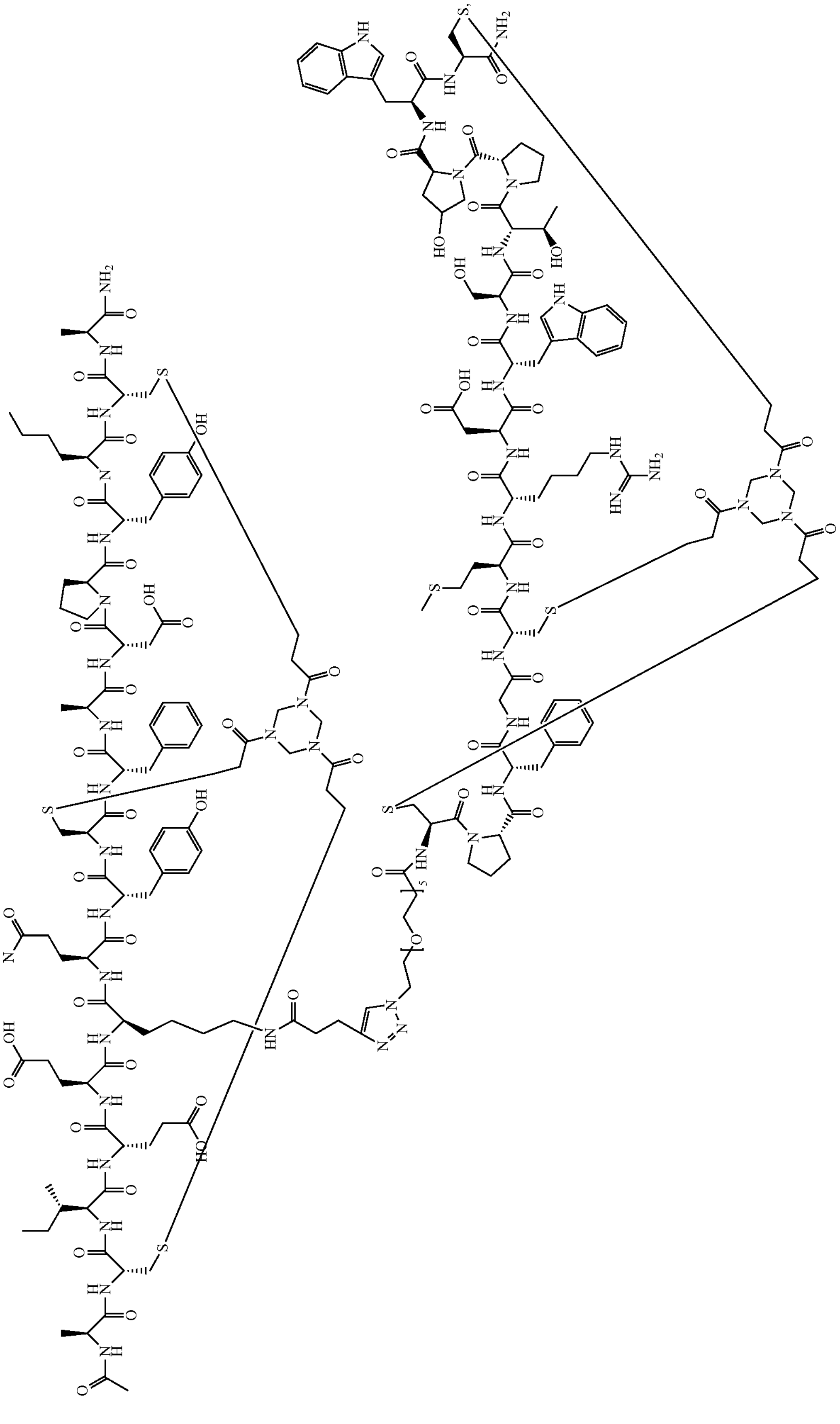

-continued
BCY11858
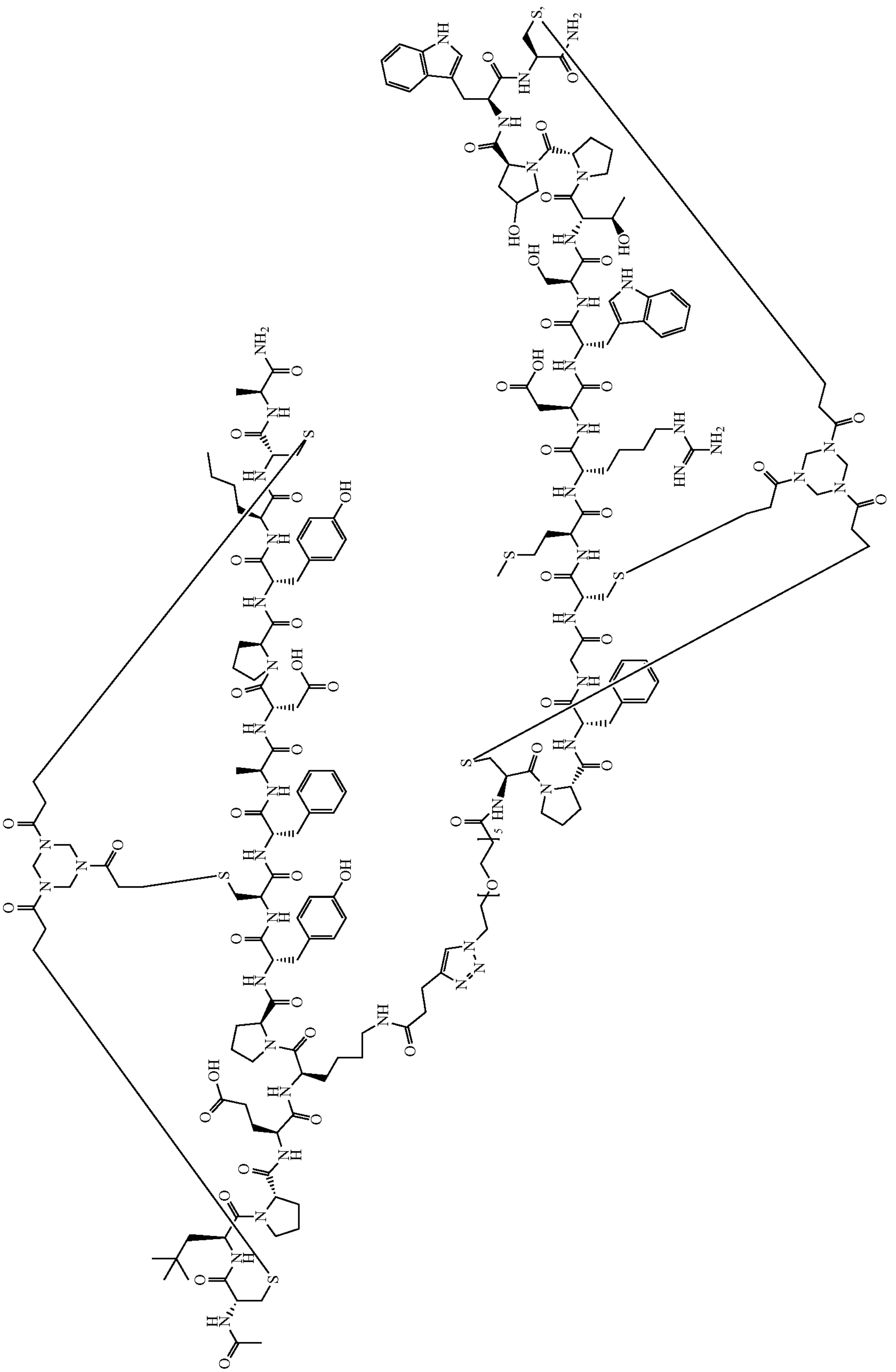
and

-continued
BCY11859
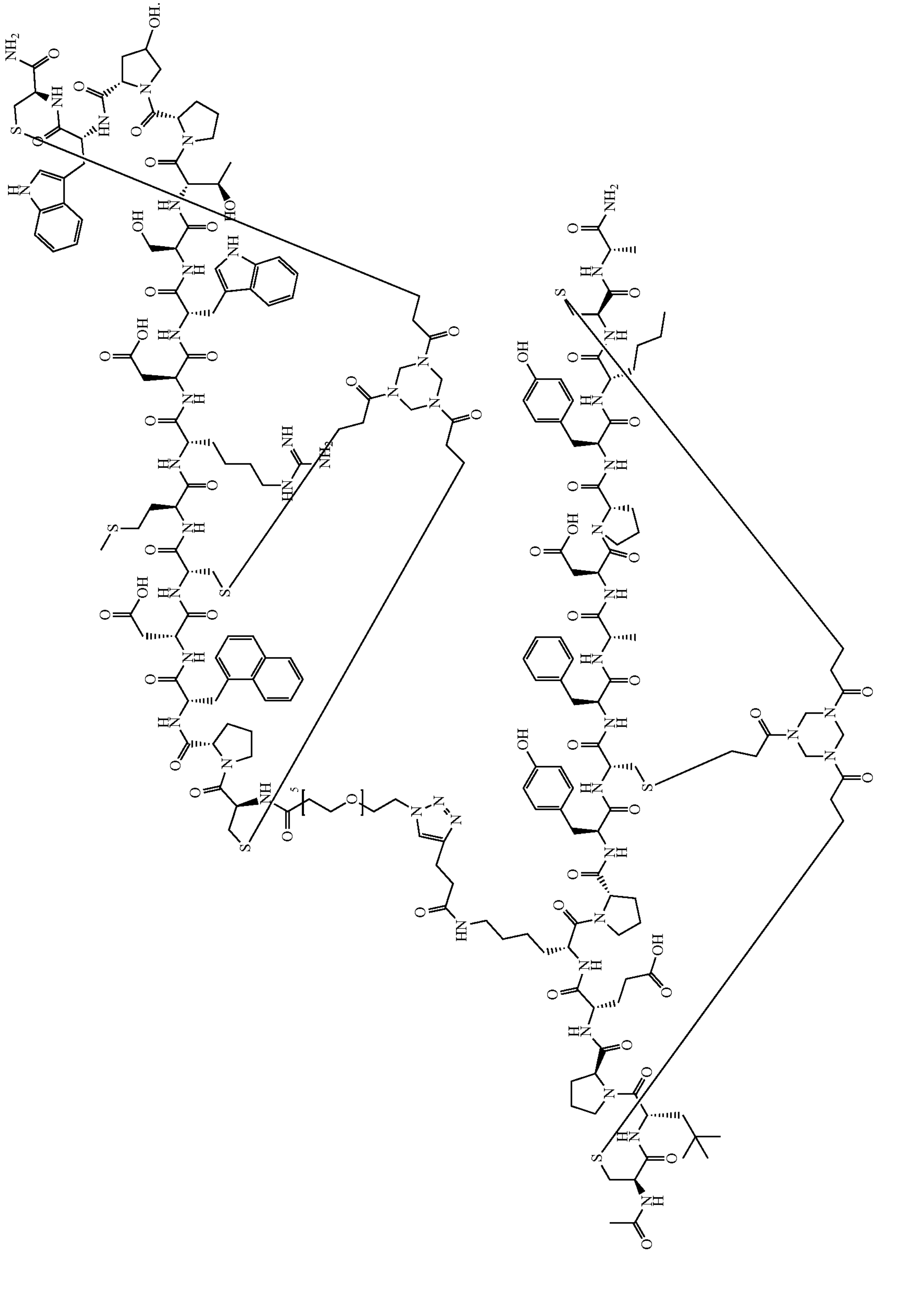

5. The heterotandem bicyclic peptide complex, or a pharmaceutically acceptable salt thereof, as defined in claim 1, wherein the linker is selected from: —$CH_2$—, -$PEG_5$-, -$PEG_{10}$-, -$PEG_{12}$-, -$PEG_{23}$-, -$PEG_{24}$-, -$PEG_{15}$-$Sar_5$-, -$PEG_{10}$-$Sar_{10}$-, -$PEG_5$-$Sar_{15}$-, -$PEG_5$-$Sar_5$-, —B-Ala-$Sar_{20}$-, —B-Ala-$Sar_{10}$-$PEG_{10}$-, —B-Ala-$Sar_5$-$PEG_{15}$-, and —B-Ala-$Sar_5$-$PEG_5$-, wherein B-Ala represents beta-alanine.

6. The heterotandem bicyclic peptide complex, or a pharmaceutically acceptable salt thereof, as defined in claim 1, wherein the molecular scaffold is 1,1',1"-(1,3,5-triazinane-1,3,5-triyl) triprop-2-en-1-one (TATA), which forms covalent bonds with the cysteine residues of the polypeptide such that two polypeptide loops are formed on the molecular scaffold.

7. The heterotandem bicyclic peptide complex, or a pharmaceutically acceptable salt thereof, as defined in claim 1, wherein the heterotandem bicyclic peptide complex is a free acid, or a pharmaceutically acceptable salt selected from the sodium, potassium, calcium, and ammonium salt.

8. A pharmaceutical composition which comprises the heterotandem bicyclic peptide complex, or a pharmaceutically acceptable salt thereof, of claim 1 in combination with one or more pharmaceutically acceptable excipients.

9. A pharmaceutical composition which comprises the heterotandem bicyclic peptide complex, or a pharmaceutically acceptable salt thereof, of claim 2 in combination with one or more pharmaceutically acceptable excipients.

10. A pharmaceutical composition which comprises the heterotandem bicyclic peptide complex, or a pharmaceutically acceptable salt thereof, of claim 3 in combination with one or more pharmaceutically acceptable excipients.

11. A pharmaceutical composition which comprises the heterotandem bicyclic peptide complex, or a pharmaceutically acceptable salt thereof, of claim 4 in combination with one or more pharmaceutically acceptable excipients.

12. A pharmaceutical composition which comprises the heterotandem bicyclic peptide complex, or a pharmaceutically acceptable salt thereof, of claim 5 in combination with one or more pharmaceutically acceptable excipients.

13. A pharmaceutical composition which comprises the heterotandem bicyclic peptide complex, or a pharmaceutically acceptable salt thereof, of claim 6 in combination with one or more pharmaceutically acceptable excipients.

14. The heterotandem bicyclic peptide complex, or a pharmaceutically acceptable salt thereof, as defined in claim 1, wherein the first and/or second peptide ligand comprises a C-terminal amide group.

15. The heterotandem bicyclic peptide complex, or a pharmaceutically acceptable salt thereof, as defined in claim 2, wherein the CD137 binding bicyclic peptide ligand comprises N- and C-terminal modifications and comprises an amino acid sequence selected from:

Ac-A-CiIEEGQYCiiFADPY[Nle]Ciii-Dap (Ac-A-(SEQ ID NO: 1)-Dap);

Ac-A-CiIEEGQYCiiFADPY[Nle]Ciii-Dap(PYA) (Ac-A-(SEQ ID NO: 1)-Dap(PYA));

Ac-Ci[tBuAla]PE[D-Ala]PYCiiFADPY[Nle]Ciii-Dap (Ac-(SEQ ID NO: 3)-Dap);

Ac-Ci[tBuAla]PE[D-Ala]PYCiiFADPY[Nle]Ciii-Dap(PYA) (Ac-(SEQ ID NO: 3)-Dap(PYA));

-continued

Ac-A-CiIEEGQYCiiF[D-Ala]DPY[Nle]Ciii-Dap (Ac-A-(SEQ ID NO: 4)-Dap);

Ac-Ci[tBuAla]PK[D-Ala]PYCiiFADPY[Nle]Ciii-A (Ac-(SEQ ID NO: 5)-A);

Ac-Ci[tBuAla]PE[D-Lys]PYCiiFADPY[Nle]Ciii-A (Ac-(SEQ ID NO: 6)-A);

Ac-Ci[tBuAla]P[K(PYA)][D-Ala]PYCiiFADPY[Nle]Ciii-A (Ac-(SEQ ID NO: 7)-A);

Ac-Ci[tBuAla]PE[D-Lys(PYA)]PYCiiFADPY[Nle]Ciii-A (Ac-(SEQ ID NO: 8)-A); and

Ac-A-CiIEE[D-Lys(PYA)]QYCiiFADPY(Nle)Ciii-A (Ac-A-(SEQ ID NO: 9)-A);

wherein Ac represents an acetyl group, Dap represents diaminopropionic acid and PYA represents 4-pentynoic acid.

16. The heterotandem bicyclic peptide complex, or a pharmaceutically acceptable salt thereof, as defined in claim 15, wherein the CD137 binding bicyclic peptide ligand comprises a C-terminal amide group.

17. The heterotandem bicyclic peptide complex, or a pharmaceutically acceptable salt thereof, as defined in claim 3, wherein the Nectin-4 binding bicyclic peptide ligand comprises a C-terminal amide group.

18. A method of treating cancer which comprises administering the heterotandem bicyclic peptide complex, or a pharmaceutically acceptable salt thereof, as defined in claim 1 to a subject in need thereof, wherein the cancer is breast cancer, lung cancer, or ovarian cancer.

19. The method of claim 18, wherein the CD137 binding bicyclic peptide ligand of the heterotandem bicyclic peptide complex, or a pharmaceutically acceptable salt thereof, comprises N- and C-terminal modifications and comprises an amino acid sequence selected from:

Ac-A-CiIEEGQYCiiFADPY[Nle]Ciii-Dap (Ac-A-(SEQ ID NO: 1)-Dap);

Ac-A-CiIEEGQYCiiFADPY[Nle]Ciii-Dap(PYA) (Ac-A-(SEQ ID NO: 1)-Dap(PYA));

Ac-Ci[tBuAla]PE[D-Ala]PYCiiFADPY[Nle]Ciii-Dap (Ac-(SEQ ID NO: 3)-Dap);

Ac-Ci[tBuAla]PE[D-Ala]PYCiiFADPY[Nle]Ciii-Dap(PYA) (Ac-(SEQ ID NO: 3)-Dap(PYA));

Ac-A-CiIEEGQYCiiF[D-Ala]DPY[Nle]Ciii-Dap (Ac-A-(SEQ ID NO: 4)-Dap);

Ac-Ci[tBuAla]PK[D-Ala]PYCiiFADPY|Nle]Ciii-A (Ac-(SEQ ID NO: 5)-A);

Ac-CiltBuAla]PE[D-Lys]PYCiiFADPY[Nle]Ciii-A (Ac-(SEQ ID NO: 6)-A);

Ac-Ci[tBuAla]P[K(PYA)|[D-Ala]PYCiiFADPY|Nle]Ciii-A (Ac-(SEQ ID NO: 7)-A);

Ac-Ci[tBuAla]PE[D-Lys(PYA)]PYCiiFADPY[Nle]Ciii-A (Ac-(SEQ ID NO: 8)-A);

Ac-A-CiIEE[D-Lys(PYA)]QYCiiFADPY(Nle)Ciii-A (Ac-A-(SEQ ID NO: 9)-A); and

[dA]-NH2 (Ac-[dA]-(SEQ ID NO: 10)-[dA]-$NH_2$);

wherein Ac represents an acetyl group, Dap represents diaminopropionic acid and PYA represents 4-pentynoic acid.

20. The method of claim 18, wherein the Nectin-4 binding bicyclic peptide ligand of the heterotandem bicyclic peptide complex, or a pharmaceutically acceptable salt thereof, comprises N-terminal modifications and comprises an amino acid sequence selected from:

CiP[1Nal][dD]CiiM[HArg]DWSTP[HyP]WCiii (SEQ ID NO: 15);

[PYA]-[B-Ala]-[Sar10]-CiP[1Nal][dD]CiiM[HArg]DWSTP[HyP]WCiii ([PYA]-[B-Ala]-[Sar10]-(SEQ ID NO: 15));

CiP[1Nal][dD]CiiM[HArg]D[dW]STP[HyP][dW]Ciii (SEQ ID NO: 16);

-continued

[PYA]-[B-Ala]-[Sar10]-CiP[1Nal][dD]CiiM[HArg]D[dW]STP[HyP][dW]Ciii ([PYA]-[B-Ala]-[Sar10]-(SEQ ID NO: 16));

Ac-CiP[1Nal][dK](Sar10-(B-Ala))CiiM[HArg]DWSTP[HyP]WCiii (Ac-(SEQ ID NO: 17)); and CiPFGCiiM[HArg]DWSTP[HyP]WCiii (SEQ ID NO: 18);

wherein PYA represents 4-pentynoic acid, B-Ala represents beta-alanine, Sar10 represents 10 sarcosine units.

21. The method of claim 18, wherein the heterotandem bicyclic peptide complex, or a pharmaceutically acceptable salt thereof, is a CD137/Nectin-4 complex selected from:

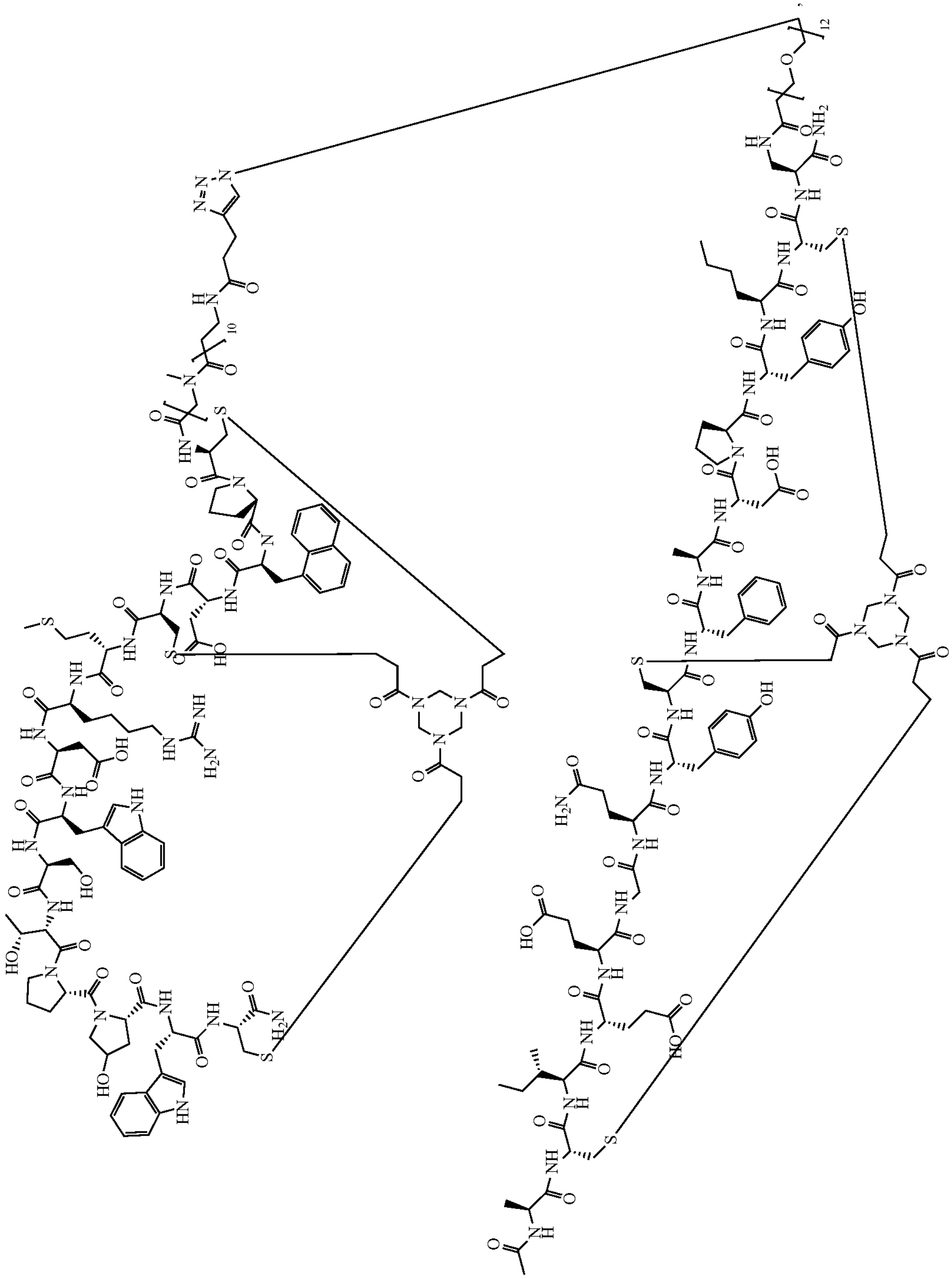
BCY8854

-continued
BCY9350
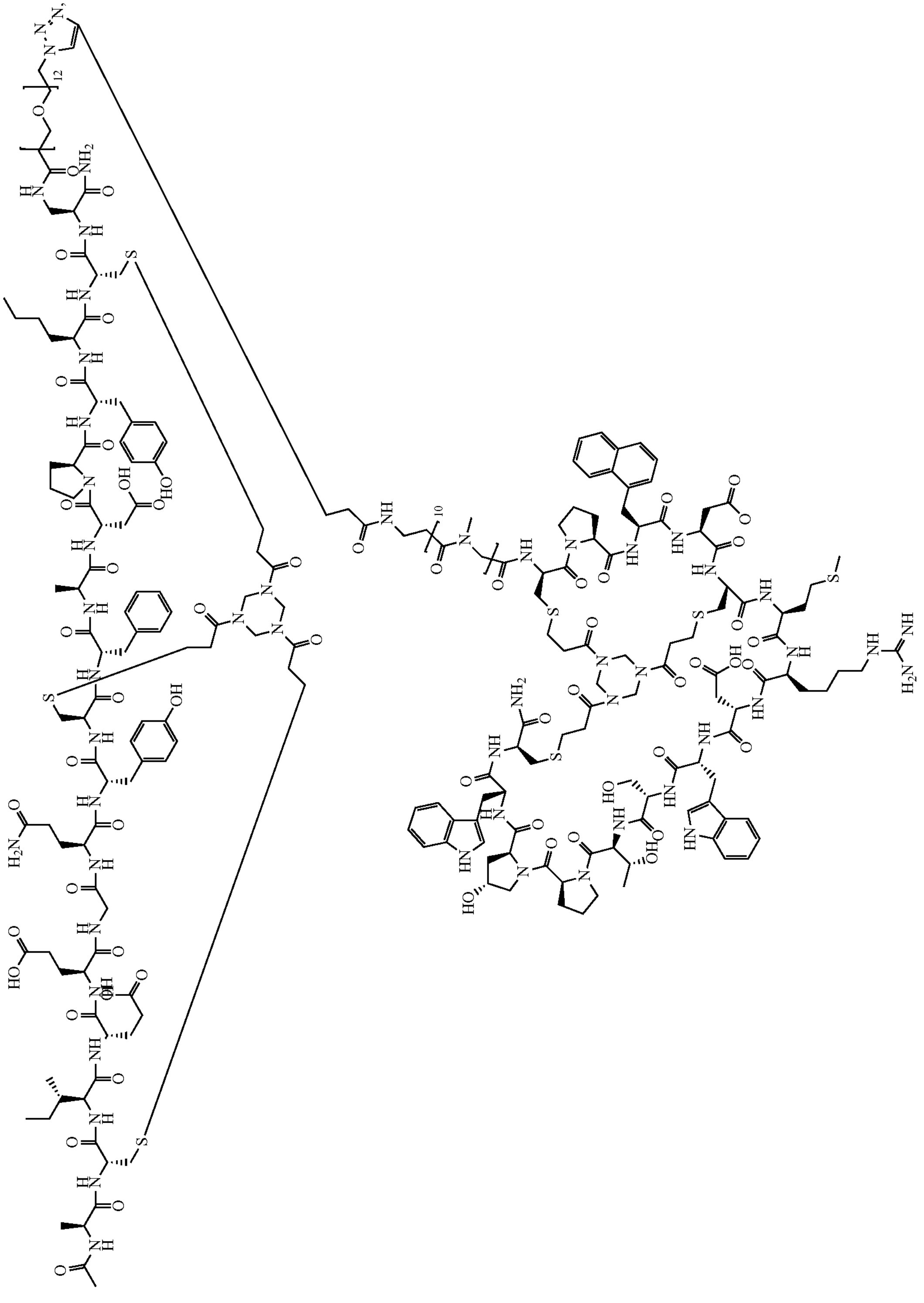

-continued
BCY9351
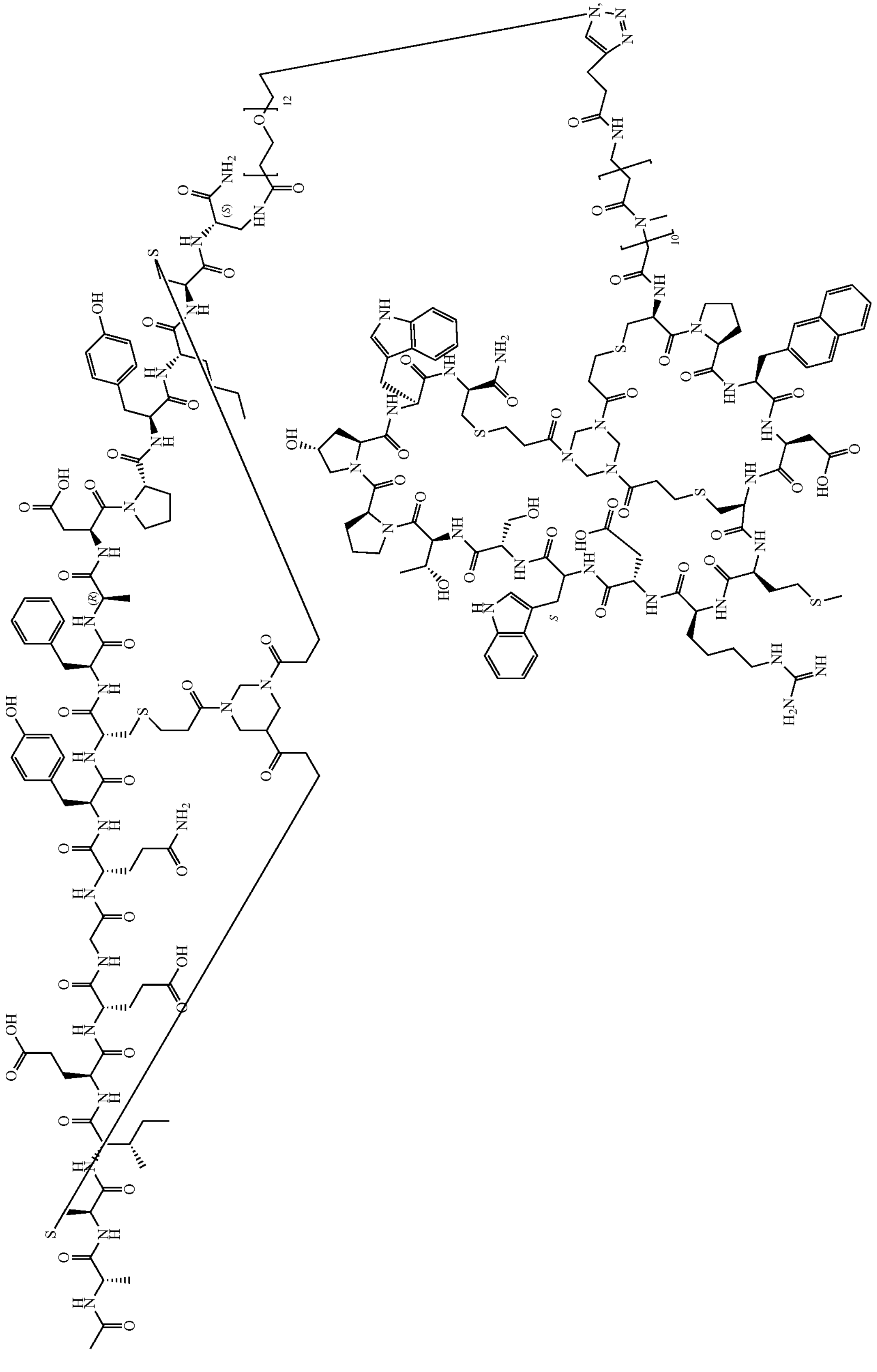

-continued
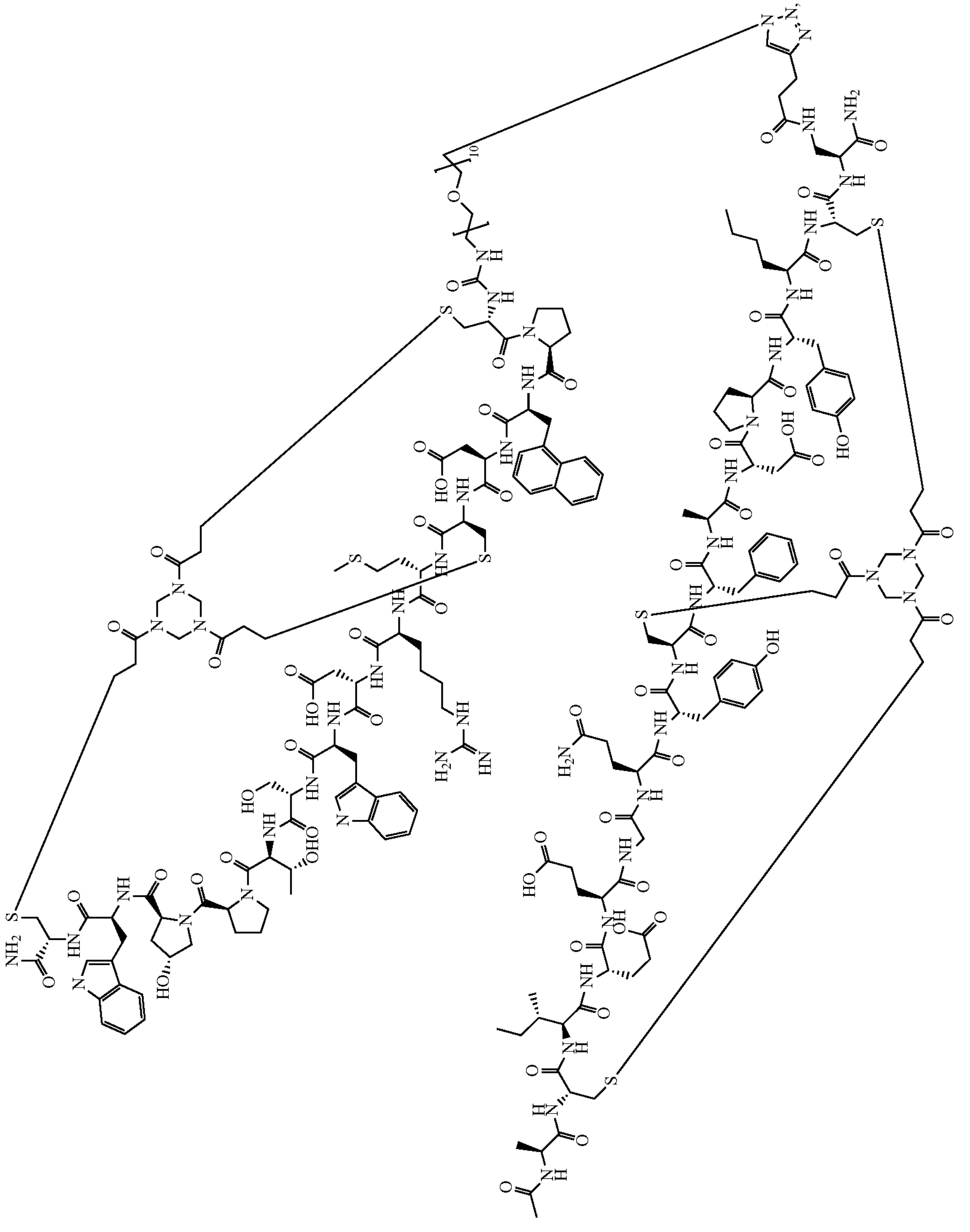
BCY9399

-continued
BCY9400
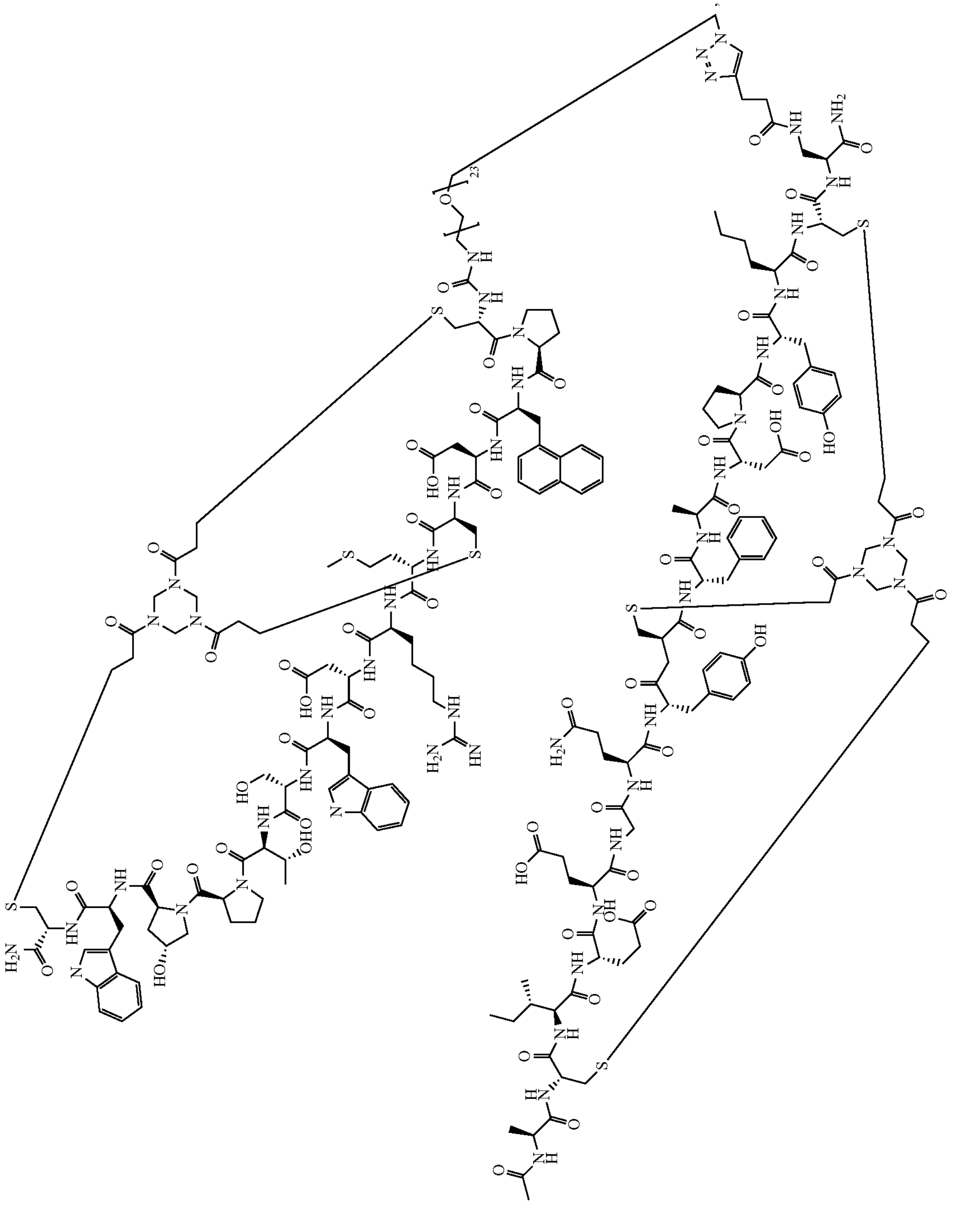

-continued
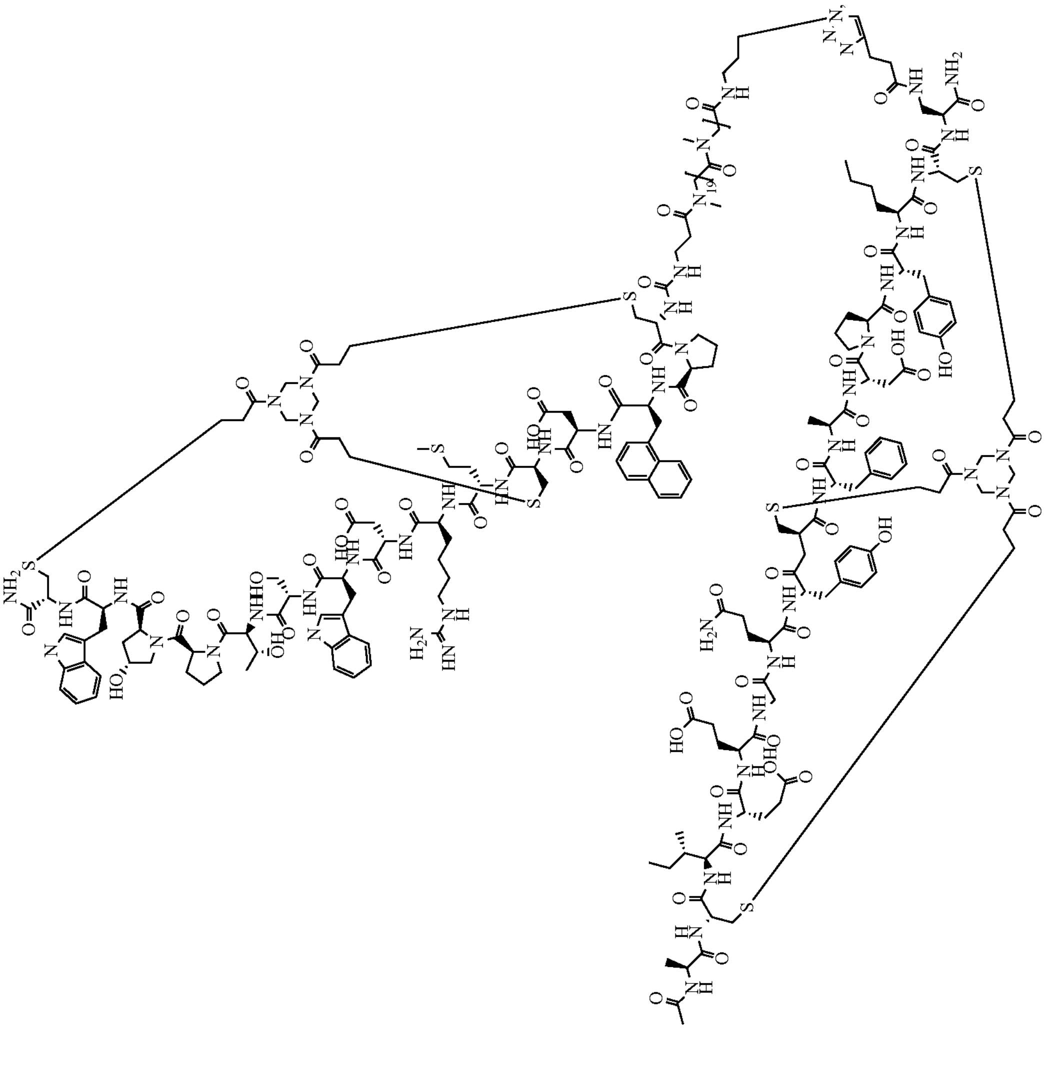
BCY9401

-continued
BCY9403
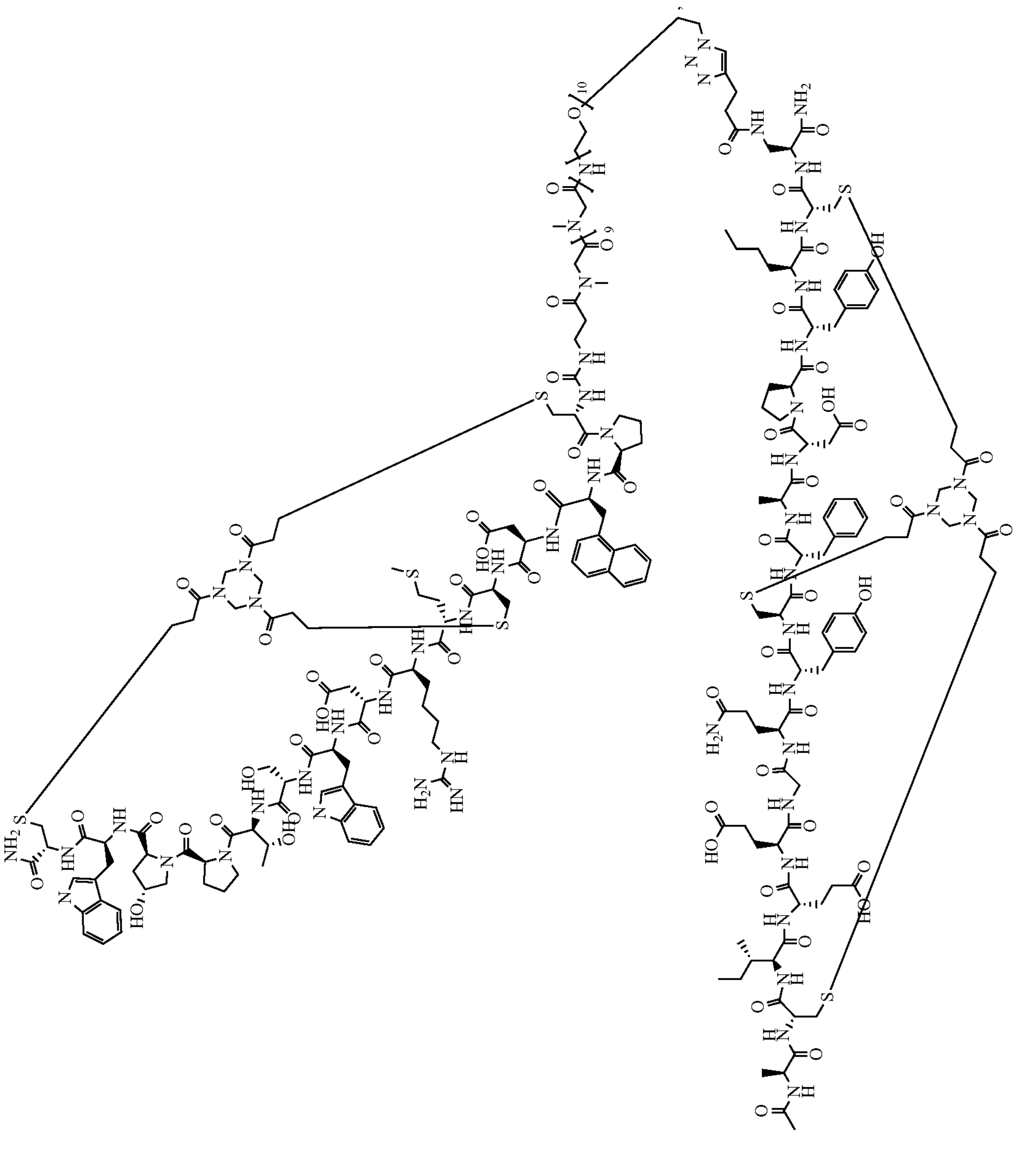

-continued
BCY9405
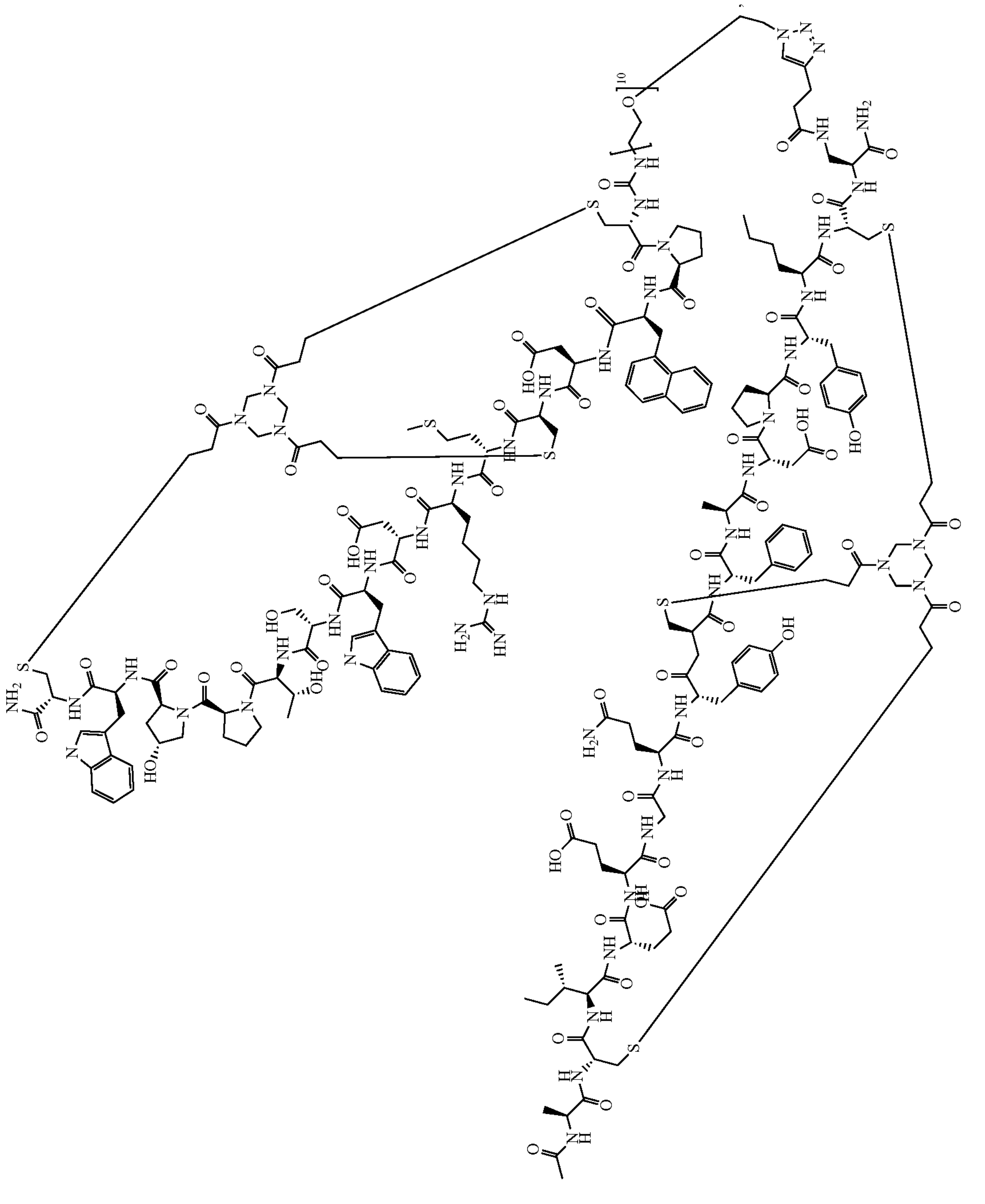

-continued
BCY9406
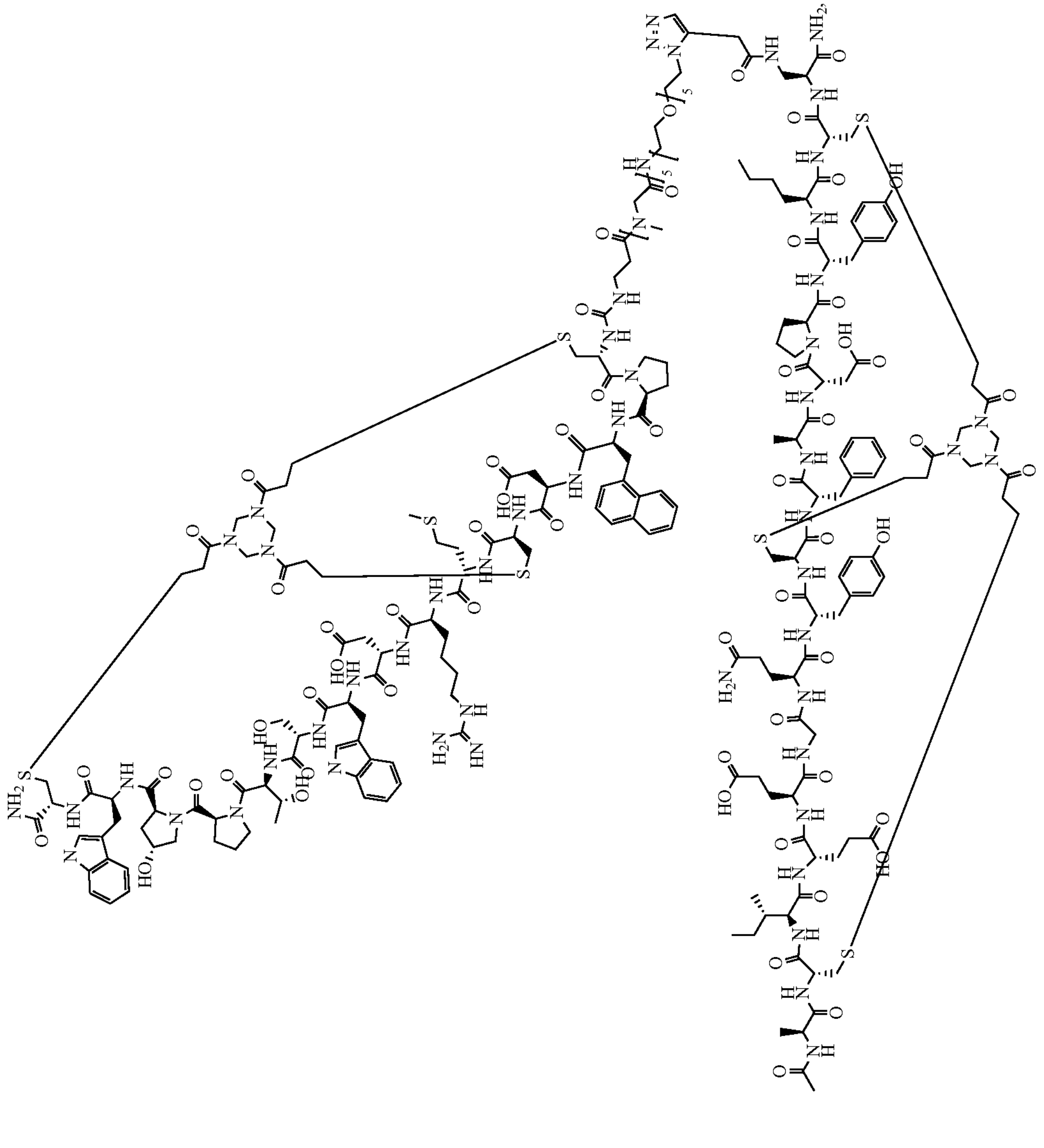

-continued
BCY9407
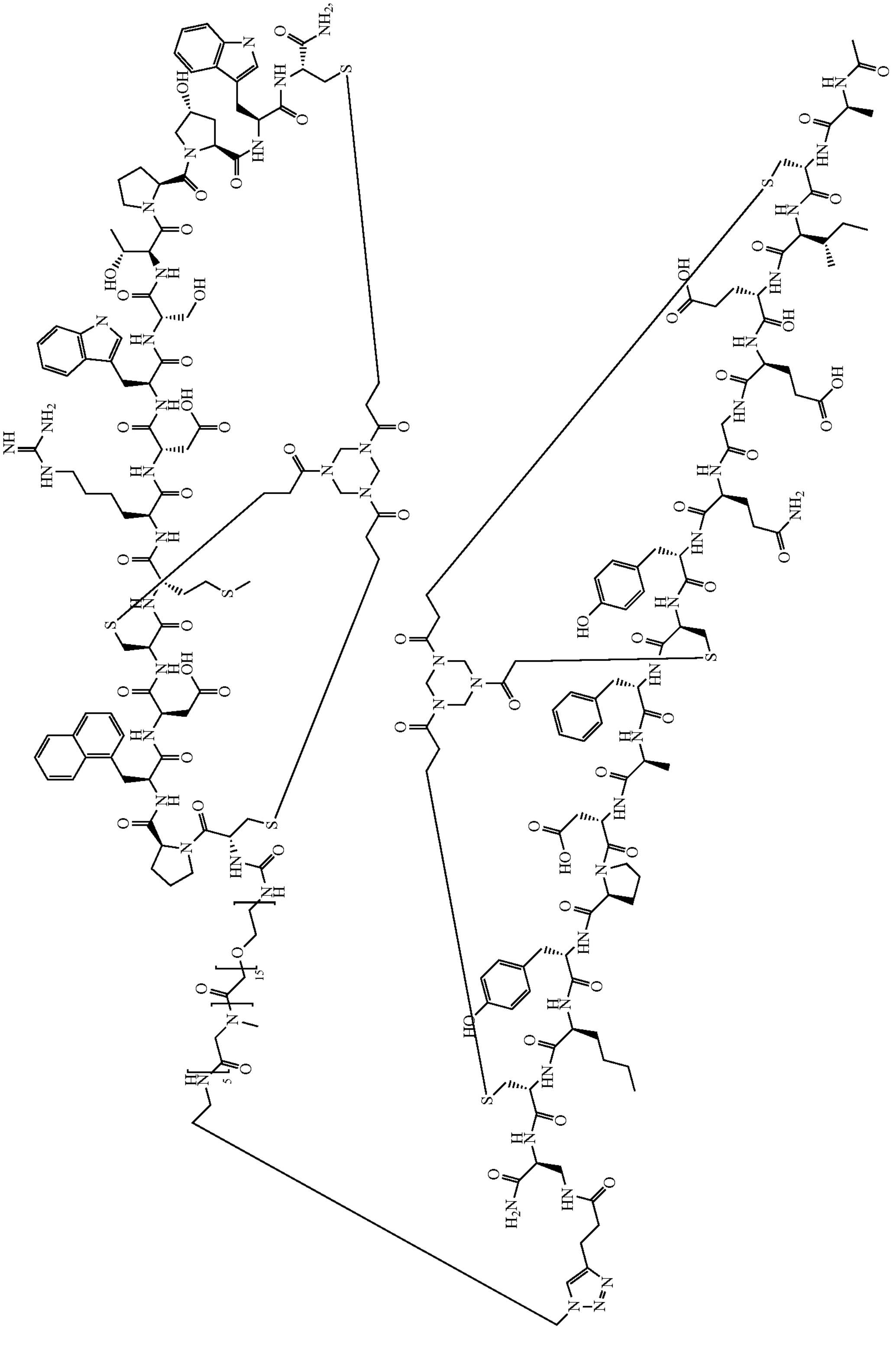

-continued
BCY9408
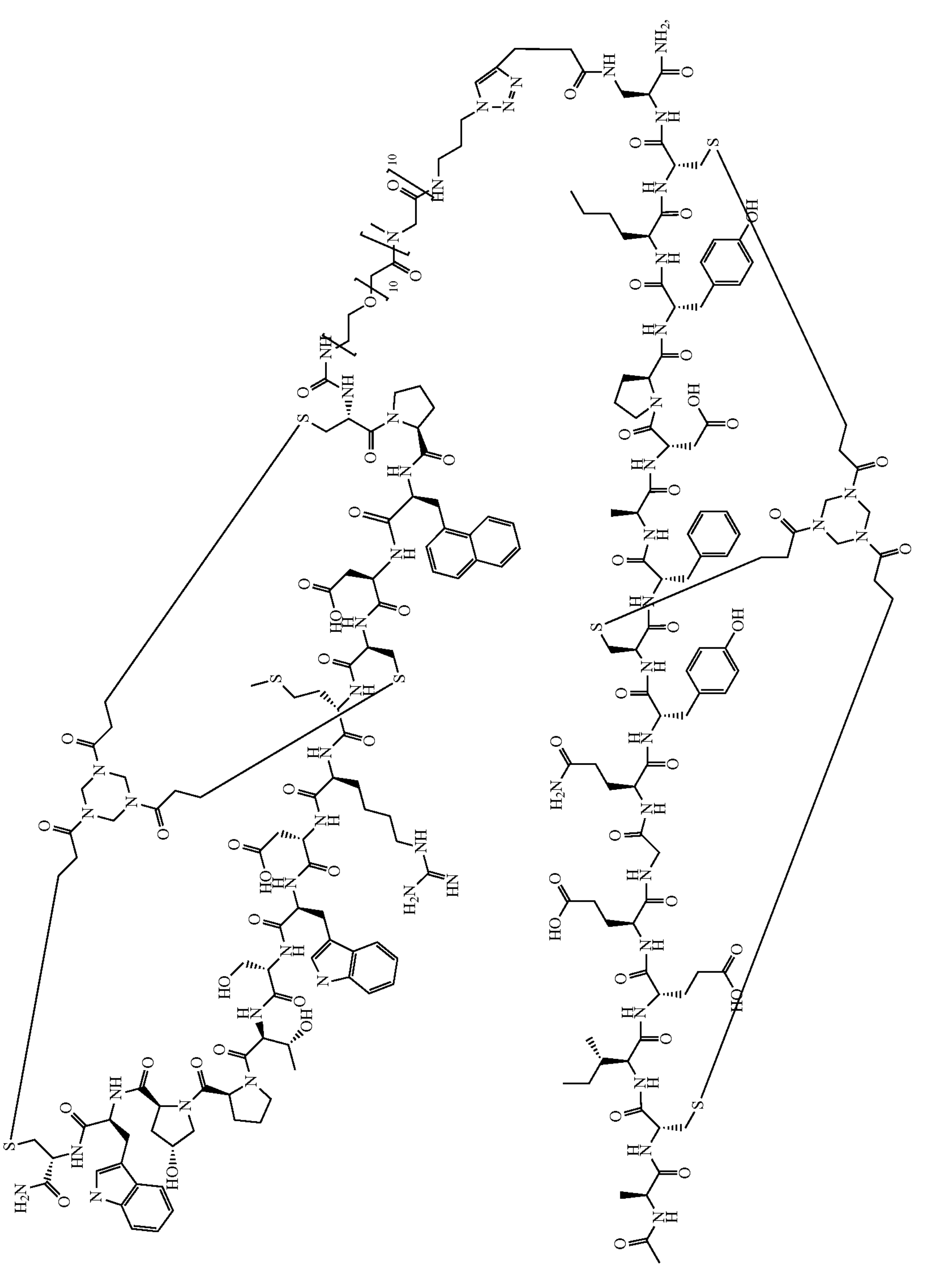

-continued
BCY9409
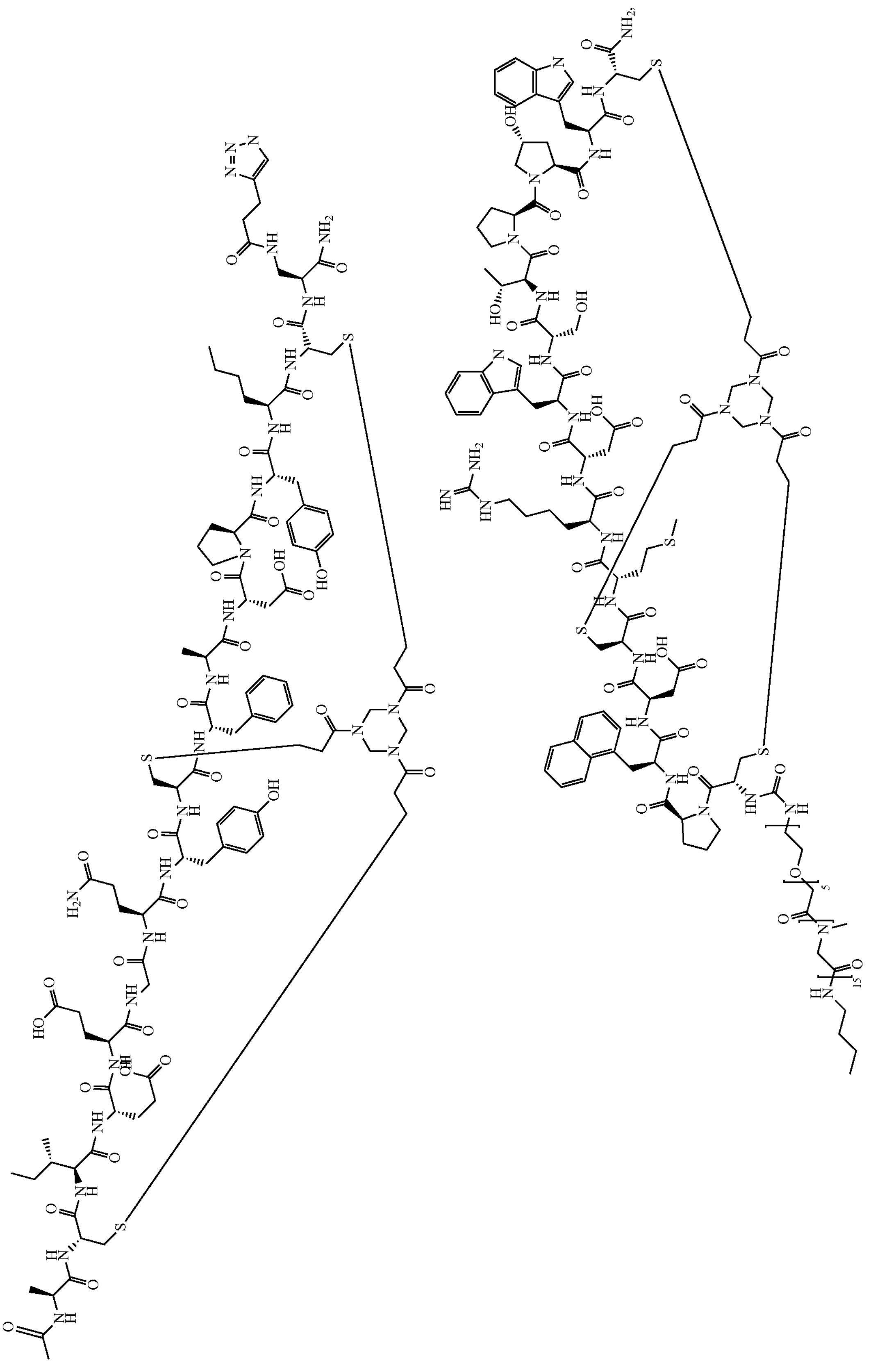

-continued
BCY9410
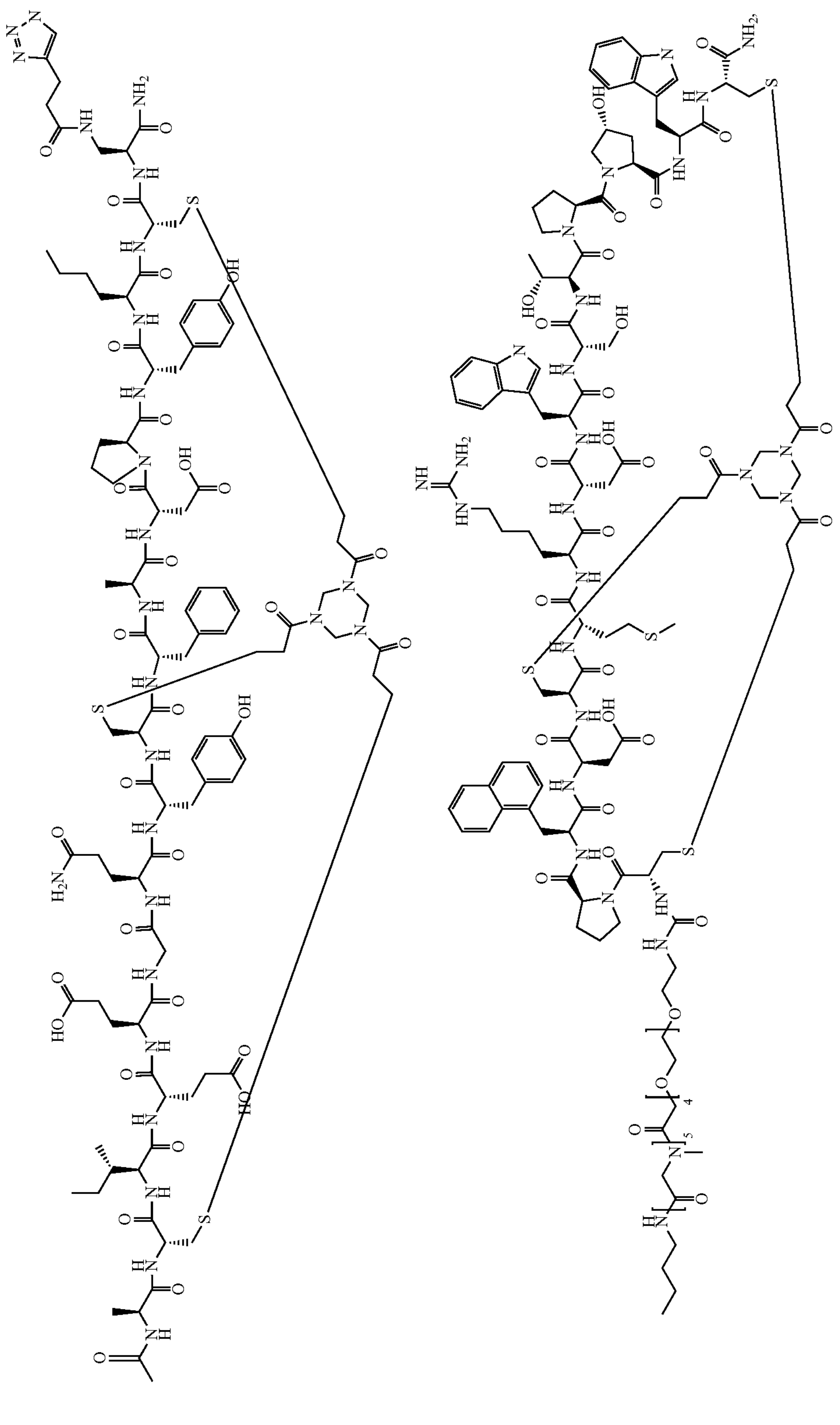

-continued
BCY9411
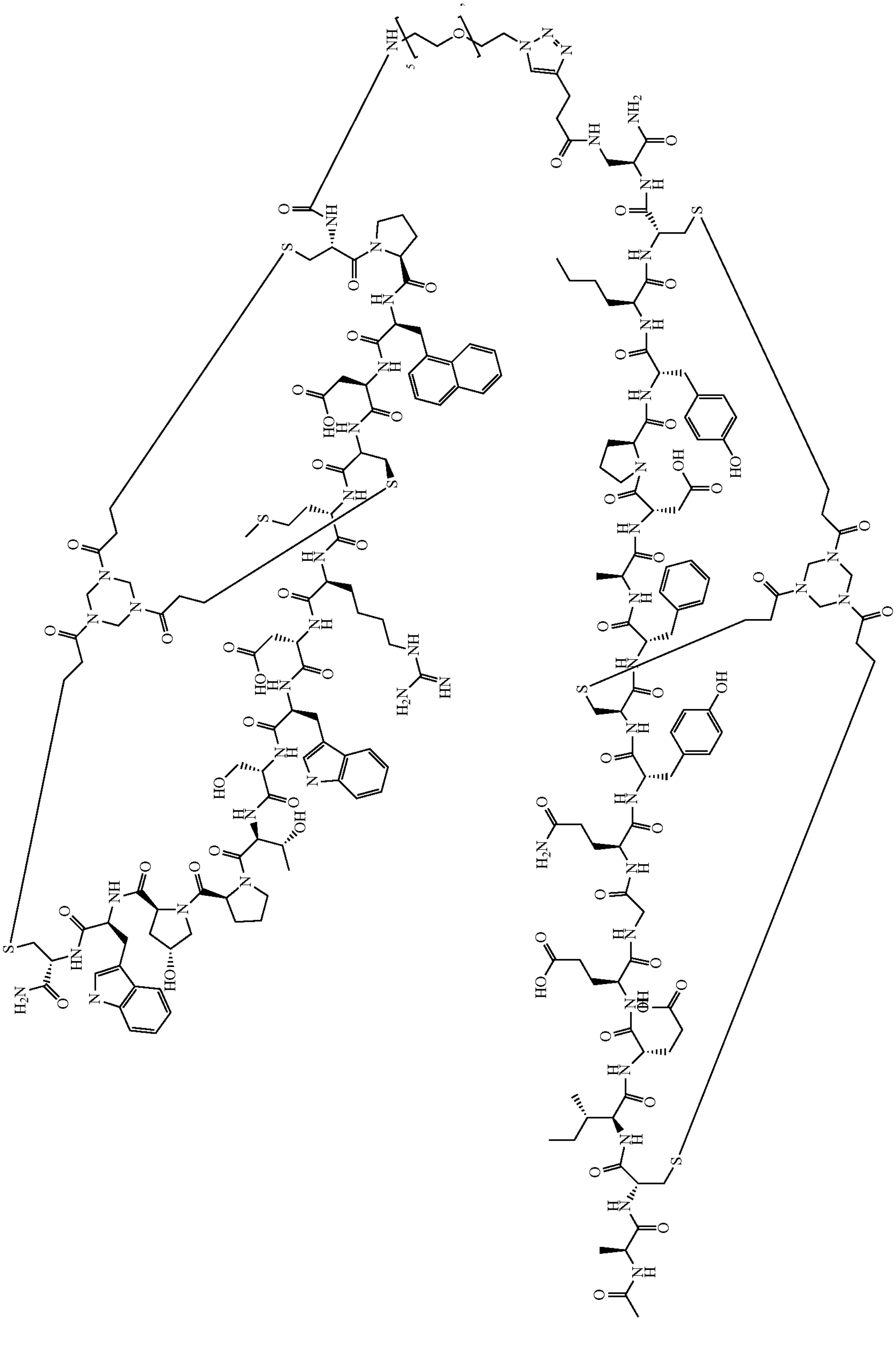

-continued
BCY9759
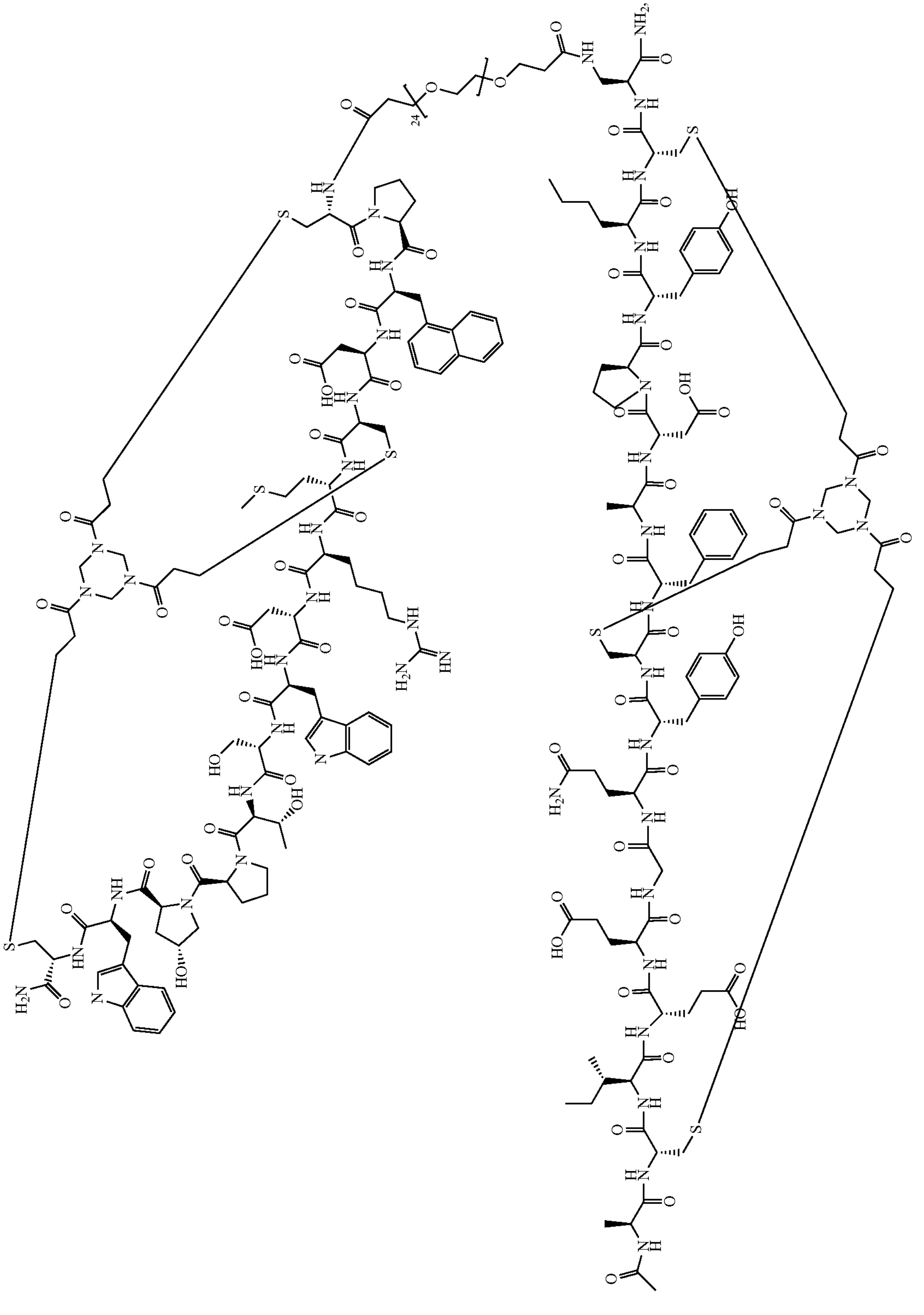

-continued
BCY10000
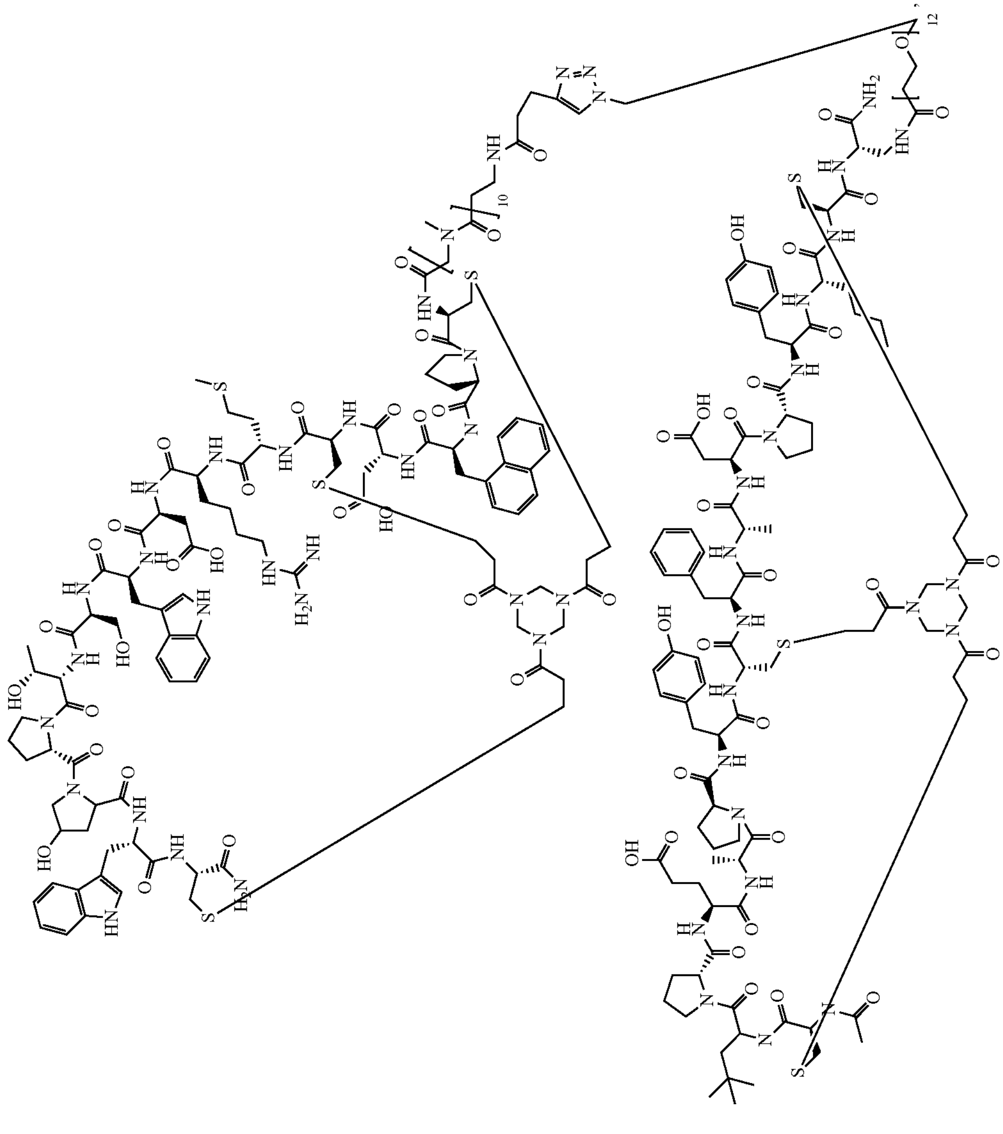

-continued
BCY10567
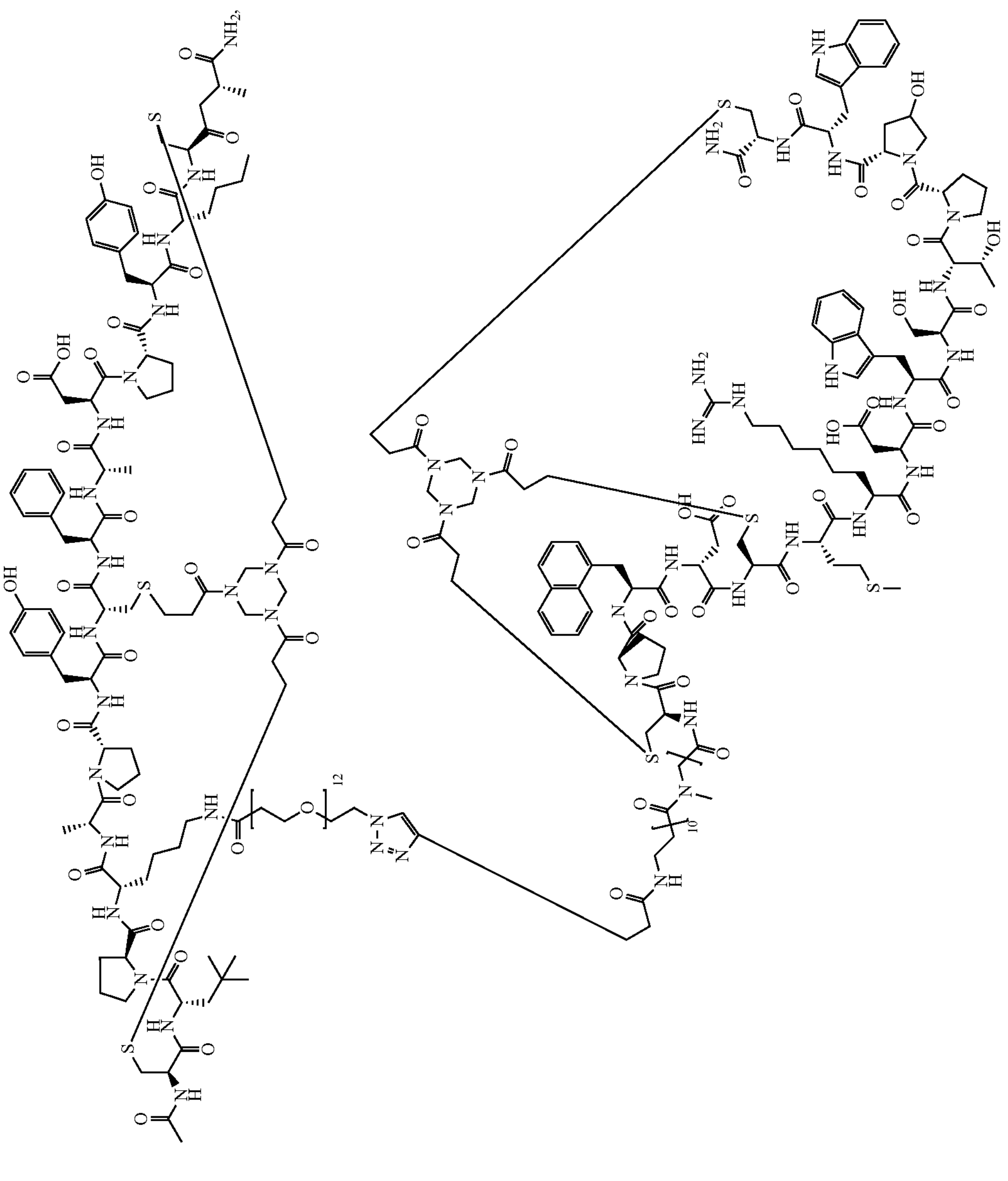

-continued
BCY10569
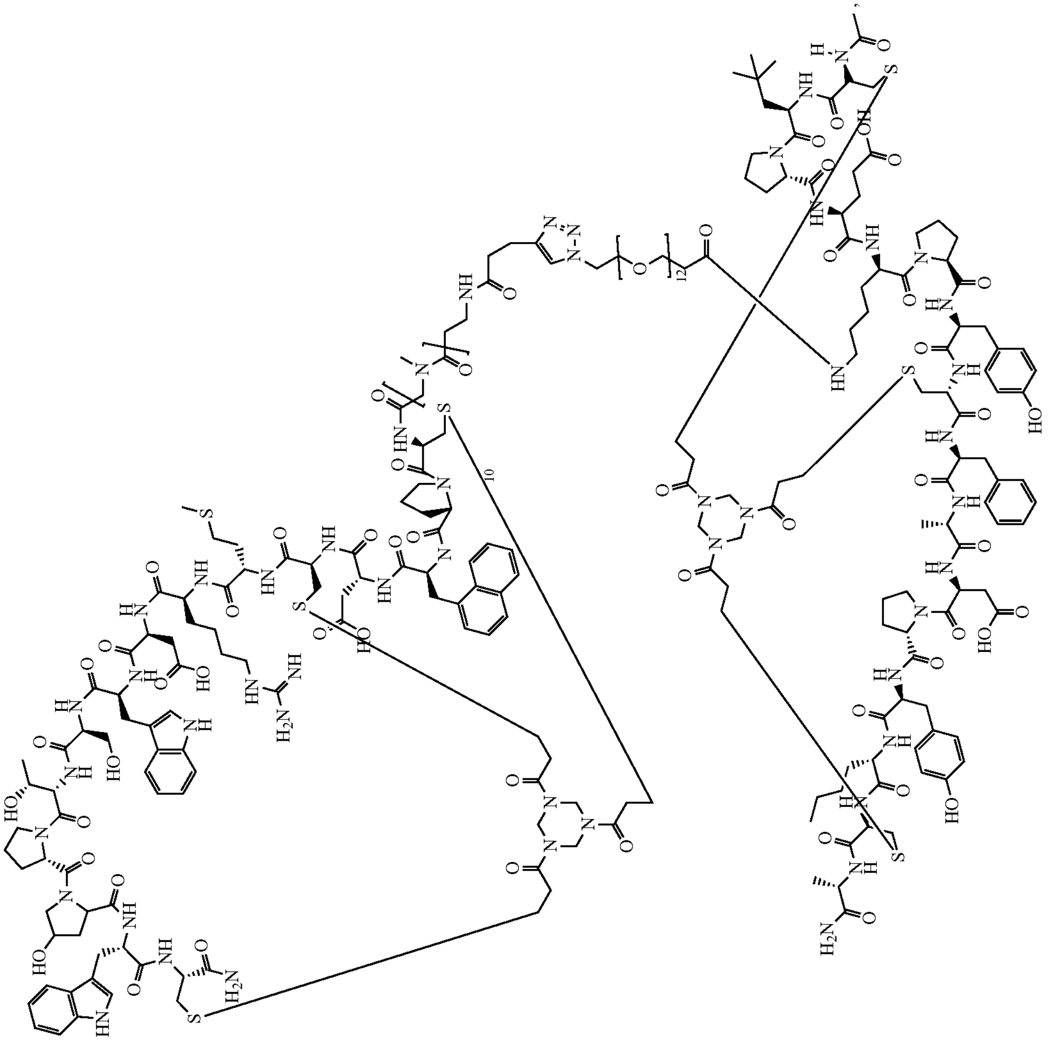

-continued
BCY105771
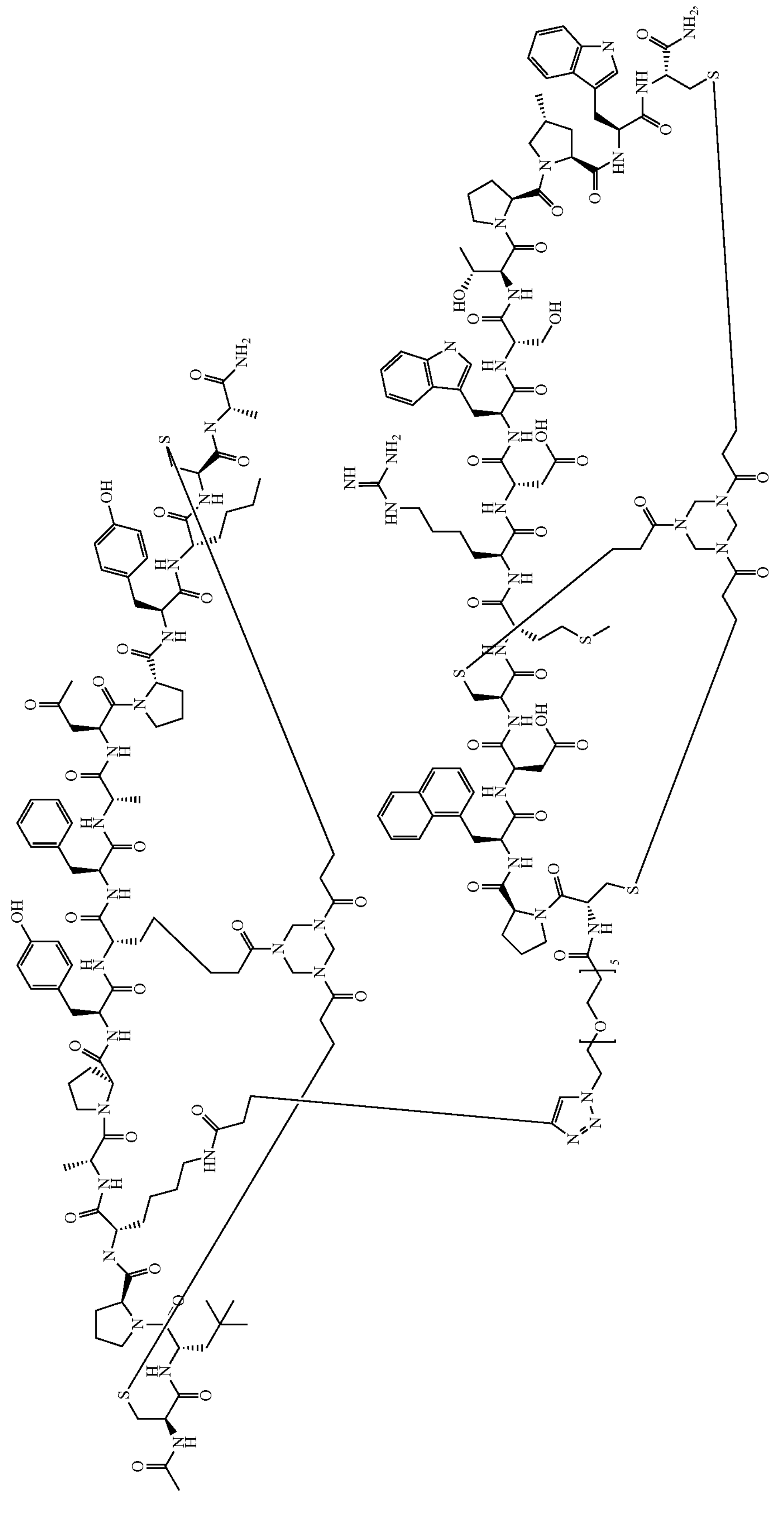

-continued
BCY10572
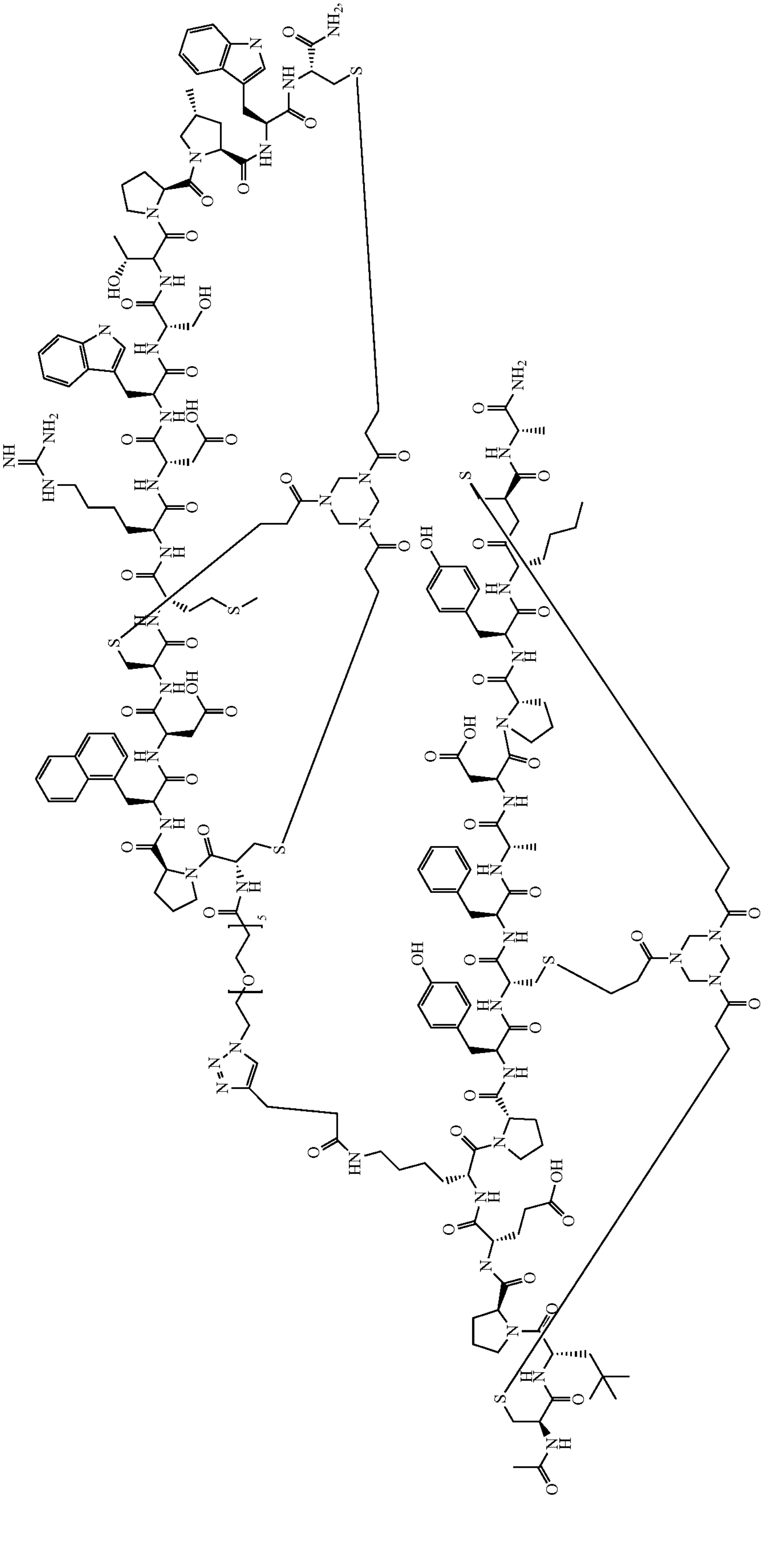

-continued
BCY10573
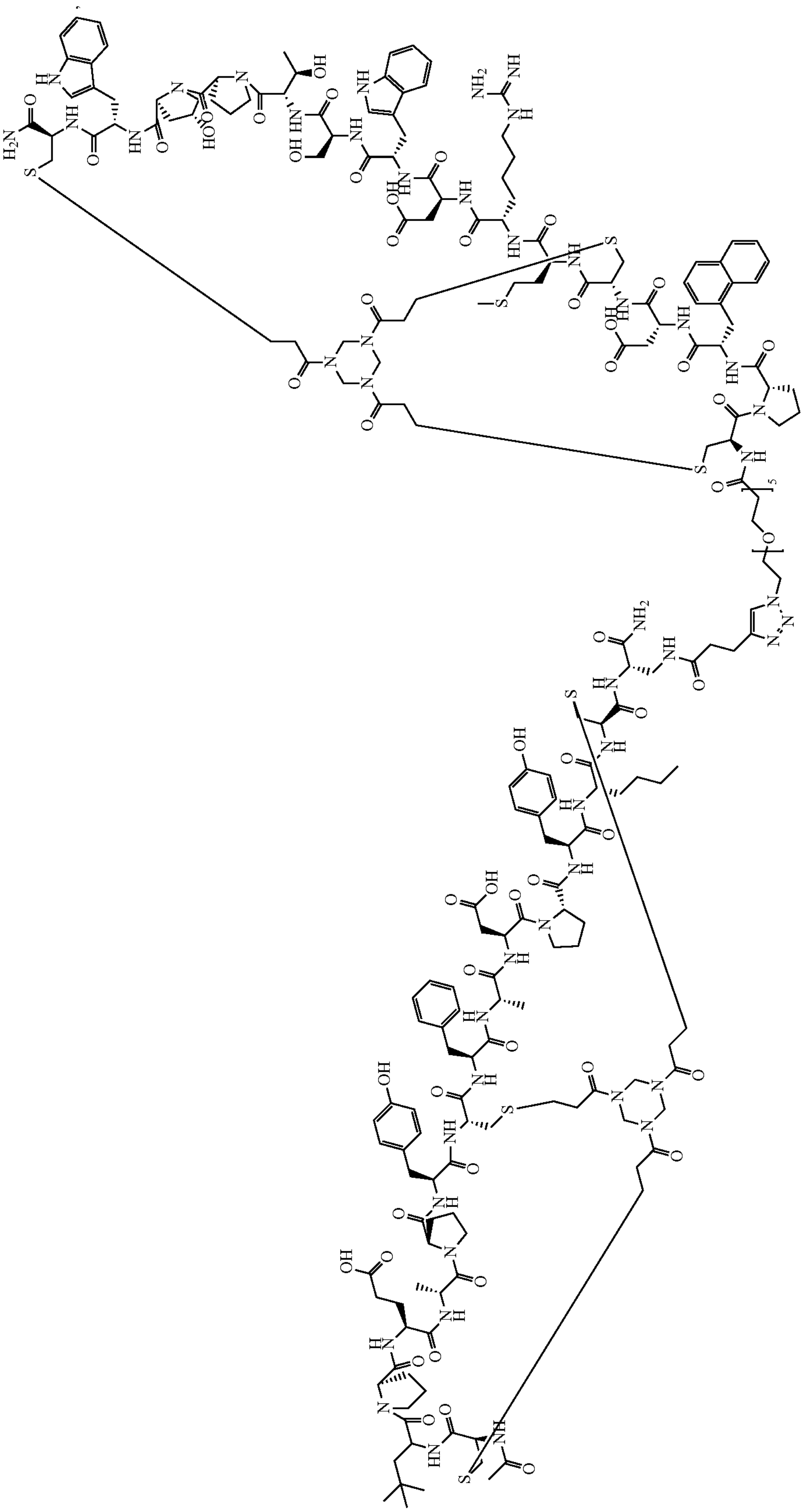

-continued
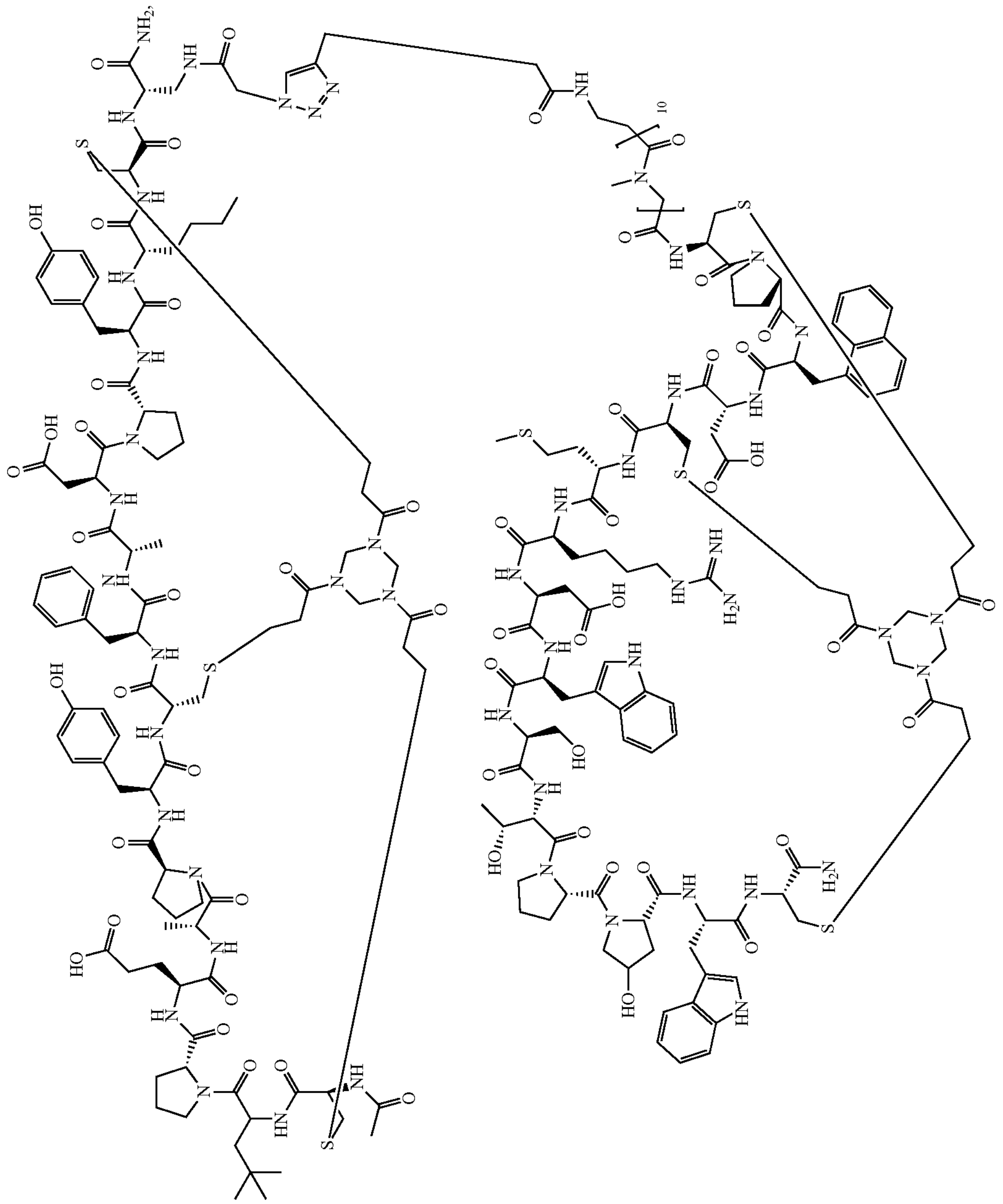
BCY10578

-continued
BCY10917
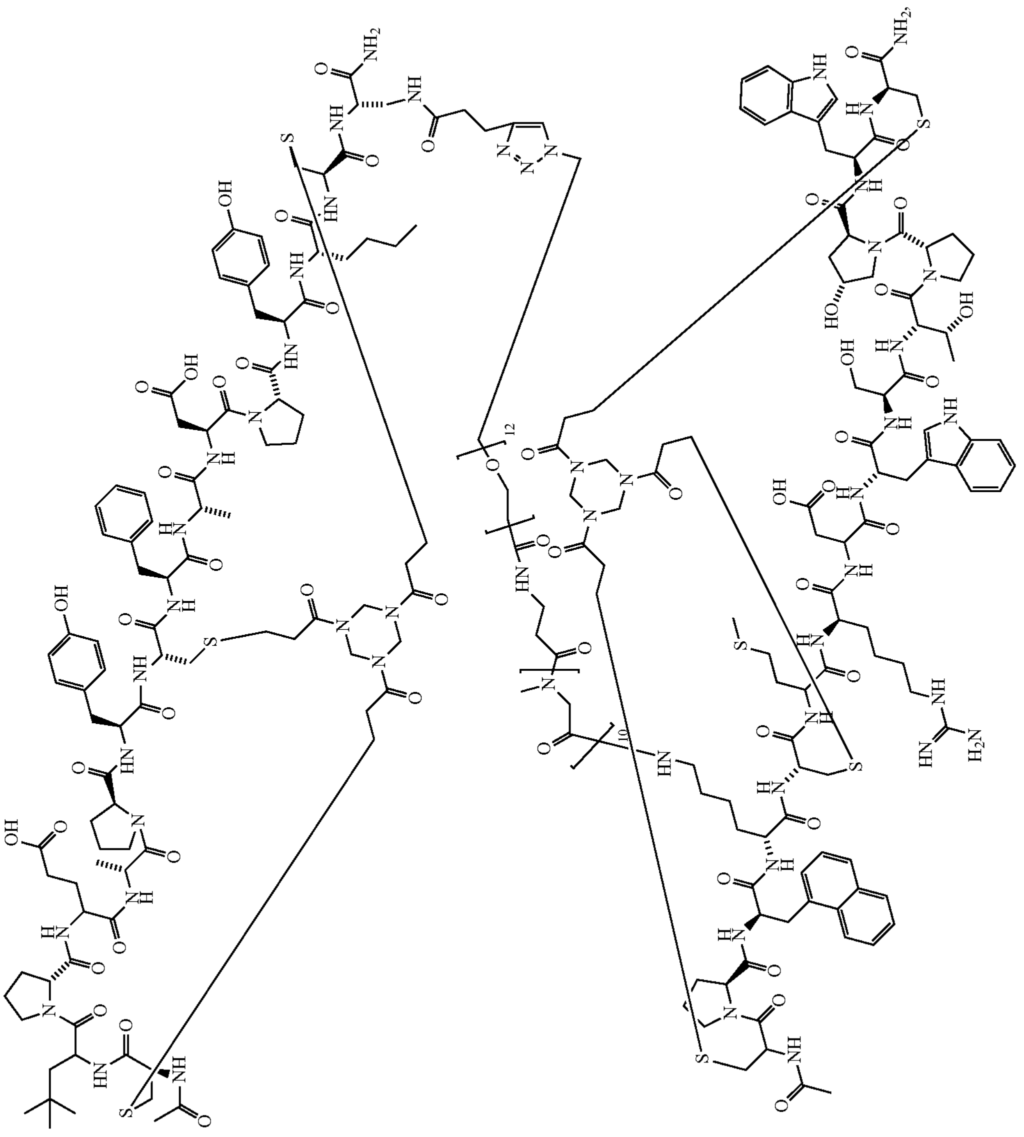

-continued
BCY11020
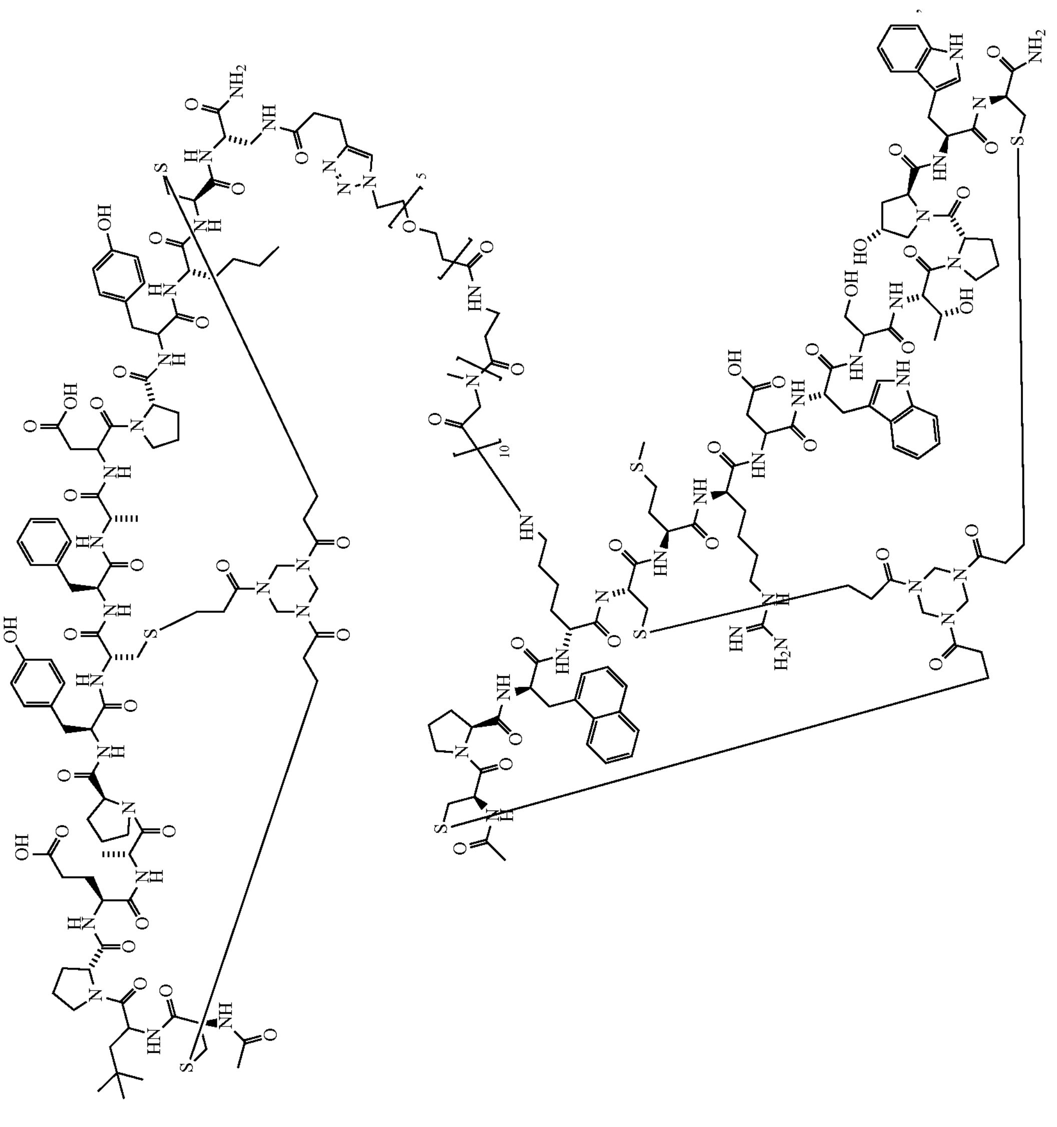

-continued
BCY11373
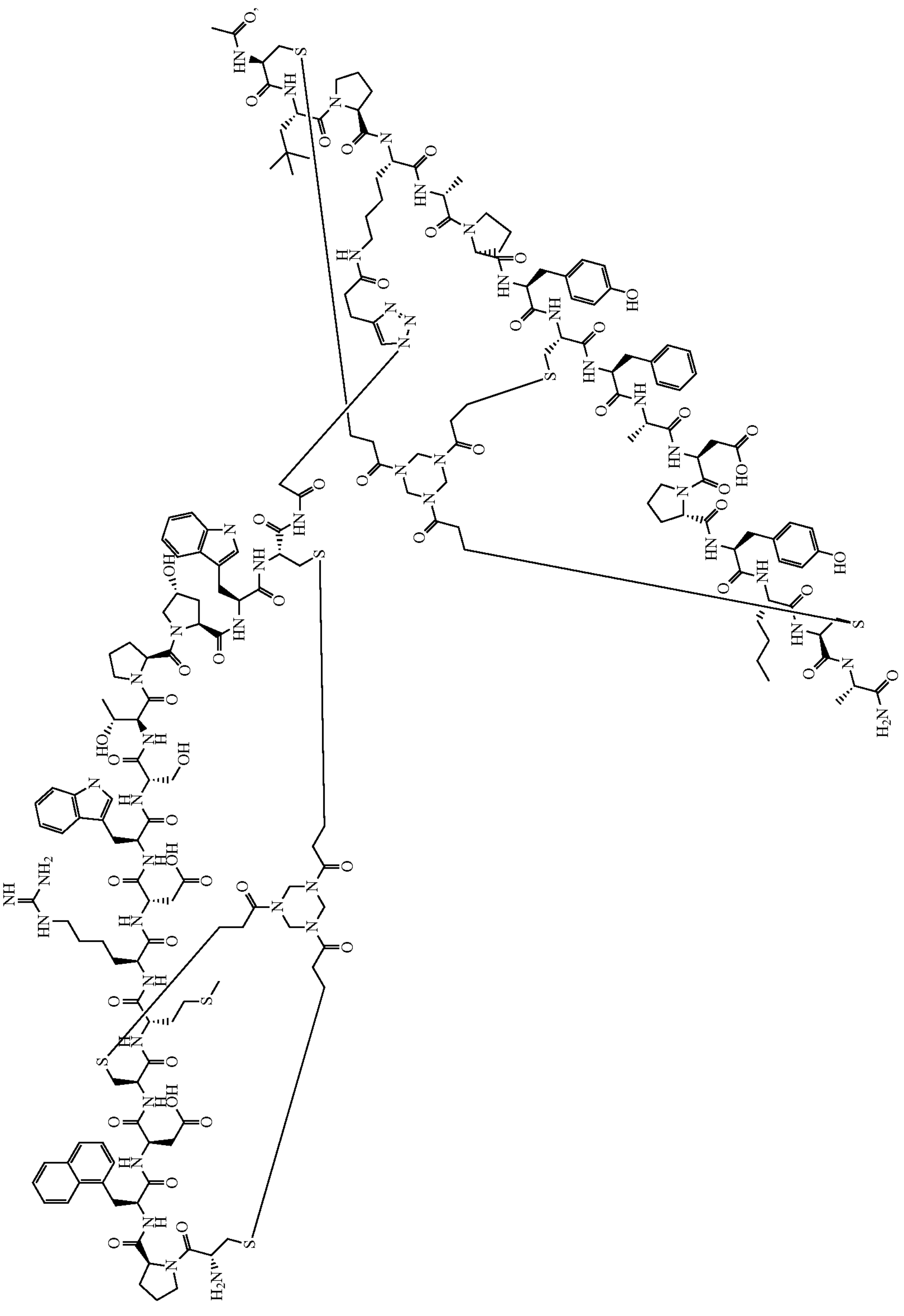

-continued
BCY11374
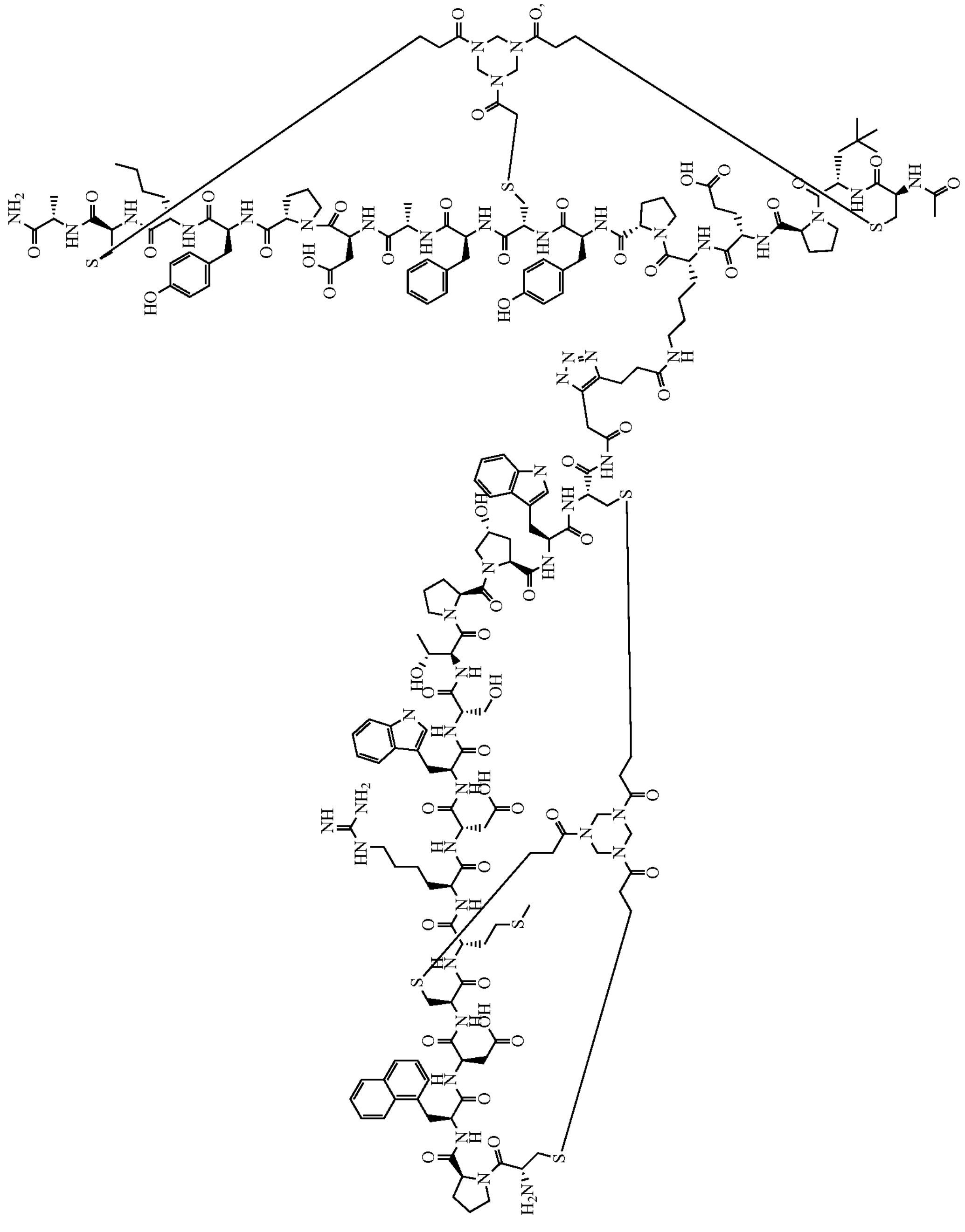

-continued
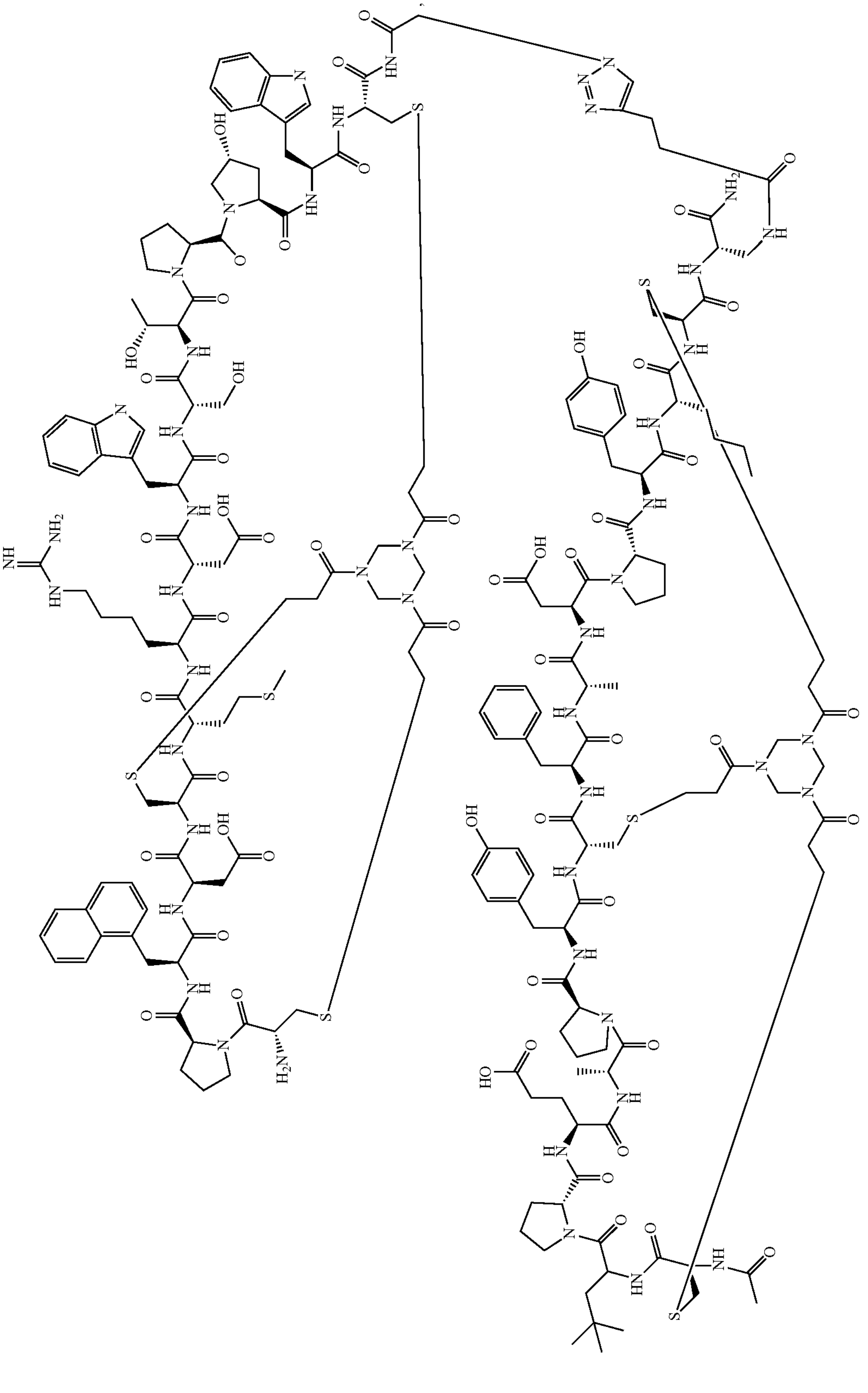
BCY11375

-continued
BCY11616
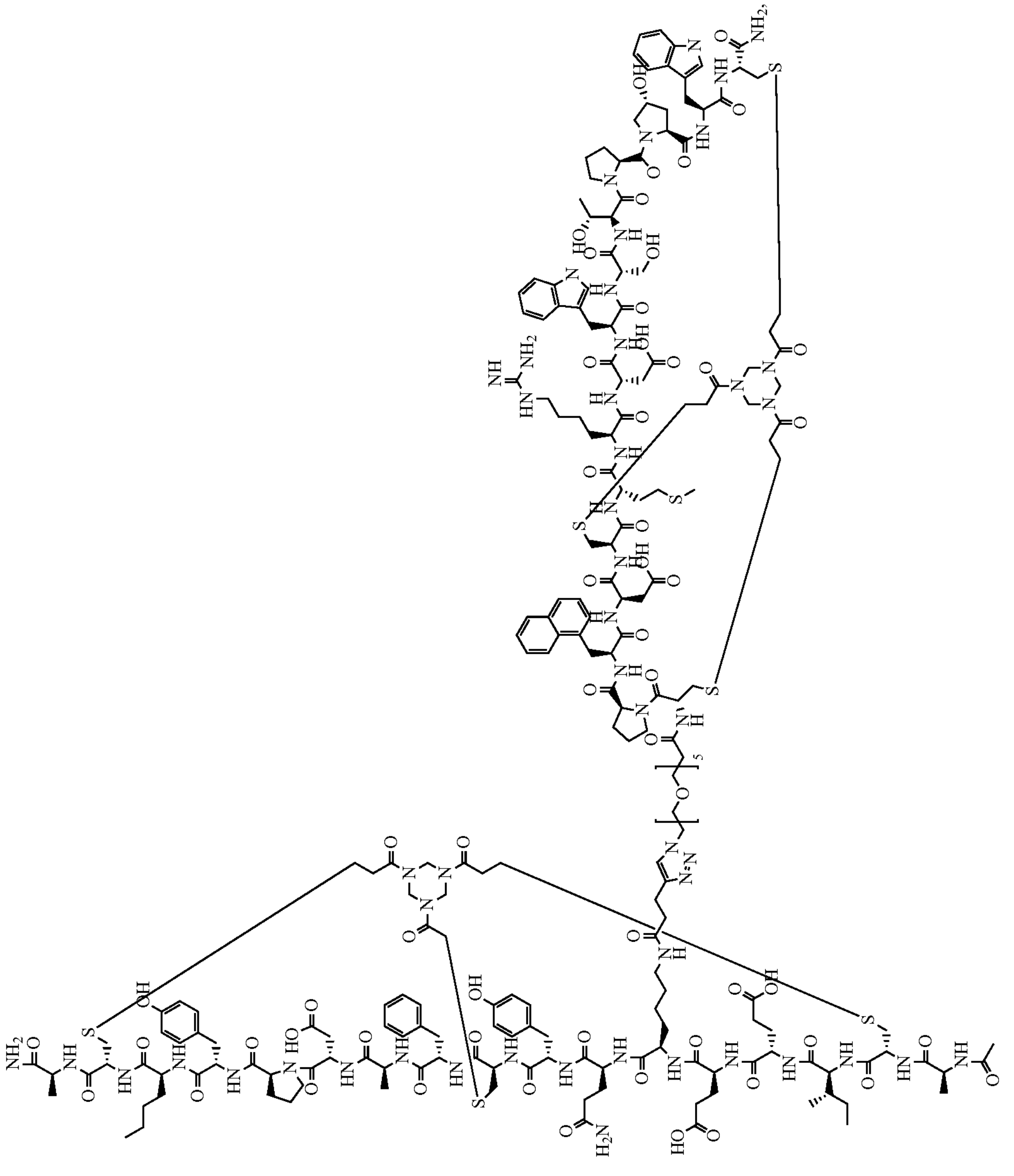

-continued
BCY11617
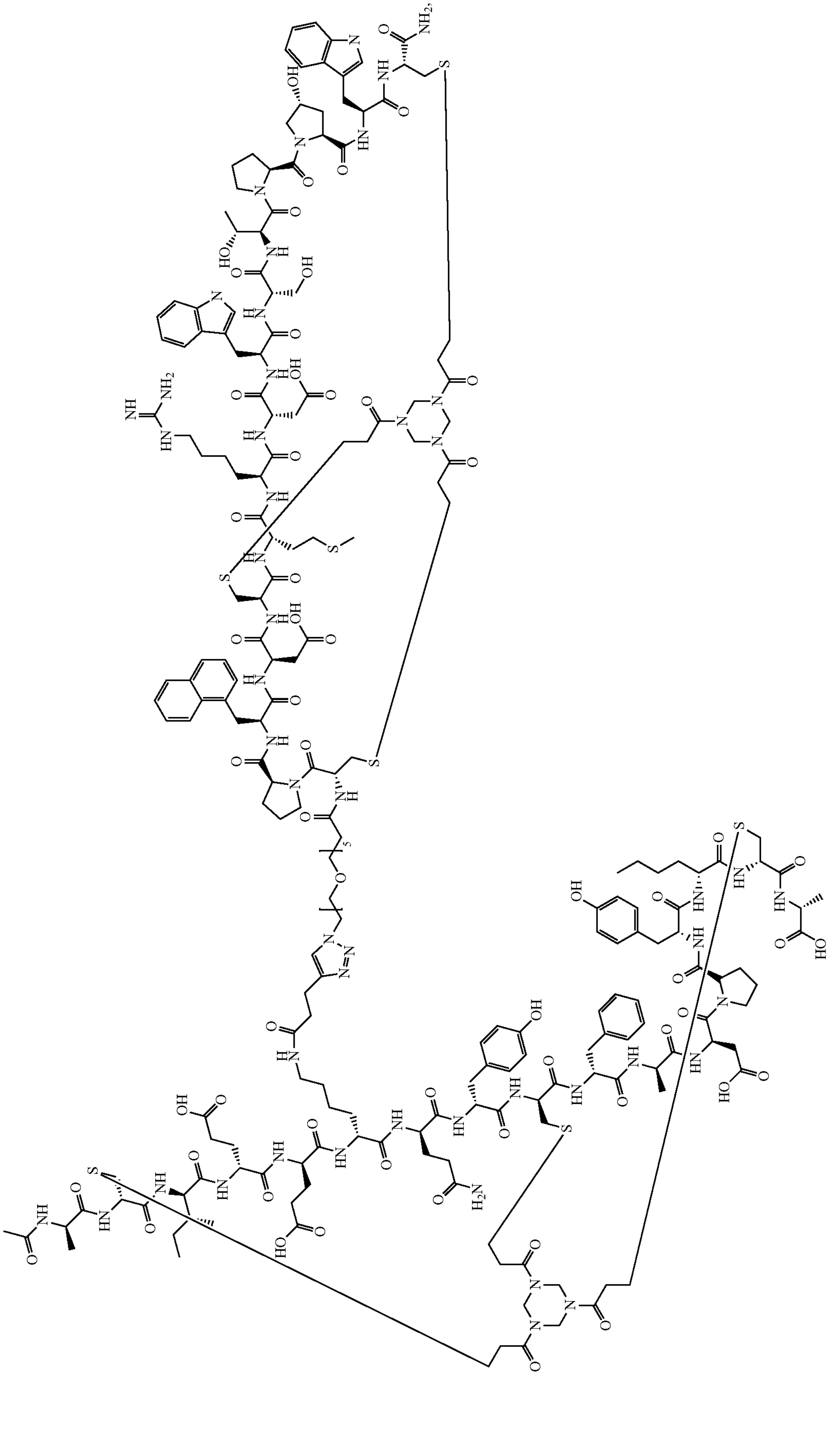

-continued
BCY11857
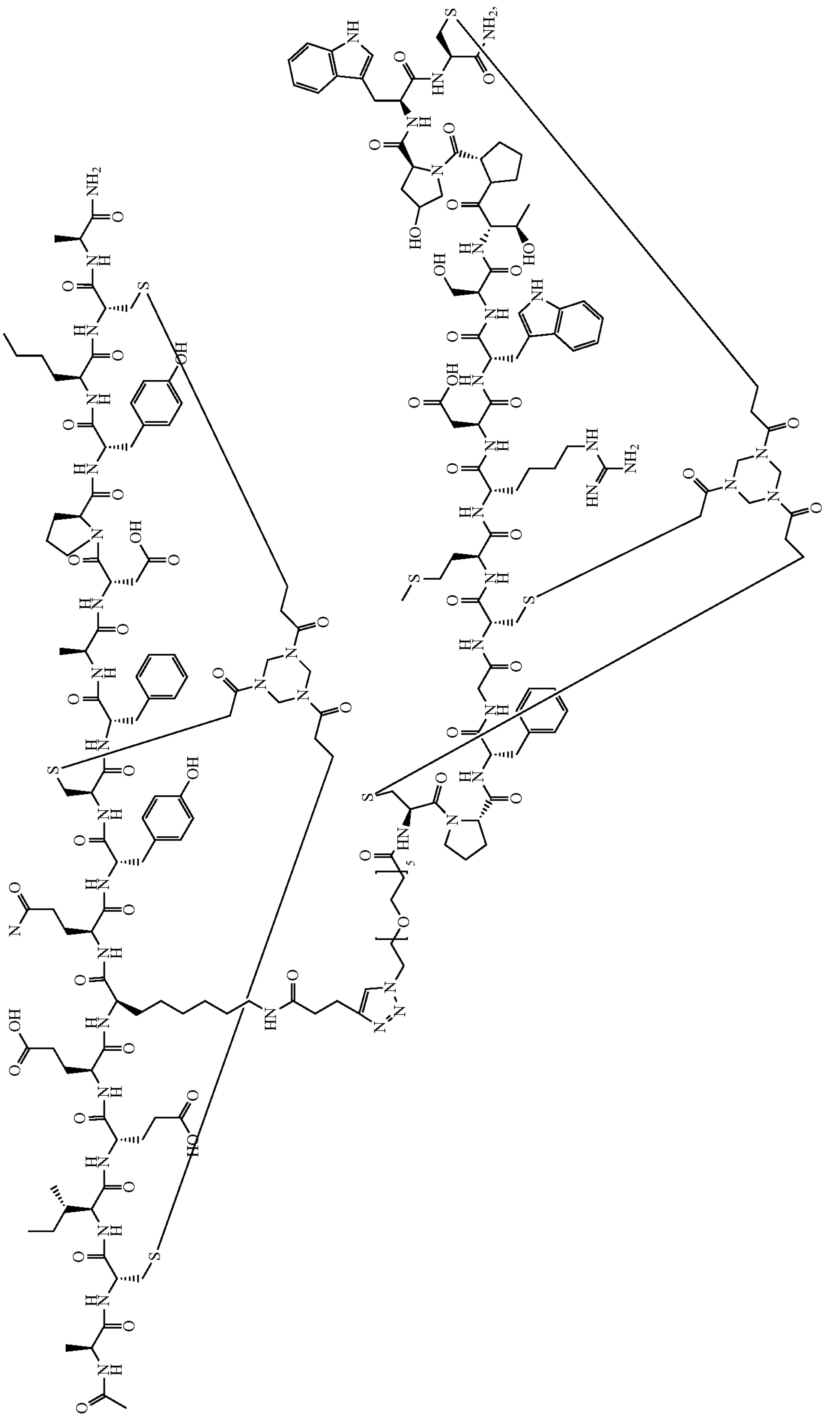

-continued
BCY11858
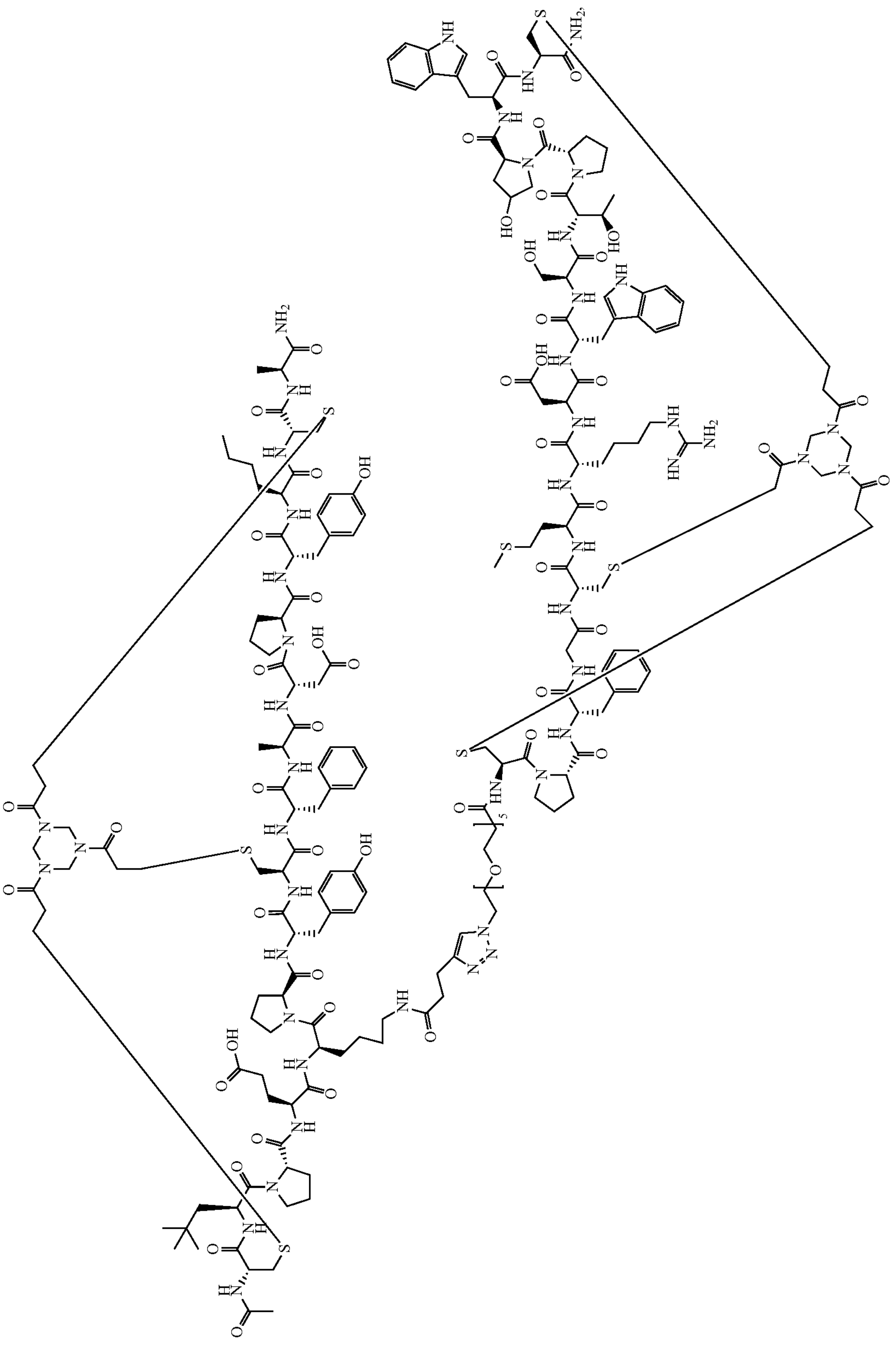
and

-continued
BCY11859
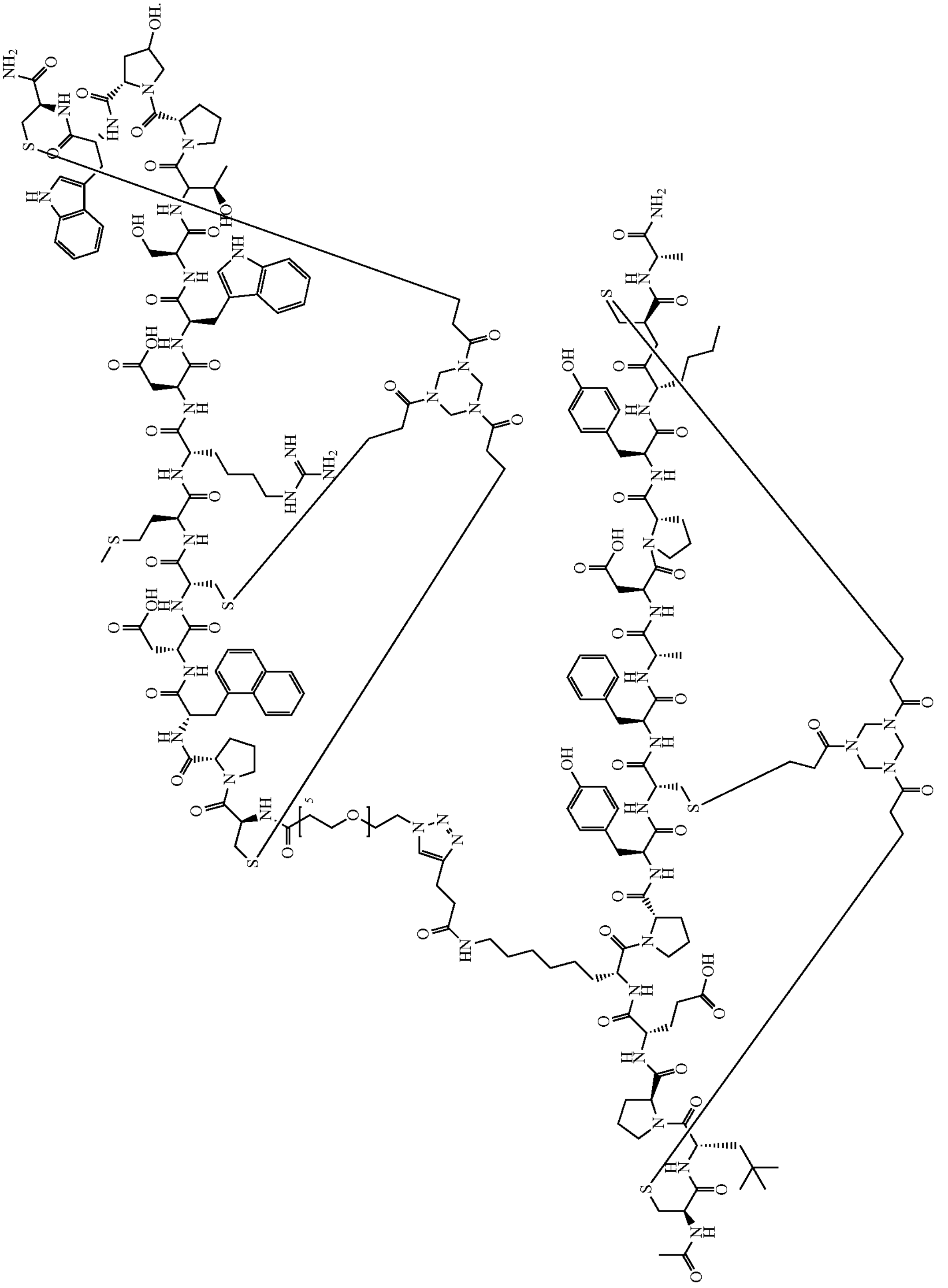

22. The method of claim 18, wherein the linker of the heterotandem bicyclic peptide complex, or a pharmaceutically acceptable salt thereof, is selected from: —$CH_2$—, -$PEG_5$-, -$PEG_{10}$-, -$PEG_{12}$-, -$PEG_{23}$-, -$PEG_{24}$-, -$PEG_{15}$-$Sar_5$-, -$PEG_{10}$-$Sar_{10}$-, -$PEG_5$-$Sar_{15}$-, -$PEG_5$-$Sar_5$-, —B-Ala-$Sar_{20}$-, —B-Ala-$Sar_{10}$-$PEG_{10}$-, —B-Ala-$Sar_5$-$PEG_{15}$-, and —B-Ala-$Sar_5$-$PEG_5$-, wherein B-Ala represents beta-alanine.

23. The method of claim 18, wherein the molecular scaffold of the heterotandem bicyclic peptide complex, or a pharmaceutically acceptable salt thereof, is 1,1',1"-(1,3,5-triazinane-1,3,5-triyl) triprop-2-en-1-one (TATA), which forms covalent bonds with the cysteine residues of the polypeptide such that two polypeptide loops are formed on the molecular scaffold.

24. The method of claim 18, wherein the heterotandem bicyclic peptide complex is a free acid, or a pharmaceutically acceptable salt selected from the sodium, potassium, calcium, and ammonium salt.

25. The method of claim 18, wherein the first and/or second peptide ligand of the heterotandem bicyclic peptide complex, or a pharmaceutically acceptable salt thereof, comprises a C-terminal amide group.

26. The method of claim 19, wherein the CD137 binding bicyclic peptide ligand of the heterotandem bicyclic peptide complex, or a pharmaceutically acceptable salt thereof, comprises N- and C-terminal modifications and comprises an amino acid sequence selected from:

Ac-A-CiIEEGQYCiiFADPY[Nle]Ciii-Dap (Ac-A-(SEQ ID NO: 1)-Dap);

Ac-A-CiIEEGQYCiiFADPY[Nle]Ciii-Dap(PYA) (Ac-A-(SEQ ID NO: 1)-Dap(PYA));

Ac-Ci[tBuAla]PE[D-Ala]PYCiiFADPY[Nle]Ciii-Dap (Ac-(SEQ ID NO: 3)-Dap);

Ac-Ci[tBuAla]PE[D-Ala]PYCiiFADPY[Nle]Ciii-Dap(PYA) (Ac-(SEQ ID NO: 3)-Dap(PYA));

Ac-A-CiIEEGQYCiiF[D-Ala]DPY[Nle]Ciii-Dap (Ac-A-(SEQ ID NO: 4)-Dap);

Ac-Ci[tBuAla]PK[D-Ala]PYCiiFADPY[Nle]Ciii-A (Ac-(SEQ ID NO: 5)-A);

Ac-Ci[tBuAla]PE[D-Lys]PYCiiFADPY[Nle]Ciii-A (Ac-(SEQ ID NO: 6)-A);

Ac-Ci[tBuAla]P[K(PYA)][D-Ala]PYCiiFADPY[Nle]Ciii-A (Ac-(SEQ ID NO: 7)-A);

Ac-Ci[tBuAla]PE[D-Lys(PYA)]PYCiiFADPY[Nle]Ciii-A (Ac-(SEQ ID NO: 8)-A); and

Ac-A-CiIEE[D-Lys(PYA)]QYCiiFADPY(Nle)Ciii-A (Ac-A-(SEQ ID NO: 9)-A);

wherein Ac represents an acetyl group, Dap represents diaminopropionic acid and PYA represents 4-pentynoic acid.

27. The method of claim 26, wherein the CD137 binding bicyclic peptide ligand of the heterotandem bicyclic peptide complex, or a pharmaceutically acceptable salt thereof, comprises a C-terminal amide group.

28. The method of claim 20, wherein the Nectin-4 binding bicyclic peptide ligand of the heterotandem bicyclic peptide complex, or a pharmaceutically acceptable salt thereof, comprises a C-terminal amide group.

* * * * *

SEQUENCE LISTING

```
<160> NUMBER OF SEQ ID NOS: 18

<210> SEQ ID NO 1
<211> LENGTH: 15
<212> TYPE: PRT
<213> ORGANISM: Artificial
<220> FEATURE:
<223> OTHER INFORMATION: Synthetic peptide
```

<220> FEATURE:
<221> NAME/KEY: Xaa
<222> LOCATION: (14)..(14)
<223> OTHER INFORMATION: Xaa is Nle

<400> SEQUENCE: 1

Cys Ile Glu Glu Gly Gln Tyr Cys Phe Ala Asp Pro Tyr Xaa Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HyP
<220> FEATURE:
<221> NAME/KEY: Xaa
<222> LOCATION: (14)..(14)
<223> OTHER INFORMATION: Xaa is HArg

<400> SEQUENCE: 2

Cys Xaa Leu Val Asn Pro Leu Cys Leu His Pro Asp Trp Xaa Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 3

Cys Xaa Pro Glu Ala Pro Tyr Cys Phe Ala Asp Pro Tyr Xaa Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 4

Cys Ile Glu Glu Gly Gln Tyr Cys Phe Ala Asp Pro Tyr Xaa Cys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)

<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 5

```
Cys Xaa Pro Lys Ala Pro Tyr Cys Phe Ala Asp Pro Tyr Xaa Cys
1               5                   10                  15
```

<210> SEQ ID NO 6
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 6

```
Cys Xaa Pro Glu Lys Pro Tyr Cys Phe Ala Asp Pro Tyr Xaa Cys
1               5                   10                  15
```

<210> SEQ ID NO 7
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (4)..(4)
<223> OTHER INFORMATION: Xaa is K(PYA)
<220> FEATURE:
<221> NAME/KEY: Xaa
<222> LOCATION: (14)..(14)
<223> OTHER INFORMATION: Xaa is Nle

<400> SEQUENCE: 7

```
Cys Xaa Pro Xaa Ala Pro Tyr Cys Phe Ala Asp Pro Tyr Xaa Cys
1               5                   10                  15
```

<210> SEQ ID NO 8
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 8

-continued

Cys Xaa Pro Glu Xaa Pro Tyr Cys Phe Ala Asp Pro Tyr Xaa Cys
1 5 10 15

<210> SEQ ID NO 9
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 9

Cys Ile Glu Glu Xaa Gln Tyr Cys Phe Ala Asp Pro Tyr Xaa Cys
1 5 10 15

<210> SEQ ID NO 10
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is K(PYA)
<220> FEATURE:
<221> NAME/KEY: Xaa
<222> LOCATION: (14)..(14)
<223> OTHER INFORMATION: Xaa is dNle

<400> SEQUENCE: 10

Cys Ile Glu Glu Xaa Gln Tyr Cys Phe Ala Asp Pro Tyr Xaa Cys
1 5 10 15

<210> SEQ ID NO 11
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is HArg

<400> SEQUENCE: 11

Cys Leu Trp Asp Pro Thr Pro Cys Ala Asn Leu His Leu Xaa Cys
1 5 10 15

<210> SEQ ID NO 12
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg

<400> SEQUENCE: 12

Cys Xaa Asp Trp Cys His Trp Thr Phe Ser His Gly His Pro Cys
1 5 10 15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Cys Ser Ala Gly Trp Leu Thr Met Cys Gln Lys Leu His Leu Cys
1 5 10 15

<210> SEQ ID NO 14
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (11)..(11)
<223> OTHER INFORMATION: Xaa is K(PYA)

<400> SEQUENCE: 14

Cys Ser Ala Gly Trp Leu Thr Met Cys Gln Xaa Leu His Leu Cys
1 5 10 15

<210> SEQ ID NO 15
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 15

Cys Pro Xaa Asp Cys Met Xaa Asp Trp Ser Thr Pro Xaa Trp Cys
1 5 10 15

<210> SEQ ID NO 16
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 16

Cys Pro Xaa Asp Cys Met Xaa Asp Trp Ser Thr Pro Xaa Trp Cys
1 5 10 15

-continued

```
<210> SEQ ID NO 17
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is 1Nal
<220> FEATURE:
<221> NAME/KEY: Xaa
<222> LOCATION: (5)..(5)
<223> OTHER INFORMATION: Xaa is (Sar10-(B-Ala))
<220> FEATURE:
<221> NAME/KEY: Xaa
<222> LOCATION: (8)..(8)
<223> OTHER INFORMATION: Xaa is HArg
<220> FEATURE:
<221> NAME/KEY: Xaa
<222> LOCATION: (14)..(14)
<223> OTHER INFORMATION: Xaa is HyP

<400> SEQUENCE: 17

Cys Pro Xaa Lys Xaa Cys Met Xaa Asp Trp Ser Thr Pro Xaa Trp Cys
1               5                   10                  15


<210> SEQ ID NO 18
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is HArg
<220> FEATURE:
<221> NAME/KEY: Xaa
<222> LOCATION: (13)..(13)
<223> OTHER INFORMATION: Xaa is HyP

<400> SEQUENCE: 18

Cys Pro Phe Gly Cys Met Xaa Asp Trp Ser Thr Pro Xaa Trp Cys
1               5                   10                  15
```